US011173196B2

(12) United States Patent
Binder

(10) Patent No.: US 11,173,196 B2
(45) **Date of Patent: *Nov. 16, 2021**

(54) VECTORS FOR EXPRESSION OF PROSTATE-ASSOCIATED ANTIGENS

(71) Applicant: Pfizer Inc., New York, NY (US)

(72) Inventor: Joseph John Binder, San Diego, CA (US)

(73) Assignee: Pfizer Inc., New York, NY (US)

( * ) Notice: Subject to any disclaimer, the term of this patent is extended or adjusted under 35 U.S.C. 154(b) by 37 days.

This patent is subject to a terminal disclaimer.

(21) Appl. No.: 16/111,120

(22) Filed: Aug. 23, 2018

(65) Prior Publication Data

US 2018/0369352 A1 Dec. 27, 2018

Related U.S. Application Data

(62) Division of application No. 15/146,578, filed on May 4, 2016, now Pat. No. 10,092,636, which is a division of application No. 14/527,226, filed on Oct. 29, 2014, now Pat. No. 9,402,901.

(60) Provisional application No. 61/898,966, filed on Nov. 1, 2013.

(51) Int. Cl.

| | |
|---|---|
| ***C07K 14/705*** | (2006.01) |
| ***A61K 39/00*** | (2006.01) |
| ***C07K 16/28*** | (2006.01) |
| ***A61K 45/06*** | (2006.01) |
| ***A61K 31/436*** | (2006.01) |
| ***A61K 31/44*** | (2006.01) |
| ***A61K 31/496*** | (2006.01) |
| ***A61K 31/506*** | (2006.01) |
| ***A61K 31/5377*** | (2006.01) |
| ***A61K 31/404*** | (2006.01) |
| ***A61K 31/7088*** | (2006.01) |
| ***A61K 39/395*** | (2006.01) |
| ***C12N 7/00*** | (2006.01) |
| ***C12N 9/64*** | (2006.01) |

(52) U.S. Cl.

CPC .... *A61K 39/001193* (2018.08); *A61K 31/404* (2013.01); *A61K 31/436* (2013.01); *A61K 31/44* (2013.01); *A61K 31/496* (2013.01); *A61K 31/506* (2013.01); *A61K 31/5377* (2013.01); *A61K 31/7088* (2013.01); *A61K 39/00* (2013.01); *A61K 39/001194* (2018.08); *A61K 39/001195* (2018.08); *A61K 39/3955* (2013.01); *A61K 39/39558* (2013.01); *A61K 45/06* (2013.01); *C07K 14/705* (2013.01); *C07K 16/2818* (2013.01); *C07K 16/2878* (2013.01); *C12N 7/00* (2013.01); *C12N 9/6424* (2013.01); *A61K 2039/505* (2013.01); *A61K 2039/53* (2013.01); *A61K 2039/55516* (2013.01); *A61K 2039/55561* (2013.01); *A61K 2039/645* (2013.01); *A61K 2039/70* (2013.01); *C07K 2317/75* (2013.01); *C07K 2319/40* (2013.01); *C12N 2710/10343* (2013.01); *C12N 2710/10371* (2013.01); *C12N 2830/006* (2013.01); *C12N 2840/20* (2013.01); *C12N 2840/203* (2013.01); *C12Y 304/21077* (2013.01)

(58) Field of Classification Search

CPC combination set(s) only.
See application file for complete search history.

(56) References Cited

U.S. PATENT DOCUMENTS

| | | | | |
|---|---|---|---|---|
| 6,083,716 | A | 7/2000 | Wilson et al. | |
| 8,216,834 | B2 * | 7/2012 | Colloca | C12N 15/86 435/320.1 |
| 9,066,898 | B2 * | 6/2015 | Binder | C07K 16/3023 |
| 9,468,672 | B2 * | 10/2016 | Binder | A61K 39/39 |
| 2005/0032730 | A1 | 2/2005 | Von Der Mulbe et al. | |
| 2005/0063975 | A1 | 3/2005 | Afar et al. | |
| 2005/0261213 | A1 * | 11/2005 | Branigan | A61K 39/0011 514/44 R |
| 2007/0065859 | A1 | 3/2007 | Wang et al. | |
| 2008/0145375 | A1 | 6/2008 | Bembridge | |
| 2010/0305196 | A1 * | 12/2010 | Probst | A61K 39/39 514/44 R |
| 2011/0081343 | A1 * | 4/2011 | Banchereau | C07K 14/4748 424/134.1 |

FOREIGN PATENT DOCUMENTS

| | | |
|---|---|---|
| CN | 102294025 | 12/2011 |
| JP | 2010 540673 | 12/2010 |
| WO | WO 00/49158 | 8/2000 |
| WO | WO 01/82963 | 11/2001 |
| WO | WO 03/004657 | 1/2003 |
| WO | WO2003/000283 | 1/2003 |
| WO | WO2003/000851 | 1/2003 |
| WO | WO 2004/067570 | 8/2004 |
| WO | WO 2005/014780 | 2/2005 |

(Continued)

OTHER PUBLICATIONS

Aurisicchio et al (Cancers, 2011, 3:3687-3713) (IDS).*

(Continued)

*Primary Examiner* — Laura B Goddard

(74) *Attorney, Agent, or Firm* — Austin W. Zhang

(57) ABSTRACT

The present disclosure provides (a) vectors comprising a multi-antigen construct encoding two, three, or more immunogenic PAA polypeptides; (b) compositions comprising the vectors, (c) methods relating to uses of the vectors and compositions for eliciting an immune response or for treating prostate cancers.

19 Claims, 13 Drawing Sheets

Specification includes a Sequence Listing.

(56) References Cited

FOREIGN PATENT DOCUMENTS

| | | |
|---|---|---|
| WO | WO 2005/016376 | 2/2005 |
| WO | WO2005/071093 | 8/2005 |
| WO | WO 2006/008154 | 1/2006 |
| WO | WO2006/078279 | 7/2006 |
| WO | WO2008/010864 | 1/2008 |
| WO | WO2008/122811 | 10/2008 |
| WO | WO 2009/052328 | 4/2009 |
| WO | WO2009046739 | 4/2009 |
| WO | WO2012/065164 | 5/2012 |
| WO | WO 2012/116714 | 9/2012 |
| WO | WO 2012/141984 | 10/2012 |
| WO | WO2015/063647 | 7/2015 |

OTHER PUBLICATIONS

Farina et al (Journal of Virology, 2001, 75:11603-11613) (IDS).*
Madan et al (Lancet Oncology, 2012, 13:501-508).*
Thakur et al (Cancers, May 2013, 5:569-590).*
Leinonen et al (Clinical Chemistry 2002, 48:2208-2216).*
Bett, A., et al., "Packaging Capacity and Stability of Human Adenovirus Type 5 Vectors", Journal of Virology,1993, 5911-5921.
Grunebach, F., et al., "New developments in dendritic cell-based vaccinations: RNA translated into clinics", Cancer Immunol Immunother, 2005, 54: 517-525.
Heiser, A. , et al., "Autologous dendritic cells transfected with prostate-specific antigen RNA stimulate CTL responses against metastatic prostate tumors", J Clin Invest, 2002;109(3):409-417.
Kyte, J., et al., "Immuno-gene therapy of cancer with tumour-mRNA transfected dendritic cells", Cancer Immunol Immunother, 2006, 55:1432-1442.
Marrari, A., et al., "Vaccination therapy in prostate cancer", Cancer Immunol Immunother, 2007, vol. 56, 429-445.
Su, Z., et al., "Enhanced Induction of Telomerase-specific CD4 T Cells Using Dendritic Cells Transfected with RNA Encoding a Chimeric Gene Product", Cancer Research, 2002, vol. 62, 5041-5048.
Dong, J., et al., "Research progress of therapeutic DNA vaccines for prostate cancer", Immunological Journal, 2013, 540-545, vol. 29.
Qin, H., et al., "Specific antitumor immune response induced by a novel DNA vaccine composed of multiple CTL and T helper cell epitopes of prostate cancer associated antigens", Immunology Letters , 2005, 85-93, vol. 99, No. 1.
EPC—International Search Report for International Application No. PCT/EP2007/008771, dated Jun. 13, 2008.
Cohen, C., et al., "Chimpanzee adenovirus CV-68 adapted as a gene delivery vector interacts with the coxsackievirus and adenovirus receptor," Journal of General Virology, (2002), pp. 151-155, vol. 83.
Farina, S., "Repllication-Defective Vector Based on a Chimpanzee Adenovirus", Journal of Virology, (2001), pp. 11603-11613, vol. 75, No. 23.
Ferraro, B., et al., "Co-delivery of PSA and PSMA DNA Vaccines With Electroporation Induces Potent Immune Responses," Human Vaccines, 2011,120-127, vol. 7.
Karan, D., et al., "Cancer Immunotherapy: a paradigm shift for prostate cancer treatment," Nat. Rev. Urology, 2012, 376-385, vol. 9.
Peruzzi, D., et al., "A novel Chimpanzee serotype-based adenoviral vector as delivery tool for cancer vaccines", Vaccine, 2009, 1293-1300, vol. 27, No. 9.
Waeckerle-Men, Ying, et al., "Dendritic cell-based multi-epitope immunotherapy of hormone-refractory prostate carcinoma", Cancer Immunology Immunotherapy, 2006, 1524-1533, vol. 55.
Roy, S., et al., "Complete nucleotide sequences and genome organization of four chimpanzee adenoviruses", Virology, (2004), pp. 361-372.
International Search Report for International Application No. PCT/IB2014/065419.
Aurisicchio, L., et al., "Emerging Cancer Vaccines: The Promise of Genetic Vectors", Cancers, 2011, pp. 3687-3713, vol. 3.
Tatsis, N., et al., "Chimpanzee-origin adenovirus vectors as vaccine carriers", Gene Therapy, 2006, 421-429, vol. 13.
Karan, D., et al, "Dual antigen target based immunotherapy for prostate cancer eliminates the growth of established tumors in mice," Immunotherapy, 2011, 735-746, vol. 3(6).
Roshorm, Y., et al., "T cells induced by recombinant chimpanzee adenovirus alone and in prime-boost regimens decrease chimeric EcoHIV/NDK challenge virus load," Immunol, 2012, 3243-3255, vol. 42.
Diab, A., et al., "DNA Immunization Against Melanoma Antigens Enhances Tumor Immunity in Mice Following Sub-Lethal Irradiation and Immune Reconstitution", Blood, abstract 104:3057.
U.S. Appl. No. 14/527,226, filed Oct. 29, 2014 (U.S. Pat. No. 9,402,901).
U.S. Appl. No. 15/146,578, filed May 4, 2016 (U.S. Pat. No. 10,092,636).
U.S. Appl. No. 13/875,162, filed May 1, 2013 (U.S. Pat. No. 9,066,898).
U.S. Appl. No. 15/207,348, filed Jul. 11, 2016.
U.S. Appl. No. 14/657,302, filed Mar. 13, 2015 (U.S. Pat. No. 9,468,672).

* cited by examiner

```
                  10                  20
------------------+-------------------+-
Q T L N F D L L K L A G D V E S N P G * P  FMDV 2A
- - E G R G S L L T C G D V E E N P G * P  TAV 2A
H Y A G Y F A D L L I H D I E T N P G * P  EMCV 2A
Q C T N Y A L L K L A G D V E S N P G * P  ERAV 2A
- A T N F S L L K Q A G D V E E N P G * P  PTV 2A
```

FIG. 2

5’UAACGUUACUGGCCGAAGCCGCUUGGAAUAAGGCCGGUGUGCGUUUGUCUAU
AUGUUAUUUUCCACCAUAUUGCCGUCUUUUGGCAAUGUGAGGGCCCGGAAACCU
GGCCCUGUCUUCUUGACGAGCAUUCCUAGGGGUCUUUCCCCUCUCGCCAAAGG
AAUGCAAGGUCUGUUGAAUGUCGUGAAGGAAGCAGUUCCUCUGGAAGCUUCUU
GAAGACAAACAACGUCUGUAGCGACCCUUUGCAGGCAGCGGAACCCCCCACCUG
GCGACAGGUGCCUCUGCGGCCAAAAGCCACGUGUAUAAGAUACACCUGCAAAGG
CGGCACAACCCCAGUGCCACGUUGUGAGUUGGAUAGUUGUGGAAAGAGUCAAAU
GGCUCUCCUCAAGCGUAUUCAACAAGGGGCUGAAGGAUGCCCAGAAGGUACCCC
AUUGUAUGGGAUCUGAUCUGGGGCCUCGGUGCACAUGCUUUACAUGUGUUUAG
UCGAGGUUAAAAAACGUCUAGGCCCCCCGAACCACGGGGACGUGGUUUUCCUUU
GAAAAACACGAUGAUAAU*<u>AUGGCCACAACCAUG3’</u>

FIG. 3

SEQUENCE LISTING

<160> NUMBER OF SEQ ID NOS: 294

<210> SEQ ID NO 1
<211> LENGTH: 750
<212> TYPE: PRT
<213> ORGANISM: Homo sapiens

<400> SEQUENCE: 1

Met Trp Asn Leu Leu His Glu Thr Asp Ser Ala Val Ala Thr Ala Arg
1               5                   10                  15

Arg Pro Arg Trp Leu Cys Ala Gly Ala Leu Val Leu Ala Gly Gly Phe
            20                  25                  30

Phe Leu Leu Gly Phe Leu Phe Gly Trp Phe Ile Lys Ser Ser Asn Glu
        35                  40                  45

Ala Thr Asn Ile Thr Pro Lys His Asn Met Lys Ala Phe Leu Asp Glu
    50                  55                  60

Leu Lys Ala Glu Asn Ile Lys Lys Phe Leu Tyr Asn Phe Thr Gln Ile
65                  70                  75                  80

Pro His Leu Ala Gly Thr Glu Gln Asn Phe Gln Leu Ala Lys Gln Ile
                85                  90                  95

Gln Ser Gln Trp Lys Glu Phe Gly Leu Asp Ser Val Glu Leu Ala His
            100                 105                 110

Tyr Asp Val Leu Leu Ser Tyr Pro Asn Lys Thr His Pro Asn Tyr Ile
        115                 120                 125

Ser Ile Ile Asn Glu Asp Gly Asn Glu Ile Phe Asn Thr Ser Leu Phe
    130                 135                 140

Glu Pro Pro Pro Pro Gly Tyr Glu Asn Val Ser Asp Ile Val Pro Pro
145                 150                 155                 160

Phe Ser Ala Phe Ser Pro Gln Gly Met Pro Glu Gly Asp Leu Val Tyr
                165                 170                 175

Val Asn Tyr Ala Arg Thr Glu Asp Phe Phe Lys Leu Glu Arg Asp Met
            180                 185                 190

Lys Ile Asn Cys Ser Gly Lys Ile Val Ile Ala Arg Tyr Gly Lys Val
        195                 200                 205

Phe Arg Gly Asn Lys Val Lys Asn Ala Gln Leu Ala Gly Ala Lys Gly
    210                 215                 220

Val Ile Leu Tyr Ser Asp Pro Ala Asp Tyr Phe Ala Pro Gly Val Lys
225                 230                 235                 240

Ser Tyr Pro Asp Gly Trp Asn Leu Pro Gly Gly Gly Val Gln Arg Gly
                245                 250                 255

Asn Ile Leu Asn Leu Asn Gly Ala Gly Asp Pro Leu Thr Pro Gly Tyr
            260                 265                 270

Pro Ala Asn Glu Tyr Ala Tyr Arg Arg Gly Ile Ala Glu Ala Val Gly
        275                 280                 285

Leu Pro Ser Ile Pro Val His Pro Ile Gly Tyr Tyr Asp Ala Gln Lys

-continued

```
    290                 295                 300

Leu Leu Glu Lys Met Gly Gly Ser Ala Pro Pro Asp Ser Ser Trp Arg
305                 310                 315                 320

Gly Ser Leu Lys Val Pro Tyr Asn Val Gly Pro Gly Phe Thr Gly Asn
                325                 330                 335

Phe Ser Thr Gln Lys Val Lys Met His Ile His Ser Thr Asn Glu Val
            340                 345                 350

Thr Arg Ile Tyr Asn Val Ile Gly Thr Leu Arg Gly Ala Val Glu Pro
        355                 360                 365

Asp Arg Tyr Val Ile Leu Gly Gly His Arg Asp Ser Trp Val Phe Gly
    370                 375                 380

Gly Ile Asp Pro Gln Ser Gly Ala Ala Val Val His Glu Ile Val Arg
385                 390                 395                 400

Ser Phe Gly Thr Leu Lys Lys Glu Gly Trp Arg Pro Arg Arg Thr Ile
                405                 410                 415

Leu Phe Ala Ser Trp Asp Ala Glu Glu Phe Gly Leu Leu Gly Ser Thr
            420                 425                 430

Glu Trp Ala Glu Glu Asn Ser Arg Leu Leu Gln Glu Arg Gly Val Ala
        435                 440                 445

Tyr Ile Asn Ala Asp Ser Ser Ile Glu Gly Asn Tyr Thr Leu Arg Val
    450                 455                 460

Asp Cys Thr Pro Leu Met Tyr Ser Leu Val His Asn Leu Thr Lys Glu
465                 470                 475                 480

Leu Lys Ser Pro Asp Glu Gly Phe Glu Gly Lys Ser Leu Tyr Glu Ser
                485                 490                 495

Trp Thr Lys Lys Ser Pro Ser Pro Glu Phe Ser Gly Met Pro Arg Ile
            500                 505                 510

Ser Lys Leu Gly Ser Gly Asn Asp Phe Glu Val Phe Phe Gln Arg Leu
        515                 520                 525

Gly Ile Ala Ser Gly Arg Ala Arg Tyr Thr Lys Asn Trp Glu Thr Asn
    530                 535                 540

Lys Phe Ser Gly Tyr Pro Leu Tyr His Ser Val Tyr Glu Thr Tyr Glu
545                 550                 555                 560

Leu Val Glu Lys Phe Tyr Asp Pro Met Phe Lys Tyr His Leu Thr Val
                565                 570                 575

Ala Gln Val Arg Gly Gly Met Val Phe Glu Leu Ala Asn Ser Ile Val
            580                 585                 590

Leu Pro Phe Asp Cys Arg Asp Tyr Ala Val Val Leu Arg Lys Tyr Ala
        595                 600                 605

Asp Lys Ile Tyr Ser Ile Ser Met Lys His Pro Gln Glu Met Lys Thr
    610                 615                 620

Tyr Ser Val Ser Phe Asp Ser Leu Phe Ser Ala Val Lys Asn Phe Thr
625                 630                 635                 640

Glu Ile Ala Ser Lys Phe Ser Glu Arg Leu Gln Asp Phe Asp Lys Ser
                645                 650                 655

Asn Pro Ile Val Leu Arg Met Met Asn Asp Gln Leu Met Phe Leu Glu
            660                 665                 670

Arg Ala Phe Ile Asp Pro Leu Gly Leu Pro Asp Arg Pro Phe Tyr Arg
        675                 680                 685

His Val Ile Tyr Ala Pro Ser Ser His Asn Lys Tyr Ala Gly Glu Ser
    690                 695                 700

Phe Pro Gly Ile Tyr Asp Ala Leu Phe Asp Ile Glu Ser Lys Val Asp
705                 710                 715                 720
```

```
Pro Ser Lys Ala Trp Gly Glu Val Lys Arg Gln Ile Tyr Val Ala Ala
                725                 730                 735

Phe Thr Val Gln Ala Ala Ala Glu Thr Leu Ser Glu Val Ala
            740                 745                 750


<210> SEQ ID NO 2
<211> LENGTH: 2250
<212> TYPE: DNA
<213> ORGANISM: Homo sapiens

<400> SEQUENCE: 2

atgtggaatc tccttcacga aaccgactcg gctgtggcca ccgcgcgccg cccgcgctgg     60

ctgtgcgctg gggcgctggt gctggcgggt ggcttctttc tcctcggctt cctcttcggg    120

tggtttataa aatcctccaa tgaagctact aacattactc caaagcataa tatgaaagca    180

tttttggatg aattgaaagc tgagaacatc aagaagttct tatataattt tacacagata    240

ccacatttag caggaacaga acaaaacttt cagcttgcaa agcaaattca atcccagtgg    300

aaagaatttg gcctggattc tgttgagcta gcacattatg atgtcctgtt gtcctaccca    360

aataagactc atcccaacta catctcaata attaatgaag atggaaatga gattttcaac    420

acatcattat ttgaaccacc tcctccagga tatgaaaatg tttcggatat tgtaccacct    480

ttcagtgctt tctctcctca aggaatgcca gagggcgatc tagtgtatgt taactatgca    540

cgaactgaag acttctttaa attggaacgg gacatgaaaa tcaattgctc tgggaaaatt    600

gtaattgcca gatatgggaa agttttcaga ggaaataagg ttaaaaatgc ccagctggca    660

ggggccaaag gagtcattct ctactccgac cctgctgact actttgctcc tggggtgaag    720

tcctatccag atggttggaa tcttcctgga ggtggtgtcc agcgtggaaa tatcctaaat    780

ctgaatggtg caggagaccc tctcacacca ggttacccag caaatgaata tgcttatagg    840

cgtggaattg cagaggctgt tggtcttcca agtattcctg ttcatccaat tggatactat    900

gatgcacaga agctcctaga aaaaatgggt ggctcagcac caccagatag cagctggaga    960

ggaagtctca aagtgcccta caatgttgga cctggcttta ctggaaactt ttctacacaa   1020

aaagtcaaga tgcacatcca ctctaccaat gaagtgacaa gaatttacaa tgtgataggt   1080

actctcagag gagcagtgga accagacaga tatgtcattc tgggaggtca ccgggactca   1140

tgggtgtttg gtggtattga ccctcagagt ggagcagctg ttgttcatga aattgtgagg   1200

agctttggaa cactgaaaaa ggaagggtgg agacctagaa gaacaatttt gtttgcaagc   1260

tgggatgcag aagaatttgg tcttcttggt tctactgagt gggcagagga gaattcaaga   1320

ctccttcaag agcgtggcgt ggcttatatt aatgctgact catctataga aggaaactac   1380

actctgagag ttgattgtac accgctgatg tacagcttgg tacacaacct aacaaaagag   1440

ctgaaaagcc ctgatgaagg ctttgaaggc aaatctcttt atgaaagttg gactaaaaaa   1500

agtccttccc cagagttcag tggcatgccc aggataagca aattgggatc tggaaatgat   1560

tttgaggtgt tcttccaacg acttggaatt gcttcaggca gagcacggta tactaaaaat   1620

tgggaaacaa acaaattcag cggctatcca ctgtatcaca gtgtctatga aacatatgag   1680

ttggtggaaa agttttatga tccaatgttt aaatatcacc tcactgtggc ccaggttcga   1740

ggagggatgg tgtttgagct agccaattcc atagtgctcc cttttgattg tcgagattat   1800

gctgtagttt taagaaagta tgctgacaaa atctacagta tttctatgaa acatccacag   1860

gaaatgaaga catacagtgt atcatttgat tcactttttt ctgcagtaaa gaattttaca   1920
```

-continued gaaattgctt ccaagttcag tgagagactc caggactttg acaaaagcaa cccaatagta 1980
ttaagaatga tgaatgatca actcatgttt ctggaaagag catttattga tccattaggg 2040
ttaccagaca ggccttttta taggcatgtc atctatgctc caagcagcca caacaagtat 2100
gcaggggagt cattcccagg aatttatgat gctctgtttg atattgaaag caaagtggac 2160
ccttccaagg cctggggaga agtgaagaga cagatttatg ttgcagcctt cacagtgcag 2220
gcagctgcag agactttgag tgaagtagcc 2250

<210> SEQ ID NO 3
<211> LENGTH: 739
<212> TYPE: PRT
<213> ORGANISM: Artificial Sequence
<220> FEATURE:
<223> OTHER INFORMATION: Synthetic Construct

<400> SEQUENCE: 3

Met Ala Ser Ala Arg Arg Pro Arg Trp Leu Cys Ala Gly Ala Leu Val
1 5 10 15

Leu Ala Gly Gly Phe Phe Leu Leu Gly Phe Leu Phe Gly Trp Phe Ile
20 25 30

Lys Ser Ser Ser Glu Ala Thr Asn Ile Ser Pro Gln His Asn Val Lys
35 40 45

Ala Phe Leu Asp Glu Met Lys Ala Glu Asn Ile Lys Lys Phe Leu Tyr
50 55 60

Leu Phe Thr Gln Ile Pro His Leu Ala Gly Thr Glu Gln Asn Phe Gln
65 70 75 80

Leu Ala Lys Gln Ile Gln Ala Glu Trp Lys Glu Phe Gly Leu Asp Ser
85 90 95

Val Glu Leu Ala His Tyr Asp Val Leu Leu Ser Tyr Pro Asn Glu Thr
100 105 110

His Pro Asn Tyr Ile Ser Ile Ile Asp Glu Asp Gly Asn Glu Ile Phe
115 120 125

Asn Thr Ser Leu Phe Glu Pro Pro Pro Pro Gly Tyr Glu Asn Ile Ser
130 135 140

Asp Val Val Pro Pro Tyr Ser Ala Phe Ser Pro Gln Gly Met Pro Glu
145 150 155 160

Gly Asp Leu Val Tyr Val Asn Tyr Ala Arg Thr Glu Asp Phe Phe Lys
165 170 175

Leu Glu Arg Glu Leu Lys Ile Asn Cys Ser Gly Lys Ile Leu Ile Ala
180 185 190

Arg Tyr Gly Lys Val Phe Arg Gly Asn Lys Val Lys Asn Ala Gln Leu
195 200 205

Ala Gly Ala Lys Gly Ile Ile Leu Tyr Ser Asp Pro Ala Asp Tyr Phe
210 215 220

Ala Pro Gly Val Lys Ser Tyr Pro Asp Gly Trp Asn Leu Pro Gly Gly
225 230 235 240

Gly Val Gln Arg Gly Asn Val Leu Asn Leu Asn Gly Ala Gly Asp Pro
245 250 255

Leu Thr Pro Gly Tyr Pro Ala Asn Glu Tyr Ala Tyr Arg Arg Glu Leu
260 265 270

Ala Glu Ala Val Gly Leu Pro Ser Ile Pro Val His Pro Ile Gly Tyr
275 280 285

Tyr Asp Ala Gln Lys Leu Leu Glu Lys Met Gly Gly Ser Ala Pro Pro
290 295 300

-continued

```
Asp Ser Ser Trp Lys Gly Ser Leu Lys Val Pro Tyr Asn Val Gly Pro
305                 310                 315                 320

Gly Phe Thr Gly Asn Phe Ser Thr Gln Lys Val Lys Met His Ile His
                325                 330                 335

Ser Thr Asn Glu Val Thr Arg Ile Tyr Asn Val Ile Gly Thr Ile Arg
            340                 345                 350

Gly Ala Val Glu Pro Asp Arg Tyr Val Ile Leu Gly Gly His Arg Asp
        355                 360                 365

Ala Trp Val Phe Gly Gly Ile Asp Pro Gln Ser Gly Ala Ala Val Val
    370                 375                 380

His Glu Ile Val Arg Ser Phe Gly Thr Leu Lys Lys Lys Gly Trp Arg
385                 390                 395                 400

Pro Arg Arg Thr Ile Ile Phe Ala Ser Trp Asp Ala Glu Glu Phe Gly
                405                 410                 415

Leu Leu Gly Ser Thr Glu Trp Ala Glu Glu Asn Ser Arg Leu Leu Gln
            420                 425                 430

Glu Arg Gly Val Ala Tyr Ile Asn Ala Asp Ser Ser Ile Glu Gly Asn
        435                 440                 445

Tyr Thr Leu Arg Val Asp Cys Thr Pro Leu Met Tyr Ser Leu Val Tyr
    450                 455                 460

Asn Leu Thr Lys Glu Leu Gln Ser Pro Asp Glu Gly Phe Glu Gly Lys
465                 470                 475                 480

Ser Leu Tyr Glu Ser Trp Thr Lys Lys Ser Pro Ser Pro Glu Phe Ser
                485                 490                 495

Gly Val Pro Arg Ile Asn Lys Leu Gly Ser Gly Asn Asp Phe Glu Val
            500                 505                 510

Phe Phe Gln Arg Leu Gly Ile Ala Ser Gly Arg Ala Arg Tyr Thr Lys
        515                 520                 525

Asn Trp Lys Thr Asn Lys Phe Ser Gly Tyr Pro Leu Tyr His Ser Val
    530                 535                 540

Tyr Glu Thr Tyr Glu Leu Val Glu Lys Phe Tyr Asp Pro Met Phe Lys
545                 550                 555                 560

Tyr His Leu Thr Val Ala Gln Val Arg Gly Gly Leu Val Phe Glu Leu
                565                 570                 575

Ala Asp Ser Ile Val Leu Pro Phe Asp Cys Gln Asp Tyr Ala Val Val
            580                 585                 590

Leu Arg Lys Tyr Ala Asp Lys Ile Tyr Asn Leu Ala Met Lys His Pro
        595                 600                 605

Glu Glu Leu Lys Thr Tyr Ser Val Ser Phe Asp Ser Leu Phe Ser Ala
    610                 615                 620

Val Lys Asn Phe Thr Glu Ile Ala Ser Lys Phe Asn Gln Arg Leu Gln
625                 630                 635                 640

Asp Phe Asp Lys Asn Asn Pro Leu Leu Val Arg Met Leu Asn Asp Gln
                645                 650                 655

Leu Met Phe Leu Glu Arg Ala Phe Val Asp Pro Leu Gly Leu Pro Asp
            660                 665                 670

Arg Pro Phe Tyr Arg His Val Ile Tyr Ala Pro Ser Ser His Asn Lys
        675                 680                 685

Tyr Ala Gly Glu Ser Phe Pro Gly Ile Tyr Asp Ala Leu Phe Asp Ile
    690                 695                 700

Glu Ser Lys Val Asp Pro Ser Lys Ala Trp Gly Glu Val Lys Arg Gln
705                 710                 715                 720

Ile Tyr Val Ala Ala Phe Thr Val Gln Ala Ala Ala Glu Thr Leu Ser
```

-continued 725 730 735

Glu Val Ala

<210> SEQ ID NO 4
<211> LENGTH: 2217
<212> TYPE: DNA
<213> ORGANISM: Artificial Sequence
<220> FEATURE:
<223> OTHER INFORMATION: Synthetic Construct

<400> SEQUENCE: 4
atggctagcg ccagacggcc cagatggctg tgcgccggag ccctggtgct ggccggagga 60
ttcttcctgc tgggcttcct gttcggctgg ttcatcaaga gcagcagcga ggccaccaac 120
atcagccccc agcacaacgt gaaggccttt ctggacgaga tgaaggccga gaacatcaag 180
aagtttctgt acctgttcac ccagatcccc cacctggccg gcaccgagca gaacttccag 240
ctggccaagc agattcaggc tgagtggaaa gagttcggcc tggacagcgt ggagctggcc 300
cactacgacg tgctgctgtc ctaccccaac gagacacacc ccaactacat cagcatcatc 360
gacgaggacg gcaacgagat tttcaacacc agcctgttcg agccccctcc ccctggctac 420
gagaacatct ccgacgtggt gccccccctac agcgccttca gccctcaggg aatgcctgaa 480
ggcgacctgg tgtacgtgaa ctacgcccgg accgaggact tcttcaagct ggaacgggag 540
ctgaagatca actgcagcgg caagatcctg atcgccagat acggcaaggt gttccggggc 600
aacaaagtga agaacgcaca gctggctgga gccaagggca tcatcctgta cagcgacccc 660
gccgactact tcgcccctgg cgtgaagtcc taccctgacg gctggaacct gcctggcggc 720
ggagtgcagc ggggcaacgt gctgaacctg aacggagccg gcgaccctct gaccccaggc 780
taccccgcca acgagtacgc ctaccggcgg gagctggccg aagccgtggg cctgcccagc 840
atccccgtgc accccatcgg ctactacgac gcccagaaac tgctggaaaa gatgggcggc 900
agcgcccctc ccgacagcag ctggaagggc agcctgaagg tgccctacaa cgtgggccct 960
ggcttcaccg gcaacttcag cacccagaaa gtgaagatgc acatccacag caccaacgaa 1020
gtgacccgga tctacaacgt gatcggcacc atcagaggcg ccgtggagcc cgacagatac 1080
gtgatcctgg gcggccaccg ggacgcctgg gtgttcggcg gcatcgaccc ccagagcgga 1140
gccgccgtgg tgcacgagat cgtgcggagc ttcggcaccc tgaagaagaa gggctggcgg 1200
cccagacgga ccatcatctt cgccagctgg gacgccgagg aattcggact gctgggctct 1260
accgagtggg ccgaggaaaa cagcagactg ctgcaggaac ggggcgtcgc ctacatcaac 1320
gccgacagct ccatcgaggg caactacacc ctgcgggtgg actgcacccc cctgatgtac 1380
agcctggtgt acaacctgac caaagagctg cagagccccg acgagggctt cgagggcaag 1440
agcctgtacg agagctggac caagaagtcc cccagccccg agttcagcgg cgtgccccgg 1500
atcaacaagc tgggcagcgg caacgacttc gaggtgttct tccagaggct gggcattgcc 1560
agcggcagag cccggtacac caagaactgg aaaaccaaca agttctccgg ctaccccctg 1620
taccacagcg tgtacgagac atacgaactg gtggagaagt tctacgaccc catgttcaag 1680
taccacctga ccgtggccca ggtccgggga gggctggtgt tcgaactggc cgacagcatc 1740
gtgctgccct tcgactgcca ggactatgct gtggtgctgc ggaagtacgc cgacaaaatc 1800
tacaacctgg ccatgaagca ccccgaggaa ctgaaaacct acagcgtgtc cttcgacagc 1860
ctgttcagcg ccgtgaagaa cttcaccgag atcgccagca agttcaacca gcggctgcag 1920
gacttcgaca agaacaaccc cctgctggtc cggatgctga acgaccagct gatgttcctg 1980

```
gaacgggcct tcgtggaccc cctgggcctg cctgaccggc ccttctaccg gcacgtgatc   2040

tatgccccca gcagccacaa caagtacgct ggcgagagct tccccggcat ctacgatgcc   2100

ctgttcgaca tcgagagcaa ggtggacccc agcaaggcct ggggcgaagt gaagcggcag   2160

atatacgtgg ccgccttcac agtgcaggcc gctgccgaga cactgagcga ggtggcc      2217


<210> SEQ ID NO 5
<211> LENGTH: 739
<212> TYPE: PRT
<213> ORGANISM: Artificial Sequence
<220> FEATURE:
<223> OTHER INFORMATION: Synthetic Construct

<400> SEQUENCE: 5

Met Ala Ser Ala Arg Arg Pro Arg Trp Leu Cys Ala Gly Ala Leu Val
1               5                   10                  15

Leu Ala Gly Gly Phe Phe Leu Leu Gly Phe Leu Phe Gly Trp Phe Ile
            20                  25                  30

Lys Ser Ser Ser Glu Ala Thr Asn Ile Thr Pro Gln His Asn Val Lys
        35                  40                  45

Ala Phe Leu Asp Glu Leu Lys Ala Glu Asn Ile Lys Lys Phe Leu Tyr
    50                  55                  60

Asn Phe Thr Gln Ile Pro His Leu Ala Gly Thr Glu Gln Asn Phe Glu
65                  70                  75                  80

Leu Ala Lys Gln Ile Gln Ala Gln Trp Lys Glu Phe Gly Leu Asp Ser
                85                  90                  95

Val Glu Leu Ser His Tyr Asp Val Leu Leu Ser Tyr Pro Asn Glu Thr
            100                 105                 110

His Pro Asn Tyr Ile Ser Ile Ile Asp Glu Asp Gly Asn Glu Ile Phe
        115                 120                 125

Asn Thr Ser Leu Phe Glu Pro Pro Pro Pro Gly Tyr Glu Asn Ile Ser
    130                 135                 140

Asp Val Val Pro Pro Tyr Ser Ala Phe Ser Pro Gln Gly Met Pro Glu
145                 150                 155                 160

Gly Asp Leu Val Tyr Val Asn Tyr Ala Arg Thr Glu Asp Phe Phe Lys
                165                 170                 175

Leu Glu Arg Asp Met Lys Ile Asn Cys Ser Gly Lys Ile Leu Ile Ala
            180                 185                 190

Arg Tyr Gly Lys Val Phe Arg Gly Asn Lys Val Lys Asn Ala Gln Leu
        195                 200                 205

Ala Gly Ala Lys Gly Ile Ile Leu Tyr Ser Asp Pro Ala Asp Tyr Phe
    210                 215                 220

Ala Pro Gly Val Lys Ser Tyr Pro Asp Gly Trp Asn Leu Pro Gly Gly
225                 230                 235                 240

Gly Val Gln Arg Gly Asn Val Leu Asn Leu Asn Gly Ala Gly Asp Pro
                245                 250                 255

Leu Thr Pro Gly Tyr Pro Ala Asn Glu Tyr Ala Tyr Arg Arg Gly Ile
            260                 265                 270

Ala Glu Ala Val Gly Leu Pro Ser Ile Pro Val His Pro Ile Gly Tyr
        275                 280                 285

Tyr Asp Ala Gln Lys Leu Leu Glu Lys Met Gly Gly Ala Ala Pro Pro
    290                 295                 300

Asp Ser Ser Trp Lys Gly Ser Leu Gln Val Pro Tyr Asn Val Gly Pro
305                 310                 315                 320
```

-continued

```
Gly Phe Thr Gly Asn Phe Ser Thr Gln Lys Val Lys Met His Ile His
                325                 330                 335

Ser Thr Asn Glu Val Thr Arg Ile Tyr Asn Val Ile Gly Thr Leu Lys
            340                 345                 350

Gly Ala Val Glu Pro Asp Arg Tyr Val Ile Leu Gly Gly His Arg Asp
        355                 360                 365

Ala Trp Val Phe Gly Gly Ile Asp Pro Gln Ser Gly Ala Ala Val Val
    370                 375                 380

His Glu Ile Val Arg Ser Phe Gly Thr Leu Lys Lys Lys Gly Trp Arg
385                 390                 395                 400

Pro Arg Arg Thr Ile Leu Phe Ala Ser Trp Asp Ala Glu Glu Phe Gly
                405                 410                 415

Leu Leu Gly Ser Thr Glu Trp Ala Glu Glu Asn Ser Arg Leu Leu Gln
            420                 425                 430

Glu Arg Gly Val Ala Tyr Ile Asn Ala Asp Ser Ser Ile Glu Gly Asn
        435                 440                 445

Tyr Thr Leu Arg Val Asp Cys Thr Pro Leu Met Tyr Ser Leu Val Tyr
    450                 455                 460

Asn Leu Thr Lys Glu Leu Gln Ser Pro Asp Glu Gly Phe Glu Gly Lys
465                 470                 475                 480

Ser Leu Phe Asp Ser Trp Thr Glu Lys Ser Pro Ser Pro Glu Phe Ser
                485                 490                 495

Gly Leu Pro Arg Ile Ser Lys Leu Gly Ser Gly Asn Asp Phe Glu Val
            500                 505                 510

Phe Phe Gln Arg Leu Gly Ile Ala Ser Gly Arg Ala Arg Tyr Thr Lys
        515                 520                 525

Asp Trp Lys Thr Ser Lys Phe Ser Gly Tyr Pro Leu Tyr His Ser Val
    530                 535                 540

Tyr Glu Thr Tyr Glu Leu Val Glu Lys Phe Tyr Asp Pro Met Phe Lys
545                 550                 555                 560

Tyr His Leu Thr Val Ala Gln Val Arg Gly Gly Ile Val Phe Glu Leu
                565                 570                 575

Ala Asn Ser Val Val Leu Pro Phe Asp Cys Gln Asp Tyr Ala Val Val
            580                 585                 590

Leu Lys Lys Tyr Ala Asp Lys Ile Tyr Asn Ile Ser Met Lys His Pro
        595                 600                 605

Gln Glu Met Lys Thr Tyr Ser Val Ser Phe Asp Ser Leu Phe Ser Ala
    610                 615                 620

Val Lys Asn Phe Thr Glu Ile Ala Ser Lys Phe Asn Gln Arg Leu Gln
625                 630                 635                 640

Asp Phe Asp Lys Asn Asn Pro Ile Leu Leu Arg Met Met Asn Asp Gln
                645                 650                 655

Leu Met Phe Leu Glu Arg Ala Phe Ile Asp Pro Leu Gly Leu Pro Asp
            660                 665                 670

Arg Pro Phe Tyr Arg His Val Ile Tyr Ala Pro Ser Ser His Asn Lys
        675                 680                 685

Tyr Ala Gly Glu Ser Phe Pro Gly Ile Tyr Asp Ala Leu Phe Asp Ile
    690                 695                 700

Glu Ser Lys Val Asp Pro Ser Lys Ala Trp Gly Glu Val Lys Arg Gln
705                 710                 715                 720

Ile Tyr Val Ala Ala Phe Thr Val Gln Ala Ala Ala Glu Thr Leu Ser
                725                 730                 735

Glu Val Ala
```

<210> SEQ ID NO 6
<211> LENGTH: 2217
<212> TYPE: DNA
<213> ORGANISM: Artificial Sequence
<220> FEATURE:
<223> OTHER INFORMATION: Synthetic Construct

<400> SEQUENCE: 6
atggctagcg ccagacggcc cagatggctg tgtgctggcg ccctggtgct ggctggcggc 60
tttttcctgc tgggcttcct gttcggctgg ttcatcaaga gcagcagcga ggccaccaac 120
atcacccccc agcacaacgt gaaggccttt ctggacgagc tgaaggccga gaatatcaag 180
aagttcctgt acaacttcac ccagatcccc cacctggccg gcaccgagca gaacttcgag 240
ctggccaagc agatccaggc ccagtggaaa gagttcggcc tggacagcgt ggaactgagc 300
cactacgacg tgctgctgag ctaccccaac gagacacacc ccaactacat cagcatcatc 360
gacgaggacg gcaacgagat tttcaacacc agcctgttcg agccccctcc acccggctac 420
gagaacatca gcgacgtggt gccccccctac agcgcattca gtccacaggg aatgcccgag 480
ggcgacctgg tgtacgtgaa ctacgcccgg accgaggact tcttcaagct ggaacgggac 540
atgaagatca actgcagcgg caagatcctg atcgccagat acggcaaggt gttccggggc 600
aacaaagtga agaacgccca gctggcaggc gccaagggca tcatcctgta cagcgacccc 660
gccgactact tcgcccctgg cgtgaagtcc taccccgacg gctggaacct gcctggcggc 720
ggagtgcaga ggggcaacgt gctgaacctg aacggcgctg gcgaccctct gacccctggc 780
taccccgcca acgagtacgc ctacagacgg ggaatcgccg aggccgtggg cctgcctagc 840
atccctgtgc accccatcgg ctactacgac gcccagaaac tgctggaaaa gatgggcgga 900
gccgcccctc ccgacagctc ttggaagggc agcctgcagg tcccctacaa cgtgggccct 960
ggcttcaccg gcaacttcag cacccagaaa gtgaagatgc acatccacag caccaacgaa 1020
gtgacccgga tctacaacgt gatcggcacc ctgaagggcg ccgtggaacc cgacagatac 1080
gtgatcctgg gcggccaccg ggacgcctgg gtgttcggag gcatcgaccc tcagagcggc 1140
gctgccgtgg tgcacgagat cgtgcggagc ttcggcacac tgaagaagaa gggctggcgg 1200
cccagacgga ccatcctgtt cgccagctgg gacgccgagg aattcggcct gctgggcagc 1260
accgagtggg ccgaggaaaa cagtcggctg ctgcaggaac ggggcgtcgc ctacatcaac 1320
gccgacagca gcatcgaggg caactacacc ctgcgggtgg actgcacccc cctgatgtac 1380
agcctggtgt acaacctgac caaagagctg cagagccccg acgagggctt cgagggcaag 1440
tccctgttcg actcctggac cgagaagtcc cccagccccg agttcagcgg cctgcccaga 1500
atcagcaagc tgggcagcgg caacgacttc gaggtgttct tccagcggct gggaatcgcc 1560
agcggcagag cccggtacac caaggactgg aaaaccagca agttctccgg ctaccccctg 1620
taccacagcg tgtacgagac atacgagctg gtggaaaagt tctacgaccc catgttcaag 1680
taccacctga ccgtggccca ggtccgaggc ggcatcgtgt tcgaactggc caacagcgtg 1740
gtgctgccat tcgattgtca ggactacgcc gtggtgctga agaagtacgc cgacaaaatc 1800
tacaacatca gcatgaagca cccccaggaa atgaaaacct acagcgtgtc cttcgacagc 1860
ctgttcagcg ccgtgaagaa tttcaccgag atcgcctcca agttcaacca gagactgcag 1920
gacttcgaca agaacaaccc catcctgctg cggatgatga acgaccagct gatgttcctg 1980
gaacgggcct tcatcgaccc cctgggcctg cccgaccggc ccttttaccg gcacgtgatc 2040

-continued

```
tatgcccca gcagccacaa caaatacgcc ggcgagagtt tccccggcat ctacgatgcc   2100

ctgttcgata tcgagagcaa ggtggacccc agcaaggcct ggggcgaagt gaagcggcag   2160

atttacgtgg ccgcattcac agtgcaggct gctgccgaga cactgagcga ggtggcc      2217


<210> SEQ ID NO 7
<211> LENGTH: 739
<212> TYPE: PRT
<213> ORGANISM: Artificial Sequence
<220> FEATURE:
<223> OTHER INFORMATION: Synthetic Construct

<400> SEQUENCE: 7

Met Ala Ser Ala Arg Arg Pro Arg Trp Leu Cys Ala Gly Ala Leu Val
1               5                   10                  15

Leu Ala Gly Gly Phe Phe Leu Leu Gly Phe Leu Phe Gly Trp Phe Ile
            20                  25                  30

Lys Ser Ser Asn Glu Ala Thr Asn Ile Thr Pro Lys His Asn Met Lys
        35                  40                  45

Ala Phe Leu Asp Glu Leu Lys Ala Glu Asn Ile Lys Lys Phe Leu Tyr
    50                  55                  60

Asn Phe Thr Gln Ile Pro His Leu Ala Gly Thr Glu Gln Asn Phe Gln
65                  70                  75                  80

Leu Ala Lys Gln Ile Gln Ser Gln Trp Lys Glu Phe Gly Leu Asp Ser
                85                  90                  95

Val Glu Leu Ala His Tyr Asp Val Leu Leu Ser Tyr Pro Asn Lys Thr
            100                 105                 110

His Pro Asn Tyr Ile Ser Ile Ile Asn Glu Asp Gly Asn Glu Ile Phe
        115                 120                 125

Asn Thr Ser Leu Phe Glu Pro Pro Pro Pro Gly Tyr Glu Asn Val Ser
    130                 135                 140

Asp Ile Val Pro Pro Phe Ser Ala Phe Ser Pro Gln Gly Met Pro Glu
145                 150                 155                 160

Gly Asp Leu Val Tyr Val Asn Tyr Ala Arg Thr Glu Asp Phe Phe Lys
                165                 170                 175

Leu Glu Arg Asp Met Lys Ile Asn Cys Ser Gly Lys Ile Val Ile Ala
            180                 185                 190

Arg Tyr Gly Lys Val Phe Arg Gly Asn Lys Val Lys Asn Ala Gln Leu
        195                 200                 205

Ala Gly Ala Lys Gly Val Ile Leu Tyr Ser Asp Pro Ala Asp Tyr Phe
    210                 215                 220

Ala Pro Gly Val Lys Ser Tyr Pro Asp Gly Trp Asn Leu Pro Gly Gly
225                 230                 235                 240

Gly Val Gln Arg Gly Asn Ile Leu Asn Leu Asn Gly Ala Gly Asp Pro
                245                 250                 255

Leu Thr Pro Gly Tyr Pro Ala Asn Glu Tyr Ala Tyr Arg Arg Gly Ile
            260                 265                 270

Ala Glu Ala Val Gly Leu Pro Ser Ile Pro Val His Pro Ile Gly Tyr
        275                 280                 285

Tyr Asp Ala Gln Lys Leu Leu Glu Lys Met Gly Gly Ser Ala Pro Pro
    290                 295                 300

Asp Ser Ser Trp Arg Gly Ser Leu Lys Val Pro Tyr Asn Val Gly Pro
305                 310                 315                 320

Gly Phe Thr Gly Asn Phe Ser Ala Gln Lys Leu Lys Leu His Ile His
                325                 330                 335
```

-continued

```
Ser Asn Thr Lys Val Thr Arg Ile Tyr Asn Val Ile Gly Thr Leu Arg
            340                 345                 350

Gly Ala Val Glu Pro Asp Arg Tyr Val Ile Leu Gly Gly His Arg Asp
        355                 360                 365

Ser Trp Val Phe Gly Gly Ile Asp Pro Gln Ser Gly Ala Ala Val Val
    370                 375                 380

His Glu Ile Val Arg Thr Phe Gly Thr Leu Lys Lys Lys Gly Trp Arg
385                 390                 395                 400

Pro Arg Arg Thr Ile Leu Phe Ala Ser Trp Asp Ala Glu Glu Phe Gly
                405                 410                 415

Leu Leu Gly Ser Thr Glu Trp Ala Glu Glu Asn Ser Arg Leu Leu Gln
            420                 425                 430

Glu Arg Gly Val Ala Tyr Ile Asn Ala Asp Ser Ser Ile Glu Gly Asn
        435                 440                 445

Tyr Thr Leu Arg Val Asp Cys Thr Pro Leu Leu His Ser Leu Val Tyr
    450                 455                 460

Asn Leu Thr Lys Glu Leu Lys Ser Pro Asp Glu Gly Phe Glu Gly Lys
465                 470                 475                 480

Ser Leu Tyr Glu Ser Trp Thr Lys Lys Ser Pro Ser Pro Glu Leu Ser
                485                 490                 495

Gly Leu Pro Arg Ile Ser Lys Leu Gly Ser Gly Asn Asp Phe Glu Val
            500                 505                 510

Phe Phe Gln Arg Leu Gly Ile Ser Ser Gly Arg Ala Arg Tyr Thr Lys
        515                 520                 525

Asp Trp Lys Thr Ser Lys Phe Ser Ser Tyr Pro Leu Tyr His Ser Ile
    530                 535                 540

Tyr Glu Thr Tyr Glu Leu Val Val Lys Phe Tyr Asp Pro Met Phe Lys
545                 550                 555                 560

Tyr His Leu Thr Val Ala Gln Val Arg Gly Gly Met Val Phe Glu Leu
                565                 570                 575

Ala Asn Ser Ile Val Leu Pro Phe Asp Cys Arg Asp Tyr Ala Val Ala
            580                 585                 590

Leu Lys Asn His Ala Glu Asn Leu Tyr Ser Ile Ser Met Lys His Pro
        595                 600                 605

Gln Glu Met Lys Thr Tyr Ser Val Ser Phe Asp Ser Leu Phe Ser Ala
    610                 615                 620

Val Lys Asn Phe Thr Glu Ile Ala Ser Lys Phe Ser Glu Arg Leu Gln
625                 630                 635                 640

Asp Phe Asp Lys Ser Asn Pro Ile Val Leu Arg Met Met Asn Asp Gln
                645                 650                 655

Leu Met Phe Leu Glu Arg Ala Phe Ile Asp Pro Leu Gly Leu Pro Asp
            660                 665                 670

Arg Pro Phe Tyr Arg His Val Ile Tyr Ala Pro Ser Ser His Asn Lys
        675                 680                 685

Tyr Ala Gly Glu Ser Phe Pro Gly Ile Tyr Asp Ala Leu Phe Asp Ile
    690                 695                 700

Glu Ser Lys Val Asp Pro Ser Lys Ala Trp Gly Glu Val Lys Arg Gln
705                 710                 715                 720

Ile Tyr Val Ala Ala Phe Thr Val Gln Ala Ala Ala Glu Thr Leu Ser
                725                 730                 735

Glu Val Ala
```

<210> SEQ ID NO 8

<211> LENGTH: 2217
<212> TYPE: DNA
<213> ORGANISM: Artificial Sequence
<220> FEATURE:
<223> OTHER INFORMATION: Synthetic Construct

<400> SEQUENCE: 8
atggctagcg ccagacggcc cagatggctg tgtgctggcg ccctggtgct ggctggcggc 60
tttttcctgc tgggcttcct gttcggctgg ttcatcaaga gcagcaacga ggccaccaac 120 atcacccccca agcacaacat gaaggccttt ctggacgagc tgaaggccga gaatatcaag 180
aagttcctgt acaacttcac ccagatcccc cacctggccg gcaccgagca gaacttccag 240
ctggccaagc agatccagag ccagtggaaa gagttcggcc tggacagcgt ggaactggcc 300
cactacgacg tgctgctgag ctaccccaac aagacccacc ccaactacat cagcatcatc 360
aacgaggacg gcaacgagat tttcaacacc agcctgttcg agccccctcc acccggctac 420
gagaacgtgt ccgacatcgt gcccccattc agcgcattca gtccacaggg aatgcccgag 480
ggcgacctgg tgtacgtgaa ctacgcccgg accgaggact tcttcaagct ggaacgggac 540
atgaagatca actgcagcgg caagatcgtg atcgccagat acggcaaggt gttccggggc 600
aacaaagtga agaacgccca gctggcaggc gccaagggcg tgatcctgta tagcgacccc 660
gccgactact tcgcccctgg cgtgaagtcc taccccgacg gctggaacct gcctggcggc 720
ggagtgcagc ggggcaacat cctgaacctg aacggcgctg gcgacccccct gacccctggc 780 tatcccgcca acgagtacgc ctacagacgg ggaatcgccg aggccgtggg cctgcctagc 840
atccctgtgc accccatcgg ctactacgac gcccagaaac tgctggaaaa gatgggcggc 900
agcgcccctc ccgatagctc ttggagaggc agcctgaagg tgccctacaa cgtgggccct 960
ggcttcaccg gcaacttcag cgcccagaag ctgaagctgc acatccacag caacaccaaa 1020
gtgacccgga tctacaacgt gatcggcacc ctgagaggcg ccgtggaacc cgacagatac 1080
gtgatcctgg gcggccaccg ggacagctgg gtgttcggcg gcatcgaccc tcagtctggc 1140
gccgctgtgg tgcacgagat cgtgcggacc tttggcaccc tgaagaagaa gggctggcgg 1200
cccagacgga ccatcctgtt cgccagctgg gacgccgagg aattcggcct gctgggcagc 1260
accgagtggg ccgaggaaaa cagtcggctg ctgcaggaac ggggcgtcgc ctacatcaac 1320
gccgacagca gcatcgaggg caactacacc ctgcgggtgg actgcacccc cctgctgcac 1380
agcctggtgt acaacctgac caaagagctg aagtccccccg acgagggctt cgagggcaag 1440
agcctgtacg agagctggac caagaagtcc cccagccccg agctgagcgg cctgcccaga 1500
atcagcaagc tgggcagcgg caacgacttc gaggtgttct tccagcggct gggcatcagc 1560
agcggcagag cccggtacac caaggactgg aaaaccagca agttcagcag ctacccccctg 1620 taccacagca tctacgagac atacgagctg gtggtcaagt tctacgaccc catgttcaag 1680
taccacctga ccgtggccca ggtccgaggc ggcatggtgt tcgagctggc caacagcatc 1740
gtgctgccct tcgactgccg ggactacgcc gtggccctga agaaccacgc cgagaacctg 1800
tacagcatca gcatgaagca cccccaggaa atgaaaacct acagcgtgtc cttcgacagc 1860
ctgttcagcg ccgtgaagaa tttcaccgag atcgcctcca agttcagcga gcggctgcag 1920
gacttcgaca agagcaaccc catcgtgctg agaatgatga acgaccagct gatgttcctg 1980
gaacgggcct tcatcgaccc cctgggcctg cccgaccggc ccttttaccg gcacgtgatc 2040 tatgcccccca gcagccacaa caaatacgcc ggcgagagtt tccccggcat ctacgatgcc 2100
ctgttcgaca tcgagagcaa ggtggacccc agcaaggcct ggggcgaagt gaagcggcag 2160
atttacgtgg ccgcattcac agtgcaggcc gctgccgaga cactgagcga ggtggcc 2217

<210> SEQ ID NO 9
<211> LENGTH: 739
<212> TYPE: PRT
<213> ORGANISM: Artificial Sequence
<220> FEATURE:
<223> OTHER INFORMATION: Synthetic Construct

<400> SEQUENCE: 9

Met Ala Ser Ala Arg Arg Pro Arg Trp Leu Cys Ala Gly Ala Leu Val
1 5 10 15

Leu Ala Gly Gly Phe Phe Leu Leu Gly Phe Leu Phe Gly Trp Phe Ile
20 25 30

Lys Ser Ser Asn Glu Ala Thr Asn Ile Thr Pro Lys His Asn Met Lys
35 40 45

Ala Phe Leu Asp Glu Leu Lys Ala Glu Asn Ile Lys Lys Phe Leu Tyr
50 55 60

Asn Phe Thr Gln Ile Pro His Leu Ala Gly Thr Glu Gln Asn Phe Gln
65 70 75 80

Leu Ala Lys Gln Ile Gln Ser Gln Trp Lys Glu Phe Gly Leu Asp Ser
85 90 95

Val Glu Leu Ala His Tyr Asp Val Leu Leu Ser Tyr Pro Asn Lys Thr
100 105 110

His Pro Asn Tyr Ile Ser Ile Ile Asn Glu Asp Gly Asn Glu Ile Phe
115 120 125

Asn Thr Ser Leu Phe Glu Pro Pro Pro Pro Gly Tyr Glu Asn Val Ser
130 135 140

Asp Ile Val Pro Pro Phe Ser Ala Phe Ser Pro Gln Gly Met Pro Glu
145 150 155 160

Gly Asp Leu Val Tyr Val Asn Tyr Ala Arg Thr Glu Asp Phe Phe Lys
165 170 175

Leu Glu Arg Asp Met Lys Ile Asn Cys Ser Gly Lys Ile Val Ile Ala
180 185 190

Arg Tyr Gly Lys Val Phe Arg Gly Asn Lys Val Lys Asn Ala Gln Leu
195 200 205

Ala Gly Ala Lys Gly Val Ile Leu Tyr Ser Asp Pro Ala Asp Tyr Phe
210 215 220

Ala Pro Gly Val Lys Ser Tyr Pro Asp Gly Trp Asn Leu Pro Gly Gly
225 230 235 240

Gly Val Gln Arg Gly Asn Ile Leu Asn Leu Asn Gly Ala Gly Asp Pro
245 250 255

Leu Thr Pro Gly Tyr Pro Ala Asn Glu Tyr Ala Tyr Arg Arg Gly Ile
260 265 270

Ala Glu Ala Val Gly Leu Pro Ser Ile Pro Val His Pro Ile Gly Tyr
275 280 285

Tyr Asp Ala Gln Lys Leu Leu Glu Lys Met Gly Gly Ser Ala Pro Pro
290 295 300

Asp Ser Ser Trp Arg Gly Ser Leu Lys Val Pro Tyr Asn Val Gly Pro
305 310 315 320

Gly Phe Thr Gly Asn Phe Ser Thr Gln Lys Val Lys Met His Ile His
325 330 335

Ser Thr Asn Glu Val Thr Arg Ile Tyr Asn Val Ile Gly Thr Leu Arg
340 345 350

```
Gly Ala Val Glu Pro Asp Arg Tyr Val Ile Leu Gly Gly His Arg Asp
        355                 360                 365

Ser Trp Val Phe Gly Gly Ile Asp Pro Gln Ser Gly Ala Ala Val Val
    370                 375                 380

His Glu Ile Val Arg Ser Phe Gly Thr Leu Lys Lys Glu Gly Trp Arg
385                 390                 395                 400

Pro Arg Arg Thr Ile Leu Phe Ala Ser Trp Asp Ala Glu Glu Phe Gly
                405                 410                 415

Leu Leu Gly Ser Thr Glu Trp Ala Glu Glu Asn Ser Arg Leu Leu Gln
            420                 425                 430

Glu Arg Gly Val Ala Tyr Ile Asn Ala Asp Ser Ser Ile Glu Gly Asn
        435                 440                 445

Tyr Thr Leu Arg Val Asp Cys Thr Pro Leu Met Tyr Ser Leu Val His
    450                 455                 460

Asn Leu Thr Lys Glu Leu Lys Ser Pro Asp Glu Gly Phe Glu Gly Lys
465                 470                 475                 480

Ser Leu Tyr Glu Ser Trp Thr Lys Lys Ser Pro Ser Pro Glu Phe Ser
                485                 490                 495

Gly Met Pro Arg Ile Ser Lys Leu Gly Ser Gly Asn Asp Phe Glu Val
            500                 505                 510

Phe Phe Gln Arg Leu Gly Ile Ala Ser Gly Arg Ala Arg Tyr Thr Lys
        515                 520                 525

Asn Trp Glu Thr Asn Lys Phe Ser Gly Tyr Pro Leu Tyr His Ser Val
    530                 535                 540

Tyr Glu Thr Tyr Glu Leu Val Glu Lys Phe Tyr Asp Pro Met Phe Lys
545                 550                 555                 560

Tyr His Leu Thr Val Ala Gln Val Arg Gly Gly Met Val Phe Glu Leu
                565                 570                 575

Ala Asn Ser Ile Val Leu Pro Phe Asp Cys Arg Asp Tyr Ala Val Val
            580                 585                 590

Leu Arg Lys Tyr Ala Asp Lys Ile Tyr Ser Ile Ser Met Lys His Pro
        595                 600                 605

Gln Glu Met Lys Thr Tyr Ser Val Ser Phe Asp Ser Leu Phe Ser Ala
    610                 615                 620

Val Lys Asn Phe Thr Glu Ile Ala Ser Lys Phe Ser Glu Arg Leu Gln
625                 630                 635                 640

Asp Phe Asp Lys Ser Asn Pro Ile Val Leu Arg Met Met Asn Asp Gln
                645                 650                 655

Leu Met Phe Leu Glu Arg Ala Phe Ile Asp Pro Leu Gly Leu Pro Asp
            660                 665                 670

Arg Pro Phe Tyr Arg His Val Ile Tyr Ala Pro Ser Ser His Asn Lys
        675                 680                 685

Tyr Ala Gly Glu Ser Phe Pro Gly Ile Tyr Asp Ala Leu Phe Asp Ile
    690                 695                 700

Glu Ser Lys Val Asp Pro Ser Lys Ala Trp Gly Glu Val Lys Arg Gln
705                 710                 715                 720

Ile Tyr Val Ala Ala Phe Thr Val Gln Ala Ala Ala Glu Thr Leu Ser
                725                 730                 735

Glu Val Ala
```

<210> SEQ ID NO 10
<211> LENGTH: 2217
<212> TYPE: DNA
<213> ORGANISM: Artificial Sequence -continued
<220> FEATURE:
<223> OTHER INFORMATION: Synthetic Construct

<400> SEQUENCE: 10

```
atggctagcg cgcgccgccc gcgctggctg tgcgctgggg cgctggtgct ggcgggtggc     60
ttctttctcc tcggcttcct cttcgggtgg tttataaaat cctccaatga agctactaac    120
attactccaa agcataatat gaaagcattt ttggatgaat tgaaagctga gaacatcaag    180
aagttcttat ataattttac acagatacca catttagcag gaacagaaca aaactttcag    240
cttgcaaagc aaattcaatc ccagtggaaa gaatttggcc tggattctgt tgagctggca    300
cattatgatg tcctgttgtc ctacccaaat aagactcatc ccaactacat ctcaataatt    360
aatgaagatg gaaatgagat tttcaacaca tcattatttg aaccacctcc tccaggatat    420
gaaaatgttt cggatattgt accacctttc agtgctttct ctcctcaagg aatgccagag    480
ggcgatctag tgtatgttaa ctatgcacga actgaagact tctttaaatt ggaacgggac    540
atgaaaatca attgctctgg gaaaattgta attgccagat atgggaaagt tttcagagga    600
aataaggtta aaaatgccca gctggcaggg gccaaaggag tcattctcta ctccgaccct    660
gctgactact ttgctcctgg ggtgaagtcc tatccagatg gttggaatct tcctggaggt    720
ggtgtccagc gtggaaatat cctaaatctg aatggtgcag gagaccctct cacaccaggt    780
tacccagcaa atgaatatgc ttataggcgt ggaattgcag aggctgttgg tcttccaagt    840
attcctgttc atccaattgg atactatgat gcacagaagc tcctagaaaa aatgggtggc    900
tcagcaccac cagatagcag ctggagagga agtctcaaag tgccctacaa tgttggacct    960
ggctttactg gaaacttttc tacacaaaaa gtcaagatgc acatccactc taccaatgaa   1020
gtgacaagaa tttacaatgt gataggtact ctcagaggag cagtggaacc agacagatat   1080
gtcattctgg gaggtcaccg ggactcatgg gtgtttggtg gtattgaccc tcagagtgga   1140
gcagctgttg ttcatgaaat tgtgaggagc tttggaacac tgaaaaagga agggtggaga   1200
cctagaagaa caattttgtt tgcaagctgg gatgcagaag aatttggtct tcttggttct   1260
actgagtggg cagaggagaa ttcaagactc cttcaagagc gtggcgtggc ttatattaat   1320
gctgactcat ctatagaagg aaactacact ctgagagttg attgtacacc gctgatgtac   1380
agcttggtac acaacctaac aaaagagctg aaaagccctg atgaaggctt tgaaggcaaa   1440
tctctttatg aaagttggac taaaaaaagt ccttccccag agttcagtgg catgcccagg   1500
ataagcaaat tgggatctgg aaatgatttt gaggtgttct tccaacgact tggaattgct   1560
tcaggcagag cacggtatac taaaaattgg gaaacaaaca aattcagcgg ctatccactg   1620
tatcacagtg tctatgaaac atatgagttg gtggaaaagt tttatgatcc aatgtttaaa   1680
tatcacctca ctgtggccca ggttcgagga gggatggtgt ttgagctggc caattccata   1740
gtgctccctt ttgattgtcg agattatgct gtagttttaa gaaagtatgc tgacaaaatc   1800
tacagtattt ctatgaaaca tccacaggaa atgaagacat acagtgtatc atttgattca   1860
ctttttctg cagtaaagaa ttttacagaa attgcttcca agttcagtga gagactccag   1920
gactttgaca aaagcaaccc aatagtatta agaatgatga atgatcaact catgtttctg   1980
gaaagagcat ttattgatcc attagggtta ccagacaggc ctttttatag gcatgtcatc   2040
tatgctccaa gcagccacaa caagtatgca ggggagtcat tcccaggaat ttatgatgct   2100
ctgtttgata ttgaaagcaa agtggaccct tccaaggcct ggggagaagt gaagagacag   2160
atttatgttg cagccttcac agtgcaggca gctgcagaga ctttgagtga agtagcc      2217
```

<210> SEQ ID NO 11
<211> LENGTH: 710
<212> TYPE: PRT
<213> ORGANISM: Artificial Sequence
<220> FEATURE:
<223> OTHER INFORMATION: Synthetic Construct

<400> SEQUENCE: 11

```
Met Ala Ser Lys Ser Ser Asn Glu Ala Thr Asn Ile Thr Pro Lys His
1               5                   10                  15

Asn Met Lys Ala Phe Leu Asp Glu Leu Lys Ala Glu Asn Ile Lys Lys
            20                  25                  30

Phe Leu Tyr Asn Phe Thr Gln Ile Pro His Leu Ala Gly Thr Glu Gln
        35                  40                  45

Asn Phe Gln Leu Ala Lys Gln Ile Gln Ser Gln Trp Lys Glu Phe Gly
    50                  55                  60

Leu Asp Ser Val Glu Leu Ala His Tyr Asp Val Leu Leu Ser Tyr Pro
65                  70                  75                  80

Asn Lys Thr His Pro Asn Tyr Ile Ser Ile Ile Asn Glu Asp Gly Asn
                85                  90                  95

Glu Ile Phe Asn Thr Ser Leu Phe Glu Pro Pro Pro Pro Gly Tyr Glu
            100                 105                 110

Asn Val Ser Asp Ile Val Pro Pro Phe Ser Ala Phe Ser Pro Gln Gly
        115                 120                 125

Met Pro Glu Gly Asp Leu Val Tyr Val Asn Tyr Ala Arg Thr Glu Asp
    130                 135                 140

Phe Phe Lys Leu Glu Arg Asp Met Lys Ile Asn Cys Ser Gly Lys Ile
145                 150                 155                 160

Val Ile Ala Arg Tyr Gly Lys Val Phe Arg Gly Asn Lys Val Lys Asn
                165                 170                 175

Ala Gln Leu Ala Gly Ala Lys Gly Val Ile Leu Tyr Ser Asp Pro Ala
            180                 185                 190

Asp Tyr Phe Ala Pro Gly Val Lys Ser Tyr Pro Asp Gly Trp Asn Leu
        195                 200                 205

Pro Gly Gly Gly Val Gln Arg Gly Asn Ile Leu Asn Leu Asn Gly Ala
    210                 215                 220

Gly Asp Pro Leu Thr Pro Gly Tyr Pro Ala Asn Glu Tyr Ala Tyr Arg
225                 230                 235                 240

Arg Gly Ile Ala Glu Ala Val Gly Leu Pro Ser Ile Pro Val His Pro
                245                 250                 255

Ile Gly Tyr Tyr Asp Ala Gln Lys Leu Leu Glu Lys Met Gly Gly Ser
            260                 265                 270

Ala Pro Pro Asp Ser Ser Trp Arg Gly Ser Leu Lys Val Pro Tyr Asn
        275                 280                 285

Val Gly Pro Gly Phe Thr Gly Asn Phe Ser Thr Gln Lys Val Lys Met
    290                 295                 300

His Ile His Ser Thr Asn Glu Val Thr Arg Ile Tyr Asn Val Ile Gly
305                 310                 315                 320

Thr Leu Arg Gly Ala Val Glu Pro Asp Arg Tyr Val Ile Leu Gly Gly
                325                 330                 335

His Arg Asp Ser Trp Val Phe Gly Gly Ile Asp Pro Gln Ser Gly Ala
            340                 345                 350

Ala Val Val His Glu Ile Val Arg Ser Phe Gly Thr Leu Lys Lys Glu
        355                 360                 365
```

```
Gly Trp Arg Pro Arg Arg Thr Ile Leu Phe Ala Ser Trp Asp Ala Glu
    370                 375                 380

Glu Phe Gly Leu Leu Gly Ser Thr Glu Trp Ala Glu Glu Asn Ser Arg
385                 390                 395                 400

Leu Leu Gln Glu Arg Gly Val Ala Tyr Ile Asn Ala Asp Ser Ser Ile
                405                 410                 415

Glu Gly Asn Tyr Thr Leu Arg Val Asp Cys Thr Pro Leu Met Tyr Ser
            420                 425                 430

Leu Val His Asn Leu Thr Lys Glu Leu Lys Ser Pro Asp Glu Gly Phe
        435                 440                 445

Glu Gly Lys Ser Leu Tyr Glu Ser Trp Thr Lys Lys Ser Pro Ser Pro
    450                 455                 460

Glu Phe Ser Gly Met Pro Arg Ile Ser Lys Leu Gly Ser Gly Asn Asp
465                 470                 475                 480

Phe Glu Val Phe Phe Gln Arg Leu Gly Ile Ala Ser Gly Arg Ala Arg
                485                 490                 495

Tyr Thr Lys Asn Trp Glu Thr Asn Lys Phe Ser Gly Tyr Pro Leu Tyr
            500                 505                 510

His Ser Val Tyr Glu Thr Tyr Glu Leu Val Glu Lys Phe Tyr Asp Pro
        515                 520                 525

Met Phe Lys Tyr His Leu Thr Val Ala Gln Val Arg Gly Gly Met Val
    530                 535                 540

Phe Glu Leu Ala Asn Ser Ile Val Leu Pro Phe Asp Cys Arg Asp Tyr
545                 550                 555                 560

Ala Val Val Leu Arg Lys Tyr Ala Asp Lys Ile Tyr Ser Ile Ser Met
                565                 570                 575

Lys His Pro Gln Glu Met Lys Thr Tyr Ser Val Ser Phe Asp Ser Leu
            580                 585                 590

Phe Ser Ala Val Lys Asn Phe Thr Glu Ile Ala Ser Lys Phe Ser Glu
        595                 600                 605

Arg Leu Gln Asp Phe Asp Lys Ser Asn Pro Ile Val Leu Arg Met Met
    610                 615                 620

Asn Asp Gln Leu Met Phe Leu Glu Arg Ala Phe Ile Asp Pro Leu Gly
625                 630                 635                 640

Leu Pro Asp Arg Pro Phe Tyr Arg His Val Ile Tyr Ala Pro Ser Ser
                645                 650                 655

His Asn Lys Tyr Ala Gly Glu Ser Phe Pro Gly Ile Tyr Asp Ala Leu
            660                 665                 670

Phe Asp Ile Glu Ser Lys Val Asp Pro Ser Lys Ala Trp Gly Glu Val
        675                 680                 685

Lys Arg Gln Ile Tyr Val Ala Ala Phe Thr Val Gln Ala Ala Ala Glu
    690                 695                 700

Thr Leu Ser Glu Val Ala
705                 710
```

<210> SEQ ID NO 12
<211> LENGTH: 2130
<212> TYPE: DNA
<213> ORGANISM: Artificial Sequence
<220> FEATURE:
<223> OTHER INFORMATION: Synthetic Construct

<400> SEQUENCE: 12

```
atggctagca aatcctccaa tgaagctact aacattactc caaagcataa tatgaaagca      60

tttttggatg aattgaaagc tgagaacatc aagaagttct tatataattt tacacagata     120
```

```
ccacatttag caggaacaga acaaaacttt cagcttgcaa agcaaattca atcccagtgg    180
aaagaatttg gcctggattc tgttgagctg gcacattatg atgtcctgtt gtcctaccca    240
aataagactc atcccaacta catctcaata attaatgaag atggaaatga gattttcaac    300
acatcattat ttgaaccacc tcctccagga tatgaaaatg tttcggatat tgtaccacct    360
ttcagtgctt tctctcctca aggaatgcca gagggcgatc tagtgtatgt taactatgca    420
cgaactgaag acttctttaa attggaacgg gacatgaaaa tcaattgctc tgggaaaatt    480
gtaattgcca gatatgggaa agttttcaga ggaaataagg ttaaaaatgc ccagctggca    540
ggggccaaag gagtcattct ctactccgac cctgctgact actttgctcc tggggtgaag    600
tcctatccag atggttggaa tcttcctgga ggtggtgtcc agcgtggaaa tatcctaaat    660
ctgaatggtg caggagaccc tctcacacca ggttacccag caaatgaata tgcttatagg    720
cgtggaattg cagaggctgt tggtcttcca agtattcctg ttcatccaat tggatactat    780
gatgcacaga agctcctaga aaaaatgggt ggctcagcac caccagatag cagctggaga    840
ggaagtctca aagtgcccta caatgttgga cctggcttta ctggaaactt ttctacacaa    900
aaagtcaaga tgcacatcca ctctaccaat gaagtgacaa gaatttacaa tgtgataggt    960
actctcagag gagcagtgga accagacaga tatgtcattc tgggaggtca ccgggactca   1020
tgggtgtttg gtggtattga ccctcagagt ggagcagctg ttgttcatga aattgtgagg   1080
agctttggaa cactgaaaaa ggaagggtgg agacctagaa gaacaatttt gtttgcaagc   1140
tgggatgcag aagaatttgg tcttcttggt tctactgagt gggcagagga gaattcaaga   1200
ctccttcaag agcgtggcgt ggcttatatt aatgctgact catctataga aggaaactac   1260
actctgagag ttgattgtac accgctgatg tacagcttgg tacacaacct aacaaaagag   1320
ctgaaaagcc ctgatgaagg ctttgaaggc aaatctcttt atgaaagttg gactaaaaaa   1380
agtccttccc cagagttcag tggcatgccc aggataagca aattgggatc tggaaatgat   1440
tttgaggtgt tcttccaacg acttggaatt gcttcaggca gagcacggta tactaaaaat   1500
tgggaaacaa acaaattcag cggctatcca ctgtatcaca gtgtctatga aacatatgag   1560
ttggtggaaa agttttatga tccaatgttt aaatatcacc tcactgtggc ccaggttcga   1620
ggagggatgg tgtttgagct ggccaattcc atagtgctcc cttttgattg tcgagattat   1680
gctgtagttt taagaaagta tgctgacaaa atctacagta tttctatgaa acatccacag   1740
gaaatgaaga catacagtgt atcatttgat tcactttttt ctgcagtaaa gaattttaca   1800
gaaattgctt ccaagttcag tgagagactc caggactttg acaaaagcaa cccaatagta   1860
ttaagaatga tgaatgatca actcatgttt ctggaaagag catttattga tccattaggg   1920
ttaccagaca ggccttttta taggcatgtc atctatgctc caagcagcca caacaagtat   1980
gcaggggagt cattcccagg aatttatgat gctctgtttg atattgaaag caaagtggac   2040
ccttccaagg cctggggaga agtgaagaga cagatttatg ttgcagcctt cacagtgcag   2100
gcagctgcag agactttgag tgaagtagcc                                    2130
```

```
<210> SEQ ID NO 13
<211> LENGTH: 732
<212> TYPE: PRT
<213> ORGANISM: Artificial Sequence
<220> FEATURE:
<223> OTHER INFORMATION: Synthetic Construct

<400> SEQUENCE: 13
```

-continued

```
Met Ala Ser Glu Thr Asp Thr Leu Leu Leu Trp Val Leu Leu Leu Trp
1               5                   10                  15

Val Pro Gly Ser Thr Gly Asp Ala Ala Lys Ser Ser Asn Glu Ala Thr
            20                  25                  30

Asn Ile Thr Pro Lys His Asn Met Lys Ala Phe Leu Asp Glu Leu Lys
        35                  40                  45

Ala Glu Asn Ile Lys Lys Phe Leu Tyr Asn Phe Thr Gln Ile Pro His
    50                  55                  60

Leu Ala Gly Thr Glu Gln Asn Phe Gln Leu Ala Lys Gln Ile Gln Ser
65                  70                  75                  80

Gln Trp Lys Glu Phe Gly Leu Asp Ser Val Glu Leu Ala His Tyr Asp
                85                  90                  95

Val Leu Leu Ser Tyr Pro Asn Lys Thr His Pro Asn Tyr Ile Ser Ile
            100                 105                 110

Ile Asn Glu Asp Gly Asn Glu Ile Phe Asn Thr Ser Leu Phe Glu Pro
        115                 120                 125

Pro Pro Pro Gly Tyr Glu Asn Val Ser Asp Ile Val Pro Pro Phe Ser
    130                 135                 140

Ala Phe Ser Pro Gln Gly Met Pro Glu Gly Asp Leu Val Tyr Val Asn
145                 150                 155                 160

Tyr Ala Arg Thr Glu Asp Phe Phe Lys Leu Glu Arg Asp Met Lys Ile
                165                 170                 175

Asn Cys Ser Gly Lys Ile Val Ile Ala Arg Tyr Gly Lys Val Phe Arg
            180                 185                 190

Gly Asn Lys Val Lys Asn Ala Gln Leu Ala Gly Ala Lys Gly Val Ile
        195                 200                 205

Leu Tyr Ser Asp Pro Ala Asp Tyr Phe Ala Pro Gly Val Lys Ser Tyr
    210                 215                 220

Pro Asp Gly Trp Asn Leu Pro Gly Gly Gly Val Gln Arg Gly Asn Ile
225                 230                 235                 240

Leu Asn Leu Asn Gly Ala Gly Asp Pro Leu Thr Pro Gly Tyr Pro Ala
                245                 250                 255

Asn Glu Tyr Ala Tyr Arg Arg Gly Ile Ala Glu Ala Val Gly Leu Pro
            260                 265                 270

Ser Ile Pro Val His Pro Ile Gly Tyr Tyr Asp Ala Gln Lys Leu Leu
        275                 280                 285

Glu Lys Met Gly Gly Ser Ala Pro Pro Asp Ser Ser Trp Arg Gly Ser
    290                 295                 300

Leu Lys Val Pro Tyr Asn Val Gly Pro Gly Phe Thr Gly Asn Phe Ser
305                 310                 315                 320

Thr Gln Lys Val Lys Met His Ile His Ser Thr Asn Glu Val Thr Arg
                325                 330                 335

Ile Tyr Asn Val Ile Gly Thr Leu Arg Gly Ala Val Glu Pro Asp Arg
            340                 345                 350

Tyr Val Ile Leu Gly Gly His Arg Asp Ser Trp Val Phe Gly Gly Ile
        355                 360                 365

Asp Pro Gln Ser Gly Ala Ala Val Val His Glu Ile Val Arg Ser Phe
    370                 375                 380

Gly Thr Leu Lys Lys Glu Gly Trp Arg Pro Arg Arg Thr Ile Leu Phe
385                 390                 395                 400

Ala Ser Trp Asp Ala Glu Glu Phe Gly Leu Leu Gly Ser Thr Glu Trp
                405                 410                 415

Ala Glu Glu Asn Ser Arg Leu Leu Gln Glu Arg Gly Val Ala Tyr Ile
```

-continued

```
            420                 425                 430

Asn Ala Asp Ser Ser Ile Glu Gly Asn Tyr Thr Leu Arg Val Asp Cys
        435                 440                 445

Thr Pro Leu Met Tyr Ser Leu Val His Asn Leu Thr Lys Glu Leu Lys
    450                 455                 460

Ser Pro Asp Glu Gly Phe Glu Gly Lys Ser Leu Tyr Glu Ser Trp Thr
465                 470                 475                 480

Lys Lys Ser Pro Ser Pro Glu Phe Ser Gly Met Pro Arg Ile Ser Lys
                485                 490                 495

Leu Gly Ser Gly Asn Asp Phe Glu Val Phe Phe Gln Arg Leu Gly Ile
            500                 505                 510

Ala Ser Gly Arg Ala Arg Tyr Thr Lys Asn Trp Glu Thr Asn Lys Phe
        515                 520                 525

Ser Gly Tyr Pro Leu Tyr His Ser Val Tyr Glu Thr Tyr Glu Leu Val
    530                 535                 540

Glu Lys Phe Tyr Asp Pro Met Phe Lys Tyr His Leu Thr Val Ala Gln
545                 550                 555                 560

Val Arg Gly Gly Met Val Phe Glu Leu Ala Asn Ser Ile Val Leu Pro
                565                 570                 575

Phe Asp Cys Arg Asp Tyr Ala Val Val Leu Arg Lys Tyr Ala Asp Lys
            580                 585                 590

Ile Tyr Ser Ile Ser Met Lys His Pro Gln Glu Met Lys Thr Tyr Ser
        595                 600                 605

Val Ser Phe Asp Ser Leu Phe Ser Ala Val Lys Asn Phe Thr Glu Ile
    610                 615                 620

Ala Ser Lys Phe Ser Glu Arg Leu Gln Asp Phe Asp Lys Ser Asn Pro
625                 630                 635                 640

Ile Val Leu Arg Met Met Asn Asp Gln Leu Met Phe Leu Glu Arg Ala
                645                 650                 655

Phe Ile Asp Pro Leu Gly Leu Pro Asp Arg Pro Phe Tyr Arg His Val
            660                 665                 670

Ile Tyr Ala Pro Ser Ser His Asn Lys Tyr Ala Gly Glu Ser Phe Pro
        675                 680                 685

Gly Ile Tyr Asp Ala Leu Phe Asp Ile Glu Ser Lys Val Asp Pro Ser
    690                 695                 700

Lys Ala Trp Gly Glu Val Lys Arg Gln Ile Tyr Val Ala Ala Phe Thr
705                 710                 715                 720

Val Gln Ala Ala Ala Glu Thr Leu Ser Glu Val Ala
                725                 730
```

<210> SEQ ID NO 14
<211> LENGTH: 2196
<212> TYPE: DNA
<213> ORGANISM: Artificial Sequence
<220> FEATURE:
<223> OTHER INFORMATION: Synthetic Construct

<400> SEQUENCE: 14

```
atggctagcg aaaccgacac tttgttgttg tgggtgcttt tgctttgggt acccggatct      60

actggtgatg ctgctaaatc ctccaatgaa gctactaaca ttactccaaa gcataatatg     120

aaagcatttt tggatgaatt gaaagctgag aacatcaaga agttcttata taattttaca     180

cagataccac atttagcagg aacagaacaa aactttcagc ttgcaaagca aattcaatcc     240

cagtggaaag aatttggcct ggattctgtt gagctagcac attatgatgt cctgttgtcc     300
```

-continued

```
tacccaaata agactcatcc caactacatc tcaataatta atgaagatgg aaatgagatt    360
ttcaacacat cattatttga accacctcct ccaggatatg aaaatgtttc ggatattgta    420
ccacctttca gtgctttctc tcctcaagga atgccagagg gcgatctagt gtatgttaac    480
tatgcacgaa ctgaagactt ctttaaattg gaacgggaca tgaaaatcaa ttgctctggg    540
aaaattgtaa ttgccagata tgggaaagtt ttcagaggaa ataaggttaa aaatgcccag    600
ctggcagggg ccaaaggagt cattctctac tccgaccctg ctgactactt tgctcctggg    660
gtgaagtcct atccagatgg ttggaatctt cctggaggtg gtgtccagcg tggaaatatc    720
ctaaatctga atggtgcagg agaccctctc acaccaggtt acccagcaaa tgaatatgct    780
tataggcgtg gaattgcaga ggctgttggt cttccaagta ttcctgttca tccaattgga    840
tactatgatg cacagaagct cctagaaaaa atgggtggct cagcaccacc agatagcagc    900
tggagaggaa gtctcaaagt gccctacaat gttggacctg gctttactgg aaacttttct    960
acacaaaaag tcaagatgca catccactct accaatgaag tgacaagaat ttacaatgtg   1020
ataggtactc tcagaggagc agtggaacca gacagatatg tcattctggg aggtcaccgg   1080
gactcatggg tgtttggtgg tattgaccct cagagtggag cagctgttgt tcatgaaatt   1140
gtgaggagct ttggaacact gaaaaaggaa gggtggagac ctagaagaac aattttgttt   1200
gcaagctggg atgcagaaga atttggtctt cttggttcta ctgagtgggc agaggagaat   1260
tcaagactcc ttcaagagcg tggcgtggct tatattaatg ctgactcatc tatagaagga   1320
aactacactc tgagagttga ttgtacaccg ctgatgtaca gcttggtaca caacctaaca   1380
aaagagctga aaagccctga tgaaggcttt gaaggcaaat ctctttatga aagttggact   1440
aaaaaaagtc cttccccaga gttcagtggc atgcccagga taagcaaatt gggatctgga   1500
aatgattttg aggtgttctt ccaacgactt ggaattgctt caggcagagc acggtatact   1560
aaaaattggg aaacaaacaa attcagcggc tatccactgt atcacagtgt ctatgaaaca   1620
tatgagttgg tggaaaagtt ttatgatcca atgtttaaat atcacctcac tgtggcccag   1680
gttcgaggag ggatggtgtt tgagctagcc aattccatag tgctcccttt tgattgtcga   1740
gattatgctg tagttttaag aaagtatgct gacaaaatct acagtatttc tatgaaacat   1800
ccacaggaaa tgaagacata cagtgtatca tttgattcac tttttctgc agtaaagaat    1860
tttacagaaa ttgcttccaa gttcagtgag agactccagg actttgacaa aagcaaccca   1920
atagtattaa gaatgatgaa tgatcaactc atgtttctgg aaagagcatt tattgatcca   1980
ttagggttac cagacaggcc tttttatagg catgtcatct atgctccaag cagccacaac   2040
aagtatgcag gggagtcatt cccaggaatt tatgatgctc tgtttgatat tgaaagcaaa   2100
gtggaccctt ccaaggcctg ggagaagtg aagagacaga tttatgttgc agccttcaca    2160
gtgcaggcag ctgcagagac tttgagtgaa gtagcc                             2196
```

<210> SEQ ID NO 15
<211> LENGTH: 263
<212> TYPE: PRT
<213> ORGANISM: Homo sapiens

<400> SEQUENCE: 15

```
Met Ala Ser Trp Val Pro Val Val Phe Leu Thr Leu Ser Val Thr Trp
1               5                   10                  15

Ile Gly Ala Ala Pro Leu Ile Leu Ser Arg Ile Val Gly Gly Trp Glu
            20                  25                  30

Cys Glu Lys His Ser Gln Pro Trp Gln Val Leu Val Ala Ser Arg Gly
```

```
        35                  40                  45

Arg Ala Val Cys Gly Gly Val Leu Val His Pro Gln Trp Val Leu Thr
    50                  55                  60

Ala Ala His Cys Ile Arg Asn Lys Ser Val Ile Leu Leu Gly Arg His
65                  70                  75                  80

Ser Leu Phe His Pro Glu Asp Thr Gly Gln Val Phe Gln Val Ser His
                85                  90                  95

Ser Phe Pro His Pro Leu Tyr Asp Met Ser Leu Leu Lys Asn Arg Phe
            100                 105                 110

Leu Arg Pro Gly Asp Asp Ser Ser His Asp Leu Met Leu Leu Arg Leu
        115                 120                 125

Ser Glu Pro Ala Glu Leu Thr Asp Ala Val Lys Val Met Asp Leu Pro
    130                 135                 140

Thr Gln Glu Pro Ala Leu Gly Thr Thr Cys Tyr Ala Ser Gly Trp Gly
145                 150                 155                 160

Ser Ile Glu Pro Glu Glu Phe Leu Thr Pro Lys Lys Leu Gln Cys Val
                165                 170                 175

Asp Leu His Val Ile Ser Asn Asp Val Cys Ala Gln Val His Pro Gln
            180                 185                 190

Lys Val Thr Lys Phe Met Leu Cys Ala Gly Arg Trp Thr Gly Gly Lys
        195                 200                 205

Ser Thr Cys Ser Gly Asp Ser Gly Gly Pro Leu Val Cys Asn Gly Val
    210                 215                 220

Leu Gln Gly Ile Thr Ser Trp Gly Ser Glu Pro Cys Ala Leu Pro Glu
225                 230                 235                 240

Arg Pro Ser Leu Tyr Thr Lys Val Val His Tyr Arg Lys Trp Ile Lys
                245                 250                 255

Asp Thr Ile Val Ala Asn Pro
            260
```

<210> SEQ ID NO 16
<211> LENGTH: 789
<212> TYPE: DNA
<213> ORGANISM: Homo sapiens

<400> SEQUENCE: 16

```
atggctagct gggtcccggt tgtcttcctc accctgtccg tgacgtggat tggcgctgcg      60
cccctcatcc tgtctcggat tgtgggaggc tgggagtgcg agaagcattc ccaaccctgg     120
caggtgcttg tggcctctcg tggcagggca gtctgcggcg gtgttctggt gcacccccag     180
tgggtcctca cagctgccca ctgcatcagg aacaaaagcg tgatcttgct gggtcggcac     240
agcttgtttc atcctgaaga cacaggccag gtatttcagg tcagccacag cttcccacac     300
ccgctctacg atatgagcct cctgaagaat cgattcctca ggccaggtga tgactccagc     360
cacgacctca tgctgctccg cctgtcagag cctgccgagc tcacggatgc tgtgaaggtc     420
atggacctgc ccacccagga gccagcactg gggaccacct gctacgcctc aggctggggc     480
agcattgaac cagaggagtt cttgaccccc aagaaacttc agtgtgtgga cctccatgtt     540
atttccaatg acgtgtgtgc gcaagttcac cctcagaagg tgaccaagtt catgctgtgt     600
gctggacgct ggacaggggg caaaagcacc tgctcgggtg attctggggg cccacttgtc     660
tgtaatggtg tgcttcaagg tatcacgtca tggggcagtg aaccatgtgc cctgcccgaa     720
aggccttccc tgtacaccaa ggtggtgcat taccggaagt ggatcaagga caccatcgtg     780
gccaacccc                                                             789
```

<210> SEQ ID NO 17
<211> LENGTH: 240
<212> TYPE: PRT
<213> ORGANISM: Artificial Sequence
<220> FEATURE:
<223> OTHER INFORMATION: Synthetic Construct

<400> SEQUENCE: 17

```
Met Ala Ser Ile Val Gly Gly Trp Glu Cys Glu Lys His Ser Gln Pro
1               5                   10                  15

Trp Gln Val Leu Val Ala Ser Arg Gly Arg Ala Val Cys Gly Gly Val
            20                  25                  30

Leu Val His Pro Gln Trp Val Leu Thr Ala Ala His Cys Ile Arg Asn
        35                  40                  45

Lys Ser Val Ile Leu Leu Gly Arg His Ser Leu Phe His Pro Glu Asp
    50                  55                  60

Thr Gly Gln Val Phe Gln Val Ser His Ser Phe Pro His Pro Leu Tyr
65                  70                  75                  80

Asp Met Ser Leu Leu Lys Asn Arg Phe Leu Arg Pro Gly Asp Asp Ser
                85                  90                  95

Ser His Asp Leu Met Leu Leu Arg Leu Ser Glu Pro Ala Glu Leu Thr
            100                 105                 110

Asp Ala Val Lys Val Met Asp Leu Pro Thr Gln Glu Pro Ala Leu Gly
        115                 120                 125

Thr Thr Cys Tyr Ala Ser Gly Trp Gly Ser Ile Glu Pro Glu Glu Phe
    130                 135                 140

Leu Thr Pro Lys Lys Leu Gln Cys Val Asp Leu His Val Ile Ser Asn
145                 150                 155                 160

Asp Val Cys Ala Gln Val His Pro Gln Lys Val Thr Lys Phe Met Leu
                165                 170                 175

Cys Ala Gly Arg Trp Thr Gly Gly Lys Ser Thr Cys Ser Gly Asp Ser
            180                 185                 190

Gly Gly Pro Leu Val Cys Asn Gly Val Leu Gln Gly Ile Thr Ser Trp
        195                 200                 205

Gly Ser Glu Pro Cys Ala Leu Pro Glu Arg Pro Ser Leu Tyr Thr Lys
    210                 215                 220

Val Val His Tyr Arg Lys Trp Ile Lys Asp Thr Ile Val Ala Asn Pro
225                 230                 235                 240
```

<210> SEQ ID NO 18
<211> LENGTH: 720
<212> TYPE: DNA
<213> ORGANISM: Artificial Sequence
<220> FEATURE:
<223> OTHER INFORMATION: Synthetic Construct

<400> SEQUENCE: 18

```
atggctagca ttgtgggagg ctgggagtgc gagaagcatt cccaaccctg gcaggtgctt      60

gtggcctctc gtggcagggc agtctgcggc ggtgttctgg tgcaccccca gtgggtcctc     120

acagctgccc actgcatcag gaacaaaagc gtgatcttgc tgggtcggca cagcttgttt     180

catcctgaag acacaggcca ggtatttcag gtcagccaca gcttcccaca cccgctctac     240

gatatgagcc tcctgaagaa tcgattcctc aggccaggtg atgactccag ccacgacctc     300

atgctgctcc gcctgtcaga gcctgccgag ctcacggatg ctgtgaaggt catggacctg     360

cccacccagg agccagcact ggggaccacc tgctacgcct caggctgggg cagcattgaa     420
```

```
ccagaggagt tcttgacccc aaagaaactt cagtgtgtgg acctccatgt tatttccaat    480

gacgtgtgtg cgcaagttca ccctcagaag gtgaccaagt tcatgctgtg tgctggacgc    540

tggacagggg gcaaaagcac ctgctcgggt gattctgggg gcccacttgt ctgtaatggt    600

gtgcttcaag gtatcacgtc atggggcagt gaaccatgtg ccctgcccga aaggccttcc    660

ctgtacacca aggtggtgca ttaccggaag tggatcaagg acaccatcgt ggccaacccc    720


<210> SEQ ID NO 19
<211> LENGTH: 281
<212> TYPE: PRT
<213> ORGANISM: Artificial Sequence
<220> FEATURE:
<223> OTHER INFORMATION: Synthetic Construct

<400> SEQUENCE: 19

Met Ala Ser Ala Arg Arg Pro Arg Trp Leu Cys Ala Gly Ala Leu Val
1               5                   10                  15

Leu Ala Gly Gly Phe Phe Leu Leu Gly Phe Leu Phe Gly Trp Phe Ile
            20                  25                  30

Lys Ser Ser Asn Glu Ala Thr Asn Ile Thr Pro Gly Ile Val Gly Gly
        35                  40                  45

Trp Glu Cys Glu Lys His Ser Gln Pro Trp Gln Val Leu Val Ala Ser
    50                  55                  60

Arg Gly Arg Ala Val Cys Gly Gly Val Leu Val His Pro Gln Trp Val
65                  70                  75                  80

Leu Thr Ala Ala His Cys Ile Arg Asn Lys Ser Val Ile Leu Leu Gly
                85                  90                  95

Arg His Ser Leu Phe His Pro Glu Asp Thr Gly Gln Val Phe Gln Val
            100                 105                 110

Ser His Ser Phe Pro His Pro Leu Tyr Asp Met Ser Leu Leu Lys Asn
        115                 120                 125

Arg Phe Leu Arg Pro Gly Asp Asp Ser Ser His Asp Leu Met Leu Leu
    130                 135                 140

Arg Leu Ser Glu Pro Ala Glu Leu Thr Asp Ala Val Lys Val Met Asp
145                 150                 155                 160

Leu Pro Thr Gln Glu Pro Ala Leu Gly Thr Thr Cys Tyr Ala Ser Gly
                165                 170                 175

Trp Gly Ser Ile Glu Pro Glu Glu Phe Leu Thr Pro Lys Lys Leu Gln
            180                 185                 190

Cys Val Asp Leu His Val Ile Ser Asn Asp Val Cys Ala Gln Val His
        195                 200                 205

Pro Gln Lys Val Thr Lys Phe Met Leu Cys Ala Gly Arg Trp Thr Gly
    210                 215                 220

Gly Lys Ser Thr Cys Ser Gly Asp Ser Gly Gly Pro Leu Val Cys Asn
225                 230                 235                 240

Gly Val Leu Gln Gly Ile Thr Ser Trp Gly Ser Glu Pro Cys Ala Leu
                245                 250                 255

Pro Glu Arg Pro Ser Leu Tyr Thr Lys Val Val His Tyr Arg Lys Trp
            260                 265                 270

Ile Lys Asp Thr Ile Val Ala Asn Pro
        275                 280


<210> SEQ ID NO 20
<211> LENGTH: 846
<212> TYPE: DNA
```

<213> ORGANISM: Artificial Sequence
<220> FEATURE:
<223> OTHER INFORMATION: Synthetic Construct

<400> SEQUENCE: 20
atggctagcg cgcgccgccc gcgctggctg tgcgctgggg cgctggtgct ggcgggtggc 60
ttctttctcc tcggcttcct cttcgggtgg tttataaaat cctccaatga agctactaac 120
attactccag gaattgtggg aggctgggag tgcgagaagc attcccaacc ctggcaggtg 180
cttgtggcct ctcgtggcag ggcagtctgc ggcggtgttc tggtgcaccc ccagtgggtc 240
ctcacagctg cccactgcat caggaacaaa agcgtgatct tgctgggtcg gcacagcttg 300
tttcatcctg aagacacagg ccaggtattt caggtcagcc acagcttccc acacccgctc 360
tacgatatga gcctcctgaa gaatcgattc ctcaggccag gtgatgactc cagccacgac 420
ctcatgctgc tccgcctgtc agagcctgcc gagctcacgg atgctgtgaa ggtcatggac 480
ctgcccaccc aggagccagc actggggacc acctgctacg cctcaggctg gggcagcatt 540
gaaccagagg agttcttgac ccccaaagaaa cttcagtgtg tggacctcca tgttatttcc 600
aatgacgtgt gtgcgcaagt tcaccctcag aaggtgacca agttcatgct gtgtgctgga 660
cgctggacag ggggcaaaag cacctgctcg ggtgattctg gggggcccact tgtctgtaat 720 ggtgtgcttc aaggtatcac gtcatggggc agtgaaccat gtgccctgcc cgaaaggcct 780
tccctgtaca ccaaggtggt gcattaccgg aagtggatca aggacaccat cgtggccaac 840
ccctga 846

<210> SEQ ID NO 21
<211> LENGTH: 125
<212> TYPE: PRT
<213> ORGANISM: Homo sapiens

<400> SEQUENCE: 21

Met Ala Ser Lys Ala Val Leu Leu Ala Leu Leu Met Ala Gly Leu Ala
1 5 10 15

Leu Gln Pro Gly Thr Ala Leu Leu Cys Tyr Ser Cys Lys Ala Gln Val
20 25 30

Ser Asn Glu Asp Cys Leu Gln Val Glu Asn Cys Thr Gln Leu Gly Glu
35 40 45

Gln Cys Trp Thr Ala Arg Ile Arg Ala Val Gly Leu Leu Thr Val Ile
50 55 60

Ser Lys Gly Cys Ser Leu Asn Cys Val Asp Asp Ser Gln Asp Tyr Tyr
65 70 75 80

Val Gly Lys Lys Asn Ile Thr Cys Cys Asp Thr Asp Leu Cys Asn Ala
85 90 95

Ser Gly Ala His Ala Leu Gln Pro Ala Ala Ala Ile Leu Ala Leu Leu
100 105 110

Pro Ala Leu Gly Leu Leu Leu Trp Gly Pro Gly Gln Leu
115 120 125

<210> SEQ ID NO 22
<211> LENGTH: 375
<212> TYPE: DNA
<213> ORGANISM: Homo sapiens

<400> SEQUENCE: 22
atggctagca aggctgtgct gcttgccctg ttgatggcag gcttggccct gcagccaggc 60
actgccctgc tgtgctactc ctgcaaagcc caggtgagca acgaggactg cctgcaggtg 120
gagaactgca cccagctggg ggagcagtgc tggaccgcgc gcatccgcgc agttggcctc 180
ctgaccgtca tcagcaaagg ctgcagcttg aactgcgtgg atgactcaca ggactactac 240
gtgggcaaga agaacatcac gtgctgtgac accgacttgt gcaacgccag cggggcccat 300
gccctgcagc cggctgccgc catccttgcg ctgctccctg cactcggcct gctgctctgg 360
ggacccggcc agcta 375

<210> SEQ ID NO 23
<211> LENGTH: 5964
<212> TYPE: DNA
<213> ORGANISM: Artificial Sequence
<220> FEATURE:
<223> OTHER INFORMATION: Synthetic Construct

<400> SEQUENCE: 23
ggcgtaatgc tctgccagtg ttacaaccaa ttaaccaatt ctgattagaa aaactcatcg 60
agcatcaaat gaaactgcaa tttattcata tcaggattat caataccata tttttgaaaa 120
agccgtttct gtaatgaagg agaaaactca ccgaggcagt tccataggat ggcaagatcc 180
tggtatcggt ctgcgattcc gactcgtcca acatcaatac aacctattaa tttcccctcg 240
tcaaaaataa ggttatcaag tgagaaatca ccatgagtga cgactgaatc cggtgagaat 300
ggcaaaagct tatgcatttc tttccagact tgttcaacag gccagccatt acgctcgtca 360
tcaaaatcac tcgcatcaac caaaccgtta ttcattcgtg attgcgcctg agcgagacga 420
aatacgcgat cgctgttaaa aggacaatta caaacaggaa tcaaatgcaa ccggcgcagg 480
aacactgcca gcgcatcaac aatattttca cctgaatcag gatattcttc taatacctgg 540
aatgctgttt tcccggggat cgcagtggtg agtaaccatg catcatcagg agtacggata 600
aaatgcttga tggtcggaag aggcataaat tccgtcagcc agtttagtct gaccatctca 660
tctgtaacat cattggcaac gctacctttg ccatgtttca gaaacaactc tggcgcatcg 720
ggcttcccat acaatcgata gattgtcgca cctgattgcc cgacattatc gcgagcccat 780
ttatacccat ataaatcagc atccatgttg gaatttaatc gcggcctcga gcaagacgtt 840
tcccgttgaa tatggctcat aacacccctt gtattactgt ttatgtaagc agacaggtcg 900
acaatattgg ctattggcca ttgcatacgt tgtatctata tcataatatg tacatttata 960
ttggctcatg tccaatatga ccgccatgtt gacattgatt attgactagt tattaatagt 1020
aatcaattac ggggtcatta gttcatagcc catatatgga gttccgcgtt acataactta 1080
cggtaaatgg cccgcctggc tgaccgccca acgacccccg cccattgacg tcaataatga 1140
cgtatgttcc catagtaacg ccaataggga ctttccattg acgtcaatgg gtggagtatt 1200
tacggtaaac tgcccacttg gcagtacatc aagtgtatca tatgccaagt ccgcccccta 1260
ttgacgtcaa tgacggtaaa tggcccgcct ggcattatgc ccagtacatg accttacggg 1320
actttcctac ttggcagtac atctacgtat tagtcatcgc tattaccatg gtgatgcggt 1380
tttggcagta caccaatggg cgtggatagc ggtttgactc acggggattt ccaagtctcc 1440
accccattga cgtcaatggg agtttgtttt ggcaccaaaa tcaacgggac tttccaaaat 1500
gtcgtaataa ccccgccccg ttgacgcaaa tgggcggtag gcgtgtacgg tgggaggtct 1560
atataagcag agctcgttta gtgaaccgtc agatcgcctg gagacgccat ccacgctgtt 1620
ttgacctcca tagaagacac cgggaccgat ccagcctccg cggccgggaa cggtgcattg 1680
gaacgcggat tccccgtgcc aagagtgact caccgtccgg atctcagcaa gcaggtatgt 1740

-continued

```
actctccagg gtgggcctgg cttccccagt caagactcca gggatttgag ggacgctgtg   1800
ggctcttctc ttacatgtac cttttgcttg cctcaaccct gactatcttc caggtcagga   1860
tcccagagtc aggggtctgt attttcctgc tggtggctcc agttcaggaa cagtaaaccc   1920
tgctccgaat attgcctctc acatctcgtc aatctccgcg aggactgggg accctgtgac   1980
gaacatggct agcgcgcgcc gcccgcgctg gctgtgcgct ggggcgctgg tgctggcggg   2040
tggcttcttt ctcctcggct tcctcttcgg gtggtttata aaatcctcca atgaagctac   2100
taacattact ccaaagcata atatgaaagc atttttggat gaattgaaag ctgagaacat   2160
caagaagttc ttatataatt ttacacagat accacattta gcaggaacag aacaaaactt   2220
tcagcttgca aagcaaattc aatcccagtg gaaagaattt ggcctggatt ctgttgagct   2280
ggcacattat gatgtcctgt tgtcctaccc aaataagact catcccaact acatctcaat   2340
aattaatgaa gatggaaatg agattttcaa cacatcatta tttgaaccac ctcctccagg   2400
atatgaaaat gtttcggata ttgtaccacc tttcagtgct ttctctcctc aaggaatgcc   2460
agagggcgat ctagtgtatg ttaactatgc acgaactgaa gacttcttta aattggaacg   2520
ggacatgaaa atcaattgct ctgggaaaat tgtaattgcc agatatggga aagttttcag   2580
aggaaataag gttaaaaatg cccagctggc aggggccaaa ggagtcattc tctactccga   2640
ccctgctgac tactttgctc ctggggtgaa gtcctatcca gatggttgga atcttcctgg   2700
aggtggtgtc cagcgtggaa atatcctaaa tctgaatggt gcaggagacc ctctcacacc   2760
aggttaccca gcaaatgaat atgcttatag gcgtggaatt gcagaggctg ttggtcttcc   2820
aagtattcct gttcatccaa ttggatacta tgatgcacag aagctcctag aaaaaatggg   2880
tggctcagca ccaccagata gcagctggag aggaagtctc aaagtgccct acaatgttgg   2940
acctggcttt actggaaact tttctacaca aaaagtcaag atgcacatcc actctaccaa   3000
tgaagtgaca agaatttaca atgtgatagg tactctcaga ggagcagtgg aaccagacag   3060
atatgtcatt ctgggaggtc accgggactc atgggtgttt ggtggtattg accctcagag   3120
tggagcagct gttgttcatg aaattgtgag gagctttgga acactgaaaa aggaagggtg   3180
gagacctaga agaacaattt tgtttgcaag ctgggatgca gaagaatttg gtcttcttgg   3240
ttctactgag tgggcagagg agaattcaag actccttcaa gagcgtggcg tggcttatat   3300
taatgctgac tcatctatag aaggaaacta cactctgaga gttgattgta caccgctgat   3360
gtacagcttg gtacacaacc taacaaaaga gctgaaaagc cctgatgaag gctttgaagg   3420
caaatctctt tatgaaagtt ggactaaaaa aagtccttcc ccagagttca gtggcatgcc   3480
caggataagc aaattgggat ctggaaatga ttttgaggtg ttcttccaac gacttggaat   3540
tgcttcaggc agagcacggt atactaaaaa ttgggaaaca aacaaattca gcggctatcc   3600
actgtatcac agtgtctatg aaacatatga gttggtggaa aagttttatg atccaatgtt   3660
taaatatcac ctcactgtgg cccaggttcg aggagggatg gtgtttgagc tggccaattc   3720
catagtgctc ccttttgatt gtcgagatta tgctgtagtt ttaagaaagt atgctgacaa   3780
aatctacagt atttctatga aacatccaca ggaaatgaag acatacagtg tatcatttga   3840
ttcacttttt tctgcagtaa agaattttac agaaattgct tccaagttca gtgagagact   3900
ccaggacttt gacaaaagca acccaatagt attaagaatg atgaatgatc aactcatgtt   3960
tctggaaaga gcatttattg atccattagg gttaccagac aggccttttt ataggcatgt   4020
catctatgct ccaagcagcc acaacaagta tgcaggggag tcattcccag gaatttatga   4080
tgctctgttt gatattgaaa gcaaagtgga cccttccaag gcctggggag aagtgaagag   4140
```

-continued acagatttat gttgcagcct tcacagtgca ggcagctgca gagactttga gtgaagtagc 4200
ctaaagatct gggccctaac aaaacaaaaa gatggggtta ttccctaaac ttcatgggtt 4260
acgtaattgg aagttggggg acattgccac aagatcatat tgtacaaaag atcaaacact 4320
gttttagaaa acttcctgta aacaggccta ttgattggaa agtatgtcaa aggattgtgg 4380
gtcttttggg ctttgctgct ccatttacac aatgtggata tcctgcctta atgcctttgt 4440
atgcatgtat acaagctaaa caggctttca ctttctcgcc aacttacaag gcctttctaa 4500
gtaaacagta catgaacctt taccccgttg ctcggcaacg gcctggtctg tgccaagtgt 4560
ttgctgacgc aacccccact ggctggggct tggccatagg ccatcagcgc atgcgtggaa 4620
cctttgtggc tcctctgccg atccatactg cggaactcct agccgcttgt tttgctcgca 4680
gccggtctgg agcaaagctc ataggaactg acaattctgt cgtcctctcg cggaaatata 4740
catcgtttcg atctacgtat gatctttttc cctctgccaa aaattatggg gacatcatga 4800
agccccttga gcatctgact tctggctaat aaaggaaatt tattttcatt gcaatagtgt 4860
gttggaattt tttgtgtctc tcactcggaa ggaattctgc attaatgaat cggccaacgc 4920
gcggggagag gcggtttgcg tattgggcgc tcttccgctt cctcgctcac tgactcgctg 4980
cgctcggtcg ttcggctgcg gcgagcggta tcagctcact caaaggcggt aatacggtta 5040
tccacagaat caggggataa cgcaggaaag aacatgtgag caaaaggcca gcaaaaggcc 5100
aggaaccgta aaaaggccgc gttgctggcg tttttccata ggctccgccc ccctgacgag 5160
catcacaaaa atcgacgctc aagtcagagg tggcgaaacc cgacaggact ataaagatac 5220
caggcgtttc cccctggaag ctccctcgtg cgctctcctg ttccgaccct gccgcttacc 5280
ggatacctgt ccgcctttct cccttcggga agcgtggcgc tttctcatag ctcacgctgt 5340
aggtatctca gttcggtgta ggtcgttcgc tccaagctgg gctgtgtgca cgaacccccc 5400
gttcagcccg accgctgcgc cttatccggt aactatcgtc ttgagtccaa cccggtaaga 5460
cacgacttat cgccactggc agcagccact ggtaacagga ttagcagagc gaggtatgta 5520
ggcggtgcta cagagttctt gaagtggtgg cctaactacg gctacactag aagaacagta 5580
tttggtatct gcgctctgct gaagccagtt accttcggaa aaagagttgg tagctcttga 5640
tccggcaaac aaaccaccgc tggtagcggt ggtttttttg tttgcaagca gcagattacg 5700
cgcagaaaaa aaggatctca agaagatcct ttgatctttt ctacggggtc tgacgctcag 5760
tggaacgaaa actcacgtta agggattttg gtcatgagat tatcaaaaag gatcttcacc 5820
tagatccttt taaattaaaa atgaagtttt aaatcaatct aaagtatata tgagtaaact 5880
tggtctgaca gttaccaatg cttaatcagt gaggcaccta tctcagcgat ctgtctattt 5940
cgttcatcca tagttgcctg actc 5964

<210> SEQ ID NO 24
<211> LENGTH: 4122
<212> TYPE: DNA
<213> ORGANISM: Artificial Sequence
<220> FEATURE:
<223> OTHER INFORMATION: Synthetic Construct

<400> SEQUENCE: 24
ggcgtaatgc tctgccagtg ttacaaccaa ttaaccaatt ctgattagaa aaactcatcg 60
agcatcaaat gaaactgcaa tttattcata tcaggattat caataccata tttttgaaaa 120
agccgtttct gtaatgaagg agaaaactca ccgaggcagt tccataggat ggcaagatcc 180

-continued

```
tggtatcggt ctgcgattcc gactcgtcca acatcaatac aacctattaa tttcccctcg    240
tcaaaaataa ggttatcaag tgagaaatca ccatgagtga cgactgaatc cggtgagaat    300
ggcaaaagct tatgcatttc tttccagact tgttcaacag gccagccatt acgctcgtca    360
tcaaaatcac tcgcatcaac caaaccgtta ttcattcgtg attgcgcctg agcgagacga    420
aatacgcgat cgctgttaaa aggacaatta caaacaggaa tcaaatgcaa ccggcgcagg    480
aacactgcca gcgcatcaac aatattttca cctgaatcag gatattcttc taatacctgg    540
aatgctgttt tcccggggat cgcagtggtg agtaaccatg catcatcagg agtacggata    600
aaatgcttga tggtcggaag aggcataaat tccgtcagcc agtttagtct gaccatctca    660
tctgtaacat cattggcaac gctacctttg ccatgtttca gaaacaactc tggcgcatcg    720
ggcttcccat acaatcgata gattgtcgca cctgattgcc cgacattatc gcgagcccat    780
ttatacccat ataaatcagc atccatgttg gaatttaatc gcggcctcga gcaagacgtt    840
tcccgttgaa tatggctcat aacacccctt gtattactgt ttatgtaagc agacaggtcg    900
acaatattgg ctattggcca ttgcatacgt tgtatctata tcataatatg tacatttata    960
ttggctcatg tccaatatga ccgccatgtt gacattgatt attgactagt tattaatagt   1020
aatcaattac ggggtcatta gttcatagcc catatatgga gttccgcgtt acataactta   1080
cggtaaatgg cccgcctggc tgaccgccca acgacccccg cccattgacg tcaataatga   1140
cgtatgttcc catagtaacg ccaataggga ctttccattg acgtcaatgg gtggagtatt   1200
tacggtaaac tgcccacttg gcagtacatc aagtgtatca tatgccaagt ccgcccccta   1260
ttgacgtcaa tgacggtaaa tggcccgcct ggcattatgc ccagtacatg accttacggg   1320
actttcctac ttggcagtac atctacgtat tagtcatcgc tattaccatg gtgatgcggt   1380
tttggcagta caccaatggg cgtggatagc ggtttgactc acggggattt ccaagtctcc   1440
accccattga cgtcaatggg agtttgtttt ggcaccaaaa tcaacgggac tttccaaaat   1500
gtcgtaataa ccccgccccg ttgacgcaaa tgggcggtag gcgtgtacgg tgggaggtct   1560
atataagcag agctcgttta gtgaaccgtc agatcgcctg gagacgccat ccacgctgtt   1620
ttgacctcca tagaagacac cgggaccgat ccagcctccg cggccgggaa cggtgcattg   1680
gaacgcggat tccccgtgcc aagagtgact caccgtccgg atctcagcaa gcaggtatgt   1740
actctccagg gtgggcctgg cttccccagt caagactcca gggatttgag ggacgctgtg   1800
ggctcttctc ttacatgtac cttttgcttg cctcaaccct gactatcttc caggtcagga   1860
tcccagagtc aggggtctgt attttcctgc tggtggctcc agttcaggaa cagtaaaccc   1920
tgctccgaat attgcctctc acatctcgtc aatctccgcg aggactgggg accctgtgac   1980
gaacatggct agcaaggctg tgctgcttgc cctgttgatg gcaggcttgg ccctgcagcc   2040
aggcactgcc ctgctgtgct actcctgcaa agcccaggtg agcaacgagg actgcctgca   2100
ggtggagaac tgcacccagc tgggggagca gtgctggacc gcgcgcatcc gcgcagttgg   2160
cctcctgacc gtcatcagca aaggctgcag cttgaactgc gtggatgact cacaggacta   2220
ctacgtgggc aagaagaaca tcacgtgctg tgacaccgac ttgtgcaacg ccagcggggc   2280
ccatgccctg cagccggctg ccgccatcct tgcgctgctc cctgcactcg gcctgctgct   2340
ctggggaccc ggccagctat agagatctgg gccctaacaa aacaaaaaga tggggttatt   2400
ccctaaactt catgggttac gtaattggaa gttgggggac attgccacaa gatcatattg   2460
tacaaaagat caaacactgt tttagaaaac ttcctgtaaa caggcctatt gattggaaag   2520
tatgtcaaag gattgtgggt cttttgggct ttgctgctcc atttacacaa tgtggatatc   2580
```

```
ctgccttaat gcctttgtat gcatgtatac aagctaaaca ggctttcact ttctcgccaa   2640

cttacaaggc ctttctaagt aaacagtaca tgaaccttta ccccgttgct cggcaacggc   2700

ctggtctgtg ccaagtgttt gctgacgcaa cccccactgg ctggggcttg gccataggcc   2760

atcagcgcat gcgtggaacc tttgtggctc ctctgccgat ccatactgcg gaactcctag   2820

ccgcttgttt tgctcgcagc cggtctggag caaagctcat aggaactgac aattctgtcg   2880

tcctctcgcg gaaatataca tcgtttcgat ctacgtatga tctttttccc tctgccaaaa   2940

attatgggga catcatgaag ccccttgagc atctgacttc tggctaataa aggaaattta   3000

ttttcattgc aatagtgtgt tggaattttt tgtgtctctc actcggaagg aattctgcat   3060

taatgaatcg gccaacgcgc ggggagaggc ggtttgcgta ttgggcgctc ttccgcttcc   3120

tcgctcactg actcgctgcg ctcggtcgtt cggctgcggc gagcggtatc agctcactca   3180

aaggcggtaa tacggttatc cacagaatca ggggataacg caggaaagaa catgtgagca   3240

aaaggccagc aaaaggccag gaaccgtaaa aaggccgcgt tgctggcgtt tttccatagg   3300

ctccgccccc ctgacgagca tcacaaaaat cgacgctcaa gtcagaggtg gcgaaacccg   3360

acaggactat aaagatacca ggcgtttccc cctggaagct ccctcgtgcg ctctcctgtt   3420

ccgaccctgc cgcttaccgg atacctgtcc gcctttctcc cttcgggaag cgtggcgctt   3480

tctcatagct cacgctgtag gtatctcagt tcggtgtagg tcgttcgctc caagctgggc   3540

tgtgtgcacg aaccccccgt tcagcccgac cgctgcgcct tatccggtaa ctatcgtctt   3600

gagtccaacc cggtaagaca cgacttatcg ccactggcag cagccactgg taacaggatt   3660

agcagagcga ggtatgtagg cggtgctaca gagttcttga agtggtggcc taactacggc   3720

tacactagaa gaacagtatt tggtatctgc gctctgctga agccagttac cttcggaaaa   3780

agagttggta gctcttgatc cggcaaacaa accaccgctg gtagcggtgg tttttttgtt   3840

tgcaagcagc agattacgcg cagaaaaaaa ggatctcaag aagatccttt gatcttttct   3900

acggggtctg acgctcagtg gaacgaaaac tcacgttaag ggattttggt catgagatta   3960

tcaaaaagga tcttcaccta gatcctttta aattaaaaat gaagttttaa atcaatctaa   4020

agtatatatg agtaaacttg gtctgacagt taccaatgct taatcagtga ggcacctatc   4080

tcagcgatct gtctatttcg ttcatccata gttgcctgac tc                      4122
```

<210> SEQ ID NO 25
<211> LENGTH: 4467
<212> TYPE: DNA
<213> ORGANISM: Artificial Sequence
<220> FEATURE:
<223> OTHER INFORMATION: Synthetic Construct

<400> SEQUENCE: 25

```
ggcgtaatgc tctgccagtg ttacaaccaa ttaaccaatt ctgattagaa aaactcatcg     60

agcatcaaat gaaactgcaa tttattcata tcaggattat caataccata tttttgaaaa    120

agccgtttct gtaatgaagg agaaaactca ccgaggcagt tccataggat ggcaagatcc    180

tggtatcggt ctgcgattcc gactcgtcca acatcaatac aacctattaa tttcccctcg    240

tcaaaaataa ggttatcaag tgagaaatca ccatgagtga cgactgaatc cggtgagaat    300

ggcaaaagct tatgcatttc tttccagact tgttcaacag gccagccatt acgctcgtca    360

tcaaaatcac tcgcatcaac caaaccgtta ttcattcgtg attgcgcctg agcgagacga    420

aatacgcgat cgctgttaaa aggacaatta caaacaggaa tcaaatgcaa ccggcgcagg    480
```

-continued

```
aacactgcca gcgcatcaac aatattttca cctgaatcag gatattcttc taatacctgg    540
aatgctgttt tcccggggat cgcagtggtg agtaaccatg catcatcagg agtacggata    600
aaatgcttga tggtcggaag aggcataaat tccgtcagcc agtttagtct gaccatctca    660
tctgtaacat cattggcaac gctacctttg ccatgtttca gaaacaactc tggcgcatcg    720
ggcttcccat acaatcgata gattgtcgca cctgattgcc cgacattatc gcgagcccat    780
ttatacccat ataaatcagc atccatgttg gaatttaatc gcggcctcga gcaagacgtt    840
tcccgttgaa tatggctcat aacacccctt gtattactgt ttatgtaagc agacaggtcg    900
acaatattgg ctattggcca ttgcatacgt tgtatctata tcataatatg tacatttata    960
ttggctcatg tccaatatga ccgccatgtt gacattgatt attgactagt tattaatagt   1020
aatcaattac ggggtcatta gttcatagcc catatatgga gttccgcgtt acataactta   1080
cggtaaatgg cccgcctggc tgaccgccca acgacccccg cccattgacg tcaataatga   1140
cgtatgttcc catagtaacg ccaataggga ctttccattg acgtcaatgg gtggagtatt   1200
tacggtaaac tgcccacttg gcagtacatc aagtgtatca tatgccaagt ccgcccccta   1260
ttgacgtcaa tgacggtaaa tggcccgcct ggcattatgc ccagtacatg accttacggg   1320
actttcctac ttggcagtac atctacgtat tagtcatcgc tattaccatg gtgatgcggt   1380
tttggcagta caccaatggg cgtggatagc ggtttgactc acggggattt ccaagtctcc   1440
accccattga cgtcaatggg agtttgtttt ggcaccaaaa tcaacgggac tttccaaaat   1500
gtcgtaataa ccccgccccg ttgacgcaaa tgggcggtag gcgtgtacgg tgggaggtct   1560
atataagcag agctcgttta gtgaaccgtc agatcgcctg gagacgccat ccacgctgtt   1620
ttgacctcca tagaagacac cgggaccgat ccagcctccg cggccgggaa cggtgcattg   1680
gaacgcggat tccccgtgcc aagagtgact caccgtccgg atctcagcaa gcaggtatgt   1740
actctccagg gtgggcctgg cttccccagt caagactcca gggatttgag ggacgctgtg   1800
ggctcttctc ttacatgtac cttttgcttg cctcaaccct gactatcttc caggtcagga   1860
tcccagagtc aggggtctgt attttcctgc tggtggctcc agttcaggaa cagtaaaccc   1920
tgctccgaat attgcctctc acatctcgtc aatctccgcg aggactgggg accctgtgac   1980
gaacatggct agcattgtgg gaggctggga gtgcgagaag cattcccaac cctggcaggt   2040
gcttgtggcc tctcgtggca gggcagtctg cggcggtgtt ctggtgcacc cccagtgggt   2100
cctcacagct gcccactgca tcaggaacaa aagcgtgatc ttgctgggtc ggcacagctt   2160
gtttcatcct gaagacacag gccaggtatt tcaggtcagc cacagcttcc cacacccgct   2220
ctacgatatg agcctcctga agaatcgatt cctcaggcca ggtgatgact ccagccacga   2280
cctcatgctg ctccgcctgt cagagcctgc cgagctcacg gatgctgtga aggtcatgga   2340
cctgcccacc caggagccag cactggggac cacctgctac gcctcaggct ggggcagcat   2400
tgaaccagag gagttcttga ccccaaagaa acttcagtgt gtggacctcc atgttatttc   2460
caatgacgtg tgtgcgcaag ttcaccctca gaaggtgacc aagttcatgc tgtgtgctgg   2520
acgctggaca gggggcaaaa gcacctgctc gggtgattct gggggcccac ttgtctgtaa   2580
tggtgtgctt caaggtatca cgtcatgggg cagtgaacca tgtgccctgc ccgaaaggcc   2640
ttccctgtac accaaggtgg tgcattaccg gaagtggatc aaggacacca tcgtggccaa   2700
cccctgaaga tctgggccct aacaaaacaa aaagatgggg ttattcccta aacttcatgg   2760
gttacgtaat tggaagttgg gggacattgc cacaagatca tattgtacaa aagatcaaac   2820
actgttttag aaaacttcct gtaaacaggc ctattgattg gaaagtatgt caaaggattg   2880
```

tgggtctttt gggctttgct gctccattta cacaatgtgg atatcctgcc ttaatgcctt 2940
tgtatgcatg tatacaagct aaacaggctt tcactttctc gccaacttac aaggcctttc 3000
taagtaaaca gtacatgaac ctttaccccg ttgctcggca acggcctggt ctgtgccaag 3060
tgtttgctga cgcaaccccc actggctggg gcttggccat aggccatcag cgcatgcgtg 3120
gaacctttgt ggctcctctg ccgatccata ctgcggaact cctagccgct tgttttgctc 3180
gcagccggtc tggagcaaag ctcataggaa ctgacaattc tgtcgtcctc tcgcggaaat 3240
atacatcgtt tcgatctacg tatgatcttt ttccctctgc caaaaattat ggggacatca 3300
tgaagcccct tgagcatctg acttctggct aataaaggaa atttattttc attgcaatag 3360
tgtgttggaa ttttttgtgt ctctcactcg gaaggaattc tgcattaatg aatcggccaa 3420
cgcgcgggga gaggcggttt gcgtattggg cgctcttccg cttcctcgct cactgactcg 3480
ctgcgctcgg tcgttcggct gcggcgagcg gtatcagctc actcaaaggc ggtaatacgg 3540
ttatccacag aatcagggga taacgcagga aagaacatgt gagcaaaagg ccagcaaaag 3600
gccaggaacc gtaaaaaggc cgcgttgctg gcgtttttcc ataggctccg cccccctgac 3660
gagcatcaca aaaatcgacg ctcaagtcag aggtggcgaa acccgacagg actataaaga 3720
taccaggcgt ttccccctgg aagctccctc gtgcgctctc ctgttccgac cctgccgctt 3780
accggatacc tgtccgcctt tctcccttcg ggaagcgtgg cgctttctca tagctcacgc 3840
tgtaggtatc tcagttcggt gtaggtcgtt cgctccaagc tgggctgtgt gcacgaaccc 3900
cccgttcagc ccgaccgctg cgccttatcc ggtaactatc gtcttgagtc caacccggta 3960
agacacgact tatcgccact ggcagcagcc actggtaaca ggattagcag agcgaggtat 4020
gtaggcggtg ctacagagtt cttgaagtgg tggcctaact acggctacac tagaagaaca 4080
gtatttggta tctgcgctct gctgaagcca gttaccttcg gaaaaagagt tggtagctct 4140
tgatccggca aacaaaccac cgctggtagc ggtggttttt ttgtttgcaa gcagcagatt 4200
acgcgcagaa aaaaaggatc tcaagaagat cctttgatct tttctacggg gtctgacgct 4260
cagtggaacg aaaactcacg ttaagggatt ttggtcatga gattatcaaa aaggatcttc 4320
acctagatcc ttttaaatta aaaatgaagt tttaaatcaa tctaaagtat atatgagtaa 4380
acttggtctg acagttacca atgcttaatc agtgaggcac ctatctcagc gatctgtcta 4440
tttcgttcat ccatagttgc ctgactc 4467

<210> SEQ ID NO 26
<211> LENGTH: 7563
<212> TYPE: DNA
<213> ORGANISM: Artificial Sequence
<220> FEATURE:
<223> OTHER INFORMATION: Synthetic Construct

<400> SEQUENCE: 26
gaattctgca ttaatgaatc ggccaacgcg cggggagagg cggtttgcgt attgggcgct 60
cttccgcttc ctcgctcact gactcgctgc gctcggtcgt tcggctgcgg cgagcggtat 120
cagctcactc aaaggcggta atacggttat ccacagaatc aggggataac gcaggaaaga 180
acatgtgagc aaaaggccag caaaaggcca ggaaccgtaa aaaggccgcg ttgctggcgt 240
ttttccatag gctccgcccc cctgacgagc atcacaaaaa tcgacgctca agtcagaggt 300
ggcgaaaccc gacaggacta taaagatacc aggcgtttcc ccctggaagc tccctcgtgc 360
gctctcctgt tccgaccctg ccgcttaccg gatacctgtc cgcctttctc ccttcgggaa 420

-continued

```
gcgtggcgct ttctcatagc tcacgctgta ggtatctcag ttcggtgtag gtcgttcgct    480
ccaagctggg ctgtgtgcac gaaccccccg ttcagcccga ccgctgcgcc ttatccggta    540
actatcgtct tgagtccaac ccggtaagac acgacttatc gccactggca gcagccactg    600
gtaacaggat tagcagagcg aggtatgtag gcggtgctac agagttcttg aagtggtggc    660
ctaactacgg ctacactaga agaacagtat ttggtatctg cgctctgctg aagccagtta    720
ccttcggaaa aagagttggt agctcttgat ccggcaaaca aaccaccgct ggtagcggtg    780
gtttttttgt ttgcaagcag cagattacgc gcagaaaaaa aggatctcaa gaagatcctt    840
tgatcttttc tacggggtct gacgctcagt ggaacgaaaa ctcacgttaa gggattttgg    900
tcatgagatt atcaaaaagg atcttcacct agatcctttt aaattaaaaa tgaagtttta    960
aatcaatcta aagtatatat gagtaaactt ggtctgacag ttaccaatgc ttaatcagtg   1020
aggcacctat ctcagcgatc tgtctatttc gttcatccat agttgcctga ctcggcgtaa   1080
tgctctgcca gtgttacaac caattaacca attctgatta gaaaaactca tcgagcatca   1140
aatgaaactg caatttattc atatcaggat tatcaatacc atatttttga aaaagccgtt   1200
tctgtaatga aggagaaaac tcaccgaggc agttccatag gatggcaaga tcctggtatc   1260
ggtctgcgat tccgactcgt ccaacatcaa tacaacctat taatttcccc tcgtcaaaaa   1320
taaggttatc aagtgagaaa tcaccatgag tgacgactga atccggtgag aatggcaaaa   1380
gcttatgcat ttctttccag acttgttcaa caggccagcc attacgctcg tcatcaaaat   1440
cactcgcatc aaccaaaccg ttattcattc gtgattgcgc ctgagcgaga cgaaatacgc   1500
gatcgctgtt aaaaggacaa ttacaaacag gaatcaaatg caaccggcgc aggaacactg   1560
ccagcgcatc aacaatattt tcacctgaat caggatattc ttctaatacc tggaatgctg   1620
ttttcccggg gatcgcagtg gtgagtaacc atgcatcatc aggagtacgg ataaaatgct   1680
tgatggtcgg aagaggcata aattccgtca gccagtttag tctgaccatc tcatctgtaa   1740
catcattggc aacgctacct ttgccatgtt tcagaaacaa ctctggcgca tcgggcttcc   1800
catacaatcg atagattgtc gcacctgatt gcccgacatt atcgcgagcc catttatacc   1860
catataaatc agcatccatg ttggaattta atcgcggcct cgagcaagac gtttcccgtt   1920
gaatatggct cataacaccc cttgtattac tgtttatgta agcagacagg gtaccaatct   1980
tccgagtgag agacacaaaa aattccaaca cactattgca atgaaaataa atttccttta   2040
ttagccagaa gtcagatgct caaggggctt catgatgtcc ccataatttt tggcagaggg   2100
aaaaagatca tacgtagatc gaaacgatgt atatttccgc gagaggacga cagaattgtc   2160
agttcctatg agctttgctc cagaccggct gcgagcaaaa caagcggcta ggagttccgc   2220
agtatggatc ggcagaggag ccacaaaggt tccacgcatg cgctgatggc ctatggccaa   2280
gccccagcca gtgggggttg cgtcagcaaa cacttggcac agaccaggcc gttgccgagc   2340
aacggggtaa aggttcatgt actgtttact tagaaaggcc ttgtaagttg gcgagaaagt   2400
gaaagcctgt ttagcttgta tacatgcata caaaggcatt aaggcaggat atccacattg   2460
tgtaaatgga gcagcaaagc ccaaaagacc cacaatcctt tgacatactt tccaatcaat   2520
aggcctgttt acaggaagtt ttctaaaaca gtgtttgatc ttttgtacaa tatgatcttg   2580
tggcaatgtc ccccaacttc caattacgta acccatgaag tttagggaat aaccccatct   2640
ttttgttttg ttagggccca gatctttagg ctacttcact caaagtctct gcagctgcct   2700
gcactgtgaa ggctgcaaca taaatctgtc tcttcacttc tccccaggcc ttggaagggt   2760
ccactttgct ttcaatatca aacagagcat cataaattcc tgggaatgac tcccctgcat   2820
```

acttgttgtg gctgcttgga gcatagatga catgcctata aaaaggcctg tctggtaacc 2880
ctaatggatc aataaatgct ctttccagaa acatgagttg atcattcatc attcttaata 2940
ctattgggtt gcttttgtca aagtcctgga gtctctcact gaacttggaa gcaatttctg 3000
taaaattctt tactgcagaa aaaagtgaat caaatgatac actgtatgtc ttcatttcct 3060
gtggatgttt catagaaata ctgtagattt tgtcagcata ctttcttaaa actacagcat 3120
aatctcgaca atcaaaaggg agcactatgg aattggccag ctcaaacacc atccctcctc 3180
gaacctgggc cacagtgagg tgatatttaa acattggatc ataaaacttt tccaccaact 3240
catatgtttc atagacactg tgatacagtg gatagccgct gaatttgttt gtttcccaat 3300
ttttagtata ccgtgctctg cctgaagcaa ttccaagtcg ttggaagaac acctcaaaat 3360
catttccaga tcccaatttg cttatcctgg gcatgccact gaactctggg gaaggacttt 3420
ttttagtcca actttcataa agagatttgc cttcaaagcc ttcatcaggg cttttcagct 3480
cttttgttag gttgtgtacc aagctgtaca tcagcggtgt acaatcaact ctcagagtgt 3540
agtttccttc tatagatgag tcagcattaa tataagccac gccacgctct tgaaggagtc 3600
ttgaattctc ctctgcccac tcagtagaac caagaagacc aaattcttct gcatcccagc 3660
ttgcaaacaa aattgttctt ctaggtctcc acccttcctt tttcagtgtt ccaaagctcc 3720
tcacaatttc atgaacaaca gctgctccac tctgagggtc aataccacca aacacccatg 3780
agtcccggtg acctcccaga atgacatatc tgtctggttc cactgctcct ctgagagtac 3840
ctatcacatt gtaaattctt gtcacttcat tggtagagtg gatgtgcatc ttgacttttt 3900
gtgtagaaaa gtttccagta aagccaggtc caacattgta gggcactttg agacttcctc 3960
tccagctgct atctggtggt gctgagccac ccattttttc taggagcttc tgtgcatcat 4020
agtatccaat tggatgaaca ggaatacttg gaagaccaac agcctctgca attccacgcc 4080
tataagcata ttcatttgct gggtaacctg gtgtgagagg gtctcctgca ccattcagat 4140
ttaggatatt tccacgctgg acaccacctc caggaagatt ccaaccatct ggataggact 4200
tcaccccagg agcaaagtag tcagcagggt cggagtagag aatgactcct ttggcccctg 4260
ccagctgggc atttttaacc ttatttcctc tgaaaacttt cccatatctg gcaattacaa 4320
ttttcccaga gcaattgatt ttcatgtccc gttccaattt aaagaagtct tcagttcgtg 4380
catagttaac atacactaga tcgccctctg gcattccttg aggagagaaa gcactgaaag 4440
gtggtacaat atccgaaaca ttttcatatc ctggaggagg tggttcaaat aatgatgtgt 4500
tgaaaatctc atttccatct tcattaatta ttgagatgta gttgggatga gtcttatttg 4560
ggtaggacaa caggacatca taatgtgcca gctcaacaga atccaggcca aattctttcc 4620
actgggattg aatttgcttt gcaagctgaa agttttgttc tgttcctgct aaatgtggta 4680
tctgtgtaaa attatataag aacttcttga tgttctcagc tttcaattca tccaaaaatg 4740
ctttcatatt atgctttgga gtaatgttag tagcttcatt ggaggatttt ataaaccacc 4800
cgaagaggaa gccgaggaga aagaagccac ccgccagcac cagcgcccca gcgcacagcc 4860
agcgcgggcg gcgcgcgcta gccatgttcg tcacagggtc cccagtcctc gcggagattg 4920
acgagatgtg agaggcaata ttcggagcag ggtttactgt tcctgaactg gagccaccag 4980
caggaaaata cagacccctg actctgggat cctgacctgg aagatagtca gggttgaggc 5040
aagcaaaagg tacatgtaag agaagagccc acagcgtccc tcaaatccct ggagtcttga 5100
ctggggaagc caggcccacc ctggagagta catacctgct tgctgagatc cggacggtga 5160

-continued

```
gtcactcttg gcacggggaa tccgcgttcc aatgcaccgt tcccggccgc ggaggctgga   5220
tcggtcccgg tgtcttctat ggaggtcaaa acagcgtgga tggcgtctcc aggcgatctg   5280
acggttcact aaacgagctc tgcttatata gacctcccac cgtacacgcc taccgcccat   5340
ttgcgtcaac ggggcggggt tattacgaca ttttggaaag tcccgttgat tttggtgctc   5400
gacctgcagg gtaccaatat tggctattgg ccattgcata cgttgtatct atatcataat   5460
atgtacattt atattggctc atgtccaata tgaccgccat gttgacattg attattgact   5520
agttattaat agtaatcaat tacggggtca ttagttcata gcccatatat ggagttccgc   5580
gttacataac ttacggtaaa tggcccgcct ggctgaccgc ccaacgaccc ccgcccattg   5640
acgtcaataa tgacgtatgt tcccatagta acgccaatag ggactttcca ttgacgtcaa   5700
tgggtggagt atttacggta aactgcccac ttggcagtac atcaagtgta tcatatgcca   5760
agtccgcccc ctattgacgt caatgacggt aaatggcccg cctggcatta tgcccagtac   5820
atgaccttac gggactttcc tacttggcag tacatctacg tattagtcat cgctattacc   5880
atggtgatgc ggttttggca gtacaccaat gggcgtggat agcggtttga ctcacgggga   5940
tttccaagtc tccaccccat tgacgtcaat gggagtttgt tttggcacca aaatcaacgg   6000
gactttccaa aatgtcgtaa taaccccgcc ccgttgacgc aaatgggcgg taggcgtgta   6060
cggtgggagg tctatataag cagagctcgt ttagtgaacc gtcagatcgc ctggagacgc   6120
catccacgct gttttgacct ccatagaaga caccgggacc gatccagcct ccgcggccgg   6180
gaacggtgca ttggaacgcg gattccccgt gccaagagtg actcaccgtc cggatctcag   6240
caagcaggta tgtactctcc agggtgggcc tggcttcccc agtcaagact ccagggattt   6300
gagggacgct gtgggctctt ctcttacatg taccttttgc ttgcctcaac cctgactatc   6360
ttccaggtca ggatcccaga gtcaggggtc tgtattttcc tgctggtggc tccagttcag   6420
gaacagtaaa ccctgctccg aatattgcct ctcacatctc gtcaatctcc gcgaggactg   6480
gggaccctgt gacgaacatg gctagcaagg ctgtgctgct tgccctgttg atggcaggct   6540
tggccctgca gccaggcact gccctgctgt gctactcctg caaagcccag gtgagcaacg   6600
aggactgcct gcaggtggag aactgcaccc agctgggga gcagtgctgg accgcgcgca   6660
tccgcgcagt tggcctcctg accgtcatca gcaaaggctg cagcttgaac tgcgtggatg   6720
actcacagga ctactacgtg ggcaagaaga acatcacgtg ctgtgacacc gacttgtgca   6780
acgccagcgg ggcccatgcc ctgcagccgg ctgccgccat ccttgcgctg ctccctgcac   6840
tcggcctgct gctctgggga cccggccagc tatagagatc tgggccctaa caaaacaaaa   6900
agatggggtt attccctaaa cttcatgggt tacgtaattg gaagttgggg gacattgcca   6960
caagatcata ttgtacaaaa gatcaaacac tgttttagaa aacttcctgt aaacaggcct   7020
attgattgga aagtatgtca aaggattgtg ggtcttttgg gctttgctgc tccatttaca   7080
caatgtggat atcctgcctt aatgcctttg tatgcatgta tacaagctaa acaggctttc   7140
actttctcgc caacttacaa ggcctttcta agtaaacagt acatgaacct ttaccccgtt   7200
gctcggcaac ggcctggtct gtgccaagtg tttgctgacg caacccccac tggctggggc   7260
ttggccatag gccatcagcg catgcgtgga acctttgtgg ctcctctgcc gatccatact   7320
gcggaactcc tagccgcttg ttttgctcgc agccggtctg gagcaaagct cataggaact   7380
gacaattctg tcgtcctctc gcggaaatat acatcgtttc gatctacgta tgatcttttt   7440
ccctctgcca aaaattatgg ggacatcatg aagccccttg agcatctgac ttctggctaa   7500
taaaggaaat ttattttcat tgcaatagtg tgttggaatt ttttgtgtct ctcactcgga   7560
```

agc 7563

<210> SEQ ID NO 27
<211> LENGTH: 6396
<212> TYPE: DNA
<213> ORGANISM: Artificial Sequence
<220> FEATURE:
<223> OTHER INFORMATION: Synthetic Construct

<400> SEQUENCE: 27
ggcgtaatgc tctgccagtg ttacaaccaa ttaaccaatt ctgattagaa aaactcatcg 60
agcatcaaat gaaactgcaa tttattcata tcaggattat caataccata tttttgaaaa 120
agccgtttct gtaatgaagg agaaaactca ccgaggcagt tccataggat ggcaagatcc 180
tggtatcggt ctgcgattcc gactcgtcca acatcaatac aacctattaa tttcccctcg 240
tcaaaaataa ggttatcaag tgagaaatca ccatgagtga cgactgaatc cggtgagaat 300
ggcaaaagct tatgcatttc tttccagact tgttcaacag gccagccatt acgctcgtca 360
tcaaaatcac tcgcatcaac caaaccgtta ttcattcgtg attgcgcctg agcgagacga 420
aatacgcgat cgctgttaaa aggacaatta caaacaggaa tcaaatgcaa ccggcgcagg 480
aacactgcca gcgcatcaac aatattttca cctgaatcag gatattcttc taatacctgg 540
aatgctgttt tcccggggat cgcagtggtg agtaaccatg catcatcagg agtacggata 600
aaatgcttga tggtcggaag aggcataaat tccgtcagcc agtttagtct gaccatctca 660
tctgtaacat cattggcaac gctacctttg ccatgtttca gaaacaactc tggcgcatcg 720
ggcttcccat acaatcgata gattgtcgca cctgattgcc cgacattatc gcgagcccat 780
ttatacccat ataaatcagc atccatgttg gaatttaatc gcggcctcga gcaagacgtt 840
tcccgttgaa tatggctcat aacacccctt gtattactgt ttatgtaagc agacaggtcg 900
acaatattgg ctattggcca ttgcatacgt tgtatctata tcataatatg tacatttata 960
ttggctcatg tccaatatga ccgccatgtt gacattgatt attgactagt tattaatagt 1020
aatcaattac ggggtcatta gttcatagcc catatatgga gttccgcgtt acataactta 1080
cggtaaatgg cccgcctggc tgaccgccca acgacccccg cccattgacg tcaataatga 1140
cgtatgttcc catagtaacg ccaataggga ctttccattg acgtcaatgg gtggagtatt 1200
tacggtaaac tgcccacttg gcagtacatc aagtgtatca tatgccaagt ccgcccccta 1260
ttgacgtcaa tgacggtaaa tggcccgcct ggcattatgc ccagtacatg accttacggg 1320
actttcctac ttggcagtac atctacgtat tagtcatcgc tattaccatg gtgatgcggt 1380
tttggcagta caccaatggg cgtggatagc ggtttgactc acggggattt ccaagtctcc 1440
accccattga cgtcaatggg agtttgtttt ggcaccaaaa tcaacgggac tttccaaaat 1500
gtcgtaataa ccccgccccg ttgacgcaaa tgggcggtag gcgtgtacgg tgggaggtct 1560
atataagcag agctcgttta gtgaaccgtc agatcgcctg gagacgccat ccacgctgtt 1620
ttgacctcca tagaagacac cgggaccgat ccagcctccg cggccgggaa cggtgcattg 1680
gaacgcggat tccccgtgcc aagagtgact caccgtccgg atctcagcaa gcaggtatgt 1740
actctccagg gtgggcctgg cttccccagt caagactcca gggatttgag ggacgctgtg 1800
ggctcttctc ttacatgtac cttttgcttg cctcaaccct gactatcttc caggtcagga 1860
tcccagagtc aggggtctgt attttcctgc tggtggctcc agttcaggaa cagtaaaccc 1920
tgctccgaat attgcctctc acatctcgtc aatctccgcg aggactgggg accctgtgac 1980

-continued

```
gaacatggct agcgcgcgcc gcccgcgctg gctgtgcgct ggggcgctgg tgctggcggg   2040
tggcttcttt ctcctcggct tcctcttcgg gtggtttata aaatcctcca atgaagctac   2100
taacattact ccaaagcata atatgaaagc atttttggat gaattgaaag ctgagaacat   2160
caagaagttc ttatataatt ttacacagat accacattta gcaggaacag aacaaaactt   2220
tcagcttgca aagcaaattc aatcccagtg gaaagaattt ggcctggatt ctgttgagct   2280
ggcacattat gatgtcctgt tgtcctaccc aaataagact catcccaact acatctcaat   2340
aattaatgaa gatggaaatg agattttcaa cacatcatta tttgaaccac ctcctccagg   2400
atatgaaaat gtttcggata ttgtaccacc tttcagtgct ttctctcctc aaggaatgcc   2460
agagggcgat ctagtgtatg ttaactatgc acgaactgaa gacttcttta aattggaacg   2520
ggacatgaaa atcaattgct ctgggaaaat tgtaattgcc agatatggga aagttttcag   2580
aggaaataag gttaaaaatg cccagctggc aggggccaaa ggagtcattc tctactccga   2640
ccctgctgac tactttgctc ctggggtgaa gtcctatcca gatggttgga atcttcctgg   2700
aggtggtgtc cagcgtggaa atatcctaaa tctgaatggt gcaggagacc ctctcacacc   2760
aggttaccca gcaaatgaat atgcttatag gcgtggaatt gcagaggctg ttggtcttcc   2820
aagtattcct gttcatccaa ttggatacta tgatgcacag aagctcctag aaaaaatggg   2880
tggctcagca ccaccagata gcagctggag aggaagtctc aaagtgccct acaatgttgg   2940
acctggcttt actggaaact tttctacaca aaaagtcaag atgcacatcc actctaccaa   3000
tgaagtgaca agaatttaca atgtgatagg tactctcaga ggagcagtgg aaccagacag   3060
atatgtcatt ctgggaggtc accgggactc atgggtgttt ggtggtattg accctcagag   3120
tggagcagct gttgttcatg aaattgtgag gagctttgga acactgaaaa aggaagggtg   3180
gagacctaga agaacaattt tgtttgcaag ctgggatgca gaagaatttg gtcttcttgg   3240
ttctactgag tgggcagagg agaattcaag actccttcaa gagcgtggcg tggcttatat   3300
taatgctgac tcatctatag aaggaaacta cactctgaga gttgattgta caccgctgat   3360
gtacagcttg gtacacaacc taacaaaaga gctgaaaagc cctgatgaag gctttgaagg   3420
caaatctctt tatgaaagtt ggactaaaaa aagtccttcc ccagagttca gtggcatgcc   3480
caggataagc aaattgggat ctggaaatga ttttgaggtg ttcttccaac gacttggaat   3540
tgcttcaggc agagcacggt atactaaaaa ttgggaaaca aacaaattca gcggctatcc   3600
actgtatcac agtgtctatg aaacatatga gttggtggaa aagttttatg atccaatgtt   3660
taaatatcac ctcactgtgg cccaggttcg aggagggatg gtgtttgagc tggccaattc   3720
catagtgctc ccttttgatt gtcgagatta tgctgtagtt ttaagaaagt atgctgacaa   3780
aatctacagt atttctatga aacatccaca ggaaatgaag acatacagtg tatcatttga   3840
ttcacttttt tctgcagtaa agaattttac agaaattgct tccaagttca gtgagagact   3900
ccaggacttt gacaaaagca acccaatagt attaagaatg atgaatgatc aactcatgtt   3960
tctggaaaga gcatttattg atccattagg gttaccagac aggccttttt ataggcatgt   4020
catctatgct ccaagcagcc acaacaagta tgcaggggag tcattcccag gaatttatga   4080
tgctctgttt gatattgaaa gcaaagtgga cccttccaag gcctggggag aagtgaagag   4140
acagatttat gttgcagcct tcacagtgca ggcagctgca gagactttga gtgaagtagc   4200
cggatccgaa ggtaggggtt cattattgac ctgtggagat gtcgaagaaa acccaggacc   4260
cgcaagcaag gctgtgctgc ttgccctgtt gatggcaggc ttggccctgc agccaggcac   4320
tgccctgctg tgctactcct gcaaagccca ggtgagcaac gaggactgcc tgcaggtgga   4380
```

gaactgcacc cagctggggg agcagtgctg gaccgcgcgc atccgcgcag ttggcctcct 4440
gaccgtcatc agcaaaggct gcagcttgaa ctgcgtggat gactcacagg actactacgt 4500
gggcaagaag aacatcacgt gctgtgacac cgacttgtgc aacgccagcg gggcccatgc 4560
cctgcagccg gctgccgcca tccttgcgct gctccctgca ctcggcctgc tgctctgggg 4620
acccggccag ctatagagat ctgggcccta acaaaacaaa aagatggggt tattccctaa 4680
acttcatggg ttacgtaatt ggaagttggg ggacattgcc acaagatcat attgtacaaa 4740
agatcaaaca ctgttttaga aaacttcctg taaacaggcc tattgattgg aaagtatgtc 4800
aaaggattgt gggtcttttg ggctttgctg ctccatttac acaatgtgga tatcctgcct 4860
taatgccttt gtatgcatgt atacaagcta aacaggcttt cactttctcg ccaacttaca 4920
aggcctttct aagtaaacag tacatgaacc tttaccccgt tgctcggcaa cggcctggtc 4980
tgtgccaagt gtttgctgac gcaaccccca ctggctgggg cttggccata ggccatcagc 5040
gcatgcgtgg aacctttgtg gctcctctgc cgatccatac tgcggaactc ctagccgctt 5100
gttttgctcg cagccggtct ggagcaaagc tcataggaac tgacaattct gtcgtcctct 5160
cgcggaaata tacatcgttt cgatctacgt atgatctttt tccctctgcc aaaaattatg 5220
gggacatcat gaagcccctt gagcatctga cttctggcta ataaaggaaa tttattttca 5280
ttgcaatagt gtgttggaat tttttgtgtc tctcactcgg aaggaattct gcattaatga 5340
atcggccaac gcgcggggag aggcggtttg cgtattgggc gctcttccgc ttcctcgctc 5400
actgactcgc tgcgctcggt cgttcggctg cggcgagcgg tatcagctca ctcaaaggcg 5460
gtaatacggt tatccacaga atcaggggat aacgcaggaa agaacatgtg agcaaaaggc 5520
cagcaaaagg ccaggaaccg taaaaaggcc gcgttgctgg cgtttttcca taggctccgc 5580
ccccctgacg agcatcacaa aaatcgacgc tcaagtcaga ggtggcgaaa cccgacagga 5640
ctataaagat accaggcgtt tccccctgga agctccctcg tgcgctctcc tgttccgacc 5700
ctgccgctta ccggatacct gtccgccttt ctcccttcgg gaagcgtggc gctttctcat 5760
agctcacgct gtaggtatct cagttcggtg taggtcgttc gctccaagct gggctgtgtg 5820
cacgaacccc ccgttcagcc cgaccgctgc gccttatccg gtaactatcg tcttgagtcc 5880
aacccggtaa gacacgactt atcgccactg gcagcagcca ctggtaacag gattagcaga 5940
gcgaggtatg taggcggtgc tacagagttc ttgaagtggt ggcctaacta cggctacact 6000
agaagaacag tatttggtat ctgcgctctg ctgaagccag ttaccttcgg aaaaagagtt 6060
ggtagctctt gatccggcaa acaaaccacc gctggtagcg gtggtttttt tgtttgcaag 6120
cagcagatta cgcgcagaaa aaaaggatct caagaagatc ctttgatctt ttctacgggg 6180
tctgacgctc agtggaacga aaactcacgt taagggattt tggtcatgag attatcaaaa 6240
aggatcttca cctagatcct tttaaattaa aaatgaagtt ttaaatcaat ctaaagtata 6300
tatgagtaaa cttggtctga cagttaccaa tgcttaatca gtgaggcacc tatctcagcg 6360
atctgtctat ttcgttcatc catagttgcc tgactc 6396

<210> SEQ ID NO 28
<211> LENGTH: 6405
<212> TYPE: DNA
<213> ORGANISM: Artificial Sequence
<220> FEATURE:
<223> OTHER INFORMATION: Synthetic Construct

<400> SEQUENCE: 28

-continued

```
ggcgtaatgc tctgccagtg ttacaaccaa ttaaccaatt ctgattagaa aaactcatcg     60
agcatcaaat gaaactgcaa tttattcata tcaggattat caataccata tttttgaaaa    120
agccgtttct gtaatgaagg agaaaactca ccgaggcagt tccataggat ggcaagatcc    180
tggtatcggt ctgcgattcc gactcgtcca acatcaatac aacctattaa tttcccctcg    240
tcaaaaataa ggttatcaag tgagaaatca ccatgagtga cgactgaatc cggtgagaat    300
ggcaaaagct tatgcatttc tttccagact tgttcaacag gccagccatt acgctcgtca    360
tcaaaatcac tcgcatcaac caaaccgtta ttcattcgtg attgcgcctg agcgagacga    420
aatacgcgat cgctgttaaa aggacaatta caaacaggaa tcaaatgcaa ccggcgcagg    480
aacactgcca gcgcatcaac aatattttca cctgaatcag gatattcttc taatacctgg    540
aatgctgttt tcccggggat cgcagtggtg agtaaccatg catcatcagg agtacggata    600
aaatgcttga tggtcggaag aggcataaat tccgtcagcc agtttagtct gaccatctca    660
tctgtaacat cattggcaac gctacctttg ccatgtttca gaaacaactc tggcgcatcg    720
ggcttcccat acaatcgata gattgtcgca cctgattgcc cgacattatc gcgagcccat    780
ttatacccat ataaatcagc atccatgttg gaatttaatc gcggcctcga gcaagacgtt    840
tcccgttgaa tatggctcat aacacccctt gtattactgt ttatgtaagc agacaggtcg    900
acaatattgg ctattggcca ttgcatacgt tgtatctata tcataatatg tacatttata    960
ttggctcatg tccaatatga ccgccatgtt gacattgatt attgactagt tattaatagt   1020
aatcaattac ggggtcatta gttcatagcc catatatgga gttccgcgtt acataactta   1080
cggtaaatgg cccgcctggc tgaccgccca acgacccccg cccattgacg tcaataatga   1140
cgtatgttcc catagtaacg ccaataggga ctttccattg acgtcaatgg gtggagtatt   1200
tacggtaaac tgcccacttg gcagtacatc aagtgtatca tatgccaagt ccgcccccta   1260
ttgacgtcaa tgacggtaaa tggcccgcct ggcattatgc ccagtacatg accttacggg   1320
actttcctac ttggcagtac atctacgtat tagtcatcgc tattaccatg gtgatgcggt   1380
tttggcagta caccaatggg cgtggatagc ggtttgactc acggggattt ccaagtctcc   1440
accccattga cgtcaatggg agtttgtttt ggcaccaaaa tcaacgggac tttccaaaat   1500
gtcgtaataa ccccgccccg ttgacgcaaa tgggcggtag gcgtgtacgg tgggaggtct   1560
atataagcag agctcgttta gtgaaccgtc agatcgcctg gagacgccat ccacgctgtt   1620
ttgacctcca tagaagacac cgggaccgat ccagcctccg cggccgggaa cggtgcattg   1680
gaacgcggat tccccgtgcc aagagtgact caccgtccgg atctcagcaa gcaggtatgt   1740
actctccagg gtgggcctgg cttccccagt caagactcca gggatttgag ggacgctgtg   1800
ggctcttctc ttacatgtac cttttgcttg cctcaaccct gactatcttc caggtcagga   1860
tcccagagtc aggggtctgt attttcctgc tggtggctcc agttcaggaa cagtaaaccc   1920
tgctccgaat attgcctctc acatctcgtc aatctccgcg aggactgggg accctgtgac   1980
gaacatggct agcaaggctg tgctgcttgc cctgttgatg gcaggcttgg ccctgcagcc   2040
aggcactgcc ctgctgtgct actcctgcaa agcccaggtg agcaacgagg actgcctgca   2100
ggtggagaac tgcacccagc tgggggagca gtgctggacc gcgcgcatcc gcgcagttgg   2160
cctcctgacc gtcatcagca aaggctgcag cttgaactgc gtggatgact cacaggacta   2220
ctacgtgggc aagaagaaca tcacgtgctg tgacaccgac ttgtgcaacg ccagcggggc   2280
ccatgccctg cagccggctg ccgccatcct tgcgctgctc cctgcactcg gcctgctgct   2340
ctggggaccc ggccagctag gatcccagac cctgaacttt gatctgctga aactggcagg   2400
```

-continued

```
cgatgtggaa agcaacccag gcccaatggc aagcgcgcgc cgcccgcgct ggctgtgcgc   2460
tggggcgctg gtgctggcgg gtggcttctt tctcctcggc ttcctcttcg ggtggtttat   2520
aaaatcctcc aatgaagcta ctaacattac tccaaagcat aatatgaaag catttttgga   2580
tgaattgaaa gctgagaaca tcaagaagtt cttatataat tttacacaga taccacattt   2640
agcaggaaca gaacaaaact ttcagcttgc aaagcaaatt caatcccagt ggaaagaatt   2700
tggcctggat tctgttgagc tggcacatta tgatgtcctg ttgtcctacc caaataagac   2760
tcatcccaac tacatctcaa taattaatga agatggaaat gagattttca acacatcatt   2820
atttgaacca cctcctccag gatatgaaaa tgtttcggat attgtaccac ctttcagtgc   2880
tttctctcct caaggaatgc cagagggcga tctagtgtat gttaactatg cacgaactga   2940
agacttcttt aaattggaac gggacatgaa aatcaattgc tctgggaaaa ttgtaattgc   3000
cagatatggg aaagttttca gaggaaataa ggttaaaaat gcccagctgg caggggccaa   3060
aggagtcatt ctctactccg accctgctga ctactttgct cctggggtga agtcctatcc   3120
agatggttgg aatcttcctg gaggtggtgt ccagcgtgga aatatcctaa atctgaatgg   3180
tgcaggagac cctctcacac caggttaccc agcaaatgaa tatgcttata ggcgtggaat   3240
tgcagaggct gttggtcttc caagtattcc tgttcatcca attggatact atgatgcaca   3300
gaagctccta gaaaaaatgg gtggctcagc accaccagat agcagctgga gaggaagtct   3360
caaagtgccc tacaatgttg gacctggctt tactggaaac ttttctacac aaaaagtcaa   3420
gatgcacatc cactctacca atgaagtgac aagaatttac aatgtgatag gtactctcag   3480
aggagcagtg gaaccagaca gatatgtcat tctgggaggt caccgggact catgggtgtt   3540
tggtggtatt gaccctcaga gtggagcagc tgttgttcat gaaattgtga ggagctttgg   3600
aacactgaaa aaggaagggt ggagacctag aagaacaatt ttgtttgcaa gctgggatgc   3660
agaagaattt ggtcttcttg gttctactga gtgggcagag gagaattcaa gactccttca   3720
agagcgtggc gtggcttata ttaatgctga ctcatctata gaaggaaact acactctgag   3780
agttgattgt acaccgctga tgtacagctt ggtacacaac ctaacaaaag agctgaaaag   3840
ccctgatgaa ggctttgaag gcaaatctct ttatgaaagt tggactaaaa aaagtccttc   3900
cccagagttc agtggcatgc ccaggataag caaattggga tctggaaatg attttgaggt   3960
gttcttccaa cgacttggaa ttgcttcagg cagagcacgg tatactaaaa attgggaaac   4020
aaacaaattc agcggctatc cactgtatca cagtgtctat gaaacatatg agttggtgga   4080
aaagttttat gatccaatgt ttaaatatca cctcactgtg gcccaggttc gaggagggat   4140
ggtgtttgag ctggccaatt ccatagtgct cccttttgat tgtcgagatt atgctgtagt   4200
tttaagaaag tatgctgaca aaatctacag tatttctatg aaacatccac aggaaatgaa   4260
gacatacagt gtatcatttg attcactttt ttctgcagta aagaatttta cagaaattgc   4320
ttccaagttc agtgagagac tccaggactt tgacaaaagc aacccaatag tattaagaat   4380
gatgaatgat caactcatgt ttctggaaag agcatttatt gatccattag ggttaccaga   4440
caggcctttt tataggcatg tcatctatgc tccaagcagc cacaacaagt atgcagggga   4500
gtcattccca ggaatttatg atgctctgtt tgatattgaa agcaaagtgg acccttccaa   4560
ggcctgggga gaagtgaaga gacagattta tgttgcagcc ttcacagtgc aggcagctgc   4620
agagactttg agtgaagtag cctaaagatc tgggccctaa caaaacaaaa agatggggtt   4680
attccctaaa cttcatgggt tacgtaattg gaagttgggg gacattgcca caagatcata   4740
```

ttgtacaaaa gatcaaacac tgttttagaa aacttcctgt aaacaggcct attgattgga 4800
aagtatgtca aaggattgtg ggtcttttgg gctttgctgc tccatttaca caatgtggat 4860
atcctgcctt aatgcctttg tatgcatgta tacaagctaa acaggctttc actttctcgc 4920
caacttacaa ggcctttcta agtaaacagt acatgaacct ttaccccgtt gctcggcaac 4980
ggcctggtct gtgccaagtg tttgctgacg caacccccac tggctggggc ttggccatag 5040
gccatcagcg catgcgtgga acctttgtgg ctcctctgcc gatccatact gcggaactcc 5100
tagccgcttg ttttgctcgc agccggtctg gagcaaagct cataggaact gacaattctg 5160
tcgtcctctc gcggaaatat acatcgtttc gatctacgta tgatcttttt ccctctgcca 5220
aaaattatgg ggacatcatg aagccccttg agcatctgac ttctggctaa taaaggaaat 5280
ttattttcat tgcaatagtg tgttggaatt ttttgtgtct ctcactcgga aggaattctg 5340
cattaatgaa tcggccaacg cgcggggaga ggcggtttgc gtattgggcg ctcttccgct 5400
tcctcgctca ctgactcgct gcgctcggtc gttcggctgc ggcgagcggt atcagctcac 5460
tcaaaggcgg taatacggtt atccacagaa tcaggggata acgcaggaaa gaacatgtga 5520
gcaaaaggcc agcaaaaggc caggaaccgt aaaaaggccg cgttgctggc gtttttccat 5580
aggctccgcc cccctgacga gcatcacaaa aatcgacgct caagtcagag gtggcgaaac 5640
ccgacaggac tataaagata ccaggcgttt ccccctggaa gctccctcgt gcgctctcct 5700
gttccgaccc tgccgcttac cggatacctg tccgcctttc tcccttcggg aagcgtggcg 5760
ctttctcata gctcacgctg taggtatctc agttcggtgt aggtcgttcg ctccaagctg 5820
ggctgtgtgc acgaaccccc cgttcagccc gaccgctgcg ccttatccgg taactatcgt 5880
cttgagtcca acccggtaag acacgactta tcgccactgg cagcagccac tggtaacagg 5940
attagcagag cgaggtatgt aggcggtgct acagagttct tgaagtggtg gcctaactac 6000
ggctacacta gaagaacagt atttggtatc tgcgctctgc tgaagccagt taccttcgga 6060
aaaagagttg gtagctcttg atccggcaaa caaaccaccg ctggtagcgg tggttttttt 6120
gtttgcaagc agcagattac gcgcagaaaa aaaggatctc aagaagatcc tttgatcttt 6180
tctacggggt ctgacgctca gtggaacgaa aactcacgtt aagggatttt ggtcatgaga 6240
ttatcaaaaa ggatcttcac ctagatcctt ttaaattaaa aatgaagttt taaatcaatc 6300
taaagtatat atgagtaaac ttggtctgac agttaccaat gcttaatcag tgaggcacct 6360
atctcagcga tctgtctatt tcgttcatcc atagttgcct gactc 6405

<210> SEQ ID NO 29
<211> LENGTH: 6750
<212> TYPE: DNA
<213> ORGANISM: Artificial Sequence
<220> FEATURE:
<223> OTHER INFORMATION: Synthetic Construct

<400> SEQUENCE: 29
ggcgtaatgc tctgccagtg ttacaaccaa ttaaccaatt ctgattagaa aaactcatcg 60
agcatcaaat gaaactgcaa tttattcata tcaggattat caataccata tttttgaaaa 120
agccgtttct gtaatgaagg agaaaactca ccgaggcagt tccataggat ggcaagatcc 180
tggtatcggt ctgcgattcc gactcgtcca acatcaatac aacctattaa tttcccctcg 240
tcaaaaataa ggttatcaag tgagaaatca ccatgagtga cgactgaatc cggtgagaat 300
ggcaaaagct tatgcatttc tttccagact tgttcaacag gccagccatt acgctcgtca 360
tcaaaatcac tcgcatcaac caaaccgtta ttcattcgtg attgcgcctg agcgagacga 420

-continued

```
aatacgcgat cgctgttaaa aggacaatta caaacaggaa tcaaatgcaa ccggcgcagg    480
aacactgcca gcgcatcaac aatattttca cctgaatcag gatattcttc taatacctgg    540
aatgctgttt tcccggggat cgcagtggtg agtaaccatg catcatcagg agtacggata    600
aaatgcttga tggtcggaag aggcataaat tccgtcagcc agtttagtct gaccatctca    660
tctgtaacat cattggcaac gctacctttg ccatgtttca gaaacaactc tggcgcatcg    720
ggcttcccat acaatcgata gattgtcgca cctgattgcc cgacattatc gcgagcccat    780
ttatacccat ataaatcagc atccatgttg gaatttaatc gcggcctcga gcaagacgtt    840
tcccgttgaa tatggctcat aacacccctt gtattactgt ttatgtaagc agacaggtcg    900
acaatattgg ctattggcca ttgcatacgt tgtatctata tcataatatg tacatttata    960
ttggctcatg tccaatatga ccgccatgtt gacattgatt attgactagt tattaatagt   1020
aatcaattac ggggtcatta gttcatagcc catatatgga gttccgcgtt acataactta   1080
cggtaaatgg cccgcctggc tgaccgccca acgacccccg cccattgacg tcaataatga   1140
cgtatgttcc catagtaacg ccaataggga ctttccattg acgtcaatgg gtggagtatt   1200
tacggtaaac tgcccacttg gcagtacatc aagtgtatca tatgccaagt ccgcccccta   1260
ttgacgtcaa tgacggtaaa tggcccgcct ggcattatgc ccagtacatg accttacggg   1320
actttcctac ttggcagtac atctacgtat tagtcatcgc tattaccatg gtgatgcggt   1380
tttggcagta caccaatggg cgtggatagc ggtttgactc acggggattt ccaagtctcc   1440
accccattga cgtcaatggg agtttgtttt ggcaccaaaa tcaacgggac tttccaaaat   1500
gtcgtaataa ccccgccccg ttgacgcaaa tgggcggtag gcgtgtacgg tgggaggtct   1560
atataagcag agctcgttta gtgaaccgtc agatcgcctg gagacgccat ccacgctgtt   1620
ttgacctcca tagaagacac cgggaccgat ccagcctccg cggccgggaa cggtgcattg   1680
gaacgcggat tccccgtgcc aagagtgact caccgtccgg atctcagcaa gcaggtatgt   1740
actctccagg gtgggcctgg cttccccagt caagactcca gggatttgag ggacgctgtg   1800
ggctcttctc ttacatgtac cttttgcttg cctcaaccct gactatcttc caggtcagga   1860
tcccagagtc aggggtctgt attttcctgc tggtggctcc agttcaggaa cagtaaaccc   1920
tgctccgaat attgcctctc acatctcgtc aatctccgcg aggactgggg accctgtgac   1980
gaacatggct agcattgtgg gaggctggga gtgcgagaag cattcccaac cctggcaggt   2040
gcttgtggcc tctcgtggca gggcagtctg cggcggtgtt ctggtgcacc cccagtgggt   2100
cctcacagct gcccactgca tcaggaacaa aagcgtgatc ttgctgggtc ggcacagctt   2160
gtttcatcct gaagacacag gccaggtatt tcaggtcagc cacagcttcc cacacccgct   2220
ctacgatatg agcctcctga agaatcgatt cctcaggcca ggtgatgact ccagccacga   2280
cctcatgctg ctccgcctgt cagagcctgc cgagctcacg gatgctgtga aggtcatgga   2340
cctgcccacc caggagccag cactggggac cacctgctac gcctcaggct ggggcagcat   2400
tgaaccagag gagttcttga ccccaaagaa acttcagtgt gtggacctcc atgttatttc   2460
caatgacgtg tgtgcgcaag ttcaccctca gaaggtgacc aagttcatgc tgtgtgctgg   2520
acgctggaca gggggcaaaa gcacctgctc gggtgattct gggggcccac ttgtctgtaa   2580
tggtgtgctt caaggtatca cgtcatgggg cagtgaacca tgtgccctgc ccgaaaggcc   2640
ttccctgtac accaaggtgg tgcattaccg gaagtggatc aaggacacca tcgtggccaa   2700
ccccggatcc cagaccctga actttgatct gctgaaactg gcaggcgatg tggaaagcaa   2760
```

```
cccaggccca atggcaagcg cgcgccgccc gcgctggctg tgcgctgggg cgctggtgct   2820
ggcgggtggc ttctttctcc tcggcttcct cttcgggtgg tttataaaat cctccaatga   2880
agctactaac attactccaa agcataatat gaaagcattt ttggatgaat tgaaagctga   2940
gaacatcaag aagttcttat ataattttac acagatacca catttagcag gaacagaaca   3000
aaactttcag cttgcaaagc aaattcaatc ccagtggaaa gaatttggcc tggattctgt   3060
tgagctggca cattatgatg tcctgttgtc ctacccaaat aagactcatc ccaactacat   3120
ctcaataatt aatgaagatg gaaatgagat tttcaacaca tcattatttg aaccacctcc   3180
tccaggatat gaaaatgttt cggatattgt accacctttc agtgctttct ctcctcaagg   3240
aatgccagag ggcgatctag tgtatgttaa ctatgcacga actgaagact tctttaaatt   3300
ggaacgggac atgaaaatca attgctctgg gaaaattgta attgccagat atgggaaagt   3360
tttcagagga aataaggtta aaaatgccca gctggcaggg gccaaaggag tcattctcta   3420
ctccgaccct gctgactact ttgctcctgg ggtgaagtcc tatccagatg gttggaatct   3480
tcctggaggt ggtgtccagc gtggaaatat cctaaatctg aatggtgcag gagaccctct   3540
cacaccaggt tacccagcaa atgaatatgc ttataggcgt ggaattgcag aggctgttgg   3600
tcttccaagt attcctgttc atccaattgg atactatgat gcacagaagc tcctagaaaa   3660
aatgggtggc tcagcaccac cagatagcag ctggagagga agtctcaaag tgccctacaa   3720
tgttggacct ggctttactg gaaacttttc tacacaaaaa gtcaagatgc acatccactc   3780
taccaatgaa gtgacaagaa tttacaatgt gataggtact ctcagaggag cagtggaacc   3840
agacagatat gtcattctgg gaggtcaccg ggactcatgg gtgtttggtg gtattgaccc   3900
tcagagtgga gcagctgttg ttcatgaaat tgtgaggagc tttggaacac tgaaaaagga   3960
agggtggaga cctagaagaa caattttgtt tgcaagctgg gatgcagaag aatttggtct   4020
tcttggttct actgagtggg cagaggagaa ttcaagactc cttcaagagc gtggcgtggc   4080
ttatattaat gctgactcat ctatagaagg aaactacact ctgagagttg attgtacacc   4140
gctgatgtac agcttggtac acaacctaac aaaagagctg aaaagccctg atgaaggctt   4200
tgaaggcaaa tctctttatg aaagttggac taaaaaaagt ccttccccag agttcagtgg   4260
catgcccagg ataagcaaat tgggatctgg aaatgatttt gaggtgttct tccaacgact   4320
tggaattgct tcaggcagag cacggtatac taaaaattgg gaaacaaaca aattcagcgg   4380
ctatccactg tatcacagtg tctatgaaac atatgagttg gtggaaaagt tttatgatcc   4440
aatgtttaaa tatcacctca ctgtggccca ggttcgagga gggatggtgt ttgagctggc   4500
caattccata gtgctccctt ttgattgtcg agattatgct gtagttttaa gaaagtatgc   4560
tgacaaaatc tacagtattt ctatgaaaca tccacaggaa atgaagacat acagtgtatc   4620
atttgattca ctttttctg cagtaaagaa ttttacagaa attgcttcca agttcagtga   4680
gagactccag gactttgaca aaagcaaccc aatagtatta agaatgatga atgatcaact   4740
catgtttctg gaaagagcat ttattgatcc attagggtta ccagacaggc ctttttatag   4800
gcatgtcatc tatgctccaa gcagccacaa caagtatgca ggggagtcat tcccaggaat   4860
ttatgatgct ctgtttgata ttgaaagcaa agtggaccct tccaaggcct ggggagaagt   4920
gaagagacag atttatgttg cagccttcac agtgcaggca gctgcagaga ctttgagtga   4980
agtagcctaa agatctgggc cctaacaaaa caaaaagatg gggttattcc ctaaacttca   5040
tgggttacgt aattggaagt tgggggacat tgccacaaga tcatattgta caaaagatca   5100
aacactgttt tagaaaactt cctgtaaaca ggcctattga ttggaaagta tgtcaaagga   5160
```

ttgtgggtct tttgggcttt gctgctccat ttacacaatg tggatatcct gccttaatgc 5220
ctttgtatgc atgtatacaa gctaaacagg ctttcacttt ctcgccaact tacaaggcct 5280
ttctaagtaa acagtacatg aacctttacc ccgttgctcg gcaacggcct ggtctgtgcc 5340
aagtgtttgc tgacgcaacc cccactggct ggggcttggc cataggccat cagcgcatgc 5400
gtggaacctt tgtggctcct ctgccgatcc atactgcgga actcctagcc gcttgttttg 5460
ctcgcagccg gtctggagca aagctcatag gaactgacaa ttctgtcgtc ctctcgcgga 5520
aatatacatc gtttcgatct acgtatgatc tttttccctc tgccaaaaat tatggggaca 5580
tcatgaagcc ccttgagcat ctgacttctg gctaataaag gaaatttatt ttcattgcaa 5640
tagtgtgttg gaattttttg tgtctctcac tcggaaggaa ttctgcatta atgaatcggc 5700
caacgcgcgg ggagaggcgg tttgcgtatt gggcgctctt ccgcttcctc gctcactgac 5760
tcgctgcgct cggtcgttcg gctgcggcga gcggtatcag ctcactcaaa ggcggtaata 5820
cggttatcca cagaatcagg ggataacgca ggaaagaaca tgtgagcaaa aggccagcaa 5880
aaggccagga accgtaaaaa ggccgcgttg ctggcgtttt tccataggct ccgcccccct 5940
gacgagcatc acaaaaatcg acgctcaagt cagaggtggc gaaacccgac aggactataa 6000
agataccagg cgtttccccc tggaagctcc ctcgtgcgct ctcctgttcc gaccctgccg 6060
cttaccggat acctgtccgc ctttctccct tcgggaagcg tggcgctttc tcatagctca 6120
cgctgtaggt atctcagttc ggtgtaggtc gttcgctcca agctgggctg tgtgcacgaa 6180
ccccccgttc agcccgaccg ctgcgcctta tccggtaact atcgtcttga gtccaacccg 6240
gtaagacacg acttatcgcc actggcagca gccactggta acaggattag cagagcgagg 6300
tatgtaggcg gtgctacaga gttcttgaag tggtggccta actacggcta cactagaaga 6360
acagtatttg gtatctgcgc tctgctgaag ccagttacct tcggaaaaag agttggtagc 6420
tcttgatccg gcaaacaaac caccgctggt agcggtggtt tttttgtttg caagcagcag 6480
attacgcgca gaaaaaaagg atctcaagaa gatcctttga tcttttctac ggggtctgac 6540
gctcagtgga acgaaaactc acgttaaggg attttggtca tgagattatc aaaaaggatc 6600
ttcacctaga tccttttaaa ttaaaaatga agttttaaat caatctaaag tatatatgag 6660
taaacttggt ctgacagtta ccaatgctta atcagtgagg cacctatctc agcgatctgt 6720
ctatttcgtt catccatagt tgcctgactc 6750

<210> SEQ ID NO 30
<211> LENGTH: 6908
<212> TYPE: DNA
<213> ORGANISM: Artificial Sequence
<220> FEATURE:
<223> OTHER INFORMATION: Synthetic Construct

<400> SEQUENCE: 30
ggcgtaatgc tctgccagtg ttacaaccaa ttaaccaatt ctgattagaa aaactcatcg 60
agcatcaaat gaaactgcaa tttattcata tcaggattat caataccata tttttgaaaa 120
agccgtttct gtaatgaagg agaaaactca ccgaggcagt tccataggat ggcaagatcc 180
tggtatcggt ctgcgattcc gactcgtcca acatcaatac aacctattaa tttcccctcg 240
tcaaaaataa ggttatcaag tgagaaatca ccatgagtga cgactgaatc cggtgagaat 300
ggcaaaagct tatgcatttc tttccagact tgttcaacag gccagccatt acgctcgtca 360
tcaaaatcac tcgcatcaac caaaccgtta ttcattcgtg attgcgcctg agcgagacga 420
aatacgcgat cgctgttaaa aggacaatta caaacaggaa tcaaatgcaa ccggcgcagg 480
aacactgcca gcgcatcaac aatattttca cctgaatcag gatattcttc taatacctgg 540
aatgctgttt tcccggggat cgcagtggtg agtaaccatg catcatcagg agtacggata 600
aaatgcttga tggtcggaag aggcataaat tccgtcagcc agtttagtct gaccatctca 660
tctgtaacat cattggcaac gctacctttg ccatgtttca gaaacaactc tggcgcatcg 720
ggcttcccat acaatcgata gattgtcgca cctgattgcc cgacattatc gcgagcccat 780
ttatacccat ataaatcagc atccatgttg gaatttaatc gcggcctcga gcaagacgtt 840
tcccgttgaa tatggctcat aacacccctt gtattactgt ttatgtaagc agacaggtcg 900
acaatattgg ctattggcca ttgcatacgt tgtatctata tcataatatg tacatttata 960
ttggctcatg tccaatatga ccgccatgtt gacattgatt attgactagt tattaatagt 1020
aatcaattac ggggtcatta gttcatagcc catatatgga gttccgcgtt acataactta 1080
cggtaaatgg cccgcctggc tgaccgccca acgacccccg cccattgacg tcaataatga 1140
cgtatgttcc catagtaacg ccaataggga ctttccattg acgtcaatgg gtggagtatt 1200
tacggtaaac tgcccacttg gcagtacatc aagtgtatca tatgccaagt ccgcccccta 1260
ttgacgtcaa tgacggtaaa tggcccgcct ggcattatgc ccagtacatg accttacggg 1320
actttcctac ttggcagtac atctacgtat tagtcatcgc tattaccatg gtgatgcggt 1380
tttggcagta caccaatggg cgtggatagc ggtttgactc acggggattt ccaagtctcc 1440
accccattga cgtcaatggg agtttgtttt ggcaccaaaa tcaacgggac tttccaaaat 1500
gtcgtaataa ccccgccccg ttgacgcaaa tgggcggtag gcgtgtacgg tgggaggtct 1560
atataagcag agctcgttta gtgaaccgtc agatcgcctg gagacgccat ccacgctgtt 1620
ttgacctcca tagaagacac cgggaccgat ccagcctccg cggccgggaa cggtgcattg 1680
gaacgcggat tccccgtgcc aagagtgact caccgtccgg atctcagcaa gcaggtatgt 1740
actctccagg gtgggcctgg cttccccagt caagactcca gggatttgag ggacgctgtg 1800
ggctcttctc ttacatgtac cttttgcttg cctcaaccct gactatcttc caggtcagga 1860
tcccagagtc aggggtctgt attttcctgc tggtggctcc agttcaggaa cagtaaaccc 1920
tgctccgaat attgcctctc acatctcgtc aatctccgcg aggactgggg accctgtgac 1980
gaacatggct agcgcgcgcc gcccgcgctg gctgtgcgct ggggcgctgg tgctggcggg 2040
tggcttcttt ctcctcggct tcctcttcgg gtggtttata aaatcctcca atgaagctac 2100
taacattact ccaaagcata atatgaaagc atttttggat gaattgaaag ctgagaacat 2160
caagaagttc ttatataatt ttacacagat accacattta gcaggaacag aacaaaactt 2220
tcagcttgca aagcaaattc aatcccagtg gaaagaattt ggcctggatt ctgttgagct 2280
ggcacattat gatgtcctgt tgtcctaccc aaataagact catcccaact acatctcaat 2340
aattaatgaa gatggaaatg agattttcaa cacatcatta tttgaaccac ctcctccagg 2400
atatgaaaat gtttcggata ttgtaccacc tttcagtgct ttctctcctc aaggaatgcc 2460
agagggcgat ctagtgtatg ttaactatgc acgaactgaa gacttcttta aattggaacg 2520
ggacatgaaa atcaattgct ctgggaaaat tgtaattgcc agatatggga aagttttcag 2580
aggaaataag gttaaaaatg cccagctggc aggggccaaa ggagtcattc tctactccga 2640
ccctgctgac tactttgctc ctggggtgaa gtcctatcca gatggttgga atcttcctgg 2700
aggtggtgtc cagcgtggaa atatcctaaa tctgaatggt gcaggagacc ctctcacacc 2760
aggttaccca gcaaatgaat atgcttatag gcgtggaatt gcagaggctg ttggtcttcc 2820
aagtattcct gttcatccaa ttggatacta tgatgcacag aagctcctag aaaaaatggg 2880
tggctcagca ccaccagata gcagctggag aggaagtctc aaagtgccct acaatgttgg 2940
acctggcttt actggaaact tttctacaca aaaagtcaag atgcacatcc actctaccaa 3000
tgaagtgaca agaatttaca atgtgatagg tactctcaga ggagcagtgg aaccagacag 3060
atatgtcatt ctgggaggtc accgggactc atgggtgttt ggtggtattg accctcagag 3120
tggagcagct gttgttcatg aaattgtgag gagctttgga acactgaaaa aggaagggtg 3180
gagacctaga agaacaattt tgtttgcaag ctgggatgca gaagaatttg gtcttcttgg 3240
ttctactgag tgggcagagg agaattcaag actccttcaa gagcgtggcg tggcttatat 3300
taatgctgac tcatctatag aaggaaacta cactctgaga gttgattgta caccgctgat 3360
gtacagcttg gtacacaacc taacaaaaga gctgaaaagc cctgatgaag gctttgaagg 3420
caaatctctt tatgaaagtt ggactaaaaa aagtccttcc ccagagttca gtggcatgcc 3480
caggataagc aaattgggat ctggaaatga ttttgaggtg ttcttccaac gacttggaat 3540
tgcttcaggc agagcacggt atactaaaaa ttgggaaaca aacaaattca gcggctatcc 3600
actgtatcac agtgtctatg aaacatatga gttggtggaa aagttttatg atccaatgtt 3660
taaatatcac ctcactgtgg cccaggttcg aggagggatg gtgtttgagc tggccaattc 3720
catagtgctc ccttttgatt gtcgagatta tgctgtagtt ttaagaaagt atgctgacaa 3780
aatctacagt atttctatga aacatccaca ggaaatgaag acatacagtg tatcatttga 3840
ttcacttttt tctgcagtaa agaattttac agaaattgct tccaagttca gtgagagact 3900
ccaggacttt gacaaaagca acccaatagt attaagaatg atgaatgatc aactcatgtt 3960
tctggaaaga gcatttattg atccattagg gttaccagac aggccttttt ataggcatgt 4020
catctatgct ccaagcagcc acaacaagta tgcaggggag tcattcccag gaatttatga 4080
tgctctgttt gatattgaaa gcaaagtgga cccttccaag gcctggggag aagtgaagag 4140
acagatttat gttgcagcct tcacagtgca ggcagctgca gagactttga gtgaagtagc 4200
ctaaagatct gaccccctaa cgttactggc cgaagccgct tggaataagg ccggtgtgcg 4260
tttgtctata tgttattttc caccatattg ccgtcttttg gcaatgtgag ggcccggaaa 4320
cctggccctg tcttcttgac gagcattcct aggggtcttt cccctctcgc caaaggaatg 4380
caaggtctgt tgaatgtcgt gaaggaagca gttcctctgg aagcttcttg aagacaaaca 4440
acgtctgtag cgaccctttg caggcagcgg aaccccccac ctggcgacag gtgcctctgc 4500
ggccaaaagc cacgtgtata agatacacct gcaaaggcgg cacaacccca gtgccacgtt 4560
gtgagttgga tagttgtgga aagagtcaaa tggctctcct caagcgtatt caacaagggg 4620
ctgaaggatg cccagaaggt accccattgt atgggatctg atctggggcc tcggtgcaca 4680
tgctttacat gtgtttagtc gaggttaaaa aacgtctagg ccccccgaac cacggggacg 4740
tggttttcct ttgaaaaaca cgatgataat atggccagca aggctgtgct gcttgccctg 4800
ttgatggcag gcttggccct gcagccaggc actgccctgc tgtgctactc ctgcaaagcc 4860
caggtgagca acgaggactg cctgcaggtg gagaactgca cccagctggg ggagcagtgc 4920
tggaccgcgc gcatccgcgc agttggcctc ctgaccgtca tcagcaaagg ctgcagcttg 4980
aactgcgtgg atgactcaca ggactactac gtgggcaaga agaacatcac gtgctgtgac 5040
accgacttgt gcaacgccag cggggcccat gccctgcagc cggctgccgc catccttgcg 5100
ctgctccctg cactcggcct gctgctctgg ggacccggcc agctataggg atctgggccc 5160
taacaaaaca aaaagatggg gttattccct aaacttcatg ggttacgtaa ttggaagttg 5220
ggggacattg ccacaagatc atattgtaca aaagatcaaa cactgtttta gaaaacttcc 5280
tgtaaacagg cctattgatt ggaaagtatg tcaaaggatt gtgggtcttt tgggctttgc 5340
tgctccattt acacaatgtg gatatcctgc cttaatgcct ttgtatgcat gtatacaagc 5400
taaacaggct ttcactttct cgccaactta caaggccttt ctaagtaaac agtacatgaa 5460
cctttacccc gttgctcggc aacggcctgg tctgtgccaa gtgtttgctg acgcaacccc 5520
cactggctgg ggcttggcca taggccatca gcgcatgcgt ggaacctttg tggctcctct 5580
gccgatccat actgcggaac tcctagccgc ttgttttgct cgcagccggt ctggagcaaa 5640
gctcatagga actgacaatt ctgtcgtcct ctcgcggaaa tatacatcgt ttcgatctac 5700
gtatgatctt tttccctctg ccaaaaatta tggggacatc atgaagcccc ttgagcatct 5760
gacttctggc taataaagga aatttatttt cattgcaata gtgtgttgga atttttgtg 5820 tctctcactc ggaaggaatt ctgcattaat gaatcggcca acgcgcgggg agaggcggtt 5880
tgcgtattgg gcgctcttcc gcttcctcgc tcactgactc gctgcgctcg gtcgttcggc 5940
tgcggcgagc ggtatcagct cactcaaagg cggtaatacg gttatccaca gaatcagggg 6000
ataacgcagg aaagaacatg tgagcaaaag gccagcaaaa ggccaggaac cgtaaaaagg 6060
ccgcgttgct ggcgtttttc cataggctcc gcccccctga cgagcatcac aaaaatcgac 6120
gctcaagtca gaggtggcga aacccgacag gactataaag ataccaggcg tttccccctg 6180
gaagctccct cgtgcgctct cctgttccga ccctgccgct taccggatac ctgtccgcct 6240
ttctcccttc gggaagcgtg gcgctttctc atagctcacg ctgtaggtat ctcagttcgg 6300
tgtaggtcgt tcgctccaag ctgggctgtg tgcacgaacc ccccgttcag cccgaccgct 6360
gcgccttatc cggtaactat cgtcttgagt ccaacccggt aagacacgac ttatcgccac 6420
tggcagcagc cactggtaac aggattagca gagcgaggta tgtaggcggt gctacagagt 6480
tcttgaagtg gtggcctaac tacggctaca ctagaagaac agtatttggt atctgcgctc 6540
tgctgaagcc agttaccttc ggaaaaagag ttggtagctc ttgatccggc aaacaaacca 6600
ccgctggtag cggtggtttt tttgtttgca agcagcagat tacgcgcaga aaaaaaggat 6660
ctcaagaaga tcctttgatc ttttctacgg ggtctgacgc tcagtggaac gaaaactcac 6720
gttaagggat tttggtcatg agattatcaa aaaggatctt cacctagatc cttttaaatt 6780
aaaaatgaag ttttaaatca atctaaagta tatatgagta aacttggtct gacagttacc 6840
aatgcttaat cagtgaggca cctatctcag cgatctgtct atttcgttca tccatagttg 6900
cctgactc 6908

<210> SEQ ID NO 31
<211> LENGTH: 6914
<212> TYPE: DNA
<213> ORGANISM: Artificial Sequence
<220> FEATURE:
<223> OTHER INFORMATION: Synthetic Construct

<400> SEQUENCE: 31
ggcgtaatgc tctgccagtg ttacaaccaa ttaaccaatt ctgattagaa aaactcatcg 60
agcatcaaat gaaactgcaa tttattcata tcaggattat caataccata tttttgaaaa 120
agccgtttct gtaatgaagg agaaaactca ccgaggcagt tccataggat ggcaagatcc 180
tggtatcggt ctgcgattcc gactcgtcca acatcaatac aacctattaa tttcccctcg 240
tcaaaaataa ggttatcaag tgagaaatca ccatgagtga cgactgaatc cggtgagaat 300
ggcaaaagct tatgcatttc tttccagact tgttcaacag gccagccatt acgctcgtca 360
tcaaaatcac tcgcatcaac caaaccgtta ttcattcgtg attgcgcctg agcgagacga 420
aatacgcgat cgctgttaaa aggacaatta caaacaggaa tcaaatgcaa ccggcgcagg 480
aacactgcca gcgcatcaac aatattttca cctgaatcag gatattcttc taatacctgg 540
aatgctgttt tcccggggat cgcagtggtg agtaaccatg catcatcagg agtacggata 600
aaatgcttga tggtcggaag aggcataaat tccgtcagcc agtttagtct gaccatctca 660
tctgtaacat cattggcaac gctacctttg ccatgtttca gaaacaactc tggcgcatcg 720
ggcttcccat acaatcgata gattgtcgca cctgattgcc cgacattatc gcgagcccat 780
ttatacccat ataaatcagc atccatgttg gaatttaatc gcggcctcga gcaagacgtt 840
tcccgttgaa tatggctcat aacacccctt gtattactgt ttatgtaagc agacaggtcg 900
acaatattgg ctattggcca ttgcatacgt tgtatctata tcataatatg tacatttata 960
ttggctcatg tccaatatga ccgccatgtt gacattgatt attgactagt tattaatagt 1020
aatcaattac ggggtcatta gttcatagcc catatatgga gttccgcgtt acataactta 1080
cggtaaatgg cccgcctggc tgaccgccca acgacccccg cccattgacg tcaataatga 1140
cgtatgttcc catagtaacg ccaataggga ctttccattg acgtcaatgg gtggagtatt 1200
tacggtaaac tgcccacttg gcagtacatc aagtgtatca tatgccaagt ccgcccccta 1260
ttgacgtcaa tgacggtaaa tggcccgcct ggcattatgc ccagtacatg accttacggg 1320
actttcctac ttggcagtac atctacgtat tagtcatcgc tattaccatg gtgatgcggt 1380
tttggcagta caccaatggg cgtggatagc ggtttgactc acggggattt ccaagtctcc 1440
accccattga cgtcaatggg agtttgtttt ggcaccaaaa tcaacgggac tttccaaaat 1500
gtcgtaataa ccccgccccg ttgacgcaaa tgggcggtag gcgtgtacgg tgggaggtct 1560
atataagcag agctcgttta gtgaaccgtc agatcgcctg gagacgccat ccacgctgtt 1620
ttgacctcca tagaagacac cgggaccgat ccagcctccg cggccgggaa cggtgcattg 1680
gaacgcggat tccccgtgcc aagagtgact caccgtccgg atctcagcaa gcaggtatgt 1740
actctccagg gtgggcctgg cttccccagt caagactcca gggatttgag ggacgctgtg 1800
ggctcttctc ttacatgtac cttttgcttg cctcaaccct gactatcttc caggtcagga 1860
tcccagagtc aggggtctgt attttcctgc tggtggctcc agttcaggaa cagtaaaccc 1920
tgctccgaat attgcctctc acatctcgtc aatctccgcg aggactgggg accctgtgac 1980
gaacatggct agcaaggctg tgctgcttgc cctgttgatg gcaggcttgg ccctgcagcc 2040
aggcactgcc ctgctgtgct actcctgcaa agcccaggtg agcaacgagg actgcctgca 2100
ggtggagaac tgcacccagc tgggggagca gtgctggacc gcgcgcatcc gcgcagttgg 2160
cctcctgacc gtcatcagca aaggctgcag cttgaactgc gtggatgact cacaggacta 2220
ctacgtgggc aagaagaaca tcacgtgctg tgacaccgac ttgtgcaacg ccagcggggc 2280
ccatgccctg cagccggctg ccgccatcct tgcgctgctc cctgcactcg gcctgctgct 2340
ctggggaccc ggccagctat agagatctga ccccctaacg ttactggccg aagccgcttg 2400
gaataaggcc ggtgtgcgtt tgtctatatg ttattttcca ccatattgcc gtcttttggc 2460
aatgtgaggg cccggaaacc tggccctgtc ttcttgacga gcattcctag gggtctttcc 2520
cctctcgcca aaggaatgca aggtctgttg aatgtcgtga aggaagcagt tcctctggaa 2580
gcttcttgaa gacaaacaac gtctgtagcg accctttgca ggcagcggaa ccccccacct 2640

```
ggcgacaggt gcctctgcgg ccaaaagcca cgtgtataag atacacctgc aaaggcggca   2700

caaccccagt gccacgttgt gagttggata gttgtggaaa gagtcaaatg gctctcctca   2760

agcgtattca acaaggggct gaaggatgcc cagaaggtac cccattgtat gggatctgat   2820

ctggggcctc ggtgcacatg ctttacatgt gtttagtcga ggttaaaaaa cgtctaggcc   2880

ccccgaacca cggggacgtg gttttccttt gaaaaacacg atgataatat ggccacaacc   2940

atggcgcgcc gcccgcgctg gctgtgcgct ggggcgctgg tgctggcggg tggcttcttt   3000

ctcctcggct tcctcttcgg gtggtttata aaatcctcca atgaagctac taacattact   3060

ccaaagcata atatgaaagc atttttggat gaattgaaag ctgagaacat caagaagttc   3120

ttatataatt ttacacagat accacattta gcaggaacag aacaaaactt tcagcttgca   3180

aagcaaattc aatcccagtg gaaagaattt ggcctggatt ctgttgagct ggcacattat   3240

gatgtcctgt tgtcctaccc aaataagact catcccaact acatctcaat aattaatgaa   3300

gatggaaatg agattttcaa cacatcatta tttgaaccac ctcctccagg atatgaaaat   3360

gtttcggata ttgtaccacc tttcagtgct ttctctcctc aaggaatgcc agagggcgat   3420

ctagtgtatg ttaactatgc acgaactgaa gacttcttta aattggaacg ggacatgaaa   3480

atcaattgct ctgggaaaat tgtaattgcc agatatggga aagttttcag aggaaataag   3540

gttaaaaatg cccagctggc aggggccaaa ggagtcattc tctactccga ccctgctgac   3600

tactttgctc ctggggtgaa gtcctatcca gatggttgga atcttcctgg aggtggtgtc   3660

cagcgtggaa atatcctaaa tctgaatggt gcaggagacc ctctcacacc aggttaccca   3720

gcaaatgaat atgcttatag gcgtggaatt gcagaggctg ttggtcttcc aagtattcct   3780

gttcatccaa ttggatacta tgatgcacag aagctcctag aaaaaatggg tggctcagca   3840

ccaccagata gcagctggag aggaagtctc aaagtgccct acaatgttgg acctggcttt   3900

actggaaact tttctacaca aaaagtcaag atgcacatcc actctaccaa tgaagtgaca   3960

agaatttaca atgtgatagg tactctcaga ggagcagtgg aaccagacag atatgtcatt   4020

ctgggaggtc accgggactc atgggtgttt ggtggtattg accctcagag tggagcagct   4080

gttgttcatg aaattgtgag gagctttgga acactgaaaa aggaagggtg gagacctaga   4140

agaacaattt tgtttgcaag ctgggatgca gaagaatttg gtcttcttgg ttctactgag   4200

tgggcagagg agaattcaag actccttcaa gagcgtggcg tggcttatat taatgctgac   4260

tcatctatag aaggaaacta cactctgaga gttgattgta caccgctgat gtacagcttg   4320

gtacacaacc taacaaaaga gctgaaaagc cctgatgaag gctttgaagg caaatctctt   4380

tatgaaagtt ggactaaaaa aagtccttcc ccagagttca gtggcatgcc caggataagc   4440

aaattgggat ctggaaatga ttttgaggtg ttcttccaac gacttggaat tgcttcaggc   4500

agagcacggt atactaaaaa ttgggaaaca aacaaattca gcggctatcc actgtatcac   4560

agtgtctatg aaacatatga gttggtggaa aagttttatg atccaatgtt taaatatcac   4620

ctcactgtgg cccaggttcg aggagggatg gtgtttgagc tggccaattc catagtgctc   4680

ccttttgatt gtcgagatta tgctgtagtt ttaagaaagt atgctgacaa aatctacagt   4740

atttctatga aacatccaca ggaaatgaag acatacagtg tatcatttga ttcacttttt   4800

tctgcagtaa agaattttac agaaattgct tccaagttca gtgagagact ccaggacttt   4860

gacaaaagca acccaatagt attaagaatg atgaatgatc aactcatgtt tctggaaaga   4920

gcatttattg atccattagg gttaccagac aggccttttt ataggcatgt catctatgct   4980

ccaagcagcc acaacaagta tgcaggggag tcattcccag gaatttatga tgctctgttt   5040
```

gatattgaaa gcaaagtgga cccttccaag gcctggggag aagtgaagag acagatttat 5100
gttgcagcct tcacagtgca ggcagctgca gagactttga gtgaagtagc ctaaagatct 5160
gggccctaac aaaacaaaaa gatggggtta ttccctaaac ttcatgggtt acgtaattgg 5220
aagttggggg acattgccac aagatcatat tgtacaaaag atcaaacact gttttagaaa 5280
acttcctgta aacaggccta ttgattggaa agtatgtcaa aggattgtgg gtcttttggg 5340
ctttgctgct ccatttacac aatgtggata tcctgcctta atgcctttgt atgcatgtat 5400
acaagctaaa caggctttca ctttctcgcc aacttacaag gcctttctaa gtaaacagta 5460
catgaacctt taccccgttg ctcggcaacg gcctggtctg tgccaagtgt ttgctgacgc 5520
aacccccact ggctggggct tggccatagg ccatcagcgc atgcgtggaa cctttgtggc 5580
tcctctgccg atccatactg cggaactcct agccgcttgt tttgctcgca gccggtctgg 5640
agcaaagctc ataggaactg acaattctgt cgtcctctcg cggaaatata catcgtttcg 5700
atctacgtat gatctttttc cctctgccaa aaattatggg gacatcatga agccccttga 5760
gcatctgact tctggctaat aaaggaaatt tattttcatt gcaatagtgt gttggaattt 5820
tttgtgtctc tcactcggaa ggaattctgc attaatgaat cggccaacgc gcggggagag 5880
gcggtttgcg tattgggcgc tcttccgctt cctcgctcac tgactcgctg cgctcggtcg 5940
ttcggctgcg gcgagcggta tcagctcact caaaggcggt aatacggtta tccacagaat 6000
caggggataa cgcaggaaag aacatgtgag caaaaggcca gcaaaaggcc aggaaccgta 6060
aaaaggccgc gttgctggcg tttttccata ggctccgccc ccctgacgag catcacaaaa 6120
atcgacgctc aagtcagagg tggcgaaacc cgacaggact ataaagatac caggcgtttc 6180
cccctggaag ctccctcgtg cgctctcctg ttccgaccct gccgcttacc ggatacctgt 6240
ccgcctttct cccttcggga agcgtggcgc tttctcatag ctcacgctgt aggtatctca 6300
gttcggtgta ggtcgttcgc tccaagctgg gctgtgtgca cgaacccccc gttcagcccg 6360
accgctgcgc cttatccggt aactatcgtc ttgagtccaa cccggtaaga cacgacttat 6420
cgccactggc agcagccact ggtaacagga ttagcagagc gaggtatgta ggcggtgcta 6480
cagagttctt gaagtggtgg cctaactacg gctacactag aagaacagta tttggtatct 6540
gcgctctgct gaagccagtt accttcggaa aaagagttgg tagctcttga tccggcaaac 6600
aaaccaccgc tggtagcggt ggtttttttg tttgcaagca gcagattacg cgcagaaaaa 6660
aaggatctca agaagatcct ttgatctttt ctacggggtc tgacgctcag tggaacgaaa 6720
actcacgtta agggattttg gtcatgagat tatcaaaaag gatcttcacc tagatccttt 6780
taaattaaaa atgaagtttt aaatcaatct aaagtatata tgagtaaact tggtctgaca 6840
gttaccaatg cttaatcagt gaggcaccta tctcagcgat ctgtctattt cgttcatcca 6900
tagttgcctg actc 6914

<210> SEQ ID NO 32
<211> LENGTH: 5411
<212> TYPE: DNA
<213> ORGANISM: Artificial Sequence
<220> FEATURE:
<223> OTHER INFORMATION: Synthetic Construct

<400> SEQUENCE: 32
ggcgtaatgc tctgccagtg ttacaaccaa ttaaccaatt ctgattagaa aaactcatcg 60
agcatcaaat gaaactgcaa tttattcata tcaggattat caataccata tttttgaaaa 120

-continued

```
agccgtttct gtaatgaagg agaaaactca ccgaggcagt tccataggat ggcaagatcc    180
tggtatcggt ctgcgattcc gactcgtcca acatcaatac aacctattaa tttcccctcg    240
tcaaaaataa ggttatcaag tgagaaatca ccatgagtga cgactgaatc cggtgagaat    300
ggcaaaagct tatgcatttc tttccagact tgttcaacag gccagccatt acgctcgtca    360
tcaaaatcac tcgcatcaac caaaccgtta ttcattcgtg attgcgcctg agcgagacga    420
aatacgcgat cgctgttaaa aggacaatta caaacaggaa tcaaatgcaa ccggcgcagg    480
aacactgcca gcgcatcaac aatattttca cctgaatcag gatattcttc taatacctgg    540
aatgctgttt tcccggggat cgcagtggtg agtaaccatg catcatcagg agtacggata    600
aaatgcttga tggtcggaag aggcataaat tccgtcagcc agtttagtct gaccatctca    660
tctgtaacat cattggcaac gctacctttg ccatgtttca gaaacaactc tggcgcatcg    720
ggcttcccat acaatcgata gattgtcgca cctgattgcc cgacattatc gcgagcccat    780
ttatacccat ataaatcagc atccatgttg gaatttaatc gcggcctcga gcaagacgtt    840
tcccgttgaa tatggctcat aacacccctt gtattactgt ttatgtaagc agacaggtcg    900
acaatattgg ctattggcca ttgcatacgt tgtatctata tcataatatg tacatttata    960
ttggctcatg tccaatatga ccgccatgtt gacattgatt attgactagt tattaatagt   1020
aatcaattac ggggtcatta gttcatagcc catatatgga gttccgcgtt acataactta   1080
cggtaaatgg cccgcctggc tgaccgccca acgacccccg cccattgacg tcaataatga   1140
cgtatgttcc catagtaacg ccaataggga ctttccattg acgtcaatgg gtggagtatt   1200
tacggtaaac tgcccacttg gcagtacatc aagtgtatca tatgccaagt ccgcccccta   1260
ttgacgtcaa tgacggtaaa tggcccgcct ggcattatgc ccagtacatg accttacggg   1320
actttcctac ttggcagtac atctacgtat tagtcatcgc tattaccatg gtgatgcggt   1380
tttggcagta caccaatggg cgtggatagc ggtttgactc acggggattt ccaagtctcc   1440
accccattga cgtcaatggg agtttgtttt ggcaccaaaa tcaacgggac tttccaaaat   1500
gtcgtaataa ccccgccccg ttgacgcaaa tgggcggtag gcgtgtacgg tgggaggtct   1560
atataagcag agctcgttta gtgaaccgtc agatcgcctg gagacgccat ccacgctgtt   1620
ttgacctcca tagaagacac cgggaccgat ccagcctccg cggccgggaa cggtgcattg   1680
gaacgcggat tccccgtgcc aagagtgact caccgtccgg atctcagcaa gcaggtatgt   1740
actctccagg gtgggcctgg cttccccagt caagactcca gggatttgag ggacgctgtg   1800
ggctcttctc ttacatgtac cttttgcttg cctcaaccct gactatcttc caggtcagga   1860
tcccagagtc aggggtctgt attttcctgc tggtggctcc agttcaggaa cagtaaaccc   1920
tgctccgaat attgcctctc acatctcgtc aatctccgcg aggactgggg accctgtgac   1980
gaacatggct agcaaggctg tgctgcttgc cctgttgatg gcaggcttgg ccctgcagcc   2040
aggcactgcc ctgctgtgct actcctgcaa agcccaggtg agcaacgagg actgcctgca   2100
ggtggagaac tgcacccagc tgggggagca gtgctggacc gcgcgcatcc gcgcagttgg   2160
cctcctgacc gtcatcagca aaggctgcag cttgaactgc gtggatgact cacaggacta   2220
ctacgtgggc aagaagaaca tcacgtgctg tgacaccgac ttgtgcaacg ccagcggggc   2280
ccatgccctg cagccggctg ccgccatcct tgcgctgctc cctgcactcg gcctgctgct   2340
ctggggaccc ggccagctat agagatctga ccccctaacg ttactggccg aagccgcttg   2400
gaataaggcc ggtgtgcgtt tgtctatatg ttattttcca ccatattgcc gtcttttggc   2460
aatgtgaggg cccggaaacc tggccctgtc ttcttgacga gcattcctag gggtctttcc   2520
```

cctctcgcca aaggaatgca aggtctgttg aatgtcgtga aggaagcagt tcctctggaa 2580
gcttcttgaa gacaaacaac gtctgtagcg accctttgca ggcagcggaa ccccccacct 2640
ggcgacaggt gcctctgcgg ccaaaagcca cgtgtataag atacacctgc aaaggcggca 2700
caaccccagt gccacgttgt gagttggata gttgtggaaa gagtcaaatg gctctcctca 2760
agcgtattca acaaggggct gaaggatgcc cagaaggtac cccattgtat gggatctgat 2820
ctggggcctc ggtgcacatg ctttacatgt gtttagtcga ggttaaaaaa cgtctaggcc 2880
ccccgaacca cggggacgtg gttttccttt gaaaaacacg atgataatat ggccagcatt 2940
gtgggaggct gggagtgcga gaagcattcc caaccctggc aggtgcttgt ggcctctcgt 3000
ggcagggcag tctgcggcgg tgttctggtg cacccccagt gggtcctcac agctgcccac 3060
tgcatcagga acaaaagcgt gatcttgctg ggtcggcaca gcttgtttca tcctgaagac 3120
acaggccagg tatttcaggt cagccacagc ttcccacacc cgctctacga tatgagcctc 3180
ctgaagaatc gattcctcag gccaggtgat gactccagcc acgacctcat gctgctccgc 3240
ctgtcagagc ctgccgagct cacggatgct gtgaaggtca tggacctgcc cacccaggag 3300
ccagcactgg ggaccacctg ctacgcctca ggctggggca gcattgaacc agaggagttc 3360
ttgaccccaa agaaacttca gtgtgtggac ctccatgtta tttccaatga cgtgtgtgcg 3420
caagttcacc ctcagaaggt gaccaagttc atgctgtgtg ctggacgctg gacagggggc 3480
aaaagcacct gctcgggtga ttctgggggc ccacttgtct gtaatggtgt gcttcaaggt 3540
atcacgtcat ggggcagtga accatgtgcc ctgcccgaaa ggccttccct gtacaccaag 3600
gtggtgcatt accggaagtg gatcaaggac accatcgtgg ccaacccctg aggatctggg 3660
ccctaacaaa acaaaaagat ggggttattc cctaaacttc atgggttacg taattggaag 3720
ttgggggaca ttgccacaag atcatattgt acaaaagatc aaacactgtt ttagaaaact 3780
tcctgtaaac aggcctattg attggaaagt atgtcaaagg attgtgggtc ttttgggctt 3840
tgctgctcca tttacacaat gtggatatcc tgccttaatg cctttgtatg catgtataca 3900
agctaaacag gctttcactt tctcgccaac ttacaaggcc tttctaagta aacagtacat 3960
gaacctttac cccgttgctc ggcaacggcc tggtctgtgc caagtgtttg ctgacgcaac 4020
ccccactggc tggggcttgg ccataggcca tcagcgcatg cgtggaacct ttgtggctcc 4080
tctgccgatc catactgcgg aactcctagc cgcttgtttt gctcgcagcc ggtctggagc 4140
aaagctcata ggaactgaca attctgtcgt cctctcgcgg aaatatacat cgtttcgatc 4200
tacgtatgat ctttttccct ctgccaaaaa ttatggggac atcatgaagc cccttgagca 4260
tctgacttct ggctaataaa ggaaatttat tttcattgca atagtgtgtt ggaatttttt 4320
gtgtctctca ctcggaagga attctgcatt aatgaatcgg ccaacgcgcg gggagaggcg 4380
gtttgcgtat tgggcgctct tccgcttcct cgctcactga ctcgctgcgc tcggtcgttc 4440
ggctgcggcg agcggtatca gctcactcaa aggcggtaat acggttatcc acagaatcag 4500
gggataacgc aggaaagaac atgtgagcaa aaggccagca aaaggccagg aaccgtaaaa 4560
aggccgcgtt gctggcgttt ttccataggc tccgcccccc tgacgagcat cacaaaaatc 4620
gacgctcaag tcagaggtgg cgaaacccga caggactata aagataccag gcgtttcccc 4680
ctggaagctc cctcgtgcgc tctcctgttc cgaccctgcc gcttaccgga tacctgtccg 4740
cctttctccc ttcgggaagc gtggcgcttt ctcatagctc acgctgtagg tatctcagtt 4800
cggtgtaggt cgttcgctcc aagctgggct gtgtgcacga accccccgtt cagcccgacc 4860
gctgcgcctt atccggtaac tatcgtcttg agtccaaccc ggtaagacac gacttatcgc 4920
cactggcagc agccactggt aacaggatta gcagagcgag gtatgtaggc ggtgctacag 4980
agttcttgaa gtggtggcct aactacggct acactagaag aacagtattt ggtatctgcg 5040
ctctgctgaa gccagttacc ttcggaaaaa gagttggtag ctcttgatcc ggcaaacaaa 5100
ccaccgctgg tagcggtggt ttttttgttt gcaagcagca gattacgcgc agaaaaaaag 5160
gatctcaaga agatcctttg atcttttcta cggggtctga cgctcagtgg aacgaaaact 5220
cacgttaagg gattttggtc atgagattat caaaaaggat cttcacctag atccttttaa 5280
attaaaaatg aagttttaaa tcaatctaaa gtatatatga gtaaacttgg tctgacagtt 5340
accaatgctt aatcagtgag gcacctatct cagcgatctg tctatttcgt tcatccatag 5400
ttgcctgact c 5411

<210> SEQ ID NO 33
<211> LENGTH: 7694
<212> TYPE: DNA
<213> ORGANISM: Artificial Sequence
<220> FEATURE:
<223> OTHER INFORMATION: Synthetic Construct

<400> SEQUENCE: 33
ggcgtaatgc tctgccagtg ttacaaccaa ttaaccaatt ctgattagaa aaactcatcg 60
agcatcaaat gaaactgcaa tttattcata tcaggattat caataccata tttttgaaaa 120
agccgtttct gtaatgaagg agaaaactca ccgaggcagt tccataggat ggcaagatcc 180
tggtatcggt ctgcgattcc gactcgtcca acatcaatac aacctattaa tttcccctcg 240
tcaaaaataa ggttatcaag tgagaaatca ccatgagtga cgactgaatc cggtgagaat 300
ggcaaaagct tatgcatttc tttccagact tgttcaacag gccagccatt acgctcgtca 360
tcaaaatcac tcgcatcaac caaaccgtta ttcattcgtg attgcgcctg agcgagacga 420
aatacgcgat cgctgttaaa aggacaatta caaacaggaa tcaaatgcaa ccggcgcagg 480
aacactgcca gcgcatcaac aatattttca cctgaatcag gatattcttc taatacctgg 540
aatgctgttt tcccggggat cgcagtggtg agtaaccatg catcatcagg agtacggata 600
aaatgcttga tggtcggaag aggcataaat tccgtcagcc agtttagtct gaccatctca 660
tctgtaacat cattggcaac gctacctttg ccatgtttca gaaacaactc tggcgcatcg 720
ggcttcccat acaatcgata gattgtcgca cctgattgcc cgacattatc gcgagcccat 780
ttatacccat ataaatcagc atccatgttg gaatttaatc gcggcctcga gcaagacgtt 840
tcccgttgaa tatggctcat aacacccctt gtattactgt ttatgtaagc agacaggtcg 900
acaatattgg ctattggcca ttgcatacgt tgtatctata tcataatatg tacatttata 960
ttggctcatg tccaatatga ccgccatgtt gacattgatt attgactagt tattaatagt 1020
aatcaattac ggggtcatta gttcatagcc catatatgga gttccgcgtt acataactta 1080
cggtaaatgg cccgcctggc tgaccgccca acgacccccg cccattgacg tcaataatga 1140
cgtatgttcc catagtaacg ccaataggga ctttccattg acgtcaatgg gtggagtatt 1200
tacggtaaac tgcccacttg gcagtacatc aagtgtatca tatgccaagt ccgcccccta 1260
ttgacgtcaa tgacggtaaa tggcccgcct ggcattatgc ccagtacatg accttacggg 1320
actttcctac ttggcagtac atctacgtat tagtcatcgc tattaccatg gtgatgcggt 1380
tttggcagta caccaatggg cgtggatagc ggtttgactc acggggattt ccaagtctcc 1440
accccattga cgtcaatggg agtttgtttt ggcaccaaaa tcaacgggac tttccaaaat 1500
gtcgtaataa ccccgccccg ttgacgcaaa tgggcggtag gcgtgtacgg tgggaggtct 1560
atataagcag agctcgttta gtgaaccgtc agatcgcctg gagacgccat ccacgctgtt 1620
ttgacctcca tagaagacac cgggaccgat ccagcctccg cggccgggaa cggtgcattg 1680
gaacgcggat tccccgtgcc aagagtgact caccgtccgg atctcagcaa gcaggtatgt 1740
actctccagg gtgggcctgg cttccccagt caagactcca gggatttgag ggacgctgtg 1800
ggctcttctc ttacatgtac cttttgcttg cctcaaccct gactatcttc caggtcagga 1860
tcccagagtc aggggtctgt attttcctgc tggtggctcc agttcaggaa cagtaaaccc 1920
tgctccgaat attgcctctc acatctcgtc aatctccgcg aggactgggg accctgtgac 1980
gaacatggct agcattgtgg gaggctggga gtgcgagaag cattcccaac cctggcaggt 2040
gcttgtggcc tctcgtggca gggcagtctg cggcggtgtt ctggtgcacc cccagtgggt 2100
cctcacagct gcccactgca tcaggaacaa aagcgtgatc ttgctgggtc ggcacagctt 2160
gtttcatcct gaagacacag gccaggtatt tcaggtcagc cacagcttcc cacacccgct 2220
ctacgatatg agcctcctga agaatcgatt cctcaggcca ggtgatgact ccagccacga 2280
cctcatgctg ctccgcctgt cagagcctgc cgagctcacg gatgctgtga aggtcatgga 2340
cctgcccacc caggagccag cactggggac cacctgctac gcctcaggct ggggcagcat 2400
tgaaccagag gagttcttga ccccaaagaa acttcagtgt gtggacctcc atgttatttc 2460
caatgacgtg tgtgcgcaag ttcaccctca gaaggtgacc aagttcatgc tgtgtgctgg 2520
acgctggaca gggggcaaaa gcacctgctc gggtgattct gggggcccac ttgtctgtaa 2580
tggtgtgctt caaggtatca cgtcatgggg cagtgaacca tgtgccctgc ccgaaaggcc 2640
ttccctgtac accaaggtgg tgcattaccg gaagtggatc aaggacacca tcgtggccaa 2700
ccccggatcc cagaccctga actttgatct gctgaaactg gcaggcgatg tggaaagcaa 2760
cccaggccca atggcaagcg cgcgccgccc gcgctggctg tgcgctgggg cgctggtgct 2820
ggcgggtggc ttctttctcc tcggcttcct cttcgggtgg tttataaaat cctccaatga 2880
agctactaac attactccaa agcataatat gaaagcattt ttggatgaat tgaaagctga 2940
gaacatcaag aagttcttat ataattttac acagatacca catttagcag gaacagaaca 3000
aaactttcag cttgcaaagc aaattcaatc ccagtggaaa gaatttggcc tggattctgt 3060
tgagctggca cattatgatg tcctgttgtc ctacccaaat aagactcatc ccaactacat 3120
ctcaataatt aatgaagatg gaaatgagat tttcaacaca tcattatttg aaccacctcc 3180
tccaggatat gaaaatgttt cggatattgt accacctttc agtgctttct ctcctcaagg 3240
aatgccagag ggcgatctag tgtatgttaa ctatgcacga actgaagact tctttaaatt 3300
ggaacgggac atgaaaatca attgctctgg gaaaattgta attgccagat atgggaaagt 3360
tttcagagga aataaggtta aaaatgccca gctggcaggg gccaaaggag tcattctcta 3420
ctccgaccct gctgactact ttgctcctgg ggtgaagtcc tatccagatg gttggaatct 3480
tcctggaggt ggtgtccagc gtggaaatat cctaaatctg aatggtgcag gagaccctct 3540
cacaccaggt tacccagcaa atgaatatgc ttataggcgt ggaattgcag aggctgttgg 3600
tcttccaagt attcctgttc atccaattgg atactatgat gcacagaagc tcctagaaaa 3660
aatgggtggc tcagcaccac cagatagcag ctggagagga agtctcaaag tgccctacaa 3720
tgttggacct ggctttactg gaaacttttc tacacaaaaa gtcaagatgc acatccactc 3780
taccaatgaa gtgacaagaa tttacaatgt gataggtact ctcagaggag cagtggaacc 3840

-continued

```
agacagatat gtcattctgg gaggtcaccg ggactcatgg gtgtttggtg gtattgaccc   3900
tcagagtgga gcagctgttg ttcatgaaat tgtgaggagc tttggaacac tgaaaaagga   3960
agggtggaga cctagaagaa caattttgtt tgcaagctgg gatgcagaag aatttggtct   4020
tcttggttct actgagtggg cagaggagaa ttcaagactc cttcaagagc gtggcgtggc   4080
ttatattaat gctgactcat ctatagaagg aaactacact ctgagagttg attgtacacc   4140
gctgatgtac agcttggtac acaacctaac aaaagagctg aaaagccctg atgaaggctt   4200
tgaaggcaaa tctctttatg aaagttggac taaaaaaagt ccttccccag agttcagtgg   4260
catgcccagg ataagcaaat tgggatctgg aaatgatttt gaggtgttct tccaacgact   4320
tggaattgct tcaggcagag cacggtatac taaaaattgg gaaacaaaca aattcagcgg   4380
ctatccactg tatcacagtg tctatgaaac atatgagttg gtggaaaagt tttatgatcc   4440
aatgtttaaa tatcacctca ctgtggccca ggttcgagga gggatggtgt ttgagctggc   4500
caattccata gtgctccctt ttgattgtcg agattatgct gtagttttaa gaaagtatgc   4560
tgacaaaatc tacagtattt ctatgaaaca tccacaggaa atgaagacat acagtgtatc   4620
atttgattca ctttttctg cagtaaagaa ttttacagaa attgcttcca agttcagtga   4680
gagactccag gactttgaca aaagcaaccc aatagtatta agaatgatga atgatcaact   4740
catgtttctg gaaagagcat ttattgatcc attagggtta ccagacaggc ctttttatag   4800
gcatgtcatc tatgctccaa gcagccacaa caagtatgca ggggagtcat tcccaggaat   4860
ttatgatgct ctgtttgata ttgaaagcaa agtggaccct tccaaggcct ggggagaagt   4920
gaagagacag atttatgttg cagccttcac agtgcaggca gctgcagaga ctttgagtga   4980
agtagcctaa agatctgacc ccctaacgtt actggccgaa gccgcttgga ataaggccgg   5040
tgtgcgtttg tctatatgtt attttccacc atattgccgt cttttggcaa tgtgagggcc   5100
cggaaacctg gccctgtctt cttgacgagc attcctaggg gtctttcccc tctcgccaaa   5160
ggaatgcaag gtctgttgaa tgtcgtgaag gaagcagttc ctctggaagc ttcttgaaga   5220
caaacaacgt ctgtagcgac cctttgcagg cagcggaacc ccccacctgg cgacaggtgc   5280
ctctgcggcc aaaagccacg tgtataagat acacctgcaa aggcggcaca accccagtgc   5340
cacgttgtga gttggatagt tgtggaaaga gtcaaatggc tctcctcaag cgtattcaac   5400
aaggggctga aggatgccca gaaggtaccc cattgtatgg gatctgatct ggggcctcgg   5460
tgcacatgct ttacatgtgt ttagtcgagg ttaaaaaacg tctaggcccc ccgaaccacg   5520
gggacgtggt tttcctttga aaaacacgat gataatatgg ccagcaaggc tgtgctgctt   5580
gccctgttga tggcaggctt ggccctgcag ccaggcactg ccctgctgtg ctactcctgc   5640
aaagcccagg tgagcaacga ggactgcctg caggtggaga actgcaccca gctgggggag   5700
cagtgctgga ccgcgcgcat ccgcgcagtt ggcctcctga ccgtcatcag caaaggctgc   5760
agcttgaact gcgtggatga ctcacaggac tactacgtgg gcaagaagaa catcacgtgc   5820
tgtgacaccg acttgtgcaa cgccagcggg gcccatgccc tgcagccggc tgccgccatc   5880
cttgcgctgc tccctgcact cggcctgctg ctctggggac ccggccagct atagggatct   5940
gggccctaac aaaacaaaaa gatggggtta ttccctaaac ttcatgggtt acgtaattgg   6000
aagttggggg acattgccac aagatcatat tgtacaaaag atcaaacact gttttagaaa   6060
acttcctgta aacaggccta ttgattggaa agtatgtcaa aggattgtgg gtcttttggg   6120
ctttgctgct ccatttacac aatgtggata tcctgcctta atgcctttgt atgcatgtat   6180
acaagctaaa caggctttca ctttctcgcc aacttacaag gcctttctaa gtaaacagta   6240
```

-continued

```
catgaacctt taccccgttg ctcggcaacg gcctggtctg tgccaagtgt ttgctgacgc   6300

aacccccact ggctggggct tggccatagg ccatcagcgc atgcgtggaa cctttgtggc   6360

tcctctgccg atccatactg cggaactcct agccgcttgt tttgctcgca gccggtctgg   6420

agcaaagctc ataggaactg acaattctgt cgtcctctcg cggaaatata catcgtttcg   6480

atctacgtat gatctttttc cctctgccaa aaattatggg gacatcatga agccccttga   6540

gcatctgact tctggctaat aaaggaaatt tattttcatt gcaatagtgt gttggaattt   6600

tttgtgtctc tcactcggaa ggaattctgc attaatgaat cggccaacgc gcggggagag   6660

gcggtttgcg tattgggcgc tcttccgctt cctcgctcac tgactcgctg cgctcggtcg   6720

ttcggctgcg gcgagcggta tcagctcact caaaggcggt aatacggtta tccacagaat   6780

caggggataa cgcaggaaag aacatgtgag caaaaggcca gcaaaaggcc aggaaccgta   6840

aaaaggccgc gttgctggcg tttttccata ggctccgccc ccctgacgag catcacaaaa   6900

atcgacgctc aagtcagagg tggcgaaacc cgacaggact ataaagatac caggcgtttc   6960

cccctggaag ctccctcgtg cgctctcctg ttccgaccct gccgcttacc ggatacctgt   7020

ccgcctttct cccttcggga agcgtggcgc tttctcatag ctcacgctgt aggtatctca   7080

gttcggtgta ggtcgttcgc tccaagctgg gctgtgtgca cgaacccccc gttcagcccg   7140

accgctgcgc cttatccggt aactatcgtc ttgagtccaa cccggtaaga cacgacttat   7200

cgccactggc agcagccact ggtaacagga ttagcagagc gaggtatgta ggcggtgcta   7260

cagagttctt gaagtggtgg cctaactacg gctacactag aagaacagta tttggtatct   7320

gcgctctgct gaagccagtt accttcggaa aaagagttgg tagctcttga tccggcaaac   7380

aaaccaccgc tggtagcggt ggtttttttg tttgcaagca gcagattacg cgcagaaaaa   7440

aaggatctca agaagatcct ttgatctttt ctacggggtc tgacgctcag tggaacgaaa   7500

actcacgtta agggattttg gtcatgagat tatcaaaaag gatcttcacc tagatccttt   7560

taaattaaaa atgaagtttt aaatcaatct aaagtatata tgagtaaact tggtctgaca   7620

gttaccaatg cttaatcagt gaggcaccta tctcagcgat ctgtctattt cgttcatcca   7680

tagttgcctg actc                                                     7694
```

```
<210> SEQ ID NO 34
<211> LENGTH: 7182
<212> TYPE: DNA
<213> ORGANISM: Artificial Sequence
<220> FEATURE:
<223> OTHER INFORMATION: Synthetic Construct

<400> SEQUENCE: 34

ggcgtaatgc tctgccagtg ttacaaccaa ttaaccaatt ctgattagaa aaactcatcg     60

agcatcaaat gaaactgcaa tttattcata tcaggattat caataccata tttttgaaaa    120

agccgtttct gtaatgaagg agaaaactca ccgaggcagt tccataggat ggcaagatcc    180

tggtatcggt ctgcgattcc gactcgtcca acatcaatac aacctattaa tttcccctcg    240

tcaaaaataa ggttatcaag tgagaaatca ccatgagtga cgactgaatc cggtgagaat    300

ggcaaaagct tatgcatttc tttccagact tgttcaacag gccagccatt acgctcgtca    360

tcaaaatcac tcgcatcaac caaaccgtta ttcattcgtg attgcgcctg agcgagacga    420

aatacgcgat cgctgttaaa aggacaatta caaacaggaa tcaaatgcaa ccggcgcagg    480

aacactgcca gcgcatcaac aatattttca cctgaatcag gatattcttc taatacctgg    540
```

-continued

```
aatgctgttt tcccggggat cgcagtggtg agtaaccatg catcatcagg agtacggata    600
aaatgcttga tggtcggaag aggcataaat tccgtcagcc agtttagtct gaccatctca    660
tctgtaacat cattggcaac gctacctttg ccatgtttca gaaacaactc tggcgcatcg    720
ggcttcccat acaatcgata gattgtcgca cctgattgcc cgacattatc gcgagcccat    780
ttatacccat ataaatcagc atccatgttg gaatttaatc gcggcctcga gcaagacgtt    840
tcccgttgaa tatggctcat aacacccctt gtattactgt ttatgtaagc agacaggtcg    900
acaatattgg ctattggcca ttgcatacgt tgtatctata tcataatatg tacatttata    960
ttggctcatg tccaatatga ccgccatgtt gacattgatt attgactagt tattaatagt   1020
aatcaattac ggggtcatta gttcatagcc catatatgga gttccgcgtt acataactta   1080
cggtaaatgg cccgcctggc tgaccgccca acgacccccg cccattgacg tcaataatga   1140
cgtatgttcc catagtaacg ccaataggga ctttccattg acgtcaatgg gtggagtatt   1200
tacggtaaac tgcccacttg gcagtacatc aagtgtatca tatgccaagt ccgcccccta   1260
ttgacgtcaa tgacggtaaa tggcccgcct ggcattatgc ccagtacatg accttacggg   1320
actttcctac ttggcagtac atctacgtat tagtcatcgc tattaccatg gtgatgcggt   1380
tttggcagta caccaatggg cgtggatagc ggtttgactc acggggattt ccaagtctcc   1440
accccattga cgtcaatggg agtttgtttt ggcaccaaaa tcaacgggac tttccaaaat   1500
gtcgtaataa ccccgccccg ttgacgcaaa tgggcggtag gcgtgtacgg tgggaggtct   1560
atataagcag agctcgttta gtgaaccgtc agatcgcctg gagacgccat ccacgctgtt   1620
ttgacctcca tagaagacac cgggaccgat ccagcctccg cggccgggaa cggtgcattg   1680
gaacgcggat tccccgtgcc aagagtgact caccgtccgg atctcagcaa gcaggtatgt   1740
actctccagg gtgggcctgg cttccccagt caagactcca gggatttgag ggacgctgtg   1800
ggctcttctc ttacatgtac cttttgcttg cctcaaccct gactatcttc caggtcagga   1860
tcccagagtc aggggtctgt attttcctgc tggtggctcc agttcaggaa cagtaaaccc   1920
tgctccgaat attgcctctc acatctcgtc aatctccgcg aggactgggg accctgtgac   1980
gaacatggct agcattgtgg gaggctggga gtgcgagaag cattcccaac cctggcaggt   2040
gcttgtggcc tctcgtggca gggcagtctg cggcggtgtt ctggtgcacc cccagtgggt   2100
cctcacagct gcccactgca tcaggaacaa aagcgtgatc ttgctgggtc ggcacagctt   2160
gtttcatcct gaagacacag gccaggtatt tcaggtcagc cacagcttcc cacacccgct   2220
ctacgatatg agcctcctga agaatcgatt cctcaggcca ggtgatgact ccagccacga   2280
cctcatgctg ctccgcctgt cagagcctgc cgagctcacg gatgctgtga aggtcatgga   2340
cctgcccacc caggagccag cactggggac cacctgctac gcctcaggct ggggcagcat   2400
tgaaccagag gagttcttga ccccaaagaa acttcagtgt gtggacctcc atgttatttc   2460
caatgacgtg tgtgcgcaag ttcaccctca gaaggtgacc aagttcatgc tgtgtgctgg   2520
acgctggaca gggggcaaaa gcacctgctc gggtgattct gggggcccac ttgtctgtaa   2580
tggtgtgctt caaggtatca cgtcatgggg cagtgaacca tgtgccctgc ccgaaaggcc   2640
ttccctgtac accaaggtgg tgcattaccg gaagtggatc aaggacacca tcgtggccaa   2700
ccccggatcc cagaccctga actttgatct gctgaaactg gcaggcgatg tggaaagcaa   2760
cccaggccca atggcaagcg cgcgccgccc gcgctggctg tgcgctgggg cgctggtgct   2820
ggcgggtggc ttctttctcc tcggcttcct cttcgggtgg tttataaaat cctccaatga   2880
agctactaac attactccaa agcataatat gaaagcattt ttggatgaat tgaaagctga   2940
```

-continued gaacatcaag aagttcttat ataattttac acagatacca catttagcag gaacagaaca 3000
aaactttcag cttgcaaagc aaattcaatc ccagtggaaa gaatttggcc tggattctgt 3060
tgagctggca cattatgatg tcctgttgtc ctacccaaat aagactcatc ccaactacat 3120
ctcaataatt aatgaagatg gaaatgagat tttcaacaca tcattatttg aaccacctcc 3180
tccaggatat gaaaatgttt cggatattgt accacctttc agtgctttct ctcctcaagg 3240
aatgccagag ggcgatctag tgtatgttaa ctatgcacga actgaagact tctttaaatt 3300
ggaacgggac atgaaaatca attgctctgg gaaaattgta attgccagat atgggaaagt 3360
tttcagagga aataaggtta aaaatgccca gctggcaggg gccaaaggag tcattctcta 3420
ctccgaccct gctgactact ttgctcctgg ggtgaagtcc tatccagatg gttggaatct 3480
tcctggaggt ggtgtccagc gtggaaatat cctaaatctg aatggtgcag gagaccctct 3540
cacaccaggt tacccagcaa atgaatatgc ttataggcgt ggaattgcag aggctgttgg 3600
tcttccaagt attcctgttc atccaattgg atactatgat gcacagaagc tcctagaaaa 3660
aatgggtggc tcagcaccac cagatagcag ctggagagga agtctcaaag tgccctacaa 3720
tgttggacct ggctttactg gaaacttttc tacacaaaaa gtcaagatgc acatccactc 3780
taccaatgaa gtgacaagaa tttacaatgt gataggtact ctcagaggag cagtggaacc 3840
agacagatat gtcattctgg gaggtcaccg ggactcatgg gtgtttggtg gtattgaccc 3900
tcagagtgga gcagctgttg ttcatgaaat tgtgaggagc tttggaacac tgaaaaagga 3960
agggtggaga cctagaagaa caattttgtt tgcaagctgg gatgcagaag aatttggtct 4020
tcttggttct actgagtggg cagaggagaa ttcaagactc cttcaagagc gtggcgtggc 4080
ttatattaat gctgactcat ctatagaagg aaactacact ctgagagttg attgtacacc 4140
gctgatgtac agcttggtac acaacctaac aaaagagctg aaaagccctg atgaaggctt 4200
tgaaggcaaa tctctttatg aaagttggac taaaaaaagt ccttccccag agttcagtgg 4260
catgcccagg ataagcaaat tgggatctgg aaatgatttt gaggtgttct tccaacgact 4320
tggaattgct tcaggcagag cacggtatac taaaaattgg gaaacaaaca aattcagcgg 4380
ctatccactg tatcacagtg tctatgaaac atatgagttg gtggaaaagt tttatgatcc 4440
aatgtttaaa tatcacctca ctgtggccca ggttcgagga gggatggtgt ttgagctggc 4500
caattccata gtgctccctt ttgattgtcg agattatgct gtagttttaa gaaagtatgc 4560
tgacaaaatc tacagtattt ctatgaaaca tccacaggaa atgaagacat acagtgtatc 4620
atttgattca ctttttctg cagtaaagaa ttttacagaa attgcttcca agttcagtga 4680
gagactccag gactttgaca aaagcaaccc aatagtatta agaatgatga atgatcaact 4740
catgtttctg gaaagagcat ttattgatcc attagggtta ccagacaggc ctttttatag 4800
gcatgtcatc tatgctccaa gcagccacaa caagtatgca ggggagtcat tcccaggaat 4860
ttatgatgct ctgtttgata ttgaaagcaa agtggaccct tccaaggcct ggggagaagt 4920
gaagagacag atttatgttg cagccttcac agtgcaggca gctgcagaga ctttgagtga 4980
agtagccgga tccgaaggta ggggttcatt attgacctgt ggagatgtcg aagaaaaccc 5040
aggacccgca agcaaggctg tgctgcttgc cctgttgatg gcaggcttgg ccctgcagcc 5100
aggcactgcc ctgctgtgct actcctgcaa agcccaggtg agcaacgagg actgcctgca 5160
ggtggagaac tgcacccagc tgggggagca gtgctggacc gcgcgcatcc gcgcagttgg 5220
cctcctgacc gtcatcagca aaggctgcag cttgaactgc gtggatgact cacaggacta 5280

```
ctacgtgggc aagaagaaca tcacgtgctg tgacaccgac ttgtgcaacg ccagcggggc   5340

ccatgccctg cagccggctg ccgccatcct tgcgctgctc cctgcactcg gcctgctgct   5400

ctggggaccc ggccagctat agagatctgg gccctaacaa aacaaaaaga tggggttatt   5460

ccctaaactt catgggttac gtaattggaa gttgggggac attgccacaa gatcatattg   5520

tacaaaagat caaacactgt tttagaaaac ttcctgtaaa caggcctatt gattggaaag   5580

tatgtcaaag gattgtgggt cttttgggct ttgctgctcc atttacacaa tgtggatatc   5640

ctgccttaat gcctttgtat gcatgtatac aagctaaaca ggctttcact ttctcgccaa   5700

cttacaaggc ctttctaagt aaacagtaca tgaaccttta ccccgttgct cggcaacggc   5760

ctggtctgtg ccaagtgttt gctgacgcaa cccccactgg ctggggcttg gccataggcc   5820

atcagcgcat gcgtggaacc tttgtggctc ctctgccgat ccatactgcg gaactcctag   5880

ccgcttgttt tgctcgcagc cggtctggag caaagctcat aggaactgac aattctgtcg   5940

tcctctcgcg gaaatataca tcgtttcgat ctacgtatga tctttttccc tctgccaaaa   6000

attatgggga catcatgaag ccccttgagc atctgacttc tggctaataa aggaaattta   6060

ttttcattgc aatagtgtgt tggaattttt tgtgtctctc actcggaagg aattctgcat   6120

taatgaatcg gccaacgcgc ggggagaggc ggtttgcgta ttgggcgctc ttccgcttcc   6180

tcgctcactg actcgctgcg ctcggtcgtt cggctgcggc gagcggtatc agctcactca   6240

aaggcggtaa tacggttatc cacagaatca ggggataacg caggaaagaa catgtgagca   6300

aaaggccagc aaaaggccag gaaccgtaaa aaggccgcgt tgctggcgtt tttccatagg   6360

ctccgccccc ctgacgagca tcacaaaaat cgacgctcaa gtcagaggtg gcgaaacccg   6420

acaggactat aaagatacca ggcgtttccc cctggaagct ccctcgtgcg ctctcctgtt   6480

ccgaccctgc cgcttaccgg atacctgtcc gcctttctcc cttcgggaag cgtggcgctt   6540

tctcatagct cacgctgtag gtatctcagt tcggtgtagg tcgttcgctc caagctgggc   6600

tgtgtgcacg aaccccccgt tcagcccgac cgctgcgcct tatccggtaa ctatcgtctt   6660

gagtccaacc cggtaagaca cgacttatcg ccactggcag cagccactgg taacaggatt   6720

agcagagcga ggtatgtagg cggtgctaca gagttcttga agtggtggcc taactacggc   6780

tacactagaa gaacagtatt tggtatctgc gctctgctga agccagttac cttcggaaaa   6840

agagttggta gctcttgatc cggcaaacaa accaccgctg gtagcggtgg tttttttgtt   6900

tgcaagcagc agattacgcg cagaaaaaaa ggatctcaag aagatccttt gatcttttct   6960

acggggtctg acgctcagtg gaacgaaaac tcacgttaag ggattttggt catgagatta   7020

tcaaaaagga tcttcaccta gatcctttta aattaaaaat gaagttttaa atcaatctaa   7080

agtatatatg agtaaacttg gtctgacagt taccaatgct taatcagtga ggcacctatc   7140

tcagcgatct gtctatttcg ttcatccata gttgcctgac tc                      7182
```

<210> SEQ ID NO 35
<211> LENGTH: 7182
<212> TYPE: DNA
<213> ORGANISM: Artificial Sequence
<220> FEATURE:
<223> OTHER INFORMATION: Synthetic Construct

<400> SEQUENCE: 35

```
ggcgtaatgc tctgccagtg ttacaaccaa ttaaccaatt ctgattagaa aaactcatcg     60

agcatcaaat gaaactgcaa tttattcata tcaggattat caataccata tttttgaaaa    120

agccgtttct gtaatgaagg agaaaactca ccgaggcagt tccataggat ggcaagatcc    180
```

-continued

```
tggtatcggt ctgcgattcc gactcgtcca acatcaatac aacctattaa tttcccctcg    240
tcaaaaataa ggttatcaag tgagaaatca ccatgagtga cgactgaatc cggtgagaat    300
ggcaaaagct tatgcatttc tttccagact tgttcaacag gccagccatt acgctcgtca    360
tcaaaatcac tcgcatcaac caaaccgtta ttcattcgtg attgcgcctg agcgagacga    420
aatacgcgat cgctgttaaa aggacaatta caaacaggaa tcaaatgcaa ccggcgcagg    480
aacactgcca gcgcatcaac aatattttca cctgaatcag gatattcttc taatacctgg    540
aatgctgttt tcccggggat cgcagtggtg agtaaccatg catcatcagg agtacggata    600
aaatgcttga tggtcggaag aggcataaat tccgtcagcc agtttagtct gaccatctca    660
tctgtaacat cattggcaac gctacctttg ccatgtttca gaaacaactc tggcgcatcg    720
ggcttcccat acaatcgata gattgtcgca cctgattgcc cgacattatc gcgagcccat    780
ttatacccat ataaatcagc atccatgttg gaatttaatc gcggcctcga gcaagacgtt    840
tcccgttgaa tatggctcat aacacccctt gtattactgt ttatgtaagc agacaggtcg    900
acaatattgg ctattggcca ttgcatacgt tgtatctata tcataatatg tacatttata    960
ttggctcatg tccaatatga ccgccatgtt gacattgatt attgactagt tattaatagt   1020
aatcaattac ggggtcatta gttcatagcc catatatgga gttccgcgtt acataactta   1080
cggtaaatgg cccgcctggc tgaccgccca acgacccccg cccattgacg tcaataatga   1140
cgtatgttcc catagtaacg ccaataggga ctttccattg acgtcaatgg gtggagtatt   1200
tacggtaaac tgcccacttg gcagtacatc aagtgtatca tatgccaagt ccgcccccta   1260
ttgacgtcaa tgacggtaaa tggcccgcct ggcattatgc ccagtacatg accttacggg   1320
actttcctac ttggcagtac atctacgtat tagtcatcgc tattaccatg gtgatgcggt   1380
tttggcagta caccaatggg cgtggatagc ggtttgactc acggggattt ccaagtctcc   1440
accccattga cgtcaatggg agtttgtttt ggcaccaaaa tcaacgggac tttccaaaat   1500
gtcgtaataa ccccgccccg ttgacgcaaa tgggcggtag gcgtgtacgg tgggaggtct   1560
atataagcag agctcgttta gtgaaccgtc agatcgcctg gagacgccat ccacgctgtt   1620
ttgacctcca tagaagacac cgggaccgat ccagcctccg cggccgggaa cggtgcattg   1680
gaacgcggat tccccgtgcc aagagtgact caccgtccgg atctcagcaa gcaggtatgt   1740
actctccagg gtgggcctgg cttccccagt caagactcca gggatttgag ggacgctgtg   1800
ggctcttctc ttacatgtac cttttgcttg cctcaaccct gactatcttc caggtcagga   1860
tcccagagtc aggggtctgt attttcctgc tggtggctcc agttcaggaa cagtaaaccc   1920
tgctccgaat attgcctctc acatctcgtc aatctccgcg aggactgggg accctgtgac   1980
gaacatggct agcattgtgg gaggctggga gtgcgagaag cattcccaac cctggcaggt   2040
gcttgtggcc tctcgtggca gggcagtctg cggcggtgtt ctggtgcacc cccagtgggt   2100
cctcacagct gcccactgca tcaggaacaa aagcgtgatc ttgctgggtc ggcacagctt   2160
gtttcatcct gaagacacag gccaggtatt tcaggtcagc cacagcttcc cacacccgct   2220
ctacgatatg agcctcctga agaatcgatt cctcaggcca ggtgatgact ccagccacga   2280
cctcatgctg ctccgcctgt cagagcctgc cgagctcacg gatgctgtga aggtcatgga   2340
cctgcccacc caggagccag cactggggac cacctgctac gcctcaggct ggggcagcat   2400
tgaaccagag gagttcttga ccccaaagaa acttcagtgt gtggacctcc atgttatttc   2460
caatgacgtg tgtgcgcaag ttcaccctca gaaggtgacc aagttcatgc tgtgtgctgg   2520
```

-continued

```
acgctggaca gggggcaaaa gcacctgctc gggtgattct gggggcccac ttgtctgtaa   2580
tggtgtgctt caaggtatca cgtcatgggg cagtgaacca tgtgccctgc ccgaaaggcc   2640
ttccctgtac accaaggtgg tgcattaccg gaagtggatc aaggacacca tcgtggccaa   2700
ccccggatcc gaaggtaggg gttcattatt gacctgtgga gatgtcgaag aaaacccagg   2760
acccgctagc aaggctgtgc tgcttgccct gttgatggca ggcttggccc tgcagccagg   2820
cactgccctg ctgtgctact cctgcaaagc ccaggtgagc aacgaggact gcctgcaggt   2880
ggagaactgc acccagctgg gggagcagtg ctggaccgcg cgcatccgcg cagttggcct   2940
cctgaccgtc atcagcaaag gctgcagctt gaactgcgtg gatgactcac aggactacta   3000
cgtgggcaag aagaacatca cgtgctgtga caccgacttg tgcaacgcca gcggggccca   3060
tgccctgcag ccggctgccg ccatccttgc gctgctccct gcactcggcc tgctgctctg   3120
gggacccggc cagctaggat cccagaccct gaactttgat ctgctgaaac tggcaggcga   3180
tgtggaaagc aacccaggcc caatggcaag cgcgcgccgc ccgcgctggc tgtgcgctgg   3240
ggcgctggtg ctggcgggtg gcttctttct cctcggcttc ctcttcgggt ggtttataaa   3300
atcctccaat gaagctacta acattactcc aaagcataat atgaaagcat tttggatga    3360
attgaaagct gagaacatca agaagttctt atataatttt acacagatac cacatttagc   3420
aggaacagaa caaaactttc agcttgcaaa gcaaattcaa tcccagtgga aagaatttgg   3480
cctggattct gttgagctgg cacattatga tgtcctgttg tcctacccaa ataagactca   3540
tcccaactac atctcaataa ttaatgaaga tggaaatgag attttcaaca catcattatt   3600
tgaaccacct cctccaggat atgaaaatgt ttcggatatt gtaccacctt tcagtgcttt   3660
ctctcctcaa ggaatgccag agggcgatct agtgtatgtt aactatgcac gaactgaaga   3720
cttctttaaa ttggaacggg acatgaaaat caattgctct gggaaaattg taattgccag   3780
atatgggaaa gttttcagag gaaataaggt taaaaatgcc cagctggcag gggccaaagg   3840
agtcattctc tactccgacc ctgctgacta ctttgctcct ggggtgaagt cctatccaga   3900
tggttggaat cttcctggag gtggtgtcca gcgtggaaat atcctaaatc tgaatggtgc   3960
aggagaccct ctcacaccag gttacccagc aaatgaatat gcttataggc gtggaattgc   4020
agaggctgtt ggtcttccaa gtattcctgt tcatccaatt ggatactatg atgcacagaa   4080
gctcctagaa aaaatgggtg gctcagcacc accagatagc agctggagag gaagtctcaa   4140
agtgccctac aatgttggac ctggctttac tggaaacttt tctacacaaa aagtcaagat   4200
gcacatccac tctaccaatg aagtgacaag aatttacaat gtgataggta ctctcagagg   4260
agcagtggaa ccagacagat atgtcattct gggaggtcac cgggactcat gggtgtttgg   4320
tggtattgac cctcagagtg gagcagctgt tgttcatgaa attgtgagga gctttggaac   4380
actgaaaaag gaagggtgga gacctagaag aacaattttg tttgcaagct gggatgcaga   4440
agaatttggt cttcttggtt ctactgagtg ggcagaggag aattcaagac tccttcaaga   4500
gcgtggcgtg gcttatatta atgctgactc atctatagaa ggaaactaca ctctgagagt   4560
tgattgtaca ccgctgatgt acagcttggt acacaaccta acaaaagagc tgaaaagccc   4620
tgatgaaggc tttgaaggca aatctcttta tgaaagttgg actaaaaaaa gtccttcccc   4680
agagttcagt ggcatgccca ggataagcaa attgggatct ggaaatgatt ttgaggtgtt   4740
cttccaacga cttggaattg cttcaggcag agcacggtat actaaaaatt gggaaacaaa   4800
caaattcagc ggctatccac tgtatcacag tgtctatgaa acatatgagt tggtggaaaa   4860
gttttatgat ccaatgttta aatatcacct cactgtggcc caggttcgag gagggatggt   4920
```

-continued

```
gtttgagctg gccaattcca tagtgctccc ttttgattgt cgagattatg ctgtagtttt   4980
aagaaagtat gctgacaaaa tctacagtat ttctatgaaa catccacagg aaatgaagac   5040
atacagtgta tcatttgatt cactttttttc tgcagtaaag aattttacag aaattgcttc   5100
caagttcagt gagagactcc aggactttga caaaagcaac ccaatagtat taagaatgat   5160
gaatgatcaa ctcatgtttc tggaaagagc atttattgat ccattagggt taccagacag   5220
gccttttat aggcatgtca tctatgctcc aagcagccac aacaagtatg caggggagtc   5280
attcccagga atttatgatg ctctgtttga tattgaaagc aaagtggacc cttccaaggc   5340
ctggggagaa gtgaagagac agatttatgt tgcagccttc acagtgcagg cagctgcaga   5400
gactttgagt gaagtagcct aaagatctgg gccctaacaa aacaaaaaga tggggttatt   5460
ccctaaactt catgggttac gtaattggaa gttgggggac attgccacaa gatcatattg   5520
tacaaaagat caaacactgt tttagaaaac ttcctgtaaa caggcctatt gattggaaag   5580
tatgtcaaag gattgtgggt cttttgggct ttgctgctcc atttacacaa tgtggatatc   5640
ctgccttaat gcctttgtat gcatgtatac aagctaaaca ggctttcact ttctcgccaa   5700
cttacaaggc ctttctaagt aaacagtaca tgaaccttta ccccgttgct cggcaacggc   5760
ctggtctgtg ccaagtgttt gctgacgcaa cccccactgg ctggggcttg gccataggcc   5820
atcagcgcat gcgtggaacc tttgtggctc ctctgccgat ccatactgcg gaactcctag   5880
ccgcttgttt tgctcgcagc cggtctggag caaagctcat aggaactgac aattctgtcg   5940
tcctctcgcg gaaatataca tcgtttcgat ctacgtatga tctttttccc tctgccaaaa   6000
attatgggga catcatgaag ccccttgagc atctgacttc tggctaataa aggaaattta   6060
ttttcattgc aatagtgtgt tggaattttt tgtgtctctc actcggaagg aattctgcat   6120
taatgaatcg gccaacgcgc ggggagaggc ggtttgcgta ttgggcgctc ttccgcttcc   6180
tcgctcactg actcgctgcg ctcggtcgtt cggctgcggc gagcggtatc agctcactca   6240
aaggcggtaa tacggttatc cacagaatca ggggataacg caggaaagaa catgtgagca   6300
aaaggccagc aaaaggccag gaaccgtaaa aaggccgcgt tgctggcgtt tttccatagg   6360
ctccgccccc ctgacgagca tcacaaaaat cgacgctcaa gtcagaggtg gcgaaacccg   6420
acaggactat aaagatacca ggcgtttccc cctggaagct ccctcgtgcg ctctcctgtt   6480
ccgaccctgc cgcttaccgg atacctgtcc gcctttctcc cttcgggaag cgtggcgctt   6540
tctcatagct cacgctgtag gtatctcagt tcggtgtagg tcgttcgctc caagctgggc   6600
tgtgtgcacg aaccccccgt tcagcccgac cgctgcgcct tatccggtaa ctatcgtctt   6660
gagtccaacc cggtaagaca cgacttatcg ccactggcag cagccactgg taacaggatt   6720
agcagagcga ggtatgtagg cggtgctaca gagttcttga agtggtggcc taactacggc   6780
tacactagaa gaacagtatt tggtatctgc gctctgctga agccagttac cttcggaaaa   6840
agagttggta gctcttgatc cggcaaacaa accaccgctg gtagcggtgg tttttttgtt   6900
tgcaagcagc agattacgcg cagaaaaaaa ggatctcaag aagatccttt gatcttttct   6960
acggggtctg acgctcagtg gaacgaaaac tcacgttaag ggattttggt catgagatta   7020
tcaaaaagga tcttcaccta gatcctttta aattaaaaat gaagttttaa atcaatctaa   7080
agtatatatg agtaaacttg gtctgacagt taccaatgct taatcagtga ggcacctatc   7140
tcagcgatct gtctatttcg ttcatccata gttgcctgac tc                      7182
```

<210> SEQ ID NO 36

<211> LENGTH: 7694
<212> TYPE: DNA
<213> ORGANISM: Artificial Sequence
<220> FEATURE:
<223> OTHER INFORMATION: Synthetic Construct

<400> SEQUENCE: 36

```
ggcgtaatgc tctgccagtg ttacaaccaa ttaaccaatt ctgattagaa aaactcatcg     60
agcatcaaat gaaactgcaa tttattcata tcaggattat caataccata tttttgaaaa    120
agccgtttct gtaatgaagg agaaaactca ccgaggcagt tccataggat ggcaagatcc    180
tggtatcggt ctgcgattcc gactcgtcca acatcaatac aacctattaa tttcccctcg    240
tcaaaaataa ggttatcaag tgagaaatca ccatgagtga cgactgaatc cggtgagaat    300
ggcaaaagct tatgcatttc tttccagact tgttcaacag gccagccatt acgctcgtca    360
tcaaaatcac tcgcatcaac caaaccgtta ttcattcgtg attgcgcctg agcgagacga    420
aatacgcgat cgctgttaaa aggacaatta caaacaggaa tcaaatgcaa ccggcgcagg    480
aacactgcca gcgcatcaac aatattttca cctgaatcag gatattcttc taatacctgg    540
aatgctgttt tcccggggat cgcagtggtg agtaaccatg catcatcagg agtacggata    600
aaatgcttga tggtcggaag aggcataaat tccgtcagcc agtttagtct gaccatctca    660
tctgtaacat cattggcaac gctacctttg ccatgtttca gaaacaactc tggcgcatcg    720
ggcttcccat acaatcgata gattgtcgca cctgattgcc cgacattatc gcgagcccat    780
ttatacccat ataaatcagc atccatgttg gaatttaatc gcggcctcga gcaagacgtt    840
tcccgttgaa tatggctcat aacacccctt gtattactgt ttatgtaagc agacaggtcg    900
acaatattgg ctattggcca ttgcatacgt tgtatctata tcataatatg tacatttata    960
ttggctcatg tccaatatga ccgccatgtt gacattgatt attgactagt tattaatagt   1020
aatcaattac ggggtcatta gttcatagcc catatatgga gttccgcgtt acataactta   1080
cggtaaatgg cccgcctggc tgaccgccca acgacccccg cccattgacg tcaataatga   1140
cgtatgttcc catagtaacg ccaataggga ctttccattg acgtcaatgg gtggagtatt   1200
tacggtaaac tgcccacttg gcagtacatc aagtgtatca tatgccaagt ccgcccccta   1260
ttgacgtcaa tgacggtaaa tggcccgcct ggcattatgc ccagtacatg accttacggg   1320
actttcctac ttggcagtac atctacgtat tagtcatcgc tattaccatg gtgatgcggt   1380
tttggcagta caccaatggg cgtggatagc ggtttgactc acggggattt ccaagtctcc   1440
accccattga cgtcaatggg agtttgtttt ggcaccaaaa tcaacgggac tttccaaaat   1500
gtcgtaataa ccccgccccg ttgacgcaaa tgggcggtag gcgtgtacgg tgggaggtct   1560
atataagcag agctcgttta gtgaaccgtc agatcgcctg gagacgccat ccacgctgtt   1620
ttgacctcca tagaagacac cgggaccgat ccagcctccg cggccgggaa cggtgcattg   1680
gaacgcggat tccccgtgcc aagagtgact caccgtccgg atctcagcaa gcaggtatgt   1740
actctccagg gtgggcctgg cttccccagt caagactcca gggatttgag ggacgctgtg   1800
ggctcttctc ttacatgtac cttttgcttg cctcaaccct gactatcttc caggtcagga   1860
tcccagagtc aggggtctgt attttcctgc tggtggctcc agttcaggaa cagtaaaccc   1920
tgctccgaat attgcctctc acatctcgtc aatctccgcg aggactgggg accctgtgac   1980
gaacatggct agcaaggctg tgctgcttgc cctgttgatg gcaggcttgg ccctgcagcc   2040
aggcactgcc ctgctgtgct actcctgcaa agcccaggtg agcaacgagg actgcctgca   2100
ggtggagaac tgcacccagc tgggggagca gtgctggacc gcgcgcatcc gcgcagttgg   2160
```

cctcctgacc gtcatcagca aaggctgcag cttgaactgc gtggatgact cacaggacta 2220
ctacgtgggc aagaagaaca tcacgtgctg tgacaccgac ttgtgcaacg ccagcggggc 2280
ccatgccctg cagccggctg ccgccatcct tgcgctgctc cctgcactcg gcctgctgct 2340
ctggggaccc ggccagctag gatcccagac cctgaacttt gatctgctga aactggcagg 2400
cgatgtggaa agcaacccag gcccaatggc aagcgcgcgc cgcccgcgct ggctgtgcgc 2460
tggggcgctg gtgctggcgg gtggcttctt tctcctcggc ttcctcttcg ggtggtttat 2520
aaaatcctcc aatgaagcta ctaacattac tccaaagcat aatatgaaag catttttgga 2580
tgaattgaaa gctgagaaca tcaagaagtt cttatataat tttacacaga taccacattt 2640
agcaggaaca gaacaaaact ttcagcttgc aaagcaaatt caatcccagt ggaaagaatt 2700
tggcctggat tctgttgagc tggcacatta tgatgtcctg ttgtcctacc caaataagac 2760
tcatcccaac tacatctcaa taattaatga agatggaaat gagattttca acacatcatt 2820
atttgaacca cctcctccag gatatgaaaa tgtttcggat attgtaccac ctttcagtgc 2880
tttctctcct caaggaatgc cagagggcga tctagtgtat gttaactatg cacgaactga 2940
agacttcttt aaattggaac gggacatgaa aatcaattgc tctgggaaaa ttgtaattgc 3000
cagatatggg aaagttttca gaggaaataa ggttaaaaat gcccagctgg caggggccaa 3060
aggagtcatt ctctactccg accctgctga ctactttgct cctggggtga agtcctatcc 3120
agatggttgg aatcttcctg gaggtggtgt ccagcgtgga aatatcctaa atctgaatgg 3180
tgcaggagac cctctcacac caggttaccc agcaaatgaa tatgcttata ggcgtggaat 3240
tgcagaggct gttggtcttc caagtattcc tgttcatcca attggatact atgatgcaca 3300
gaagctccta gaaaaaatgg gtggctcagc accaccagat agcagctgga gaggaagtct 3360
caaagtgccc tacaatgttg gacctggctt tactggaaac ttttctacac aaaaagtcaa 3420
gatgcacatc cactctacca atgaagtgac aagaatttac aatgtgatag gtactctcag 3480
aggagcagtg gaaccagaca gatatgtcat tctgggaggt caccgggact catgggtgtt 3540
tggtggtatt gaccctcaga gtggagcagc tgttgttcat gaaattgtga ggagctttgg 3600
aacactgaaa aaggaagggt ggagacctag aagaacaatt ttgtttgcaa gctgggatgc 3660
agaagaattt ggtcttcttg gttctactga gtgggcagag gagaattcaa gactccttca 3720
agagcgtggc gtggcttata ttaatgctga ctcatctata gaaggaaact acactctgag 3780
agttgattgt acaccgctga tgtacagctt ggtacacaac ctaacaaaag agctgaaaag 3840
ccctgatgaa ggctttgaag gcaaatctct ttatgaaagt tggactaaaa aaagtccttc 3900
cccagagttc agtggcatgc ccaggataag caaattggga tctggaaatg attttgaggt 3960
gttcttccaa cgacttggaa ttgcttcagg cagagcacgg tatactaaaa attgggaaac 4020
aaacaaattc agcggctatc cactgtatca cagtgtctat gaaacatatg agttggtgga 4080
aaagttttat gatccaatgt ttaaatatca cctcactgtg gcccaggttc gaggagggat 4140
ggtgtttgag ctggccaatt ccatagtgct ccccttttgat tgtcgagatt atgctgtagt 4200
tttaagaaag tatgctgaca aaatctacag tatttctatg aaacatccac aggaaatgaa 4260
gacatacagt gtatcatttg attcactttt ttctgcagta aagaatttta cagaaattgc 4320
ttccaagttc agtgagagac tccaggactt tgacaaaagc aacccaatag tattaagaat 4380
gatgaatgat caactcatgt ttctggaaag agcatttatt gatccattag ggttaccaga 4440
caggcctttt tataggcatg tcatctatgc tccaagcagc cacaacaagt atgcagggga 4500

-continued

```
gtcattccca ggaatttatg atgctctgtt tgatattgaa agcaaagtgg acccttccaa   4560
ggcctgggga gaagtgaaga gacagattta tgttgcagcc ttcacagtgc aggcagctgc   4620
agagactttg agtgaagtag cctaaagatc tgacccccta acgttactgg ccgaagccgc   4680
ttggaataag gccggtgtgc gtttgtctat atgttatttt ccaccatatt gccgtctttt   4740
ggcaatgtga gggcccggaa acctggccct gtcttcttga cgagcattcc taggggtctt   4800
tcccctctcg ccaaaggaat gcaaggtctg ttgaatgtcg tgaaggaagc agttcctctg   4860
gaagcttctt gaagacaaac aacgtctgta gcgacccttt gcaggcagcg gaacccccca   4920
cctggcgaca ggtgcctctg cggccaaaag ccacgtgtat aagatacacc tgcaaaggcg   4980
gcacaacccc agtgccacgt tgtgagttgg atagttgtgg aaagagtcaa atggctctcc   5040
tcaagcgtat tcaacaaggg gctgaaggat gcccagaagg taccccattg tatgggatct   5100
gatctggggc ctcggtgcac atgctttaca tgtgtttagt cgaggttaaa aaacgtctag   5160
gccccccgaa ccacggggac gtggttttcc tttgaaaaac acgatgataa tatggccagc   5220
attgtgggag gctgggagtg cgagaagcat tcccaaccct ggcaggtgct tgtggcctct   5280
cgtggcaggg cagtctgcgg cggtgttctg gtgcaccccc agtgggtcct cacagctgcc   5340
cactgcatca ggaacaaaag cgtgatcttg ctgggtcggc acagcttgtt tcatcctgaa   5400
gacacaggcc aggtatttca ggtcagccac agcttcccac acccgctcta cgatatgagc   5460
ctcctgaaga atcgattcct caggccaggt gatgactcca gccacgacct catgctgctc   5520
cgcctgtcag agcctgccga gctcacggat gctgtgaagg tcatggacct gcccacccag   5580
gagccagcac tggggaccac ctgctacgcc tcaggctggg gcagcattga accagaggag   5640
ttcttgaccc caaagaaact tcagtgtgtg gacctccatg ttatttccaa tgacgtgtgt   5700
gcgcaagttc accctcagaa ggtgaccaag ttcatgctgt gtgctggacg ctggacaggg   5760
ggcaaaagca cctgctcggg tgattctggg ggcccacttg tctgtaatgg tgtgcttcaa   5820
ggtatcacgt catggggcag tgaaccatgt gccctgcccg aaaggccttc cctgtacacc   5880
aaggtggtgc attaccggaa gtggatcaag gacaccatcg tggccaaccc ctgaggatct   5940
gggccctaac aaaacaaaaa gatggggtta ttccctaaac ttcatgggtt acgtaattgg   6000
aagttggggg acattgccac aagatcatat tgtacaaaag atcaaacact gttttagaaa   6060
acttcctgta aacaggccta ttgattggaa agtatgtcaa aggattgtgg gtcttttggg   6120
ctttgctgct ccatttacac aatgtggata tcctgcctta atgcctttgt atgcatgtat   6180
acaagctaaa caggctttca ctttctcgcc aacttacaag gcctttctaa gtaaacagta   6240
catgaacctt taccccgttg ctcggcaacg gcctggtctg tgccaagtgt ttgctgacgc   6300
aacccccact ggctggggct tggccatagg ccatcagcgc atgcgtggaa cctttgtggc   6360
tcctctgccg atccatactg cggaactcct agccgcttgt tttgctcgca gccggtctgg   6420
agcaaagctc ataggaactg acaattctgt cgtcctctcg cggaaatata catcgtttcg   6480
atctacgtat gatctttttc cctctgccaa aaattatggg gacatcatga agccccttga   6540
gcatctgact tctggctaat aaaggaaatt tattttcatt gcaatagtgt gttggaattt   6600
tttgtgtctc tcactcggaa ggaattctgc attaatgaat cggccaacgc gcggggagag   6660
gcggtttgcg tattgggcgc tcttccgctt cctcgctcac tgactcgctg cgctcggtcg   6720
ttcggctgcg gcgagcggta tcagctcact caaaggcggt aatacggtta tccacagaat   6780
caggggataa cgcaggaaag aacatgtgag caaaaggcca gcaaaaggcc aggaaccgta   6840
aaaaggccgc gttgctggcg tttttccata ggctccgccc ccctgacgag catcacaaaa   6900
```

```
atcgacgctc aagtcagagg tggcgaaacc cgacaggact ataaagatac caggcgtttc   6960

cccctggaag ctccctcgtg cgctctcctg ttccgaccct gccgcttacc ggatacctgt   7020

ccgcctttct cccttcggga agcgtggcgc tttctcatag ctcacgctgt aggtatctca   7080

gttcggtgta ggtcgttcgc tccaagctgg gctgtgtgca cgaacccccc gttcagcccg   7140

accgctgcgc cttatccggt aactatcgtc ttgagtccaa cccggtaaga cacgacttat   7200

cgccactggc agcagccact ggtaacagga ttagcagagc gaggtatgta ggcggtgcta   7260

cagagttctt gaagtggtgg cctaactacg gctacactag aagaacagta tttggtatct   7320

gcgctctgct gaagccagtt accttcggaa aaagagttgg tagctcttga tccggcaaac   7380

aaaccaccgc tggtagcggt ggtttttttg tttgcaagca gcagattacg cgcagaaaaa   7440

aaggatctca agaagatcct ttgatctttt ctacggggtc tgacgctcag tggaacgaaa   7500

actcacgtta agggattttg gtcatgagat tatcaaaaag gatcttcacc tagatccttt   7560

taaattaaaa atgaagtttt aaatcaatct aaagtatata tgagtaaact tggtctgaca   7620

gttaccaatg cttaatcagt gaggcaccta tctcagcgat ctgtctattt cgttcatcca   7680

tagttgcctg actc                                                     7694
```

<210> SEQ ID NO 37
<211> LENGTH: 8461
<212> TYPE: DNA
<213> ORGANISM: Artificial Sequence
<220> FEATURE:
<223> OTHER INFORMATION: Synthetic Construct

<400> SEQUENCE: 37

```
catcatcaat aatatacctt attttggatt gaagccaata tgataatgag ggggtggagt     60

ttgtgacgtg gcgcggggcg tgggaacggg gcgggtgacg tagtagtgtg gcggaagtgt    120

gatgttgcaa gtgtggcgga acacatgtaa gcgacggatg tggcaaaagt gacgtttttg    180

gtgtgcgccg gtgtacacag gaagtgacaa ttttcgcgcg gttttaggcg gatgttgtag    240

taaatttggg cgtaaccgag taagatttgg ccattttcgc gggaaaactg aataagagga    300

agtgaaatct gaataatttt gtgttactca tagcgcgtaa tactgtaata gtaatcaatt    360

acggggtcat tagttcatag cccatatatg gagttccgcg ttacataact tacggtaaat    420

ggcccgcctg gctgaccgcc caacgacccc cgcccattga cgtcaataat gacgtatgtt    480

cccatagtaa cgccaatagg gactttccat tgacgtcaat gggtggagta tttacggtaa    540

actgcccact tggcagtaca tcaagtgtat catatgccaa gtacgccccc tattgacgtc    600

aatgacggta aatggcccgc ctggcattat gcccagtaca tgaccttatg ggactttcct    660

acttggcagt acatctacgt attagtcatc gctattacca tggtgatgcg gttttggcag    720

tacatcaatg ggcgtggata gcggtttgac tcacggggat ttccaagtct ccaccccatt    780

gacgtcaatg ggagtttgtt ttggcaccaa aatcaacggg actttccaaa atgtcgtaac    840

aactccgccc cattgacgca aatgggcggt aggcgtgtac ggtgggaggt ctatataagc    900

agagctggtt tagtgaaccg tcagatccgc tagagatcca ccatggctag cggtgccccg    960

acgttgcccc ctgcctggca gccctttctc aaggaccacc gcatctctac attcaagaac   1020

tggcccttct tggagggctg cgcctgcgcc ccggagcgga tggccgaggc tggcttcatc   1080

cactgcccca ctgagaacga gccagacttg gcccagtgtt tcttctgctt caaggagctg   1140

gaaggctggg agccagatga cgaccccata gaggaacata aaaagcattc gtccggttgc   1200
```

-continued

```
gctttccttt ctgtcaagaa gcagtttgaa gaattaaccc ttggtgaatt tttgaaactg   1260
gacagagaaa gagccaagaa caaaattgca aaggaaacca acaataagaa gaaagaattt   1320
gaggaaactg cggagaaagt gcgccgtgcc atcgagcagc tggctgccat ggattagaga   1380
tctgaccccc taacgttact ggccgaagcc gcttggaata aggccggtgt gcgtttgtct   1440
atatgttatt ttccaccata ttgccgtctt ttggcaatgt gagggcccgg aaacctggcc   1500
ctgtcttctt gacgagcatt cctaggggtc tttcccctct cgccaaagga atgcaaggtc   1560
tgttgaatgt cgtgaaggaa gcagttcctc tggaagcttc ttgaagacaa acaacgtctg   1620
tagcgaccct ttgcaggcag cggaaccccc cacctggcga caggtgcctc tgcggccaaa   1680
agccacgtgt ataagataca cctgcaaagg cggcacaacc ccagtgccac gttgtgagtt   1740
ggatagttgt ggaaagagtc aaatggctct cctcaagcgt attcaacaag gggctgaagg   1800
atgcccagaa ggtaccccat tgtatgggat ctgatctggg gcctcggtgc acatgcttta   1860
catgtgttta gtcgaggtta aaaaacgtct aggccccccg aaccacgggg acgtggtttt   1920
cctttgaaaa acacgataat atggcggccg ctcgagccta agcttctaga taagatatcc   1980
gatccaccgg atctagataa ctgatcataa tcagccatac cacatttgta gaggttttac   2040
ttgctttaaa aaacctccca cacctccccc tgaacctgaa acataaaatg aatgcaattg   2100
ttgttgttaa cttgtttatt gcagcttata atggttacaa ataaagcaat agcatcacaa   2160
atttcacaaa taaagcattt ttttcactgc attctagttg tggtttgtcc aaactcatca   2220
atgtatctta acgcggatct gggcgtggtt aagggtggga aagaatatat aaggtggggg   2280
tcttatgtag ttttgtatct gttttgcagc agccgccgcc gccatgagca ccaactcgtt   2340
tgatggaagc attgtgagct catatttgac aacgcgcatg cccccatggg ccggggtgcg   2400
tcagaatgtg atgggctcca gcattgatgg tcgccccgtc ctgcccgcaa actctactac   2460
cttgacctac gagaccgtgt ctggaacgcc gttggagact gcagcctccg ccgccgcttc   2520
agccgctgca gccaccgccc gcgggattgt gactgacttt gctttcctga gcccgcttgc   2580
aagcagtgca gcttcccgtt catccgcccg cgatgacaag ttgacggctc ttttggcaca   2640
attggattct ttgacccggg aacttaatgt cgtttctcag cagctgttgg atctgcgcca   2700
gcaggtttct gccctgaagg cttcctcccc tcccaatgcg gtttaaaaca taaataaaaa   2760
accagactct gtttggattt ggatcaagca agtgtcttgc tgtctttatt taggggtttt   2820
gcgcgcgcgg taggcccggg accagcggtc tcggtcgttg agggtcctgt gtattttttc   2880
caggacgtgg taaaggtgac tctggatgtt cagatacatg ggcataagcc cgtctctggg   2940
gtggaggtag caccactgca gagcttcatg ctgcggggtg gtgttgtaga tgatccagtc   3000
gtagcaggag cgctgggcgt ggtgcctaaa aatgtctttc agtagcaagc tgattgccag   3060
gggcaggccc ttggtgtaag tgtttacaaa gcggttaagc tgggatgggt gcatacgtgg   3120
ggatatgaga tgcatcttgg actgtatttt taggttggct atgttcccag ccatatccct   3180
ccggggattc atgttgtgca gaaccaccag cacagtgtat ccggtgcact tgggaaattt   3240
gtcatgtagc ttagaaggaa atgcgtggaa gaacttggag acgcccttgt gacctccaag   3300
attttccatg cattcgtcca taatgatggc aatgggccca cgggcggcgg cctgggcgaa   3360
gatatttctg ggatcactaa cgtcatagtt gtgttccagg atgagatcgt cataggccat   3420
ttttacaaag cgcgggcgga gggtgccaga ctgcggtata atggttccat ccggcccagg   3480
ggcgtagtta ccctcacaga tttgcatttc ccacgctttg agttcagatg gggggatcat   3540
gtctacctgc ggggcgatga agaaaacggt ttccggggta ggggagatca gctgggaaga   3600
```

-continued

```
aagcaggttc ctgagcagct gcgacttacc gcagccggtg ggcccgtaaa tcacacctat   3660
taccggctgc aactggtagt taagagagct gcagctgccg tcatccctga gcaggggggc   3720
cacttcgtta agcatgtccc tgactcgcat gttttccctg accaaatccg ccagaaggcg   3780
ctcgccgccc agcgatagca gttcttgcaa ggaagcaaag tttttcaacg gtttgagacc   3840
gtccgccgta ggcatgcttt tgagcgtttg accaagcagt tccaggcggt cccacagctc   3900
ggtcacctgc tctacggcat ctcgatccag catatctcct cgtttcgcgg gttggggcgg   3960
ctttcgctgt acggcagtag tcggtgctcg tccagacggg ccagggtcat gtctttccac   4020
gggcgcaggg tcctcgtcag cgtagtctgg gtcacggtga aggggtgcgc tccgggctgc   4080
gcgctggcca gggtgcgctt gaggctggtc ctgctggtgc tgaagcgctg ccggtcttcg   4140
ccctgcgcgt cggccaggta gcatttgacc atggtgtcat agtccagccc ctccgcggcg   4200
tggcccttgg cgcgcagctt gcccttggag gaggcgccgc acgaggggca gtgcagactt   4260
ttgagggcgt agagcttggg cgcgagaaat accgattccg gggagtaggc atccgcgccg   4320
caggccccgc agacggtctc gcattccacg agccaggtga gctctggccg ttcggggtca   4380
aaaaccaggt ttcccccatg ctttttgatg cgtttcttac ctctggtttc catgagccgg   4440
tgtccacgct cggtgacgaa aaggctgtcc gtgtccccgt atacagactt gagagggagt   4500
ttaaacgaat tcaatagctt gttgcatggg cggcgatata aaatgcaagg tgctgctcaa   4560
aaaatcaggc aaagcctcgc gcaaaaaaga aagcacatcg tagtcatgct catgcagata   4620
aaggcaggta agctccggaa ccaccacaga aaaagacacc atttttctct caaacatgtc   4680
tgcgggtttc tgcataaaca caaaataaaa taacaaaaaa acatttaaac attagaagcc   4740
tgtcttacaa caggaaaaac aacccttata agcataagac ggactacggc catgccggcg   4800
tgaccgtaaa aaaactggtc accgtgatta aaaagcacca ccgacagctc ctcggtcatg   4860
tccggagtca taatgtaaga ctcggtaaac acatcaggtt gattcacatc ggtcagtgct   4920
aaaaagcgac cgaaatagcc cgggggaata catacccgca ggcgtagaga caacattaca   4980
gcccccatag gaggtataac aaaattaata ggagagaaaa acacataaac acctgaaaaa   5040
ccctcctgcc taggcaaaat agcaccctcc cgctccagaa caacatacag cgcttccaca   5100
gcggcagcca taacagtcag ccttaccagt aaaaaagaaa acctattaaa aaaacaccac   5160
tcgacacggc accagctcaa tcagtcacag tgtaaaaaag ggccaagtgc agagcgagta   5220
tatataggac taaaaaatga cgtaacggtt aaagtccaca aaaaacaccc agaaaaccgc   5280
acgcgaacct acgcccagaa acgaaagcca aaaaacccac aacttcctca aatcgtcact   5340
tccgttttcc cacgttacgt cacttcccat tttaagaaaa ctacaattcc caacacatac   5400
aagttactcc gccctaaaac ctacgtcacc cgccccgttc ccacgccccg cgccacgtca   5460
caaactccac cccctcatta tcatattggc ttcaatccaa aataaggtat attattgatg   5520
atgttaatta acatgcatgg atccatatgc ggtgtgaaat accgcacaga tgcgtaagga   5580
gaaaataccg catcaggcgc tcttccgctt cctcgctcac tgactcgctg cgctcggtcg   5640
ttcggctgcg gcgagcggta tcagctcact caaaggcggt aatacggtta tccacagaat   5700
caggggataa cgcaggaaag aacatgtgag caaaaggcca gcaaaaggcc aggaaccgta   5760
aaaaggccgc gttgctggcg tttttccata ggctccgccc ccctgacgag catcacaaaa   5820
atcgacgctc aagtcagagg tggcgaaacc cgacaggact ataaagatac caggcgtttc   5880
cccctggaag ctccctcgtg cgctctcctg ttccgaccct gccgcttacc ggatacctgt   5940
```

-continued

```
ccgcctttct cccttcggga agcgtggcgc tttctcatag ctcacgctgt aggtatctca   6000
gttcggtgta ggtcgttcgc tccaagctgg gctgtgtgca cgaacccccc gttcagcccg   6060
accgctgcgc cttatccggt aactatcgtc ttgagtccaa cccggtaaga cacgacttat   6120
cgccactggc agcagccact ggtaacagga ttagcagagc gaggtatgta ggcggtgcta   6180
cagagttctt gaagtggtgg cctaactacg gctacactag aaggacagta tttggtatct   6240
gcgctctgct gaagccagtt accttcggaa aaagagttgg tagctcttga tccggcaaac   6300
aaaccaccgc tggtagcggt ggtttttttg tttgcaagca gcagattacg cgcagaaaaa   6360
aaggatctca agaagatcct ttgatctttt ctacggggtc tgacgctcag tggaacgaaa   6420
actcacgtta agggattttg gtcatgagat tatcaaaaag gatcttcacc tagatccttt   6480
taaattaaaa atgaagtttt aaatcaatct aaagtatata tgagtaaact tggtctgaca   6540
gttaccaatg cttaatcagt gaggcaccta tctcagcgat ctgtctattt cgttcatcca   6600
tagttgcctg actccccgtc gtgtagataa ctacgatacg ggagggctta ccatctggcc   6660
ccagtgctgc aatgataccg cgagacccac gctcaccggc tccagattta tcagcaataa   6720
accagccagc cggaagggcc gagcgcagaa gtggtcctgc aactttatcc gcctccatcc   6780
agtctattaa ttgttgccgg gaagctagag taagtagttc gccagttaat agtttgcgca   6840
acgttgttgc cattgctgca gccatgagat tatcaaaaag gatcttcacc tagatccttt   6900
tcacgtagaa agccagtccg cagaaacggt gctgaccccg gatgaatgtc agctactggg   6960
ctatctggac aagggaaaac gcaagcgcaa agagaaagca ggtagcttgc agtgggctta   7020
catggcgata gctagactgg gcggttttat ggacagcaag cgaaccggaa ttgccagctg   7080
gggcgccctc tggtaaggtt gggaagccct gcaaagtaaa ctggatggct ttcttgccgc   7140
caaggatctg atggcgcagg ggatcaagct ctgatcaaga gacaggatga ggatcgtttc   7200
gcatgattga acaagatgga ttgcacgcag gttctccggc cgcttgggtg gagaggctat   7260
tcggctatga ctgggcacaa cagacaatcg gctgctctga tgccgccgtg ttccggctgt   7320
cagcgcaggg gcgcccggtt ctttttgtca agaccgacct gtccggtgcc ctgaatgaac   7380
tgcaagacga ggcagcgcgg ctatcgtggc tggccacgac gggcgttcct tgcgcagctg   7440
tgctcgacgt tgtcactgaa gcgggaaggg actggctgct attgggcgaa gtgccggggc   7500
aggatctcct gtcatctcac cttgctcctg ccgagaaagt atccatcatg gctgatgcaa   7560
tgcggcggct gcatacgctt gatccggcta cctgcccatt cgaccaccaa gcgaaacatc   7620
gcatcgagcg agcacgtact cggatggaag ccggtcttgt cgatcaggat gatctggacg   7680
aagagcatca ggggctcgcg ccagccgaac tgttcgccag gctcaaggcg agcatgcccg   7740
acggcgagga tctcgtcgtg acccatggcg atgcctgctt gccgaatatc atggtggaaa   7800
atggccgctt ttctggattc atcgactgtg gccggctggg tgtggcggac cgctatcagg   7860
acatagcgtt ggctacccgt gatattgctg aagagcttgg cggcgaatgg gctgaccgct   7920
tcctcgtgct ttacggtatc gccgctcccg attcgcagcg catcgccttc tatcgccttc   7980
ttgacgagtt cttctgaatt ttgttaaaat ttttgttaaa tcagctcatt ttttaaccaa   8040
taggccgaaa tcggcaccat cccttataaa tcaaaagaat agaccgagat agggttgagt   8100
gttgttccag tttggaacaa gagtccacta ttaaagaacg tggactccaa cgtcaaaggg   8160
cgaaaaaccg tctatcaggg cgatggccca ctacgtgaac catcacccta atcaagtttt   8220
ttgtggtcga ggtgccgtaa agcactaaat cggaacccta aagggagccc ccgatttaga   8280
gcttgacggg gaaagccggc gaacgtggcg agaaaggaag ggaagaaagc gaaaggagcg   8340
```

```
ggcgctaggg cgctggcaag tgtagcggtc acgctgcgcg taaccaccac acccgcgcgc   8400

ttaatgcgcc gctacagggc gcgtccattc gccattcagg atcgaattaa ttcttaatta   8460

a                                                                   8461


<210> SEQ ID NO 38
<211> LENGTH: 956
<212> TYPE: PRT
<213> ORGANISM: Artificial Sequence
<220> FEATURE:
<223> OTHER INFORMATION: Synthetic Construct

<400> SEQUENCE: 38

Met Ala Ser Glu Leu Ala Ala Leu Cys Arg Trp Gly Leu Leu Leu Ala
1               5                   10                  15

Leu Leu Pro Pro Gly Ala Ala Ser Thr Gln Val Cys Thr Gly Thr Asp
            20                  25                  30

Met Lys Leu Arg Leu Pro Ala Ser Pro Glu Thr His Leu Asp Met Leu
        35                  40                  45

Arg His Leu Tyr Gln Gly Cys Gln Val Val Gln Gly Asn Leu Glu Leu
    50                  55                  60

Thr Tyr Leu Pro Thr Asn Ala Ser Leu Ser Phe Leu Gln Asp Ile Gln
65                  70                  75                  80

Glu Val Gln Gly Tyr Val Leu Ile Ala His Asn Gln Val Arg Gln Val
                85                  90                  95

Pro Leu Gln Arg Leu Arg Ile Val Arg Gly Thr Gln Leu Phe Glu Asp
            100                 105                 110

Asn Tyr Ala Leu Ala Val Leu Asp Asn Gly Asp Pro Leu Asp Ser Val
        115                 120                 125

Ala Pro Ala Ala Gly Ala Thr Pro Gly Gly Leu Gln Glu Leu Gln Leu
    130                 135                 140

Arg Ser Leu Thr Glu Ile Leu Lys Gly Gly Val Leu Ile Arg Arg Ser
145                 150                 155                 160

Pro Gln Leu Cys His Gln Asp Thr Val Leu Trp Glu Asp Val Phe Arg
                165                 170                 175

Lys Asn Asn Gln Leu Ala Leu Val Leu Met Asp Thr Asn Arg Ser Arg
            180                 185                 190

Ala Cys His Pro Cys Ala Pro Met Cys Lys Ala Asn His Cys Trp Gly
        195                 200                 205

Glu Ser Ser Gln Asp Cys Gln Thr Leu Thr Arg Thr Ile Cys Thr Ser
    210                 215                 220

Ala Cys Ala Arg Cys Lys Ala Pro Leu Pro Thr Asp Cys Cys His Glu
225                 230                 235                 240

Gln Cys Ala Ala Gly Cys Thr Gly Pro Lys His Ser Asp Cys Leu Ala
                245                 250                 255

Cys Leu His Phe Asn His Ser Gly Ile Cys Glu Leu His Cys Pro Ala
            260                 265                 270

Leu Val Thr Tyr Asn Thr Asp Thr Phe Glu Ser Met Pro Asn Pro Glu
        275                 280                 285

Gly Arg Tyr Thr Phe Gly Ala Ser Cys Val Thr Ala Cys Pro Tyr Asn
    290                 295                 300

Tyr Leu Ser Thr Asp Val Gly Ser Cys Thr Leu Val Cys Pro Leu His
305                 310                 315                 320

Asn Gln Glu Val Thr Ala Glu Asp Gly Thr Gln Arg Cys Glu Lys Cys
                325                 330                 335
```

-continued

Ser Lys Pro Cys Ala Arg Val Cys Tyr Gly Leu Gly Met Glu His Leu
340 345 350

Arg Glu Ala Arg Ala Ile Thr Ser Ala Asn Val Gln Asp Phe Val Gly
355 360 365

Cys Lys Lys Ile Phe Gly Ser Leu Ala Phe Leu Pro Glu Ser Phe Asp
370 375 380

Gly Asp Pro Ala Ser Gly Thr Ala Pro Leu Gln Pro Glu Gln Leu Gln
385 390 395 400

Val Phe Glu Thr Leu Glu Glu Ile Thr Gly Tyr Leu Tyr Ile Ser Ala
405 410 415

Trp Pro Asp Ser Phe Pro Asn Leu Ser Val Phe Gln Asn Leu Arg Val
420 425 430

Ile Arg Gly Arg Ile Leu His Asn Gly Ala Tyr Ser Leu Thr Leu Gln
435 440 445

Gly Leu Gly Ile Ser Trp Leu Gly Leu Arg Ser Leu Gln Glu Leu Gly
450 455 460

Ser Gly Leu Ala Leu Val His Arg Asn Ala Arg Leu Cys Phe Val His
465 470 475 480

Thr Val Pro Trp Asp Gln Leu Phe Arg Asn Pro His Gln Ala Leu Leu
485 490 495

His Ser Gly Asn Arg Pro Glu Glu Asp Cys Val Gly Glu Gly Phe Val
500 505 510

Cys Tyr Ser Leu Cys Ala His Gly His Cys Trp Gly Pro Gly Pro Thr
515 520 525

Gln Cys Val Asn Cys Ser His Phe Leu Arg Gly Gln Glu Cys Val Glu
530 535 540

Glu Cys Arg Val Leu Gln Gly Leu Pro Arg Glu Tyr Val Asn Ala Arg
545 550 555 560

His Cys Leu Pro Cys His Pro Glu Cys Gln Pro Gln Asn Gly Ser Val
565 570 575

Thr Cys Phe Gly Pro Glu Ala Asp Gln Cys Val Ala Cys Ala His Tyr
580 585 590

Lys Asp Pro Pro Phe Cys Val Ala Arg Cys Pro Ser Gly Val Lys Pro
595 600 605

Asp Leu Ser Tyr Met Pro Ile Trp Lys Phe Pro Asp Glu Glu Gly Ala
610 615 620

Cys Gln Pro Cys Pro Ile Asn Cys Thr His Ser Cys Val Asp Leu Asp
625 630 635 640

Asp Lys Gly Cys Pro Ala Glu Gln Arg Ala Ser Pro Leu Thr Ser Ile
645 650 655

Ile Ser Ala Val Val Gly Ile Leu Leu Val Val Val Leu Gly Val Val
660 665 670

Phe Gly Ile Leu Ile Lys Arg Arg Gln Gln Lys Ile Arg Lys Tyr Thr
675 680 685

Met Arg Arg Asn Glu Asp Leu Gly Pro Ser Ser Pro Met Asp Ser Thr
690 695 700

Phe Tyr Arg Ser Leu Leu Glu Asp Glu Asp Met Gly Glu Leu Val Asp
705 710 715 720

Ala Glu Glu Tyr Leu Val Pro Gln Gln Gly Phe Phe Cys Pro Asp Pro
725 730 735

Thr Pro Gly Thr Gly Ser Thr Ala His Arg Arg His Arg Ser Ser Ser
740 745 750

```
Ala Arg Asn Gly Gly Gly Asp Leu Thr Leu Gly Met Glu Pro Ser Gly
        755                 760                 765

Glu Gly Pro Pro Arg Ser Pro Arg Ala Pro Ser Glu Gly Thr Gly Ser
    770                 775                 780

Asp Val Phe Asp Gly Asp Leu Ala Val Gly Val Thr Lys Gly Leu Gln
785                 790                 795                 800

Ser Leu Ser Pro Gln Asp Leu Ser Pro Leu Gln Arg Tyr Ser Glu Asp
                805                 810                 815

Pro Thr Leu Pro Leu Pro Ser Glu Thr Asp Gly Lys Val Ala Pro Leu
            820                 825                 830

Ser Cys Ser Pro Gln Pro Glu Phe Val Asn Gln Ser Asp Val Gln Pro
        835                 840                 845

Lys Ser Pro Leu Thr Pro Glu Gly Pro Pro Ser Pro Ala Arg Pro Thr
    850                 855                 860

Gly Ala Thr Leu Glu Arg Ala Lys Thr Leu Ser Pro Gly Lys Asn Gly
865                 870                 875                 880

Val Val Lys Asp Val Phe Thr Phe Gly Gly Ala Val Glu Asn Pro Glu
                885                 890                 895

Phe Leu Ala Pro Arg Glu Gly Thr Ala Ser Pro Pro His Pro Ser Pro
            900                 905                 910

Ala Phe Ser Pro Ala Phe Asp Asn Leu Phe Phe Trp Asp Gln Asn Ser
        915                 920                 925

Ser Glu Gln Gly Pro Pro Pro Ser Asn Phe Glu Gly Thr Pro Thr Ala
    930                 935                 940

Glu Asn Pro Glu Phe Leu Gly Leu Asp Val Pro Val
945                 950                 955


<210> SEQ ID NO 39
<211> LENGTH: 2871
<212> TYPE: DNA
<213> ORGANISM: Artificial Sequence
<220> FEATURE:
<223> OTHER INFORMATION: Synthetic Construct

<400> SEQUENCE: 39

atggctagcg agctggccgc cctgtgtaga tggggactgc tgctggctct gctgcctcct      60

ggagccgctt ctacacaggt ctgcaccggc accgacatga agctgagact gcccgccagc     120

cccgagacac acctggacat gctgcggcac ctgtaccagg gctgccaggt ggtccagggg     180

aatctggaac tgacctacct gcccaccaac gccagcctga gcttcctgca ggacatccag     240

gaagtgcagg gctacgtcct gatcgcccac aaccaggtcc gccaggtgcc cctgcagcgg     300

ctgagaatcg tgcggggcac ccagctgttc gaggacaact acgccctggc cgtgctggac     360

aacggcgacc ctctggatag cgtggcccct gctgctgggg ctacacctgg cggactgcag     420

gaactgcagc tgcggagcct gaccgagatc ctgaagggcg gcgtgctgat caggcggagc     480

cctcagctgt gccaccagga caccgtgctg tgggaggacg tgttccggaa gaacaaccag     540

ctggccctcg tgctgatgga caccaacaga agccgggcct gccacccctg cgcccccatg     600

tgcaaggcca atcactgctg gggagagagc agccaggact gccagaccct gacccggacc     660

atctgcacca gcgcctgcgc cagatgcaag gcccccctgc ctaccgactg ctgccacgaa     720

cagtgcgccg ctggctgcac cggccccaag cacagcgatt gcctggcctg cctgcacttc     780

aaccacagcg gcatctgcga gctgcactgc cctgccctgg tgacatacaa caccgacacc     840

ttcgagagca tgcccaaccc cgagggccgg tacaccttcg gcgccagctg tgtgaccgcc     900
```

-continued

```
tgcccctaca actacctgag caccgacgtg ggcagctgca ccctggtgtg cccccctgcac    960

aaccaggaag tgaccgccga ggacggcacc cagagatgcg agaagtgcag caagccttgc   1020

gccagagtgt gctacggcct gggcatggaa cacctgagag aggccagagc catcaccagc   1080

gccaacgtgc aggacttcgt gggctgcaag aagattttcg gctccctggc cttcctgccc   1140

gagagcttcg acggcgatcc tgcctctggc accgcccctc tgcagcctga gcagctgcag   1200

gtcttcgaga cactggaaga gatcaccggc tacctgtaca tcagcgcctg gcccgacagc   1260

ttccccaacc tgagcgtgtt ccagaacctg agagtgatcc ggggcagaat cctgcacaac   1320

ggcgcctaca gcctgaccct gcagggcctg ggaatcagct ggctgggcct gcggagcctg   1380

caggaactgg gatctggcct ggctctggtg caccggaacg cccggctgtg cttcgtgcac   1440

accgtgccct gggaccagct gttcagaaac cccccaccagg ctctgctgca cagcggcaac   1500

cggcccgaag aggattgcgt gggcgagggc ttcgtgtgct actccctgtg cgcccacggc   1560

cactgttggg gacctggccc tacccagtgc gtgaactgca gccacttcct gcggggccaa   1620

gaatgcgtgg aagagtgccg ggtgctgcag ggactgcccc gggaatacgt gaacgccaga   1680

cactgcctgc cttgccaccc cgagtgccag ccccagaatg gcagcgtgac ctgcttcgga   1740

cccgaggccg atcagtgtgt ggcctgcgcc cactacaagg acccccccatt ctgcgtggcc   1800

agatgcccca gcggcgtgaa gcccgacctg agctacatgc ccatctggaa gttccccgac   1860

gaggaaggcg cctgccagcc ttgccccatc aactgcaccc acagctgcgt ggacctggac   1920

gacaagggct gccctgccga gcagagagcc agcccccctga ccagcatcat cagcgccgtg   1980

gtgggaatcc tgctggtggt ggtgctgggc gtggtgttcg gcatcctgat caagcggcgg   2040

cagcagaaga tccggaagta caccatgcgg cggaacgagg acctgggccc ctctagcccc   2100

atggacagca ccttctaccg gtccctgctg gaagatgagg acatgggcga gctggtggac   2160

gccgaggaat acctggtgcc tcagcagggc ttcttctgcc ccgaccctac ccctggcacc   2220

ggctctaccg cccacagacg gcacagaagc agcagcgcca gaaacggcgg aggcgacctg   2280

accctgggaa tggaacctag cggcgaggga cctcccagaa gccctagagc cctagcgag    2340

ggcaccggca gcgacgtgtt cgatggcgat ctggccgtgg gcgtgaccaa gggactgcag   2400

agcctgagcc cccaggacct gtccccccctg cagagataca gcgaggaccc caccctgccc   2460

ctgcccagcg agacagatgg caaggtggcc cccctgagct gcagccctca gcccgagttc   2520

gtgaaccaga gcgacgtgca gcccaagtcc cccctgacac ccgagggacc tccaagccct   2580

gccagaccta ccggcgccac cctggaaaga gccaagaccc tgagccccgg caagaacggc   2640

gtggtgaaag acgtgttcac cttcggaggc gccgtggaaa accccgagtt cctggccccc   2700

agagagggca cagccagccc tccacacccc agcccagcct tctcccccgc cttcgacaac   2760

ctgttcttct gggaccagaa cagcagcgag cagggcccac cccccagcaa tttcgagggc   2820

acccccaccg ccgagaatcc tgagttcctg ggcctggacg tgcccgtgtg a            2871
```

<210> SEQ ID NO 40
<211> LENGTH: 471
<212> TYPE: PRT
<213> ORGANISM: Artificial Sequence
<220> FEATURE:
<223> OTHER INFORMATION: Synthetic Construct

<400> SEQUENCE: 40

```
Met Asp Trp Thr Trp Arg Ile Leu Phe Leu Val Ala Ala Ala Thr Gly
1               5                   10                  15
```

-continued

```
Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Gly Tyr Tyr Met His Trp Val Arg Gln Ala Pro Gly Gln Gly Leu
    50                  55                  60

Glu Trp Met Gly Trp Ile Asn Pro Asp Ser Gly Gly Thr Asn Tyr Ala
65                  70                  75                  80

Gln Lys Phe Gln Gly Arg Val Thr Met Thr Arg Asp Thr Ser Ile Ser
                85                  90                  95

Thr Ala Tyr Met Glu Leu Asn Arg Leu Arg Ser Asp Asp Thr Ala Val
            100                 105                 110

Tyr Tyr Cys Ala Arg Asp Gln Pro Leu Gly Tyr Cys Thr Asn Gly Val
        115                 120                 125

Cys Ser Tyr Phe Asp Tyr Trp Gly Gln Gly Thr Leu Val Thr Val Ser
    130                 135                 140

Ser Ala Ser Thr Lys Gly Pro Ser Val Phe Pro Leu Ala Pro Cys Ser
145                 150                 155                 160

Arg Ser Thr Ser Glu Ser Thr Ala Ala Leu Gly Cys Leu Val Lys Asp
                165                 170                 175

Tyr Phe Pro Glu Pro Val Thr Val Ser Trp Asn Ser Gly Ala Leu Thr
            180                 185                 190

Ser Gly Val His Thr Phe Pro Ala Val Leu Gln Ser Ser Gly Leu Tyr
        195                 200                 205

Ser Leu Ser Ser Val Val Thr Val Pro Ser Ser Asn Phe Gly Thr Gln
    210                 215                 220

Thr Tyr Thr Cys Asn Val Asp His Lys Pro Ser Asn Thr Lys Val Asp
225                 230                 235                 240

Lys Thr Val Glu Arg Lys Cys Cys Val Glu Cys Pro Pro Cys Pro Ala
                245                 250                 255

Pro Pro Val Ala Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Gln Phe Asn Trp Tyr Val Asp
    290                 295                 300

Gly Val Glu Val His Asn Ala Lys Thr Lys Pro Arg Glu Glu Gln Phe
305                 310                 315                 320

Asn Ser Thr Phe Arg Val Val Ser Val Leu Thr Val Val His Gln Asp
                325                 330                 335

Trp Leu Asn Gly Lys Glu Tyr Lys Cys Lys Val Ser Asn Lys Gly Leu
            340                 345                 350

Pro Ala Pro Ile Glu Lys Thr Ile Ser Lys Thr Lys Gly Gln Pro Arg
        355                 360                 365

Glu Pro Gln Val Tyr Thr Leu Pro Pro Ser Arg Glu Glu Met Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Met Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
```

```
        435                 440                 445

Cys Ser Val Met His Glu Ala Leu His Asn His Tyr Thr Gln Lys Ser
    450                 455                 460

Leu Ser Leu Ser Pro Gly Lys
465                 470


<210> SEQ ID NO 41
<211> LENGTH: 234
<212> TYPE: PRT
<213> ORGANISM: Artificial Sequence
<220> FEATURE:
<223> OTHER INFORMATION: Synthetic Construct

<400> SEQUENCE: 41

Met Arg Leu Pro Ala Gln Leu Leu Gly Leu Leu Leu Leu Trp Phe Pro
1               5                   10                  15

Gly Ser Arg Cys Asp Ile Gln Met Thr Gln Ser Pro Ser Ser Val Ser
            20                  25                  30

Ala Ser Val Gly Asp Arg Val Thr Ile Thr Cys Arg Ala Ser Gln Gly
        35                  40                  45

Ile Tyr Ser Trp Leu Ala Trp Tyr Gln Gln Lys Pro Gly Lys Ala Pro
    50                  55                  60

Asn Leu Leu Ile Tyr Thr Ala Ser Thr Leu Gln Ser Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Gln Gln Ala Asn
            100                 105                 110

Ile Phe Pro Leu Thr Phe Gly Gly Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230


<210> SEQ ID NO 42
<211> LENGTH: 451
<212> TYPE: PRT
<213> ORGANISM: Artificial Sequence
<220> FEATURE:
<223> OTHER INFORMATION: Synthetic Construct

<400> SEQUENCE: 42

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30
```

-continued

```
Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Pro Arg Gly Ala Thr Leu Tyr Tyr Tyr Tyr Tyr Gly Met
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Asn Phe Gly Thr Gln Thr Tyr Thr Cys
        195                 200                 205

Asn Val Asp His Lys Pro Ser Asn Thr Lys Val Asp Lys Thr Val Glu
    210                 215                 220

Arg Lys Cys Cys Val Glu Cys Pro Pro Cys Pro Ala Pro Pro Val Ala
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Phe
    290                 295                 300

Arg Val Val Ser Val Leu Thr Val Val His Gln Asp Trp Leu Asn Gly
305                 310                 315                 320

Lys Glu Tyr Lys Cys Lys Val Ser Asn Lys Gly Leu Pro Ala Pro Ile
                325                 330                 335

Glu Lys Thr Ile Ser Lys Thr Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Met Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
```

450

<210> SEQ ID NO 43
<211> LENGTH: 214
<212> TYPE: PRT
<213> ORGANISM: Artificial Sequence
<220> FEATURE:
<223> OTHER INFORMATION: Synthetic Construct

<400> SEQUENCE: 43

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asn Ser Tyr
            20                  25                  30

Leu Asp Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Thr Pro Phe
                85                  90                  95

Thr Phe Gly Pro Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 44
<211> LENGTH: 24
<212> TYPE: DNA
<213> ORGANISM: Artificial Sequence
<220> FEATURE:
<223> OTHER INFORMATION: Synthetic Construct

<400> SEQUENCE: 44

```
tcgtcgtttt gtcgttttgt cgtt                                             24
```

<210> SEQ ID NO 45
<211> LENGTH: 21
<212> TYPE: DNA
<213> ORGANISM: Artificial Sequence
<220> FEATURE:
<223> OTHER INFORMATION: Synthetic Construct

<400> SEQUENCE: 45

```
tcgtcgtttt tcggtgcttt t                                                21
```

<210> SEQ ID NO 46
<211> LENGTH: 21
<212> TYPE: DNA
<213> ORGANISM: Artificial Sequence
<220> FEATURE:
<223> OTHER INFORMATION: Synthetic Construct

<400> SEQUENCE: 46
tcgtcgtttt tcggtcgttt t 21

<210> SEQ ID NO 47
<211> LENGTH: 239
<212> TYPE: PRT
<213> ORGANISM: Artificial Sequence
<220> FEATURE:
<223> OTHER INFORMATION: Synthetic Construct

<400> SEQUENCE: 47

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235
```

<210> SEQ ID NO 48
<211> LENGTH: 185
<212> TYPE: PRT
<213> ORGANISM: Orthohepadnavirus hepatitis B virus

<400> SEQUENCE: 48

```
Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30
```

```
Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Glu Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Gly Arg Ser Pro Arg Arg
145                 150                 155                 160

Arg Thr Pro Ser Pro Arg Arg Arg Arg Ser Gln Ser Pro Arg Arg Arg
                165                 170                 175

Arg Ser Gln Ser Arg Glu Ser Gln Cys
            180                 185
```

<210> SEQ ID NO 49
<211> LENGTH: 226
<212> TYPE: PRT
<213> ORGANISM: Orthohepadnavirus hepatitis B virus

<400> SEQUENCE: 49

```
Met Glu Asn Ile Thr Ser Gly Phe Leu Gly Pro Leu Leu Val Leu Gln
1               5                   10                  15

Ala Gly Phe Phe Leu Leu Thr Arg Ile Leu Thr Ile Pro Gln Ser Leu
            20                  25                  30

Asp Ser Trp Trp Thr Ser Leu Asn Phe Leu Gly Gly Ser Pro Val Cys
        35                  40                  45

Leu Gly Gln Asn Ser Gln Ser Pro Thr Ser Asn His Ser Pro Thr Ser
    50                  55                  60

Cys Pro Pro Ile Cys Pro Gly Tyr Arg Trp Met Cys Leu Arg Arg Phe
65                  70                  75                  80

Ile Ile Phe Leu Phe Ile Leu Leu Leu Cys Leu Ile Phe Leu Leu Val
                85                  90                  95

Leu Leu Asp Tyr Gln Gly Met Leu Pro Val Cys Pro Leu Ile Pro Gly
            100                 105                 110

Ser Thr Thr Thr Ser Thr Gly Pro Cys Lys Thr Cys Thr Thr Pro Ala
        115                 120                 125

Gln Gly Asn Ser Met Phe Pro Ser Cys Cys Cys Thr Lys Pro Thr Asp
    130                 135                 140

Gly Asn Cys Thr Cys Ile Pro Ile Pro Ser Ser Trp Ala Phe Ala Lys
145                 150                 155                 160

Tyr Leu Trp Glu Trp Ala Ser Val Arg Phe Ser Trp Leu Ser Leu Leu
                165                 170                 175

Val Pro Phe Val Gln Trp Phe Val Gly Leu Ser Pro Thr Val Trp Leu
            180                 185                 190

Ser Ala Ile Trp Met Met Trp Tyr Trp Gly Pro Ser Leu Tyr Ser Ile
        195                 200                 205

Val Ser Pro Phe Ile Pro Leu Leu Pro Ile Phe Phe Cys Leu Trp Val
```

210                 215                 220

Tyr Ile
225

<210> SEQ ID NO 50
<211> LENGTH: 737
<212> TYPE: PRT
<213> ORGANISM: Artificial Sequence
<220> FEATURE:
<223> OTHER INFORMATION: Synthetic Construct

<400> SEQUENCE: 50

Met Ala Ser Glu Thr Asp Thr Leu Leu Leu Trp Val Leu Leu Leu Trp
1               5                   10                  15

Val Pro Gly Ser Thr Gly Asp Ala Ala His His His His His His Lys
            20                  25                  30

Ser Ser Ser Glu Ala Thr Asn Ile Thr Pro Lys His Asn Met Lys Ala
        35                  40                  45

Phe Leu Asp Glu Leu Lys Ala Glu Asn Ile Lys Lys Phe Leu His Asn
    50                  55                  60

Phe Thr Gln Ile Pro His Leu Ala Gly Thr Glu Gln Asn Phe Gln Leu
65                  70                  75                  80

Ala Lys Gln Ile Gln Ser Gln Trp Lys Glu Phe Gly Leu Asp Ser Val
                85                  90                  95

Glu Leu Thr His Tyr Asp Val Leu Leu Ser Tyr Pro Asn Lys Thr His
            100                 105                 110

Pro Asn Tyr Ile Ser Ile Ile Asn Glu Asp Gly Asn Glu Ile Phe Asn
        115                 120                 125

Thr Ser Leu Phe Glu Pro Pro Pro Ala Gly Tyr Glu Asn Val Ser Asp
    130                 135                 140

Ile Val Pro Pro Phe Ser Ala Phe Ser Pro Gln Gly Met Pro Glu Gly
145                 150                 155                 160

Asp Leu Val Tyr Val Asn Tyr Ala Arg Thr Glu Asp Phe Phe Lys Leu
                165                 170                 175

Glu Arg Asp Met Lys Ile Asn Cys Ser Gly Lys Ile Val Ile Ala Arg
            180                 185                 190

Tyr Gly Lys Val Phe Arg Gly Asn Lys Val Lys Asn Ala Gln Leu Ala
        195                 200                 205

Gly Ala Thr Gly Val Ile Leu Tyr Ser Asp Pro Ala Asp Tyr Phe Ala
    210                 215                 220

Pro Gly Val Lys Ser Tyr Pro Asp Gly Trp Asn Leu Pro Gly Gly Gly
225                 230                 235                 240

Val Gln Arg Gly Asn Ile Leu Asn Leu Asn Gly Ala Gly Asp Pro Leu
                245                 250                 255

Thr Pro Gly Tyr Pro Ala Asn Glu Tyr Ala Tyr Arg Arg Gly Ile Ala
            260                 265                 270

Glu Ala Val Gly Leu Pro Ser Ile Pro Val His Pro Ile Gly Tyr Tyr
        275                 280                 285

Asp Ala Gln Lys Leu Leu Glu Lys Met Gly Gly Ser Ala Ser Pro Asp
    290                 295                 300

Ser Ser Trp Arg Gly Ser Leu Lys Val Pro Tyr Asn Val Gly Pro Gly
305                 310                 315                 320

Phe Thr Gly Asn Phe Ser Thr Gln Lys Val Lys Met His Ile His Ser
                325                 330                 335

Thr Ser Glu Val Thr Arg Ile Tyr Asn Val Ile Gly Thr Leu Arg Gly

```
            340                 345                 350

Ala Val Glu Pro Asp Arg Tyr Val Ile Leu Gly Gly His Arg Asp Ser
        355                 360                 365

Trp Val Phe Gly Gly Ile Asp Pro Gln Ser Gly Ala Ala Val Val His
    370                 375                 380

Glu Ile Val Arg Ser Phe Gly Thr Leu Lys Lys Glu Gly Trp Arg Pro
385                 390                 395                 400

Arg Arg Thr Ile Leu Phe Ala Ser Trp Asp Ala Glu Glu Phe Gly Leu
                405                 410                 415

Leu Gly Ser Thr Glu Trp Ala Glu Glu Asn Ser Arg Leu Leu Gln Glu
            420                 425                 430

Arg Gly Val Ala Tyr Ile Asn Ala Asp Ser Ser Ile Glu Gly Asn Tyr
        435                 440                 445

Thr Leu Arg Val Asp Cys Thr Pro Leu Met Tyr Ser Leu Val Tyr Asn
    450                 455                 460

Leu Thr Lys Glu Leu Glu Ser Pro Asp Glu Gly Phe Glu Gly Lys Ser
465                 470                 475                 480

Leu Tyr Glu Ser Trp Thr Lys Ser Pro Ser Pro Glu Phe Ser Gly Met
                485                 490                 495

Pro Arg Ile Ser Lys Leu Gly Ser Gly Asn Asp Phe Glu Val Phe Phe
            500                 505                 510

Gln Arg Leu Gly Ile Ala Ser Gly Arg Ala Arg Tyr Thr Lys Asn Trp
        515                 520                 525

Glu Thr Asn Lys Phe Ser Ser Tyr Pro Leu Tyr His Ser Val Tyr Glu
    530                 535                 540

Thr Tyr Glu Leu Val Glu Lys Phe Tyr Asp Pro Met Phe Lys Tyr His
545                 550                 555                 560

Leu Thr Val Ala Gln Val Arg Gly Gly Met Val Phe Glu Leu Ala Asn
                565                 570                 575

Ser Val Val Leu Pro Phe Asp Cys Arg Asp Tyr Ala Val Val Leu Arg
            580                 585                 590

Lys Tyr Ala Asp Lys Ile Tyr Asn Ile Ser Met Lys His Pro Gln Glu
        595                 600                 605

Met Lys Thr Tyr Ser Val Ser Phe Asp Ser Leu Phe Ser Ala Val Lys
    610                 615                 620

Asn Phe Thr Glu Ile Ala Ser Lys Phe Ser Glu Arg Leu Arg Asp Phe
625                 630                 635                 640

Asp Lys Ser Asn Pro Ile Leu Leu Arg Met Met Asn Asp Gln Leu Met
                645                 650                 655

Phe Leu Glu Arg Ala Phe Ile Asp Pro Leu Gly Leu Pro Asp Arg Pro
            660                 665                 670

Phe Tyr Arg His Val Ile Tyr Ala Pro Ser Ser His Asn Lys Tyr Ala
        675                 680                 685

Gly Glu Ser Phe Pro Gly Ile Tyr Asp Ala Leu Phe Asp Ile Glu Ser
    690                 695                 700

Lys Val Asp Pro Ser Gln Ala Trp Gly Glu Val Lys Arg Gln Ile Ser
705                 710                 715                 720

Ile Ala Thr Phe Thr Val Gln Ala Ala Ala Glu Thr Leu Ser Glu Val
                725                 730                 735

Ala
```

<210> SEQ ID NO 51
<211> LENGTH: 9

```
<212> TYPE: PRT
<213> ORGANISM: Artificial Sequence
<220> FEATURE:
<223> OTHER INFORMATION: Synthetic Construct

<400> SEQUENCE: 51

Thr Tyr Val Pro Ala Asn Ala Ser Leu
1               5


<210> SEQ ID NO 52
<211> LENGTH: 15
<212> TYPE: PRT
<213> ORGANISM: Artificial Sequence
<220> FEATURE:
<223> OTHER INFORMATION: Synthetic Construct

<400> SEQUENCE: 52

Asp Met Val Leu Trp Lys Asp Val Phe Arg Lys Asn Asn Gln Leu
1               5                   10                  15


<210> SEQ ID NO 53
<211> LENGTH: 9
<212> TYPE: PRT
<213> ORGANISM: Artificial Sequence
<220> FEATURE:
<223> OTHER INFORMATION: Synthetic Construct

<400> SEQUENCE: 53

Ser Tyr Val Asn Thr Asn Met Gly Leu
1               5


<210> SEQ ID NO 54
<211> LENGTH: 957
<212> TYPE: PRT
<213> ORGANISM: Artificial Sequence
<220> FEATURE:
<223> OTHER INFORMATION: Synthetic Construct

<400> SEQUENCE: 54

Met Ala Ser Glu Leu Ala Ala Trp Cys Arg Trp Gly Phe Leu Leu Ala
1               5                   10                  15

Leu Leu Pro Pro Gly Ile Ala Gly Thr Gln Val Cys Thr Gly Thr Asp
            20                  25                  30

Met Lys Leu Arg Leu Pro Ala Ser Pro Glu Thr His Leu Asp Met Leu
        35                  40                  45

Arg His Leu Tyr Gln Gly Cys Gln Val Val Gln Gly Asn Leu Glu Leu
    50                  55                  60

Thr Tyr Val Pro Ala Asn Ala Ser Leu Ser Phe Leu Gln Asp Ile Gln
65                  70                  75                  80

Glu Val Gln Gly Tyr Met Leu Ile Ala His Asn Gln Val Lys Arg Val
                85                  90                  95

Pro Leu Gln Arg Leu Arg Ile Val Arg Gly Thr Gln Leu Phe Glu Asp
            100                 105                 110

Lys Tyr Ala Leu Ala Val Leu Asp Asn Arg Asp Pro Gln Asp Asn Val
        115                 120                 125

Ala Ala Ser Thr Pro Gly Arg Thr Pro Glu Gly Leu Arg Glu Leu Gln
    130                 135                 140

Leu Arg Ser Leu Thr Glu Ile Leu Lys Gly Gly Val Leu Ile Arg Gly
145                 150                 155                 160

Asn Pro Gln Leu Cys Tyr Gln Asp Met Val Leu Trp Lys Asp Val Phe
                165                 170                 175
```

-continued

```
Arg Lys Asn Asn Gln Leu Ala Pro Val Asp Ile Asp Thr Asn Arg Ser
            180                 185                 190

Arg Ala Cys Pro Pro Cys Ala Pro Ala Cys Lys Asp Asn His Cys Trp
        195                 200                 205

Gly Glu Ser Pro Glu Asp Cys Gln Ile Leu Thr Gly Thr Ile Cys Thr
    210                 215                 220

Ser Gly Cys Ala Arg Cys Lys Gly Arg Leu Pro Thr Asp Cys Cys His
225                 230                 235                 240

Glu Gln Cys Ala Ala Gly Cys Thr Gly Pro Lys His Ser Asp Cys Leu
                245                 250                 255

Ala Cys Leu His Phe Asn His Ser Gly Ile Cys Glu Leu His Cys Pro
            260                 265                 270

Ala Leu Val Thr Tyr Asn Thr Asp Thr Phe Glu Ser Met His Asn Pro
        275                 280                 285

Glu Gly Arg Tyr Thr Phe Gly Ala Ser Cys Val Thr Thr Cys Pro Tyr
    290                 295                 300

Asn Tyr Leu Ser Thr Glu Val Gly Ser Cys Thr Leu Val Cys Pro Pro
305                 310                 315                 320

Asn Asn Gln Glu Val Thr Ala Glu Asp Gly Thr Gln Arg Cys Glu Lys
                325                 330                 335

Cys Ser Lys Pro Cys Ala Arg Val Cys Tyr Gly Leu Gly Met Glu His
            340                 345                 350

Leu Arg Gly Ala Arg Ala Ile Thr Ser Asp Asn Val Gln Glu Phe Asp
        355                 360                 365

Gly Cys Lys Lys Ile Phe Gly Ser Leu Ala Phe Leu Pro Glu Ser Phe
    370                 375                 380

Asp Gly Asp Pro Ser Ser Gly Ile Ala Pro Leu Arg Pro Glu Gln Leu
385                 390                 395                 400

Gln Val Phe Glu Thr Leu Glu Glu Ile Thr Gly Tyr Leu Tyr Ile Ser
                405                 410                 415

Ala Trp Pro Asp Ser Leu Arg Asp Leu Ser Val Phe Gln Asn Leu Arg
            420                 425                 430

Ile Ile Arg Gly Arg Ile Leu His Asp Gly Ala Tyr Ser Leu Thr Leu
        435                 440                 445

Gln Gly Leu Gly Ile His Ser Leu Gly Leu Arg Ser Leu Arg Glu Leu
    450                 455                 460

Gly Ser Gly Leu Ala Leu Ile His Arg Asn Ala His Leu Cys Phe Val
465                 470                 475                 480

His Thr Val Pro Trp Asp Gln Leu Phe Arg Asn Pro His Gln Ala Leu
                485                 490                 495

Leu His Ser Gly Asn Arg Pro Glu Glu Asp Cys Gly Leu Glu Gly Leu
            500                 505                 510

Val Cys Asn Ser Leu Cys Ala His Gly His Cys Trp Gly Pro Gly Pro
        515                 520                 525

Thr Gln Cys Val Asn Cys Ser His Phe Leu Arg Gly Gln Glu Cys Val
    530                 535                 540

Glu Glu Cys Arg Val Trp Lys Gly Leu Pro Arg Glu Tyr Val Ser Asp
545                 550                 555                 560

Lys Arg Cys Leu Pro Cys His Pro Glu Cys Gln Pro Gln Asn Ser Ser
                565                 570                 575

Glu Thr Cys Phe Gly Ser Glu Ala Asp Gln Cys Ala Ala Cys Ala His
            580                 585                 590

Tyr Lys Asp Ser Ser Ser Cys Val Ala Arg Cys Pro Ser Gly Val Lys
```

595 600 605

Pro Asp Leu Ser Tyr Met Pro Ile Trp Lys Tyr Pro Asp Glu Glu Gly
610 615 620

Ile Cys Gln Pro Cys Pro Ile Asn Cys Thr His Ser Cys Val Asp Leu
625 630 635 640

Asp Glu Arg Gly Cys Pro Ala Glu Gln Arg Ala Ser Pro Val Thr Phe
645 650 655

Ile Ile Ala Thr Val Val Gly Val Leu Leu Phe Leu Ile Leu Val Val
660 665 670

Val Val Gly Ile Leu Ile Lys Arg Arg Arg Gln Lys Ile Arg Lys Tyr
675 680 685

Thr Met Arg Arg Asn Glu Asp Leu Gly Pro Ser Ser Pro Met Asp Ser
690 695 700

Thr Phe Tyr Arg Ser Leu Leu Glu Asp Asp Asp Met Gly Asp Leu Val
705 710 715 720

Asp Ala Glu Glu Tyr Leu Val Pro Gln Gln Gly Phe Phe Ser Pro Asp
725 730 735

Pro Thr Pro Gly Thr Gly Ser Thr Ala His Arg Arg His Arg Ser Ser
740 745 750

Ser Thr Arg Ser Gly Gly Gly Glu Leu Thr Leu Gly Leu Glu Pro Ser
755 760 765

Glu Glu Gly Pro Pro Arg Ser Pro Leu Ala Pro Ser Glu Gly Ala Gly
770 775 780

Ser Asp Val Phe Asp Gly Asp Leu Ala Met Gly Val Thr Lys Gly Leu
785 790 795 800

Gln Ser Leu Ser Pro His Asp Leu Ser Pro Leu Gln Arg Tyr Ser Glu
805 810 815

Asp Pro Thr Leu Pro Leu Pro Pro Glu Thr Asp Gly Tyr Val Ala Pro
820 825 830

Leu Ala Cys Ser Pro Gln Pro Glu Phe Val Asn Gln Ser Glu Val Gln
835 840 845

Pro Gln Pro Pro Leu Thr Pro Glu Gly Pro Leu Pro Pro Val Arg Pro
850 855 860

Ala Gly Ala Thr Leu Glu Arg Pro Lys Thr Leu Ser Pro Gly Lys Asn
865 870 875 880

Gly Val Val Lys Asp Val Phe Ala Phe Gly Gly Ala Val Glu Asn Pro
885 890 895

Glu Phe Leu Val Pro Arg Glu Gly Thr Ala Ser Pro Pro His Pro Ser
900 905 910

Pro Ala Phe Ser Pro Ala Phe Asp Asn Leu Phe Phe Trp Asp Gln Asn
915 920 925

Ser Ser Glu Gln Gly Pro Pro Pro Ser Asn Phe Glu Gly Thr Pro Thr
930 935 940

Ala Glu Asn Pro Glu Phe Leu Gly Leu Asp Val Pro Val
945 950 955

<210> SEQ ID NO 55
<211> LENGTH: 739
<212> TYPE: PRT
<213> ORGANISM: Artificial Sequence
<220> FEATURE:
<223> OTHER INFORMATION: Synthetic Construct

<400> SEQUENCE: 55

Met Ala Ser Ala Arg Arg Pro Arg Trp Leu Cys Ala Gly Ala Leu Val

-continued

```
1               5                   10                  15

Leu Ala Gly Gly Phe Phe Leu Leu Gly Phe Leu Phe Gly Trp Phe Ile
            20                  25                  30

Lys Ser Ser Ser Glu Ala Thr Asn Ile Thr Pro Lys His Asn Met Lys
        35                  40                  45

Ala Phe Leu Asp Glu Leu Lys Ala Glu Asn Ile Lys Lys Phe Leu His
    50                  55                  60

Asn Phe Thr Gln Ile Pro His Leu Ala Gly Thr Glu Gln Asn Phe Gln
65                  70                  75                  80

Leu Ala Lys Gln Ile Gln Ser Gln Trp Lys Glu Phe Gly Leu Asp Ser
                85                  90                  95

Val Glu Leu Thr His Tyr Asp Val Leu Leu Ser Tyr Pro Asn Lys Thr
            100                 105                 110

His Pro Asn Tyr Ile Ser Ile Ile Asn Glu Asp Gly Asn Glu Ile Phe
        115                 120                 125

Asn Thr Ser Leu Phe Glu Pro Pro Pro Ala Gly Tyr Glu Asn Val Ser
    130                 135                 140

Asp Ile Val Pro Pro Phe Ser Ala Phe Ser Pro Gln Gly Met Pro Glu
145                 150                 155                 160

Gly Asp Leu Val Tyr Val Asn Tyr Ala Arg Thr Glu Asp Phe Phe Lys
                165                 170                 175

Leu Glu Arg Asp Met Lys Ile Asn Cys Ser Gly Lys Ile Val Ile Ala
            180                 185                 190

Arg Tyr Gly Lys Val Phe Arg Gly Asn Lys Val Lys Asn Ala Gln Leu
        195                 200                 205

Ala Gly Ala Thr Gly Val Ile Leu Tyr Ser Asp Pro Ala Asp Tyr Phe
    210                 215                 220

Ala Pro Gly Val Lys Ser Tyr Pro Asp Gly Trp Asn Leu Pro Gly Gly
225                 230                 235                 240

Gly Val Gln Arg Gly Asn Ile Leu Asn Leu Asn Gly Ala Gly Asp Pro
                245                 250                 255

Leu Thr Pro Gly Tyr Pro Ala Asn Glu Tyr Ala Tyr Arg Arg Gly Ile
            260                 265                 270

Ala Glu Ala Val Gly Leu Pro Ser Ile Pro Val His Pro Ile Gly Tyr
        275                 280                 285

Tyr Asp Ala Gln Lys Leu Leu Glu Lys Met Gly Gly Ser Ala Ser Pro
    290                 295                 300

Asp Ser Ser Trp Arg Gly Ser Leu Lys Val Pro Tyr Asn Val Gly Pro
305                 310                 315                 320

Gly Phe Thr Gly Asn Phe Ser Thr Gln Lys Val Lys Met His Ile His
                325                 330                 335

Ser Thr Ser Glu Val Thr Arg Ile Tyr Asn Val Ile Gly Thr Leu Arg
            340                 345                 350

Gly Ala Val Glu Pro Asp Arg Tyr Val Ile Leu Gly Gly His Arg Asp
        355                 360                 365

Ser Trp Val Phe Gly Gly Ile Asp Pro Gln Ser Gly Ala Ala Val Val
    370                 375                 380

His Glu Ile Val Arg Ser Phe Gly Thr Leu Lys Lys Glu Gly Trp Arg
385                 390                 395                 400

Pro Arg Arg Thr Ile Leu Phe Ala Ser Trp Asp Ala Glu Glu Phe Gly
                405                 410                 415

Leu Leu Gly Ser Thr Glu Trp Ala Glu Glu Asn Ser Arg Leu Leu Gln
            420                 425                 430
```

```
Glu Arg Gly Val Ala Tyr Ile Asn Ala Asp Ser Ser Ile Glu Gly Asn
        435                 440                 445

Tyr Thr Leu Arg Val Asp Cys Thr Pro Leu Met Tyr Ser Leu Val Tyr
    450                 455                 460

Asn Leu Thr Lys Glu Leu Glu Ser Pro Asp Glu Gly Phe Glu Gly Lys
465                 470                 475                 480

Ser Leu Tyr Glu Ser Trp Thr Lys Lys Ser Pro Ser Pro Glu Phe Ser
                485                 490                 495

Gly Met Pro Arg Ile Ser Lys Leu Gly Ser Gly Asn Asp Phe Glu Val
            500                 505                 510

Phe Phe Gln Arg Leu Gly Ile Ala Ser Gly Arg Ala Arg Tyr Thr Lys
        515                 520                 525

Asn Trp Glu Thr Asn Lys Phe Ser Ser Tyr Pro Leu Tyr His Ser Val
    530                 535                 540

Tyr Glu Thr Tyr Glu Leu Val Glu Lys Phe Tyr Asp Pro Met Phe Lys
545                 550                 555                 560

Tyr His Leu Thr Val Ala Gln Val Arg Gly Gly Met Val Phe Glu Leu
                565                 570                 575

Ala Asn Ser Val Val Leu Pro Phe Asp Cys Arg Asp Tyr Ala Val Val
            580                 585                 590

Leu Arg Lys Tyr Ala Asp Lys Ile Tyr Asn Ile Ser Met Lys His Pro
        595                 600                 605

Gln Glu Met Lys Thr Tyr Ser Val Ser Phe Asp Ser Leu Phe Ser Ala
    610                 615                 620

Val Lys Asn Phe Thr Glu Ile Ala Ser Lys Phe Ser Glu Arg Leu Arg
625                 630                 635                 640

Asp Phe Asp Lys Ser Asn Pro Ile Leu Leu Arg Met Met Asn Asp Gln
                645                 650                 655

Leu Met Phe Leu Glu Arg Ala Phe Ile Asp Pro Leu Gly Leu Pro Asp
            660                 665                 670

Arg Pro Phe Tyr Arg His Val Ile Tyr Ala Pro Ser Ser His Asn Lys
        675                 680                 685

Tyr Ala Gly Glu Ser Phe Pro Gly Ile Tyr Asp Ala Leu Phe Asp Ile
    690                 695                 700

Glu Ser Lys Val Asp Pro Ser Gln Ala Trp Gly Glu Val Lys Arg Gln
705                 710                 715                 720

Ile Ser Ile Ala Thr Phe Thr Val Gln Ala Ala Ala Glu Thr Leu Ser
                725                 730                 735

Glu Val Ala
```

<210> SEQ ID NO 56
<211> LENGTH: 2217
<212> TYPE: DNA
<213> ORGANISM: Artificial Sequence
<220> FEATURE:
<223> OTHER INFORMATION: Synthetic Construct

<400> SEQUENCE: 56

```
atggctagcg ctagaaggcc cagatggctg tgcgctggcg ccctggtgct ggctggcgga     60

ttcttcctgc tgggcttcct gttcggctgg ttcatcaagt cctccagcga ggccaccaac    120

atcacccccca agcacaacat gaaggccttt ctggacgagc tgaaggccga gaatatcaag    180

aagttcctgc acaacttcac ccagatcccc cacctggccg gcaccgagca gaacttccag    240

ctggccaagc agatccagtc ccagtggaaa gagttcggcc tggactccgt ggaactgacc    300
```

cactacgacg tgctgctgtc ctaccccaac aagacccacc ccaactacat ctccatcatc 360
aacgaggacg gcaacgaaat cttcaacacc tccctgttcg agcccccacc agccggctac 420
gagaacgtgt ccgacatcgt gcccccattc tccgcattca gtccacaagg catgcccgag 480
ggcgacctgg tgtacgtgaa ctacgccagg accgaggact tcttcaagct ggaaagggac 540
atgaagatca actgctccgg caagatcgtg atcgccagat acggcaaggt gttcaggggc 600
aacaaagtga agaacgctca gctggctggg gccaccggcg tgatcctgta ctctgacccc 660
gccgactact tcgccccagg cgtgaagtcc taccccgacg gctggaacct gccaggtggc 720
ggagtgcaga ggggcaacat cctgaacctg aacggcgctg gcgacccccct gaccccagga 780 taccccgcca acgagtacgc ctacagaaga ggaatcgccg aggccgtggg cctgccctct 840
atcccagtgc accccatcgg ctactacgac gcccagaaac tgctggaaaa gatgggcggc 900
tccgcctccc ccgactcctc ttggagaggc tccctgaagg tgccctacaa cgtgggccca 960
ggcttcaccg gcaacttctc cacccagaaa gtgaagatgc acatccactc cacctccgaa 1020
gtgaccagga tctacaacgt gatcggcacc ctgagaggcg ccgtggaacc cgacagatac 1080
gtgatcctgg gcggccacag ggacagctgg gtgttcggcg gcatcgaccc acagtctggc 1140
gccgctgtgg tgcacgagat cgtgcggtcc ttcggaaccc tgaagaaaga gggatggcgc 1200
cccagaagga caatcctgtt cgcctcctgg gacgccgagg aattcggcct gctgggatcc 1260
accgagtggg ccgaggaaaa ctccaggctg ctgcaggaaa ggggcgtcgc ctacatcaac 1320
gccgactcct ccatcgaggg caactacacc ctgagggtgg actgcacccc cctgatgtac 1380
tccctggtgt acaacctgac caaagagctg gaatccccccg acgagggctt cgagggcaag 1440
tccctgtacg agtcctggac caagaagtcc ccatcccccg agttctccgg catgcccagg 1500
atctccaagc tgggctccgg caacgacttc gaggtgttct tccagaggct gggaatcgcc 1560
tccggcaggg ccagatacac caagaactgg gagacaaaca agttctcctc ctaccccctg 1620
taccactccg tgtacgaaac ctacgagctg gtggaaaagt tctacgaccc catgttcaag 1680
taccacctga ccgtggccca ggtccgcgga ggcatggtgt tcgagctggc caactccgtg 1740
gtgctgccct tcgactgcag agactatgct gtggtgctga ggaagtacgc cgacaaaatc 1800
tacaacatct ccatgaagca cccccaggaa atgaagacct actccgtgtc cttcgactcc 1860
ctgttctccg ccgtgaagaa tttcaccgag atcgcctcca agttctccga gaggctgagg 1920
gacttcgaca agtccaaccc catcctgctg aggatgatga acgaccagct gatgttcctg 1980
gaaagggcct tcatcgaccc cctgggcctg ccagacaggc ccttctacag gcacgtgatc 2040
tacgccccat cctcccacaa caaatacgcc ggcgagtcct tccccggcat ctacgatgcc 2100
ctgttcgaca tcgagtccaa ggtggacccc tcccaggctt ggggcgaagt gaagaggcag 2160
atcagtatcg ccacattcac agtgcaggcc gctgccgaaa ccctgtccga ggtggcc 2217

<210> SEQ ID NO 57
<211> LENGTH: 36519
<212> TYPE: DNA
<213> ORGANISM: Simian adenovirus type 25

<400> SEQUENCE: 57
ccatcttcaa taatatacct caaacttttt gtgcgcgtta atatgcaaat gaggcgtttg 60
aatttgggga ggaagggcgg tgattggtcg agggatgagc gaccgttagg ggcggggcga 120
gtgacgtttt gatgacgtgg ttgcgaggag gagccagttt gcaagttctc gtgggaaaag 180

-continued

```
tgacgtcaaa cgaggtgtgg tttgaacacg gaaatactca attttcccgc gctctctgac    240
aggaaatgag gtgtttctgg gcggatgcaa gtgaaaacgg gccattttcg cgcgaaaact    300
gaatgaggaa gtgaaaatct gagtaatttc gcgtttatgg cagggaggag tatttgccga    360
gggccgagta gactttgacc gattacgtgg gggtttcgat taccgtgttt ttcacctaaa    420
tttccgcgta cggtgtcaaa gtccggtgtt tttacgtagg tgtcagctga tcgccagggt    480
atttaaacct gcgctctcca gtcaagaggc cactcttgag tgccagcgag aagagttttc    540
tcctccgcgc cgcgagtcag atctacactt tgaaagatga ggcacctgag agacctgccc    600
gatgagaaaa tcatcatcgc ttccgggaac gagattctgg aactggtggt aaatgccatg    660
atgggcgacg accctccgga gccccccacc ccatttgaga caccttcgct gcacgatttg    720
tatgatctgg aggtggatgt gcccgaggac gatcccaatg aggaggcggt aaatgatttt    780
tttagcgatg ccgcgctgct agctgccgag gaggcttcga gctctagctc agacagcgac    840
tcttcactgc atacccctag acccggcaga ggtgagaaaa agatccccga gcttaaaggg    900
gaagagatgg acttgcgctg ctatgaggaa tgcttgcccc cgagcgatga tgaggacgag    960
caggcgatcc agaacgcagc gagccaggga gtgcaagccg ccagcgagag ctttgcgctg   1020
gactgcccgc ctctgcccgg acacggctgt aagtcttgtg aatttcatcg catgaatact   1080
ggagataaag ctgtgttgtg tgcactttgc tatatgagag cttacaacca ttgtgtttac   1140
agtaagtgtg attaagttga actttagagg gaggcagaga gcagggtgac tgggcgatga   1200
ctggtttatt tatgtatata tgttctttat ataggtcccg tctctgacgc agatgatgag   1260
acccccacta caaagtccac ttcgtcaccc ccagaaattg gcacatctcc acctgagaat   1320
attgttagac cagttcctgt tagagccact gggaggagag cagctgtgga atgtttggat   1380
gacttgctac agggtggggt tgaacctttg gacttgtgta cccggaaacg ccccaggcac   1440
taagtgccac acatgtgtgt ttacttgagg tgatgtcagt atttataggg tgtggagtgc   1500
aataaaaaat gtgttgactt taagtgcgtg gtttatgact caggggtggg gactgtgagt   1560
atataagcag gtgcagacct gtgtggttag ctcagagcgg catggagatt tggacggtct   1620
tggaagactt tcacaagact agacagctgc tagagaacgc ctcgaacgga gtctcttacc   1680
tgtggagatt ctgcttcggt ggcgacctag ctaggctagt ctacagggcc aaacaggatt   1740
atagtgaaca atttgaggtt attttgagag agtgttctgg tctttttgac gctcttaact   1800
tgggccatca gtctcacttt aaccagagga tttcgagagc ccttgatttt actactcctg   1860
gcagaaccac tgcagcagta gccttttttg cttttattct tgacaaatgg agtcaagaaa   1920
cccatttcag cagggattac cagctggatt tcttagcagt agctttgtgg agaacatgga   1980
agtgccagcg cctgaatgca atctccggct acttgccggt acagccgcta gacactctga   2040
ggatcctgaa tctccaggag agtcccaggg cacgccaacg tcgccagcag cagcagcagg   2100
aggaggatca agaagagaac ccgagagccg gcctggaccc tccggcggag gaggaggagt   2160
agctgacctg tttcctgaac tgcgccgggt gctgactagg tcttcgagtg gtcgggagag   2220
ggggattaag cgggagaggc atgatgagac taatcacaga actgaactga ctgtgggtct   2280
gatgagtcgc aagcgcccag aaacagtgtg gtggcatgag gtgcagtcga ctggcacaga   2340
tgaggtgtcg gtgatgcatg agaggttttc tctagaacaa gtcaagactt gttggttaga   2400
gcctgaggat gattgggagg tagccatcag gaattatgcc aagctggctc tgaggccaga   2460
caagaagtac aagattacta agctgataaa tatcagaaat gcctgctaca tctcagggaa   2520
tggggctgaa gtggagatct gtctccagga aagggtggct ttcagatgct gcatgatgaa   2580
```

tatgtacccg ggagtggtgg gcatggatgg ggttaccttt atgaacatga ggttcagggg 2640
agatgggtat aatggcacgg tctttatggc caataccaag ctgacagtcc atggctgctc 2700
cttctttggg tttaataaca cctgcatcga ggcctggggt caggtcggtg tgaggggctg 2760
cagtttttca gccaactgga tgggggtcgt gggcaggacc aagagtatgc tgtccgtgaa 2820
gaaatgcttg tttgagaggt gccacctggg ggtgatgagc gagggcgaag ccagaatccg 2880
ccactgcgcc tctaccgaga cgggctgctt tgtgctgtgc aagggcaatg ctaagatcaa 2940
gcataatatg atctgtggag cctcggacga gcgcggctac cagatgctga cctgcgccgg 3000
cgggaacagc catatgctgg ccaccgtaca tgtggcttcc catgctcgca agccctggcc 3060
cgagttcgag cacaatgtca tgaccaggtg caatatgcat ctggggtccc gccgaggcat 3120
gttcatgccc taccagtgca acctgaatta tgtgaaggtg ctgctggagc ccgatgccat 3180
gtccagagtg agcctgacgg gggtgtttga catgaatgtg gaggtgtgga agattctgag 3240
atatgatgaa tccaagacca ggtgccgagc ctgcgagtgc ggagggaagc atgccaggtt 3300
ccagcccgtg tgtgtggatg tgacggagga cctgcgaccc gatcatttgg tgttgccctg 3360
caccgggacg gagttcggtt ccagcgggga agaatctgac tagagtgagt agtgttctgg 3420
ggcgggggag gacctgcatg agggccagaa taactgaaat ctgtgctttt ctgtgtgttg 3480
cagcagcatg agcggaagcg gctcctttga gggaggggta ttcagccctt atctgacggg 3540
gcgtctcccc tcctgggcgg gagtgcgtca gaatgtgatg ggatccacgg tggacggccg 3600
gcccgtgcag cccgcgaact cttcaaccct gacctatgca accctgagct cttcgtcgtt 3660
ggacgcagct gccgccgcag ctgctgcatc tgccgccagc gccgtgcgcg gaatggccat 3720
gggcgccggc tactacggca ctctggtggc caactcgagt tccaccaata atcccgccag 3780
cctgaacgag gagaagctgt tgctgctgat ggcccagctc gaggccttga cccagcgcct 3840
gggcgagctg acccagcagg tggctcagct gcaggagcag acgcgggccg cggttgccac 3900
ggtgaaatcc aaataaaaaa tgaatcaata aataaacgga gacggttgtt gattttaaca 3960
cagagtctga atctttattt gatttttcgc gcgcggtagg ccctggacca ccggtctcga 4020
tcattgagca cccggtggat cttttccagg acccggtaga ggtgggcttg gatgttgagg 4080
tacatgggca tgagcccgtc ccgggggtgg aggtagctcc attgcagggc ctcgtgctcg 4140
ggggtggtgt tgtaaatcac ccagtcatag caggggcgca gggcatggtg ttgcacaata 4200
tctttgagga ggagactgat ggccacgggc agccctttgg tgtaggtgtt tacaaatctg 4260
ttgagctggg agggatgcat gcggggggag atgaggtgca tcttggcctg gatcttgaga 4320
ttggcgatgt taccgcccag atcccgcctg gggttcatgt tgtgcaggac caccagcacg 4380
gtgtatccgg tgcacttggg gaatttatca tgcaacttgg aagggaaggc gtgaaagaat 4440
ttggcgacgc ctttgtgccc gcccaggttt tccatgcact catccatgat gatggcgatg 4500
ggcccgtggg cggcggcctg ggcaaagacg tttcgggggt cggacacatc atagttgtgg 4560
tcctgggtga ggtcatcata ggccatttta atgaatttgg ggcggagggt gccggactgg 4620
gggacaaagg taccctcgat cccgggggcg tagttcccct cacagatctg catctcccag 4680
gctttgagct cggagggggg gatcatgtcc acctgcgggg cgataaagaa cacggtttcc 4740
ggggcggggg agatgagctg ggccgaaagc aagttccgga gcagctggga cttgccgcag 4800
ccggtggggc cgtagatgac cccgatgacc ggctgcaggt ggtagttgag ggagagacag 4860
ctgccgtcct cccggaggag gggggccacc tcgttcatca tctcgcgcac gtgcatgttc 4920

-continued

```
tcgcgcacca gttccgccag gaggcgctct ccccccaggg ataggagctc ctggagcgag   4980
gcgaagtttt tcagcggctt gagtccgtcg gccatgggca ttttggagag ggtttgttgc   5040
aagagttcca ggcggtccca gagctcggtg atgtgctcta cggcatctcg atccagcaga   5100
cctcctcgtt tcgcgggttg ggacggctgc gggagtaggg caccagacga tgggcgtcca   5160
gcgcagccag ggtccggtcc ttccagggtc gcagcgtccg cgtcagggtg gtctccgtca   5220
cggtgaaggg gtgcgcgccg ggctgggcgc ttgcgagggt gcgcttcagg ctcatccggc   5280
tggtcgaaaa ccgctcccga tcggcgccct gcgcgtcggc caggtagcaa ttgaccatga   5340
gttcgtagtt gagcgcctcg gccgcgtggc ctttggcgcg gagcttacct ttggaagtct   5400
gcccgcaggc gggacagagg agggacttga gggcgtagag cttgggggcg aggaagacgg   5460
actcgggggc gtaggcgtcc gcgccgcagt gggcgcagac ggtctcgcac tccacgagcc   5520
aggtgaggtc gggctggtcg gggtcaaaaa ccagtttccc gccgttcttt ttgatgcgtt   5580
tcttaccttt ggtctccatg agctcgtgtc cccgctgggt gacaaagagg ctgtccgtgt   5640
ccccgtagac cgactttatg ggccggtcct cgagcggtgt gccgcggtcc tcctcgtaga   5700
ggaaccccgc ccactccgag acgaaagccc gggtccaggc cagcacgaag gaggccacgt   5760
gggacgggta gcggtcgttg tccaccagcg ggtccacctt ttccagggta tgcaaacaca   5820
tgtcccccto gtccacatcc aggaaggtga ttggcttgta agtgtaggcc acgtgaccgg   5880
gggtcccggc cggggggta taaaagggtg cgggtccctg ctcgtcctca ctgtcttccg   5940
gatcgctgtc caggagcgcc agctgttggg gtaggtattc cctctcgaag gcgggcatga   6000
cctcggcact caggttgtca gtttctagaa acgaggagga tttgatattg acggtgccgg   6060
cggagatgcc tttcaagagc ccctcgtcca tctggtcaga aaagacgatc tttttgttgt   6120
cgagcttggt ggcgaaggag ccgtagaggg cgttggagag gagcttggcg atggagcgca   6180
tggtctggtt tttttccttg tcggcgcgct ccttggcggc gatgttgagc tgcacgtact   6240
cgcgcgccac gcacttccat tcggggaaga cggtggtcag ctcgtcgggc acgattctga   6300
cctgccagcc ccgattatgc agggtgatga ggtccacact ggtggccacc tcgccgcgca   6360
ggggctcatt agtccagcag aggcgtccgc ccttgcgcga gcagaagggg ggcagggggt   6420
ccagcatgac ctcgtcgggg gggtcggcat cgatggtgaa gatgccgggc aggaggtcgg   6480
ggtcaaagta gctgatggaa gtggccagat cgtccagggc agcttgccat tcgcgcacgg   6540
ccagcgcgcg ctcgtaggga ctgaggggcg tgccccaggg catgggatgg gtaagcgcgg   6600
aggcgtacat gccgcagatg tcgtagacgt agaggggctc ctcgaggatg ccgatgtagg   6660
tggggtagca gcgccccccg cggatgctgg cgcgcacgta gtcatacagc tcgtgcgagg   6720
gggcgaggag ccccgggccc aggttggtgc gactgggctt ttcggcgcgg tagacgatct   6780
ggcggaaaat ggcatgcgag ttggaggaga tggtgggcct ttggaagatg ttgaagtggg   6840
cgtggggcag tccgaccgag tcgcggatga agtgggcgta ggagtcttgc agcttggcga   6900
cgagctcggc ggtgactagg acgtccagag cgcagtagtc gagggtctcc tggatgatgt   6960
catacttgag ctgtcccttt tgtttccaca gctcgcggtt gagaaggaac tcttcgcggt   7020
ccttccagta ctcttcgagg gggaacccgt cctgatctgc acggtaagag cctagcatgt   7080
agaactggtt gacggccttg taggcgcagc agcccttctc cacggggagg gcgtaggcct   7140
gggcggcctt gcgcagggag gtgtgcgtga gggcgaaagt gtccctgacc atgaccttga   7200
ggaactggtg cttgaagtcg atatcgtcgc agcccccctg ctcccagagc tggaagtccg   7260
tgcgcttctt gtaggcgggg ttgggcaaag cgaaagtaac atcgttgaag aggatcttgc   7320
```

-continued

```
ccgcgcgggg cataaagttg cgagtgatgc ggaaaggttg gggcacctcg gcccggttgt   7380
tgatgacctg ggcggcgagc acgatctcgt cgaagccgtt gatgttgtgg cccacgatgt   7440
agagttccac gaatcgcgga cggcccttga cgtggggcag tttcttgagc tcctcgtagg   7500
tgagctcgtc ggggtcgctg agcccgtgct gctcgagcgc ccagtcggcg agatgggggt   7560
tggcgcggag gaaggaagtc cagagatcca cggccagggc ggtttgcaga cggtcccggt   7620
actgacggaa ctgctgcccg acggccattt tttcgggggt gacgcagtag aaggtgcggg   7680
ggtccccgtg ccagcgatcc catttgagct ggagggcgag atcgagggcg agctcgacga   7740
gccggtcgtc cccggagagt ttcatgacca gcatgaaggg gacgagctgc ttgccgaagg   7800
accccatcca ggtgtaggtt tccacatcgt aggtgaggaa gagcctttcg gtgcgaggat   7860
gcgagccgat ggggaagaac tggatctcct gccaccaatt ggaggaatgg ctgttgatgt   7920
gatggaagta gaaatgccga cggcgcgccg aacactcgtg cttgtgttta tacaagcggc   7980
cacagtgctc gcaacgctgc acgggatgca cgtgctgcac gagctgtacc tgagttcctt   8040
tgacgaggaa tttcagtggg aagtggagtc gtggcgcctg catctcgtgc tgtactacgt   8100
cgtggtggtc ggcctggccc tcttctgcct cgatggtggt catgctgacg agcccgcgcg   8160
ggaggcaggt ccagacctcg gcgcgagcgg gtcggagagc gaggacgagg gcgcgcaggc   8220
cggagctgtc cagggtcctg agacgctgcg gagtcaggtc agtgggcagc ggcggcgcgc   8280
ggttgacttg caggagtttt tccagggcgc gcgggaggtc cagatggtac ttgatctcca   8340
ccgcgccatt ggtggcgacg tcgatggctt gcagggtccc gtgcccctgg ggtgtgacca   8400
ccgtccccg tttcttcttg ggcggctggg gcgacggggg cggtgcctct tccatggtta   8460
gaagcggcgg cgaggacgcg cgccgggcgg caggggcggc tcggggcccg gaggcagggg   8520
cggcaggggc acgtcggcgc cgcgcgcggg taggttctgg tactgcgccc ggagaagact   8580
ggcgtgagcg acgacgcgac ggttgacgtc ctggatctga cgcctctggg tgaaggccac   8640
gggacccgtg agtttgaacc tgaaagagag ttcgacagaa tcaatctcgg tatcgttgac   8700
ggcggcctgc cgcaggatct cttgcacgtc gcccgagttg tcctggtagg cgatctcggt   8760
catgaactgc tcgatctcct cctcttgaag gtctccgcgg ccggcgcgct ccacggtggc   8820
cgcgaggtcg ttggagatgc ggcccatgag ctgcgagaag gcgttcatgc ccgcctcgtt   8880
ccagacgcgg ctgtagacca cgacgccctc gggatcgccg gcgcgcatga ccacctgggc   8940
gaggttgagc tccacgtggc gcgtgaagac cgcgtagttg cagaggcgct ggtagaggta   9000
gttgagcgtg gtggcgatgt gctcggtgac gaagaaatac atgatccagc ggcggagcgg   9060
catctcgctg acgtcgccca gcgcctccaa acgttccatg gcctcgtaaa agtccacggc   9120
gaagttgaaa aactgggagt tgcgcgccga gacggtcaac tcctcctcca gaagacggat   9180
gagctcggcg atggtggcgc gcacctcgcg ctcgaaggcc cccgggagtt cctccacttc   9240
ctcttcttcc tcctccacta acatctcttc tacttcctcc tcaggcggca gtggtggcgg   9300
gggagggggc ctgcgtcgcc ggcggcgcac gggcagacgg tcgatgaagc gctcgatggt   9360
ctcgccgcgc cggcgtcgca tggtctcggt gacggcgcgc ccgtcctcgc ggggccgcag   9420
cgtgaagacg ccgccgcgca tctccaggtg gccgggggggg tccccgttgg gcagggagag   9480
ggcgctgacg atgcatctta tcaattgccc cgtagggact ccgcgcaagg acctgagcgt   9540
ctcgagatcc acgggatctg aaaaccgctg aacgaaggct tcgagccagt cgcagtcgca   9600
aggtaggctg agcacggttt cttctggcgg gtcatgttgg ttgggagcgg ggcgggcgat   9660
```

-continued

```
gctgctggtg atgaagttga aataggcggt tctgagacgg cggatggtgg cgaggagcac   9720
caggtctttg ggcccggctt gctggatgcg cagacggtcg gccatgcccc aggcgtggtc   9780
ctgacacctg gccaggtcct tgtagtagtc ctgcatgagc cgctccacgg gcacctcctc   9840
ctcgcccgcg cggccgtgca tgcgcgtgag cccgaagccg cgctggggct ggacgagcgc   9900
caggtcggcg acgacgcgct cggcgaggat ggcttgctgg atctgggtga gggtggtctg   9960
gaagtcatca aagtcgacga agcggtggta ggctccggtg ttgatggtgt aggagcagtt  10020
ggccatgacg gaccagttga cggtctggtg gcccggacgc acgagctcgt ggtacttgag  10080
gcgcgagtag gcgcgcgtgt cgaagatgta gtcgttgcag gtgcgcacca ggtactggta  10140
gccgatgagg aagtgcggcg gcggctggcg gtagagcggc catcgctcgg tggcgggggc  10200
gccgggcgcg aggtcctcga gcatggtgcg gtggtagccg tagatgtacc tggacatcca  10260
ggtgatgccg gcggcggtgg tggaggcgcg cgggaactcg cggacgcggt tccagatgtt  10320
gcgcagcggc aggaagtagt tcatggtggg cacggtctgg cccgtgaggc gcgcgcagtc  10380
gtggatgctc tatacgggca aaaacgaaag cggtcagcgg ctcgactccg tggcctggag  10440
gctaagcgaa cgggttgggc tgcgcgtgta ccccggttcg aatctcgaat caggctggag  10500
ccgcagctaa cgtggtattg gcactcccgt ctcgacccaa gcctgcacca accctccagg  10560
atacggaggc gggtcgtttt gcaacttttt tttggaggcc ggatgagact agtaagcgcg  10620
gaaagcggcc gaccgcgatg gctcgctgcc gtagtctgga gaagaatcgc cagggttgcg  10680
ttgcggtgtg ccccggttcg aggccggccg gattccgcgg ctaacgaggg cgtggctgcc  10740
ccgtcgtttc caagacccca tagccagccg acttctccag ttacggagcg agcccctctt  10800
ttgttttgtt tgtttttgcc agatgcatcc cgtactgcgg cagatgcgcc cccaccaccc  10860
tccaccgcaa caacagcccc ctccacagcc ggcgcttctg cccccgcccc agcagcaact  10920
tccagccacg accgccgcgg ccgccgtgag cggggctgga cagagttatg atcaccagct  10980
ggccttggaa gagggcgagg ggctggcgcg cctgggggcg tcgtcgccgg agcggcaccc  11040
gcgcgtgcag atgaaaaggg acgctcgcga ggcctacgtg cccaagcaga acctgttcag  11100
agacaggagc ggcgaggagc ccgaggagat gcgcgcggcc cggttccacg cggggcggga  11160
gctgcggcgc ggcctggacc gaaagagggt gctgagggac gaggatttcg aggcggacga  11220
gctgacgggg atcagccccg cgcgcgcgca cgtggccgcg gccaacctgg tcacggcgta  11280
cgagcagacc gtgaaggagg agagcaactt ccaaaaatcc ttcaacaacc acgtgcgcac  11340
cctgatcgcg cgcgaggagg tgaccctggg cctgatgcac ctgtgggacc tgctggaggc  11400
catcgtgcag aaccccacca gcaagccgct gacggcgcag ctgttcctgg tggtgcagca  11460
tagtcgggac aacgaagcgt tcagggaggc gctgctgaat atcaccgagc ccgagggccg  11520
ctggctcctg gacctggtga acattctgca gagcatcgtg gtgcaggagc gcgggctgcc  11580
gctgtccgag aagctggcgg ccatcaactt ctcggtgctg agtttgggca agtactacgc  11640
taggaagatc tacaagaccc cgtacgtgcc catagacaag gaggtgaaga tcgacgggtt  11700
ttacatgcgc atgaccctga aagtgctgac cctgagcgac gatctggggg tgtaccgcaa  11760
cgacaggatg caccgtgcgg tgagcgccag caggcggcgc gagctgagcg accaggagct  11820
gatgcatagt ctgcagcggg ccctgaccgg ggccgggacc gagggggaga gctactttga  11880
catgggcgcg gacctgcact ggcagcccag ccgccgggcc ttggaggcgg cggcaggacc  11940
ctacgtagaa gaggtggacg atgaggtgga cgaggagggc gagtacctgg aagactgatg  12000
gcgcgaccgt atttttgcta gatgcaacaa caacagccac ctcctgatcc cgcgatgcgg  12060
```

gcggcgctgc agagccagcc gtccggcatt aactcctcgg acgattggac ccaggccatg 12120
caacgcatca tggcgctgac gacccgcaac cccgaagcct ttagacagca gccccaggcc 12180
aaccggctct cggccatcct ggaggccgtg gtgccctcgc gctccaaccc cacgcacgag 12240
aaggtcctgg ccatcgtgaa cgcgctggtg gagaacaagg ccatccgcgg cgacgaggcc 12300
ggcctggtgt acaacgcgct gctggagcgc gtggcccgct acaacagcac caacgtgcag 12360
accaacctgg accgcatggt gaccgacgtg cgcgaggccg tggcccagcg cgagcggttc 12420
caccgcgagt ccaacctggg atccatggtg gcgctgaacg ccttcctcag cacccagccc 12480
gccaacgtgc cccggggcca ggaggactac accaacttca tcagcgccct gcgcctgatg 12540
gtgaccgagg tgccccagag cgaggtgtac cagtccgggc cggactactt cttccagacc 12600
agtcgccagg gcttgcagac cgtgaacctg agccaggctt tcaagaactt gcagggcctg 12660
tggggcgtgc aggccccggt cggggaccgc gcgacggtgt cgagcctgct gacgccgaac 12720
tcgcgcctgc tgctgctgct ggtggccccc ttcacggaca gcggcagcat caaccgcaac 12780
tcgtacctgg gctacctgat taacctgtac cgcgaggcca tcggccaggc gcacgtggac 12840
gagcagacct accaggagat cacccacgtg agccgcgccc tgggccagga cgacccgggc 12900
aacctggaag ccaccctgaa ctttttgctg accaaccggt cgcagaagat cccgccccag 12960
tacgcgctca gcaccgagga ggagcgcatc ctgcgttacg tgcagcagag cgtgggcctg 13020
ttcctgatgc aggagggggc cacccccagc gccgcgctcg acatgaccgc gcgcaacatg 13080
gagcccagca tgtacgccag caaccgcccg ttcatcaata aactgatgga ctacttgcat 13140
cgggcggccg ccatgaactc tgactatttc accaacgcca tcctgaatcc ccactggctc 13200
ccgccgccgg ggttctacac gggcgagtac gacatgcccg accccaatga cgggttcctg 13260
tgggacgatg tggacagcag cgtgttctcc ccccgaccgg gtgctaacga gcgccccttg 13320
tggaagaagg aaggcagcga ccgacgcccg tcctcggcgc tgtccggccg cgagggtgct 13380
gccgcggcgg tgcccgaggc cgccagtcct ttcccgagct tgcccttctc gctgaacagt 13440
atccgcagca gcgagctggg caggatcacg cgcccgcgct tgctgggcga agaggagtac 13500
ttgaatgact cgctgttgag acccgagcgg gagaagaact tccccaataa cgggatagaa 13560
agcctggtgg acaagatgag ccgctggaag acgtatgcgc aggagcacag ggacgatccc 13620
cgggcgtcgc agggggccac gagccggggc agcgccgccc gtaaacgccg gtggcacgac 13680
aggcagcggg gacagatgtg ggacgatgag gactccgccg acgacagcag cgtgttggac 13740
ttgggtggga gtggtaaccc gttcgctcac ctgcgccccc gtatcgggcg catgatgtaa 13800
gagaaaccga aaataaatga tactcaccaa ggccatggcg accagcgtgc gttcgtttct 13860
tctctgttgt tgttgtatct agtatgatga ggcgtgcgta cccggagggt cctcctccct 13920
cgtacgagag cgtgatgcag caggcgatgg cggcggcggc gatgcagccc ccgctggagg 13980
ctccttacgt gcccccgcgg tacctggcgc ctacggaggg gcggaacagc attcgttact 14040
cggagctggc acccttgtac gataccaccc ggttgtacct ggtggacaac aagtcggcgg 14100
acatcgcctc gctgaactac cagaacgacc acagcaactt cctgaccacc gtggtgcaga 14160
acaatgactt cacccccacg gaggccagca cccagaccat caactttgac gagcgctcgc 14220
ggtggggcgg ccagctgaaa accatcatgc acaccaacat gcccaacgtg aacgagttca 14280
tgtacagcaa caagttcaag gcgcgggtga tggtctcccg caagaccccc aatggggtga 14340
cagtgacaga ggattatgat ggtagtcagg atgagctgaa gtatgaatgg gtggaatttg 14400
agctgcccga aggcaacttc tcggtgacca tgaccatcga cctgatgaac aacgccatca 14460
tcgacaatta cttggcggtg gggcggcaga acggggtgct ggagagcgac atcggcgtga 14520
agttcgacac taggaacttc aggctgggct gggaccccgt gaccgagctg gtcatgcccg 14580
gggtgtacac caacgaggct ttccatcccg atattgtctt gctgcccggc tgcggggtgg 14640
acttcaccga gagccgcctc agcaacctgc tgggcattcg caagaggcag cccttccagg 14700
aaggcttcca gatcatgtac gaggatctgg aggggggcaa catccccgcg ctcctggatg 14760
tcgacgccta tgagaaaagc aaggaggatg cagcagctga agcaactgca gccgtagcta 14820
ccgcctctac cgaggtcagg ggcgataatt ttgcaagcgc cgcagcagtg gcagcggccg 14880
aggcggctga aaccgaaagt aagatagtca ttcagccggt ggagaaggat agcaagaaca 14940
ggagctacaa cgtactaccg gacaagataa acaccgccta ccgcagctgg tacctagcct 15000
acaactatgg cgaccccgag aagggcgtgc gctcctggac gctgctcacc acctcggacg 15060
tcacctgcgg cgtggagcaa gtctactggt cgctgcccga catgatgcaa gacccggtca 15120
ccttccgctc cacgcgtcaa gttagcaact acccggtggt gggcgccgag ctcctgcccg 15180
tctactccaa gagcttcttc aacgagcagg ccgtctactc gcagcagctg cgcgccttca 15240
cctcgcttac gcacgtcttc aaccgcttcc ccgagaacca gatcctcgtc cgcccgcccg 15300
cgcccaccat taccaccgtc agtgaaaacg ttcctgctct cacagatcac gggaccctgc 15360
cgctgcgcag cagtatccgg ggagtccagc gcgtgaccgt tactgacgcc agacgccgca 15420
cctgccccta cgtctacaag gccctgggca tagtcgcgcc gcgcgtcctc tcgagccgca 15480
ccttctaaat gtccattctc atctcgccca gtaataacac cggttggggc ctgcgcgcgc 15540
ccagcaagat gtacggaggc gctcgccaac gctccacgca acaccccgtg cgcgtgcgcg 15600
ggcacttccg cgctccctgg ggcgccctca agggccgcgt gcggtcgcgc accaccgtcg 15660
acgacgtgat cgaccaggtg gtggccgacg cgcgcaacta cacccccgcc gccgcgcccg 15720
tctccaccgt ggacgccgtc atcgacagcg tggtggcgga cgcgcgccgg tacgcccgcg 15780
ccaagagccg gcggcggcgc atcgcccggc ggcaccggag cacccccgcc atgcgcgcgg 15840
cgcgagcctt gctgcgcagg gccaggcgca cgggacgcag ggccatgctc agggcggcca 15900
gacgcgcggc ttcaggcgcc agcgccggca ggacccggag acgcgcggcc acggcggcgg 15960
cagcggccat cgccagcatg tcccgcccgc ggcgagggaa cgtgtactgg gtgcgcgacg 16020
ccgccaccgg tgtgcgcgtg cccgtgcgca cccgcccccc tcgcacttga agatgttcac 16080
ttcgcgatgt tgatgtgtcc cagcggcgag gaggatgtcc aagcgcaaat tcaaggaaga 16140
gatgctccag gtcatcgcgc ctgagatcta cggccctgcg gtggtgaagg aggaaagaaa 16200
gccccgcaaa atcaagcggg tcaaaaagga caaaaaggaa gaagaaagtg atgtggacgg 16260
attggtggag tttgtgcgcg agttcgcccc ccggcggcgc gtgcagtggc gcgggcggaa 16320
ggtgcaaccg gtgctgagac ccggcaccac cgtggtcttc acgcccggcg agcgctccgg 16380
caccgcttcc aagcgctcct acgacgaggt gtacggggat gatgatattc tggagcaggc 16440
ggccgagcgc ctgggcgagt ttgcttacgg caagcgcagc cgttccgcac cgaaggaaga 16500
ggcggtgtcc atcccgctgg accacggcaa ccccacgccg agcctcaagc ccgtgacctt 16560
gcagcaggtg ctgccgaccg cggcgccgcg ccgggggttc aagcgcgagg gcgaggatct 16620
gtaccccacc atgcagctga tggtgcccaa gcgccagaag ctggaagacg tgctggagac 16680
catgaaggtg gacccggacg tgcagcccga ggtcaaggtg cggcccatca agcaggtggc 16740
cccgggcctg ggcgtgcaga ccgtggacat caagattccc acggagccca tggaaacgca 16800

-continued gaccgagccc atgatcaagc ccagcaccag caccatggag gtgcagacgg atccctggat 16860
gccatcggct cctagtcgaa gaccccggcg caagtacggc gcggccagcc tgctgatgcc 16920
caactacgcg ctgcatcctt ccatcatccc cacgccgggc taccgcggca cgcgcttcta 16980
ccgcggtcat accagcagcc gccgccgcaa gaccaccact cgccgccgcc gtcgccgcac 17040
cgccgctgca accacccctg ccgccctggt gcggagagtg taccgccgcg gccgcgcacc 17100
tctgaccctg ccgcgcgcgc gctaccaccc gagcatcgcc atttaaactt tcgccagctt 17160
tgcagatcaa tggccctcac atgccgcctt cgcgttccca ttacgggcta ccgaggaaga 17220
aaaccgcgcc gtagaaggct ggcggggaac gggatgcgtc gccaccacca ccggcggcgg 17280
cgcgccatca gcaagcggtt ggggggaggc ttcctgcccg cgctgatccc catcatcgcc 17340
gcggcgatcg gggcgatccc cggcattgct tccgtggcgg tgcaggcctc tcagcgccac 17400
tgagacacac ttggaaacat cttgtaataa acccatggac tctgacgctc ctggtcctgt 17460
gatgtgtttt cgtagacaga tggaagacat caatttttcg tccctggctc cgcgacacgg 17520
cacgcggccg ttcatgggca cctggagcga catcggcacc agccaactga acgggggcgc 17580
cttcaattgg agcagtctct ggagcgggct taagaatttc gggtccacgc ttaaaaccta 17640
tggcagcaag gcgtggaaca gcaccacagg gcaggcgctg agggataagc tgaaagagca 17700
gaacttccag cagaaggtgg tcgatgggct cgcctcgggc atcaacgggg tggtggacct 17760
ggccaaccag gccgtgcagc ggcagatcaa cagccgcctg gacccggtgc cgcccgccgg 17820
ctccgtggag atgccgcagg tggaggagga gctgcctccc ctggacaagc ggggcgagaa 17880
gcgaccccgc cccgatgcgg aggagacgct gctgacgcac acggacgagc cgcccccgta 17940
cgaggaggcg gtgaaactgg gtctgcccac cacgcggccc atcgcgcccc tggccaccgg 18000
ggtgctgaaa cccgaaaagc ccgcgaccct ggacttgcct cctccccagc cttcccgccc 18060
ctctacagtg gctaagcccc tgccgccggt ggccgtggcc cgcgcgcgac ccgggggcac 18120
cgcccgccct catgcgaact ggcagagcac tctgaacagc atcgtgggtc tgggagtgca 18180
gagtgtgaag cgccgccgct gctattaaac ctaccgtagc gcttaacttg cttgtctgtg 18240
tgtgtatgta ttatgtcgcc gccgccgctg tccaccagaa ggaggagtga agaggcgcgt 18300
cgccgagttg caagatggcc accccatcga tgctgcccca gtgggcgtac atgcacatcg 18360
ccggacagga cgcttcggag tacctgagtc cgggtctggt gcagtttgcc cgcgccacag 18420
acacctactt cagtctgggg aacaagttta ggaaccccac ggtggcgccc acgcacgatg 18480
tgaccaccga ccgcagccag cggctgacgc tgcgcttcgt gcccgtggac cgcgaggaca 18540
acacctactc gtacaaagtg cgctacacgc tggccgtggg cgacaaccgc gtgctggaca 18600
tggccagcac ctactttgac atccgcggcg tgctggatcg gggccctagc ttcaaaccct 18660
actccggcac cgcctacaac agtctggccc ccaagggagc acccaacact tgtcagtgga 18720
catataaagc cgatggtgaa actgccacag aaaaaaccta tacatatgga aatgcacccg 18780
tgcagggcat taacatcaca aaagatggta ttcaacttgg aactgacacc gatgatcagc 18840
caatctacgc agataaaacc tatcagcctg aacctcaagt gggtgatgct gaatggcatg 18900
acatcactgg tactgatgaa aagtatggag gcagagctct taagcctgat accaaaatga 18960
agccttgtta tggttctttt gccaagccta ctaataaaga aggaggtcag gcaaatgtga 19020
aaacaggaac aggcactact aaagaatatg acatagacat ggctttcttt gacaacagaa 19080
gtgcggctgc tgctggccta gctccagaaa ttgttttgta tactgaaaat gtggatttgg 19140

-continued

```
aaactccaga tacccatatt gtatacaaag caggcacaga tgacagcagc tcttctatta  19200
atttgggtca gcaagccatg cccaacagac ctaactacat tggtttcaga gacaacttta  19260
tcgggctcat gtactacaac agcactggca atatgggggt gctggccggt caggcttctc  19320
agctgaatgc tgtggttgac ttgcaagaca gaaacaccga gctgtcctac cagctcttgc  19380
ttgactctct gggtgacaga acccggtatt tcagtatgtg gaatcaggcg gtggacagct  19440
atgatcctga tgtgcgcatt attgaaaatc atggtgtgga ggatgaactt cccaactatt  19500
gtttccctct ggatgctgtt ggcagaacag atacttatca gggaattaag gctaatggaa  19560
ctgatcaaac cacatggacc aaagatgaca gtgtcaatga tgctaatgag ataggcaagg  19620
gtaatccatt cgccatggaa atcaacatcc aagccaacct gtggaggaac ttcctctacg  19680
ccaacgtggc cctgtacctg cccgactctt acaagtacac gccggccaat gttaccctgc  19740
ccaccaacac caacacctac gattacatga acggccgggt ggtggcgccc tcgctggtgg  19800
actcctacat caacatcggg gcgcgctggt cgctggatcc catggacaac gtgaacccct  19860
tcaaccacca ccgcaatgcg gggctgcgct accgctccat gctcctgggc aacgggcgct  19920
acgtgccctt ccacatccag gtgccccaga aatttttcgc catcaagagc ctcctgctcc  19980
tgcccgggtc ctacacctac gagtggaact tccgcaagga cgtcaacatg atcctgcaga  20040
gctccctcgg caacgacctg cgcacggacg gggcctccat ctccttcacc agcatcaacc  20100
tctacgccac cttcttcccc atggcgcaca acacggcctc cacgctcgag gccatgctgc  20160
gcaacgacac caacgaccag tccttcaacg actacctctc ggcggccaac atgctctacc  20220
ccatcccggc caacgccacc aacgtgccca tctccatccc ctcgcgcaac tgggccgcct  20280
tccgcggctg gtccttcacg cgtctcaaga ccaaggagac gccctcgctg ggctccgggt  20340
tcgaccccta cttcgtctac tcgggctcca tcccctacct cgacggcacc ttctacctca  20400
accacacctt caagaaggtc tccatcacct tcgactcctc cgtcagctgg cccggcaacg  20460
accggctcct gacgcccaac gagttcgaaa tcaagcgcac cgtcgacggc gagggctaca  20520
acgtggccca gtgcaacatg accaaggact ggttcctggt ccagatgctg gcccactaca  20580
acatcggcta ccagggcttc tacgtgcccg agggctacaa ggaccgcatg tactccttct  20640
tccgcaactt ccagcccatg agccgccagg tggtggacga ggtcaactac aaggactacc  20700
aggccgtcac cctggcctac cagcacaaca actcgggctt cgtcggctac ctcgcgccca  20760
ccatgcgcca gggccagccc taccccgcca actaccccta cccgctcatc ggcaagagcg  20820
ccgtcaccag cgtcacccag aaaaagttcc tctgcgacag ggtcatgtgg cgcatcccct  20880
tctccagcaa cttcatgtcc atgggcgcgc tcaccgacct cggccagaac atgctctatg  20940
ccaactccgc ccacgcgcta gacatgaatt tcgaagtcga ccccatggat gagtccaccc  21000
ttctctatgt tgtcttcgaa gtcttcgacg tcgtccgagt gcaccagccc caccgcggcg  21060
tcatcgaggc cgtctacctg cgcaccccct tctcggccgg taacgccacc acctaagctc  21120
ttgcttcttg caagccatgg ccgcgggctc cggcgagcag gagctcaggg ccatcatccg  21180
cgacctgggc tgcgggccct acttcctggg caccttcgat aagcgcttcc cgggattcat  21240
ggccccgcac aagctggcct gcgccatcgt caacacggcc ggccgcgaga ccgggggcga  21300
gcactggctg gccttcgcct ggaacccgcg ctcgaacacc tgctacctct tcgacccctt  21360
cgggttctcg gacgagcgcc tcaagcagat ctaccagttc gagtacgagg gcctgctgcg  21420
ccgcagcgcc ctggccaccg aggaccgctg cgtcaccctg gaaaagtcca cccagaccgt  21480
gcagggtccg cgctcggccg cctgcgggct cttctgctgc atgttcctgc acgccttcgt  21540
```

-continued

```
gcactggccc gaccgcccca tggacaagaa ccccaccatg aacttgctga cgggggtgcc  21600
caacggcatg ctccagtcgc cccaggtgga acccaccctg cgccgcaacc aggaggcgct  21660
ctaccgcttc ctcaactccc actccgccta ctttcgctcc caccgcgcgc gcatcgagaa  21720
ggccaccgcc ttcgaccgca tgaatcaaga catgtaaacc gtgtgtgtat gttaaatgtc  21780
tttaataaac agcactttca tgttacacat gcatctgaga tgatttattt agaaatcgaa  21840
agggttctgc cgggtctcgg catggcccgc gggcagggac acgttgcgga actggtactt  21900
ggccagccac ttgaactcgg ggatcagcag tttgggcagc ggggtgtcgg ggaaggagtc  21960
ggtccacagc ttccgcgtca gttgcagggc gcccagcagg tcgggcgcgg agatcttgaa  22020
atcgcagttg ggacccgcgt tctgcgcgcg ggagttgcgg tacacggggt tgcagcactg  22080
gaacaccatc agggccgggt gcttcacgct cgccagcacc gtcgcgtcgg tgatgctctc  22140
cacgtcgagg tcctcggcgt tggccatccc gaagggggtc atcttgcagg tctgccttcc  22200
catggtgggc acgcacccgg gcttgtggtt gcaatcgcag tgcaggggga tcagcatcat  22260
ctgggcctgg tcggcgttca tccccgggta catggccttc atgaaagcct ccaattgcct  22320
gaacgcctgc tgggccttgg ctccctcggt gaagaagacc ccgcaggact tgctagagaa  22380
ctggttggtg gcgcacccgg cgtcgtgcac gcagcagcgc gcgtcgttgt tggccagctg  22440
caccacgctg cgcccccagc ggttctgggt gatcttggcc cggtcggggt tctccttcag  22500
cgcgcgctgc ccgttctcgc tcgccacatc catctcgatc atgtgctcct tctggatcat  22560
ggtggtcccg tgcaggcacc gcagcttgcc ctcggcctcg gtgcacccgt gcagccacag  22620
cgcgcacccg gtgcactccc agttcttgtg ggcgatctgg gaatgcgcgt gcacgaagcc  22680
ctgcaggaag cggcccatca tggtggtcag ggtcttgttg ctagtgaagg tcagcggaat  22740
gccgcggtgc tcctcgttga tgtacaggtg gcagatgcgg cggtacacct cgccctgctc  22800
gggcatcagc tggaagttgg ctttcaggtc ggtctccacg cggtagcggt ccatcagcat  22860
agtcatgatt tccataccct tctcccaggc cgagacgatg ggcaggctca tagggttctt  22920
caccatcatc ttagcgctag cagccgcggc caggggggtcg ctctcgtcca gggtctcaaa  22980
gctccgcttg ccgtccttct cggtgatccg caccgggggg tagctgaagc ccacggccgc  23040
cagctcctcc tcggcctgtc tttcgtcctc gctgtcctgg ctgacgtcct gcaggaccac  23100
atgcttggtc ttgcggggtt tcttcttggg cggcagcggc ggcggagatg ttggagatgg  23160
cgagggggag cgcgagttct cgctcaccac tactatctct tcctcttctt ggtccgaggc  23220
cacgcggcgg taggtatgtc tcttcggggg cagaggcgga ggcgacgggc tctcgccgcc  23280
gcgacttggc ggatggctgg cagagcccct tccgcgttcg ggggtgcgct cccggcggcg  23340
ctctgactga cttcctccgc ggccggccat tgtgttctcc tagggaggaa caacaagcat  23400
ggagactcag ccatcgccaa cctcgccatc tgccccccacc gccgacgaga agcagcagca  23460
gcagaatgaa agcttaaccg ccccgccgcc cagccccgcc acctccgacg cggccgtccc  23520
agacatgcaa gagatggagg aatccatcga gattgacctg ggctatgtga cgcccgcgga  23580
gcacgaggag gagctggcag tgcgcttttc acaagaagag atacaccaag aacagccaga  23640
gcaggaagca gagaatgagc agagtcaggc tgggctcgag catgacggcg actacctcca  23700
cctgagcggg ggggaggacg cgctcatcaa gcatctggcc cggcaggcca ccatcgtcaa  23760
ggatgcgctg ctcgaccgca ccgaggtgcc cctcagcgtg gaggagctca gccgcgccta  23820
cgagttgaac ctcttctcgc cgcgcgtgcc ccccaagcgc cagcccaatg gcacctgcga  23880
```

```
gcccaacccg cgcctcaact tctacccggt cttcgcggtg cccgaggccc tggccaccta  23940
ccacatcttt ttcaagaacc aaaagatccc cgtctcctgc cgcgccaacc gcacccgcgc  24000
cgacgccctt ttcaacctgg gtcccggcgc ccgcctacct gatatcgcct ccttggaaga  24060
ggttcccaag atcttcgagg gtctgggcag cgacgagact cgggccgcga acgctctgca  24120
aggagaagga ggagagcatg agcaccacag cgccctggtc gagttggaag gcgacaacgc  24180
gcggctggcg gtgctcaaac gcacggtcga gctgacccat ttcgcctacc cggctctgaa  24240
cctgcccccc aaagtcatga gcgcggtcat ggaccaggtg ctcatcaagc gcgcgtcgcc  24300
catctccgag gacgagggca tgcaagactc cgaggagggc aagcccgtgg tcagcgacga  24360
gcagctggcc cggtggctgg gtcctaatgc tagtccccag agtttggaag agcggcgcaa  24420
actcatgatg gccgtggtcc tggtgaccgt ggagctggag tgcctgcgcc gcttcttcgc  24480
cgacgcggag accctgcgca aggtcgagga gaacctgcac tacctcttca ggcacgggtt  24540
cgtgcgccag gcctgcaaga tctccaacgt ggagctgacc aacctggtct cctacatggg  24600
catcttgcac gagaaccgcc tggggcagaa cgtgctgcac accaccctgc gcggggaggc  24660
ccggcgcgac tacatccgcg actgcgtcta cctctacctc tgccacacct ggcagacggg  24720
catgggcgtg tggcagcagt gtctggagga gcagaacctg aaagagctct gcaagctcct  24780
gcagaagaac ctcaagggtc tgtggaccgg gttcgacgag cgcaccaccg cctcggacct  24840
ggccgacctc attttccccg agcgcctcag gctgacgctg cgcaacggcc tgcccgactt  24900
tatgagccaa agcatgttgc aaaactttcg ctctttcatc ctcgaacgct ccggaatcct  24960
gcccgccacc tgctccgcgc tgccctcgga cttcgtgccg ctgaccttcc gcgagtgccc  25020
cccgccgctg tggagccact gctacctgct gcgcctggcc aactacctgg cctaccactc  25080
ggacgtgatc gaggacgtca gcggcgaggg cctgctcgag tgccactgcc gctgcaacct  25140
ctgcacgccg caccgctccc tggcctgcaa cccccagctg ctgagcgaga cccagatcat  25200
cggcaccttc gagttgcaag ggcccagcga aggcgagggt tcagccgcca agggggggtct  25260
gaaactcacc ccggggctgt ggacctcggc ctacttgcgc aagttcgtgc ccgaggacta  25320
ccatcccttc gagatcaggt tctacgagga ccaatcccat ccgcccaagg ccgagctgtc  25380
ggcctgcgtc atcacccagg gggcgatcct ggcccaattg caagccatcc agaaatcccg  25440
ccaagaattc ttgctgaaaa agggccgcgg ggtctacctc gacccccaga ccggtgagga  25500
gctcaacccc ggcttccccc aggatgcccc gaggaaacaa gaagctgaaa gtggagctgc  25560
cgcccgtgga ggatttggag gaagactggg agaacagcag tcaggcagag gaggaggaga  25620
tggaggaaga ctgggacagc actcaggcag aggaggacag cctgcaagac agtctggagg  25680
aagacgagga ggaggcagag gaggaggtgg aagaagcagc cgccgccaga ccgtcgtcct  25740
cggcggggga gaaagcaagc agcacggata ccatctccgc tccgggtcgg ggtcccgctc  25800
gaccacacag tagatgggac gagaccggac gattcccgaa ccccaccacc cagaccggta  25860
agaaggagcg gcagggatac aagtcctggc gggggcacaa aaacgccatc gtctcctgct  25920
tgcaggcctg cgggggcaac atctccttca cccggcgcta cctgctcttc caccgcgggg  25980
tgaactttcc ccgcaacatc ttgcattact accgtcacct ccacagcccc tactacttcc  26040
aagaagaggc agcagcagca gaaaaagacc agcagaaaac cagcagctag aaaatccaca  26100
gcggcggcag caggtggact gaggatcgcg gcgaacgagc cggcgcaaac ccgggagctg  26160
aggaaccgga tctttcccac cctctatgcc atcttccagc agagtcgggg gcaggagcag  26220
gaactgaaag tcaagaaccg ttctctgcgc tcgctcaccc gcagttgtct gtatcacaag  26280
```

```
agcgaagacc aacttcagcg cactctcgag gacgccgagg ctctcttcaa caagtactgc  26340
gcgctcactc ttaaagagta gcccgcgccc gcccagtcgc agaaaaaggc gggaattacg  26400
tcacctgtgc ccttcgccct agccgcctcc acccatcatc atgagcaaag agattcccac  26460
gccttacatg tggagctacc agccccagat gggcctggcc gccggtgccg cccaggacta  26520
ctccacccgc atgaattggc tcagcgccgg gcccgcgatg atctcacggg tgaatgacat  26580
ccgcgcccac cgaaaccaga tactcctaga acagtcagcg ctcaccgcca cgccccgcaa  26640
tcacctcaat ccgcgtaatt ggcccgccgc cctggtgtac caggaaattc cccagcccac  26700
gaccgtacta cttccgcgag acgcccaggc cgaagtccag ctgactaact caggtgtcca  26760
gctggcgggc ggcgccaccc tgtgtcgtca ccgccccgct cagggtataa agcggctggt  26820
gatccggggc agaggcacac agctcaacga cgaggtggtg agctcttcgc tgggtctgcg  26880
acctgacgga gtcttccaac tcgccggatc ggggagatct tccttcacgc ctcgtcaggc  26940
cgtcctgact ttggagagtt cgtcctcgca gccccgctcg ggtggcatcg gcactctcca  27000
gttcgtggag gagttcactc cctcggtcta cttcaacccc ttctccggct cccccggcca  27060
ctacccggac gagttcatcc cgaacttcga cgccatcagc gagtcggtgg acggctacga  27120
ttgaatgtcc catggtggcg cagctgacct agctcggctt cgacacctgg accactgccg  27180
ccgcttccgc tgcttcgctc gggatctcgc cgagtttgcc tactttgagc tgcccgagga  27240
gcaccctcag ggcccggccc acggagtgcg gatcgtcgtc gaagggggcc tcgactccca  27300
cctgcttcgg atcttcagcc agcgtccgat cctggtcgag cgcgagcaag gacagaccct  27360
tctgactctg tactgcatct gcaaccaccc cggcctgcat gaaagtcttt gttgtctgct  27420
gtgtactgag tataataaaa gctgagatca gcgactactc cggacttccg tgtgttcctg  27480
aatccatcaa ccagtctttg ttcttcaccg ggaacgagac cgagctccag ctccagtgta  27540
agccccacaa gaagtacctc acctggctgt tccagggctc cccgatcgcc gttgtcaacc  27600
actgcgacaa cgacggagtc ctgctgagcg gccctgccaa ccttactttt tccacccgca  27660
gaagcaagct ccagctcttc caacccttcc tccccgggac ctatcagtgc gtctcgggac  27720
cctgccatca caccttccac ctgatcccga ataccacagc gtcgctcccc gctactaaca  27780
accaaactaa cctccaccaa cgccaccgtc gcgacctttc tgaatctaat actaccaccc  27840
acaccggagg tgagctccga ggtcaaccaa cctctgggat ttactacggc ccctgggagg  27900
tggttgggtt aatagcgcta ggcctagttg cgggtgggct tttggttctc tgctacctat  27960
acctcccttg ctgttcgtac ttagtggtgc tgtgttgctg gtttaagaaa tggggaagat  28020
caccctagtg agctgcggtg cgctggtggc ggtgttgctt tcgattgtgg gactgggcgg  28080
tgcggctgta gtgaaggaga aggccgatcc ctgcttgcat ttcaatccca acaaatgcca  28140
gctgagtttt cagcccgatg gcaatcggtg cgcggtactg atcaagtgcg gatgggaatg  28200
cgagaacgtg agaatcgagt acaataacaa gactcggaac aatactctcg cgtccgtgtg  28260
gcagcccggg gaccccgagt ggtacaccgt ctctgtcccc ggtgctgacg gctccccgcg  28320
caccgtgaat aatactttca tttttgcgca catgtgcgac acggtcatgt ggatgagcaa  28380
gcagtacgat atgtggcccc ccacgaagga gaacatcgtg gtcttctcca tcgcttacag  28440
cctgtgcacg gcgctaatca ccgctatcgt gtgcctgagc attcacatgc tcatcgctat  28500
tcgccccaga aataatgccg aaaaagaaaa acagccataa cgtttttttt cacacctttt  28560
tcagaccatg gcctctgtta aatttttgct tttatttgcc agtctcattg ccgtcattca  28620
```

-continued

```
tggaatgagt aatgagaaaa ttactattta cactggcact aatcacacat tgaaaggtcc  28680
agaaaaagcc acagaagttt catggtattg ttattttaat gaatcagatg tatctactga  28740
actctgtgga aacaataaca aaaaaaatga gagcattact ctcatcaagt ttcaatgtgg  28800
atctgactta accctaatta acatcactag agactatgta ggtatgtatt atggaactac  28860
agcaggcatt tcggacatgg aattttatca agtttctgtg tctgaaccca ccacgcctag  28920
aatgaccaca accacaaaaa ctacacctgt taccactatg cagctcacta ccaataacat  28980
ttttgccatg cgtcaaatgg tcaacaatag cactcaaccc accccaccca gtgaggaaat  29040
tcccaaatcc atgattggca ttattgttgc tgtagtggtg tgcatgttga tcatcgcctt  29100
gtgcatggtg tactatgcct tctgctacag aaagcacaga ctgaacgaca agctggaaca  29160
cttactaagt gttgaatttt aattttttag aaccatgaag atcctaggcc ttttaatttt  29220
ttctatcatt acctctgctc tatgcaattc tgacaatgag gacgttactg tcgttgtcgg  29280
atcaaattat acactgaaag gtccagcgaa gggtatgctt tcgtggtatt gctattttgg  29340
atctgacact acagaaactg aattatgcaa tcttaagaat ggcaaaattc aaaattctaa  29400
aattaacaat tatatatgca atggtactga tctgatactc ctcaatatca cgaaatcata  29460
tgctggcagt tacacctgcc ctggagatga tgctgacagt atgatttttt acaaagtaac  29520
tgttgttgat cccactactc cacctccacc caccacaact actcacacca cacacacaga  29580
tcaaaccgca gcagaggagg cagcaaagtt agccttgcag gtccaagaca gttcatttgt  29640
tggcattacc cctacacctg atcagcggtg tccggggctg ctagtcagcg gcattgtcgg  29700
tgtgctttcg ggattagcag tcataatcat ctgcatgttc atttttgctt gctgctatag  29760
aaggctttac cgacaaaaat cagacccact gctgaacctc tatgtttaat tttttccaga  29820
gtcatgaagg cagttagcgc tctagttttt tgttctttga ttggcattgt tttttgcaat  29880
cctattccta aagttagctt tattaaagat gtgaatgtta ctgagggggg caatgtgaca  29940
ctggtaggtg tagagggtgc tgaaaacacc acctggacaa aataccacct caatgggtgg  30000
aaagatattt gcaattggag tgtattagtt tatacatgtg agggagttaa tcttaccatt  30060
gtcaatgcca cctcagctca aaatggtaga attcaaggac aaagtgtcag tgtatctaat  30120
gggtatttta cccaacatac ttttatctat gacgttaaag tcataccact gcctacgcct  30180
agcccaccta gcactaccac acagacaacc cacactacac agacaaccac atacagtaca  30240
ttaaatcagc ctaccaccac tacagcagca gaggttgcca gctcgtctgg ggtccgagtg  30300
gcatttttga tgtgggcccc atctagcagt cccactgcta gtaccaatga gcagactact  30360
gaatttttgt ccactgtcga gagccacacc acagctacct ccagtgcctt ctctagcacc  30420
gccaatctct cctcgctttc ctctacacca atcagtcccg ctactactcc tagccccgct  30480
cctcttccca ctcccctgaa gcaaacagac ggcggcatgc aatggcagat caccctgctc  30540
attgtgatcg ggttggtcat cctggccgtg ttgctctact acatcttctg ccgccgcatt  30600
cccaacgcgc accgcaagcc ggtctacaag cccatcattg tcgggcagcc ggagccgctt  30660
caggtggaag gggtctaagg gaatcttctc ttctctttta cagtatggtg attgaactat  30720
gattcctaga caattcttga tcactattct tatctgcctc ctccaagtct gtgccaccct  30780
cgctctggtg gccaacgcca gtccagactg tattgggccc ttcgcctcct acgtgctctt  30840
tgccttcacc acctgcatct gctgctgtag catagtctgc ctgcttatca ccttcttcca  30900
gttcattgac tggatctttg tgcgcatcgc ctacctgcgc caccaccccc agtaccgcga  30960
ccagcgagtg gcgcggctgc tcaggctcct ctgataagca tgcgggctct gctacttctc  31020
```

gcgcttctgc tgttagtgct cccccgtccc gtcgaccccc ggtcccccac ccagtccccc 31080
gaggaggtcc gcaaatgcaa attccaagaa ccctggaaat tcctcaaatg ctaccgccaa 31140
aaatcagaca tgcatcccag ctggatcatg atcattggga tcgtgaacat tctggcctgc 31200
accctcatct cctttgtgat ttacccctgc tttgactttg gttggaactc gccagaggcg 31260
ctctatctcc cgcctgaacc tgacacacca ccacagcaac ctcaggcaca cgcactacca 31320
ccactacagc ctaggccaca atacatgccc atattagact atgaggccga gccacagcga 31380
cccatgctcc ccgctattag ttacttcaat ctaaccggcg gagatgactg acccactggc 31440
caacaacaac gtcaacgacc ttctcctgga catggacggc cgcgcctcgg agcagcgact 31500
cgcccaactt cgcattcgcc agcagcagga gagagccgtc aaggagctgc aggatgcggt 31560
ggccatccac cagtgcaaga gaggcatctt ctgcctggtg aaacaggcca agatctccta 31620
cgaggtcact ccaaacgacc atcgcctctc ctacgagctc ctgcagcagc gccagaagtt 31680
cacctgcctg gtcggagtca accccatcgt catcacccag cagtctggcg ataccaaggg 31740
gtgcatccac tgctcctgcg actcccccga ctgcgtccac actctgatca agaccctctg 31800
cggcctccgc gacctcctcc ccatgaacta atcacccccct tatccagtga aataaagatc 31860
atattgatga tgattttaca gaaataaaaa ataatcattt gatttgaaat aaagatacaa 31920
tcatattgat gatttgagtt taacaaaaaa ataaagaatc acttacttga aatctgatac 31980
caggtctctg tccatgtttt ctgccaacac cacttcactc ccctcttccc agctctggta 32040
ctgcaggccc cggcgggctg caaacttcct ccacacgctg aaggggatgt caaattcctc 32100
ctgtccctca atcttcattt tatcttctat cagatgtcca aaaagcgcgt ccgggtggat 32160
gatgacttcg accccgtcta cccctacgat gcagacaacg caccgaccgt gcccttcatc 32220
aacccccccct tcgtctcttc agatggattc caagagaagc ccctgggggt gttgtccctg 32280
cgactggccg accccgtcac caccaagaac ggggaaatca ccctcaagct gggagagggg 32340
gtggacctcg attcctcggg aaaactcatc tccaacacgg ccaccaaggc cgccgcccct 32400
ctcagttttt ccaacaacac catttccctt aacatggatc accccttttta cactaaagat 32460
ggaaaattat ccttacaagt ttctccacca ttaaatatac tgagaacaag cattctaaac 32520
acactagctt taggttttgg atcaggttta ggactccgtg gctctgcctt ggcagtacag 32580
ttagtctctc cacttacatt tgatactgat ggaaacataa agcttacctt agacagaggt 32640
ttgcatgtta caacaggaga tgcaattgaa agcaacataa gctgggctaa aggtttaaaa 32700
tttgaagatg gagccatagc aaccaacatt ggaaatgggt tagagtttgg aagcagtagt 32760
acagaaacag gtgttgatga tgcttaccca atccaagtta aacttggatc tggccttagc 32820
tttgacagta caggagccat aatggctggt aacaaagaag acgataaact cactttgtgg 32880
acaacacctg atccatcacc aaactgtcaa atactcgcag aaaatgatgc aaaactaaca 32940
ctttgcttga ctaaatgtgg tagtcaaata ctggccactg tgtcagtctt agttgtagga 33000
agtggaaacc taaaccccat tactggcacc gtaagcagtg ctcaggtgtt tctacgtttt 33060
gatgcaaacg gtgttctttt aacagaacat tctacactaa aaaaatactg gggtataggg 33120
cagggagata gcatagatgg cactccatat accaatgctg taggattcat gcccaattta 33180
aaagcttatc caaagtcaca aagttctact actaaaaata atatagtagg gcaagtatac 33240
atgaatggag atgtttcaaa acctatgctt ctcactataa ccctcaatgg tactgatgac 33300
agcaacagta catattcaat gtcattttca tacacctgga ctaatggaag ctatgttgga 33360

-continued

```
gcaacatttg gggctaactc ttataccttc tcatacatcg cccaagaatg aacactgtat  33420
cccaccctgc atgccaaccc ttcccacccc actctgtgga acaaactctg aaacacaaaa  33480
taaaataaag ttcaagtgtt ttattgattc aacagtttta caggattcga gcagttattt  33540
ttcctccacc ctcccaggac atggaataca ccaccctctc cccccgcaca gccttgaaca  33600
tctgaatgcc attggtgatg gacatgcttt tggtctccac gttccacaca gtttcagagc  33660
gagccagtct cgggtcggtc agggagatga aaccctccgg gcactcccgc atctgcacct  33720
cacagctcaa cagctgagga ttgtcctcgg tggtcgggat cacggttatc tggaagaagc  33780
agaagagcgg cggtgggaat catagtccgc gaacgggatc ggccggtggt gtcgcatcag  33840
gccccgcagc agtcgctgcc gccgccgctc cgtcaagctg ctgctcaggg ggtccgggtc  33900
cagggactcc ctcagcatga tgcccacggc cctcagcatc agtcgtctgg tgcggcgggc  33960
gcagcagcgc atgcggatct cgctcaggtc gctgcagtac gtgcaacaca gaaccaccag  34020
gttgttcaac agtccatagt tcaacacgct ccagccgaaa ctcatcgcgg gaaggatgct  34080
acccacgtgg ccgtcgtacc agatcctcag gtaaatcaag tggtgccccc tccagaacac  34140
gctgcccacg tacatgatct ccttgggcat gtggcggttc accacctccc ggtaccacat  34200
caccctctgg ttgaacatgc agccccggat gatcctgcgg aaccacaggg ccagcaccgc  34260
cccgcccgcc atgcagcgaa gagaccccgg gtcccggcaa tggcaatgga ggacccaccg  34320
ctcgtacccg tggatcatct gggagctgaa caagtctatg ttggcacagc acaggcatat  34380
gctcatgcat ctcttcagca ctctcaactc ctcgggggtc aaaaccatat cccagggcac  34440
ggggaactct tgcaggacag cgaaccccgc agaacagggc aatcctcgca cagaacttac  34500
attgtgcatg gacagggtat cgcaatcagg cagcaccggg tgatcctcca ccagagaagc  34560
gcgggtctcg gtctcctcac agcgtggtaa gggggccggc cgatacgggt gatggcggga  34620
cgcggctgat cgtgttcgcg accgtgtcat gatgcagttg ctttcggaca ttttcgtact  34680
tgctgtagca gaacctggtc cgggcgctgc acaccgatcg ccggcggcgg tctcggcgct  34740
tggaacgctc ggtgttgaaa ttgtaaaaca gccactctct cagaccgtgc agcagatcta  34800
gggcctcagg agtgatgaag atcccatcat gcctgatggc tctgatcaca tcgaccaccg  34860
tggaatgggc cagacccagc cagatgatgc aattttgttg ggtttcggtg acggcggggg  34920
agggaagaac aggaagaacc atgattaact tttaatccaa acggtctcgg agtacttcaa  34980
aatgaagatc gcggagatgg cacctctcgc ccccgctgtg ttggtggaaa ataacagcca  35040
ggtcaaaggt gatacggttc tcgagatgtt ccacggtggc ttccagcaaa gcctccacgc  35100
gcacatccag aaacaagaca atagcgaaag cgggagggtt ctctaattcc tcaatcatca  35160
tgttacactc ctgcaccatc cccagataat tttcattttt ccagccttga atgattcgaa  35220
ctagttcgtg aggtaaatcc aagccagcca tgataaagag ctcgcgcaga gcgccctcca  35280
ccggcattct taagcacacc ctcataattc caagatattc tgctcctggt tcacctgcag  35340
cagattgaca agcggaatat caaaatctct gccgcgatcc ctgagctcct ccctcagcaa  35400
taactgtaag tactctttca tatcctctcc gaaattttta gccataggac caccaggaat  35460
aagattaggg caagccacag tacagataaa ccgaagtcct ccccagtgag cattgccaaa  35520
tgcaagactg ctataagcat gctggctaga cccggtgata tcttccagat aactggacag  35580
aaaatcgccc aggcaatttt taagaaaatc aacaaaagaa aaatcctcca ggtggacgtt  35640
tagagcctcg ggaacaacga tgaagtaaat gcaagcggtg cgttccagca tggttagtta  35700
gctgatctgt agaaaaaaca aaaatgaaca ttaaaccatg ctagcctggc gaacaggtgg  35760
```

gtaaatcgtt ctctccagca ccaggcaggc cacggggtct ccggcgcgac cctcgtaaaa 35820
attgtcgcta tgattgaaaa ccatcacaga gagacgttcc cggtggccgg cgtgaatgat 35880
tcgacaagat gaatacaccc ccggaacatt ggcgtccgcg agtgaaaaaa agcgcccgag 35940
gaagcaataa ggcactacaa tgctcagtct caagtccagc aaagcgatgc catgcggatg 36000
aagcacaaaa ttctcaggtg cgtacaaaat gtaattactc ccctcctgca caggcagcaa 36060
agcccccgat ccctccaggt acacatacaa agcctcagcg tccatagctt accgagcagc 36120
agcacacaac aggcgcaaga gtcagagaaa ggctgagctc taacctgtcc acccgctctc 36180
tgctcaatat atagcccaga tctacactga cgtaaaggcc aaagtctaaa aatacccgcc 36240
aaataatcac acacgcccag cacacgccca gaaaccggtg acacactcaa aaaaatacgc 36300
gcacttcctc aaacgcccaa aactgccgtc atttccgggt tcccacgcta cgtcatcaaa 36360
acacgacttt caaattccgt cgaccgttaa aaacgtcacc cgccccgccc ctaacggtcg 36420
cccgtctctc agccaatcag cgccccgcat ccccaaattc aaacacctca tttgcatatt 36480
aacgcgcaca aaaagtttga ggtatattat tgatgatgg 36519

<210> SEQ ID NO 58
<211> LENGTH: 34819
<212> TYPE: DNA
<213> ORGANISM: Artificial Sequence
<220> FEATURE:
<223> OTHER INFORMATION: Synthetic Construct

<400> SEQUENCE: 58
ttaattaacc atcttcaata atatacctca aactttttgt gcgcgttaat atgcaaatga 60
ggcgtttgaa tttggggagg aagggcggtg attggtcgag ggatgagcga ccgttagggg 120
cggggcgagt gacgttttga tgacgtggtt gcgaggagga gccagtttgc aagttctcgt 180
gggaaaagtg acgtcaaacg aggtgtggtt tgaacacgga aatactcaat tttcccgcgc 240
tctctgacag gaaatgaggt gtttctgggc ggatgcaagt gaaaacgggc cattttcgcg 300
cgaaaactga atgaggaagt gaaaatctga gtaatttcgc gtttatggca gggaggagta 360
tttgccgagg gccgagtaga ctttgaccga ttacgtgggg gtttcgatta ccgtgttttt 420
cacctaaatt tccgcgtacg gtgtcaaagt ccggtgtttt tactactgta atagtaatca 480
attacggggt cattagttca tagcccatat atggagttcc gcgttacata acttacggta 540
aatggcccgc ctggctgacc gcccaacgac ccccgcccat tgacgtcaat aatgacgtat 600
gttcccatag taacgccaat agggactttc cattgacgtc aatgggtgga gtatttacgg 660
taaactgccc acttggcagt acatcaagtg tatcatatgc caagtacgcc ccctattgac 720
gtcaatgacg gtaaatggcc cgcctggcat tatgcccagt acatgacctt atgggacttt 780
cctacttggc agtacatcta cgtattagtc atcgctatta ccatggtgat gcggttttgg 840
cagtacatca atgggcgtgg atagcggttt gactcacggg gatttccaag tctccacccc 900
attgacgtca atgggagttt gttttggcac caaaatcaac gggactttcc aaaatgtcgt 960
aacaactccg ccccattgac gcaaatgggc ggtaggcgtg tacggtggga ggtctatata 1020
agcagagctg tccctatcag tgatagagat ctccctatca gtgatagaga gtttagtgaa 1080
ccgtcagatc cgctagggta ccaacatggc tagcatcgtc ggagggtggg agtgcgaaaa 1140
gcactcacag ccatggcagg tcctggtcgc ctcgcgcgga cgcgccgtgt gtggaggtgt 1200
gctggtccac ccgcagtggg tgttgactgc ggcccattgc atcagaaata agtccgtgat 1260

-continued cctcttgggg agacattccc tgtttcaccc cgaagatact ggacaggtgt tccaagtgag 1320
ccactccttc ccgcatccac tgtacgacat gagcctgctg aagaaccgct ttctgcggcc 1380
aggggacgac tcatcacacg atttgatgct gcttcggctc tcggaaccgg ccgagctcac 1440
cgacgcagtg aaggtcatgg acctccctac gcaagagcct gctctcggta ccacttgtta 1500
cgcatcggga tggggctcca tcgagccgga agaattcctg accccgaaaa agctgcagtg 1560
cgtggatctg cacgtgattt cgaatgacgt gtgcgcgcaa gtgcatccac aaaaggtcac 1620
taagttcatg ctgtgcgccg gaaggtggac cggcggaaaa tcgacctgtt ccggcgacag 1680
cggaggccca ctcgtgtgca acggtgtgct gcagggcatc actagctggg gatcagaacc 1740
gtgcgcgctt ccggagcggc cctcgctcta cacgaaggtg gtgcactacc gcaaatggat 1800
taaagatacc atcgtcgcaa accctggatc cgaaggtagg ggttcattat tgacctgtgg 1860
agatgtcgaa gaaaacccag gacccgctag caaagcagtg ctgctggcgc tcctgatggc 1920
tggactcgcg ctgcagcctg gaaccgccct gctctgttac tcgtgcaagg cccaagtctc 1980
gaatgaggac tgtttgcaag tggaaaactg cacccagctc ggagaacaat gctggactgc 2040
acggatccgc gctgtcggcc tgctgaccgt gatctccaaa gggtgctcat tgaactgcgt 2100
ggacgatagc caggactact acgtgggaaa gaagaatatc acttgttgcg acacggatct 2160
ttgcaacgcg tccggagcgc acgccctgca gccagcagcc gccattctgg ccctgcttcc 2220
ggccctgggg ttgctgctct ggggtccggg ccagctcgga tcccagaccc tgaactttga 2280
tctgctgaaa ctggcaggcg atgtggaaag caacccaggc ccaatggcta gcgctcgcag 2340
accgcggtgg ctgtgtgcag gggcgctcgt cctggcgggt ggcttctttt tgctcggctt 2400
tcttttcgga tggttcatca aatcgtcaaa cgaagctacc aatatcaccc cgaagcacaa 2460
catgaaggcc tttctggatg agctgaaggc tgagaacatt aagaagttcc tctacaactt 2520
cacccagatc ccacatttgg cgggcactga gcagaacttt cagttggcta agcagatcca 2580
gagccagtgg aaggaattcg gcctggactc cgtcgagctg gcgcattacg atgtgctgct 2640
gagctaccct aataagactc atccgaacta tatctcgatt atcaatgagg acggaaacga 2700
aatctttaac acgtccctct tcgagccgcc accgcctgga tacgagaacg tgtcagatat 2760
cgtgcctccg ttctcggcct tctcgcccca gggaatgccc gaaggggacc tggtgtacgt 2820
gaactacgca aggaccgagg acttcttcaa gttggagcgg gatatgaaga tcaattgcag 2880
cggaaagatc gtcatcgccc gctacggcaa agtgttccgc ggcaacaagg tgaagaatgc 2940
acagttggca ggcgccaagg gcgtcatcct ctactcggat cctgccgact acttcgctcc 3000
tggcgtgaaa tcctaccctg atggttggaa tctgccagga ggaggggtgc agaggggaaa 3060
tatcctgaac ctgaacggtg ccggtgaccc acttactccg ggttacccgg ccaacgaata 3120
cgcgtacagg cggggtatcg cggaagccgt cggactgccg tccatcccgg tccatccgat 3180
tggttactac gacgcccaga agctcctcga aaagatggga ggcagcgccc ctccggactc 3240
gtcatggaga ggctcgctga aggtgccata caacgtggga cccggattca ctggaaattt 3300
cagcactcaa aaagtgaaga tgcacattca ctccactaac gaagtcacca ggatctacaa 3360
cgtcatcgga accctccggg gagcggtgga accggaccgc tacgtgatcc tcggtggaca 3420
ccgggatagc tgggtgttcg gaggaatcga tcctcaatcg ggcgcagccg tcgtccatga 3480
aatcgtcagg tcctttggta ctcttaagaa ggagggctgg cgccctagac gcactattct 3540
gttcgcctcg tgggatgccg aagaatttgg tctgctcggc agcaccgaat gggctgagga 3600
aaactcccgc ctgctccaag aacgcggagt ggcgtacatc aatgccgact catccatcga 3660
aggaaactac acgctgcggg tggactgcac tccactgatg tactcgctcg tgcacaacct 3720
gaccaaagaa ctcaaatccc cagacgaagg attcgaggga aaatcgctgt acgagtcgtg 3780
gaccaagaag agcccatccc cggagttcag cgggatgccg cggatctcaa agctcggatc 3840
aggaaatgat ttcgaagtgt tctttcagag gctgggaatt gcgtcgggaa gggctcggta 3900
cacgaaaaac tgggaaacta acaagttctc gggataccg ctgtaccact cggtgtatga 3960
aacttacgaa ctggtggaga aattctacga tcctatgttt aagtaccacc tgactgtggc 4020
ccaagtgaga ggcggaatgg tgttcgagtt ggccaattca attgtgctgc cattcgattg 4080
ccgcgactac gccgtggtgc tgagaaagta cgcagacaaa atctactcaa tcagcatgaa 4140
gcacccacaa gagatgaaaa cctactcagt ctccttcgac tccctcttct ccgcggtgaa 4200
gaacttcacc gagatcgcga gcaaattctc ggagcgcctt caagatttg acaaatccaa 4260 tccgatcgtc ctccgcatga tgaatgacca gctcatgttt ctcgaacggg ccttcatcga 4320
tccactggga cttccggacc ggccgtttta ccgccacgtg atctacgcgc cctcgtcgca 4380
taacaagtat gctggagaga gcttcccggg tatctacgac gcattgttcg acattgagtc 4440
caaggtggat ccgtccaaag cctggggtga agtgaagcgc caaatctacg tggcggcctt 4500
taccgtccag gcggcagcag aaaccttgag cgaggtggct tgactcgagc ctaagcttct 4560
agataagata tccgatccac cggatctaga taactgatca taatcagcca taccacattt 4620
gtagaggttt tacttgcttt aaaaaacctc ccacacctcc ccctgaacct gaaacataaa 4680
atgaatgcaa ttgttgttgt taacttgttt attgcagctt ataatggtta caaataaagc 4740
aatagcatca caaatttcac aaataaagca tttttttcac tgcattctag ttgtggtttg 4800
tccaaactca tcaatgtatc ttatatgctg gccaccgtac atgtggcttc ccatgctcgc 4860
aagccctggc ccgagttcga gcacaatgtc atgaccaggt gcaatatgca tctggggtcc 4920
cgccgaggca tgttcatgcc ctaccagtgc aacctgaatt atgtgaaggt gctgctggag 4980
cccgatgcca tgtccagagt gagcctgacg gggtgtttg acatgaatgt ggaggtgtgg 5040
aagattctga gatatgatga atccaagacc aggtgccgag cctgcgagtg cggagggaag 5100
catgccaggt tccagcccgt gtgtgtggat gtgacggagg acctgcgacc cgatcatttg 5160
gtgttgccct gcaccgggac ggagttcggt tccagcgggg aagaatctga ctagagtgag 5220
tagtgttctg gggcggggga ggacctgcat gagggccaga ataactgaaa tctgtgcttt 5280
tctgtgtgtt gcagcagcat gagcggaagc ggctcctttg agggaggggt attcagccct 5340
tatctgacgg ggcgtctccc ctcctgggcg ggagtgcgtc agaatgtgat gggatccacg 5400
gtggacggcc ggcccgtgca gcccgcgaac tcttcaaccc tgacctatgc aaccctgagc 5460
tcttcgtcgt tggacgcagc tgccgccgca gctgctgcat ctgccgccag cgccgtgcgc 5520
ggaatggcca tgggcgccgg ctactacggc actctggtgg ccaactcgag ttccaccaat 5580
aatcccgcca gcctgaacga ggagaagctg ttgctgctga tggcccagct cgaggccttg 5640
acccagcgcc tgggcgagct gacccagcag gtggctcagc tgcaggagca gacgcgggcc 5700
gcggttgcca cggtgaaatc caaataaaaa atgaatcaat aaataaacgg agacggttgt 5760
tgattttaac acagagtctg aatctttatt tgatttttcg cgcgcggtag gccctggacc 5820
accggtctcg atcattgagc acccggtgga tcttttccag gacccggtag aggtgggctt 5880
ggatgttgag gtacatgggc atgagcccgt cccgggggtg gaggtagctc cattgcaggg 5940
cctcgtgctc gggggtggtg ttgtaaatca cccagtcata gcaggggcgc agggcatggt 6000

```
gttgcacaat atctttgagg aggagactga tggccacggg cagccctttg gtgtaggtgt   6060
ttacaaatct gttgagctgg gagggatgca tgcgggggga gatgaggtgc atcttggcct   6120
ggatcttgag attggcgatg ttaccgccca gatcccgcct ggggttcatg ttgtgcagga   6180
ccaccagcac ggtgtatccg gtgcacttgg ggaatttatc atgcaacttg gaagggaagg   6240
cgtgaaagaa tttggcgacg cctttgtgcc cgcccaggtt ttccatgcac tcatccatga   6300
tgatggcgat gggcccgtgg gcggcggcct gggcaaagac gtttcggggg tcggacacat   6360
catagttgtg gtcctgggtg aggtcatcat aggccatttt aatgaatttg gggcggaggg   6420
tgccggactg gggggacaaag gtaccctcga tcccgggggc gtagttcccc tcacagatct   6480
gcatctccca ggctttgagc tcggaggggg ggatcatgtc cacctgcggg gcgataaaga   6540
acacggtttc cggggcgggg gagatgagct gggccgaaag caagttccgg agcagctggg   6600
acttgccgca gccggtgggg ccgtagatga ccccgatgac cggctgcagg tggtagttga   6660
gggagagaca gctgccgtcc tcccggagga ggggggccac ctcgttcatc atctcgcgca   6720
cgtgcatgtt ctcgcgcacc agttccgcca ggaggcgctc tccccccagg gataggagct   6780
cctggagcga ggcgaagttt ttcagcggct tgagtccgtc ggccatgggc attttggaga   6840
gggtttgttg caagagttcc aggcggtccc agagctcggt gatgtgctct acggcatctc   6900
gatccagcag acctcctcgt ttcgcgggtt gggacggctg cgggagtagg gcaccagacg   6960
atgggcgtcc agcgcagcca gggtccggtc cttccagggt cgcagcgtcc gcgtcagggt   7020
ggtctccgtc acggtgaagg ggtgcgcgcc gggctgggcg cttgcgaggg tgcgcttcag   7080
gctcatccgg ctggtcgaaa accgctcccg atcggcgccc tgcgcgtcgg ccaggtagca   7140
attgaccatg agttcgtagt tgagcgcctc ggccgcgtgg cctttggcgc ggagcttacc   7200
tttggaagtc tgcccgcagg cgggacagag gagggacttg agggcgtaga gcttgggggc   7260
gaggaagacg gactcggggg cgtaggcgtc cgcgccgcag tgggcgcaga cggtctcgca   7320
ctccacgagc caggtgaggt cgggctggtc ggggtcaaaa accagtttcc cgccgttctt   7380
tttgatgcgt ttcttacctt tggtctccat gagctcgtgt ccccgctggg tgacaaagag   7440
gctgtccgtg tccccgtaga ccgactttat gggccggtcc tcgagcggtg tgccgcggtc   7500
ctcctcgtag aggaaccccg cccactccga gacgaaagcc cgggtccagg ccagcacgaa   7560
ggaggccacg tgggacgggt agcggtcgtt gtccaccagc gggtccacct tttccagggt   7620
atgcaaacac atgtccccct cgtccacatc caggaaggtg attggcttgt aagtgtaggc   7680
cacgtgaccg gggtcccgg ccggggggt ataaaagggt gcgggtccct gctcgtcctc   7740
actgtcttcc ggatcgctgt ccaggagcgc cagctgttgg ggtaggtatt ccctctcgaa   7800
ggcgggcatg acctcggcac tcaggttgtc agtttctaga aacgaggagg atttgatatt   7860
gacggtgccg gcggagatgc ctttcaagag cccctcgtcc atctggtcag aaaagacgat   7920
ctttttgttg tcgagcttgg tggcgaagga gccgtagagg gcgttggaga ggagcttggc   7980
gatggagcgc atggtctggt ttttttcctt gtcggcgcgc tccttggcgg cgatgttgag   8040
ctgcacgtac tcgcgcgcca cgcacttcca ttcggggaag acggtggtca gctcgtcggg   8100
cacgattctg acctgccagc cccgattatg cagggtgatg aggtccacac tggtggccac   8160
ctcgccgcgc aggggctcat tagtccagca gaggcgtccg cccttgcgcg agcagaaggg   8220
gggcaggggg tccagcatga cctcgtcggg ggggtcggca tcgatggtga agatgccggg   8280
caggaggtcg gggtcaaagt agctgatgga agtggccaga tcgtccaggg cagcttgcca   8340
ttcgcgcacg gccagcgcgc gctcgtaggg actgaggggc gtgccccagg gcatgggatg   8400
```

ggtaagcgcg gaggcgtaca tgccgcagat gtcgtagacg tagaggggct cctcgaggat 8460
gccgatgtag gtggggtagc agcgcccccc gcggatgctg gcgcgcacgt agtcatacag 8520
ctcgtgcgag ggggcgagga gccccgggcc caggttggtg cgactgggct tttcggcgcg 8580
gtagacgatc tggcggaaaa tggcatgcga gttggaggag atggtgggcc tttggaagat 8640
gttgaagtgg gcgtggggca gtccgaccga gtcgcggatg aagtgggcgt aggagtcttg 8700
cagcttggcg acgagctcgg cggtgactag gacgtccaga gcgcagtagt cgagggtctc 8760
ctggatgatg tcatacttga gctgtccctt ttgtttccac agctcgcggt tgagaaggaa 8820
ctcttcgcgg tccttccagt actcttcgag ggggaacccg tcctgatctg cacggtaaga 8880
gcctagcatg tagaactggt tgacggcctt gtaggcgcag cagcccttct ccacggggag 8940
ggcgtaggcc tgggcggcct tgcgcaggga ggtgtgcgtg agggcgaaag tgtccctgac 9000
catgaccttg aggaactggt gcttgaagtc gatatcgtcg cagccccct gctcccagag 9060
ctggaagtcc gtgcgcttct tgtaggcggg gttgggcaaa gcgaaagtaa catcgttgaa 9120
gaggatcttg cccgcgcggg gcataaagtt gcgagtgatg cggaaaggtt ggggcacctc 9180
ggcccggttg ttgatgacct gggcggcgag cacgatctcg tcgaagccgt tgatgttgtg 9240
gcccacgatg tagagttcca cgaatcgcgg acggcccttg acgtggggca gtttcttgag 9300
ctcctcgtag gtgagctcgt cggggtcgct gagcccgtgc tgctcgagcg cccagtcggc 9360
gagatggggg ttggcgcgga ggaaggaagt ccagagatcc acggccaggg cggtttgcag 9420
acggtcccgg tactgacgga actgctgccc gacggccatt ttttcggggg tgacgcagta 9480
gaaggtgcgg gggtccccgt gccagcgatc ccatttgagc tggagggcga gatcgagggc 9540
gagctcgacg agccggtcgt ccccggagag tttcatgacc agcatgaagg ggacgagctg 9600
cttgccgaag gaccccatcc aggtgtaggt ttccacatcg taggtgagga agagcctttc 9660
ggtgcgagga tgcgagccga tggggaagaa ctggatctcc tgccaccaat tggaggaatg 9720
gctgttgatg tgatggaagt agaaatgccg acggcgcgcc gaacactcgt gcttgtgttt 9780
atacaagcgg ccacagtgct cgcaacgctg cacgggatgc acgtgctgca cgagctgtac 9840
ctgagttcct ttgacgagga atttcagtgg gaagtggagt cgtggcgcct gcatctcgtg 9900
ctgtactacg tcgtggtggt cggcctggcc ctcttctgcc tcgatggtgg tcatgctgac 9960
gagcccgcgc gggaggcagg tccagacctc ggcgcgagcg ggtcggagag cgaggacgag 10020
ggcgcgcagg ccggagctgt ccagggtcct gagacgctgc ggagtcaggt cagtgggcag 10080
cggcggcgcg cggttgactt gcaggagttt ttccagggcg cgcgggaggt ccagatggta 10140
cttgatctcc accgcgccat tggtggcgac gtcgatggct tgcagggtcc cgtgcccctg 10200
ggtgtgacc accgtccccc gtttcttctt gggcggctgg ggcgacgggg gcggtgcctc 10260
ttccatggtt agaagcggcg gcgaggacgc gcgccgggcg gcaggggcgg ctcggggccc 10320
ggaggcaggg gcggcagggg cacgtcggcg ccgcgcgcgg gtaggttctg gtactgcgcc 10380
cggagaagac tggcgtgagc gacgacgcga cggttgacgt cctggatctg acgcctctgg 10440
gtgaaggcca cgggacccgt gagtttgaac ctgaaagaga gttcgacaga atcaatctcg 10500
gtatcgttga cggcggcctg ccgcaggatc tcttgcacgt cgcccgagtt gtcctggtag 10560
gcgatctcgg tcatgaactg ctcgatctcc tcctcttgaa ggtctccgcg gccggcgcgc 10620
tccacggtgg ccgcgaggtc gttggagatg cggcccatga gctgcgagaa ggcgttcatg 10680
cccgcctcgt tccagacgcg gctgtagacc acgacgccct cgggatcgcg ggcgcgcatg 10740

-continued

```
accacctggg cgaggttgag ctccacgtgg cgcgtgaaga ccgcgtagtt gcagaggcgc  10800
tggtagaggt agttgagcgt ggtggcgatg tgctcggtga cgaagaaata catgatccag  10860
cggcggagcg gcatctcgct gacgtcgccc agcgcctcca aacgttccat ggcctcgtaa  10920
aagtccacgg cgaagttgaa aaactgggag ttgcgcgccg agacggtcaa ctcctcctcc  10980
agaagacgga tgagctcggc gatggtggcg cgcacctcgc gctcgaaggc cccgggagt  11040
tcctccactt cctcttcttc ctcctccact aacatctctt ctacttcctc ctcaggcggc  11100
agtggtggcg ggggaggggg cctgcgtcgc cggcggcgca cgggcagacg gtcgatgaag  11160
cgctcgatgg tctcgccgcg ccggcgtcgc atggtctcgg tgacggcgcg cccgtcctcg  11220
cggggccgca gcgtgaagac gccgccgcgc atctccaggt ggccgggggg gtccccgttg  11280
ggcagggaga gggcgctgac gatgcatctt atcaattgcc ccgtagggac tccgcgcaag  11340
gacctgagcg tctcgagatc cacgggatct gaaaaccgct gaacgaaggc ttcgagccag  11400
tcgcagtcgc aaggtaggct gagcacggtt tcttctggcg ggtcatgttg gttgggagcg  11460
gggcgggcga tgctgctggt gatgaagttg aaataggcgg ttctgagacg gcggatggtg  11520
gcgaggagca ccaggtcttt gggcccggct tgctggatgc gcagacggtc ggccatgccc  11580
caggcgtggt cctgacacct ggccaggtcc ttgtagtagt cctgcatgag ccgctccacg  11640
ggcacctcct cctcgcccgc gcggccgtgc atgcgcgtga gcccgaagcc gcgctggggc  11700
tggacgagcg ccaggtcggc gacgacgcgc tcggcgagga tggcttgctg gatctgggtg  11760
agggtggtct ggaagtcatc aaagtcgacg aagcggtggt aggctccggt gttgatggtg  11820
taggagcagt tggccatgac ggaccagttg acggtctggt ggcccggacg cacgagctcg  11880
tggtacttga ggcgcgagta ggcgcgcgtg tcgaagatgt agtcgttgca ggtgcgcacc  11940
aggtactggt agccgatgag gaagtgcggc ggcggctggc ggtagagcgg ccatcgctcg  12000
gtggcggggg cgccgggcgc gaggtcctcg agcatggtgc ggtggtagcc gtagatgtac  12060
ctggacatcc aggtgatgcc ggcggcggtg gtggaggcgc gcgggaactc gcggacgcgg  12120
ttccagatgt tgcgcagcgg caggaagtag ttcatggtgg gcacggtctg gcccgtgagg  12180
cgcgcgcagt cgtggatgct ctatacgggc aaaaacgaaa gcggtcagcg gctcgactcc  12240
gtggcctgga ggctaagcga acgggttggg ctgcgcgtgt accccggttc gaatctcgaa  12300
tcaggctgga gccgcagcta acgtggtatt ggcactcccg tctcgaccca agcctgcacc  12360
aaccctccag gatacggagg cgggtcgttt tgcaactttt ttttggaggc cggatgagac  12420
tagtaagcgc ggaaagcggc cgaccgcgat ggctcgctgc cgtagtctgg agaagaatcg  12480
ccagggttgc gttgcggtgt gccccggttc gaggccggcc ggattccgcg gctaacgagg  12540
gcgtggctgc cccgtcgttt ccaagacccc atagccagcc gacttctcca gttacggagc  12600
gagcccctct tttgttttgt ttgtttttgc cagatgcatc ccgtactgcg gcagatgcgc  12660
ccccaccacc ctccaccgca acaacagccc cctccacagc cggcgcttct gcccccgccc  12720
cagcagcaac ttccagccac gaccgccgcg gccgccgtga gcggggctgg acagagttat  12780
gatcaccagc tggccttgga agagggcgag gggctggcgc gcctgggggc gtcgtcgccg  12840
gagcggcacc cgcgcgtgca gatgaaaagg gacgctcgcg aggcctacgt gcccaagcag  12900
aacctgttca gagacaggag cggcgaggag cccgaggaga tgcgcgcggc ccggttccac  12960
gcggggcggg agctgcggcg cggcctggac cgaaagaggg tgctgaggga cgaggatttc  13020
gaggcggacg agctgacggg gatcagcccc gcgcgcgcgc acgtggccgc ggccaacctg  13080
gtcacggcgt acgagcagac cgtgaaggag gagagcaact tccaaaaatc cttcaacaac  13140
```

-continued

```
cacgtgcgca ccctgatcgc gcgcgaggag gtgaccctgg gcctgatgca cctgtgggac  13200
ctgctggagg ccatcgtgca gaaccccacc agcaagccgc tgacggcgca gctgttcctg  13260
gtggtgcagc atagtcggga caacgaagcg ttcagggagg cgctgctgaa tatcaccgag  13320
cccgagggcc gctggctcct ggacctggtg aacattctgc agagcatcgt ggtgcaggag  13380
cgcgggctgc cgctgtccga gaagctggcg gccatcaact tctcggtgct gagtttgggc  13440
aagtactacg ctaggaagat ctacaagacc ccgtacgtgc ccatagacaa ggaggtgaag  13500
atcgacgggt tttacatgcg catgaccctg aaagtgctga ccctgagcga cgatctgggg  13560
gtgtaccgca acgacaggat gcaccgtgcg gtgagcgcca gcaggcggcg cgagctgagc  13620
gaccaggagc tgatgcatag tctgcagcgg gccctgaccg gggccgggac cgagggggag  13680
agctactttg acatgggcgc ggacctgcac tggcagccca gccgccgggc cttggaggcg  13740
gcggcaggac cctacgtaga agaggtggac gatgaggtgg acgaggaggg cgagtacctg  13800
gaagactgat ggcgcgaccg tatttttgct agatgcaaca acaacagcca cctcctgatc  13860
ccgcgatgcg ggcggcgctg cagagccagc cgtccggcat taactcctcg gacgattgga  13920
cccaggccat gcaacgcatc atggcgctga cgacccgcaa ccccgaagcc tttagacagc  13980
agccccaggc caaccggctc tcggccatcc tggaggccgt ggtgccctcg cgctccaacc  14040
ccacgcacga gaaggtcctg gccatcgtga acgcgctggt ggagaacaag gccatccgcg  14100
gcgacgaggc cggcctggtg tacaacgcgc tgctggagcg cgtggcccgc tacaacagca  14160
ccaacgtgca gaccaacctg gaccgcatgg tgaccgacgt gcgcgaggcc gtggcccagc  14220
gcgagcggtt ccaccgcgag tccaacctgg gatccatggt ggcgctgaac gccttcctca  14280
gcacccagcc cgccaacgtg ccccggggcc aggaggacta caccaacttc atcagcgccc  14340
tgcgcctgat ggtgaccgag gtgccccaga gcgaggtgta ccagtccggg ccggactact  14400
tcttccagac cagtcgccag ggcttgcaga ccgtgaacct gagccaggct ttcaagaact  14460
tgcagggcct gtggggcgtg caggccccgg tcggggaccg cgcgacggtg tcgagcctgc  14520
tgacgccgaa ctcgcgcctg ctgctgctgc tggtggcccc cttcacggac agcggcagca  14580
tcaaccgcaa ctcgtacctg ggctacctga ttaacctgta ccgcgaggcc atcggccagg  14640
cgcacgtgga cgagcagacc taccaggaga tcacccacgt gagccgcgcc ctgggccagg  14700
acgacccggg caacctggaa gccaccctga actttttgct gaccaaccgg tcgcagaaga  14760
tcccgcccca gtacgcgctc agcaccgagg aggagcgcat cctgcgttac gtgcagcaga  14820
gcgtgggcct gttcctgatg caggaggggg ccacccccag cgccgcgctc gacatgaccg  14880
cgcgcaacat ggagcccagc atgtacgcca gcaaccgccc gttcatcaat aaactgatgg  14940
actacttgca tcgggcggcc gccatgaact ctgactattt caccaacgcc atcctgaatc  15000
cccactggct cccgccgccg gggttctaca cgggcgagta cgacatgccc gaccccaatg  15060
acgggttcct gtgggacgat gtggacagca gcgtgttctc cccccgaccg ggtgctaacg  15120
agcgcccctt gtggaagaag gaaggcagcg accgacgccc gtcctcggcg ctgtccggcc  15180
gcgagggtgc tgccgcggcg gtgcccgagg ccgccagtcc tttcccgagc ttgcccttct  15240
cgctgaacag tatccgcagc agcgagctgg gcaggatcac gcgcccgcgc ttgctgggcg  15300
aagaggagta cttgaatgac tcgctgttga gacccgagcg ggagaagaac ttccccaata  15360
acgggataga aagcctggtg gacaagatga gccgctggaa gacgtatgcg caggagcaca  15420
gggacgatcc ccgggcgtcg caggggggcca cgagccgggg cagcgccgcc cgtaaacgcc  15480
```

-continued

```
ggtggcacga caggcagcgg ggacagatgt gggacgatga ggactccgcc gacgacagca  15540
gcgtgttgga cttgggtggg agtggtaacc cgttcgctca cctgcgcccc cgtatcgggc  15600
gcatgatgta agagaaaccg aaaataaatg atactcacca aggccatggc gaccagcgtg  15660
cgttcgtttc ttctctgttg ttgttgtatc tagtatgatg aggcgtgcgt acccggaggg  15720
tcctcctccc tcgtacgaga gcgtgatgca gcaggcgatg gcggcggcgg cgatgcagcc  15780
cccgctggag gctccttacg tgcccccgcg gtacctggcg cctacggagg ggcggaacag  15840
cattcgttac tcggagctgg cacccttgta cgataccacc cggttgtacc tggtggacaa  15900
caagtcggcg gacatcgcct cgctgaacta ccagaacgac cacagcaact tcctgaccac  15960
cgtggtgcag aacaatgact tcacccccac ggaggccagc acccagacca tcaactttga  16020
cgagcgctcg cggtggggcg gccagctgaa aaccatcatg cacaccaaca tgcccaacgt  16080
gaacgagttc atgtacagca acaagttcaa ggcgcgggtg atggtctccc gcaagacccc  16140
caatggggtg acagtgacag aggattatga tggtagtcag gatgagctga agtatgaatg  16200
ggtggaattt gagctgcccg aaggcaactt ctcggtgacc atgaccatcg acctgatgaa  16260
caacgccatc atcgacaatt acttggcggt ggggcggcag aacggggtgc tggagagcga  16320
catcggcgtg aagttcgaca ctaggaactt caggctgggc tgggaccccg tgaccgagct  16380
ggtcatgccc ggggtgtaca ccaacgaggc tttccatccc gatattgtct tgctgcccgg  16440
ctgcggggtg gacttcaccg agagccgcct cagcaacctg ctgggcattc gcaagaggca  16500
gcccttccag gaaggcttcc agatcatgta cgaggatctg gaggggggca acatccccgc  16560
gctcctggat gtcgacgcct atgagaaaag caaggaggat gcagcagctg aagcaactgc  16620
agccgtagct accgcctcta ccgaggtcag ggcgataaat tttgcaagcg ccgcagcagt  16680
ggcagcggcc gaggcggctg aaaccgaaag taagatagtc attcagccgg tggagaagga  16740
tagcaagaac aggagctaca acgtactacc ggacaagata aacaccgcct accgcagctg  16800
gtacctagcc tacaactatg gcgaccccga gaagggcgtg cgctcctgga cgctgctcac  16860
cacctcggac gtcacctgcg gcgtggagca agtctactgg tcgctgcccg acatgatgca  16920
agacccggtc accttccgct ccacgcgtca agttagcaac tacccggtgg tgggcgccga  16980
gctcctgccc gtctactcca agagcttctt caacgagcag gccgtctact cgcagcagct  17040
gcgcgccttc acctcgctta cgcacgtctt caaccgcttc cccgagaacc agatcctcgt  17100
ccgcccgccc gcgcccacca ttaccaccgt cagtgaaaac gttcctgctc tcacagatca  17160
cgggaccctg ccgctgcgca gcagtatccg gggagtccag cgcgtgaccg ttactgacgc  17220
cagacgccgc acctgcccct acgtctacaa ggccctgggc atagtcgcgc cgcgcgtcct  17280
ctcgagccgc accttctaaa tgtccattct catctcgccc agtaataaca ccggttgggg  17340
cctgcgcgcg cccagcaaga tgtacggagg cgctcgccaa cgctccacgc aacaccccgt  17400
gcgcgtgcgc gggcacttcc gcgctccctg gggcgccctc aagggccgcg tgcggtcgcg  17460
caccaccgtc gacgacgtga tcgaccaggt ggtggccgac gcgcgcaact acaccccccgc  17520
cgccgcgccc gtctccaccg tggacgccgt catcgacagc gtggtggccg acgcgcgccg  17580
gtacgcccgc gccaagagcc ggcggcggcg catcgcccgg cggcaccgga gcacccccgc  17640
catgcgcgcg gcgcgagcct tgctgcgcag ggccaggcgc acgggacgca gggccatgct  17700
cagggcggcc agacgcgcgg cttcaggcgc cagcgccggc aggacccgga gacgcgcggc  17760
cacggcggcg gcagcggcca tcgccagcat gtcccgcccg cggcgaggga acgtgtactg  17820
ggtgcgcgac gccgccaccg gtgtgcgcgt gcccgtgcgc acccgccccc ctcgcacttg  17880
```

aagatgttca cttcgcgatg ttgatgtgtc ccagcggcga ggaggatgtc caagcgcaaa 17940
ttcaaggaag agatgctcca ggtcatcgcg cctgagatct acggccctgc ggtggtgaag 18000
gaggaaagaa agccccgcaa aatcaagcgg gtcaaaaagg acaaaaagga agaagaaagt 18060
gatgtggacg gattggtgga gtttgtgcgc gagttcgccc cccggcggcg cgtgcagtgg 18120
cgcgggcgga aggtgcaacc ggtgctgaga cccggcacca ccgtggtctt cacgcccggc 18180
gagcgctccg gcaccgcttc caagcgctcc tacgacgagg tgtacgggga tgatgatatt 18240
ctggagcagg cggccgagcg cctgggcgag tttgcttacg gcaagcgcag ccgttccgca 18300
ccgaaggaag aggcggtgtc catcccgctg gaccacggca accccacgcc gagcctcaag 18360
cccgtgacct tgcagcaggt gctgccgacc gcggcgccgc gccgggggtt caagcgcgag 18420
ggcgaggatc tgtaccccac catgcagctg atggtgccca agcgccagaa gctggaagac 18480
gtgctggaga ccatgaaggt ggacccggac gtgcagcccg aggtcaaggt gcggcccatc 18540
aagcaggtgg ccccgggcct gggcgtgcag accgtggaca tcaagattcc cacggagccc 18600
atggaaacgc agaccgagcc catgatcaag cccagcacca gcaccatgga ggtgcagacg 18660
gatccctgga tgccatcggc tcctagtcga agaccccggc gcaagtacgg cgcggccagc 18720
ctgctgatgc ccaactacgc gctgcatcct tccatcatcc ccacgccggg ctaccgcggc 18780
acgcgcttct accgcggtca taccagcagc cgccgccgca agaccaccac tcgccgccgc 18840
cgtcgccgca ccgccgctgc aaccacccct gccgccctgg tgcggagagt gtaccgccgc 18900
ggccgcgcac ctctgaccct gccgcgcgcg cgctaccacc cgagcatcgc catttaaact 18960
ttcgcctgct ttgcagatca atggccctca catgccgcct tcgcgttccc attacgggct 19020
accgaggaag aaaaccgcgc cgtagaaggc tggcggggaa cgggatgcgt cgccaccacc 19080
accggcggcg gcgcgccatc agcaagcggt tgggggggagg cttcctgccc gcgctgatcc 19140
ccatcatcgc cgcggcgatc ggggcgatcc ccggcattgc ttccgtggcg gtgcaggcct 19200
ctcagcgcca ctgagacaca cttggaaaca tcttgtaata aaccaatgga ctctgacgct 19260
cctggtcctg tgatgtgttt tcgtagacag atggaagaca tcaatttttc gtccctggct 19320
ccgcgacacg gcacgcggcc gttcatgggc acctggagcg acatcggcac cagccaactg 19380
aacgggggcg ccttcaattg gagcagtctc tggagcgggc ttaagaattt cgggtccacg 19440
cttaaaacct atggcagcaa ggcgtggaac agcaccacag ggcaggcgct gagggataag 19500
ctgaaagagc agaacttcca gcagaaggtg gtcgatgggc tcgcctcggg catcaacggg 19560
gtggtggacc tggccaacca ggccgtgcag cggcagatca acagccgcct ggacccggtg 19620
ccgcccgccg gctccgtgga gatgccgcag gtggaggagg agctgcctcc cctggacaag 19680
cggggcgaga agcgaccccg ccccgatgcg gaggagacgc tgctgacgca cacggacgag 19740
ccgccccccgt acgaggaggc ggtgaaactg ggtctgccca ccacgcggcc catcgcgccc 19800
ctggccaccg gggtgctgaa acccgaaaag cccgcgaccc tggacttgcc tcctccccag 19860
ccttcccgcc cctctacagt ggctaagccc ctgccgccgg tggccgtggc ccgcgcgcga 19920
cccgggggca ccgcccgccc tcatgcgaac tggcagagca ctctgaacag catcgtgggt 19980
ctgggagtgc agagtgtgaa gcgccgccgc tgctattaaa cctaccgtag cgcttaactt 20040
gcttgtctgt gtgtgtatgt attatgtcgc cgccgccgct gtccaccaga aggaggagtg 20100
aagaggcgcg tcgccgagtt gcaagatggc caccccatcg atgctgcccc agtgggcgta 20160
catgcacatc gccggacagg acgcttcgga gtacctgagt ccgggtctgg tgcagtttgc 20220

-continued

```
ccgcgccaca gacacctact tcagtctggg gaacaagttt aggaacccca cggtggcgcc  20280
cacgcacgat gtgaccaccg accgcagcca gcggctgacg ctgcgcttcg tgcccgtgga  20340
ccgcgaggac aacacctact cgtacaaagt gcgctacacg ctggccgtgg gcgacaaccg  20400
cgtgctggac atggccagca cctactttga catccgcggc gtgctggatc ggggccctag  20460
cttcaaaccc tactccggca ccgcctacaa cagtctggcc cccaagggag cacccaacac  20520
ttgtcagtgg acatataaag ccgatggtga aactgccaca gaaaaaacct atacatatgg  20580
aaatgcaccc gtgcagggca ttaacatcac aaaagatggt attcaacttg gaactgacac  20640
cgatgatcag ccaatctacg cagataaaac ctatcagcct gaacctcaag tgggtgatgc  20700
tgaatggcat gacatcactg gtactgatga aaagtatgga ggcagagctc ttaagcctga  20760
taccaaaatg aagccttgtt atggttcttt tgccaagcct actaataaag aaggaggtca  20820
ggcaaatgtg aaaacaggaa caggcactac taaagaatat gacatagaca tggctttctt  20880
tgacaacaga agtgcggctg ctgctggcct agctccagaa attgttttgt atactgaaaa  20940
tgtggatttg gaaactccag atacccatat tgtatacaaa gcaggcacag atgacagcag  21000
ctcttctatt aatttgggtc agcaagccat gcccaacaga cctaactaca ttggtttcag  21060
agacaacttt atcgggctca tgtactacaa cagcactggc aatatggggg tgctggccgg  21120
tcaggcttct cagctgaatg ctgtggttga cttgcaagac agaaacaccg agctgtccta  21180
ccagctcttg cttgactctc tgggtgacag aacccggtat ttcagtatgt ggaatcaggc  21240
ggtggacagc tatgatcctg atgtgcgcat tattgaaaat catggtgtgg aggatgaact  21300
tcccaactat tgtttccctc tggatgctgt tggcagaaca gatacttatc agggaattaa  21360
ggctaatgga actgatcaaa ccacatggac caaagatgac agtgtcaatg atgctaatga  21420
gataggcaag ggtaatccat tcgccatgga aatcaacatc caagccaacc tgtggaggaa  21480
cttcctctac gccaacgtgg ccctgtacct gcccgactct tacaagtaca cgccggccaa  21540
tgttaccctg cccaccaaca ccaacaccta cgattacatg aacggccggg tggtggcgcc  21600
ctcgctggtg gactcctaca tcaacatcgg ggcgcgctgg tcgctggatc ccatggacaa  21660
cgtgaacccc ttcaaccacc accgcaatgc ggggctgcgc taccgctcca tgctcctggg  21720
caacgggcgc tacgtgccct tccacatcca ggtgccccag aaatttttcg ccatcaagag  21780
cctcctgctc ctgcccgggt cctacaccta cgagtggaac ttccgcaagg acgtcaacat  21840
gatcctgcag agctccctcg gcaacgacct gcgcacggac ggggcctcca tctccttcac  21900
cagcatcaac ctctacgcca ccttcttccc catggcgcac aacacggcct ccacgctcga  21960
ggccatgctg cgcaacgaca ccaacgacca gtccttcaac gactacctct cggcggccaa  22020
catgctctac cccatcccgg ccaacgccac caacgtgccc atctccatcc cctcgcgcaa  22080
ctgggccgcc ttccgcggct ggtccttcac gcgtctcaag accaaggaga cgccctcgct  22140
gggctccggg ttcgacccct acttcgtcta ctcgggctcc atcccctacc tcgacggcac  22200
cttctacctc aaccacacct tcaagaaggt ctccatcacc ttcgactcct ccgtcagctg  22260
gcccggcaac gaccggctcc tgacgcccaa cgagttcgaa atcaagcgca ccgtcgacgg  22320
cgagggctac aacgtggccc agtgcaacat gaccaaggac tggttcctgg tccagatgct  22380
ggcccactac aacatcggct accagggctt ctacgtgccc gagggctaca aggaccgcat  22440
gtactccttc ttccgcaact tccagcccat gagccgccag gtggtggacg aggtcaacta  22500
caaggactac caggccgtca ccctggccta ccagcacaac aactcgggct tcgtcggcta  22560
cctcgcgccc accatgcgcc agggccagcc ctaccccgcc aactacccct acccgctcat  22620
```

```
cggcaagagc gccgtcacca gcgtcaccca gaaaaagttc ctctgcgaca gggtcatgtg  22680
gcgcatcccc ttctccagca acttcatgtc catgggcgcg ctcaccgacc tcggccagaa  22740
catgctctat gccaactccg cccacgcgct agacatgaat ttcgaagtcg accccatgga  22800
tgagtccacc cttctctatg ttgtcttcga agtcttcgac gtcgtccgag tgcaccagcc  22860
ccaccgcggc gtcatcgagg ccgtctacct gcgcaccccc ttctcggccg gtaacgccac  22920
cacctaagct cttgcttctt gcaagccatg gccgcgggct ccggcgagca ggagctcagg  22980
gccatcatcc gcgacctggg ctgcgggccc tacttcctgg gcaccttcga taagcgcttc  23040
ccgggattca tggccccgca caagctggcc tgcgccatcg tcaacacggc cggccgcgag  23100
accgggggcg agcactggct ggccttcgcc tggaacccgc gctcgaacac ctgctacctc  23160
ttcgacccct tcgggttctc ggacgagcgc ctcaagcaga tctaccagtt cgagtacgag  23220
ggcctgctgc gccgcagcgc cctggccacc gaggaccgct gcgtcaccct ggaaaagtcc  23280
acccagaccg tgcagggtcc gcgctcggcc gcctgcgggc tcttctgctg catgttcctg  23340
cacgccttcg tgcactggcc cgaccgcccc atggacaaga accccaccat gaacttgctg  23400
acgggggtgc ccaacggcat gctccagtcg ccccaggtgg aacccaccct gcgccgcaac  23460
caggaggcgc tctaccgctt cctcaactcc cactccgcct actttcgctc ccaccgcgcg  23520
cgcatcgaga aggccaccgc cttcgaccgc atgaatcaag acatgtaaac cgtgtgtgta  23580
tgttaaatgt ctttaataaa cagcactttc atgttacaca tgcatctgag atgatttatt  23640
tagaaatcga aagggttctg ccgggtctcg gcatggcccg cgggcaggga cacgttgcgg  23700
aactggtact tggccagcca cttgaactcg gggatcagca gtttgggcag cggggtgtcg  23760
gggaaggagt cggtccacag cttccgcgtc agttgcaggg cgcccagcag gtcgggcgcg  23820
gagatcttga aatcgcagtt gggacccgcg ttctgcgcgc gggagttgcg gtacacgggg  23880
ttgcagcact ggaacaccat cagggccggg tgcttcacgc tcgccagcac cgtcgcgtcg  23940
gtgatgctct ccacgtcgag gtcctcggcg ttggccatcc cgaagggggt catcttgcag  24000
gtctgccttc ccatggtggg cacgcacccg ggcttgtggt tgcaatcgca gtgcaggggg  24060
atcagcatca tctgggcctg gtcggcgttc atccccgggt acatggcctt catgaaagcc  24120
tccaattgcc tgaacgcctg ctgggccttg gctccctcgg tgaagaagac cccgcaggac  24180
ttgctagaga actggttggt ggcgcacccg gcgtcgtgca cgcagcagcg cgcgtcgttg  24240
ttggccagct gcaccacgct gcgcccccag cggttctggg tgatcttggc ccggtcgggg  24300
ttctccttca gcgcgcgctg cccgttctcg ctcgccacat ccatctcgat catgtgctcc  24360
ttctggatca tggtggtccc gtgcaggcac cgcagcttgc cctcggcctc ggtgcacccg  24420
tgcagccaca gcgcgcaccc ggtgcactcc cagttcttgt gggcgatctg ggaatgcgcg  24480
tgcacgaagc cctgcaggaa gcggcccatc atggtggtca gggtcttgtt gctagtgaag  24540
gtcagcggaa tgccgcggtg ctcctcgttg atgtacaggt ggcagatgcg gcggtacacc  24600
tcgccctgct cgggcatcag ctggaagttg gctttcaggt cggtctccac gcggtagcgg  24660
tccatcagca tagtcatgat ttccataccc ttctcccagg ccgagacgat gggcaggctc  24720
atagggttct tcaccatcat cttagcgcta gcagccgcgg ccagggggtc gctctcgtcc  24780
agggtctcaa agctccgctt gccgtccttc tcggtgatcc gcaccggggg gtagctgaag  24840
cccacggccg ccagctcctc ctcggcctgt ctttcgtcct cgctgtcctg gctgacgtcc  24900
tgcaggacca catgcttggt cttgcggggt ttcttcttgg gcggcagcgg cggcggagat  24960
```

gttggagatg gcgaggggga gcgcgagttc tcgctcacca ctactatctc ttcctcttct 25020
tggtccgagg ccacgcggcg gtaggtatgt ctcttcgggg gcagaggcgg aggcgacggg 25080
ctctcgccgc cgcgacttgg cggatggctg gcagagcccc ttccgcgttc gggggtgcgc 25140
tcccggcggc gctctgactg acttcctccg cggccggcca ttgtgttctc ctagggagga 25200
acaacaagca tggagactca gccatcgcca acctcgccat ctgcccccac cgccgacgag 25260
aagcagcagc agcagaatga aagcttaacc gccccgccgc ccagccccgc cacctccgac 25320
gcggccgtcc cagacatgca agagatggag gaatccatcg agattgacct gggctatgtg 25380
acgcccgcgg agcacgagga ggagctggca gtgcgctttt cacaagaaga gatacaccaa 25440
gaacagccag agcaggaagc agagaatgag cagagtcagg ctgggctcga gcatgacggc 25500
gactacctcc acctgagcgg gggggaggac gcgctcatca agcatctggc ccggcaggcc 25560
accatcgtca aggatgcgct gctcgaccgc accgaggtgc ccctcagcgt ggaggagctc 25620
agccgcgcct acgagttgaa cctcttctcg ccgcgcgtgc cccccaagcg ccagcccaat 25680
ggcacctgcg agcccaaccc gcgcctcaac ttctacccgg tcttcgcggt gcccgaggcc 25740
ctggccacct accacatctt tttcaagaac caaaagatcc ccgtctcctg ccgcgccaac 25800
cgcacccgcg ccgacgccct tttcaacctg ggtcccggcg cccgcctacc tgatatcgcc 25860
tccttggaag aggttcccaa gatcttcgag ggtctgggca gcgacgagac tcgggccgcg 25920
aacgctctgc aaggagaagg aggagagcat gagcaccaca gcgccctggt cgagttggaa 25980
ggcgacaacg cgcggctggc ggtgctcaaa cgcacggtcg agctgaccca tttcgcctac 26040
ccggctctga acctgccccc caaagtcatg agcgcggtca tggaccaggt gctcatcaag 26100
cgcgcgtcgc ccatctccga ggacgagggc atgcaagact ccgaggaggg caagcccgtg 26160
gtcagcgacg agcagctggc ccggtggctg ggtcctaatg ctagtcccca gagtttggaa 26220
gagcggcgca aactcatgat ggccgtggtc ctggtgaccg tggagctgga gtgcctgcgc 26280
cgcttcttcg ccgacgcgga gaccctgcgc aaggtcgagg agaacctgca ctacctcttc 26340
aggcacgggt tcgtgcgcca ggcctgcaag atctccaacg tggagctgac caacctggtc 26400
tcctacatgg gcatcttgca cgagaaccgc ctggggcaga acgtgctgca caccaccctg 26460
cgcggggagg cccggcgcga ctacatccgc gactgcgtct acctctacct ctgccacacc 26520
tggcagacgg gcatgggcgt gtggcagcag tgtctggagg agcagaacct gaaagagctc 26580
tgcaagctcc tgcagaagaa cctcaagggt ctgtggaccg ggttcgacga gcgcaccacc 26640
gcctcggacc tggccgacct cattttcccc gagcgcctca ggctgacgct gcgcaacggc 26700
ctgcccgact ttatgagcca aagcatgttg caaaactttc gctctttcat cctcgaacgc 26760
tccggaatcc tgcccgccac ctgctccgcg ctgccctcgg acttcgtgcc gctgaccttc 26820
cgcgagtgcc ccccgccgct gtggagccac tgctacctgc tgcgcctggc caactacctg 26880
gcctaccact cggacgtgat cgaggacgtc agcggcgagg gcctgctcga gtgccactgc 26940
cgctgcaacc tctgcacgcc gcaccgctcc ctggcctgca acccccagct gctgagcgag 27000
acccagatca tcggcacctt cgagttgcaa gggcccagcg aaggcgaggg ttcagccgcc 27060
aagggggggtc tgaaactcac cccggggctg tggacctcgg cctacttgcg caagttcgtg 27120
cccgaggact accatccctt cgagatcagg ttctacgagg accaatccca tccgcccaag 27180
gccgagctgt cggcctgcgt catcacccag ggggcgatcc tggcccaatt gcaagccatc 27240
cagaaatccc gccaagaatt cttgctgaaa aagggccgcg gggtctacct cgacccccag 27300
accggtgagg agctcaaccc cggcttcccc caggatgccc cgaggaaaca agaagctgaa 27360

```
agtggagctg ccgcccgtgg aggatttgga ggaagactgg gagaacagca gtcaggcaga  27420
ggaggaggag atggaggaag actgggacag cactcaggca gaggaggaca gcctgcaaga  27480
cagtctggag gaagacgagg aggaggcaga ggaggaggtg gaagaagcag ccgccgccag  27540
accgtcgtcc tcggcggggg agaaagcaag cagcacggat accatctccg ctccgggtcg  27600
gggtcccgct cgaccacaca gtagatggga cgagaccgga cgattcccga accccaccac  27660
ccagaccggt aagaaggagc ggcagggata caagtcctgg cgggggcaca aaaacgccat  27720
cgtctcctgc ttgcaggcct gcgggggcaa catctccttc acccggcgct acctgctctt  27780
ccaccgcggg gtgaactttc cccgcaacat cttgcattac taccgtcacc tccacagccc  27840
ctactacttc caagaagagg cagcagcagc agaaaaagac cagcagaaaa ccagcagcta  27900
gaaaatccac agcggcggca gcaggtggac tgaggatcgc ggcgaacgag ccggcgcaaa  27960
cccgggagct gaggaaccgg atctttccca ccctctatgc catcttccag cagagtcggg  28020
ggcaggagca ggaactgaaa gtcaagaacc gttctctgcg ctcgctcacc cgcagttgtc  28080
tgtatcacaa gagcgaagac caacttcagc gcactctcga ggacgccgag gctctcttca  28140
acaagtactg cgcgctcact cttaaagagt agcccgcgcc cgcccagtcg cagaaaaagg  28200
cgggaattac gtcacctgtg cccttcgccc tagccgcctc cacccatcat catgagcaaa  28260
gagattccca cgccttacat gtggagctac cagccccaga tgggcctggc cgccggtgcc  28320
gcccaggact actccacccg catgaattgg ctcagcgccg ggcccgcgat gatctcacgg  28380
gtgaatgaca tccgcgccca ccgaaaccag atactcctag aacagtcagc gctcaccgcc  28440
acgccccgca atcacctcaa tccgcgtaat tggcccgccg ccctggtgta ccaggaaatt  28500
ccccagccca cgaccgtact acttccgcga gacgcccagg ccgaagtcca gctgactaac  28560
tcaggtgtcc agctggcggg cggcgccacc ctgtgtcgtc accgccccgc tcagggtata  28620
aagcggctgg tgatccgggg cagaggcaca cagctcaacg acgaggtggt gagctcttcg  28680
ctgggtctgc gacctgacgg agtcttccaa ctcgccggat cggggagatc ttccttcacg  28740
cctcgtcagg ccgtcctgac tttggagagt tcgtcctcgc agccccgctc gggtggcatc  28800
ggcactctcc agttcgtgga ggagttcact ccctcggtct acttcaaccc cttctccggc  28860
tcccccggcc actacccgga cgagttcatc ccgaacttcg acgccatcag cgagtcggtg  28920
gacggctacg attgaatgtc ccatggtggc gcagctgacc tagctcggct tcgacacctg  28980
gaccactgcc gccgcttccg ctgcttcgct cgggatctcg ccgagtttgc ctactttgag  29040
ctgcccgagg agcaccctca gggcccggcc cacggagtgc ggatcgtcgt cgaagggggc  29100
ctcgactccc acctgcttcg gatcttcagc cagcgtccga tcctggtcga gcgcgagcaa  29160
ggacagaccc ttctgactct gtactgcatc tgcaaccacc ccggcctgca tgaaagtctt  29220
tgttgtctgc tgtgtactga gtataataaa agctgagatc agcgactact ccggacttcc  29280
gtgtgttcct gaatccatca accagtcttt gttcttcacc gggaacgaga ccgagctcca  29340
gctccagtgt aagccccaca agaagtacct cacctggctg ttccagggct ccccgatcgc  29400
cgttgtcaac cactgcgaca acgacggagt cctgctgagc ggccctgcca accttacttt  29460
ttccacccgc agaagcaagc tccagctctt ccaacccttc ctccccggga cctatcagtg  29520
cgtctcggga ccctgccatc acaccttcca cctgatcccg aataccacag cgtcgctccc  29580
cgctactaac aaccaaacta acctccacca acgccaccgt cgctaggcca caatacatgc  29640
ccatattaga ctatgaggcc gagccacagc gacccatgct ccccgctatt agttacttca  29700
```

-continued

```
atctaaccgg cggagatgac tgacccactg gccaacaaca acgtcaacga ccttctcctg  29760
gacatggacg gccgcgcctc ggagcagcga ctcgcccaac ttcgcattcg ccagcagcag  29820
gagagagccg tcaaggagct gcaggatgcg gtggccatcc accagtgcaa gagaggcatc  29880
ttctgcctgg tgaaacaggc caagatctcc tacgaggtca ctccaaacga ccatcgcctc  29940
tcctacgagc tcctgcagca gcgccagaag ttcacctgcc tggtcggagt caaccccatc  30000
gtcatcaccc agcagtctgg cgataccaag ggtgcatcc actgctcctg cgactccccc  30060
gactgcgtcc acactctgat caagaccctc tgcggcctcc gcgacctcct ccccatgaac  30120
taatcacccc cttatccagt gaaataaaga tcatattgat gatgatttta cagaaataaa  30180
aaataatcat ttgatttgaa ataaagatac aatcatattg atgatttgag tttaacaaaa  30240
aaataaagaa tcacttactt gaaatctgat accaggtctc tgtccatgtt ttctgccaac  30300
accacttcac tcccctcttc ccagctctgg tactgcaggc cccggcgggc tgcaaacttc  30360
ctccacacgc tgaaggggat gtcaaattcc tcctgtccct caatcttcat tttatcttct  30420
atcagatgtc caaaaagcgc gtccgggtgg atgatgactt cgaccccgtc taccccctacg  30480
atgcagacaa cgcaccgacc gtgcccttca tcaacccccc cttcgtctct tcagatggat  30540
tccaagagaa gcccctgggg gtgttgtccc tgcgactggc cgaccccgtc accaccaaga  30600
acggggaaat caccctcaag ctgggagagg gggtggacct cgattcctcg ggaaaactca  30660
tctccaacac ggccaccaag gccgccgccc ctctcagttt ttccaacaac accatttccc  30720
ttaacatgga tcacccctttt tacactaaag atggaaaatt atccttacaa gtttctccac  30780
cattaaatat actgagaaca agcattctaa acacactagc tttaggtttt ggatcaggtt  30840
taggactccg tggctctgcc ttggcagtac agttagtctc tccacttaca tttgatactg  30900
atggaaacat aaagcttacc ttagacagag gtttgcatgt tacaacagga gatgcaattg  30960
aaagcaacat aagctgggct aaaggtttaa aatttgaaga tggagccata gcaaccaaca  31020
ttggaaatgg gttagagttt ggaagcagta gtacagaaac aggtgttgat gatgcttacc  31080
caatccaagt taaacttgga tctggcctta gctttgacag tacaggagcc ataatggctg  31140
gtaacaaaga agacgataaa ctcactttgt ggacaacacc tgatccatca ccaaactgtc  31200
aaatactcgc agaaaatgat gcaaaactaa cactttgctt gactaaatgt ggtagtcaaa  31260
tactggccac tgtgtcagtc ttagttgtag gaagtggaaa cctaaacccc attactggca  31320
ccgtaagcag tgctcaggtg tttctacgtt ttgatgcaaa cggtgttctt ttaacagaac  31380
attctacact aaaaaaatac tgggggtata ggcagggaga tagcatagat ggcactccat  31440
ataccaatgc tgtaggattc atgcccaatt taaaagctta tccaaagtca caaagttcta  31500
ctactaaaaa taatatagta gggcaagtat acatgaatgg agatgtttca aaacctatgc  31560
ttctcactat aaccctcaat ggtactgatg acagcaacag tacatattca atgtcatttt  31620
catacacctg gactaatgga agctatgttg gagcaacatt tggggctaac tcttatacct  31680
tctcatacat cgcccaagaa tgaacactgt atcccaccct gcatgccaac ccttcccacc  31740
ccactctgtg gaacaaactc tgaaacacaa aataaaataa agttcaagtg ttttattgat  31800
tcaacagttt tacaggattc gagcagttat ttttcctcca ccctcccagg acatggaata  31860
caccaccctc tccccccgca cagccttgaa catctgaatg ccattggtga tggacatgct  31920
tttggtctcc acgttccaca cagtttcaga gcgagccagt ctcgggtcgg tcagggagat  31980
gaaaccctcc gggcactccc gcatctgcac ctcacagctc aacagctgag gattgtcctc  32040
ggtggtcggg atcacggtta tctggaagaa gcagaagagc ggcggtggga atcatagtcc  32100
```

gcgaacggga tcggccggtg gtgtcgcatc aggccccgca gcagtcgctg ccgccgccgc 32160
tccgtcaagc tgctgctcag ggggtccggg tccagggact ccctcagcat gatgcccacg 32220
gccctcagca tcagtcgtct ggtgcggcgg gcgcagcagc gcatgcggat ctcgctcagg 32280
tcgctgcagt acgtgcaaca cagaaccacc aggttgttca acagtccata gttcaacacg 32340
ctccagccga aactcatcgc gggaaggatg ctacccacgt ggccgtcgta ccagatcctc 32400
aggtaaatca agtggtgccc cctccagaac acgctgccca cgtacatgat ctccttgggc 32460
atgtggcggt tcaccacctc ccggtaccac atcaccctct ggttgaacat gcagccccgg 32520
atgatcctgc ggaaccacag ggccagcacc gccccgcccg ccatgcagcg aagagacccc 32580
gggtcccggc aatggcaatg gaggacccac cgctcgtacc cgtggatcat ctgggagctg 32640
aacaagtcta tgttggcaca gcacaggcat atgctcatgc atctcttcag cactctcaac 32700
tcctcggggg tcaaaaccat atcccagggc acggggaact cttgcaggac agcgaacccc 32760
gcagaacagg gcaatcctcg cacagaactt acattgtgca tggacagggt atcgcaatca 32820
ggcagcaccg ggtgatcctc caccagagaa gcgcgggtct cggtctcctc acagcgtggt 32880
aagggggccg gccgatacgg gtgatggcgg gacgcggctg atcgtgttcg cgaccgtgtc 32940
atgatgcagt tgctttcgga cattttcgta cttgctgtag cagaacctgg tccgggcgct 33000
gcacaccgat cgccggcggc ggtctcggcg cttggaacgc tcggtgttga aattgtaaaa 33060
cagccactct ctcagaccgt gcagcagatc tagggcctca ggagtgatga agatcccatc 33120
atgcctgatg gctctgatca catcgaccac cgtggaatgg gccagaccca gccagatgat 33180
gcaattttgt tgggtttcgg tgacggcggg ggagggaaga acaggaagaa ccatgattaa 33240
cttttaatcc aaacggtctc ggagtacttc aaaatgaaga tcgcggagat ggcacctctc 33300
gcccccgctg tgttggtgga aaataacagc caggtcaaag gtgatacggt tctcgagatg 33360
ttccacggtg gcttccagca aagcctccac gcgcacatcc agaaacaaga caatagcgaa 33420
agcgggaggg ttctctaatt cctcaatcat catgttacac tcctgcacca tccccagata 33480
attttcattt ttccagcctt gaatgattcg aactagttcc tgaggtaaat ccaagccagc 33540
catgataaag agctcgcgca gagcgccctc caccggcatt cttaagcaca ccctcataat 33600
tccaagatat tctgctcctg gttcacctgc agcagattga caagcggaat atcaaaatct 33660
ctgccgcgat ccctgagctc ctccctcagc aataactgta agtactcttt catatcctct 33720
ccgaaatttt tagccatagg accaccagga ataagattag ggcaagccac agtacagata 33780
aaccgaagtc ctccccagtg agcattgcca aatgcaagac tgctataagc atgctggcta 33840
gacccggtga tatcttccag ataactggac agaaaatcgc ccaggcaatt tttaagaaaa 33900
tcaacaaaag aaaaatcctc caggtggacg tttagagcct cgggaacaac gatgaagtaa 33960
atgcaagcgg tgcgttccag catggttagt tagctgatct gtagaaaaaa caaaaatgaa 34020
cattaaacca tgctagcctg gcgaacaggt gggtaaatcg ttctctccag caccaggcag 34080
gccacggggt ctccggcgcg accctcgtaa aaattgtcgc tatgattgaa aaccatcaca 34140
gagagacgtt cccggtggcc ggcgtgaatg attcgacaag atgaatacac ccccggaaca 34200
ttggcgtccg cgagtgaaaa aaagcgcccg aggaagcaat aaggcactac aatgctcagt 34260
ctcaagtcca gcaaagcgat gccatgcgga tgaagcacaa aattctcagg tgcgtacaaa 34320
atgtaattac tcccctcctg cacaggcagc aaagcccccg atccctccag gtacacatac 34380
aaagcctcag cgtccatagc ttaccgagca gcagcacaca acaggcgcaa gagtcagaga 34440

```
aaggctgagc tctaacctgt ccacccgctc tctgctcaat atatagccca gatctacact  34500

gacgtaaagg ccaaagtcta aaaatacccg ccaaataatc acacacgccc agcacacgcc  34560

cagaaaccgg tgacacactc aaaaaaatac gcgcacttcc tcaaacgccc aaaactgccg  34620

tcatttccgg gttcccacgc tacgtcatca aaacacgact ttcaaattcc gtcgaccgtt  34680

aaaaacgtca cccgccccgc ccctaacggt cgcccgtctc tcagccaatc agcgccccgc  34740

atccccaaat tcaaacacct catttgcata ttaacgcgca caaaaagttt gaggtatatt  34800

attgatgatg gttaattaa                                               34819
```

<210> SEQ ID NO 59
<211> LENGTH: 568
<212> TYPE: DNA
<213> ORGANISM: Artificial Sequence
<220> FEATURE:
<223> OTHER INFORMATION: Synthetic Construct

<400> SEQUENCE: 59

```
taacgttact ggccgaagcc gcttggaata aggccggtgt gcgtttgtct atatgttatt     60

ttccaccata ttgccgtctt ttggcaatgt gagggcccgg aaacctggcc ctgtcttctt    120

gacgagcatt cctaggggtc tttcccctct cgccaaagga atgcaaggtc tgttgaatgt    180

cgtgaaggaa gcagttcctc tggaagcttc ttgaagacaa acaacgtctg tagcgaccct    240

ttgcaggcag cggaaccccc cacctggcga caggtgcctc tgcggccaaa agccacgtgt    300

ataagataca cctgcaaagg cggcacaacc ccagtgccac gttgtgagtt ggatagttgt    360

ggaaagagtc aaatggctct cctcaagcgt attcaacaag gggctgaagg atgcccagaa    420

ggtaccccat tgtatgggat ctgatctggg gcctcggtgc acatgcttta catgtgttta    480

gtcgaggtta aaaaacgtct aggccccccg aaccacgggg acgtggtttt cctttgaaaa    540

acacgatgat aatatggcca caaccatg                                       568
```

<210> SEQ ID NO 60
<211> LENGTH: 1145
<212> TYPE: PRT
<213> ORGANISM: Artificial Sequence
<220> FEATURE:
<223> OTHER INFORMATION: Synthetic Construct

<400> SEQUENCE: 60

```
Met Ala Ser Ile Val Gly Gly Trp Glu Cys Glu Lys His Ser Gln Pro
1               5                   10                  15

Trp Gln Val Leu Val Ala Ser Arg Gly Arg Ala Val Cys Gly Gly Val
            20                  25                  30

Leu Val His Pro Gln Trp Val Leu Thr Ala Ala His Cys Ile Arg Asn
        35                  40                  45

Lys Ser Val Ile Leu Leu Gly Arg His Ser Leu Phe His Pro Glu Asp
    50                  55                  60

Thr Gly Gln Val Phe Gln Val Ser His Ser Phe Pro His Pro Leu Tyr
65                  70                  75                  80

Asp Met Ser Leu Leu Lys Asn Arg Phe Leu Arg Pro Gly Asp Asp Ser
                85                  90                  95

Ser His Asp Leu Met Leu Leu Arg Leu Ser Glu Pro Ala Glu Leu Thr
            100                 105                 110

Asp Ala Val Lys Val Met Asp Leu Pro Thr Gln Glu Pro Ala Leu Gly
        115                 120                 125

Thr Thr Cys Tyr Ala Ser Gly Trp Gly Ser Ile Glu Pro Glu Glu Phe
```

-continued

```
    130                 135                 140

Leu Thr Pro Lys Lys Leu Gln Cys Val Asp Leu His Val Ile Ser Asn
145                 150                 155                 160

Asp Val Cys Ala Gln Val His Pro Gln Lys Val Thr Lys Phe Met Leu
                165                 170                 175

Cys Ala Gly Arg Trp Thr Gly Gly Lys Ser Thr Cys Ser Gly Asp Ser
            180                 185                 190

Gly Gly Pro Leu Val Cys Asn Gly Val Leu Gln Gly Ile Thr Ser Trp
        195                 200                 205

Gly Ser Glu Pro Cys Ala Leu Pro Glu Arg Pro Ser Leu Tyr Thr Lys
    210                 215                 220

Val Val His Tyr Arg Lys Trp Ile Lys Asp Thr Ile Val Ala Asn Pro
225                 230                 235                 240

Gly Ser Glu Gly Arg Gly Ser Leu Leu Thr Cys Gly Asp Val Glu Glu
                245                 250                 255

Asn Pro Gly Pro Ala Ser Lys Ala Val Leu Leu Ala Leu Leu Met Ala
            260                 265                 270

Gly Leu Ala Leu Gln Pro Gly Thr Ala Leu Leu Cys Tyr Ser Cys Lys
        275                 280                 285

Ala Gln Val Ser Asn Glu Asp Cys Leu Gln Val Glu Asn Cys Thr Gln
    290                 295                 300

Leu Gly Glu Gln Cys Trp Thr Ala Arg Ile Arg Ala Val Gly Leu Leu
305                 310                 315                 320

Thr Val Ile Ser Lys Gly Cys Ser Leu Asn Cys Val Asp Asp Ser Gln
                325                 330                 335

Asp Tyr Tyr Val Gly Lys Lys Asn Ile Thr Cys Cys Asp Thr Asp Leu
            340                 345                 350

Cys Asn Ala Ser Gly Ala His Ala Leu Gln Pro Ala Ala Ala Ile Leu
        355                 360                 365

Ala Leu Leu Pro Ala Leu Gly Leu Leu Leu Trp Gly Pro Gly Gln Leu
    370                 375                 380

Gly Ser Gln Thr Leu Asn Phe Asp Leu Leu Lys Leu Ala Gly Asp Val
385                 390                 395                 400

Glu Ser Asn Pro Gly Pro Met Ala Ser Ala Arg Arg Pro Arg Trp Leu
                405                 410                 415

Cys Ala Gly Ala Leu Val Leu Ala Gly Gly Phe Phe Leu Leu Gly Phe
            420                 425                 430

Leu Phe Gly Trp Phe Ile Lys Ser Ser Asn Glu Ala Thr Asn Ile Thr
        435                 440                 445

Pro Lys His Asn Met Lys Ala Phe Leu Asp Glu Leu Lys Ala Glu Asn
    450                 455                 460

Ile Lys Lys Phe Leu Tyr Asn Phe Thr Gln Ile Pro His Leu Ala Gly
465                 470                 475                 480

Thr Glu Gln Asn Phe Gln Leu Ala Lys Gln Ile Gln Ser Gln Trp Lys
                485                 490                 495

Glu Phe Gly Leu Asp Ser Val Glu Leu Ala His Tyr Asp Val Leu Leu
            500                 505                 510

Ser Tyr Pro Asn Lys Thr His Pro Asn Tyr Ile Ser Ile Ile Asn Glu
        515                 520                 525

Asp Gly Asn Glu Ile Phe Asn Thr Ser Leu Phe Glu Pro Pro Pro Pro
    530                 535                 540

Gly Tyr Glu Asn Val Ser Asp Ile Val Pro Pro Phe Ser Ala Phe Ser
545                 550                 555                 560
```

-continued

```
Pro Gln Gly Met Pro Glu Gly Asp Leu Val Tyr Val Asn Tyr Ala Arg
                565                 570                 575

Thr Glu Asp Phe Phe Lys Leu Glu Arg Asp Met Lys Ile Asn Cys Ser
            580                 585                 590

Gly Lys Ile Val Ile Ala Arg Tyr Gly Lys Val Phe Arg Gly Asn Lys
        595                 600                 605

Val Lys Asn Ala Gln Leu Ala Gly Ala Lys Gly Val Ile Leu Tyr Ser
    610                 615                 620

Asp Pro Ala Asp Tyr Phe Ala Pro Gly Val Lys Ser Tyr Pro Asp Gly
625                 630                 635                 640

Trp Asn Leu Pro Gly Gly Gly Val Gln Arg Gly Asn Ile Leu Asn Leu
                645                 650                 655

Asn Gly Ala Gly Asp Pro Leu Thr Pro Gly Tyr Pro Ala Asn Glu Tyr
            660                 665                 670

Ala Tyr Arg Arg Gly Ile Ala Glu Ala Val Gly Leu Pro Ser Ile Pro
        675                 680                 685

Val His Pro Ile Gly Tyr Tyr Asp Ala Gln Lys Leu Leu Glu Lys Met
    690                 695                 700

Gly Gly Ser Ala Pro Pro Asp Ser Ser Trp Arg Gly Ser Leu Lys Val
705                 710                 715                 720

Pro Tyr Asn Val Gly Pro Gly Phe Thr Gly Asn Phe Ser Thr Gln Lys
                725                 730                 735

Val Lys Met His Ile His Ser Thr Asn Glu Val Thr Arg Ile Tyr Asn
            740                 745                 750

Val Ile Gly Thr Leu Arg Gly Ala Val Glu Pro Asp Arg Tyr Val Ile
        755                 760                 765

Leu Gly Gly His Arg Asp Ser Trp Val Phe Gly Gly Ile Asp Pro Gln
    770                 775                 780

Ser Gly Ala Ala Val Val His Glu Ile Val Arg Ser Phe Gly Thr Leu
785                 790                 795                 800

Lys Lys Glu Gly Trp Arg Pro Arg Arg Thr Ile Leu Phe Ala Ser Trp
                805                 810                 815

Asp Ala Glu Glu Phe Gly Leu Leu Gly Ser Thr Glu Trp Ala Glu Glu
            820                 825                 830

Asn Ser Arg Leu Leu Gln Glu Arg Gly Val Ala Tyr Ile Asn Ala Asp
        835                 840                 845

Ser Ser Ile Glu Gly Asn Tyr Thr Leu Arg Val Asp Cys Thr Pro Leu
    850                 855                 860

Met Tyr Ser Leu Val His Asn Leu Thr Lys Glu Leu Lys Ser Pro Asp
865                 870                 875                 880

Glu Gly Phe Glu Gly Lys Ser Leu Tyr Glu Ser Trp Thr Lys Lys Ser
                885                 890                 895

Pro Ser Pro Glu Phe Ser Gly Met Pro Arg Ile Ser Lys Leu Gly Ser
            900                 905                 910

Gly Asn Asp Phe Glu Val Phe Phe Gln Arg Leu Gly Ile Ala Ser Gly
        915                 920                 925

Arg Ala Arg Tyr Thr Lys Asn Trp Glu Thr Asn Lys Phe Ser Gly Tyr
    930                 935                 940

Pro Leu Tyr His Ser Val Tyr Glu Thr Tyr Glu Leu Val Glu Lys Phe
945                 950                 955                 960

Tyr Asp Pro Met Phe Lys Tyr His Leu Thr Val Ala Gln Val Arg Gly
                965                 970                 975
```

```
Gly Met Val Phe Glu Leu Ala Asn Ser Ile Val Leu Pro Phe Asp Cys
            980                 985                 990

Arg Asp Tyr Ala Val Val Leu Arg  Lys Tyr Ala Asp Lys  Ile Tyr Ser
        995                 1000                1005

Ile Ser  Met Lys His Pro Gln  Glu Met Lys Thr Tyr  Ser Val Ser
    1010                 1015                 1020

Phe Asp  Ser Leu Phe Ser Ala  Val Lys Asn Phe Thr  Glu Ile Ala
    1025                 1030                 1035

Ser Lys  Phe Ser Glu Arg Leu  Gln Asp Phe Asp Lys  Ser Asn Pro
    1040                 1045                 1050

Ile Val  Leu Arg Met Met Asn  Asp Gln Leu Met Phe  Leu Glu Arg
    1055                 1060                 1065

Ala Phe  Ile Asp Pro Leu Gly  Leu Pro Asp Arg Pro  Phe Tyr Arg
    1070                 1075                 1080

His Val  Ile Tyr Ala Pro Ser  Ser His Asn Lys Tyr  Ala Gly Glu
    1085                 1090                 1095

Ser Phe  Pro Gly Ile Tyr Asp  Ala Leu Phe Asp Ile  Glu Ser Lys
    1100                 1105                 1110

Val Asp  Pro Ser Lys Ala Trp  Gly Glu Val Lys Arg  Gln Ile Tyr
    1115                 1120                 1125

Val Ala  Ala Phe Thr Val Gln  Ala Ala Ala Glu Thr  Leu Ser Glu
    1130                 1135                 1140

Val Ala
    1145
```

<210> SEQ ID NO 61
<211> LENGTH: 3435
<212> TYPE: DNA
<213> ORGANISM: Artificial Sequence
<220> FEATURE:
<223> OTHER INFORMATION: Synthetic Construct

<400> SEQUENCE: 61

```
atggctagca tcgtcggagg gtgggagtgc gaaaagcact cacagccatg gcaggtcctg      60

gtcgcctcgc gcggacgcgc cgtgtgtgga ggtgtgctgg tccacccgca gtgggtgttg     120

actgcggccc attgcatcag aaataagtcc gtgatcctct tggggagaca ttccctgttt     180

caccccgaag atactggaca ggtgttccaa gtgagccact ccttcccgca tccactgtac     240

gacatgagcc tgctgaagaa ccgctttctg cggccagggg acgactcatc acacgatttg     300

atgctgcttc ggctctcgga accggccgag ctcaccgacg cagtgaaggt catggacctc     360

cctacgcaag agcctgctct cggtaccact tgttacgcat cgggatgggg ctccatcgag     420

ccggaagaat tcctgacccc gaaaaagctg cagtgcgtgg atctgcacgt gatttcgaat     480

gacgtgtgcg cgcaagtgca tccacaaaag gtcactaagt tcatgctgtg cgccggaagg     540

tggaccggcg gaaaatcgac ctgttccggc gacagcggag gcccactcgt gtgcaacggt     600

gtgctgcagg gcatcactag ctggggatca gaaccgtgcg cgcttccgga gcggccctcg     660

ctctacacga aggtggtgca ctaccgcaaa tggattaaag ataccatcgt cgcaaaccct     720

ggatccgaag gtaggggttc attattgacc tgtggagatg tcgaagaaaa cccaggaccc     780

gctagcaaag cagtgctgct ggcgctcctg atggctggac tcgcgctgca gcctggaacc     840

gccctgctct gttactcgtg caaggcccaa gtctcgaatg aggactgttt gcaagtggaa     900

aactgcaccc agctcggaga acaatgctgg actgcacgga tccgcgctgt cggcctgctg     960

accgtgatct ccaaagggtg ctcattgaac tgcgtggacg atagccagga ctactacgtg    1020
```

ggaaagaaga atatcacttg ttgcgacacg gatctttgca acgcgtccgg agcgcacgcc 1080
ctgcagccag cagccgccat tctggccctg cttccggccc tggggttgct gctctggggt 1140
ccgggccagc tcggatccca gaccctgaac tttgatctgc tgaaactggc aggcgatgtg 1200
gaaagcaacc caggcccaat ggctagcgct cgcagaccgc ggtggctgtg tgcaggggcg 1260
ctcgtcctgg cgggtggctt ctttttgctc ggctttcttt tcggatggtt catcaaatcg 1320
tcaaacgaag ctaccaatat caccccgaag cacaacatga aggcctttct ggatgagctg 1380
aaggctgaga acattaagaa gttcctctac aacttcaccc agatcccaca tttggcgggc 1440
actgagcaga actttcagtt ggctaagcag atccagagcc agtggaagga attcggcctg 1500
gactccgtcg agctggcgca ttacgatgtg ctgctgagct accctaataa gactcatccg 1560
aactatatct cgattatcaa tgaggacgga aacgaaatct ttaacacgtc cctcttcgag 1620
ccgccaccgc ctggatacga gaacgtgtca gatatcgtgc ctccgttctc ggccttctcg 1680
ccccagggaa tgcccgaagg ggacctggtg tacgtgaact acgcaaggac cgaggacttc 1740
ttcaagttgg agcgggatat gaagatcaat tgcagcggaa agatcgtcat cgcccgctac 1800
ggcaaagtgt tccgcggcaa caaggtgaag aatgcacagt tggcaggcgc caagggcgtc 1860
atcctctact cggatcctgc cgactacttc gctcctggcg tgaaatccta ccctgatggt 1920
tggaatctgc caggaggagg ggtgcagagg ggaaatatcc tgaacctgaa cggtgccggt 1980
gacccactta ctccgggtta cccggccaac gaatacgcgt acaggcgggg tatcgcggaa 2040
gccgtcggac tgccgtccat cccggtccat ccgattggtt actacgacgc ccagaagctc 2100
ctcgaaaaga tgggaggcag cgcccctccg gactcgtcat ggagaggctc gctgaaggtg 2160
ccatacaacg tgggacccgg attcactgga aatttcagca ctcaaaaagt gaagatgcac 2220
attcactcca ctaacgaagt caccaggatc tacaacgtca tcggaaccct ccggggagcg 2280
gtggaaccgg accgctacgt gatcctcggt ggacaccggg atagctgggt gttcggagga 2340
atcgatcctc aatcgggcgc agccgtcgtc catgaaatcg tcaggtcctt tggtactctt 2400
aagaaggagg gctggcgccc tagacgcact attctgttcg cctcgtggga tgccgaagaa 2460
tttggtctgc tcggcagcac cgaatgggct gaggaaaact cccgcctgct ccaagaacgc 2520
ggagtggcgt acatcaatgc cgactcatcc atcgaaggaa actacacgct gcgggtggac 2580
tgcactccac tgatgtactc gctcgtgcac aacctgacca aagaactcaa atccccagac 2640
gaaggattcg agggaaaatc gctgtacgag tcgtggacca agaagagccc atccccggag 2700
ttcagcggga tgccgcggat ctcaaagctc ggatcaggaa atgatttcga agtgttcttt 2760
cagaggctgg gaattgcgtc gggaagggct cggtacacga aaaactggga aactaacaag 2820
ttctcgggat acccgctgta ccactcggtg tatgaaactt acgaactggt ggagaaattc 2880
tacgatccta tgtttaagta ccacctgact gtggcccaag tgagaggcgg aatggtgttc 2940
gagttggcca attcaattgt gctgccattc gattgccgcg actacgccgt ggtgctgaga 3000
aagtacgcag acaaaatcta ctcaatcagc atgaagcacc cacaagagat gaaaacctac 3060
tcagtctcct tcgactccct cttctccgcg gtgaagaact tcaccgagat cgcgagcaaa 3120
ttctcggagc gccttcaaga ttttgacaaa tccaatccga tcgtcctccg catgatgaat 3180
gaccagctca tgtttctcga acgggccttc atcgatccac tgggacttcc ggaccggccg 3240
ttttaccgcc acgtgatcta cgcgccctcg tcgcataaca agtatgctgg agagagcttc 3300
ccgggtatct acgacgcatt gttcgacatt gagtccaagg tggatccgtc caaagcctgg 3360
ggtgaagtga agcgccaaat ctacgtggcg gcctttaccg tccaggcggc agcagaaacc 3420
ttgagcgagg tggct 3435

<210> SEQ ID NO 62
<211> LENGTH: 7182
<212> TYPE: DNA
<213> ORGANISM: Artificial Sequence
<220> FEATURE:
<223> OTHER INFORMATION: Synthetic Construct

<400> SEQUENCE: 62
ggcgtaatgc tctgccagtg ttacaaccaa ttaaccaatt ctgattagaa aaactcatcg 60
agcatcaaat gaaactgcaa tttattcata tcaggattat caataccata tttttgaaaa 120
agccgtttct gtaatgaagg agaaaactca ccgaggcagt tccataggat ggcaagatcc 180
tggtatcggt ctgcgattcc gactcgtcca acatcaatac aacctattaa tttcccctcg 240
tcaaaaataa ggttatcaag tgagaaatca ccatgagtga cgactgaatc cggtgagaat 300
ggcaaaagct tatgcatttc tttccagact tgttcaacag gccagccatt acgctcgtca 360
tcaaaatcac tcgcatcaac caaaccgtta ttcattcgtg attgcgcctg agcgagacga 420
aatacgcgat cgctgttaaa aggacaatta caaacaggaa tcaaatgcaa ccggcgcagg 480
aacactgcca gcgcatcaac aatattttca cctgaatcag gatattcttc taatacctgg 540
aatgctgttt tcccggggat cgcagtggtg agtaaccatg catcatcagg agtacggata 600
aaatgcttga tggtcggaag aggcataaat tccgtcagcc agtttagtct gaccatctca 660
tctgtaacat cattggcaac gctacctttg ccatgtttca gaaacaactc tggcgcatcg 720
ggcttcccat acaatcgata gattgtcgca cctgattgcc cgacattatc gcgagcccat 780
ttatacccat ataaatcagc atccatgttg gaatttaatc gcggcctcga gcaagacgtt 840
tcccgttgaa tatggctcat aacacccctt gtattactgt ttatgtaagc agacaggtcg 900
acaatattgg ctattggcca ttgcatacgt tgtatctata tcataatatg tacatttata 960
ttggctcatg tccaatatga ccgccatgtt gacattgatt attgactagt tattaatagt 1020
aatcaattac ggggtcatta gttcatagcc catatatgga gttccgcgtt acataactta 1080
cggtaaatgg cccgcctggc tgaccgccca acgacccccg cccattgacg tcaataatga 1140
cgtatgttcc catagtaacg ccaataggga ctttccattg acgtcaatgg gtggagtatt 1200
tacggtaaac tgcccacttg gcagtacatc aagtgtatca tatgccaagt ccgcccccta 1260
ttgacgtcaa tgacggtaaa tggcccgcct ggcattatgc ccagtacatg accttacggg 1320
actttcctac ttggcagtac atctacgtat tagtcatcgc tattaccatg gtgatgcggt 1380
tttggcagta caccaatggg cgtggatagc ggtttgactc acggggattt ccaagtctcc 1440
accccattga cgtcaatggg agtttgtttt ggcaccaaaa tcaacgggac tttccaaaat 1500
gtcgtaataa ccccgccccg ttgacgcaaa tgggcggtag gcgtgtacgg tgggaggtct 1560
atataagcag agctcgttta gtgaaccgtc agatcgcctg gagacgccat ccacgctgtt 1620
ttgacctcca tagaagacac cgggaccgat ccagcctccg cggccgggaa cggtgcattg 1680
gaacgcggat tccccgtgcc aagagtgact caccgtccgg atctcagcaa gcaggtatgt 1740
actctccagg gtgggcctgg cttccccagt caagactcca gggatttgag ggacgctgtg 1800
ggctcttctc ttacatgtac cttttgcttg cctcaaccct gactatcttc caggtcagga 1860
tcccagagtc aggggtctgt attttcctgc tggtggctcc agttcaggaa cagtaaaccc 1920
tgctccgaat attgcctctc acatctcgtc aatctccgcg aggactgggg accctgtgac 1980

-continued

```
gaacatggct agcatcgtcg gagggtggga gtgcgaaaag cactcacagc catggcaggt   2040
cctggtcgcc tcgcgcggac gcgccgtgtg tggaggtgtg ctggtccacc cgcagtgggt   2100
gttgactgcg gcccattgca tcagaaataa gtccgtgatc ctcttgggga gacattccct   2160
gtttcacccc gaagatactg gacaggtgtt ccaagtgagc cactccttcc cgcatccact   2220
gtacgacatg agcctgctga agaaccgctt tctgcggcca ggggacgact catcacacga   2280
tttgatgctg cttcggctct cggaaccggc cgagctcacc gacgcagtga aggtcatgga   2340
cctccctacg caagagcctg ctctcggtac cacttgttac gcatcgggat ggggctccat   2400
cgagccggaa gaattcctga ccccgaaaaa gctgcagtgc gtggatctgc acgtgatttc   2460
gaatgacgtg tgcgcgcaag tgcatccaca aaaggtcact aagttcatgc tgtgcgccgg   2520
aaggtggacc ggcggaaaat cgacctgttc cggcgacagc ggaggcccac tcgtgtgcaa   2580
cggtgtgctg cagggcatca ctagctgggg atcagaaccg tgcgcgcttc cggagcggcc   2640
ctcgctctac acgaaggtgg tgcactaccg caaatggatt aaagatacca tcgtcgcaaa   2700
ccctggatcc gaaggtaggg gttcattatt gacctgtgga gatgtcgaag aaaacccagg   2760
acccgctagc aaagcagtgc tgctggcgct cctgatggct ggactcgcgc tgcagcctgg   2820
aaccgccctg ctctgttact cgtgcaaggc ccaagtctcg aatgaggact gtttgcaagt   2880
ggaaaactgc acccagctcg gagaacaatg ctggactgca cggatccgcg ctgtcggcct   2940
gctgaccgtg atctccaaag ggtgctcatt gaactgcgtg gacgatagcc aggactacta   3000
cgtgggaaag aagaatatca cttgttgcga cacggatctt tgcaacgcgt ccggagcgca   3060
cgccctgcag ccagcagccg ccattctggc cctgcttccg gccctggggt tgctgctctg   3120
gggtccgggc cagctcggat cccagaccct gaactttgat ctgctgaaac tggcaggcga   3180
tgtggaaagc aacccaggcc caatggctag cgctcgcaga ccgcggtggc tgtgtgcagg   3240
ggcgctcgtc ctggcgggtg gcttcttttt gctcggcttt cttttcggat ggttcatcaa   3300
atcgtcaaac gaagctacca atatcacccc gaagcacaac atgaaggcct ttctggatga   3360
gctgaaggct gagaacatta agaagttcct ctacaacttc acccagatcc cacatttggc   3420
gggcactgag cagaactttc agttggctaa gcagatccag agccagtgga aggaattcgg   3480
cctggactcc gtcgagctgg cgcattacga tgtgctgctg agctacccta ataagactca   3540
tccgaactat atctcgatta tcaatgagga cggaaacgaa atctttaaca cgtccctctt   3600
cgagccgcca ccgcctggat acgagaacgt gtcagatatc gtgcctccgt tctcggcctt   3660
ctcgccccag ggaatgcccg aaggggacct ggtgtacgtg aactacgcaa ggaccgagga   3720
cttcttcaag ttggagcggg atatgaagat caattgcagc ggaaagatcg tcatcgcccg   3780
ctacggcaaa gtgttccgcg gcaacaaggt gaagaatgca cagttggcag gcgccaaggg   3840
cgtcatcctc tactcggatc ctgccgacta cttcgctcct ggcgtgaaat cctaccctga   3900
tggttggaat ctgccaggag gaggggtgca gaggggaaat atcctgaacc tgaacggtgc   3960
cggtgaccca cttactccgg gttacccggc caacgaatac gcgtacaggc ggggtatcgc   4020
ggaagccgtc ggactgccgt ccatcccggt ccatccgatt ggttactacg acgcccagaa   4080
gctcctcgaa aagatgggag gcagcgcccc tccggactcg tcatggagag gctcgctgaa   4140
ggtgccatac aacgtgggac ccggattcac tggaaatttc agcactcaaa aagtgaagat   4200
gcacattcac tccactaacg aagtcaccag gatctacaac gtcatcggaa ccctccgggg   4260
agcggtggaa ccggaccgct acgtgatcct cggtggacac cgggatagct gggtgttcgg   4320
```

-continued

```
aggaatcgat cctcaatcgg gcgcagccgt cgtccatgaa atcgtcaggt cctttggtac   4380
tcttaagaag gagggctggc gccctagacg cactattctg ttcgcctcgt gggatgccga   4440
agaatttggt ctgctcggca gcaccgaatg ggctgaggaa aactcccgcc tgctccaaga   4500
acgcggagtg gcgtacatca atgccgactc atccatcgaa ggaaactaca cgctgcgggt   4560
ggactgcact ccactgatgt actcgctcgt gcacaacctg accaaagaac tcaaatcccc   4620
agacgaagga ttcgagggaa aatcgctgta cgagtcgtgg accaagaaga gcccatcccc   4680
ggagttcagc gggatgccgc ggatctcaaa gctcggatca ggaaatgatt tcgaagtgtt   4740
ctttcagagg ctgggaattg cgtcgggaag ggctcggtac acgaaaaact gggaaactaa   4800
caagttctcg ggatacccgc tgtaccactc ggtgtatgaa acttacgaac tggtggagaa   4860
attctacgat cctatgttta agtaccacct gactgtggcc caagtgagag gcggaatggt   4920
gttcgagttg gccaattcaa ttgtgctgcc attcgattgc cgcgactacg ccgtggtgct   4980
gagaaagtac gcagacaaaa tctactcaat cagcatgaag cacccacaag agatgaaaac   5040
ctactcagtc tccttcgact ccctcttctc cgcggtgaag aacttcaccg agatcgcgag   5100
caaattctcg gagcgccttc aagattttga caaatccaat ccgatcgtcc tccgcatgat   5160
gaatgaccag ctcatgtttc tcgaacgggc cttcatcgat ccactgggac ttccggaccg   5220
gccgttttac cgccacgtga tctacgcgcc ctcgtcgcat aacaagtatg ctggagagag   5280
cttcccgggt atctacgacg cattgttcga cattgagtcc aaggtggatc cgtccaaagc   5340
ctggggtgaa gtgaagcgcc aaatctacgt ggcggccttt accgtccagg cggcagcaga   5400
aaccttgagc gaggtggctt aaagatctgg gccctaacaa aacaaaaaga tggggttatt   5460
ccctaaactt catgggttac gtaattggaa gttgggggac attgccacaa gatcatattg   5520
tacaaaagat caaacactgt tttagaaaac ttcctgtaaa caggcctatt gattggaaag   5580
tatgtcaaag gattgtgggt cttttgggct ttgctgctcc atttacacaa tgtggatatc   5640
ctgccttaat gcctttgtat gcatgtatac aagctaaaca ggctttcact ttctcgccaa   5700
cttacaaggc ctttctaagt aaacagtaca tgaaccttta ccccgttgct cggcaacggc   5760
ctggtctgtg ccaagtgttt gctgacgcaa cccccactgg ctggggcttg gccataggcc   5820
atcagcgcat gcgtggaacc tttgtggctc ctctgccgat ccatactgcg gaactcctag   5880
ccgcttgttt tgctcgcagc cggtctggag caaagctcat aggaactgac aattctgtcg   5940
tcctctcgcg gaaatataca tcgtttcgat ctacgtatga tctttttccc tctgccaaaa   6000
attatgggga catcatgaag ccccttgagc atctgacttc tggctaataa aggaaattta   6060
ttttcattgc aatagtgtgt tggaattttt tgtgtctctc actcggaagg aattctgcat   6120
taatgaatcg gccaacgcgc ggggagaggc ggtttgcgta ttgggcgctc ttccgcttcc   6180
tcgctcactg actcgctgcg ctcggtcgtt cggctgcggc gagcggtatc agctcactca   6240
aaggcggtaa tacggttatc cacagaatca ggggataacg caggaaagaa catgtgagca   6300
aaaggccagc aaaaggccag gaaccgtaaa aaggccgcgt tgctggcgtt tttccatagg   6360
ctccgccccc ctgacgagca tcacaaaaat cgacgctcaa gtcagaggtg gcgaaacccg   6420
acaggactat aaagatacca ggcgtttccc cctggaagct ccctcgtgcg ctctcctgtt   6480
ccgaccctgc cgcttaccgg atacctgtcc gcctttctcc cttcgggaag cgtggcgctt   6540
tctcatagct cacgctgtag gtatctcagt tcggtgtagg tcgttcgctc caagctgggc   6600
tgtgtgcacg aaccccccgt tcagcccgac cgctgcgcct tatccggtaa ctatcgtctt   6660
gagtccaacc cggtaagaca cgacttatcg ccactggcag cagccactgg taacaggatt   6720
```

agcagagcga ggtatgtagg cggtgctaca gagttcttga agtggtggcc taactacggc 6780
tacactagaa gaacagtatt tggtatctgc gctctgctga agccagttac cttcggaaaa 6840
agagttggta gctcttgatc cggcaaacaa accaccgctg gtagcggtgg tttttttgtt 6900
tgcaagcagc agattacgcg cagaaaaaaa ggatctcaag aagatccttt gatcttttct 6960
acggggtctg acgctcagtg gaacgaaaac tcacgttaag ggattttggt catgagatta 7020
tcaaaaagga tcttcaccta gatcctttta aattaaaaat gaagttttaa atcaatctaa 7080
agtatatatg agtaaacttg gtctgacagt taccaatgct taatcagtga ggcacctatc 7140
tcagcgatct gtctatttcg ttcatccata gttgcctgac tc 7182

<210> SEQ ID NO 63
<211> LENGTH: 34803
<212> TYPE: DNA
<213> ORGANISM: Artificial Sequence
<220> FEATURE:
<223> OTHER INFORMATION: Synthetic Construct

<400> SEQUENCE: 63
ccatcttcaa taatatacct caaacttttt gtgcgcgtta atatgcaaat gaggcgtttg 60
aatttgggga ggaagggcgg tgattggtcg agggatgagc gaccgttagg ggcggggcga 120
gtgacgtttt gatgacgtgg ttgcgaggag gagccagttt gcaagttctc gtgggaaaag 180
tgacgtcaaa cgaggtgtgg tttgaacacg gaaatactca attttcccgc gctctctgac 240
aggaaatgag gtgtttctgg gcggatgcaa gtgaaaacgg gccattttcg cgcgaaaact 300
gaatgaggaa gtgaaaatct gagtaatttc gcgtttatgg cagggaggag tatttgccga 360
gggccgagta gactttgacc gattacgtgg gggtttcgat taccgtgttt ttcacctaaa 420
tttccgcgta cggtgtcaaa gtccggtgtt tttactactg taatagtaat caattacggg 480
gtcattagtt catagcccat atatggagtt ccgcgttaca taacttacgg taaatggccc 540
gcctggctga ccgcccaacg acccccgccc attgacgtca ataatgacgt atgttcccat 600
agtaacgcca atagggactt tccattgacg tcaatgggtg gagtatttac ggtaaactgc 660
ccacttggca gtacatcaag tgtatcatat gccaagtacg ccccctattg acgtcaatga 720
cggtaaatgg cccgcctggc attatgccca gtacatgacc ttatgggact ttcctacttg 780
gcagtacatc tacgtattag tcatcgctat taccatggtg atgcggtttt ggcagtacat 840
caatgggcgt ggatagcggt ttgactcacg gggatttcca agtctccacc ccattgacgt 900
caatgggagt ttgttttggc accaaaatca acgggacttt ccaaaatgtc gtaacaactc 960
cgccccattg acgcaaatgg gcggtaggcg tgtacggtgg gaggtctata taagcagagc 1020
tgtccctatc agtgatagag atctccctat cagtgataga gagtttagtg aaccgtcaga 1080
tccgctaggg taccaacatg gctagcatcg tcggagggtg ggagtgcgaa aagcactcac 1140
agccatggca ggtcctggtc gcctcgcgcg gacgcgccgt gtgtggaggt gtgctggtcc 1200
acccgcagtg ggtgttgact gcggcccatt gcatcagaaa taagtccgtg atcctcttgg 1260
ggagacattc cctgtttcac cccgaagata ctggacaggt gttccaagtg agccactcct 1320
tcccgcatcc actgtacgac atgagcctgc tgaagaaccg ctttctgcgg ccaggggacg 1380
actcatcaca cgatttgatg ctgcttcggc tctcggaacc ggccgagctc accgacgcag 1440
tgaaggtcat ggacctccct acgcaagagc ctgctctcgg taccacttgt tacgcatcgg 1500
gatggggctc catcgagccg gaagaattcc tgaccccgaa aaagctgcag tgcgtggatc 1560

-continued

```
tgcacgtgat ttcgaatgac gtgtgcgcgc aagtgcatcc acaaaaggtc actaagttca   1620
tgctgtgcgc cggaaggtgg accggcggaa aatcgacctg ttccggcgac agcggaggcc   1680
cactcgtgtg caacggtgtg ctgcagggca tcactagctg gggatcagaa ccgtgcgcgc   1740
ttccggagcg gccctcgctc tacacgaagg tggtgcacta ccgcaaatgg attaaagata   1800
ccatcgtcgc aaaccctgga tccgaaggta ggggttcatt attgacctgt ggagatgtcg   1860
aagaaaaccc aggacccgct agcaaagcag tgctgctggc gctcctgatg gctggactcg   1920
cgctgcagcc tggaaccgcc ctgctctgtt actcgtgcaa ggcccaagtc tcgaatgagg   1980
actgtttgca agtggaaaac tgcacccagc tcggagaaca atgctggact gcacggatcc   2040
gcgctgtcgg cctgctgacc gtgatctcca aagggtgctc attgaactgc gtggacgata   2100
gccaggacta ctacgtggga aagaagaata tcacttgttg cgacacggat ctttgcaacg   2160
cgtccggagc gcacgccctg cagccagcag ccgccattct ggccctgctt ccggccctgg   2220
ggttgctgct ctggggtccg ggccagctcg gatcccagac cctgaacttt gatctgctga   2280
aactggcagg cgatgtggaa agcaacccag gcccaatggc tagcgctcgc agaccgcggt   2340
ggctgtgtgc aggggcgctc gtcctggcgg gtggcttctt tttgctcggc tttctttcg    2400
gatggttcat caaatcgtca aacgaagcta ccaatatcac cccgaagcac aacatgaagg   2460
cctttctgga tgagctgaag gctgagaaca ttaagaagtt cctctacaac ttcacccaga   2520
tcccacattt ggcgggcact gagcagaact ttcagttggc taagcagatc cagagccagt   2580
ggaaggaatt cggcctggac tccgtcgagc tggcgcatta cgatgtgctg ctgagctacc   2640
ctaataagac tcatccgaac tatatctcga ttatcaatga ggacggaaac gaaatcttta   2700
acacgtccct cttcgagccg ccaccgcctg gatacgagaa cgtgtcagat atcgtgcctc   2760
cgttctcggc cttctcgccc cagggaatgc ccgaagggga cctggtgtac gtgaactacg   2820
caaggaccga ggacttcttc aagttggagc gggatatgaa gatcaattgc agcggaaaga   2880
tcgtcatcgc ccgctacggc aaagtgttcc gcggcaacaa ggtgaagaat gcacagttgg   2940
caggcgccaa gggcgtcatc ctctactcgg atcctgccga ctacttcgct cctggcgtga   3000
aatcctaccc tgatggttgg aatctgccag gaggaggggt gcagagggga aatatcctga   3060
acctgaacgg tgccggtgac ccacttactc cgggttaccc ggccaacgaa tacgcgtaca   3120
ggcggggtat cgcggaagcc gtcggactgc cgtccatccc ggtccatccg attggttact   3180
acgacgccca gaagctcctc gaaaagatgg gaggcagcgc ccctccggac tcgtcatgga   3240
gaggctcgct gaaggtgcca tacaacgtgg gacccggatt cactggaaat ttcagcactc   3300
aaaaagtgaa gatgcacatt cactccacta acgaagtcac caggatctac aacgtcatcg   3360
gaaccctccg gggagcggtg gaaccggacc gctacgtgat cctcggtgga caccgggata   3420
gctgggtgtt cggaggaatc gatcctcaat cgggcgcagc cgtcgtccat gaaatcgtca   3480
ggtcctttgg tactcttaag aaggagggct ggcgccctag acgcactatt ctgttcgcct   3540
cgtgggatgc cgaagaattt ggtctgctcg gcagcaccga atgggctgag gaaaactccc   3600
gcctgctcca agaacgcgga gtggcgtaca tcaatgccga ctcatccatc gaaggaaact   3660
acacgctgcg ggtggactgc actccactga tgtactcgct cgtgcacaac ctgaccaaag   3720
aactcaaatc cccagacgaa ggattcgagg gaaaatcgct gtacgagtcg tggaccaaga   3780
agagcccatc cccggagttc agcgggatgc cgcggatctc aaagctcgga tcaggaaatg   3840
atttcgaagt gttctttcag aggctgggaa ttgcgtcggg aagggctcgg tacacgaaaa   3900
actgggaaac taacaagttc tcgggatacc cgctgtacca ctcggtgtat gaaacttacg   3960
```

-continued aactggtgga gaaattctac gatcctatgt ttaagtacca cctgactgtg gcccaagtga 4020
gaggcggaat ggtgttcgag ttggccaatt caattgtgct gccattcgat tgccgcgact 4080
acgccgtggt gctgagaaag tacgcagaca aaatctactc aatcagcatg aagcacccac 4140
aagagatgaa aacctactca gtctccttcg actccctctt ctccgcggtg aagaacttca 4200
ccgagatcgc gagcaaattc tcggagcgcc ttcaagattt tgacaaatcc aatccgatcg 4260
tcctccgcat gatgaatgac cagctcatgt ttctcgaacg ggccttcatc gatccactgg 4320
gacttccgga ccggccgttt taccgccacg tgatctacgc gccctcgtcg cataacaagt 4380
atgctggaga gagcttcccg ggtatctacg acgcattgtt cgacattgag tccaaggtgg 4440
atccgtccaa agcctggggt gaagtgaagc gccaaatcta cgtggcggcc tttaccgtcc 4500
aggcggcagc agaaaccttg agcgaggtgg cttgactcga gcctaagctt ctagataaga 4560
tatccgatcc accggatcta gataactgat cataatcagc cataccacat ttgtagaggt 4620
tttacttgct ttaaaaaacc tcccacacct ccccctgaac ctgaaacata aaatgaatgc 4680
aattgttgtt gttaacttgt ttattgcagc ttataatggt tacaaataaa gcaatagcat 4740
cacaaatttc acaaataaag catttttttc actgcattct agttgtggtt tgtccaaact 4800
catcaatgta tcttatatgc tggccaccgt acatgtggct tcccatgctc gcaagccctg 4860
gcccgagttc gagcacaatg tcatgaccag gtgcaatatg catctggggt cccgccgagg 4920
catgttcatg ccctaccagt gcaacctgaa ttatgtgaag gtgctgctgg agcccgatgc 4980
catgtccaga gtgagcctga cgggggtgtt tgacatgaat gtggaggtgt ggaagattct 5040
gagatatgat gaatccaaga ccaggtgccg agcctgcgag tgcggaggga agcatgccag 5100
gttccagccc gtgtgtgtgg atgtgacgga ggacctgcga cccgatcatt tggtgttgcc 5160
ctgcaccggg acggagttcg gttccagcgg ggaagaatct gactagagtg agtagtgttc 5220
tggggcgggg gaggacctgc atgagggcca gaataactga aatctgtgct tttctgtgtg 5280
ttgcagcagc atgagcggaa gcggctcctt tgagggaggg gtattcagcc cttatctgac 5340
ggggcgtctc ccctcctggg cgggagtgcg tcagaatgtg atgggatcca cggtggacgg 5400
ccggcccgtg cagcccgcga actcttcaac cctgacctat gcaaccctga gctcttcgtc 5460
gttggacgca gctgccgccg cagctgctgc atctgccgcc agcgccgtgc gcggaatggc 5520
catgggcgcc ggctactacg gcactctggt ggccaactcg agttccacca ataatcccgc 5580
cagcctgaac gaggagaagc tgttgctgct gatggcccag ctcgaggcct tgacccagcg 5640
cctgggcgag ctgacccagc aggtggctca gctgcaggag cagacgcggg ccgcggttgc 5700
cacggtgaaa tccaaataaa aaatgaatca ataaataaac ggagacggtt gttgatttta 5760
acacagagtc tgaatcttta tttgattttt cgcgcgcggt aggccctgga ccaccggtct 5820
cgatcattga gcacccggtg gatcttttcc aggacccggt agaggtgggc ttggatgttg 5880
aggtacatgg gcatgagccc gtcccggggg tggaggtagc tccattgcag ggcctcgtgc 5940
tcgggggtgg tgttgtaaat cacccagtca tagcaggggc gcagggcatg gtgttgcaca 6000
atatctttga ggaggagact gatggccacg ggcagccctt tggtgtaggt gtttacaaat 6060
ctgttgagct gggagggatg catgcggggg gagatgaggt gcatcttggc ctggatcttg 6120
agattggcga tgttaccgcc cagatcccgc ctggggttca tgttgtgcag gaccaccagc 6180
acggtgtatc cggtgcactt ggggaattta tcatgcaact tggaagggaa ggcgtgaaag 6240
aatttggcga cgcctttgtg cccgcccagg ttttccatgc actcatccat gatgatggcg 6300

-continued

```
atgggcccgt gggcggcggc ctgggcaaag acgtttcggg ggtcggacac atcatagttg   6360
tggtcctggg tgaggtcatc ataggccatt ttaatgaatt tggggcggag ggtgccggac   6420
tgggggacaa aggtaccctc gatcccgggg gcgtagttcc cctcacagat ctgcatctcc   6480
caggctttga gctcggaggg ggggatcatg tccacctgcg ggcgataaa gaacacggtt   6540
tccggggcgg gggagatgag ctgggccgaa agcaagttcc ggagcagctg ggacttgccg   6600
cagccggtgg ggccgtagat gaccccgatg accggctgca ggtggtagtt gagggagaga   6660
cagctgccgt cctcccggag gagggggggcc acctcgttca tcatctcgcg cacgtgcatg   6720
ttctcgcgca ccagttccgc caggaggcgc tctcccccca gggataggag ctcctggagc   6780
gaggcgaagt ttttcagcgg cttgagtccg tcggccatgg gcattttgga gagggtttgt   6840
tgcaagagtt ccaggcggtc ccagagctcg gtgatgtgct ctacggcatc tcgatccagc   6900
agacctcctc gtttcgcggg ttgggacggc tgcgggagta gggcaccaga cgatgggcgt   6960
ccagcgcagc cagggtccgg tccttccagg gtcgcagcgt ccgcgtcagg gtggtctccg   7020
tcacggtgaa ggggtgcgcg ccgggctggg cgcttgcgag ggtgcgcttc aggctcatcc   7080
ggctggtcga aaaccgctcc cgatcggcgc cctgcgcgtc ggccaggtag caattgacca   7140
tgagttcgta gttgagcgcc tcggccgcgt ggcctttggc gcggagctta cctttggaag   7200
tctgcccgca ggcgggacag aggagggact tgagggcgta gagcttgggg gcgaggaaga   7260
cggactcggg ggcgtaggcg tccgcgccgc agtgggcgca gacggtctcg cactccacga   7320
gccaggtgag gtcgggctgg tcggggtcaa aaaccagttt cccgccgttc tttttgatgc   7380
gtttcttacc tttggtctcc atgagctcgt gtccccgctg ggtgacaaag aggctgtccg   7440
tgtccccgta gaccgacttt atgggccggt cctcgagcgg tgtgccgcgg tcctcctcgt   7500
agaggaaccc cgcccactcc gagacgaaag cccgggtcca ggccagcacg aaggaggcca   7560
cgtgggacgg gtagcggtcg ttgtccacca gcgggtccac cttttccagg gtatgcaaac   7620
acatgtcccc ctcgtccaca tccaggaagg tgattggctt gtaagtgtag gccacgtgac   7680
cgggggtccc ggccgggggg gtataaaagg gtgcgggtcc ctgctcgtcc tcactgtctt   7740
ccggatcgct gtccaggagc gccagctgtt ggggtaggta ttccctctcg aaggcgggca   7800
tgacctcggc actcaggttg tcagtttcta gaaacgagga ggatttgata ttgacggtgc   7860
cggcggagat gcctttcaag agcccctcgt ccatctggtc agaaaagacg atctttttgt   7920
tgtcgagctt ggtggcgaag gagccgtaga gggcgttgga gaggagcttg gcgatggagc   7980
gcatggtctg gttttttttcc ttgtcggcgc gctccttggc ggcgatgttg agctgcacgt   8040
actcgcgcgc cacgcacttc cattcgggga agacggtggt cagctcgtcg ggcacgattc   8100
tgacctgcca gccccgatta tgcagggtga tgaggtccac actggtggcc acctcgccgc   8160
gcaggggctc attagtccag cagaggcgtc cgcccttgcg cgagcagaag gggggcaggg   8220
ggtccagcat gacctcgtcg ggggggtcgg catcgatggt gaagatgccg ggcaggaggt   8280
cggggtcaaa gtagctgatg gaagtggcca gatcgtccag ggcagcttgc cattcgcgca   8340
cggccagcgc gcgctcgtag ggactgaggg gcgtgcccca gggcatggga tgggtaagcg   8400
cggaggcgta catgccgcag atgtcgtaga cgtagagggg ctcctcgagg atgccgatgt   8460
aggtggggta gcagcgcccc ccgcggatgc tggcgcgcac gtagtcatac agctcgtgcg   8520
agggggcgag gagccccggg cccaggttgg tgcgactggg cttttcggcg cggtagacga   8580
tctggcggaa aatggcatgc gagttggagg agatggtggg cctttggaag atgttgaagt   8640
gggcgtgggg cagtccgacc gagtcgcgga tgaagtgggc gtaggagtct tgcagcttgg   8700
```

-continued

```
cgacgagctc ggcggtgact aggacgtcca gagcgcagta gtcgagggtc tcctggatga   8760
tgtcatactt gagctgtccc ttttgtttcc acagctcgcg gttgagaagg aactcttcgc   8820
ggtccttcca gtactcttcg agggggaacc cgtcctgatc tgcacggtaa gagcctagca   8880
tgtagaactg gttgacggcc ttgtaggcgc agcagccctt ctccacgggg agggcgtagg   8940
cctgggcggc cttgcgcagg gaggtgtgcg tgagggcgaa agtgtccctg accatgacct   9000
tgaggaactg gtgcttgaag tcgatatcgt cgcagccccc ctgctcccag agctggaagt   9060
ccgtgcgctt cttgtaggcg gggttgggca aagcgaaagt aacatcgttg aagaggatct   9120
tgcccgcgcg gggcataaag ttgcgagtga tgcggaaagg ttggggcacc tcggcccggt   9180
tgttgatgac ctgggcggcg agcacgatct cgtcgaagcc gttgatgttg tggcccacga   9240
tgtagagttc cacgaatcgc ggacggccct tgacgtgggg cagtttcttg agctcctcgt   9300
aggtgagctc gtcggggtcg ctgagcccgt gctgctcgag cgcccagtcg gcgagatggg   9360
ggttggcgcg gaggaaggaa gtccagagat ccacggccag ggcggtttgc agacggtccc   9420
ggtactgacg gaactgctgc ccgacggcca tttttcggg ggtgacgcag tagaaggtgc   9480
gggggtcccc gtgccagcga tcccatttga gctggagggc gagatcgagg gcgagctcga   9540
cgagccggtc gtccccggag agtttcatga ccagcatgaa ggggacgagc tgcttgccga   9600
aggaccccat ccaggtgtag gtttccacat cgtaggtgag gaagagcctt tcggtgcgag   9660
gatgcgagcc gatggggaag aactggatct cctgccacca attggaggaa tggctgttga   9720
tgtgatggaa gtagaaatgc cgacggcgcg ccgaacactc gtgcttgtgt ttatacaagc   9780
ggccacagtg ctcgcaacgc tgcacgggat gcacgtgctg cacgagctgt acctgagttc   9840
ctttgacgag gaatttcagt gggaagtgga gtcgtggcgc ctgcatctcg tgctgtacta   9900
cgtcgtggtg gtcggcctgg ccctcttctg cctcgatggt ggtcatgctg acgagcccgc   9960
gcgggaggca ggtccagacc tcggcgcgag cgggtcggag agcgaggacg agggcgcgca  10020
ggccggagct gtccagggtc ctgagacgct gcggagtcag gtcagtgggc agcggcggcg  10080
cgcggttgac ttgcaggagt ttttccaggg cgcgcgggag gtccagatgg tacttgatct  10140
ccaccgcgcc attggtggcg acgtcgatgg cttgcagggt cccgtgcccc tggggtgtga  10200
ccaccgtccc ccgtttcttc ttgggcggct ggggcgacgg gggcggtgcc tcttccatgg  10260
ttagaagcgg cggcgaggac gcgcgccggg cggcaggggc ggctcggggc ccggaggcag  10320
gggcggcagg ggcacgtcgg cgccgcgcgc gggtaggttc tggtactgcg cccggagaag  10380
actggcgtga gcgacgacgc gacggttgac gtcctggatc tgacgcctct gggtgaaggc  10440
cacgggaccc gtgagtttga acctgaaaga gagttcgaca gaatcaatct cggtatcgtt  10500
gacggcggcc tgccgcagga tctcttgcac gtcgcccgag ttgtcctggt aggcgatctc  10560
ggtcatgaac tgctcgatct cctcctcttg aaggtctccg cggccggcgc gctccacggt  10620
ggccgcgagg tcgttggaga tgcggcccat gagctgcgag aaggcgttca tgcccgcctc  10680
gttccagacg cggctgtaga ccacgacgcc ctcgggatcg cgggcgcgca tgaccacctg  10740
ggcgaggttg agctccacgt ggcgcgtgaa gaccgcgtag ttgcagaggc gctggtagag  10800
gtagttgagc gtggtggcga tgtgctcggt gacgaagaaa tacatgatcc agcggcggag  10860
cggcatctcg ctgacgtcgc ccagcgcctc caaacgttcc atggcctcgt aaaagtccac  10920
ggcgaagttg aaaaactggg agttgcgcgc cgagacggtc aactcctcct ccagaagacg  10980
gatgagctcg gcgatggtgg cgcgcacctc gcgctcgaag gcccccggga gttcctccac  11040
```

```
ttcctcttct tcctcctcca ctaacatctc ttctacttcc tcctcaggcg gcagtggtgg  11100
cgggggaggg ggcctgcgtc gccggcggcg cacgggcaga cggtcgatga agcgctcgat  11160
ggtctcgccg cgccggcgtc gcatggtctc ggtgacggcg cgcccgtcct cgcggggccg  11220
cagcgtgaag acgccgccgc gcatctccag gtggccgggg gggtccccgt tgggcaggga  11280
gagggcgctg acgatgcatc ttatcaattg ccccgtaggg actccgcgca aggacctgag  11340
cgtctcgaga tccacgggat ctgaaaaccg ctgaacgaag gcttcgagcc agtcgcagtc  11400
gcaaggtagg ctgagcacgg tttcttctgg cgggtcatgt tggttgggag cggggcgggc  11460
gatgctgctg gtgatgaagt tgaaataggc ggttctgaga cggcggatgg tggcgaggag  11520
caccaggtct ttgggcccgg cttgctggat gcgcagacgg tcggccatgc cccaggcgtg  11580
gtcctgacac ctggccaggt ccttgtagta gtcctgcatg agccgctcca cgggcacctc  11640
ctcctcgccc gcgcggccgt gcatgcgcgt gagcccgaag ccgcgctggg gctggacgag  11700
cgccaggtcg gcgacgacgc gctcggcgag gatggcttgc tggatctggg tgagggtggt  11760
ctggaagtca tcaaagtcga cgaagcggtg gtaggctccg gtgttgatgg tgtaggagca  11820
gttggccatg acggaccagt tgacggtctg gtggcccgga cgcacgagct cgtggtactt  11880
gaggcgcgag taggcgcgcg tgtcgaagat gtagtcgttg caggtgcgca ccaggtactg  11940
gtagccgatg aggaagtgcg gcggcggctg gcggtagagc ggccatcgct cggtggcggg  12000
ggcgccgggc gcgaggtcct cgagcatggt gcggtggtag ccgtagatgt acctggacat  12060
ccaggtgatg ccggcggcgg tggtggaggc gcgcgggaac tcgcggacgc ggttccagat  12120
gttgcgcagc ggcaggaagt agttcatggt gggcacggtc tggcccgtga ggcgcgcgca  12180
gtcgtggatg ctctatacgg gcaaaaacga aagcggtcag cggctcgact ccgtggcctg  12240
gaggctaagc gaacgggttg ggctgcgcgt gtaccccggt tcgaatctcg aatcaggctg  12300
gagccgcagc taacgtggta ttggcactcc cgtctcgacc caagcctgca ccaaccctcc  12360
aggatacgga ggcgggtcgt tttgcaactt ttttttggag gccggatgag actagtaagc  12420
gcggaaagcg gccgaccgcg atggctcgct gccgtagtct ggagaagaat cgccagggtt  12480
gcgttgcggt gtgccccggt tcgaggccgg ccggattccg cggctaacga gggcgtggct  12540
gccccgtcgt ttccaagacc ccatagccag ccgacttctc cagttacgga gcgagcccct  12600
cttttgtttt gtttgttttt gccagatgca tcccgtactg cggcagatgc gcccccacca  12660
ccctccaccg caacaacagc cccctccaca gccggcgctt ctgcccccgc cccagcagca  12720
acttccagcc acgaccgccg cggccgccgt gagcggggct ggacagagtt atgatcacca  12780
gctggccttg gaagagggcg aggggctggc gcgcctgggg gcgtcgtcgc cggagcggca  12840
cccgcgcgtg cagatgaaaa gggacgctcg cgaggcctac gtgcccaagc agaacctgtt  12900
cagagacagg agcggcgagg agcccgagga gatgcgcgcg gcccggttcc acgcggggcg  12960
ggagctgcgg cgcggcctgg accgaaagag ggtgctgagg gacgaggatt tcgaggcgga  13020
cgagctgacg gggatcagcc ccgcgcgcgc gcacgtggcc gcggccaacc tggtcacggc  13080
gtacgagcag accgtgaagg aggagagcaa cttccaaaaa tccttcaaca accacgtgcg  13140
caccctgatc gcgcgcgagg aggtgaccct gggcctgatg cacctgtggg acctgctgga  13200
ggccatcgtg cagaacccca ccagcaagcc gctgacggcg cagctgttcc tggtggtgca  13260
gcatagtcgg gacaacgaag cgttcaggga ggcgctgctg aatatcaccg agcccgaggg  13320
ccgctggctc ctggacctgg tgaacattct gcagagcatc gtggtgcagg agcgcgggct  13380
gccgctgtcc gagaagctgg cggccatcaa cttctcggtg ctgagtttgg gcaagtacta  13440
```

cgctaggaag atctacaaga ccccgtacgt gcccatagac aaggaggtga agatcgacgg 13500
gttttacatg cgcatgaccc tgaaagtgct gaccctgagc gacgatctgg gggtgtaccg 13560
caacgacagg atgcaccgtg cggtgagcgc cagcaggcgg cgcgagctga gcgaccagga 13620
gctgatgcat agtctgcagc gggccctgac cggggccggg accgaggggg agagctactt 13680
tgacatgggc gcggacctgc actggcagcc cagccgccgg gccttggagg cggcggcagg 13740
accctacgta gaagaggtgg acgatgaggt ggacgaggag ggcgagtacc tggaagactg 13800
atggcgcgac cgtatttttg ctagatgcaa caacaacagc cacctcctga tcccgcgatg 13860
cgggcggcgc tgcagagcca gccgtccggc attaactcct cggacgattg gacccaggcc 13920
atgcaacgca tcatggcgct gacgacccgc aaccccgaag cctttagaca gcagccccag 13980
gccaaccggc tctcggccat cctggaggcc gtggtgccct cgcgctccaa ccccacgcac 14040
gagaaggtcc tggccatcgt gaacgcgctg gtggagaaca aggccatccg cggcgacgag 14100
gccggcctgg tgtacaacgc gctgctggag cgcgtggccc gctacaacag caccaacgtg 14160
cagaccaacc tggaccgcat ggtgaccgac gtgcgcgagg ccgtggccca gcgcgagcgg 14220
ttccaccgcg agtccaacct gggatccatg gtggcgctga acgccttcct cagcacccag 14280
cccgccaacg tgccccgggg ccaggaggac tacaccaact tcatcagcgc cctgcgcctg 14340
atggtgaccg aggtgcccca gagcgaggtg taccagtccg ggccggacta cttcttccag 14400
accagtcgcc agggcttgca gaccgtgaac ctgagccagg ctttcaagaa cttgcagggc 14460
ctgtggggcg tgcaggcccc ggtcggggac cgcgcgacgg tgtcgagcct gctgacgccg 14520
aactcgcgcc tgctgctgct gctggtggcc cccttcacgg acagcggcag catcaaccgc 14580
aactcgtacc tgggctacct gattaacctg taccgcgagg ccatcggcca ggcgcacgtg 14640
gacgagcaga cctaccagga gatcacccac gtgagccgcg ccctgggcca ggacgacccg 14700
ggcaacctgg aagccaccct gaactttttg ctgaccaacc ggtcgcagaa gatcccgccc 14760
cagtacgcgc tcagcaccga ggaggagcgc atcctgcgtt acgtgcagca gagcgtgggc 14820
ctgttcctga tgcaggaggg ggccaccccc agcgccgcgc tcgacatgac cgcgcgcaac 14880
atggagccca gcatgtacgc cagcaaccgc ccgttcatca ataaactgat ggactacttg 14940
catcgggcgg ccgccatgaa ctctgactat ttcaccaacg ccatcctgaa tccccactgg 15000
ctcccgccgc cggggttcta cacgggcgag tacgacatgc ccgaccccaa tgacgggttc 15060
ctgtgggacg atgtggacag cagcgtgttc tccccccgac cgggtgctaa cgagcgcccc 15120
ttgtggaaga aggaaggcag cgaccgacgc ccgtcctcgg cgctgtccgg ccgcgagggt 15180
gctgccgcgg cggtgcccga ggccgccagt cctttcccga gcttgccctt ctcgctgaac 15240
agtatccgca gcagcgagct gggcaggatc acgcgcccgc gcttgctggg cgaagaggag 15300
tacttgaatg actcgctgtt gagacccgag cgggagaaga acttccccaa taacgggata 15360
gaaagcctgg tggacaagat gagccgctgg aagacgtatg cgcaggagca cagggacgat 15420
ccccgggcgt cgcagggggc cacgagccgg ggcagcgccg cccgtaaacg ccggtggcac 15480
gacaggcagc ggggacagat gtgggacgat gaggactccg ccgacgacag cagcgtgttg 15540
gacttgggtg ggagtggtaa cccgttcgct cacctgcgcc cccgtatcgg gcgcatgatg 15600
taagagaaac cgaaaataaa tgatactcac caaggccatg gcgaccagcg tgcgttcgtt 15660
tcttctctgt tgttgttgta tctagtatga tgaggcgtgc gtacccggag ggtcctcctc 15720
cctcgtacga gagcgtgatg cagcaggcga tggcggcggc ggcgatgcag cccccgctgg 15780

-continued

```
aggctcctta cgtgcccccg cggtacctgg cgcctacgga ggggcggaac agcattcgtt  15840
actcggagct ggcacccttg tacgatacca cccggttgta cctggtggac aacaagtcgg  15900
cggacatcgc ctcgctgaac taccagaacg accacagcaa cttcctgacc accgtggtgc  15960
agaacaatga cttcaccccc acggaggcca gcacccagac catcaacttt gacgagcgct  16020
cgcggtgggg cggccagctg aaaaccatca tgcacaccaa catgcccaac gtgaacgagt  16080
tcatgtacag caacaagttc aaggcgcggg tgatggtctc ccgcaagacc cccaatgggg  16140
tgacagtgac agaggattat gatggtagtc aggatgagct gaagtatgaa tgggtggaat  16200
ttgagctgcc cgaaggcaac ttctcggtga ccatgaccat cgacctgatg aacaacgcca  16260
tcatcgacaa ttacttggcg gtggggcggc agaacggggt gctggagagc gacatcggcg  16320
tgaagttcga cactaggaac ttcaggctgg gctgggaccc cgtgaccgag ctggtcatgc  16380
ccggggtgta caccaacgag gctttccatc ccgatattgt cttgctgccc ggctgcgggg  16440
tggacttcac cgagagccgc ctcagcaacc tgctgggcat tcgcaagagg cagcccttcc  16500
aggaaggctt ccagatcatg tacgaggatc tggagggggg caacatcccc gcgctcctgg  16560
atgtcgacgc ctatgagaaa agcaaggagg atgcagcagc tgaagcaact gcagccgtag  16620
ctaccgcctc taccgaggtc aggggcgata attttgcaag cgccgcagca gtggcagcgg  16680
ccgaggcggc tgaaaccgaa agtaagatag tcattcagcc ggtggagaag gatagcaaga  16740
acaggagcta caacgtacta ccggacaaga taaacaccgc ctaccgcagc tggtacctag  16800
cctacaacta tggcgacccc gagaagggcg tgcgctcctg gacgctgctc accacctcgg  16860
acgtcacctg cggcgtggag caagtctact ggtcgctgcc cgacatgatg caagacccgg  16920
tcaccttccg ctccacgcgt caagttagca actacccggt ggtgggcgcc gagctcctgc  16980
ccgtctactc caagagcttc ttcaacgagc aggccgtcta ctcgcagcag ctgcgcgcct  17040
tcacctcgct tacgcacgtc ttcaaccgct tccccgagaa ccagatcctc gtccgcccgc  17100
ccgcgcccac cattaccacc gtcagtgaaa acgttcctgc tctcacagat cacgggaccc  17160
tgccgctgcg cagcagtatc cggggagtcc agcgcgtgac cgttactgac gccagacgcc  17220
gcacctgccc ctacgtctac aaggccctgg gcatagtcgc gccgcgcgtc ctctcgagcc  17280
gcaccttcta aatgtccatt ctcatctcgc ccagtaataa caccggttgg ggcctgcgcg  17340
cgcccagcaa gatgtacgga ggcgctcgcc aacgctccac gcaacacccc gtgcgcgtgc  17400
gcgggcactt ccgcgctccc tggggcgccc tcaagggccg cgtgcggtcg cgcaccaccg  17460
tcgacgacgt gatcgaccag gtggtggccg acgcgcgcaa ctacaccccc gccgccgcgc  17520
ccgtctccac cgtggacgcc gtcatcgaca gcgtggtggc cgacgcgcgc cggtacgccc  17580
gcgccaagag ccggcggcgg cgcatcgccc ggcggcaccg gagcaccccc gccatgcgcg  17640
cggcgcgagc cttgctgcgc agggccaggc gcacgggacg cagggccatg ctcagggcgg  17700
ccagacgcgc ggcttcaggc gccagcgccg gcaggacccg gagacgcgcg gccacggcgg  17760
cggcagcggc catcgccagc atgtcccgcc cgcggcgagg gaacgtgtac tgggtgcgcg  17820
acgccgccac cggtgtgcgc gtgcccgtgc gcacccgccc ccctcgcact tgaagatgtt  17880
cacttcgcga tgttgatgtg tcccagcggc gaggaggatg tccaagcgca aattcaagga  17940
agagatgctc caggtcatcg cgcctgagat ctacggccct gcggtggtga aggaggaaag  18000
aaagccccgc aaaatcaagc gggtcaaaaa ggacaaaaag gaagaagaaa gtgatgtgga  18060
cggattggtg gagtttgtgc gcgagttcgc cccccggcgg cgcgtgcagt ggcgcgggcg  18120
gaaggtgcaa ccggtgctga gacccggcac caccgtggtc ttcacgcccg gcgagcgctc  18180
```

cggcaccgct tccaagcgct cctacgacga ggtgtacggg gatgatgata ttctggagca 18240
ggcggccgag cgcctgggcg agtttgctta cggcaagcgc agccgttccg caccgaagga 18300
agaggcggtg tccatcccgc tggaccacgg caaccccacg ccgagcctca agcccgtgac 18360
cttgcagcag gtgctgccga ccgcggcgcc gcgccggggg ttcaagcgcg agggcgagga 18420
tctgtacccc accatgcagc tgatggtgcc caagcgccag aagctggaag acgtgctgga 18480
gaccatgaag gtggacccgg acgtgcagcc cgaggtcaag gtgcggccca tcaagcaggt 18540
ggccccgggc ctgggcgtgc agaccgtgga catcaagatt cccacggagc ccatggaaac 18600
gcagaccgag cccatgatca agcccagcac cagcaccatg gaggtgcaga cggatccctg 18660
gatgccatcg gctcctagtc gaagaccccg gcgcaagtac ggcgcggcca gcctgctgat 18720
gcccaactac gcgctgcatc cttccatcat ccccacgccg ggctaccgcg gcacgcgctt 18780
ctaccgcggt cataccagca gccgccgccg caagaccacc actcgccgcc gccgtcgccg 18840
caccgccgct gcaaccaccc ctgccgccct ggtgcggaga gtgtaccgcc gcggccgcgc 18900
acctctgacc ctgccgcgcg cgcgctacca cccgagcatc gccatttaaa ctttcgcctg 18960
ctttgcagat caatggccct cacatgccgc cttcgcgttc ccattacggg ctaccgagga 19020
agaaaaccgc gccgtagaag gctggcgggg aacgggatgc gtcgccacca ccaccggcgg 19080
cggcgcgcca tcagcaagcg gttgggggga ggcttcctgc ccgcgctgat ccccatcatc 19140
gccgcggcga tcggggcgat ccccggcatt gcttccgtgg cggtgcaggc ctctcagcgc 19200
cactgagaca cacttggaaa catcttgtaa taaaccaatg gactctgacg ctcctggtcc 19260
tgtgatgtgt tttcgtagac agatggaaga catcaatttt tcgtccctgg ctccgcgaca 19320
cggcacgcgg ccgttcatgg gcacctggag cgacatcggc accagccaac tgaacggggg 19380
cgccttcaat tggagcagtc tctggagcgg gcttaagaat ttcgggtcca cgcttaaaac 19440
ctatggcagc aaggcgtgga acagcaccac agggcaggcg ctgagggata agctgaaaga 19500
gcagaacttc cagcagaagg tggtcgatgg gctcgcctcg ggcatcaacg gggtggtgga 19560
cctggccaac caggccgtgc agcggcagat caacagccgc ctggacccgg tgccgcccgc 19620
cggctccgtg gagatgccgc aggtggagga ggagctgcct cccctggaca agcggggcga 19680
gaagcgaccc cgccccgatg cggaggagac gctgctgacg cacacggacg agccgccccc 19740
gtacgaggag gcggtgaaac tgggtctgcc caccacgcgg cccatcgcgc ccctggccac 19800
cggggtgctg aaacccgaaa agcccgcgac cctggacttg cctcctcccc agccttcccg 19860
cccctctaca gtggctaagc cctgccgcc ggtggccgtg gcccgcgcgc gacccggggg 19920
caccgcccgc cctcatgcga actggcagag cactctgaac agcatcgtgg gtctgggagt 19980
gcagagtgtg aagcgccgcc gctgctatta aacctaccgt agcgcttaac ttgcttgtct 20040
gtgtgtgtat gtattatgtc gccgccgccg ctgtccacca gaaggaggag tgaagaggcg 20100
cgtcgccgag ttgcaagatg gccaccccat cgatgctgcc ccagtgggcg tacatgcaca 20160
tcgccggaca ggacgcttcg gagtacctga gtccgggtct ggtgcagttt gcccgcgcca 20220
cagacaccta cttcagtctg gggaacaagt ttaggaaccc cacggtggcg cccacgcacg 20280
atgtgaccac cgaccgcagc cagcggctga cgctgcgctt cgtgcccgtg gaccgcgagg 20340
acaacaccta ctcgtacaaa gtgcgctaca cgctggccgt gggcgacaac cgcgtgctgg 20400
acatggccag cacctacttt gacatccgcg gcgtgctgga tcggggccct agcttcaaac 20460
cctactccgg caccgcctac aacagtctgg cccccaaggg agcacccaac acttgtcagt 20520

-continued

```
ggacatataa agccgatggt gaaactgcca cagaaaaaac ctatacatat ggaaatgcac  20580
ccgtgcaggg cattaacatc acaaaagatg gtattcaact tggaactgac accgatgatc  20640
agccaatcta cgcagataaa acctatcagc ctgaacctca agtgggtgat gctgaatggc  20700
atgacatcac tggtactgat gaaaagtatg gaggcagagc tcttaagcct gataccaaaa  20760
tgaagccttg ttatggttct tttgccaagc ctactaataa agaaggaggt caggcaaatg  20820
tgaaaacagg aacaggcact actaaagaat atgacataga catggctttc tttgacaaca  20880
gaagtgcggc tgctgctggc ctagctccag aaattgtttt gtatactgaa aatgtggatt  20940
tggaaactcc agatacccat attgtataca aagcaggcac agatgacagc agctcttcta  21000
ttaatttggg tcagcaagcc atgcccaaca gacctaacta cattggtttc agagacaact  21060
ttatcgggct catgtactac aacagcactg gcaatatggg ggtgctggcc ggtcaggctt  21120
ctcagctgaa tgctgtggtt gacttgcaag acagaaacac cgagctgtcc taccagctct  21180
tgcttgactc tctgggtgac agaacccggt atttcagtat gtggaatcag gcggtggaca  21240
gctatgatcc tgatgtgcgc attattgaaa atcatggtgt ggaggatgaa cttcccaact  21300
attgtttccc tctggatgct gttggcagaa cagatactta tcagggaatt aaggctaatg  21360
gaactgatca aaccacatgg accaaagatg acagtgtcaa tgatgctaat gagataggca  21420
agggtaatcc attcgccatg gaaatcaaca tccaagccaa cctgtggagg aacttcctct  21480
acgccaacgt ggccctgtac ctgcccgact cttacaagta cacgccggcc aatgttaccc  21540
tgcccaccaa caccaacacc tacgattaca tgaacggccg ggtggtggcg ccctcgctgg  21600
tggactccta catcaacatc ggggcgcgct ggtcgctgga tcccatggac aacgtgaacc  21660
ccttcaacca ccaccgcaat gcggggctgc gctaccgctc catgctcctg ggcaacgggc  21720
gctacgtgcc cttccacatc caggtgcccc agaaattttt cgccatcaag agcctcctgc  21780
tcctgcccgg gtcctacacc tacgagtgga acttccgcaa ggacgtcaac atgatcctgc  21840
agagctccct cggcaacgac ctgcgcacgg acggggcctc catctccttc accagcatca  21900
acctctacgc caccttcttc cccatggcgc acaacacggc ctccacgctc gaggccatgc  21960
tgcgcaacga caccaacgac cagtccttca acgactacct ctcggcggcc aacatgctct  22020
accccatccc ggccaacgcc accaacgtgc ccatctccat cccctcgcgc aactgggccg  22080
ccttccgcgg ctggtccttc acgcgtctca agaccaagga gacgccctcg ctgggctccg  22140
ggttcgaccc ctacttcgtc tactcgggct ccatccccta cctcgacggc accttctacc  22200
tcaaccacac cttcaagaag gtctccatca ccttcgactc ctccgtcagc tggcccggca  22260
acgaccggct cctgacgccc aacgagttcg aaatcaagcg caccgtcgac ggcgagggct  22320
acaacgtggc ccagtgcaac atgaccaagg actggttcct ggtccagatg ctggcccact  22380
acaacatcgg ctaccagggc ttctacgtgc ccgagggcta caaggaccgc atgtactcct  22440
tcttccgcaa cttccagccc atgagccgcc aggtggtgga cgaggtcaac tacaaggact  22500
accaggccgt caccctggcc taccagcaca acaactcggg cttcgtcggc tacctcgcgc  22560
ccaccatgcg ccagggccag ccctaccccg ccaactaccc ctacccgctc atcggcaaga  22620
gcgccgtcac cagcgtcacc cagaaaaagt tcctctgcga cagggtcatg tggcgcatcc  22680
ccttctccag caacttcatg tccatgggcg cgctcaccga cctcggccag aacatgctct  22740
atgccaactc cgcccacgcg ctagacatga atttcgaagt cgaccccatg gatgagtcca  22800
cccttctcta tgttgtcttc gaagtcttcg acgtcgtccg agtgcaccag ccccaccgcg  22860
gcgtcatcga ggccgtctac ctgcgcaccc ccttctcggc cggtaacgcc accacctaag  22920
```

```
ctcttgcttc ttgcaagcca tggccgcggg ctccggcgag caggagctca gggccatcat  22980
ccgcgacctg ggctgcgggc cctacttcct gggcaccttc gataagcgct tcccgggatt  23040
catggccccg cacaagctgg cctgcgccat cgtcaacacg gccggccgcg agaccggggg  23100
cgagcactgg ctggccttcg cctggaaccc gcgctcgaac acctgctacc tcttcgaccc  23160
cttcgggttc tcggacgagc gcctcaagca gatctaccag ttcgagtacg agggcctgct  23220
gcgccgcagc gccctggcca ccgaggaccg ctgcgtcacc ctggaaaagt ccacccagac  23280
cgtgcagggt ccgcgctcgg ccgcctgcgg gctcttctgc tgcatgttcc tgcacgcctt  23340
cgtgcactgg cccgaccgcc ccatggacaa gaaccccacc atgaacttgc tgacgggggt  23400
gcccaacggc atgctccagt cgccccaggt ggaacccacc ctgcgccgca accaggaggc  23460
gctctaccgc ttcctcaact cccactccgc ctactttcgc tcccaccgcg cgcgcatcga  23520
gaaggccacc gccttcgacc gcatgaatca agacatgtaa accgtgtgtg tatgttaaat  23580
gtctttaata aacagcactt tcatgttaca catgcatctg agatgattta tttagaaatc  23640
gaaagggttc tgccgggtct cggcatggcc cgcgggcagg gacacgttgc ggaactggta  23700
cttggccagc cacttgaact cggggatcag cagtttgggc agcggggtgt cggggaagga  23760
gtcggtccac agcttccgcg tcagttgcag ggcgcccagc aggtcgggcg cggagatctt  23820
gaaatcgcag ttgggacccg cgttctgcgc gcgggagttg cggtacacgg ggttgcagca  23880
ctggaacacc atcagggccg ggtgcttcac gctcgccagc accgtcgcgt cggtgatgct  23940
ctccacgtcg aggtcctcgg cgttggccat cccgaagggg gtcatcttgc aggtctgcct  24000
tcccatggtg ggcacgcacc cgggcttgtg gttgcaatcg cagtgcaggg ggatcagcat  24060
catctgggcc tggtcggcgt tcatccccgg gtacatggcc ttcatgaaag cctccaattg  24120
cctgaacgcc tgctgggcct tggctccctc ggtgaagaag accccgcagg acttgctaga  24180
gaactggttg gtggcgcacc cggcgtcgtg cacgcagcag cgcgcgtcgt tgttggccag  24240
ctgcaccacg ctgcgccccc agcggttctg ggtgatcttg gcccggtcgg ggttctcctt  24300
cagcgcgcgc tgcccgttct cgctcgccac atccatctcg atcatgtgct ccttctggat  24360
catggtggtc ccgtgcaggc accgcagctt gccctcggcc tcggtgcacc cgtgcagcca  24420
cagcgcgcac ccggtgcact cccagttctt gtgggcgatc tgggaatgcg cgtgcacgaa  24480
gccctgcagg aagcggccca tcatggtggt cagggtcttg ttgctagtga aggtcagcgg  24540
aatgccgcgg tgctcctcgt tgatgtacag gtggcagatg cggcggtaca cctcgccctg  24600
ctcgggcatc agctggaagt tggctttcag gtcggtctcc acgcggtagc ggtccatcag  24660
catagtcatg atttccatac ccttctccca ggccgagacg atgggcaggc tcatagggtt  24720
cttcaccatc atcttagcgc tagcagccgc ggccaggggg tcgctctcgt ccagggtctc  24780
aaagctccgc ttgccgtcct tctcggtgat ccgcaccggg gggtagctga agcccacggc  24840
cgccagctcc tcctcggcct gtctttcgtc ctcgctgtcc tggctgacgt cctgcaggac  24900
cacatgcttg gtcttgcggg gtttcttctt gggcggcagc ggcggcggag atgttggaga  24960
tggcgagggg gagcgcgagt tctcgctcac cactactatc tcttcctctt cttggtccga  25020
ggccacgcgg cggtaggtat gtctcttcgg gggcagaggc ggaggcgacg ggctctcgcc  25080
gccgcgactt ggcggatggc tggcagagcc ccttccgcgt tcgggggtgc gctcccggcg  25140
gcgctctgac tgacttcctc cgcggccggc cattgtgttc tcctagggag gaacaacaag  25200
catggagact cagccatcgc caacctcgcc atctgccccc accgccgacg agaagcagca  25260
```

```
gcagcagaat gaaagcttaa ccgccccgcc gcccagcccc gccacctccg acgcggccgt  25320
cccagacatg caagagatgg aggaatccat cgagattgac ctgggctatg tgacgcccgc  25380
ggagcacgag gaggagctgg cagtgcgctt ttcacaagaa gagatacacc aagaacagcc  25440
agagcaggaa gcagagaatg agcagagtca ggctgggctc gagcatgacg gcgactacct  25500
ccacctgagc ggggggggagg acgcgctcat caagcatctg gcccggcagg ccaccatcgt  25560
caaggatgcg ctgctcgacc gcaccgaggt gcccctcagc gtggaggagc tcagccgcgc  25620
ctacgagttg aacctcttct cgccgcgcgt gccccccaag cgccagccca atggcacctg  25680
cgagcccaac ccgcgcctca acttctaccc ggtcttcgcg gtgcccgagg ccctggccac  25740
ctaccacatc tttttcaaga accaaaagat ccccgtctcc tgccgcgcca accgcacccg  25800
cgccgacgcc cttttcaacc tgggtcccgg cgcccgccta cctgatatcg cctccttgga  25860
agaggttccc aagatcttcg agggtctggg cagcgacgag actcgggccg cgaacgctct  25920
gcaaggagaa ggaggagagc atgagcacca cagcgccctg gtcgagttgg aaggcgacaa  25980
cgcgcggctg gcggtgctca aacgcacggt cgagctgacc catttcgcct acccggctct  26040
gaacctgccc cccaaagtca tgagcgcggt catggaccag gtgctcatca agcgcgcgtc  26100
gcccatctcc gaggacgagg gcatgcaaga ctccgaggag ggcaagcccg tggtcagcga  26160
cgagcagctg gcccggtggc tgggtcctaa tgctagtccc cagagtttgg aagagcggcg  26220
caaactcatg atggccgtgg tcctggtgac cgtggagctg gagtgcctgc gccgcttctt  26280
cgccgacgcg gagaccctgc gcaaggtcga ggagaacctg cactacctct tcaggcacgg  26340
gttcgtgcgc caggcctgca agatctccaa cgtggagctg accaacctgg tctcctacat  26400
gggcatcttg cacgagaacc gcctggggca gaacgtgctg cacaccaccc tgcgcgggga  26460
ggcccggcgc gactacatcc gcgactgcgt ctacctctac ctctgccaca cctggcagac  26520
gggcatgggc gtgtggcagc agtgtctgga ggagcagaac ctgaaagagc tctgcaagct  26580
cctgcagaag aacctcaagg gtctgtggac cgggttcgac gagcgcacca ccgcctcgga  26640
cctggccgac ctcattttcc ccgagcgcct caggctgacg ctgcgcaacg gcctgcccga  26700
ctttatgagc caaagcatgt tgcaaaactt tcgctctttc atcctcgaac gctccggaat  26760
cctgcccgcc acctgctccg cgctgccctc ggacttcgtg ccgctgacct tccgcgagtg  26820
ccccccgccg ctgtggagcc actgctacct gctgcgcctg gccaactacc tggcctacca  26880
ctcggacgtg atcgaggacg tcagcggcga gggcctgctc gagtgccact gccgctgcaa  26940
cctctgcacg ccgcaccgct ccctggcctg caacccccag ctgctgagcg agacccagat  27000
catcggcacc ttcgagttgc aagggcccag cgaaggcgag ggttcagccg ccaagggggg  27060
tctgaaactc accccggggc tgtggacctc ggcctacttg cgcaagttcg tgcccgagga  27120
ctaccatccc ttcgagatca ggttctacga ggaccaatcc catccgccca aggccgagct  27180
gtcggcctgc gtcatcaccc agggggcgat cctggcccaa ttgcaagcca tccagaaatc  27240
ccgccaagaa ttcttgctga aaaagggccg cggggtctac ctcgaccccc agaccggtga  27300
ggagctcaac cccggcttcc cccaggatgc cccgaggaaa caagaagctg aaagtggagc  27360
tgccgcccgt ggaggatttg gaggaagact gggagaacag cagtcaggca gaggaggagg  27420
agatggagga agactgggac agcactcagg cagaggagga cagcctgcaa gacagtctgg  27480
aggaagacga ggaggaggca gaggaggagg tggaagaagc agccgccgcc agaccgtcgt  27540
cctcggcggg ggagaaagca agcagcacgg ataccatctc cgctccgggt cggggtcccg  27600
ctcgaccaca cagtagatgg gacgagaccg gacgattccc gaaccccacc acccagaccg  27660
```

```
gtaagaagga gcggcaggga tacaagtcct ggcgggggca caaaaacgcc atcgtctcct  27720
gcttgcaggc ctgcgggggc aacatctcct tcacccggcg ctacctgctc ttccaccgcg  27780
gggtgaactt tccccgcaac atcttgcatt actaccgtca cctccacagc ccctactact  27840
tccaagaaga ggcagcagca gcagaaaaag accagcagaa aaccagcagc tagaaaatcc  27900
acagcggcgg cagcaggtgg actgaggatc gcggcgaacg agccggcgca aacccgggag  27960
ctgaggaacc ggatctttcc caccctctat gccatcttcc agcagagtcg gggggcaggag  28020
caggaactga aagtcaagaa ccgttctctg cgctcgctca cccgcagttg tctgtatcac  28080
aagagcgaag accaacttca gcgcactctc gaggacgccg aggctctctt caacaagtac  28140
tgcgcgctca ctcttaaaga gtagcccgcg cccgcccagt cgcagaaaaa ggcgggaatt  28200
acgtcacctg tgcccttcgc cctagccgcc tccacccatc atcatgagca aagagattcc  28260
cacgccttac atgtggagct accagcccca gatgggcctg gccgccggtg ccgcccagga  28320
ctactccacc cgcatgaatt ggctcagcgc cgggcccgcg atgatctcac gggtgaatga  28380
catccgcgcc caccgaaacc agatactcct agaacagtca gcgctcaccg ccacgccccg  28440
caatcacctc aatccgcgta attggcccgc cgccctggtg taccaggaaa ttccccagcc  28500
cacgaccgta ctacttccgc gagacgccca ggccgaagtc cagctgacta actcaggtgt  28560
ccagctggcg ggcggcgcca ccctgtgtcg tcaccgcccc gctcagggta taaagcggct  28620
ggtgatccgg ggcagaggca cacagctcaa cgacgaggtg gtgagctctt cgctgggtct  28680
gcgacctgac ggagtcttcc aactcgccgg atcggggaga tcttccttca cgcctcgtca  28740
ggccgtcctg actttggaga gttcgtcctc gcagccccgc tcgggtggca tcggcactct  28800
ccagttcgtg gaggagttca ctccctcggt ctacttcaac cccttctccg gctcccccgg  28860
ccactacccg gacgagttca tcccgaactt cgacgccatc agcgagtcgg tggacggcta  28920
cgattgaatg tcccatggtg gcgcagctga cctagctcgg cttcgacacc tggaccactg  28980
ccgccgcttc cgctgcttcg ctcgggatct cgccgagttt gcctactttg agctgcccga  29040
ggagcaccct cagggcccgg cccacggagt gcggatcgtc gtcgaagggg gcctcgactc  29100
ccacctgctt cggatcttca gccagcgtcc gatcctggtc gagcgcgagc aaggacagac  29160
ccttctgact ctgtactgca tctgcaacca ccccggcctg catgaaagtc tttgttgtct  29220
gctgtgtact gagtataata aaagctgaga tcagcgacta ctccggactt ccgtgtgttc  29280
ctgaatccat caaccagtct ttgttcttca ccgggaacga gaccgagctc cagctccagt  29340
gtaagcccca caagaagtac ctcacctggc tgttccaggg ctccccgatc gccgttgtca  29400
accactgcga caacgacgga gtcctgctga gcggccctgc caaccttact ttttccaccc  29460
gcagaagcaa gctccagctc ttccaaccct tcctccccgg gacctatcag tgcgtctcgg  29520
gaccctgcca tcacaccttc cacctgatcc cgaataccac agcgtcgctc cccgctacta  29580
acaaccaaac taacctccac caacgccacc gtcgctaggc cacaatacat gcccatatta  29640
gactatgagg ccgagccaca gcgacccatg ctccccgcta ttagttactt caatctaacc  29700
ggcggagatg actgacccac tggccaacaa caacgtcaac gaccttctcc tggacatgga  29760
cggccgcgcc tcggagcagc gactcgccca acttcgcatt cgccagcagc aggagagagc  29820
cgtcaaggag ctgcaggatg cggtggccat ccaccagtgc aagagaggca tcttctgcct  29880
ggtgaaacag gccaagatct cctacgaggt cactccaaac gaccatcgcc tctcctacga  29940
gctcctgcag cagcgccaga agttcacctg cctggtcgga gtcaacccca tcgtcatcac  30000
```

```
ccagcagtct ggcgatacca aggggtgcat ccactgctcc tgcgactccc ccgactgcgt  30060
ccacactctg atcaagaccc tctgcggcct ccgcgacctc ctccccatga actaatcacc  30120
cccttatcca gtgaaataaa gatcatattg atgatgattt tacagaaata aaaaataatc  30180
atttgatttg aaataaagat acaatcatat tgatgatttg agtttaacaa aaaaataaag  30240
aatcacttac ttgaaatctg ataccaggtc tctgtccatg ttttctgcca acaccacttc  30300
actcccctct tcccagctct ggtactgcag gccccggcgg gctgcaaact tcctccacac  30360
gctgaagggg atgtcaaatt cctcctgtcc ctcaatcttc attttatctt ctatcagatg  30420
tccaaaaagc gcgtccgggt ggatgatgac ttcgaccccg tctacccccta cgatgcagac  30480
aacgcaccga ccgtgccctt catcaacccc cccttcgtct cttcagatgg attccaagag  30540
aagcccctgg gggtgttgtc cctgcgactg gccgaccccg tcaccaccaa gaacggggaa  30600
atcaccctca agctgggaga gggggtggac ctcgattcct cgggaaaact catctccaac  30660
acggccacca aggccgccgc ccctctcagt ttttccaaca acaccatttc ccttaacatg  30720
gatcacccct tttacactaa agatggaaaa ttatccttac aagtttctcc accattaaat  30780
atactgagaa caagcattct aaacacacta gctttaggtt ttggatcagg tttaggactc  30840
cgtggctctg ccttggcagt acagttagtc tctccactta catttgatac tgatggaaac  30900
ataaagctta ccttagacag aggtttgcat gttacaacag gagatgcaat tgaaagcaac  30960
ataagctggg ctaaaggttt aaaatttgaa gatggagcca tagcaaccaa cattggaaat  31020
gggttagagt ttggaagcag tagtacagaa acaggtgttg atgatgctta cccaatccaa  31080
gttaaacttg gatctggcct tagctttgac agtacaggag ccataatggc tggtaacaaa  31140
gaagacgata aactcacttt gtggacaaca cctgatccat caccaaactg tcaaatactc  31200
gcagaaaatg atgcaaaact aacactttgc ttgactaaat gtggtagtca aatactggcc  31260
actgtgtcag tcttagttgt aggaagtgga aacctaaacc ccattactgg caccgtaagc  31320
agtgctcagg tgtttctacg ttttgatgca aacggtgttc ttttaacaga acattctaca  31380
ctaaaaaaat actgggggta taggcaggga gatagcatag atggcactcc atataccaat  31440
gctgtaggat tcatgcccaa tttaaaagct tatccaaagt cacaaagttc tactactaaa  31500
aataatatag tagggcaagt atacatgaat ggagatgttt caaaacctat gcttctcact  31560
ataaccctca atggtactga tgacagcaac agtacatatt caatgtcatt ttcatacacc  31620
tggactaatg gaagctatgt tggagcaaca tttggggcta actcttatac cttctcatac  31680
atcgcccaag aatgaacact gtatcccacc ctgcatgcca acccttccca ccccactctg  31740
tggaacaaac tctgaaacac aaaataaaat aaagttcaag tgttttattg attcaacagt  31800
tttacaggat tcgagcagtt atttttcctc caccctccca ggacatggaa tacaccaccc  31860
tctccccccg cacagccttg aacatctgaa tgccattggt gatggacatg cttttggtct  31920
ccacgttcca cacagtttca gagcgagcca gtctcgggtc ggtcagggag atgaaaccct  31980
ccgggcactc ccgcatctgc acctcacagc tcaacagctg aggattgtcc tcggtggtcg  32040
ggatcacggt tatctggaag aagcagaaga gcggcggtgg gaatcatagt ccgcgaacgg  32100
gatcggccgg tggtgtcgca tcaggccccg cagcagtcgc tgccgccgcc gctccgtcaa  32160
gctgctgctc agggggtccg ggtccaggga ctccctcagc atgatgccca cggccctcag  32220
catcagtcgt ctggtgcggc gggcgcagca gcgcatgcgg atctcgctca ggtcgctgca  32280
gtacgtgcaa cacagaacca ccaggttgtt caacagtcca tagttcaaca cgctccagcc  32340
gaaactcatc gcgggaagga tgctacccac gtggccgtcg taccagatcc tcaggtaaat  32400
```

caagtggtgc cccctccaga acacgctgcc cacgtacatg atctccttgg gcatgtggcg 32460
gttcaccacc tcccggtacc acatcaccct ctggttgaac atgcagcccc ggatgatcct 32520
gcggaaccac agggccagca ccgccccgcc cgccatgcag cgaagagacc ccgggtcccg 32580
gcaatggcaa tggaggaccc accgctcgta cccgtggatc atctgggagc tgaacaagtc 32640
tatgttggca cagcacaggc atatgctcat gcatctcttc agcactctca actcctcggg 32700
ggtcaaaacc atatcccagg gcacggggaa ctcttgcagg acagcgaacc ccgcagaaca 32760
gggcaatcct cgcacagaac ttacattgtg catggacagg gtatcgcaat caggcagcac 32820
cgggtgatcc tccaccagag aagcgcgggt ctcggtctcc tcacagcgtg gtaagggggc 32880
cggccgatac gggtgatggc gggacgcggc tgatcgtgtt cgcgaccgtg tcatgatgca 32940
gttgctttcg gacattttcg tacttgctgt agcagaacct ggtccgggcg ctgcacaccg 33000
atcgccggcg gcggtctcgg cgcttggaac gctcggtgtt gaaattgtaa aacagccact 33060
ctctcagacc gtgcagcaga tctagggcct caggagtgat gaagatccca tcatgcctga 33120
tggctctgat cacatcgacc accgtggaat gggccagacc cagccagatg atgcaatttt 33180
gttgggtttc ggtgacggcg ggggagggaa gaacaggaag aaccatgatt aacttttaat 33240
ccaaacggtc tcggagtact tcaaaatgaa gatcgcggag atggcacctc tcgcccccgc 33300
tgtgttggtg gaaaataaca gccaggtcaa aggtgatacg gttctcgaga tgttccacgg 33360
tggcttccag caaagcctcc acgcgcacat ccagaaacaa gacaatagcg aaagcgggag 33420
ggttctctaa ttcctcaatc atcatgttac actcctgcac catccccaga taattttcat 33480
ttttccagcc ttgaatgatt cgaactagtt cctgaggtaa atccaagcca gccatgataa 33540
agagctcgcg cagagcgccc tccaccggca ttcttaagca caccctcata attccaagat 33600
attctgctcc tggttcacct gcagcagatt gacaagcgga atatcaaaat ctctgccgcg 33660
atccctgagc tcctccctca gcaataactg taagtactct ttcatatcct ctccgaaatt 33720
tttagccata ggaccaccag gaataagatt agggcaagcc acagtacaga taaaccgaag 33780
tcctccccag tgagcattgc caaatgcaag actgctataa gcatgctggc tagacccggt 33840
gatatcttcc agataactgg acagaaaatc gcccaggcaa tttttaagaa aatcaacaaa 33900
agaaaaatcc tccaggtgga cgtttagagc ctcgggaaca acgatgaagt aaatgcaagc 33960
ggtgcgttcc agcatggtta gttagctgat ctgtagaaaa aacaaaaatg aacattaaac 34020
catgctagcc tggcgaacag gtgggtaaat cgttctctcc agcaccaggc aggccacggg 34080
gtctccggcg cgaccctcgt aaaaattgtc gctatgattg aaaaccatca cagagagacg 34140
ttcccggtgg ccggcgtgaa tgattcgaca agatgaatac acccccggaa cattggcgtc 34200
cgcgagtgaa aaaaagcgcc cgaggaagca ataaggcact acaatgctca gtctcaagtc 34260
cagcaaagcg atgccatgcg gatgaagcac aaaattctca ggtgcgtaca aaatgtaatt 34320
actcccctcc tgcacaggca gcaaagcccc cgatccctcc aggtacacat acaaagcctc 34380
agcgtccata gcttaccgag cagcagcaca caacaggcgc aagagtcaga gaaaggctga 34440
gctctaacct gtccacccgc tctctgctca atatatagcc cagatctaca ctgacgtaaa 34500
ggccaaagtc taaaaatacc cgccaaataa tcacacacgc ccagcacacg cccagaaacc 34560
ggtgacacac tcaaaaaaat acgcgcactt cctcaaacgc ccaaaactgc cgtcatttcc 34620
gggttcccac gctacgtcat caaaacacga ctttcaaatt ccgtcgaccg ttaaaaacgt 34680
cacccgcccc gcccctaacg gtcgcccgtc tctcagccaa tcagcgcccc gcatccccaa 34740
attcaaacgc ctcatttgca tattaacgcg cacaaaaagt ttgaggtata ttattgatga 34800
tgg 34803

<210> SEQ ID NO 64
<211> LENGTH: 1145
<212> TYPE: PRT
<213> ORGANISM: Artificial Sequence
<220> FEATURE:
<223> OTHER INFORMATION: Synthetic Construct

<400> SEQUENCE: 64

Met Ala Ser Ile Val Gly Gly Trp Glu Cys Glu Lys His Ser Gln Pro
1 5 10 15

Trp Gln Val Leu Val Ala Ser Arg Gly Arg Ala Val Cys Gly Gly Val
20 25 30

Leu Val His Pro Gln Trp Val Leu Thr Ala Ala His Cys Ile Arg Asn
35 40 45

Lys Ser Val Ile Leu Leu Gly Arg His Ser Leu Phe His Pro Glu Asp
50 55 60

Thr Gly Gln Val Phe Gln Val Ser His Ser Phe Pro His Pro Leu Tyr
65 70 75 80

Asp Met Ser Leu Leu Lys Asn Arg Phe Leu Arg Pro Gly Asp Asp Ser
85 90 95

Ser His Asp Leu Met Leu Leu Arg Leu Ser Glu Pro Ala Glu Leu Thr
100 105 110

Asp Ala Val Lys Val Met Asp Leu Pro Thr Gln Glu Pro Ala Leu Gly
115 120 125

Thr Thr Cys Tyr Ala Ser Gly Trp Gly Ser Ile Glu Pro Glu Glu Phe
130 135 140

Leu Thr Pro Lys Lys Leu Gln Cys Val Asp Leu His Val Ile Ser Asn
145 150 155 160

Asp Val Cys Ala Gln Val His Pro Gln Lys Val Thr Lys Phe Met Leu
165 170 175

Cys Ala Gly Arg Trp Thr Gly Gly Lys Ser Thr Cys Ser Gly Asp Ser
180 185 190

Gly Gly Pro Leu Val Cys Asn Gly Val Leu Gln Gly Ile Thr Ser Trp
195 200 205

Gly Ser Glu Pro Cys Ala Leu Pro Glu Arg Pro Ser Leu Tyr Thr Lys
210 215 220

Val Val His Tyr Arg Lys Trp Ile Lys Asp Thr Ile Val Ala Asn Pro
225 230 235 240

Gly Ser Gln Thr Leu Asn Phe Asp Leu Leu Lys Leu Ala Gly Asp Val
245 250 255

Glu Ser Asn Pro Gly Pro Met Ala Ser Ala Arg Arg Pro Arg Trp Leu
260 265 270

Cys Ala Gly Ala Leu Val Leu Ala Gly Gly Phe Phe Leu Leu Gly Phe
275 280 285

Leu Phe Gly Trp Phe Ile Lys Ser Ser Asn Glu Ala Thr Asn Ile Thr
290 295 300

Pro Lys His Asn Met Lys Ala Phe Leu Asp Glu Leu Lys Ala Glu Asn
305 310 315 320

Ile Lys Lys Phe Leu Tyr Asn Phe Thr Gln Ile Pro His Leu Ala Gly
325 330 335

Thr Glu Gln Asn Phe Gln Leu Ala Lys Gln Ile Gln Ser Gln Trp Lys
340 345 350

```
Glu Phe Gly Leu Asp Ser Val Glu Leu Ala His Tyr Asp Val Leu Leu
        355                 360                 365

Ser Tyr Pro Asn Lys Thr His Pro Asn Tyr Ile Ser Ile Ile Asn Glu
    370                 375                 380

Asp Gly Asn Glu Ile Phe Asn Thr Ser Leu Phe Glu Pro Pro Pro Pro
385                 390                 395                 400

Gly Tyr Glu Asn Val Ser Asp Ile Val Pro Pro Phe Ser Ala Phe Ser
                405                 410                 415

Pro Gln Gly Met Pro Glu Gly Asp Leu Val Tyr Val Asn Tyr Ala Arg
            420                 425                 430

Thr Glu Asp Phe Phe Lys Leu Glu Arg Asp Met Lys Ile Asn Cys Ser
        435                 440                 445

Gly Lys Ile Val Ile Ala Arg Tyr Gly Lys Val Phe Arg Gly Asn Lys
    450                 455                 460

Val Lys Asn Ala Gln Leu Ala Gly Ala Lys Gly Val Ile Leu Tyr Ser
465                 470                 475                 480

Asp Pro Ala Asp Tyr Phe Ala Pro Gly Val Lys Ser Tyr Pro Asp Gly
                485                 490                 495

Trp Asn Leu Pro Gly Gly Gly Val Gln Arg Gly Asn Ile Leu Asn Leu
            500                 505                 510

Asn Gly Ala Gly Asp Pro Leu Thr Pro Gly Tyr Pro Ala Asn Glu Tyr
        515                 520                 525

Ala Tyr Arg Arg Gly Ile Ala Glu Ala Val Gly Leu Pro Ser Ile Pro
    530                 535                 540

Val His Pro Ile Gly Tyr Tyr Asp Ala Gln Lys Leu Leu Glu Lys Met
545                 550                 555                 560

Gly Gly Ser Ala Pro Pro Asp Ser Ser Trp Arg Gly Ser Leu Lys Val
                565                 570                 575

Pro Tyr Asn Val Gly Pro Gly Phe Thr Gly Asn Phe Ser Thr Gln Lys
            580                 585                 590

Val Lys Met His Ile His Ser Thr Asn Glu Val Thr Arg Ile Tyr Asn
        595                 600                 605

Val Ile Gly Thr Leu Arg Gly Ala Val Glu Pro Asp Arg Tyr Val Ile
    610                 615                 620

Leu Gly Gly His Arg Asp Ser Trp Val Phe Gly Gly Ile Asp Pro Gln
625                 630                 635                 640

Ser Gly Ala Ala Val Val His Glu Ile Val Arg Ser Phe Gly Thr Leu
                645                 650                 655

Lys Lys Glu Gly Trp Arg Pro Arg Arg Thr Ile Leu Phe Ala Ser Trp
            660                 665                 670

Asp Ala Glu Glu Phe Gly Leu Leu Gly Ser Thr Glu Trp Ala Glu Glu
        675                 680                 685

Asn Ser Arg Leu Leu Gln Glu Arg Gly Val Ala Tyr Ile Asn Ala Asp
    690                 695                 700

Ser Ser Ile Glu Gly Asn Tyr Thr Leu Arg Val Asp Cys Thr Pro Leu
705                 710                 715                 720

Met Tyr Ser Leu Val His Asn Leu Thr Lys Glu Leu Lys Ser Pro Asp
                725                 730                 735

Glu Gly Phe Glu Gly Lys Ser Leu Tyr Glu Ser Trp Thr Lys Lys Ser
            740                 745                 750

Pro Ser Pro Glu Phe Ser Gly Met Pro Arg Ile Ser Lys Leu Gly Ser
        755                 760                 765
```

```
Gly Asn Asp Phe Glu Val Phe Phe Gln Arg Leu Gly Ile Ala Ser Gly
    770                 775                 780

Arg Ala Arg Tyr Thr Lys Asn Trp Glu Thr Asn Lys Phe Ser Gly Tyr
785                 790                 795                 800

Pro Leu Tyr His Ser Val Tyr Glu Thr Tyr Glu Leu Val Glu Lys Phe
                805                 810                 815

Tyr Asp Pro Met Phe Lys Tyr His Leu Thr Val Ala Gln Val Arg Gly
            820                 825                 830

Gly Met Val Phe Glu Leu Ala Asn Ser Ile Val Leu Pro Phe Asp Cys
        835                 840                 845

Arg Asp Tyr Ala Val Val Leu Arg Lys Tyr Ala Asp Lys Ile Tyr Ser
    850                 855                 860

Ile Ser Met Lys His Pro Gln Glu Met Lys Thr Tyr Ser Val Ser Phe
865                 870                 875                 880

Asp Ser Leu Phe Ser Ala Val Lys Asn Phe Thr Glu Ile Ala Ser Lys
                885                 890                 895

Phe Ser Glu Arg Leu Gln Asp Phe Asp Lys Ser Asn Pro Ile Val Leu
            900                 905                 910

Arg Met Met Asn Asp Gln Leu Met Phe Leu Glu Arg Ala Phe Ile Asp
        915                 920                 925

Pro Leu Gly Leu Pro Asp Arg Pro Phe Tyr Arg His Val Ile Tyr Ala
    930                 935                 940

Pro Ser Ser His Asn Lys Tyr Ala Gly Glu Ser Phe Pro Gly Ile Tyr
945                 950                 955                 960

Asp Ala Leu Phe Asp Ile Glu Ser Lys Val Asp Pro Ser Lys Ala Trp
                965                 970                 975

Gly Glu Val Lys Arg Gln Ile Tyr Val Ala Ala Phe Thr Val Gln Ala
            980                 985                 990

Ala Ala Glu Thr Leu Ser Glu Val  Ala Gly Ser Glu Gly  Arg Gly Ser
        995                 1000                1005

Leu Leu  Thr Cys Gly Asp Val  Glu Glu Asn Pro Gly  Pro Ala Ser
    1010                1015                1020

Lys Ala  Val Leu Leu Ala Leu  Leu Met Ala Gly Leu  Ala Leu Gln
    1025                1030                1035

Pro Gly  Thr Ala Leu Leu Cys  Tyr Ser Cys Lys Ala  Gln Val Ser
    1040                1045                1050

Asn Glu  Asp Cys Leu Gln Val  Glu Asn Cys Thr Gln  Leu Gly Glu
    1055                1060                1065

Gln Cys  Trp Thr Ala Arg Ile  Arg Ala Val Gly Leu  Leu Thr Val
    1070                1075                1080

Ile Ser  Lys Gly Cys Ser Leu  Asn Cys Val Asp Asp  Ser Gln Asp
    1085                1090                1095

Tyr Tyr  Val Gly Lys Lys Asn  Ile Thr Cys Cys Asp  Thr Asp Leu
    1100                1105                1110

Cys Asn  Ala Ser Gly Ala His  Ala Leu Gln Pro Ala  Ala Ala Ile
    1115                1120                1125

Leu Ala  Leu Leu Pro Ala Leu  Gly Leu Leu Leu Trp  Gly Pro Gly
    1130                1135                1140

Gln Leu
    1145
```

<210> SEQ ID NO 65
<211> LENGTH: 3435
<212> TYPE: DNA

-continued

<213> ORGANISM: Artificial Sequence
<220> FEATURE:
<223> OTHER INFORMATION: Synthetic Construct

<400> SEQUENCE: 65

```
atggctagca tcgtcggagg gtgggagtgc gaaaagcact cacagccatg gcaggtcctg     60

gtcgcctcgc gcggacgcgc cgtgtgtgga ggtgtgctgg tccacccgca gtgggtgttg    120

actgcggccc attgcatcag aaataagtcc gtgatcctct tggggagaca ttccctgttt    180

caccccgaag atactggaca ggtgttccaa gtgagccact ccttcccgca tccactgtac    240

gacatgagcc tgctgaagaa ccgctttctg cggccagggg acgactcatc acacgatttg    300

atgctgcttc ggctctcgga accggccgag ctcaccgacg cagtgaaggt catggacctc    360

cctacgcaag agcctgctct cggtaccact tgttacgcat cgggatgggg ctccatcgag    420

ccggaagaat tcctgacccc gaaaaagctg cagtgcgtgg atctgcacgt gatttcgaat    480

gacgtgtgcg cgcaagtgca tccacaaaag gtcactaagt tcatgctgtg cgccggaagg    540

tggaccggcg gaaaatcgac ctgttccggc gacagcggag gcccactcgt gtgcaacggt    600

gtgctgcagg gcatcactag ctggggatca gaaccgtgcg cgcttccgga gcggccctcg    660

ctctacacga aggtggtgca ctaccgcaaa tggattaaag ataccatcgt cgcaaaccct    720

ggatcccaga ccctgaactt tgatctgctg aaactggcag gcgatgtgga aagcaaccca    780

ggcccaatgg ctagcgctcg cagaccgcgg tggctgtgtg caggggcgct cgtcctggcg    840

ggtggcttct tttgctcgg ctttctttc ggatggttca tcaaatcgtc aaacgaagct     900

accaatatca ccccgaagca caacatgaag gcctttctgg atgagctgaa ggctgagaac    960

attaagaagt tcctctacaa cttcacccag atcccacatt tggcgggcac tgagcagaac   1020

tttcagttgg ctaagcagat ccagagccag tggaaggaat tcggcctgga ctccgtcgag   1080

ctggcgcatt acgatgtgct gctgagctac cctaataaga ctcatccgaa ctatatctcg   1140

attatcaatg aggacggaaa cgaaatcttt aacacgtccc tcttcgagcc gccaccgcct   1200

ggatacgaga acgtgtcaga tatcgtgcct ccgttctcgg ccttctcgcc ccagggaatg   1260

cccgaagggg acctggtgta cgtgaactac gcaaggaccg aggacttctt caagttggag   1320

cgggatatga agatcaattg cagcggaaag atcgtcatcg cccgctacgg caaagtgttc   1380

cgcggcaaca aggtgaagaa tgcacagttg gcaggcgcca agggcgtcat cctctactcg   1440

gatcctgccg actacttcgc tcctggcgtg aaatcctacc ctgatggttg gaatctgcca   1500

ggaggagggg tgcagagggg aaatatcctg aacctgaacg gtgccggtga cccacttact   1560

ccgggttacc cggccaacga atacgcgtac aggcggggta tcgcggaagc cgtcggactg   1620

ccgtccatcc cggtccatcc gattggttac tacgacgccc agaagctcct cgaaaagatg   1680

ggaggcagcg cccctccgga ctcgtcatgg agaggctcgc tgaaggtgcc atacaacgtg   1740

ggacccggat tcactggaaa tttcagcact caaaaagtga agatgcacat tcactccact   1800

aacgaagtca ccaggatcta caacgtcatc ggaaccctcc ggggagcggt ggaaccggac   1860

cgctacgtga tcctcggtgg acaccgggat agctgggtgt tcggaggaat cgatcctcaa   1920

tcgggcgcag ccgtcgtcca tgaaatcgtc aggtcctttg gtactcttaa gaaggagggc   1980

tggcgcccta gacgcactat tctgttcgcc tcgtgggatg ccgaagaatt tggtctgctc   2040

ggcagcaccg aatgggctga ggaaaactcc cgcctgctcc aagaacgcgg agtggcgtac   2100

atcaatgccg actcatccat cgaaggaaac tacacgctgc gggtggactg cactccactg   2160

atgtactcgc tcgtgcacaa cctgaccaaa gaactcaaat ccccagacga aggattcgag   2220
```

```
ggaaaatcgc tgtacgagtc gtggaccaag aagagcccat ccccggagtt cagcgggatg   2280
ccgcggatct caaagctcgg atcaggaaat gatttcgaag tgttctttca gaggctggga   2340
attgcgtcgg gaagggctcg gtacacgaaa aactgggaaa ctaacaagtt ctcgggatac   2400
ccgctgtacc actcggtgta tgaaacttac gaactggtgg agaaattcta cgatcctatg   2460
tttaagtacc acctgactgt ggcccaagtg agaggcggaa tggtgttcga gttggccaat   2520
tcaattgtgc tgccattcga ttgccgcgac tacgccgtgg tgctgagaaa gtacgcagac   2580
aaaatctact caatcagcat gaagcaccca caagagatga aacctactc agtctccttc   2640
gactccctct tctccgcggt gaagaacttc accgagatcg cgagcaaatt ctcggagcgc   2700
cttcaagatt ttgacaaatc caatccgatc gtcctccgca tgatgaatga ccagctcatg   2760
tttctcgaac gggccttcat cgatccactg ggacttccgg accggccgtt ttaccgccac   2820
gtgatctacg cgccctcgtc gcataacaag tatgctggag agagcttccc gggtatctac   2880
gacgcattgt tcgacattga gtccaaggtg gatccgtcca aagcctgggg tgaagtgaag   2940
cgccaaatct acgtggcggc ctttaccgtc caggcggcag cagaaacctt gagcgaggtg   3000
gctggatccg aaggtagggg ttcattattg acctgtggag atgtcgaaga aaacccagga   3060
cccgctagca aagcagtgct gctggcgctc ctgatggctg gactcgcgct gcagcctgga   3120
accgccctgc tctgttactc gtgcaaggcc caagtctcga atgaggactg tttgcaagtg   3180
gaaaactgca cccagctcgg agaacaatgc tggactgcac ggatccgcgc tgtcggcctg   3240
ctgaccgtga tctccaaagg gtgctcattg aactgcgtgg acgatagcca ggactactac   3300
gtgggaaaga agaatatcac ttgttgcgac acggatcttt gcaacgcgtc cggagcgcac   3360
gccctgcagc cagcagccgc cattctggcc ctgcttccgg ccctggggtt gctgctctgg   3420
ggtccgggcc agctc                                                    3435
```

<210> SEQ ID NO 66
<211> LENGTH: 3947
<212> TYPE: DNA
<213> ORGANISM: Artificial Sequence
<220> FEATURE:
<223> OTHER INFORMATION: Synthetic Construct

<400> SEQUENCE: 66

```
atggctagca aagcagtgct gctggcgctc ctgatggctg gactcgcgct gcagcctgga     60
accgccctgc tctgttactc gtgcaaggcc caagtctcga atgaggactg tttgcaagtg    120
gaaaactgca cccagctcgg agaacaatgc tggactgcac ggatccgcgc tgtcggcctg    180
ctgaccgtga tctccaaagg gtgctcattg aactgcgtgg acgatagcca ggactactac    240
gtgggaaaga agaatatcac ttgttgcgac acggatcttt gcaacgcgtc cggagcgcac    300
gccctgcagc cagcagccgc cattctggcc ctgcttccgg ccctggggtt gctgctctgg    360
ggtccgggcc agctcggatc ccagaccctg aactttgatc tgctgaaact ggcaggcgat    420
gtggaaagca acccaggccc aatggctagc gctcgcagac cgcggtggct gtgtgcaggg    480
gcgctcgtcc tggcgggtgg cttctttttg ctcggctttc ttttcggatg gttcatcaaa    540
tcgtcaaacg aagctaccaa tatcaccccg aagcacaaca tgaaggcctt tctggatgag    600
ctgaaggctg agaacattaa gaagttcctc tacaacttca cccagatccc acatttggcg    660
ggcactgagc agaactttca gttggctaag cagatccaga gccagtggaa ggaattcggc    720
ctggactccg tcgagctggc gcattacgat gtgctgctga gctaccctaa taagactcat    780
```

-continued

```
ccgaactata tctcgattat caatgaggac ggaaacgaaa tctttaacac gtccctcttc    840
gagccgccac cgcctggata cgagaacgtg tcagatatcg tgcctccgtt ctcggccttc    900
tcgccccagg gaatgcccga aggggacctg gtgtacgtga actacgcaag gaccgaggac    960
ttcttcaagt tggagcggga tatgaagatc aattgcagcg gaaagatcgt catcgcccgc   1020
tacggcaaag tgttccgcgg caacaaggtg aagaatgcac agttggcagg cgccaagggc   1080
gtcatcctct actcggatcc tgccgactac ttcgctcctg gcgtgaaatc ctaccctgat   1140
ggttggaatc tgccaggagg aggggtgcag aggggaaata tcctgaacct gaacggtgcc   1200
ggtgacccac ttactccggg ttacccggcc aacgaatacg cgtacaggcg ggtatcgcg    1260
gaagccgtcg gactgccgtc catcccggtc catccgattg gttactacga cgcccagaag   1320
ctcctcgaaa agatgggagg cagcgcccct ccggactcgt catggagagg ctcgctgaag   1380
gtgccataca acgtgggacc cggattcact ggaaatttca gcactcaaaa agtgaagatg   1440
cacattcact ccactaacga agtcaccagg atctacaacg tcatcggaac cctccgggga   1500
gcggtggaac cggaccgcta cgtgatcctc ggtggacacc gggatagctg ggtgttcgga   1560
ggaatcgatc ctcaatcggg cgcagccgtc gtccatgaaa tcgtcaggtc ctttggtact   1620
cttaagaagg agggctggcg ccctagacgc actattctgt tcgcctcgtg ggatgccgaa   1680
gaatttggtc tgctcggcag caccgaatgg gctgaggaaa actcccgcct gctccaagaa   1740
cgcggagtgg cgtacatcaa tgccgactca tccatcgaag gaaactacac gctgcgggtg   1800
gactgcactc cactgatgta ctcgctcgtg cacaacctga ccaaagaact caaatcccca   1860
gacgaaggat tcgagggaaa atcgctgtac gagtcgtgga ccaagaagag cccatccccg   1920
gagttcagcg ggatgccgcg gatctcaaag ctcggatcag gaaatgattt cgaagtgttc   1980
tttcagaggc tgggaattgc gtcgggaagg gctcggtaca cgaaaaactg ggaaactaac   2040
aagttctcgg gatacccgct gtaccactcg gtgtatgaaa cttacgaact ggtggagaaa   2100
ttctacgatc ctatgtttaa gtaccacctg actgtggccc aagtgagagg cggaatggtg   2160
ttcgagttgg ccaattcaat tgtgctgcca ttcgattgcc gcgactacgc cgtggtgctg   2220
agaaagtacg cagacaaaat ctactcaatc agcatgaagc acccacaaga gatgaaaacc   2280
tactcagtct ccttcgactc cctcttctcc gcggtgaaga acttcaccga gatcgcgagc   2340
aaattctcgg agcgccttca agattttgac aaatccaatc cgatcgtcct ccgcatgatg   2400
aatgaccagc tcatgtttct cgaacgggcc ttcatcgatc cactgggact tccggaccgg   2460
ccgttttacc gccacgtgat ctacgcgccc tcgtcgcata acaagtatgc tggagagagc   2520
ttcccgggta tctacgacgc attgttcgac attgagtcca aggtggatcc gtccaaagcc   2580
tggggtgaag tgaagcgcca aatctacgtg gcggccttta ccgtccaggc ggcagcagaa   2640
accttgagcg aggtggcttg aagatctgac cccctaacgt tactggccga agccgcttgg   2700
aataaggccg gtgtgcgttt gtctatatgt tattttccac catattgccg tcttttggca   2760
atgtgagggc ccggaaacct ggccctgtct tcttgacgag cattcctagg ggtctttccc   2820
ctctcgccaa aggaatgcaa ggtctgttga atgtcgtgaa ggaagcagtt cctctggaag   2880
cttcttgaag acaaacaacg tctgtagcga ccctttgcag gcagcggaac cccccacctg   2940
gcgacaggtg cctctgcggc caaaagccac gtgtataaga tacacctgca aaggcggcac   3000
aaccccagtg ccacgttgtg agttggatag ttgtggaaag agtcaaatgg ctctcctcaa   3060
gcgtattcaa caaggggctg aaggatgccc agaaggtacc ccattgtatg ggatctgatc   3120
tggggcctcg gtgcacatgc tttacatgtg tttagtcgag gttaaaaaac gtctaggccc   3180
```

```
cccgaaccac ggggacgtgg ttttcctttg aaaaacacga tgataatatg gctagcatcg    3240

tcggagggtg ggagtgcgaa aagcactcac agccatggca ggtcctggtc gcctcgcgcg    3300

gacgcgccgt gtgtggaggt gtgctggtcc acccgcagtg ggtgttgact gcggcccatt    3360

gcatcagaaa taagtccgtg atcctcttgg ggagacattc cctgtttcac cccgaagata    3420

ctggacaggt gttccaagtg agccactcct tcccgcatcc actgtacgac atgagcctgc    3480

tgaagaaccg ctttctgcgg ccaggggacg actcatcaca cgatttgatg ctgcttcggc    3540

tctcggaacc ggccgagctc accgacgcag tgaaggtcat ggacctccct acgcaagagc    3600

ctgctctcgg taccacttgt tacgcatcgg gatggggctc catcgagccg gaagaattcc    3660

tgaccccgaa aaagctgcag tgcgtggatc tgcacgtgat ttcgaatgac gtgtgcgcgc    3720

aagtgcatcc acaaaaggtc actaagttca tgctgtgcgc cggaaggtgg accggcggaa    3780

aatcgacctg ttccggcgac agcggaggcc cactcgtgtg caacggtgtg ctgcagggca    3840

tcactagctg gggatcagaa ccgtgcgcgc ttccggagcg gccctcgctc tacacgaagg    3900

tggtgcacta ccgcaaatgg attaaagata ccatcgtcgc aaaccct                  3947
```

<210> SEQ ID NO 67
<211> LENGTH: 21
<212> TYPE: PRT
<213> ORGANISM: Artificial Sequence
<220> FEATURE:
<223> OTHER INFORMATION: Synthetic Construct

<400> SEQUENCE: 67

Val Lys Gln Thr Leu Asn Phe Asp Leu Leu Lys Leu Ala Gly Asp Val
1               5                   10                  15

Glu Ser Asn Pro Gly
            20

<210> SEQ ID NO 68
<211> LENGTH: 19
<212> TYPE: PRT
<213> ORGANISM: Artificial Sequence
<220> FEATURE:
<223> OTHER INFORMATION: Synthetic Construct

<400> SEQUENCE: 68

Gln Cys Thr Asn Tyr Ala Leu Leu Lys Leu Ala Gly Asp Val Glu Ser
1               5                   10                  15

Asn Pro Gly

<210> SEQ ID NO 69
<211> LENGTH: 18
<212> TYPE: PRT
<213> ORGANISM: Artificial Sequence
<220> FEATURE:
<223> OTHER INFORMATION: Synthetic Construct

<400> SEQUENCE: 69

Ala Thr Asn Phe Ser Leu Leu Lys Gln Ala Gly Asp Val Glu Glu Asn
1               5                   10                  15

Pro Gly

<210> SEQ ID NO 70
<211> LENGTH: 19
<212> TYPE: PRT
<213> ORGANISM: Artificial Sequence
<220> FEATURE:

-continued

<223> OTHER INFORMATION: Synthetic Construct

<400> SEQUENCE: 70

His Tyr Ala Gly Tyr Phe Ala Asp Leu Leu Ile His Asp Ile Glu Thr
1 5 10 15

Asn Pro Gly

<210> SEQ ID NO 71
<211> LENGTH: 24
<212> TYPE: PRT
<213> ORGANISM: Artificial Sequence
<220> FEATURE:
<223> OTHER INFORMATION: Synthetic Construct

<400> SEQUENCE: 71

Gly Ile Phe Asn Ala His Tyr Ala Gly Tyr Phe Ala Asp Leu Leu Ile
1 5 10 15

His Asp Ile Glu Thr Asn Pro Gly
20

<210> SEQ ID NO 72
<211> LENGTH: 24
<212> TYPE: PRT
<213> ORGANISM: Artificial Sequence
<220> FEATURE:
<223> OTHER INFORMATION: Synthetic Construct

<400> SEQUENCE: 72

Lys Ala Val Arg Gly Tyr His Ala Asp Tyr Tyr Lys Gln Arg Leu Ile
1 5 10 15

His Asp Val Glu Met Asn Pro Gly
20

<210> SEQ ID NO 73
<211> LENGTH: 19
<212> TYPE: PRT
<213> ORGANISM: Artificial Sequence
<220> FEATURE:
<223> OTHER INFORMATION: Synthetic Construct

<400> SEQUENCE: 73

Gly Ala Thr Asn Phe Ser Leu Leu Lys Leu Ala Gly Asp Val Glu Leu
1 5 10 15

Asn Pro Gly

<210> SEQ ID NO 74
<211> LENGTH: 17
<212> TYPE: PRT
<213> ORGANISM: Artificial Sequence
<220> FEATURE:
<223> OTHER INFORMATION: Synthetic Construct

<400> SEQUENCE: 74

Glu Gly Arg Gly Ser Leu Leu Thr Cys Gly Asp Val Glu Glu Asn Pro
1 5 10 15

Gly

<210> SEQ ID NO 75
<211> LENGTH: 18
<212> TYPE: PRT
<213> ORGANISM: Artificial Sequence
<220> FEATURE:
<223> OTHER INFORMATION: Synthetic Construct

<400> SEQUENCE: 75

Ala Ala Arg Gln Met Leu Leu Leu Leu Ser Gly Asp Val Glu Thr Asn
1               5                   10                  15

Pro Gly

<210> SEQ ID NO 76
<211> LENGTH: 19
<212> TYPE: PRT
<213> ORGANISM: Artificial Sequence
<220> FEATURE:
<223> OTHER INFORMATION: Synthetic Construct

<400> SEQUENCE: 76

Phe Leu Arg Lys Arg Thr Gln Leu Leu Met Ser Gly Asp Val Glu Ser
1               5                   10                  15

Asn Pro Gly

<210> SEQ ID NO 77
<211> LENGTH: 19
<212> TYPE: PRT
<213> ORGANISM: Artificial Sequence
<220> FEATURE:
<223> OTHER INFORMATION: Synthetic Construct

<400> SEQUENCE: 77

Gly Ser Trp Thr Asp Ile Leu Leu Leu Leu Ser Gly Asp Val Glu Thr
1               5                   10                  15

Asn Pro Gly

<210> SEQ ID NO 78
<211> LENGTH: 19
<212> TYPE: PRT
<213> ORGANISM: Artificial Sequence
<220> FEATURE:
<223> OTHER INFORMATION: Synthetic Construct

<400> SEQUENCE: 78

Thr Arg Ala Glu Ile Glu Asp Glu Leu Ile Arg Ala Gly Ile Glu Ser
1               5                   10                  15

Asn Pro Gly

<210> SEQ ID NO 79
<211> LENGTH: 19
<212> TYPE: PRT
<213> ORGANISM: Artificial Sequence
<220> FEATURE:
<223> OTHER INFORMATION: Synthetic Construct

<400> SEQUENCE: 79

Ala Lys Phe Gln Ile Asp Lys Ile Leu Ile Ser Gly Asp Val Glu Leu
1               5                   10                  15

Asn Pro Gly

<210> SEQ ID NO 80
<211> LENGTH: 19
<212> TYPE: PRT
<213> ORGANISM: Artificial Sequence
<220> FEATURE:
<223> OTHER INFORMATION: Synthetic Construct

<400> SEQUENCE: 80

Ser Lys Phe Gln Ile Asp Lys Ile Leu Ile Ser Gly Asp Ile Glu Leu
1               5                   10                  15

Asn Pro Gly

<210> SEQ ID NO 81
<211> LENGTH: 19
<212> TYPE: PRT
<213> ORGANISM: Artificial Sequence
<220> FEATURE:
<223> OTHER INFORMATION: Synthetic Construct

<400> SEQUENCE: 81

Ser Ser Ile Ile Arg Thr Lys Met Leu Val Ser Gly Asp Val Glu Glu
1 5 10 15

Asn Pro Gly

<210> SEQ ID NO 82
<211> LENGTH: 19
<212> TYPE: PRT
<213> ORGANISM: Artificial Sequence
<220> FEATURE:
<223> OTHER INFORMATION: Synthetic Construct

<400> SEQUENCE: 82

Cys Asp Ala Gln Arg Gln Lys Leu Leu Leu Ser Gly Asp Ile Glu Gln
1 5 10 15

Asn Pro Gly

<210> SEQ ID NO 83
<211> LENGTH: 23
<212> TYPE: DNA
<213> ORGANISM: Artificial Sequence
<220> FEATURE:
<223> OTHER INFORMATION: Synthetic Construct

<400> SEQUENCE: 83
cgttgacgca aatgggcggt agg 23

<210> SEQ ID NO 84
<211> LENGTH: 30
<212> TYPE: DNA
<213> ORGANISM: Artificial Sequence
<220> FEATURE:
<223> OTHER INFORMATION: Synthetic Construct

<400> SEQUENCE: 84
tcagagatct gaccccctaa cgttactggc 30

<210> SEQ ID NO 85
<211> LENGTH: 29
<212> TYPE: DNA
<213> ORGANISM: Artificial Sequence
<220> FEATURE:
<223> OTHER INFORMATION: Synthetic Construct

<400> SEQUENCE: 85
tataggatcc tcaggggttg gccacgatg 29

<210> SEQ ID NO 86
<211> LENGTH: 47
<212> TYPE: DNA
<213> ORGANISM: Artificial Sequence
<220> FEATURE:
<223> OTHER INFORMATION: Synthetic Construct

<400> SEQUENCE: 86
gaaaaacacg atgataatat ggccagcatt gtgggaggct gggagtg 47

<210> SEQ ID NO 87
<211> LENGTH: 51
<212> TYPE: DNA
<213> ORGANISM: Artificial Sequence
<220> FEATURE:
<223> OTHER INFORMATION: Synthetic Construct

<400> SEQUENCE: 87
ccacaatgct ggccatatta tcatcgtgtt tttcaaagga aaaccacgtc c 51

<210> SEQ ID NO 88
<211> LENGTH: 59
<212> TYPE: DNA
<213> ORGANISM: Artificial Sequence
<220> FEATURE:
<223> OTHER INFORMATION: Synthetic Construct

<400> SEQUENCE: 88
catctccaca ggtcaataat gaacccctac cttcggatcc ggctacttca ctcaaagtc 59

<210> SEQ ID NO 89
<211> LENGTH: 71
<212> TYPE: DNA
<213> ORGANISM: Artificial Sequence
<220> FEATURE:
<223> OTHER INFORMATION: Synthetic Construct

<400> SEQUENCE: 89
gttcattatt gacctgtgga gatgtcgaag aaaacccagg acccgcaagc aaggctgtgc 60
tgcttgccct g 71

<210> SEQ ID NO 90
<211> LENGTH: 34
<212> TYPE: DNA
<213> ORGANISM: Artificial Sequence
<220> FEATURE:
<223> OTHER INFORMATION: Synthetic Construct

<400> SEQUENCE: 90
ttgcctctca catctcgtca atctccgcga ggac 34

<210> SEQ ID NO 91
<211> LENGTH: 36
<212> TYPE: DNA
<213> ORGANISM: Artificial Sequence
<220> FEATURE:
<223> OTHER INFORMATION: Synthetic Construct

<400> SEQUENCE: 91
gatcttttgt acaatatgat cttgtggcaa tgtccc 36

<210> SEQ ID NO 92
<211> LENGTH: 28
<212> TYPE: DNA
<213> ORGANISM: Artificial Sequence
<220> FEATURE:
<223> OTHER INFORMATION: Synthetic Construct

<400> SEQUENCE: 92
tataggatcc ctatagctgg ccgggtcc 28

<210> SEQ ID NO 93
<211> LENGTH: 39

<212> TYPE: DNA
<213> ORGANISM: Artificial Sequence
<220> FEATURE:
<223> OTHER INFORMATION: Synthetic Construct

<400> SEQUENCE: 93
cacgatgata atatggccag caaggctgtg ctgcttgcc 39

<210> SEQ ID NO 94
<211> LENGTH: 53
<212> TYPE: DNA
<213> ORGANISM: Artificial Sequence
<220> FEATURE:
<223> OTHER INFORMATION: Synthetic Construct

<400> SEQUENCE: 94
cacagccttg ctggccatat tatcatcgtg tttttcaaag gaaaaccacg tcc 53

<210> SEQ ID NO 95
<211> LENGTH: 31
<212> TYPE: DNA
<213> ORGANISM: Artificial Sequence
<220> FEATURE:
<223> OTHER INFORMATION: Synthetic Construct

<400> SEQUENCE: 95
tataggatcc tagctggccg ggtccccaga g 31

<210> SEQ ID NO 96
<211> LENGTH: 92
<212> TYPE: DNA
<213> ORGANISM: Artificial Sequence
<220> FEATURE:
<223> OTHER INFORMATION: Synthetic Construct

<400> SEQUENCE: 96
atatgctagc gggtcctggg ttttcttcga catctccaca ggtcaataat gaacccctac 60
cttcggatcc ggggttggcc acgatggtgt cc 92

<210> SEQ ID NO 97
<211> LENGTH: 24
<212> TYPE: DNA
<213> ORGANISM: Artificial Sequence
<220> FEATURE:
<223> OTHER INFORMATION: Synthetic Construct

<400> SEQUENCE: 97
ctgtgacgaa catggctagc aagg 24

<210> SEQ ID NO 98
<211> LENGTH: 29
<212> TYPE: DNA
<213> ORGANISM: Artificial Sequence
<220> FEATURE:
<223> OTHER INFORMATION: Synthetic Construct

<400> SEQUENCE: 98
attatcatcg tgtttttcaa aggaaaacc 29

<210> SEQ ID NO 99
<211> LENGTH: 43
<212> TYPE: DNA
<213> ORGANISM: Artificial Sequence
<220> FEATURE:
<223> OTHER INFORMATION: Synthetic Construct

<400> SEQUENCE: 99
aaacacgatg ataatatggc cacaaccatg gcgcgccgcc cgc        43

<210> SEQ ID NO 100
<211> LENGTH: 26
<212> TYPE: DNA
<213> ORGANISM: Artificial Sequence
<220> FEATURE:
<223> OTHER INFORMATION: Synthetic Construct

<400> SEQUENCE: 100
ttttgttagg gcccagatct ttaggc        26

<210> SEQ ID NO 101
<211> LENGTH: 30
<212> TYPE: DNA
<213> ORGANISM: Artificial Sequence
<220> FEATURE:
<223> OTHER INFORMATION: Synthetic Construct

<400> SEQUENCE: 101
gacgaacatg gctagcattg tgggaggctg        30

<210> SEQ ID NO 102
<211> LENGTH: 70
<212> TYPE: DNA
<213> ORGANISM: Artificial Sequence
<220> FEATURE:
<223> OTHER INFORMATION: Synthetic Construct

<400> SEQUENCE: 102
ccacatcgcc tgccagtttc agcagatcaa agttcagggt ctgggatccg gggttggcca        60
cgatggtgtc        70

<210> SEQ ID NO 103
<211> LENGTH: 71
<212> TYPE: DNA
<213> ORGANISM: Artificial Sequence
<220> FEATURE:
<223> OTHER INFORMATION: Synthetic Construct

<400> SEQUENCE: 103
gatctgctga aactggcagg cgatgtggaa agcaacccag gcccaatggc aagcgcgcgc        60
cgcccgcgct g        71

<210> SEQ ID NO 104
<211> LENGTH: 38
<212> TYPE: DNA
<213> ORGANISM: Artificial Sequence
<220> FEATURE:
<223> OTHER INFORMATION: Synthetic Construct

<400> SEQUENCE: 104
gttagggccc agatctttag gctacttcac tcaaagtc        38

<210> SEQ ID NO 105
<211> LENGTH: 61
<212> TYPE: DNA
<213> ORGANISM: Artificial Sequence
<220> FEATURE:
<223> OTHER INFORMATION: Synthetic Construct

<400> SEQUENCE: 105
cttgtattac tgtttatgta agcagacagg gtaccaatat tggctattgg ccattgcata        60
c 61

<210> SEQ ID NO 106
<211> LENGTH: 61
<212> TYPE: DNA
<213> ORGANISM: Artificial Sequence
<220> FEATURE:
<223> OTHER INFORMATION: Synthetic Construct

<400> SEQUENCE: 106
gtatgcaatg gccaatagcc aatattggta ccctgtctgc ttacataaac agtaatacaa 60
g 61

<210> SEQ ID NO 107
<211> LENGTH: 45
<212> TYPE: DNA
<213> ORGANISM: Artificial Sequence
<220> FEATURE:
<223> OTHER INFORMATION: Synthetic Construct

<400> SEQUENCE: 107
catgcatggg taccaatctt ccgagtgaga gacacaaaaa attcc 45

<210> SEQ ID NO 108
<211> LENGTH: 42
<212> TYPE: DNA
<213> ORGANISM: Artificial Sequence
<220> FEATURE:
<223> OTHER INFORMATION: Synthetic Construct

<400> SEQUENCE: 108
gatcgatcgg taccctgcag gtcgagcacc aaaatcaacg gg 42

<210> SEQ ID NO 109
<211> LENGTH: 49
<212> TYPE: DNA
<213> ORGANISM: Artificial Sequence
<220> FEATURE:
<223> OTHER INFORMATION: Synthetic Construct

<400> SEQUENCE: 109
gtttatgtaa gcagacaggt cgacccatag agcccaccgc atccccagc 49

<210> SEQ ID NO 110
<211> LENGTH: 50
<212> TYPE: DNA
<213> ORGANISM: Artificial Sequence
<220> FEATURE:
<223> OTHER INFORMATION: Synthetic Construct

<400> SEQUENCE: 110
tggccaatag ccaatattgt cgactgggtc gaggtgagcc ccacgttctg 50

<210> SEQ ID NO 111
<211> LENGTH: 15
<212> TYPE: PRT
<213> ORGANISM: Artificial Sequence
<220> FEATURE:
<223> OTHER INFORMATION: Synthetic Construct

<400> SEQUENCE: 111

Val Val Phe Leu Thr Leu Ser Val Thr Trp Ile Gly Ala Ala Pro
1 5 10 15

<210> SEQ ID NO 112
<211> LENGTH: 15
<212> TYPE: PRT
<213> ORGANISM: Artificial Sequence
<220> FEATURE:
<223> OTHER INFORMATION: Synthetic Construct

<400> SEQUENCE: 112

Thr Leu Ser Val Thr Trp Ile Gly Ala Ala Pro Leu Ile Leu Ser
1 5 10 15

<210> SEQ ID NO 113
<211> LENGTH: 15
<212> TYPE: PRT
<213> ORGANISM: Artificial Sequence
<220> FEATURE:
<223> OTHER INFORMATION: Synthetic Construct

<400> SEQUENCE: 113

Ser Val Thr Trp Ile Gly Ala Ala Pro Leu Ile Leu Ser Arg Ile
1 5 10 15

<210> SEQ ID NO 114
<211> LENGTH: 15
<212> TYPE: PRT
<213> ORGANISM: Artificial Sequence
<220> FEATURE:
<223> OTHER INFORMATION: Synthetic Construct

<400> SEQUENCE: 114

Thr Trp Ile Gly Ala Ala Pro Leu Ile Leu Ser Arg Ile Val Gly
1 5 10 15

<210> SEQ ID NO 115
<211> LENGTH: 15
<212> TYPE: PRT
<213> ORGANISM: Artificial Sequence
<220> FEATURE:
<223> OTHER INFORMATION: Synthetic Construct

<400> SEQUENCE: 115

Ile Gly Ala Ala Pro Leu Ile Leu Ser Arg Ile Val Gly Gly Trp
1 5 10 15

<210> SEQ ID NO 116
<211> LENGTH: 15
<212> TYPE: PRT
<213> ORGANISM: Artificial Sequence
<220> FEATURE:
<223> OTHER INFORMATION: Synthetic Construct

<400> SEQUENCE: 116

Ala Ala Pro Leu Ile Leu Ser Arg Ile Val Gly Gly Trp Glu Cys
1 5 10 15

<210> SEQ ID NO 117
<211> LENGTH: 15
<212> TYPE: PRT
<213> ORGANISM: Artificial Sequence
<220> FEATURE:
<223> OTHER INFORMATION: Synthetic Construct

<400> SEQUENCE: 117

Pro Leu Ile Leu Ser Arg Ile Val Gly Gly Trp Glu Cys Glu Lys
1 5 10 15

<210> SEQ ID NO 118

-continued

<211> LENGTH: 15
<212> TYPE: PRT
<213> ORGANISM: Artificial Sequence
<220> FEATURE:
<223> OTHER INFORMATION: Synthetic Construct

<400> SEQUENCE: 118

Ile Leu Ser Arg Ile Val Gly Gly Trp Glu Cys Glu Lys His Ser
1 5 10 15

<210> SEQ ID NO 119
<211> LENGTH: 15
<212> TYPE: PRT
<213> ORGANISM: Artificial Sequence
<220> FEATURE:
<223> OTHER INFORMATION: Synthetic Construct

<400> SEQUENCE: 119

Ser Arg Ile Val Gly Gly Trp Glu Cys Glu Lys His Ser Gln Pro
1 5 10 15

<210> SEQ ID NO 120
<211> LENGTH: 15
<212> TYPE: PRT
<213> ORGANISM: Artificial Sequence
<220> FEATURE:
<223> OTHER INFORMATION: Synthetic Construct

<400> SEQUENCE: 120

Ile Val Gly Gly Trp Glu Cys Glu Lys His Ser Gln Pro Trp Gln
1 5 10 15

<210> SEQ ID NO 121
<211> LENGTH: 15
<212> TYPE: PRT
<213> ORGANISM: Artificial Sequence
<220> FEATURE:
<223> OTHER INFORMATION: Synthetic Construct

<400> SEQUENCE: 121

Gly Gly Trp Glu Cys Glu Lys His Ser Gln Pro Trp Gln Val Leu
1 5 10 15

<210> SEQ ID NO 122
<211> LENGTH: 15
<212> TYPE: PRT
<213> ORGANISM: Artificial Sequence
<220> FEATURE:
<223> OTHER INFORMATION: Synthetic Construct

<400> SEQUENCE: 122

Trp Glu Cys Glu Lys His Ser Gln Pro Trp Gln Val Leu Val Ala
1 5 10 15

<210> SEQ ID NO 123
<211> LENGTH: 15
<212> TYPE: PRT
<213> ORGANISM: Artificial Sequence
<220> FEATURE:
<223> OTHER INFORMATION: Synthetic Construct

<400> SEQUENCE: 123

Cys Glu Lys His Ser Gln Pro Trp Gln Val Leu Val Ala Ser Arg
1 5 10 15

<210> SEQ ID NO 124
<211> LENGTH: 15

-continued

<212> TYPE: PRT
<213> ORGANISM: Artificial Sequence
<220> FEATURE:
<223> OTHER INFORMATION: Synthetic Construct

<400> SEQUENCE: 124

Lys His Ser Gln Pro Trp Gln Val Leu Val Ala Ser Arg Gly Arg
1 5 10 15

<210> SEQ ID NO 125
<211> LENGTH: 15
<212> TYPE: PRT
<213> ORGANISM: Artificial Sequence
<220> FEATURE:
<223> OTHER INFORMATION: Synthetic Construct

<400> SEQUENCE: 125

Ser Gln Pro Trp Gln Val Leu Val Ala Ser Arg Gly Arg Ala Val
1 5 10 15

<210> SEQ ID NO 126
<211> LENGTH: 15
<212> TYPE: PRT
<213> ORGANISM: Artificial Sequence
<220> FEATURE:
<223> OTHER INFORMATION: Synthetic Construct

<400> SEQUENCE: 126

Pro Trp Gln Val Leu Val Ala Ser Arg Gly Arg Ala Val Cys Gly
1 5 10 15

<210> SEQ ID NO 127
<211> LENGTH: 15
<212> TYPE: PRT
<213> ORGANISM: Artificial Sequence
<220> FEATURE:
<223> OTHER INFORMATION: Synthetic Construct

<400> SEQUENCE: 127

Gln Val Leu Val Ala Ser Arg Gly Arg Ala Val Cys Gly Gly Val
1 5 10 15

<210> SEQ ID NO 128
<211> LENGTH: 15
<212> TYPE: PRT
<213> ORGANISM: Artificial Sequence
<220> FEATURE:
<223> OTHER INFORMATION: Synthetic Construct

<400> SEQUENCE: 128

Leu Val Ala Ser Arg Gly Arg Ala Val Cys Gly Gly Val Leu Val
1 5 10 15

<210> SEQ ID NO 129
<211> LENGTH: 15
<212> TYPE: PRT
<213> ORGANISM: Artificial Sequence
<220> FEATURE:
<223> OTHER INFORMATION: Synthetic Construct

<400> SEQUENCE: 129

Ala Ser Arg Gly Arg Ala Val Cys Gly Gly Val Leu Val His Pro
1 5 10 15

<210> SEQ ID NO 130
<211> LENGTH: 15
<212> TYPE: PRT

<213> ORGANISM: Artificial Sequence
<220> FEATURE:
<223> OTHER INFORMATION: Synthetic Construct

<400> SEQUENCE: 130

Arg Gly Arg Ala Val Cys Gly Gly Val Leu Val His Pro Gln Trp
1 5 10 15

<210> SEQ ID NO 131
<211> LENGTH: 15
<212> TYPE: PRT
<213> ORGANISM: Artificial Sequence
<220> FEATURE:
<223> OTHER INFORMATION: Synthetic Construct

<400> SEQUENCE: 131

Arg Ala Val Cys Gly Gly Val Leu Val His Pro Gln Trp Val Leu
1 5 10 15

<210> SEQ ID NO 132
<211> LENGTH: 15
<212> TYPE: PRT
<213> ORGANISM: Artificial Sequence
<220> FEATURE:
<223> OTHER INFORMATION: Synthetic Construct

<400> SEQUENCE: 132

Val Cys Gly Gly Val Leu Val His Pro Gln Trp Val Leu Thr Ala
1 5 10 15

<210> SEQ ID NO 133
<211> LENGTH: 15
<212> TYPE: PRT
<213> ORGANISM: Artificial Sequence
<220> FEATURE:
<223> OTHER INFORMATION: Synthetic Construct

<400> SEQUENCE: 133

Gly Gly Val Leu Val His Pro Gln Trp Val Leu Thr Ala Ala His
1 5 10 15

<210> SEQ ID NO 134
<211> LENGTH: 15
<212> TYPE: PRT
<213> ORGANISM: Artificial Sequence
<220> FEATURE:
<223> OTHER INFORMATION: Synthetic Construct

<400> SEQUENCE: 134

Val Leu Val His Pro Gln Trp Val Leu Thr Ala Ala His Cys Ile
1 5 10 15

<210> SEQ ID NO 135
<211> LENGTH: 15
<212> TYPE: PRT
<213> ORGANISM: Artificial Sequence
<220> FEATURE:
<223> OTHER INFORMATION: Synthetic Construct

<400> SEQUENCE: 135

Val His Pro Gln Trp Val Leu Thr Ala Ala His Cys Ile Arg Asn
1 5 10 15

<210> SEQ ID NO 136
<211> LENGTH: 15
<212> TYPE: PRT
<213> ORGANISM: Artificial Sequence
<220> FEATURE:
<223> OTHER INFORMATION: Synthetic Construct

<400> SEQUENCE: 136

Pro Gln Trp Val Leu Thr Ala Ala His Cys Ile Arg Asn Lys Ser
1 5 10 15

<210> SEQ ID NO 137
<211> LENGTH: 15
<212> TYPE: PRT
<213> ORGANISM: Artificial Sequence
<220> FEATURE:
<223> OTHER INFORMATION: Synthetic Construct

<400> SEQUENCE: 137

Trp Val Leu Thr Ala Ala His Cys Ile Arg Asn Lys Ser Val Ile
1 5 10 15

<210> SEQ ID NO 138
<211> LENGTH: 15
<212> TYPE: PRT
<213> ORGANISM: Artificial Sequence
<220> FEATURE:
<223> OTHER INFORMATION: Synthetic Construct

<400> SEQUENCE: 138

Leu Thr Ala Ala His Cys Ile Arg Asn Lys Ser Val Ile Leu Leu
1 5 10 15

<210> SEQ ID NO 139
<211> LENGTH: 15
<212> TYPE: PRT
<213> ORGANISM: Artificial Sequence
<220> FEATURE:
<223> OTHER INFORMATION: Synthetic Construct

<400> SEQUENCE: 139

Ala Ala His Cys Ile Arg Asn Lys Ser Val Ile Leu Leu Gly Arg
1 5 10 15

<210> SEQ ID NO 140
<211> LENGTH: 15
<212> TYPE: PRT
<213> ORGANISM: Artificial Sequence
<220> FEATURE:
<223> OTHER INFORMATION: Synthetic Construct

<400> SEQUENCE: 140

His Cys Ile Arg Asn Lys Ser Val Ile Leu Leu Gly Arg His Ser
1 5 10 15

<210> SEQ ID NO 141
<211> LENGTH: 15
<212> TYPE: PRT
<213> ORGANISM: Artificial Sequence
<220> FEATURE:
<223> OTHER INFORMATION: Synthetic Construct

<400> SEQUENCE: 141

Ile Arg Asn Lys Ser Val Ile Leu Leu Gly Arg His Ser Leu Phe
1 5 10 15

<210> SEQ ID NO 142
<211> LENGTH: 15
<212> TYPE: PRT
<213> ORGANISM: Artificial Sequence
<220> FEATURE:

<223> OTHER INFORMATION: Synthetic Construct

<400> SEQUENCE: 142

Asn Lys Ser Val Ile Leu Leu Gly Arg His Ser Leu Phe His Pro
1 5 10 15

<210> SEQ ID NO 143
<211> LENGTH: 15
<212> TYPE: PRT
<213> ORGANISM: Artificial Sequence
<220> FEATURE:
<223> OTHER INFORMATION: Synthetic Construct

<400> SEQUENCE: 143

Ser Val Ile Leu Leu Gly Arg His Ser Leu Phe His Pro Glu Asp
1 5 10 15

<210> SEQ ID NO 144
<211> LENGTH: 15
<212> TYPE: PRT
<213> ORGANISM: Artificial Sequence
<220> FEATURE:
<223> OTHER INFORMATION: Synthetic Construct

<400> SEQUENCE: 144

Ile Leu Leu Gly Arg His Ser Leu Phe His Pro Glu Asp Thr Gly
1 5 10 15

<210> SEQ ID NO 145
<211> LENGTH: 15
<212> TYPE: PRT
<213> ORGANISM: Artificial Sequence
<220> FEATURE:
<223> OTHER INFORMATION: Synthetic Construct

<400> SEQUENCE: 145

Leu Gly Arg His Ser Leu Phe His Pro Glu Asp Thr Gly Gln Val
1 5 10 15

<210> SEQ ID NO 146
<211> LENGTH: 15
<212> TYPE: PRT
<213> ORGANISM: Artificial Sequence
<220> FEATURE:
<223> OTHER INFORMATION: Synthetic Construct

<400> SEQUENCE: 146

Arg His Ser Leu Phe His Pro Glu Asp Thr Gly Gln Val Phe Gln
1 5 10 15

<210> SEQ ID NO 147
<211> LENGTH: 15
<212> TYPE: PRT
<213> ORGANISM: Artificial Sequence
<220> FEATURE:
<223> OTHER INFORMATION: Synthetic Construct

<400> SEQUENCE: 147

Ser Leu Phe His Pro Glu Asp Thr Gly Gln Val Phe Gln Val Ser
1 5 10 15

<210> SEQ ID NO 148
<211> LENGTH: 15
<212> TYPE: PRT
<213> ORGANISM: Artificial Sequence
<220> FEATURE:
<223> OTHER INFORMATION: Synthetic Construct

<400> SEQUENCE: 148

Phe His Pro Glu Asp Thr Gly Gln Val Phe Gln Val Ser His Ser
1 5 10 15

<210> SEQ ID NO 149
<211> LENGTH: 15
<212> TYPE: PRT
<213> ORGANISM: Artificial Sequence
<220> FEATURE:
<223> OTHER INFORMATION: Synthetic Construct

<400> SEQUENCE: 149

Pro Glu Asp Thr Gly Gln Val Phe Gln Val Ser His Ser Phe Pro
1 5 10 15

<210> SEQ ID NO 150
<211> LENGTH: 15
<212> TYPE: PRT
<213> ORGANISM: Artificial Sequence
<220> FEATURE:
<223> OTHER INFORMATION: Synthetic Construct

<400> SEQUENCE: 150

Asp Thr Gly Gln Val Phe Gln Val Ser His Ser Phe Pro His Pro
1 5 10 15

<210> SEQ ID NO 151
<211> LENGTH: 15
<212> TYPE: PRT
<213> ORGANISM: Artificial Sequence
<220> FEATURE:
<223> OTHER INFORMATION: Synthetic Construct

<400> SEQUENCE: 151

Gly Gln Val Phe Gln Val Ser His Ser Phe Pro His Pro Leu Tyr
1 5 10 15

<210> SEQ ID NO 152
<211> LENGTH: 15
<212> TYPE: PRT
<213> ORGANISM: Artificial Sequence
<220> FEATURE:
<223> OTHER INFORMATION: Synthetic Construct

<400> SEQUENCE: 152

Val Phe Gln Val Ser His Ser Phe Pro His Pro Leu Tyr Asp Met
1 5 10 15

<210> SEQ ID NO 153
<211> LENGTH: 15
<212> TYPE: PRT
<213> ORGANISM: Artificial Sequence
<220> FEATURE:
<223> OTHER INFORMATION: Synthetic Construct

<400> SEQUENCE: 153

Gln Val Ser His Ser Phe Pro His Pro Leu Tyr Asp Met Ser Leu
1 5 10 15

<210> SEQ ID NO 154
<211> LENGTH: 15
<212> TYPE: PRT
<213> ORGANISM: Artificial Sequence
<220> FEATURE:
<223> OTHER INFORMATION: Synthetic Construct

<400> SEQUENCE: 154

Ser His Ser Phe Pro His Pro Leu Tyr Asp Met Ser Leu Leu Lys
1               5                   10                  15

<210> SEQ ID NO 155
<211> LENGTH: 15
<212> TYPE: PRT
<213> ORGANISM: Artificial Sequence
<220> FEATURE:
<223> OTHER INFORMATION: Synthetic Construct

<400> SEQUENCE: 155

Ser Phe Pro His Pro Leu Tyr Asp Met Ser Leu Leu Lys Asn Arg
1               5                   10                  15

<210> SEQ ID NO 156
<211> LENGTH: 15
<212> TYPE: PRT
<213> ORGANISM: Artificial Sequence
<220> FEATURE:
<223> OTHER INFORMATION: Synthetic Construct

<400> SEQUENCE: 156

Pro His Pro Leu Tyr Asp Met Ser Leu Leu Lys Asn Arg Phe Leu
1               5                   10                  15

<210> SEQ ID NO 157
<211> LENGTH: 15
<212> TYPE: PRT
<213> ORGANISM: Artificial Sequence
<220> FEATURE:
<223> OTHER INFORMATION: Synthetic Construct

<400> SEQUENCE: 157

Pro Leu Tyr Asp Met Ser Leu Leu Lys Asn Arg Phe Leu Arg Pro
1               5                   10                  15

<210> SEQ ID NO 158
<211> LENGTH: 15
<212> TYPE: PRT
<213> ORGANISM: Artificial Sequence
<220> FEATURE:
<223> OTHER INFORMATION: Synthetic Construct

<400> SEQUENCE: 158

Tyr Asp Met Ser Leu Leu Lys Asn Arg Phe Leu Arg Pro Gly Asp
1               5                   10                  15

<210> SEQ ID NO 159
<211> LENGTH: 15
<212> TYPE: PRT
<213> ORGANISM: Artificial Sequence
<220> FEATURE:
<223> OTHER INFORMATION: Synthetic Construct

<400> SEQUENCE: 159

Met Ser Leu Leu Lys Asn Arg Phe Leu Arg Pro Gly Asp Asp Ser
1               5                   10                  15

<210> SEQ ID NO 160
<211> LENGTH: 15
<212> TYPE: PRT
<213> ORGANISM: Artificial Sequence
<220> FEATURE:
<223> OTHER INFORMATION: Synthetic Construct

<400> SEQUENCE: 160

Leu Leu Lys Asn Arg Phe Leu Arg Pro Gly Asp Asp Ser Ser His
1 5 10 15

<210> SEQ ID NO 161
<211> LENGTH: 15
<212> TYPE: PRT
<213> ORGANISM: Artificial Sequence
<220> FEATURE:
<223> OTHER INFORMATION: Synthetic Construct

<400> SEQUENCE: 161

Lys Asn Arg Phe Leu Arg Pro Gly Asp Asp Ser Ser His Asp Leu
1 5 10 15

<210> SEQ ID NO 162
<211> LENGTH: 15
<212> TYPE: PRT
<213> ORGANISM: Artificial Sequence
<220> FEATURE:
<223> OTHER INFORMATION: Synthetic Construct

<400> SEQUENCE: 162

Arg Phe Leu Arg Pro Gly Asp Asp Ser Ser His Asp Leu Met Leu
1 5 10 15

<210> SEQ ID NO 163
<211> LENGTH: 15
<212> TYPE: PRT
<213> ORGANISM: Artificial Sequence
<220> FEATURE:
<223> OTHER INFORMATION: Synthetic Construct

<400> SEQUENCE: 163

Leu Arg Pro Gly Asp Asp Ser Ser His Asp Leu Met Leu Leu Arg
1 5 10 15

<210> SEQ ID NO 164
<211> LENGTH: 15
<212> TYPE: PRT
<213> ORGANISM: Artificial Sequence
<220> FEATURE:
<223> OTHER INFORMATION: Synthetic Construct

<400> SEQUENCE: 164

Pro Gly Asp Asp Ser Ser His Asp Leu Met Leu Leu Arg Leu Ser
1 5 10 15

<210> SEQ ID NO 165
<211> LENGTH: 15
<212> TYPE: PRT
<213> ORGANISM: Artificial Sequence
<220> FEATURE:
<223> OTHER INFORMATION: Synthetic Construct

<400> SEQUENCE: 165

Asp Asp Ser Ser His Asp Leu Met Leu Leu Arg Leu Ser Glu Pro
1 5 10 15

<210> SEQ ID NO 166
<211> LENGTH: 15
<212> TYPE: PRT
<213> ORGANISM: Artificial Sequence
<220> FEATURE:
<223> OTHER INFORMATION: Synthetic Construct

<400> SEQUENCE: 166

Ser Ser His Asp Leu Met Leu Leu Arg Leu Ser Glu Pro Ala Glu
1 5 10 15

<210> SEQ ID NO 167
<211> LENGTH: 15
<212> TYPE: PRT
<213> ORGANISM: Artificial Sequence
<220> FEATURE:
<223> OTHER INFORMATION: Synthetic Construct

<400> SEQUENCE: 167

His Asp Leu Met Leu Leu Arg Leu Ser Glu Pro Ala Glu Leu Thr
1 5 10 15

<210> SEQ ID NO 168
<211> LENGTH: 15
<212> TYPE: PRT
<213> ORGANISM: Artificial Sequence
<220> FEATURE:
<223> OTHER INFORMATION: Synthetic Construct

<400> SEQUENCE: 168

Leu Met Leu Leu Arg Leu Ser Glu Pro Ala Glu Leu Thr Asp Ala
1 5 10 15

<210> SEQ ID NO 169
<211> LENGTH: 15
<212> TYPE: PRT
<213> ORGANISM: Artificial Sequence
<220> FEATURE:
<223> OTHER INFORMATION: Synthetic Construct

<400> SEQUENCE: 169

Leu Leu Arg Leu Ser Glu Pro Ala Glu Leu Thr Asp Ala Val Lys
1 5 10 15

<210> SEQ ID NO 170
<211> LENGTH: 15
<212> TYPE: PRT
<213> ORGANISM: Artificial Sequence
<220> FEATURE:
<223> OTHER INFORMATION: Synthetic Construct

<400> SEQUENCE: 170

Arg Leu Ser Glu Pro Ala Glu Leu Thr Asp Ala Val Lys Val Met
1 5 10 15

<210> SEQ ID NO 171
<211> LENGTH: 15
<212> TYPE: PRT
<213> ORGANISM: Artificial Sequence
<220> FEATURE:
<223> OTHER INFORMATION: Synthetic Construct

<400> SEQUENCE: 171

Ser Glu Pro Ala Glu Leu Thr Asp Ala Val Lys Val Met Asp Leu
1 5 10 15

<210> SEQ ID NO 172
<211> LENGTH: 15
<212> TYPE: PRT
<213> ORGANISM: Artificial Sequence
<220> FEATURE:
<223> OTHER INFORMATION: Synthetic Construct

<400> SEQUENCE: 172

Pro Ala Glu Leu Thr Asp Ala Val Lys Val Met Asp Leu Pro Thr 1 5 10 15

<210> SEQ ID NO 173
<211> LENGTH: 15
<212> TYPE: PRT
<213> ORGANISM: Artificial Sequence
<220> FEATURE:
<223> OTHER INFORMATION: Synthetic Construct

<400> SEQUENCE: 173

Glu Leu Thr Asp Ala Val Lys Val Met Asp Leu Pro Thr Gln Glu
1 5 10 15

<210> SEQ ID NO 174
<211> LENGTH: 15
<212> TYPE: PRT
<213> ORGANISM: Artificial Sequence
<220> FEATURE:
<223> OTHER INFORMATION: Synthetic Construct

<400> SEQUENCE: 174

Thr Asp Ala Val Lys Val Met Asp Leu Pro Thr Gln Glu Pro Ala
1 5 10 15

<210> SEQ ID NO 175
<211> LENGTH: 15
<212> TYPE: PRT
<213> ORGANISM: Artificial Sequence
<220> FEATURE:
<223> OTHER INFORMATION: Synthetic Construct

<400> SEQUENCE: 175

Ala Val Lys Val Met Asp Leu Pro Thr Gln Glu Pro Ala Leu Gly
1 5 10 15

<210> SEQ ID NO 176
<211> LENGTH: 15
<212> TYPE: PRT
<213> ORGANISM: Artificial Sequence
<220> FEATURE:
<223> OTHER INFORMATION: Synthetic Construct

<400> SEQUENCE: 176

Lys Val Met Asp Leu Pro Thr Gln Glu Pro Ala Leu Gly Thr Thr
1 5 10 15

<210> SEQ ID NO 177
<211> LENGTH: 15
<212> TYPE: PRT
<213> ORGANISM: Artificial Sequence
<220> FEATURE:
<223> OTHER INFORMATION: Synthetic Construct

<400> SEQUENCE: 177

Met Asp Leu Pro Thr Gln Glu Pro Ala Leu Gly Thr Thr Cys Tyr
1 5 10 15

<210> SEQ ID NO 178
<211> LENGTH: 15
<212> TYPE: PRT
<213> ORGANISM: Artificial Sequence
<220> FEATURE:
<223> OTHER INFORMATION: Synthetic Construct

<400> SEQUENCE: 178

Leu Pro Thr Gln Glu Pro Ala Leu Gly Thr Thr Cys Tyr Ala Ser
1 5 10 15

<210> SEQ ID NO 179
<211> LENGTH: 15
<212> TYPE: PRT
<213> ORGANISM: Artificial Sequence
<220> FEATURE:
<223> OTHER INFORMATION: Synthetic Construct

<400> SEQUENCE: 179

Thr Gln Glu Pro Ala Leu Gly Thr Thr Cys Tyr Ala Ser Gly Trp
1 5 10 15

<210> SEQ ID NO 180
<211> LENGTH: 15
<212> TYPE: PRT
<213> ORGANISM: Artificial Sequence
<220> FEATURE:
<223> OTHER INFORMATION: Synthetic Construct

<400> SEQUENCE: 180

Glu Pro Ala Leu Gly Thr Thr Cys Tyr Ala Ser Gly Trp Gly Ser
1 5 10 15

<210> SEQ ID NO 181
<211> LENGTH: 15
<212> TYPE: PRT
<213> ORGANISM: Artificial Sequence
<220> FEATURE:
<223> OTHER INFORMATION: Synthetic Construct

<400> SEQUENCE: 181

Ala Leu Gly Thr Thr Cys Tyr Ala Ser Gly Trp Gly Ser Ile Glu
1 5 10 15

<210> SEQ ID NO 182
<211> LENGTH: 15
<212> TYPE: PRT
<213> ORGANISM: Artificial Sequence
<220> FEATURE:
<223> OTHER INFORMATION: Synthetic Construct

<400> SEQUENCE: 182

Gly Thr Thr Cys Tyr Ala Ser Gly Trp Gly Ser Ile Glu Pro Glu
1 5 10 15

<210> SEQ ID NO 183
<211> LENGTH: 15
<212> TYPE: PRT
<213> ORGANISM: Artificial Sequence
<220> FEATURE:
<223> OTHER INFORMATION: Synthetic Construct

<400> SEQUENCE: 183

Thr Cys Tyr Ala Ser Gly Trp Gly Ser Ile Glu Pro Glu Glu Phe
1 5 10 15

<210> SEQ ID NO 184
<211> LENGTH: 15
<212> TYPE: PRT
<213> ORGANISM: Artificial Sequence
<220> FEATURE:
<223> OTHER INFORMATION: Synthetic Construct

<400> SEQUENCE: 184

Tyr Ala Ser Gly Trp Gly Ser Ile Glu Pro Glu Glu Phe Leu Thr
1 5 10 15

<210> SEQ ID NO 185
<211> LENGTH: 15
<212> TYPE: PRT
<213> ORGANISM: Artificial Sequence
<220> FEATURE:
<223> OTHER INFORMATION: Synthetic Construct

<400> SEQUENCE: 185

Ser Gly Trp Gly Ser Ile Glu Pro Glu Glu Phe Leu Thr Pro Lys
1 5 10 15

<210> SEQ ID NO 186
<211> LENGTH: 15
<212> TYPE: PRT
<213> ORGANISM: Artificial Sequence
<220> FEATURE:
<223> OTHER INFORMATION: Synthetic Construct

<400> SEQUENCE: 186

Trp Gly Ser Ile Glu Pro Glu Glu Phe Leu Thr Pro Lys Lys Leu
1 5 10 15

<210> SEQ ID NO 187
<211> LENGTH: 15
<212> TYPE: PRT
<213> ORGANISM: Artificial Sequence
<220> FEATURE:
<223> OTHER INFORMATION: Synthetic Construct

<400> SEQUENCE: 187

Ser Ile Glu Pro Glu Glu Phe Leu Thr Pro Lys Lys Leu Gln Cys
1 5 10 15

<210> SEQ ID NO 188
<211> LENGTH: 15
<212> TYPE: PRT
<213> ORGANISM: Artificial Sequence
<220> FEATURE:
<223> OTHER INFORMATION: Synthetic Construct

<400> SEQUENCE: 188

Glu Pro Glu Glu Phe Leu Thr Pro Lys Lys Leu Gln Cys Val Asp
1 5 10 15

<210> SEQ ID NO 189
<211> LENGTH: 15
<212> TYPE: PRT
<213> ORGANISM: Artificial Sequence
<220> FEATURE:
<223> OTHER INFORMATION: Synthetic Construct

<400> SEQUENCE: 189

Glu Glu Phe Leu Thr Pro Lys Lys Leu Gln Cys Val Asp Leu His
1 5 10 15

<210> SEQ ID NO 190
<211> LENGTH: 15
<212> TYPE: PRT
<213> ORGANISM: Artificial Sequence
<220> FEATURE:
<223> OTHER INFORMATION: Synthetic Construct

<400> SEQUENCE: 190

Phe Leu Thr Pro Lys Lys Leu Gln Cys Val Asp Leu His Val Ile
1 5 10 15

<210> SEQ ID NO 191
<211> LENGTH: 15
<212> TYPE: PRT
<213> ORGANISM: Artificial Sequence
<220> FEATURE:
<223> OTHER INFORMATION: Synthetic Construct

<400> SEQUENCE: 191

Thr Pro Lys Lys Leu Gln Cys Val Asp Leu His Val Ile Ser Asn
1 5 10 15

<210> SEQ ID NO 192
<211> LENGTH: 15
<212> TYPE: PRT
<213> ORGANISM: Artificial Sequence
<220> FEATURE:
<223> OTHER INFORMATION: Synthetic Construct

<400> SEQUENCE: 192

Lys Lys Leu Gln Cys Val Asp Leu His Val Ile Ser Asn Asp Val
1 5 10 15

<210> SEQ ID NO 193
<211> LENGTH: 15
<212> TYPE: PRT
<213> ORGANISM: Artificial Sequence
<220> FEATURE:
<223> OTHER INFORMATION: Synthetic Construct

<400> SEQUENCE: 193

Leu Gln Cys Val Asp Leu His Val Ile Ser Asn Asp Val Cys Ala
1 5 10 15

<210> SEQ ID NO 194
<211> LENGTH: 15
<212> TYPE: PRT
<213> ORGANISM: Artificial Sequence
<220> FEATURE:
<223> OTHER INFORMATION: Synthetic Construct

<400> SEQUENCE: 194

Cys Val Asp Leu His Val Ile Ser Asn Asp Val Cys Ala Gln Val
1 5 10 15

<210> SEQ ID NO 195
<211> LENGTH: 15
<212> TYPE: PRT
<213> ORGANISM: Artificial Sequence
<220> FEATURE:
<223> OTHER INFORMATION: Synthetic Construct

<400> SEQUENCE: 195

Asp Leu His Val Ile Ser Asn Asp Val Cys Ala Gln Val His Pro
1 5 10 15

<210> SEQ ID NO 196
<211> LENGTH: 15
<212> TYPE: PRT
<213> ORGANISM: Artificial Sequence
<220> FEATURE:
<223> OTHER INFORMATION: Synthetic Construct

<400> SEQUENCE: 196

His Val Ile Ser Asn Asp Val Cys Ala Gln Val His Pro Gln Lys
1 5 10 15

<210> SEQ ID NO 197

<211> LENGTH: 15
<212> TYPE: PRT
<213> ORGANISM: Artificial Sequence
<220> FEATURE:
<223> OTHER INFORMATION: Synthetic Construct

<400> SEQUENCE: 197

Ile Ser Asn Asp Val Cys Ala Gln Val His Pro Gln Lys Val Thr
1 5 10 15

<210> SEQ ID NO 198
<211> LENGTH: 15
<212> TYPE: PRT
<213> ORGANISM: Artificial Sequence
<220> FEATURE:
<223> OTHER INFORMATION: Synthetic Construct

<400> SEQUENCE: 198

Asn Asp Val Cys Ala Gln Val His Pro Gln Lys Val Thr Lys Phe
1 5 10 15

<210> SEQ ID NO 199
<211> LENGTH: 15
<212> TYPE: PRT
<213> ORGANISM: Artificial Sequence
<220> FEATURE:
<223> OTHER INFORMATION: Synthetic Construct

<400> SEQUENCE: 199

Val Cys Ala Gln Val His Pro Gln Lys Val Thr Lys Phe Met Leu
1 5 10 15

<210> SEQ ID NO 200
<211> LENGTH: 15
<212> TYPE: PRT
<213> ORGANISM: Artificial Sequence
<220> FEATURE:
<223> OTHER INFORMATION: Synthetic Construct

<400> SEQUENCE: 200

Ala Gln Val His Pro Gln Lys Val Thr Lys Phe Met Leu Cys Ala
1 5 10 15

<210> SEQ ID NO 201
<211> LENGTH: 15
<212> TYPE: PRT
<213> ORGANISM: Artificial Sequence
<220> FEATURE:
<223> OTHER INFORMATION: Synthetic Construct

<400> SEQUENCE: 201

Val His Pro Gln Lys Val Thr Lys Phe Met Leu Cys Ala Gly Arg
1 5 10 15

<210> SEQ ID NO 202
<211> LENGTH: 15
<212> TYPE: PRT
<213> ORGANISM: Artificial Sequence
<220> FEATURE:
<223> OTHER INFORMATION: Synthetic Construct

<400> SEQUENCE: 202

Pro Gln Lys Val Thr Lys Phe Met Leu Cys Ala Gly Arg Trp Thr
1 5 10 15

<210> SEQ ID NO 203
<211> LENGTH: 15

<212> TYPE: PRT
<213> ORGANISM: Artificial Sequence
<220> FEATURE:
<223> OTHER INFORMATION: Synthetic Construct

<400> SEQUENCE: 203

Lys Val Thr Lys Phe Met Leu Cys Ala Gly Arg Trp Thr Gly Gly
1 5 10 15

<210> SEQ ID NO 204
<211> LENGTH: 15
<212> TYPE: PRT
<213> ORGANISM: Artificial Sequence
<220> FEATURE:
<223> OTHER INFORMATION: Synthetic Construct

<400> SEQUENCE: 204

Thr Lys Phe Met Leu Cys Ala Gly Arg Trp Thr Gly Gly Lys Ser
1 5 10 15

<210> SEQ ID NO 205
<211> LENGTH: 15
<212> TYPE: PRT
<213> ORGANISM: Artificial Sequence
<220> FEATURE:
<223> OTHER INFORMATION: Synthetic Construct

<400> SEQUENCE: 205

Phe Met Leu Cys Ala Gly Arg Trp Thr Gly Gly Lys Ser Thr Cys
1 5 10 15

<210> SEQ ID NO 206
<211> LENGTH: 15
<212> TYPE: PRT
<213> ORGANISM: Artificial Sequence
<220> FEATURE:
<223> OTHER INFORMATION: Synthetic Construct

<400> SEQUENCE: 206

Leu Cys Ala Gly Arg Trp Thr Gly Gly Lys Ser Thr Cys Ser Gly
1 5 10 15

<210> SEQ ID NO 207
<211> LENGTH: 15
<212> TYPE: PRT
<213> ORGANISM: Artificial Sequence
<220> FEATURE:
<223> OTHER INFORMATION: Synthetic Construct

<400> SEQUENCE: 207

Ala Gly Arg Trp Thr Gly Gly Lys Ser Thr Cys Ser Gly Asp Ser
1 5 10 15

<210> SEQ ID NO 208
<211> LENGTH: 15
<212> TYPE: PRT
<213> ORGANISM: Artificial Sequence
<220> FEATURE:
<223> OTHER INFORMATION: Synthetic Construct

<400> SEQUENCE: 208

Arg Trp Thr Gly Gly Lys Ser Thr Cys Ser Gly Asp Ser Gly Gly
1 5 10 15

<210> SEQ ID NO 209
<211> LENGTH: 15
<212> TYPE: PRT

<213> ORGANISM: Artificial Sequence
<220> FEATURE:
<223> OTHER INFORMATION: Synthetic Construct

<400> SEQUENCE: 209

Thr Gly Gly Lys Ser Thr Cys Ser Gly Asp Ser Gly Gly Pro Leu
1 5 10 15

<210> SEQ ID NO 210
<211> LENGTH: 15
<212> TYPE: PRT
<213> ORGANISM: Artificial Sequence
<220> FEATURE:
<223> OTHER INFORMATION: Synthetic Construct

<400> SEQUENCE: 210

Gly Lys Ser Thr Cys Ser Gly Asp Ser Gly Gly Pro Leu Val Cys
1 5 10 15

<210> SEQ ID NO 211
<211> LENGTH: 15
<212> TYPE: PRT
<213> ORGANISM: Artificial Sequence
<220> FEATURE:
<223> OTHER INFORMATION: Synthetic Construct

<400> SEQUENCE: 211

Ser Thr Cys Ser Gly Asp Ser Gly Gly Pro Leu Val Cys Asn Gly
1 5 10 15

<210> SEQ ID NO 212
<211> LENGTH: 15
<212> TYPE: PRT
<213> ORGANISM: Artificial Sequence
<220> FEATURE:
<223> OTHER INFORMATION: Synthetic Construct

<400> SEQUENCE: 212

Cys Ser Gly Asp Ser Gly Gly Pro Leu Val Cys Asn Gly Val Leu
1 5 10 15

<210> SEQ ID NO 213
<211> LENGTH: 15
<212> TYPE: PRT
<213> ORGANISM: Artificial Sequence
<220> FEATURE:
<223> OTHER INFORMATION: Synthetic Construct

<400> SEQUENCE: 213

Gly Asp Ser Gly Gly Pro Leu Val Cys Asn Gly Val Leu Gln Gly
1 5 10 15

<210> SEQ ID NO 214
<211> LENGTH: 15
<212> TYPE: PRT
<213> ORGANISM: Artificial Sequence
<220> FEATURE:
<223> OTHER INFORMATION: Synthetic Construct

<400> SEQUENCE: 214

Ser Gly Gly Pro Leu Val Cys Asn Gly Val Leu Gln Gly Ile Thr
1 5 10 15

<210> SEQ ID NO 215
<211> LENGTH: 15
<212> TYPE: PRT
<213> ORGANISM: Artificial Sequence
<220> FEATURE:
<223> OTHER INFORMATION: Synthetic Construct

<400> SEQUENCE: 215

Gly Pro Leu Val Cys Asn Gly Val Leu Gln Gly Ile Thr Ser Trp
1 5 10 15

<210> SEQ ID NO 216
<211> LENGTH: 15
<212> TYPE: PRT
<213> ORGANISM: Artificial Sequence
<220> FEATURE:
<223> OTHER INFORMATION: Synthetic Construct

<400> SEQUENCE: 216

Leu Val Cys Asn Gly Val Leu Gln Gly Ile Thr Ser Trp Gly Ser
1 5 10 15

<210> SEQ ID NO 217
<211> LENGTH: 15
<212> TYPE: PRT
<213> ORGANISM: Artificial Sequence
<220> FEATURE:
<223> OTHER INFORMATION: Synthetic Construct

<400> SEQUENCE: 217

Cys Asn Gly Val Leu Gln Gly Ile Thr Ser Trp Gly Ser Glu Pro
1 5 10 15

<210> SEQ ID NO 218
<211> LENGTH: 15
<212> TYPE: PRT
<213> ORGANISM: Artificial Sequence
<220> FEATURE:
<223> OTHER INFORMATION: Synthetic Construct

<400> SEQUENCE: 218

Gly Val Leu Gln Gly Ile Thr Ser Trp Gly Ser Glu Pro Cys Ala
1 5 10 15

<210> SEQ ID NO 219
<211> LENGTH: 15
<212> TYPE: PRT
<213> ORGANISM: Artificial Sequence
<220> FEATURE:
<223> OTHER INFORMATION: Synthetic Construct

<400> SEQUENCE: 219

Leu Gln Gly Ile Thr Ser Trp Gly Ser Glu Pro Cys Ala Leu Pro
1 5 10 15

<210> SEQ ID NO 220
<211> LENGTH: 15
<212> TYPE: PRT
<213> ORGANISM: Artificial Sequence
<220> FEATURE:
<223> OTHER INFORMATION: Synthetic Construct

<400> SEQUENCE: 220

Gly Ile Thr Ser Trp Gly Ser Glu Pro Cys Ala Leu Pro Glu Arg
1 5 10 15

<210> SEQ ID NO 221
<211> LENGTH: 15
<212> TYPE: PRT
<213> ORGANISM: Artificial Sequence
<220> FEATURE:

<223> OTHER INFORMATION: Synthetic Construct

<400> SEQUENCE: 221

Thr Ser Trp Gly Ser Glu Pro Cys Ala Leu Pro Glu Arg Pro Ser
1 5 10 15

<210> SEQ ID NO 222
<211> LENGTH: 15
<212> TYPE: PRT
<213> ORGANISM: Artificial Sequence
<220> FEATURE:
<223> OTHER INFORMATION: Synthetic Construct

<400> SEQUENCE: 222

Trp Gly Ser Glu Pro Cys Ala Leu Pro Glu Arg Pro Ser Leu Tyr
1 5 10 15

<210> SEQ ID NO 223
<211> LENGTH: 15
<212> TYPE: PRT
<213> ORGANISM: Artificial Sequence
<220> FEATURE:
<223> OTHER INFORMATION: Synthetic Construct

<400> SEQUENCE: 223

Ser Glu Pro Cys Ala Leu Pro Glu Arg Pro Ser Leu Tyr Thr Lys
1 5 10 15

<210> SEQ ID NO 224
<211> LENGTH: 15
<212> TYPE: PRT
<213> ORGANISM: Artificial Sequence
<220> FEATURE:
<223> OTHER INFORMATION: Synthetic Construct

<400> SEQUENCE: 224

Pro Cys Ala Leu Pro Glu Arg Pro Ser Leu Tyr Thr Lys Val Val
1 5 10 15

<210> SEQ ID NO 225
<211> LENGTH: 15
<212> TYPE: PRT
<213> ORGANISM: Artificial Sequence
<220> FEATURE:
<223> OTHER INFORMATION: Synthetic Construct

<400> SEQUENCE: 225

Ala Leu Pro Glu Arg Pro Ser Leu Tyr Thr Lys Val Val His Tyr
1 5 10 15

<210> SEQ ID NO 226
<211> LENGTH: 15
<212> TYPE: PRT
<213> ORGANISM: Artificial Sequence
<220> FEATURE:
<223> OTHER INFORMATION: Synthetic Construct

<400> SEQUENCE: 226

Pro Glu Arg Pro Ser Leu Tyr Thr Lys Val Val His Tyr Arg Lys
1 5 10 15

<210> SEQ ID NO 227
<211> LENGTH: 15
<212> TYPE: PRT
<213> ORGANISM: Artificial Sequence
<220> FEATURE:
<223> OTHER INFORMATION: Synthetic Construct

<400> SEQUENCE: 227

Arg Pro Ser Leu Tyr Thr Lys Val Val His Tyr Arg Lys Trp Ile
1 5 10 15

<210> SEQ ID NO 228
<211> LENGTH: 15
<212> TYPE: PRT
<213> ORGANISM: Artificial Sequence
<220> FEATURE:
<223> OTHER INFORMATION: Synthetic Construct

<400> SEQUENCE: 228

Ser Leu Tyr Thr Lys Val Val His Tyr Arg Lys Trp Ile Lys Asp
1 5 10 15

<210> SEQ ID NO 229
<211> LENGTH: 15
<212> TYPE: PRT
<213> ORGANISM: Artificial Sequence
<220> FEATURE:
<223> OTHER INFORMATION: Synthetic Construct

<400> SEQUENCE: 229

Tyr Thr Lys Val Val His Tyr Arg Lys Trp Ile Lys Asp Thr Ile
1 5 10 15

<210> SEQ ID NO 230
<211> LENGTH: 15
<212> TYPE: PRT
<213> ORGANISM: Artificial Sequence
<220> FEATURE:
<223> OTHER INFORMATION: Synthetic Construct

<400> SEQUENCE: 230

Lys Val Val His Tyr Arg Lys Trp Ile Lys Asp Thr Ile Val Ala
1 5 10 15

<210> SEQ ID NO 231
<211> LENGTH: 15
<212> TYPE: PRT
<213> ORGANISM: Artificial Sequence
<220> FEATURE:
<223> OTHER INFORMATION: Synthetic Construct

<400> SEQUENCE: 231

Val His Tyr Arg Lys Trp Ile Lys Asp Thr Ile Val Ala Asn Pro
1 5 10 15

<210> SEQ ID NO 232
<211> LENGTH: 13
<212> TYPE: PRT
<213> ORGANISM: Artificial Sequence
<220> FEATURE:
<223> OTHER INFORMATION: Synthetic Construct

<400> SEQUENCE: 232

Tyr Arg Lys Trp Ile Lys Asp Thr Ile Val Ala Asn Pro
1 5 10

<210> SEQ ID NO 233
<211> LENGTH: 11
<212> TYPE: PRT
<213> ORGANISM: Artificial Sequence
<220> FEATURE:
<223> OTHER INFORMATION: Synthetic Construct

<400> SEQUENCE: 233

Lys Trp Ile Lys Asp Thr Ile Val Ala Asn Pro
1 5 10

<210> SEQ ID NO 234
<211> LENGTH: 15
<212> TYPE: PRT
<213> ORGANISM: Artificial Sequence
<220> FEATURE:
<223> OTHER INFORMATION: Synthetic Construct

<400> SEQUENCE: 234

Met Lys Ala Val Leu Leu Ala Leu Leu Met Ala Gly Leu Ala Leu
1 5 10 15

<210> SEQ ID NO 235
<211> LENGTH: 15
<212> TYPE: PRT
<213> ORGANISM: Artificial Sequence
<220> FEATURE:
<223> OTHER INFORMATION: Synthetic Construct

<400> SEQUENCE: 235

Ala Val Leu Leu Ala Leu Leu Met Ala Gly Leu Ala Leu Gln Pro
1 5 10 15

<210> SEQ ID NO 236
<211> LENGTH: 15
<212> TYPE: PRT
<213> ORGANISM: Artificial Sequence
<220> FEATURE:
<223> OTHER INFORMATION: Synthetic Construct

<400> SEQUENCE: 236

Leu Leu Ala Leu Leu Met Ala Gly Leu Ala Leu Gln Pro Gly Thr
1 5 10 15

<210> SEQ ID NO 237
<211> LENGTH: 15
<212> TYPE: PRT
<213> ORGANISM: Artificial Sequence
<220> FEATURE:
<223> OTHER INFORMATION: Synthetic Construct

<400> SEQUENCE: 237

Ala Leu Leu Met Ala Gly Leu Ala Leu Gln Pro Gly Thr Ala Leu
1 5 10 15

<210> SEQ ID NO 238
<211> LENGTH: 15
<212> TYPE: PRT
<213> ORGANISM: Artificial Sequence
<220> FEATURE:
<223> OTHER INFORMATION: Synthetic Construct

<400> SEQUENCE: 238

Leu Met Ala Gly Leu Ala Leu Gln Pro Gly Thr Ala Leu Leu Cys
1 5 10 15

<210> SEQ ID NO 239
<211> LENGTH: 15
<212> TYPE: PRT
<213> ORGANISM: Artificial Sequence
<220> FEATURE:
<223> OTHER INFORMATION: Synthetic Construct

<400> SEQUENCE: 239

Ala Gly Leu Ala Leu Gln Pro Gly Thr Ala Leu Leu Cys Tyr Ser
1 5 10 15

<210> SEQ ID NO 240
<211> LENGTH: 15
<212> TYPE: PRT
<213> ORGANISM: Artificial Sequence
<220> FEATURE:
<223> OTHER INFORMATION: Synthetic Construct

<400> SEQUENCE: 240

Leu Ala Leu Gln Pro Gly Thr Ala Leu Leu Cys Tyr Ser Cys Lys
1 5 10 15

<210> SEQ ID NO 241
<211> LENGTH: 15
<212> TYPE: PRT
<213> ORGANISM: Artificial Sequence
<220> FEATURE:
<223> OTHER INFORMATION: Synthetic Construct

<400> SEQUENCE: 241

Leu Gln Pro Gly Thr Ala Leu Leu Cys Tyr Ser Cys Lys Ala Gln
1 5 10 15

<210> SEQ ID NO 242
<211> LENGTH: 15
<212> TYPE: PRT
<213> ORGANISM: Artificial Sequence
<220> FEATURE:
<223> OTHER INFORMATION: Synthetic Construct

<400> SEQUENCE: 242

Pro Gly Thr Ala Leu Leu Cys Tyr Ser Cys Lys Ala Gln Val Ser
1 5 10 15

<210> SEQ ID NO 243
<211> LENGTH: 15
<212> TYPE: PRT
<213> ORGANISM: Artificial Sequence
<220> FEATURE:
<223> OTHER INFORMATION: Synthetic Construct

<400> SEQUENCE: 243

Thr Ala Leu Leu Cys Tyr Ser Cys Lys Ala Gln Val Ser Asn Glu
1 5 10 15

<210> SEQ ID NO 244
<211> LENGTH: 15
<212> TYPE: PRT
<213> ORGANISM: Artificial Sequence
<220> FEATURE:
<223> OTHER INFORMATION: Synthetic Construct

<400> SEQUENCE: 244

Leu Leu Cys Tyr Ser Cys Lys Ala Gln Val Ser Asn Glu Asp Cys
1 5 10 15

<210> SEQ ID NO 245
<211> LENGTH: 15
<212> TYPE: PRT
<213> ORGANISM: Artificial Sequence
<220> FEATURE:
<223> OTHER INFORMATION: Synthetic Construct

<400> SEQUENCE: 245

Cys Tyr Ser Cys Lys Ala Gln Val Ser Asn Glu Asp Cys Leu Gln
1 5 10 15

<210> SEQ ID NO 246
<211> LENGTH: 15
<212> TYPE: PRT
<213> ORGANISM: Artificial Sequence
<220> FEATURE:
<223> OTHER INFORMATION: Synthetic Construct

<400> SEQUENCE: 246

Ser Cys Lys Ala Gln Val Ser Asn Glu Asp Cys Leu Gln Val Glu
1 5 10 15

<210> SEQ ID NO 247
<211> LENGTH: 15
<212> TYPE: PRT
<213> ORGANISM: Artificial Sequence
<220> FEATURE:
<223> OTHER INFORMATION: Synthetic Construct

<400> SEQUENCE: 247

Lys Ala Gln Val Ser Asn Glu Asp Cys Leu Gln Val Glu Asn Cys
1 5 10 15

<210> SEQ ID NO 248
<211> LENGTH: 15
<212> TYPE: PRT
<213> ORGANISM: Artificial Sequence
<220> FEATURE:
<223> OTHER INFORMATION: Synthetic Construct

<400> SEQUENCE: 248

Gln Val Ser Asn Glu Asp Cys Leu Gln Val Glu Asn Cys Thr Gln
1 5 10 15

<210> SEQ ID NO 249
<211> LENGTH: 15
<212> TYPE: PRT
<213> ORGANISM: Artificial Sequence
<220> FEATURE:
<223> OTHER INFORMATION: Synthetic Construct

<400> SEQUENCE: 249

Ser Asn Glu Asp Cys Leu Gln Val Glu Asn Cys Thr Gln Leu Gly
1 5 10 15

<210> SEQ ID NO 250
<211> LENGTH: 15
<212> TYPE: PRT
<213> ORGANISM: Artificial Sequence
<220> FEATURE:
<223> OTHER INFORMATION: Synthetic Construct

<400> SEQUENCE: 250

Glu Asp Cys Leu Gln Val Glu Asn Cys Thr Gln Leu Gly Glu Gln
1 5 10 15

<210> SEQ ID NO 251
<211> LENGTH: 15
<212> TYPE: PRT
<213> ORGANISM: Artificial Sequence
<220> FEATURE:
<223> OTHER INFORMATION: Synthetic Construct

<400> SEQUENCE: 251

Cys Leu Gln Val Glu Asn Cys Thr Gln Leu Gly Glu Gln Cys Trp 1 5 10 15

<210> SEQ ID NO 252
<211> LENGTH: 15
<212> TYPE: PRT
<213> ORGANISM: Artificial Sequence
<220> FEATURE:
<223> OTHER INFORMATION: Synthetic Construct

<400> SEQUENCE: 252

Gln Val Glu Asn Cys Thr Gln Leu Gly Glu Gln Cys Trp Thr Ala
1 5 10 15

<210> SEQ ID NO 253
<211> LENGTH: 15
<212> TYPE: PRT
<213> ORGANISM: Artificial Sequence
<220> FEATURE:
<223> OTHER INFORMATION: Synthetic Construct

<400> SEQUENCE: 253

Glu Asn Cys Thr Gln Leu Gly Glu Gln Cys Trp Thr Ala Arg Ile
1 5 10 15

<210> SEQ ID NO 254
<211> LENGTH: 15
<212> TYPE: PRT
<213> ORGANISM: Artificial Sequence
<220> FEATURE:
<223> OTHER INFORMATION: Synthetic Construct

<400> SEQUENCE: 254

Cys Thr Gln Leu Gly Glu Gln Cys Trp Thr Ala Arg Ile Arg Ala
1 5 10 15

<210> SEQ ID NO 255
<211> LENGTH: 15
<212> TYPE: PRT
<213> ORGANISM: Artificial Sequence
<220> FEATURE:
<223> OTHER INFORMATION: Synthetic Construct

<400> SEQUENCE: 255

Gln Leu Gly Glu Gln Cys Trp Thr Ala Arg Ile Arg Ala Val Gly
1 5 10 15

<210> SEQ ID NO 256
<211> LENGTH: 15
<212> TYPE: PRT
<213> ORGANISM: Artificial Sequence
<220> FEATURE:
<223> OTHER INFORMATION: Synthetic Construct

<400> SEQUENCE: 256

Gly Glu Gln Cys Trp Thr Ala Arg Ile Arg Ala Val Gly Leu Leu
1 5 10 15

<210> SEQ ID NO 257
<211> LENGTH: 15
<212> TYPE: PRT
<213> ORGANISM: Artificial Sequence
<220> FEATURE:
<223> OTHER INFORMATION: Synthetic Construct

<400> SEQUENCE: 257

Gln Cys Trp Thr Ala Arg Ile Arg Ala Val Gly Leu Leu Thr Val
1 5 10 15

<210> SEQ ID NO 258
<211> LENGTH: 15
<212> TYPE: PRT
<213> ORGANISM: Artificial Sequence
<220> FEATURE:
<223> OTHER INFORMATION: Synthetic Construct

<400> SEQUENCE: 258

Trp Thr Ala Arg Ile Arg Ala Val Gly Leu Leu Thr Val Ile Ser
1 5 10 15

<210> SEQ ID NO 259
<211> LENGTH: 15
<212> TYPE: PRT
<213> ORGANISM: Artificial Sequence
<220> FEATURE:
<223> OTHER INFORMATION: Synthetic Construct

<400> SEQUENCE: 259

Ala Arg Ile Arg Ala Val Gly Leu Leu Thr Val Ile Ser Lys Gly
1 5 10 15

<210> SEQ ID NO 260
<211> LENGTH: 15
<212> TYPE: PRT
<213> ORGANISM: Artificial Sequence
<220> FEATURE:
<223> OTHER INFORMATION: Synthetic Construct

<400> SEQUENCE: 260

Ile Arg Ala Val Gly Leu Leu Thr Val Ile Ser Lys Gly Cys Ser
1 5 10 15

<210> SEQ ID NO 261
<211> LENGTH: 15
<212> TYPE: PRT
<213> ORGANISM: Artificial Sequence
<220> FEATURE:
<223> OTHER INFORMATION: Synthetic Construct

<400> SEQUENCE: 261

Ala Val Gly Leu Leu Thr Val Ile Ser Lys Gly Cys Ser Leu Asn
1 5 10 15

<210> SEQ ID NO 262
<211> LENGTH: 15
<212> TYPE: PRT
<213> ORGANISM: Artificial Sequence
<220> FEATURE:
<223> OTHER INFORMATION: Synthetic Construct

<400> SEQUENCE: 262

Gly Leu Leu Thr Val Ile Ser Lys Gly Cys Ser Leu Asn Cys Val
1 5 10 15

<210> SEQ ID NO 263
<211> LENGTH: 15
<212> TYPE: PRT
<213> ORGANISM: Artificial Sequence
<220> FEATURE:
<223> OTHER INFORMATION: Synthetic Construct

<400> SEQUENCE: 263

Leu Thr Val Ile Ser Lys Gly Cys Ser Leu Asn Cys Val Asp Asp
1 5 10 15

<210> SEQ ID NO 264
<211> LENGTH: 15
<212> TYPE: PRT
<213> ORGANISM: Artificial Sequence
<220> FEATURE:
<223> OTHER INFORMATION: Synthetic Construct

<400> SEQUENCE: 264

Val Ile Ser Lys Gly Cys Ser Leu Asn Cys Val Asp Asp Ser Gln
1 5 10 15

<210> SEQ ID NO 265
<211> LENGTH: 15
<212> TYPE: PRT
<213> ORGANISM: Artificial Sequence
<220> FEATURE:
<223> OTHER INFORMATION: Synthetic Construct

<400> SEQUENCE: 265

Ser Lys Gly Cys Ser Leu Asn Cys Val Asp Asp Ser Gln Asp Tyr
1 5 10 15

<210> SEQ ID NO 266
<211> LENGTH: 15
<212> TYPE: PRT
<213> ORGANISM: Artificial Sequence
<220> FEATURE:
<223> OTHER INFORMATION: Synthetic Construct

<400> SEQUENCE: 266

Gly Cys Ser Leu Asn Cys Val Asp Asp Ser Gln Asp Tyr Tyr Val
1 5 10 15

<210> SEQ ID NO 267
<211> LENGTH: 15
<212> TYPE: PRT
<213> ORGANISM: Artificial Sequence
<220> FEATURE:
<223> OTHER INFORMATION: Synthetic Construct

<400> SEQUENCE: 267

Ser Leu Asn Cys Val Asp Asp Ser Gln Asp Tyr Tyr Val Gly Lys
1 5 10 15

<210> SEQ ID NO 268
<211> LENGTH: 15
<212> TYPE: PRT
<213> ORGANISM: Artificial Sequence
<220> FEATURE:
<223> OTHER INFORMATION: Synthetic Construct

<400> SEQUENCE: 268

Asn Cys Val Asp Asp Ser Gln Asp Tyr Tyr Val Gly Lys Lys Asn
1 5 10 15

<210> SEQ ID NO 269
<211> LENGTH: 15
<212> TYPE: PRT
<213> ORGANISM: Artificial Sequence
<220> FEATURE:
<223> OTHER INFORMATION: Synthetic Construct

<400> SEQUENCE: 269

Val Asp Asp Ser Gln Asp Tyr Tyr Val Gly Lys Lys Asn Ile Thr
1 5 10 15

<210> SEQ ID NO 270
<211> LENGTH: 15
<212> TYPE: PRT
<213> ORGANISM: Artificial Sequence
<220> FEATURE:
<223> OTHER INFORMATION: Synthetic Construct

<400> SEQUENCE: 270

Asp Ser Gln Asp Tyr Tyr Val Gly Lys Lys Asn Ile Thr Cys Cys
1               5                   10                  15

<210> SEQ ID NO 271
<211> LENGTH: 15
<212> TYPE: PRT
<213> ORGANISM: Artificial Sequence
<220> FEATURE:
<223> OTHER INFORMATION: Synthetic Construct

<400> SEQUENCE: 271

Gln Asp Tyr Tyr Val Gly Lys Lys Asn Ile Thr Cys Cys Asp Thr
1               5                   10                  15

<210> SEQ ID NO 272
<211> LENGTH: 15
<212> TYPE: PRT
<213> ORGANISM: Artificial Sequence
<220> FEATURE:
<223> OTHER INFORMATION: Synthetic Construct

<400> SEQUENCE: 272

Tyr Tyr Val Gly Lys Lys Asn Ile Thr Cys Cys Asp Thr Asp Leu
1               5                   10                  15

<210> SEQ ID NO 273
<211> LENGTH: 15
<212> TYPE: PRT
<213> ORGANISM: Artificial Sequence
<220> FEATURE:
<223> OTHER INFORMATION: Synthetic Construct

<400> SEQUENCE: 273

Val Gly Lys Lys Asn Ile Thr Cys Cys Asp Thr Asp Leu Cys Asn
1               5                   10                  15

<210> SEQ ID NO 274
<211> LENGTH: 15
<212> TYPE: PRT
<213> ORGANISM: Artificial Sequence
<220> FEATURE:
<223> OTHER INFORMATION: Synthetic Construct

<400> SEQUENCE: 274

Lys Lys Asn Ile Thr Cys Cys Asp Thr Asp Leu Cys Asn Ala Ser
1               5                   10                  15

<210> SEQ ID NO 275
<211> LENGTH: 15
<212> TYPE: PRT
<213> ORGANISM: Artificial Sequence
<220> FEATURE:
<223> OTHER INFORMATION: Synthetic Construct

<400> SEQUENCE: 275

Asn Ile Thr Cys Cys Asp Thr Asp Leu Cys Asn Ala Ser Gly Ala
1               5                   10                  15

<210> SEQ ID NO 276

-continued

<211> LENGTH: 15
<212> TYPE: PRT
<213> ORGANISM: Artificial Sequence
<220> FEATURE:
<223> OTHER INFORMATION: Synthetic Construct

<400> SEQUENCE: 276

Thr Cys Cys Asp Thr Asp Leu Cys Asn Ala Ser Gly Ala His Ala
1               5                   10                  15

<210> SEQ ID NO 277
<211> LENGTH: 15
<212> TYPE: PRT
<213> ORGANISM: Artificial Sequence
<220> FEATURE:
<223> OTHER INFORMATION: Synthetic Construct

<400> SEQUENCE: 277

Cys Asp Thr Asp Leu Cys Asn Ala Ser Gly Ala His Ala Leu Gln
1               5                   10                  15

<210> SEQ ID NO 278
<211> LENGTH: 15
<212> TYPE: PRT
<213> ORGANISM: Artificial Sequence
<220> FEATURE:
<223> OTHER INFORMATION: Synthetic Construct

<400> SEQUENCE: 278

Thr Asp Leu Cys Asn Ala Ser Gly Ala His Ala Leu Gln Pro Ala
1               5                   10                  15

<210> SEQ ID NO 279
<211> LENGTH: 15
<212> TYPE: PRT
<213> ORGANISM: Artificial Sequence
<220> FEATURE:
<223> OTHER INFORMATION: Synthetic Construct

<400> SEQUENCE: 279

Leu Cys Asn Ala Ser Gly Ala His Ala Leu Gln Pro Ala Ala Ala
1               5                   10                  15

<210> SEQ ID NO 280
<211> LENGTH: 15
<212> TYPE: PRT
<213> ORGANISM: Artificial Sequence
<220> FEATURE:
<223> OTHER INFORMATION: Synthetic Construct

<400> SEQUENCE: 280

Asn Ala Ser Gly Ala His Ala Leu Gln Pro Ala Ala Ala Ile Leu
1               5                   10                  15

<210> SEQ ID NO 281
<211> LENGTH: 15
<212> TYPE: PRT
<213> ORGANISM: Artificial Sequence
<220> FEATURE:
<223> OTHER INFORMATION: Synthetic Construct

<400> SEQUENCE: 281

Ser Gly Ala His Ala Leu Gln Pro Ala Ala Ala Ile Leu Ala Leu
1               5                   10                  15

<210> SEQ ID NO 282
<211> LENGTH: 15

<212> TYPE: PRT
<213> ORGANISM: Artificial Sequence
<220> FEATURE:
<223> OTHER INFORMATION: Synthetic Construct

<400> SEQUENCE: 282

Ala His Ala Leu Gln Pro Ala Ala Ala Ile Leu Ala Leu Leu Pro
1 5 10 15

<210> SEQ ID NO 283
<211> LENGTH: 15
<212> TYPE: PRT
<213> ORGANISM: Artificial Sequence
<220> FEATURE:
<223> OTHER INFORMATION: Synthetic Construct

<400> SEQUENCE: 283

Ala Leu Gln Pro Ala Ala Ala Ile Leu Ala Leu Leu Pro Ala Leu
1 5 10 15

<210> SEQ ID NO 284
<211> LENGTH: 15
<212> TYPE: PRT
<213> ORGANISM: Artificial Sequence
<220> FEATURE:
<223> OTHER INFORMATION: Synthetic Construct

<400> SEQUENCE: 284

Gln Pro Ala Ala Ala Ile Leu Ala Leu Leu Pro Ala Leu Gly Leu
1 5 10 15

<210> SEQ ID NO 285
<211> LENGTH: 15
<212> TYPE: PRT
<213> ORGANISM: Artificial Sequence
<220> FEATURE:
<223> OTHER INFORMATION: Synthetic Construct

<400> SEQUENCE: 285

Ala Ala Ala Ile Leu Ala Leu Leu Pro Ala Leu Gly Leu Leu Leu
1 5 10 15

<210> SEQ ID NO 286
<211> LENGTH: 15
<212> TYPE: PRT
<213> ORGANISM: Artificial Sequence
<220> FEATURE:
<223> OTHER INFORMATION: Synthetic Construct

<400> SEQUENCE: 286

Ala Ile Leu Ala Leu Leu Pro Ala Leu Gly Leu Leu Leu Trp Gly
1 5 10 15

<210> SEQ ID NO 287
<211> LENGTH: 15
<212> TYPE: PRT
<213> ORGANISM: Artificial Sequence
<220> FEATURE:
<223> OTHER INFORMATION: Synthetic Construct

<400> SEQUENCE: 287

Leu Ala Leu Leu Pro Ala Leu Gly Leu Leu Leu Trp Gly Pro Gly
1 5 10 15

<210> SEQ ID NO 288
<211> LENGTH: 15
<212> TYPE: PRT

<213> ORGANISM: Artificial Sequence
<220> FEATURE:
<223> OTHER INFORMATION: Synthetic Construct

<400> SEQUENCE: 288

Leu Leu Pro Ala Leu Gly Leu Leu Leu Trp Gly Pro Gly Gln Leu
1               5                   10                  15

<210> SEQ ID NO 289
<211> LENGTH: 13
<212> TYPE: PRT
<213> ORGANISM: Artificial Sequence
<220> FEATURE:
<223> OTHER INFORMATION: Synthetic Construct

<400> SEQUENCE: 289

Pro Ala Leu Gly Leu Leu Leu Trp Gly Pro Gly Gln Leu
1               5                   10

<210> SEQ ID NO 290
<211> LENGTH: 568
<212> TYPE: RNA
<213> ORGANISM: Artificial Sequence
<220> FEATURE:
<223> OTHER INFORMATION: Synthetic Construct

<400> SEQUENCE: 290
uaacguuacu ggccgaagcc gcuuggaaua aggccggugu gcguuugucu auauguuauu 60
uuccaccaua uugccgucuu uuggcaaugu gagggcccgg aaaccuggcc cugucuucuu 120
gacgagcauu ccuagggguc uuuccccucu cgccaaagga augcaagguc uguugaaugu 180
cgugaaggaa gcaguuccuc uggaagcuuc uugaagacaa acaacgucug uagcgacccu 240
uugcaggcag cggaaccccc caccuggcga caggugccuc ugcggccaaa agccacgugu 300
auaagauaca ccugcaaagg cggcacaacc ccagugccac guugugaguu ggauaguugu 360
ggaaagaguc aaauggcucu ccucaagcgu auucaacaag gggcugaagg augcccagaa 420
gguaccccau uguaugggau cugaucuggg gccucggugc acaugcuuua cauguguuua 480
gucgagguua aaaaacgucu aggccccccg aaccacgggg acgugguuuu ccuuugaaaa 540
acacgaugau aauauggcca caaccaug 568

<210> SEQ ID NO 291
<211> LENGTH: 24
<212> TYPE: DNA
<213> ORGANISM: Artificial Sequence
<220> FEATURE:
<223> OTHER INFORMATION: Synthetic Construct

<400> SEQUENCE: 291
tcgtcgtttt gtcgttttgt cgtt 24

<210> SEQ ID NO 292
<211> LENGTH: 21
<212> TYPE: DNA
<213> ORGANISM: Artificial Sequence
<220> FEATURE:
<223> OTHER INFORMATION: Synthetic Construct

<400> SEQUENCE: 292
tcgtcgtttt tcggtgcttt t 21

<210> SEQ ID NO 293
<211> LENGTH: 21

-continued

```
<212> TYPE: DNA
<213> ORGANISM: Artificial Sequence
<220> FEATURE:
<223> OTHER INFORMATION: Synthetic Construct

<400> SEQUENCE: 293

tcgtcgtttt tcggtcgttt t                                              21


<210> SEQ ID NO 294
<211> LENGTH: 20
<212> TYPE: PRT
<213> ORGANISM: Artificial Sequence
<220> FEATURE:
<223> OTHER INFORMATION: Synthetic Construct

<400> SEQUENCE: 294

Glu Thr Asp Thr Leu Leu Leu Trp Val Leu Leu Leu Trp Val Pro Gly
1               5                   10                  15

Ser Thr Gly Asp
            20
```

VECTORS FOR EXPRESSION OF PROSTATE-ASSOCIATED ANTIGENS

CROSS-REFERENCE TO RELATED APPLICATIONS

This application is a division of application Ser. No. 15/146,578 filed on May 4, 2016, now U.S. Pat. No. 9,402,901, which is a division of application Ser. No. 14/527,226 filed on Oct. 29, 2014, now U.S. Pat. No. 9,402,901, which claims the benefit of U.S. Provisional Application No. 61/898,966 filed on Nov. 1, 2013. The disclosure of each of application Ser. Nos. 15/146,578, 14/527,226, and U.S. Provisional Application No. 61/898,966 is incorporated herein by reference in its entirety.

REFERENCE TO SEQUENCE LISTING

This application is being filed along with a sequence listing in electronic format. The sequence listing is provided as a file in .txt format entitled "PC72055C_UPDATED12222020_SEQListing_ST25.txt", created on Dec. 22, 2020 and having a size of 492 KB. The sequence listing contained in the .txt file is part of the specification and is herein incorporated by reference in its entirety.

FIELD OF THE INVENTION

The present invention relates generally to immunotherapy and specifically to vaccines and methods for treating or preventing neoplastic disorders.

BACKGROUND OF THE INVENTION

Prostate cancer is the second most commonly diagnosed cancer and the fourth leading cause of cancer-related death in men in the developed countries worldwide. Various prostate-associated antigens (PAA), such as prostate-specific antigen (PSA), prostate-specific membrane antigen (PSMA), and prostate stem cell antigen (PSCA) have been shown to be overexpressed by prostate cancer cells as compared to normal counterparts. These antigens, therefore, represent possible targets for inducing specific immune responses against cancers expressing the antigens via the use of vaccine-based immunotherapy. (See e.g. Marrari, A., M. lero, et al. (2007). "Vaccination therapy in prostate cancer." Cancer Immunol Immunother 56(4): 429-45)

PSCA is a 123-amino acid membrane protein. The native full length human PSCA consists of amino acids 1 and 4-125 of SEQ ID NO:21 (without the alanine and serine residues at the second and third position respectively). PSCA has high tissue specificity and is expressed on more than 85% of prostate cancer specimens, with expression levels increasing with higher Gleason scores and androgen independence. It is expressed in 80-100% of bone metastasis of prostate cancer patients.

PSA is a kallikrein-like serine protease that is produced exclusively by the columnar epithelial cells lining the acini and ducts of the prostate gland. PSA mRNA is translated as an inactive 261-amino acid preproPSA precursor. Prepro-PSA has 24 additional residues that constitute the pre-region (the signal polypeptide) and the propolypeptide. Release of the propolypeptide results in the 237- amino acid, mature extracellular form, which is enzymatically active. The full length sequence of the native human PSA consists of amino acids 4-263 of SEQ ID NO: 15. PSA is organ-specific and, as a result, it is produced by the epithelial cells of benign prostatic hyperplastic (BPH) tissue, primary prostate cancer tissue, and metastatic prostate cancer tissue.

PSMA, also known as Folate hydrolase 1 (FOLH1), is composed of 750 amino acids. The amino acid sequence of the full length human PSMA is provided in SEQ ID NO:1. PSMA includes a cytoplasmic domain (amino acids 1-19), a transmembrane domain (amino acids 20-43), and an extracellular domain (amino acids 44-750). PSMA was found to be expressed in prostate cancer cells it at 1000-fold higher levels than normal tissues. It is abundantly expressed on neovasculature of a variety of other solid tumors such as colon, breast, liver, bladder, pancreas, lung, renal cancers as well as melanoma and sarcomas. Thus, PSMA is considered a target not only specific for prostate cancer cells but also a pan-carcinoma target for other cancers.

While a large number of tumor-associated antigens have been identified and many of these antigens have been explored as protein-based or DNA-based vaccines for the treatment or prevention of cancers, most clinical trials so far have failed to produce a therapeutic product. One of the challenges in developing cancer vaccines resides in the fact that the cancer antigens are usually self-derived and, therefore, poorly immunogenic because the immune system is self-regulated not to recognize self-proteins. Accordingly, a need exists for a method to enhance the immunogenicity or therapeutic effect of cancer vaccines.

Numerous approaches have been explored for enhancing the immunogenicity or enhancing anti-tumor efficacy of cancer vaccines. One of such approach involves the use of various immune modulators, such as TLR agonists, TNFR agonists, CTLA-4 inhibitors, and protein kinase inhibitors.

Toll-like receptors (TLRs) are type 1 membrane receptors that are expressed on hematopoietic and non-hematopoietic cells. At least 11 members have been identified in the TLR family. These receptors are characterized by their capacity to recognize pathogen-associated molecular patterns (PAMP) expressed by pathogenic organisms. These receptors in the innate immune systems exert control over the polarity of the ensuing acquired immune response. Among the TLRs, TLR9 has been extensively investigated for its functions in immune responses. Stimulation of the TLR9 receptor directs antigen-presenting cells (APCs) towards priming potent, $T_H1$-dominated T-cell responses, by increasing the production of pro-inflammatory cytokines and the presentation of co-stimulatory molecules to T cells. CpG oligonucleotides, ligands for TLR9, were found to be a class of potent immunostimulatory factors. CpG therapy has been tested against a wide variety of tumor models in mice, and has consistently been shown to promote tumor inhibition or regression.

Cytotoxic T-Lymphocyte Antigen 4 (CTLA-4) is a member of the immunoglobulin superfamily and is expressed on the surface of Helper T cells. CTLA-4 is a negative regulator of CD28 dependent T cell activation, and acts as an inhibitory checkpoint for the adaptive immune response. Similar to the T-cell costimulatory protein CD28, CTLA-4 binds to CD80 and CD86 on antigen-presenting cells. CTLA-4 transmits an inhibitory signal to T cells, whereas CD28 transmits a stimulatory signal. Human antibodies against human CTLA-4 have been described as immunostimulation modulators in a number of disease conditions, such as treating or preventing viral and bacterial infection and for treating cancer (WO 01/14424 and WO 00/37504). Various preclinical studies have shown that CTLA-4 blockade by monoclonal antibodies enhances the host immune response against immunogenic tumors, and can even reject established tumors. Two fully human anti-human CTLA-4 monoclonal antibodies (mAbs), ipilimumab (MDX-010) and Tremelimumab (also known as CP-675206), have been investigated in clinical trials in the treatment of various types of solid tumors.

The tumor necrosis factor (TNF) superfamily is a group of cytokines that engage specific cognate cell surface receptors, the TNF receptor (TNFR) superfamily. Members of the tumor necrosis factor superfamily act through ligand-mediated trimerization, causing recruitment of several intracellular adaptors to activate multiple signal transduction pathways, such as apoptosis, NF-kB pathway, JNK pathway, as well as immune and inflammatory responses. Examples of the TNF superfamily include CD40 ligands, OX40 ligands, 4-1BB ligands, CD27, CD30 ligand (CD153), TNF- alpha, TNF- beta, RANK ligands, LT- alpha, LT- beta, GITR ligands, and LIGHT. The TNFR superfamily includes, for example, CD40, OX40, 4-1BB, CD70 (CD27 ligand), CD30, TNFR2, RANK, LT- beta R, HVEM, GITR, TROY, and RELT. Among the TNF members, CD40 agonists, including various CD40 agonistic antibodies, such as the fully human agonist CD40 monoclonal antibody CP870893, have been extensively explored for usage in therapies.

Protein kinases are a family of enzymes that catalyze the phosphorylation of specific residues in proteins. A number of kinase inhibitors have been investigated in clinical investigation for use in anti-cancer therapies, which includes, for example, MK0457, VX-680, ZD6474, MLN8054, AZD2171, SNS-032, PTK787/ZK222584, Sorafenib (BAY43-9006), SU5416, SU6668 AMG706, Zactima (ZD6474), MP-412, Dasatinib, CEP-701, (Lestaurtinib), XL647, XL999, Tykerb, (Lapatinib), MLN518, (formerly known as CT53518), PKC412, ST1571, AMN107, AEE 788, OSI-930, OSI-817, Sunitinib malate (Sutent; SU11248), Vatalanib (PTK787/ZK 222584), SNS-032, SNS-314 and Axitinib (AG-013736). Gefitinib and Erlotinib are two orally available EGFR-TKIs.

SUMMARY OF THE INVENTION

The present disclosure relates to vectors constructed from chimpanzee adenovirus ChAd68 genomic sequences for expression of two or more immunogenic PAA polypeptides. The vector comprises (1) a C68 DNA sequence, (2) a multi-antigen construct for expression of two or more immunogenic PAA polypeptides, and (3) regulatory sequences that control the transcription and translation of the antigen products (i.e., the immunogenic PAA polypeptides). The C68 DNA sequence included in the vector is derived from C68 genomic sequence by functional deletion of one or more viral genes but is sufficient for production of an infectious viral particle. In a particular embodiment, the C68 DNA sequence used in the vector is the entire C68 genome with only functional deletions in the E1 and E3 regions.

The multi-antigen construct carried by the vector comprises nucleotide sequences encoding two or more immunogenic PAA polypeptides selected from immunogenic PSMA polypeptide, immunogenic PSA polypeptide, and immunogenic PSCA polypeptide. In some embodiments, the multi-antigen construct carried by the vector comprises (1) a nucleotide sequence encoding at least one immunogenic PSMA polypeptide, (2) a nucleotide sequence encoding at least one immunogenic PSA polypeptide, and (3) a nucleotide sequence encoding at least one immunogenic PSCA polypeptide. The multi-antigen constructs may also include separator sequences that enable expression of separate PAA polypeptides encoded by the construct. Examples of separator sequences include 2A peptide sequences and IRESs. In some embodiments, the vector comprises a multi-antigen construct having one of the following structures:

(1) PSA-F2A-PSMA-mIRES-PSCA;
(2) PSA-F2A-PSMA-T2A-PSCA;
(3) PSA-T2A-PSCA-F2A-PSMA; and
(4) PSCA-F2A-PSMA-mIRES-PSA.

In some embodiments, the nucleotide sequence encoding the immunogenic PSA polypeptide comprises nucleotides 1115-1825 of SEQ ID NO:58 or comprises nucleotides 1106-1825 of SEQ ID NO:58, the nucleotide sequence encoding the immunogenic PSCA polypeptide comprises nucleotides 1892-2257 of SEQ ID NO:58 or comprises nucleotides 1886-2257 of SEQ ID NO:58, and the nucleotide sequence encoding the immunogenic PSMA polypeptide comprises nucleotides 2333-4543 of SEQ ID NO:58 or comprises nucleotides 2324-4543 of SEQ ID NO:58. In some specific embodiments, the multi-antigen construct comprises nucleotide sequence selected from the group consisting of SEQ ID NOs:33, 34, 35, and 36. In a particular embodiment, the multi-antigen construct comprises a nucleotide sequence that encodes a polypeptide sequence of SEQ ID NO:60. In another particular embodiment, the multi-antigen construct comprises a nucleotide sequence of SEQ ID NO:61.

The present disclosure also provides compositions comprising the vectors. In some embodiments, the composition is an immunogenic composition useful for eliciting an immune response against a PAA in a mammal, such as a mouse, dog, monkey, or human. In some embodiments, the composition is a vaccine composition useful for immunization of a mammal, such as a human, for inhibiting abnormal cell proliferation, for providing protection against the development of cancer (used as a prophylactic), or for treatment of disorders (used as a therapeutic) associated with PAA over-expression, such as cancer, particularly prostate cancer.

The present disclosure further relates to methods of using the vectors or compositions for eliciting an immune response against a PAA, or for treating cancers, such as prostate cancers, in a mammal, particularly a human. In some embodiments, the vectors or compositions, including vaccine compositions, are administered to the mammal, particularly human, in combination with one or more immune modulators that enhance the immunogenicity or effect of the vectors or compositions. In some particular embodiments, the method involves co-administration of a vaccine provided by the present invention in combination with at least one immune-suppressive-cell inhibitor and at least one immune-effector-cell enhancer.

BRIEF DESCRIPTION OF THE DRAWINGS

FIG. 2. Amino acid alignment of five viral 2A cassettes (FMDV 2A, ERAV 2A, PTV 2A, EMCV 2A, and TAV 2A). The skipped glycine-proline bonds are indicated by asterisks. The amino acid sequence of FMDV 2A, ERAV 2A, PTV 2A, EMCV 2A, and TAV 2A is set forth in SEQ ID NOs: 67, 68, 69, 70, and 74, respectively.

FIG. 3. Sequence of the preferred EMCV IRES (SEQ ID NO:290). The translation initiation site is indicated by the asterisk. The minimal IRES element excludes the underlined first 5 codons of the EMCV L protein.

DETAILED DESCRIPTION OF THE INVENTION

Figure 1:
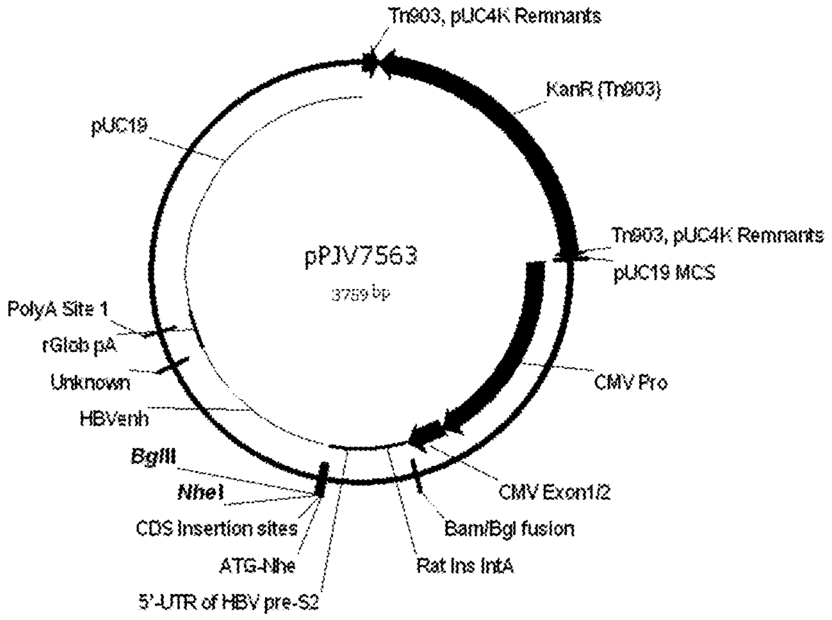
FIG. 1. Schematic illustration of PJV7563 vector.

A. DEFINITIONS The term "adjuvant" refers to a substance that is capable of enhancing, accelerating, or prolonging an immune response elicited by a vaccine immunogen.

The term "agonist" refers to a substance which promotes (induces, causes, enhances or increases) the activity of another molecule or a receptor. The term agonist encompasses substances which bind receptor (e.g., an antibody, a homolog of a natural ligand from another species) and substances which promote receptor function without binding thereto (e.g., by activating an associated protein).

The term "antagonist" or "inhibitor" refers to a substance that partially or fully blocks, inhibits, or neutralizes a biological activity of another molecule or receptor.

The term "co-administration" refers to administration of two or more agents to the same subject during a treatment period. The two or more agents may be encompassed in a single formulation and thus be administered simultaneously. Alternatively, the two or more agents may be in separate physical formulations and administered separately, either sequentially or simultaneously, to the subject. The term "administered simultaneously" or "simultaneous administration" means that the administration of the first agent and that of a second agent overlap in time with each other, while the term "administered sequentially" or "sequential administration" means that the administration of the first agent and that of a second agent does not overlap in time with each other. The term "cytosolic" means that, after a nucleotide sequence encoding a particular polypeptide is expressed by a host cell, the expressed polypeptide is retained inside the host cell.

The terms "degenerate variant" refers to a nucleotide, sequence that has substitutions of bases as compared to a reference nucleotide sequence but, due to degeneracy of the genetic code, encodes the same amino acid sequence as the reference nucleotide sequence.

The term "effective amount" refers to an amount administered to a mammal that is sufficient to cause a desired effect in the mammal.

The term "fragment" of a given polypeptide refers to a polypeptide that is shorter than the given polypeptide and shares 100% identity with the sequence of the given polypeptide.

The term "identical" or percent "identity," in the context of two or more nucleic acid or polypeptide sequences, refers to two or more sequences or subsequences that are the same or have a specified percentage of amino acid residues or nucleotides that are the same, when compared and aligned for maximum correspondence.

The term "immune-effector-cell enhancer" or "IEC enhancer" refers to a substance capable of increasing or enhancing the number, quality, or function of one or more types of immune effector cells of a mammal. Examples of immune effector cells include cytolytic CD8 T cells, CD40 T cells, NK cells, and B cells.

The term "immune modulator" refers to a substance capable of altering (e.g., inhibiting, decreasing, increasing, enhancing or stimulating) the working of any component of the innate, humoral or cellular immune system of a mammal. Thus, the term "immune modulator" encompasses the "immune-effector-cell enhancer" as defined herein and the "immune-suppressive-cell inhibitor" as defined herein, as well as substance that affects other components of the immune system of a mammal.

The term "immune response" refers to any detectable response to a particular substance (such as an antigen or immunogen) by the immune system of a host vertebrate animal, including, but not limited to, innate immune responses (e.g., activation of Toll receptor signaling cascade), cell-mediated immune responses (e.g., responses mediated by T cells, such as antigen-specific T cells, and non-specific cells of the immune system), and humoral immune responses (e.g., responses mediated by B cells, such as generation and secretion of antibodies into the plasma, lymph, and/or tissue fluids). Examples of immune responses include an alteration (e.g., increase) in Toll-like receptor activation, lymphokine (e.g., cytokine (e.g., Th1, Th2 or Th17 type cytokines) or chemokine) expression or secretion, macrophage activation, dendritic cell activation, T cell (e.g., CD4+ or CD8+ T cell) activation, NK cell activation, B cell activation (e.g., antibody generation and/or secretion), binding of an immunogen (e.g., antigen (e.g., immunogenic polypolypeptide)) to an MHC molecule, induction of a cytotoxic T lymphocyte ("CTL") response, induction of a B cell response (e.g., antibody production), and, expansion (e.g., growth of a population of cells) of cells of the immune system (e.g., T cells and B cells), and increased processing and presentation of antigen by antigen presenting cells. The term "immune response" also encompasses any detectable response to a particular substance (such as an antigen or immunogen) by one or more components of the immune system of a vertebrate animal in vitro.

The term "immunogenic" refers to the ability of a substance to cause, elicit, stimulate, or induce an immune response, or to improve, enhance, increase or prolong a pre-existing immune response, against a particular antigen, whether alone or when linked to a carrier, in the presence or absence of an adjuvant.

The term "immunogenic PSA polypeptide" refers to a polypeptide that is immunogenic against human PSA protein or against cells expressing human PSA protein.

The term "immunogenic PSCA polypeptide" refers to a polypeptide that is immunogenic against human PSCA protein or against cells expressing human PSCA protein.

The term "immunogenic PSMA polypeptide" refers to a polypeptide that is immunogenic against human PSMA protein or against cells expressing human PSMA protein.

The term "immunogenic PAA polypeptide" refers to an "immunogenic PSA polypeptide," an "immunogenic PSCA polypeptide," or an "immunogenic PSMA polypeptide" as defined herein above.

The term "immune-suppressive-cell inhibitor" or "ISC inhibitor" refers to a substance capable of reducing or suppressing the number or function of immune suppressive cells of a mammal. Examples of immune suppressive cells include regulatory T cells ("T regs"), myeloid-derived suppressor cells, and tumor-associated macrophages.

The term "intradermal administration," or "administered intradermally," in the context of administering a substance, such as a therapeutic agent or an immune modulator, to a mammal including a human, refers to the delivery of the substance into the dermis layer of the skin of the mammal. The skin of a mammal is composed of three layers-the epidermis, dermis, and subcutaneous layer. The epidermis is the relatively thin, tough, outer layer of the skin. Most of the cells in the epidermis are keratinocytes. The dermis, the skin's next layer, is a thick layer of fibrous and elastic tissue (made mostly of collagen, elastin, and fibrillin) that gives the skin its flexibility and strength. The dermis contains nerve endings, sweat glands and oil (sebaceous) glands, hair follicles, and blood vessels. The dermis varies in thickness depending on the location of the skin. In humans it is about 0.3 mm on the eyelid and about 3.0 mm on the back. The subcutaneous layer is made up of fat and connective tissue that houses larger blood vessels and nerves. The thickness of this layer varies throughout the body and from person to person. The term "intradermal administration" refers to delivery of a substance to the inside of the dermis layer. In contrast, "subcutaneous administration" refers to the administration of a substance into the subcutaneous layer and "topical administration" refers to the administration of a substance onto the surface of the skin.

The term "local administration" or "administered locally" encompasses "topical administration," "intradermal administration," and "subcutaneous administration," each as defined herein above. This term also encompasses "intratumoral administration": which refers to administration of a substance to the inside of a tumor. Local administration is intended to allow for high local concentrations around the site of administration for a period of time until systemic biodistribution has been achieved with of the administered substance, while "systemic administration" is intended for the administered substance to be absorbed into the blood and attain systemic exposure rapidly by being distributed through the circulatory system to organs or tissues throughout the body.

The term "mammal" refers to any animal species of the Mammalia class. Examples of mammals include: humans; non-human primates such as monkeys; laboratory animals such as rats, mice, guinea pigs; domestic animals such as cats, dogs, rabbits, cattle, sheep, goats, horses, and pigs; and captive wild animals such as lions, tigers, elephants, and the like.

The term "membrane-bound" means that after a nucleotide sequence encoding a particular polypeptide is expressed by a host cell, the expressed polypeptide is bound to, attached to, or otherwise associated with, the membrane of the cell.

The term "neoplastic disorder" refers to a condition in which cells proliferate at an abnormally high and uncontrolled rate, the rate exceeding and uncoordinated with that of the surrounding normal tissues. It usually results in a solid lesion or lump known as "tumor." This term encompasses benign and malignant neoplastic disorders. The term "malignant neoplastic disorder", which is used interchangeably with the term "cancer" in the present disclosure, refers to a neoplastic disorder characterized by the ability of the tumor cells to spread to other locations in the body (known as "metastasis"). The term "benign neoplastic disorder" refers to a neoplastic disorder in which the tumor cells lack the ability to metastasize.

The term "operably linked" refers to a juxtaposition wherein the components so described are in a relationship permitting them to function in their intended manner. A control sequence "operably linked" to a transgene is ligated in such a way that expression of the transgene is achieved under conditions compatible with the control sequences.

The term "pharmaceutically acceptable excipient" refers to a substance in an immunogenic or vaccine composition, other than the active ingredients (e.g., the antigen, antigen-coding nucleic acid, immune modulator, or adjuvant) that is compatible with the active ingredients and does not cause significant untoward effect in subjects to whom it is administered.

The terms "peptide," "polypeptide," and "protein" are used interchangeably herein, and refer to a polymeric form of amino acids of any length, which can include coded and non-coded amino acids, chemically, or biochemically modified or derivatized amino acids, and polypeptides having modified polypeptide backbones.

The term "preventing" or "prevent" refers to (a) keeping a disorder from occurring or (b) delaying the onset of a disorder or onset of symptoms of a disorder.

The term "prostate-associated-antigen" (or PAA) refers to the TAA (as defined herein) that is specifically expressed on prostate tumor cells or expressed at a higher frequency or density by tumor cells than by non-tumor cells of the same tissue type. Examples of PAA include PSA, PSCA, and PSMA.

The term "secreted" in the context of a polypeptide means that after a nucleotide sequence encoding the polypeptide is expressed by a host cell, the expressed polypeptide is secreted outside of the host cell.

The term "suboptimal dose" when used to describe the amount of an immune modulator, such as a protein kinase inhibitor, refers to a dose of the immune modulator that is below the minimum amount required to produce the desired therapeutic effect for the disease being treated when the immune modulator is administered alone to a patient.

The term "treating," "treatment," or "treat" refers to abrogating a disorder, reducing the severity of a disorder, or reducing the severity or occurrence frequency of a symptom of a disorder.

The term "tumor-associated antigen" or "TAA" refers to an antigen which is specifically expressed by tumor cells or expressed at a higher frequency or density by tumor cells than by non-tumor cells of the same tissue type. Tumor-associated antigens may be antigens not normally expressed by the host; they may be mutated, truncated, misfolded, or otherwise abnormal manifestations of molecules normally expressed by the host; they may be identical to molecules normally expressed but expressed at abnormally high levels; or they may be expressed in a context or milieu that is abnormal. Tumor-associated antigens may be, for example, proteins or protein fragments, complex carbohydrates, gangliosides, haptens, nucleic acids, or any combination of these or other biological molecules.

The term "vaccine" refers to an immunogenic composition for administration to a mammal for eliciting an immune response against a particular antigen.

The term "vector" refers to a nucleic acid molecule capable of transporting or transferring a foreign nucleic acid molecule. The foreign nucleic acid molecule is referred to as "insert" or "transgene." A vector generally consists of an insert and a larger sequence that serves as the backbone of the vector. The term "vector" encompasses both expression vectors and transcription vectors. The term "expression vector" refers to a vector capable of expressing the insert in the target cell. It generally contains control sequences, such as enhancer, promoter, and terminator sequences, that drive expression of the insert. The term "transcription vector" refers to a vector capable of being transcribed but not translated. Transcription vectors are used to amplify their insert. Based on the structure or origin of vectors, major types of vectors include plasmid vectors, cosmid vectors, phage vectors such as lambda phage, viral vectors such as adenovirus (Ad) vectors, and artificial chromosomes.

B. VECTORS CONTAINING A MULTI-ANTIGEN CONSTRUCT In one aspect, the present disclosure provides a voral vector constructed from the genome of chimpanzee adenovirus ChAd68 for expression of two or more immunogenic PAA polypeptides. Chimpanzee adenovirus ChAd68 is also referred in the literature as simian adenovirus 25, C68, Chad68, SAdV25, PanAd9, or Pan9. For convenience, the chimpanzee adenovirus ChAd68 may be referred to in this specification as "C68" and the viral vector constructed from the genome of chimpanzee adenovirus ChAd68 is referred to as "C68 vector." The full length genomic sequence of C68 is available from Genbank (Accession Number AC_000011.1) and is provided in SEQ ID NO:57. In addition, the full length genomic sequence of C68 and location of the adenovirus genes E1a, E1b, E2a, E2b, E3, E4, 11, 12, L3, L4, and L5 are also provided in U.S. Pat. No. 6,083,716.

The C68 vector provided by the present disclosure comprises (1) a C68 DNA sequence, and (2) a multi-antigen construct for expression of two or more immunogenic PAA polypeptides. The vector may also contain non-native regulatory sequences that control the transcription and translation of the antigen products. The non-native regulatory sequences refer to sequences that are not part of the C68 genome. The C68 DNA sequence, multi-antigen construct, and regulatory sequences are operably linked to each other.

The C68 vector can be replication-competent, conditionally replication-competent, or replication-deficient. A replication-competent C68 vector can replicate in typical host cells, i.e., cells typically capable of being infected by an adenovirus. A replication-competent viral vector can have one or more mutations as compared to the wild-type adenovirus (e.g., one or more deletions, insertions, and/or substitutions) in the adenoviral genome that do not inhibit viral replication in host cells. A conditionally-replicating C68 vector is viral vector that has been engineered to replicate under pre-determined conditions. For example, replication-essential gene functions, e.g., gene functions encoded by the adenoviral early regions, can be operably linked to an inducible, repressible, or tissue-specific transcription control sequence, e.g., promoter. A replication-deficient C68 vector is a viral vector that requires complementation of one or more gene functions or regions of the viral genome that are required for replication, as a result of, for example, a deficiency in one or more replication-essential gene function or regions, such that the vector does not replicate in typical host cells, especially those in a human to be infected by the vector.

The vectors are useful for cloning or expressing the immunogenic PAA polypeptides, or for delivering the multi-antigen construct in a composition, such as a vaccine, to a host cell or to a host animal, such as a human. In some particular embodiments, the present disclosure provides a vector selected from the group consisting of (i) a vector comprising or consisting of the nucleotide sequence of SEQ ID NO:58; (ii) a vector comprising or consisting of nucleotides 9—34811 of SEQ ID NO:58; and (iii) a vector comprising or consisting of the nucleotide sequence of SEQ ID NO:63.

The C68 vector provided by the present disclosure also encompasses functional variants of the vectors specifically described or exemplified in the present disclosure. A "functional variant" refers a vector that contains mutations (e.g., additions, deletions, or substitutions) relative to the sequence of a vector ("parent vector") specifically described or exemplified in the present disclosure but retains the function or property of the parent vector. For example, functional variant may comprise codon-optimized sequence corresponding to a parent vector exemplified in the present disclosure.

B1. The C68 DNA Sequence

The term "C68 DNA sequence" refers to a DNA sequence that is part of the C68 genomic sequence. The C68 DNA sequence included in the vector is derived from C68 genomic sequence by functional deletion of one or more viral genes or genomic regions. The term "functional deletion" means that a sufficient amount of the gene region of the virus is removed or otherwise changed, e.g., by mutation or modification, so that the gene region is no longer capable of producing functional products of gene expression or is otherwise performing its normal function. Deletion of an entire gene region often is not required for disruption of a replication-essential gene function. However, for the purpose of providing sufficient space in the C68 genome for one or more transgenes, removal of a majority of one or more gene regions may be desirable. While deletion of genetic material is preferred, mutation of genetic material by addition or substitution also is appropriate for disrupting gene function.

In some embodiments, the C68 DNA sequence of the vector is derived from the C68 genomic sequence by functionally deleting the entire, or a sufficient portion of, the adenoviral immediate early gene E1a and delayed early gene E1 b. In other embodiments, in addition to the functional deletion of E1a and E1 b, functional deletion may also be made to one or more other genes, such as the delayed early gene E2a, delayed early gene E3, E4, any of the late genes L1 through L5, the intermediate genes IX, and IVa2. Thus, the C68 DNA sequence for use in the construction of the vector of the invention may contain deletions in E1 only. Alternatively, deletions of entire genes or portions thereof effective to destroy their biological activity may be used in any combination. For example, in one exemplary vector, the C68 DNA sequence is derived from the C68 genomic sequence by functional deletions of the E1 genes and the E4 gene, or of the E1, E2a and E3 genes, or of the E1 and E3 genes, or of E1, E2a and E4 genes, with or without deletion of E3, and so on. In addition, such deletions may be used in combination with other mutations, such as temperature-sensitive mutations, to achieve a desired result. In a particular embodiment, the C68 DNA sequence is the entire C68 genome with only functional deletions in the E1 and E3 regions.

In some particular embodiments, the functional deletion of E1 gene is accomplished by deletion of nucleotides 577-3403 of SEQ ID NO:57 or by deletion of nucleotides 456-3012 of SEQ ID NO:57, and the functional deletion of E3 gene is accomplished by deletion of nucleotides 27125-31831 of SEQ ID NO:57 or by deletion of nucleotides 27812-31330 of SEQ ID NO:57. In other particular embodiments, the C68 DNA sequence included in the vector comprises nucleodtides 3013-27811 of SEQ ID NO:57. In still other particular embodiments, the C68 DNA sequence included in the vector comprises nucleodtides 3013-27811 and 31331-36519 of SEQ ID NO:57.

The multi-antigen construct may be inserted into any deleted region of the adenovirus genome. The multi-antigen construct may also be inserted into an existing gene region to disrupt the function of that region. In some embodiments, the multi-antigen construct is inserted in the place of the deleted E1 gene.

B2. The Multi-antigen Constructs

The term “multi-antigen construct” refers to a nucleic acid molecule or sequence that encodes two or more PAA polypeptides. Such molecules or sequences may also be referred to as “multi-antigen vaccine” or “multi-antigen plasmid” in the present disclosure. A multi-antigen construct can carry two coding nucleotide sequences wherein each of the coding nucleotide sequences expresses an individual immunogenic PAA polypeptide. Such a construct is also referred to as “dual antigen construct,” “dual antigen vaccine,” or “dual antigen plasmid” in this disclosure. A multi-antigen construct can also carry three coding nucleotide sequences wherein each of the coding nucleotide sequences expresses an individual immunogenic PAA polypeptide. Such a construct is also referred to as “triple antigen construct,” “triple antigen vaccine,” or “triple antigen plasmid” in this disclosure. The individual PAA polypeptides encoded by a multi-antigen construct may be immunogenic against the same antigen, such as PSMA, PSA, or PSCA. For example, a dual antigen construct may express two different PAA antigens that are both immunogenic against PSMA. The individual PAA polypeptides encoded by a multi-antigen construct may be immunogenic against different antigens, for example, a dual antigen construct may express two PAA polypeptides that are immunogenic against PSMA and PSA, respectively. It is preferred that a multi-antigen construct encodes two or more individual PAA polypeptides that are immunogenic against different antigens.

In some embodiments, the multi-antigen construct encodes at least two immunogenic PAA polypeptides in any one of the following combinations:

1) an immunogenic PSMA polypeptide and an immunogenic PSA polypeptide;

2) an immunogenic PSMA polypeptide and an immunogenic PSCA polypeptide; and 3) an immunogenic PSA polypeptide and an immunogenic PSCA polypeptide.

In some particular embodiments, the multi-antigen construct encodes at least one immunogenic PSMA polypeptide, at least one immunogenic PSA polypeptide, and at least one immunogenic PSCA polypeptide.

The immunogenic PSMA polypeptide expressed by a multi-antigen construct may be cytosolic, secreted, or membrane-bound, but preferably membrane-bound. In some embodiments, the immunogenic PSMA polypeptide comprises an amino acid sequence selected from the group consisting of:

1) the amino acid sequence of SEQ ID NO:1,
2) amino acids 15-750 of SEQ ID NO:1;
3) the amino acid sequence of SEQ ID NO:3;
4) the amino acid sequence of SEQ ID NO:5;
5) the amino acid sequence of SEQ ID NO:7;
6) amino acids 4-739 of SEQ ID NO:3;
7) amino acids 4-739 of SEQ ID NO:5;
8) amino acids 4-739 of SEQ ID NO:7;
9) the amino acid sequence of SEQ ID NO:9; and
10) amino acids 4-739 of SEQ ID NO:9.

The immunogenic PSA polypeptide expressed by a multi-antigen construct may be cytosolic, secreted, or membrane-bound, but preferably cytosolic. In some embodiments, the immunogenic PSA polypeptide comprises an amino acid sequence selected from the group consisting of:

1) amino acids 27-263 of SEQ ID NO: 15;
2) the amino acid sequence of SEQ ID NO:17; and
3) amino acids 4-240 of SEQ ID NO:17.

The immunogenic PSCA polypeptide expressed by a multi-antigen construct may be the full length human PSCA protein. In some embodiments, the immunogenic PSCA polypeptide comprises an amino acid sequence selected from the group consisting of:

1) the amino acid sequence of SEQ ID NO:21;
2) amino acids 2-125 of SEQ ID NO;21; and
3) amino acids 4-125 of SEQ ID NO:21.

In some other embodiments, the multi-antigen construct encodes at least one immunogenic PSA polypeptide, at least one immunogenic PSCA polypeptide, and at least one immunogenic PSMA polypeptide, wherein the immunogenic PSA polypeptide comprises the amino acid sequence of SEQ ID NO:17 or amino acids 4-240 of SEQ ID NO:17, wherein the immunogenic PSCA polypeptide comprises the amino acid sequence of SEQ ID NO:21 or amino acids 2-125 of SEQ ID NO:21, and wherein the immunogenic PSMA polypeptide comprises an amino acid sequence selected from the group consisting of:

1) amino acids 15-750 of SEQ ID NO: 1;
2) amino acids 4-739 of SEQ ID NO:9; and
3) the amino acid sequence of SEQ ID NO: 9.

In some particular embodiments, the multi-antigen construct comprises a nucleotide sequence that encodes the amino acid sequence of SEQ ID NO:60 or 64.

In some particular embodiments, the multi-antigen construct comprises: (i) a nucleotide sequence encoding an immunogenic PSA polypeptide, (ii) a nucleotide sequence encoding an immunogenic PSCA polypeptide, and (iii) a nucleotide sequence encoding an immunogenic PSMA polypeptide, wherein:

(1) the nucleotide sequence encoding the immunogenic PSA polypeptide is selected from the group consisting of: (i) nucleotide sequence of SEQ ID NO:18; (ii) nucleotide sequence of SEQ ID NO:20; (iii) nucleotide sequence comprising nucleotides 10-720 of SEQ ID NO:18; (iv) nucleotide sequence comprising nucleotides 1115-1825 of SEQ ID NO:58 or SEQ ID NO:63; (v) nucleotide sequence comprising nucleotides 1106-1825 of SEQ ID NO:58 or SEQ ID NO:63; and (vi) a degerate variant of any of the nucleotide sequences provided in (i)-(v) above.

(2) the nucleotide sequence encoding the immunogenic PSCA polypeptide is selected from the group consisting of: (i) the nucleotide sequence of SEQ ID NO:22; (ii) a nucleotide sequence comprising nucleotides 10-375 of SEQ ID NO:22; (iii) a nucleotide sequence comprising nucleotides 1892-2257 of SEQ ID NO:58 or SEQ ID NO:63; (iv) a nucleotide sequence comprising nucleotides 1886-2257 of SEQ ID NO:58 or SEQ ID NO:63; and (v) a degerate variant of any of the nucleotide sequences provided in (i)-(iv) above; and (3) the nucleotide sequence encoding the immunogenic PSMA polypeptide is selected from the group consisting of: (i) the nucleotide sequence comprising nucleotides 43-2250 of SEQ ID NO:2; (ii) the nucleotide sequence of SEQ ID NO:4; (iii) the nucleotide sequence of SEQ ID NO:6; (iv) the nucleotide sequence of SEQ ID NO:8; (v) the nucleotide sequence of SEQ ID NO:10; (vi) a nucleotide sequence comprising nucleotides 10-2217 of SEQ ID NO:4; (vii) a nucleotide sequence comprising nucleotides 10-2217 of SEQ ID NO:6; (viii) a nucleotide sequence comprising nucleotides 10-2217 of SEQ ID NO:8; (ix) a nucleotide sequence comprising nucleotides 10-2217 of SEQ ID NO:10; (x) the nucleotide sequence comprising nucleotides 2333-4543 of SEQ ID NO:58 or SEQ ID NO:63; (xi) the nucleotide sequence comprising nucleotides 2324-4543 of SEQ ID NO:58 or SEQ ID NO:63; and (xii) a degerate variant of any of the nucleotide sequences provided in (i)-(xi) above.

In another specific embodiment, the multi-antigen construct comprises a nucleotide sequence encoding an immunogenic PSA polypeptide, a nucleotide sequence encoding an immunogenic PSCA polypeptide, and a nucleotide sequence encoding an immunogenic PSMA polypeptide, wherein: the nucleotide sequence encoding the immunogenic PSA polypeptide comprises nucleotides 1106-1825 of SEQ ID NO:58 or SEQ ID NO:63; the nucleotide sequence encoding the immunogenic PSCA polypeptide comprises nucleotides 1886-2257 of SEQ ID NO:58 or SEQ ID NO:62; and the nucleotide sequence encoding the immunogenic PSMA polypeptide comprises nucleotides 2324-4543 of SEQ ID NO:58 or SEQ ID NO:63.

In order to enable expression of separate immunogenic PAA polypeptides from a single multi-antigen construct carried by the vector, intervening sequences are included between the sequences that encode the individual immunogenic PAA polypeptides (i.e., PSA, PSCA, and PSMA polypeptides). These intervening sequences enable the separate translation of the downstream immunogenic PAA polypeptide. Such an intervening sequence is referred to as "separator sequence" in the specification. Any sequences that can be used for the co-expression of multiple polypeptides from a single vector may be used as separator sequences in the vector provided by the present disclosure. Examples of useful separator sequences includes internal ribosomal entry sites (IRESs) and 2A peptide sequences.

2A peptide and 2A peptide-like sequences, also referred to as cleavage cassettes or CHYSELs (cis-acting hydrolase elements), are approximately 20 amino acids long with a highly conserved carboxy terminal D-V/I-EXNPGP motif (FIG. 2). The sequences are rare in nature, most commonly found in viruses such as Foot-and-mouth disease virus (FMDV), Equine rhinitis A virus (ERAV), Encephalomyocarditis virus (EMCV), Porcine teschovirus (PTV), and Thosea asigna virus (TAV) (Luke, G. A., P. de Felipe, et al. (2008). "Occurrence, function and evolutionary origins of '2A-like' sequences in virus genomes." J Gen Virol 89(Pt 4): 1036-1042). With a 2A-based multi-antigen expression strategy, genes encoding multiple target antigens are linked together in a single open reading frame, separated by 2A sequences. The entire open reading frame is cloned into a vector with a single promoter and terminator. Upon delivery of the constructs to a host cell, mRNA encoding the multiple antigens is transcribed and translated as a single polyprotein. During translation of the 2A sequences, ribosomes skip the bond between the C-terminal glycine and proline. The ribosomal skipping acts like a cotranslational autocatalytic "cleavage" that releases upstream from downstream proteins. General information regarding use of various 2A peptide sequences in vectors co-expressing multiple polypeptides may be found in Andrea L. Szymczak & Darrio AA Vignali: Development of 2A peptide-based strategies in the design of multicistronic vectors. Expert Opinion Biol. Ther. (2005)5(5) 627-638, the disclosure of which is incorporated herein by reference. The incorporation of a 2A sequence between two protein antigens results in the addition of ~20 amino acids onto the C-terminus of the upstream polypeptide and 1 amino acid (proline) to the N-terminus of downstream protein. In an adaptation of this methodology, protease cleavage sites can be incorporated at the N terminus of the 2A cassette such that ubiquitous proteases will cleave the cassette from the upstream protein (Fang, J., S. Yi, et al. (2007). "An antibody delivery system for regulated expression of therapeutic levels of monoclonal antibodies in vivo." Mol Ther 15(6): 1153-1159).

Examples of specific 2A-peptide sequences that may be used in the present invention are disclosed in Andrea L. Szymczak & Darrio AA Vignali: Development of 2A peptide-based strategies in the design of multicistronic vectors. Expert Opinion Biol. Ther. (2005)5(5) 627-638, and are provided in Table 1.

TABLE 1

2A-peptide Sequences

| Virus | 2A-peptide Sequence | SEQ ID NO |
|---|---|---|
| Foot and mouse disease virus (FMDV) | VKQTLNFDLLKLAGDVESNPG | 67 |
| Equine rhinitis A virus (ERAV) | QCTNYALLKLAGDVESNPG | 68 |

TABLE 1-continued

| 2A-peptide Sequences | | |
|---|---|---|
| Virus | 2A-peptide Sequence | SEQ ID NO |
| Porcine teschovirus-1 (PTV1) | ATNF-SLLKQAGDVEENPG | 69 |
| Encephalomyocarditis virus (EMCV) | HYAGYFADLLIHDIETNPG | 70 |
| Encephalomyocarditis B variant (EMC-B) | GIFN-AHYAGYFADLLIHD IETNPG | 71 |
| Theiler murine encephalomyelitis GD7 (TME-GD7) | KAVRGYHADYYKQRLIHDV EMNPG | 72 |
| Equine rhinitis B virus (ERBV) | GATNF-SLLKLAGDVELNP G | 73 |
| *Thosea asigna* virus (TAV) | EGRGSLLTCGDVEENPG | 74 |
| *Drosophilia* C (DrosC) | AARQMLLLLSGDVETNPG | 75 |
| Cricket paralysis virus (CrPV) | FLRKRTQLLMSGDVESNPG | 76 |
| Acute bee paralysis virus (ABPV) | GSWTDILLLLSGDVETNPG | 77 |
| Infectious flacherie virus (IFV) | TRAEUEDELIRAGIESNPG | 78 |
| Porcine rotavirus | AKFQIDKILISGDVELNPG | 79 |
| Human rotavirus | SKFQIDKILISGDIELNPG | 80 |
| *T. brucei* TSR1 | SSIIRTKMLVSGDVEENPG | 81 |
| *T. cruzi* AP endonuclease | CDAQRQKLLLSGDIEQNPG | 82 |

Internal ribosomal entry sites (IRESs) are RNA elements (FIG. 3) found in the 5' untranslated regions of certain RNA molecules (Bonnal, S., C. Boutonnet, et al. (2003). "IRESdb: the Internal Ribosome Entry Site database." Nucleic Acids Res 31(1): 427-428). They attract eukaryotic ribosomes to the RNA to facilitate translation of downstream open reading frames. Unlike normal cellular 7-methyl-guanosine cap-dependent translation, IRES-mediated translation can initiate at AUG codons far within an RNA molecule. The highly efficient process can be exploited for use in multi-cistronic expression vectors (Bochkov, Y. A. and A. C. Palmenberg (2006). "Translational efficiency of EMCV IRES in bicistronic vectors is dependent upon IRES sequence and gene location." Biotechniques 41(3): 283-284, 286, 288). The RNA sequence of a preferred EMCV IRES (pIRES) is provided in FIG. 3 and SEQ ID NO:290, which has the corresponding DNA sequence of SEQ ID NO:59. The minimal EMCV IRES (mIRES) excludes the underlined first five codons of the EMCV L protein as shown in FIG. 3. Typically, two transgenes are inserted into a vector between a promoter and transcription terminator as two separate open reading frames separated by an IRES. Upon delivery of the constructs to a host cell, a single long transcript encoding both transgenes will be transcribed. The first ORF will be translated in the traditional cap-dependent manner, terminating at a stop codon upstream of the IRES. The second ORF will be translated in a cap-independent manner using the IRES. In this way, two independent proteins can be produced from a single mRNA transcribed from a vector with a single expression cassette. In some embodiments, the multi-antigen construct comprises a EMCV IRES comprising nucleotides 1-553 of SEQ ID NO:59.

Typically, only one separator sequence is needed between two immunogenic PAA polypeptide-coding sequences on a multi-antigen construct. The order of the separator sequences and the nucleotide sequences encoding the PAA polypeptides on a multi-antigen construct is shown in formula (I):PAA1-SS1-PAA2-SS2-PAA3 (I)

Wherein: (i) PAA1, PAA2, and PAA3 each is a nucleotide sequence encoding an immunogenic PSA polypeptide, a nucleotide sequence encoding immunogenic PSCA polypeptide, or a nucleotide sequence encoding immunogenic PSMA polypeptide, provided that PAA1, PAA2, and PAA3 encode different PAA polypeptides, and (ii) SS1 and SS2 are separator sequences and can be same or different.

In some embodiments, the vector comprises a multi-antigen construct of formula (I) wherein:

(i) PAA1 is a nucleotide sequence encoding an immunogenic PSA polypeptide; (ii) PAA2 is a nucleotide sequence encoding an immunogenic PSCA or PSMA polypeptide. (where PAA2 is nucleotide sequence encoding an immunogenic PSCA, then PAA3 is a nucleotide sequence encoding an immunogenic PSMA, or Vice Versa);

(iii) SS1 is a 2A-peptide sequence; and (iv) SS2 is a 2A-peptide sequence or an IRES.

In some particular embodiments, the multi-antigen construct has a structure selected from the group consisting of:

(1) PSA-F2A-PSMA-mIRES-PSCA;

(2) PSA-F2A-PSMA-T2A-PSCA;

(3) PSA-T2A-PSCA-F2A-PSMA; and (4) PSCA-F2A-PSMA-mIRES-PSA In a specific embodiment, the vector comprises a multi-antigen construct having a structure of formula (I):

PAA1-SS1-PAA2-SS2-PAA3 (I)

wherein:

(i) PAA1 is a nucleotide sequence encoding an immunogenic PSA polypeptide and comprises nucleotides 1115-1825 SEQ ID NO: 58 or comprises 1106-1114 of SEQ ID NO: 58 or 63;

(ii) PAA2 is a nucleotide sequence encoding an immunogenic PSCA polypeptide and comprises nucleotides 1892-2257 of SEQ ID NO: 58 or comprises 1886-2257 of SEQ ID NO: 58 or 63;

(iii) PAA3 is a nucleotide sequence encoding an immunogenic PSMA polypeptide and comprises nucleotides 2333-4543 SEQ ID NO: 58 or comprises 2324-4543 of SEQ ID NO: 58 or 63;

(iv) SS1 is a nucleotide sequence encoding T2A; and (v) SS2 is a nucleotide sequence encoding F2A.

The multi-antigen construct may also include a linker sequence positioned between a nucleotide sequence encoding an immunogenic PAA polypeptide (i.e, an immunogenic PSA, PSCA, or PSMA polypeptide) and a down-stream separator sequence. One example of such a linker sequence is a nucleotide sequence encoding glycine-serine.

In some particular embodiments, the multi-antigen construct comprises a nucleotide sequence that encodes an amino acid sequence of SEQ ID NO:60 or encodes an amino acid sequence of SEQ ID NO:61. In a particular embodiment, the multi-antigen construct comprises a nucleotide sequence selected from the groups consisting of nucleotide sequence of SEQ ID NO:61, nucleotide sequence of SEQ ID NO:65, nucleotide sequence of SEQ ID NO:66, and degenerate variant of any of the nucleotide sequences.

B3. Regulatory Sequences In addition to the separator sequences and linker sequences described herein above, the vector may comprise other non-native regulatory sequences to drive the efficient expression of the encoded PAA polypeptides. Examples of the regulatory sequences includes (1) transcription initiation, termination, promoter, and enhancer sequences; (2) efficient RNA processing signals such as splicing and polyadenylation signals; (3) sequences that stabilize cytoplasmic mRNA; (4) sequences that enhance translation efficiency (i.e., Kozak consensus sequence); (5) sequences that enhance protein stability; and (6) sequences that enhance protein secretion. Examples of promoter systems that can be used in the vectors provided by the present disclosure to drive efficient expression in mammalian cells include SV40 promoter, chicken B actin promoter, human elongation factor promoter, human cytomegalovirus (CMV) promoter, simian CMV promoter, murine CMV promoter, psudorabies promoter, Rous Sarcoma Virus promoter, phosphoglycerate kinase promoter, murine leukemia virus LTR promoter, avian leukosis virus LTR promoter, mouse mammary tumor virus LTR promoter, moloney murine leukemia virus LTR promoter, plasminogen activator inhibitor promoter, CYR61, adenovirus major late promoter, mouse metallothionein promoter, mouse phosphoenol-pyruvate carboxykinase promoter, bovine B-lactoglobulin promoter, bovine prolactin promoter, ubiquitin C promoter, and herpes simplex virus thymidine kinase promoter. Examples of transcription termination signals include SV40 polyadenylation (polyA); bovine growth hormone polyA; rabbit B globin polyA; HSV thymidine kinase, glycoprotein B, and glycoprotein D; HPV E and L, and synthetic terminators.

In some embodiments, the C68 vectors comprise a human cytomegalovirus (CMV) promoter, optionally with the CMV enhancer, and a SV40 polyA.

C. COMPOSITIONS COMPRISING A VECTOR CARRYING A MULTI-ANTIGEN CONSTRUCT (VECTOR COMPOSITIONS) The present disclosure also provides a composition comprising a vector provided by the present disclosure (herein "vector composition"). The vector compositions are useful for eliciting an immune response against a PAA protein in vitro or in vivo in a mammal, including a human. The vector composition may comprise the vectors alone, or may further comprise an excipient.

In some embodiments, the vector composition is a pharmaceutical composition, which comprises a vector provided by the present disclosure and a pharmaceutically acceptable excipient. Suitable excipients for pharmaceutical compositions are known in the arts. The excipients may include aqueous solutions, non aqueous solutions, suspensions, and emulsions. Examples of non-aqueous excipients include propylene glycol, polyethylene glycol, vegetable oils such as olive oil, and injectable organic esters such as ethyl oleate. Examples of aqueous excipient include water, alcoholic/aqueous solutions, emulsions or suspensions, including saline and buffered media. Suitable excipients also include agents that assist in cellular uptake of the vector.

In some embodiments, the pharmaceutical composition is a vaccine composition for administration to humans for inhibiting abnormal cell proliferation, providing protection against the development of cancer (used as a prophylactic), or for treatment of cancer (used as a therapeutic) associated with a PAA over—expression, or for eliciting an immune response to a particular human PAA, such as PSMA, PSA, and PSCA. The vaccine composition may further comprise one or more adjuvants. Examples of adjuvants that may be included in the vaccine compositions are provided herein below.

D. USES OF THE VECTORS AND VECTOR COMPOSITIONS In other aspects, the present disclosure provides methods of using the vector or composition comprising the vectors described herein above.

In one aspect, the present disclosure provides a method of eliciting an immune response against a PAA in a mammal, particularly a human, comprising administering to the mammal an effective amount of (1) a vector containing a multi-antigen construct, or (2) a composition comprising such vectors.

In another aspect, the present disclosure provides a method of inhibiting abnormal cell proliferation in a human, wherein the abnormal cell proliferation is associated with over-expression of a PAA. The method comprises administering to the mammal an effective amount of (1) a vector containing a multi-antigen construct encoding two or more immunogenic PAA polypeptides, or (2) a composition comprising such vectors. In some embodiments, the method is for inhibiting abnormal cell proliferation in prostate in a human. In a particular embodiment, the present disclosure provides a method of inhibiting abnormal cell proliferation in prostate over-expressing PSMA. In some embodiments, the disclosure provides a method of treating prostate cancer in a human, comprising administering to the human an effective amount of a (1) a vector containing a multi-antigen construct or (2) a composition comprising such vectors. In a preferred embodiment, the multi-antigen construct is a triple antigen construct that encodes an immunogenic PSMA polypeptide, an immunogenic PSA polypeptide, and an immunogenic PSCA polypeptide.

The vectors or vector compositions can be administered to an animal, including human, by a number of methods known in the art. Examples of suitable methods include: (1) intramuscular, intradermal, intraepidermal, intravenous, intraarterial, subcutaneous, or intraperitoneal administration, (2) oral administration, and (3) topical application (such as ocular, intranasal, and intravaginal application). One particular method of intradermal or intraepidermal administration of a nucleic acid vaccine composition involves the use of gene gun delivery technology, such the Particle Mediated Epidermal Delivery (PMED™) vaccine delivery device marketed by PowderMed. Another particular method for intramuscular administration of a nucleic acid vaccine is injection followed by electroporation.

The effective amount of the vector or vector composition to be administered in a given method can be readily determined by a person skilled in the art and will depend on a number of factors. In a method of treating cancer, such as prostate cancer, factors that may be considered in determining the effective amount include, but not limited: (1) the subject to be treated, including the subject's immune status and health, (2) the severity or stage of the cancer to be treated, (3) the specific immunogenic PAA polypeptides expressed, (4) the degree of protection or treatment desired, (5) the administration method and schedule, (6) formulations used, and (7) co-administration of other therapeutic agents (such as adjuvants or immune modulators). For example, the effective amounts of the vector may be in the range of 2 μg/dose-10 mg/dose when the nucleic acid vaccine composition is formulated as an aqueous solution and administered by hypodermic needle injection or pneumatic injection, whereas only 16 ng/dose-16 μg/dose may be required when the nucleic acid is prepared as coated gold beads and delivered using a gene gun technology.

The vectors or vector compositions, including vaccine compositions, provided by the present disclosure may be used together with one or more adjuvants. Examples of suitable adjuvants include: (1) oil-in-water emulsion formulations (with or without other specific immunostimulating agents such as muramyl polypeptides or bacterial cell wall components), such as MF59™ (containing 5% Squalene, 0.5% Tween 80, and 0.5% sorbitan trioleate) and SAF (containing 10% Squalene, 0.4% Tween 80, 5% pluronic-blocked polymer L121, and thr-MDP); (2) saponin adjuvants, such as QS21, STIMULON™ (Cambridge Bioscience, Worcester, Mass.), Abisco® (Isconova, Sweden), or Iscomatrix® (Commonwealth Serum Laboratories, Australia); (3) complete Freund's Adjuvant (CFA) and incomplete Freund's Adjuvant (IFA); (4) oligonucleotides comprising CpG motifs, i.e. containing at least one CG dinucleotide, where the cytosine is unmethylated (e.g., Krieg, Vaccine (2000) 19:618-622; Krieg, *Curr Opin Mol Ther* (2001) 3:15-24; WO 98/40100, WO 98/55495, WO 98/37919 and WO 98/52581); and (5) metal salt including aluminum salts (such as alum, aluminum phosphate, aluminum hydroxide); (12) a saponin and an oil-in-water emulsion (e.g. WO 99/11241).

The vectors or vector compositions provided by the present disclosure may be used together with one or more immune modulators. In a further aspect, the present disclosure provides a method of treating prostate cancer in a mammal, particularly a human, the method comprising administering to the mammal: (1) an effective amount of a vector, vector composition, or vaccine provided by the present invention; (2) an effective amount of at least one immune-suppressive-cell inhibitor (ISC inhibitor); and (3) an effective amount of at least one immune-effector-cell enhancer (IEC enhancer). This method is also referred to as "vaccine-based immunotherapy regimen" (or "VBIR") in the present disclosure.

The IEC enhancers and ISC inhibitors may be administered by any suitable methods and routes, including (1) systemic administration such as intravenous, intramuscular, or oral administration, and (2) local administration such intradermal and subcutaneous administration. Where appropriate or suitable, local administration is generally preferred over systemic administration. Local administration of any IEC enhancer and ISC inhibitor can be carried out at any location of the body of the mammal that is suitable for local administration of pharmaceuticals; however, it is more preferable that these immune modulators are administered locally at close proximity to the vaccine draining lymph node.

Two or more specific IEC enhancers from a single class of IEC enhancers (for examples, two CTLA-antagonists) may be administered in combination with the ISC inhibitors. In addition, two or more specific IEC enhancers from two or more different classes of IEC enhancers (for example, one CTLA-4 antagonist and one TLR agonist, or one CTLA-4 antagonist and one PD-1 antagonist) may be administered together. Similarly, two or more specific ISC inhibitors from a single class of ISC inhibitors (for examples, two or more protein kinase inhibitors) may be administered in combination with the IEC enhancers. In addition, two or more specific ISC inhibitors from two or more different classes of ISC inhibitors (for example, one protein kinase inhibitor and one COX-2 inhibitor) may be administered together.

The vectors or vector compositions may be administered simultaneously or sequentially with any or all of the immune modulators (i.e., ISC inhibitors and IEC enhancers) used. Similarly, when two or more immune modulators are used, they may be administered simultaneously or sequentially with respect to each other. In some embodiments, a vector or vector composition is administered simultaneously (e.g., in a mixture) with respect to one immune modulator, but sequentially with respect to one or more additional immune modulators. Co-administration of the vector or vector composition and the immune modulators can include cases in which the vaccine and at least one immune modulator are administered so that each is present at the administration site, such as vaccine draining lymph node, at the same time, even though the antigen and the immune modulators are not administered simultaneously. Co-administration of the vaccine and the immune modulators also can include cases in which the vaccine or the immune modulator is cleared from the administration site, but at least one cellular effect of the cleared vaccine or immune modulator persists at the administration site, such as vaccine draining lymph node, at least until one or more additional immune modulators are administered to the administration site. In cases where a nucleic acid vaccine is administered in combination with a CpG, the vaccine and CpG may be contained in a single formulation and administered together by any suitable method. In some embodiments, the nucleic acid vaccine and CpG in a co-formulation (mixture) is administered by intramuscular injection in combination with electroporation.

Any ISC inhibitors may be used in combination with the vectors or vector compositions provided by the present invention. Examples of classes of ISC inhibitors include PD-1/PD-L1 antagonists, protein kinase inhibitors, cyclooxygenase-2 (COX-2) inhibitors, phosphodiesterase type 5 (PDES) inhibitors, and DNA crosslinkers. Examples PD-1/PD-L1 antagonists include anti-PD-1 and PD-L1 monoclonal antibodies Examples of COX-2 inhibitors include celecoxib and rofecoxib. Examples of PDES inhibitors include avanafil, lodenafil, mirodenafil, sildenafil, tadalafil, vardenafil, udenafil, and zaprinast. An example of DNA crosslinkers is cyclophosphamide. Examples of specific protein kinase inhibitors are described in details below.

The term "protein kinase inhibitor" refers to any substance that acts as a selective or non-selective inhibitor of a protein kinase. The term "protein kinases" refers to the enzymes that catalyze the transfer of the terminal phosphate of adenosine triphosphate to tyrosine, serine or threonine residues in protein substrates. Protein kinases include receptor tyrosine kinases and non-receptor tyrosine kinases. Examples of receptor tyrosine kinases include EGFR (e.g., EGFR/HER1/ErbB1, HER2/Neu/ErbB2, HER3/ErbB3, HER4/ErbB4), INSR (insulin receptor), IGF-IR, IGF-II1R, IRR (insulin receptor-related receptor), PDGFR (e.g., PDGFRA, PDGFRB), c-KIT/SCFR, VEGFR-1/FLT-1, VEGFR-2/FLK-1/KDR, VEGFR-3/FLT-4, FLT-3/FLK-2, CSF-1R, FGFR 1-4, CCK4, TRK A-C, MET, RON, EPHA 1-8, EPHB 1-6, AXL, MER, TYRO3, TIE, TEK, RYK, DDR 1-2, RET, c-ROS, LTK (leukocyte tyrosine kinase), ALK (anaplastic lymphoma kinase), ROR 1-2, MUSK, AATYK 1-3, and RTK 106. Examples of non-receptor tyrosine kinases include BCR-ABL, Src, Frk, Btk, Csk, Abl, Zap70, Fes/Fps, Fak, Jak, Ack, and LIMK. In the vaccine-based immunotherapy regimen provided by the present disclosure, the protein kinase inhibitors are administered to the mammal at a suboptimal dose. The term "suboptimal dose" refers to the dose amount that is below the minimum effective dose when the tyrosine kinase inhibitor is administered in a monotherapy (i.e., where the protein kinase inhibitor is administered alone without any other therapeutic agents) for the target neoplastic disorder.

Examples of specific protein kinase inhibitors suitable for use in the vaccine-based immunotherapy regimen include lapatinib, AZD 2171, ET18OCH 3, indirubin-3'-oxime, NSC-154020, PD 169316, quercetin, roscovitine, triciribine, ZD1839, 5-lodotubercidin, adaphostin, aloisine, alsterpaullone, aminogenistein, API-2, apigenin, arctigenin, ARRY-334543, axitinib, AY-22989, AZD 2171, Bisindolylmaleimide IX, CCI-779, chelerythrine, DMPQ, DRB, edelfosine, ENMD-981693, erbstatin analog, erlotinib, fasudil, gefitinib (ZD1839), H-7, H-8, H-89, HA-100, HA-1004, HA-1077, HA-1100, hydroxyfasudil, kenpaullone, KN-62, KY12420, LFM-A13, luteolin, LY294002, LY-294002, mallotoxin, ML-9, MLN608, NSC-226080, NSC-231634, NSC-664704, NSC-680410, NU6102, olomoucine, oxindole I, PD 153035, PD 98059, phloridzin, piceatannol, picropodophyllin, PKI, PP1, PP2, PTK787/ZK222584, PTK787/ZK-222584, purvalanol A, rapamune, rapamycin, Ro 31-8220, rottlerin, SB202190, SB203580, sirolimus, SL327, SP600125, staurosporine, STI-571, SU1498, SU4312, SU5416, semaxanib, SU6656, SU6668, syk inhibitor, TBB, TCN, tyrphostin AG 1024, tyrphostin AG 490, tyrphostin AG 825, tyrphostin AG 957, U0126, W-7, wortmannin, Y-27632, zactima, ZM 252868, gefitinib, sunitinib malate, erlotinib, lapatinib, canertinib, semaxinib, vatalanib, sorafenib, imatinib, dasatinib, leflunomide, vandetanib, and nilotinib. In some embodiments, the protein kinase inhibitor is a multi-kinase inhibitor, which is an inhibitor that acts on more than one specific kinase. Examples of multi-kinase inhibitors include imatinib, sorafenib, lapatinib, BIRB-796, and AZD-1152, AMG706, zactima, MP-412, sorafenib, dasatinib, lestaurtinib, XL647, XL999, lapatinib, MLN518, (also known as CT53518), PKC412, ST1571, AEE 788, OSI-930, OSI-817, sunitinib malate, erlotinib, gefitinib, axitinib, bosutinib, temsirolismus and nilotinib. In some particular embodiments, the tyrosine kinase inhibitor is sunitinib, sorafenib, or a pharmaceutically acceptable salt or derivative (such as a malate or a tosylate) of sunitinib or sorafenib.

Sunitinib malate, which is marketed by Pfizer Inc. under the trade name SUTENT, is described chemically as butanedioic acid, hydroxy-, (2S)—, compound with N-[2-(diethylamino)ethyl]-5-[(Z)-(5-fluoro-1,2-dihydro-2-oxo-3H-indol-3-ylidine)methyl]-2,4-dimethyl-1H-pyrrole-3-carboxamide (1:1). The compound, its synthesis, and particular polymorphs are described in U.S. Pat. No. 6,573,293, U.S. Patent Publication Nos. 2003-0229229, 2003-0069298 and 2005-0059824, and in J. M. Manley, M. J. Kalman, B. G. Conway, C. C. Ball, J. L Havens and R. Vaidyanathan, "Early Amidation Approach to 3-[(4-amido) pyrrol-2-yl]-2-indolinones," J. Org. Chew. 68, 6447-6450 (2003). Formulations of sunitinib and its L-malate salt are described in PCT Publication No. WO 2004/024127. Sunitinib malate has been approved in the U.S. for the treatment of gastrointestinal stromal tumor, advanced renal cell carcinoma, and progressive, well-differentiated pancreatic neuroendocrine tumors in patients with unresectable locally advanced or metastatic disease. The recommended dose of sunitinib malate for gastrointestinal stromal tumor (GIST) and advanced renal cell carcinoma (RCC) for humans is 50 mg taken orally once daily, on a schedule of 4 weeks on treatment followed by 2 weeks off (Schedule 4/2). The recommended dose of sunitinib malate for pancreatic neuroendocrine tumors (pNET) is 37.5 mg taken orally once daily.

In the vaccine-based immunotherapy regimen, sunitinib malate may be administered orally in a single dose or multiple doses. Typically, sunitinib malate is delivered for two, three, four or more consecutive weekly doses followed by a "off" period of about 1 or 2 weeks, or more where no sunitinib malate is delivered. In one embodiment, the doses are delivered for about 4 weeks, with 2 weeks off. In another embodiment, the sunitinib malate is delivered for two weeks, with 1 week off. However, it may also be delivered without a "off" period for the entire treatment period. The effective amount of sunitinib malate administered orally to a human in the vaccine-based immunotherapy regimen is typically below 40 mg per person per dose. For example, it may be administered orally at 37.5, 31.25, 25, 18.75, 12.5, 6.25 mg per person per day. In some embodiments, sunitinib malate is administered orally in the range of 1-25 mg per person per dose. In some other embodiments, sunitinib malate is administered orally in the range of 6.25, 12.5, or 18.75 mg per person per dose. Other dosage regimens and variations are foreseeable, and will be determined through physician guidance.

Sorafenib tosylate, which is marketed under the trade name NEXAVAR, is also a multi-kinase inhibitor. Its chemical name is 4-(4-{3-[4-Chloro-3-(trifluoromethyl) phenyl] ureido}phenoxy)-N-methylpyrid-ine-2-carboxamide. It is approved in the U.S. for the treatment of primary kidney cancer (advanced renal cell carcinoma) and advanced primary liver cancer (hepatocellular carcinoma). The recommended daily dose is 400 mg taken orally twice daily. In the vaccine-based immunotherapy regimen provided by the present disclosure, the effective amount of sorafenib tosylate administered orally is typically below 400 mg per person per day. In some embodiments, the effective amount of sorafenib tosylate administered orally is in the range of 10-300 mg per person per day. In some other embodiments, the effective amount of sorafenib tosylate administered orally is between 10-200 mg per person per day, such as 10, 20, 60, 80, 100, 120, 140, 160, 180, or 200 mg per person per day.

Axitinib, which is marketed under the trade name INLYTA, is a selective inhibitor of VEGF receptors 1, 2, and 3. Its chemical name is (N-Methyl-2-[3-((E)-2-pyridin-2-yl-vinyl)-1H-indazol-6-ylsulfanyl]-benzamide. It is approved for the treatment of advanced renal cell carcinoma after failure of one prior systemic therapy. The starting dose is 5 mg orally twice daily. Dose adjustments can be made based on individual safety and tolerability. In the vaccine-based immunotherapy regimen provided by the present disclosure, the effective amount of axitinib administered orally is typically below 5 mg twice daily. In some other embodiments, the effective amount of axitinib administered orally is between 1-5 mg twice daily. In some other embodiments, the effective amount of axitinib administered orally is between 1, 2, 3, 4, or 5 mg twice daily.

In the vaccine-based immunotherapy regimens any IEC enhancers may be used. They may be small molecules or large molecules (such as protein, polypeptide, DNA, RNA, and antibody). Examples of IEC enhancers that may be used include TNFR agonists, CTLA-4 antagonists, TLR agonists, programmed cell death protein 1 (PD-1) antagonists (such as anti-PD-1 antibody CT-011), and programmed cell death protein 1 ligand 1 (PD-L1) antagonists (such as BMS-936559), lymphocyte-activation gene 3 (LAG3) antagonists, and T cell Immunoglobulin- and mucin-domain-containing molecule-3 (TIM-3) antagonists. Examples of specific TNFR agonists, CTLA-4 antagonists, and TLR agonists are provided in details herein below.

TNFR Agonists.

Examples of TNFR agonists include agonists of OX40, 4-1BB (such as BMS-663513), GITR (such as TRX518), and CD40. Examples of specific CD40 agonists are described in details herein below.

CD40 agonists are substances that bind to a CD40 receptor on a cell and are capable of increasing one or more CD40 or CD40L associated activities. Thus, CD40 "agonists" encompass CD40 "ligands".

Examples of CD40 agonists include CD40 agonistic antibodies, fragments CD40 agonistic antibodies, CD40 ligands (CD40L), and fragments and derivatives of CD40L such as oligomeric (e.g., bivalent, trimeric CD40L), fusion proteins containing and variants thereof.

CD40 ligands for use in the present invention include any peptide, polypeptide or protein, or a nucleic acid encoding a peptide, polypeptide or protein that can bind to and activate one or more CD40 receptors on a cell. Suitable CD40 ligands are described, for example, in U.S. Pat. Nos. 6,482,411; 6,410,711; 6,391,637; and 5,981,724, all of which patents and application and the CD40L sequences disclosed therein are incorporated by reference in their entirety herein. Although human CD40 ligands will be preferred for use in human therapy, CD40 ligands from any species may be used in the invention. For use in other animal species, such as in veterinary embodiments, a species of CD40 ligand matched to the animal being treated will be preferred. In certain embodiments, the CD40 ligand is a gp39 peptide or protein oligomer, including naturally forming gp39 peptide, polypeptide or protein oligomers, as well as gp39 peptides, polypeptides, proteins (and encoding nucleic acids) that comprise an oligomerization sequence. While oligomers such as dimers, trimers and tetramers are preferred in certain aspects of the invention, in other aspects of the invention larger oligomeric structures are contemplated for use, so long as the oligomeric structure retains the ability to bind to and activate one or more CD40 receptor(s).

In certain other embodiments, the CD40 agonist is an anti-CD40 antibody, or antigen-binding fragment thereof. The antibody can be a human, humanized or part-human chimeric anti-CD40 antibody. Examples of specific anti-CD40 monoclonal antibodies include the G28-5, mAb89, EA-5 or S2C6 monoclonal antibody, and CP870893. In a particular embodiment, the anti-CD40 agonist antibody is CP870893 or dacetuzumab (SGN-40).

CP-870,893 is a fully human agonistic CD40 monoclonal antibody (mAb) that has been investigated clinically as an anti-tumor therapy. The structure and preparation of CP870,893 is disclosed in WO2003041070 (where the antibody is identified by the internal identified "21.4.1"). The amino acid sequences of the heavy chain and light chain of CP-870,893 are set forth in SEQ ID NO: 40 and SEQ ID NO: 41, respectively.

In clinical trials, CP870,893 was administered by intravenous infusion at doses generally in the ranges of 0.05-0.25 mg/kg per infusion. In a phase I clinical study, the maximum tolerated dose (MTD) of CP-870893 was estimated to be 0.2 mg/kg and the dose-limiting toxicities included grade 3 CRS and grade 3 urticaria. [Jens Ruter et al.: Immune modulation with weekly dosing of an agonist CD40 antibody in a phase I study of patients with advanced solid tumors. [Cancer Biology & Therapy 10:10, 983-993; Nov. 15, 2010.]. In the vaccine-based immunotherapy regimen provided by the present disclosure, CP-870,893 can be administered intradermally, subcutaneously, or topically. It is preferred that it is administered intradermally. The effective amount of CP870893 to be administered in the regimen is generally below 0.2 mg/kg, typically in the range of 0.01 mg-0.15 mg/kg, or 0.05-0.1 mg/kg.

Dacetuzumab (also known as SGN-40 or huS2C6; CAS number 88-486-59-9) is another anti-CD40 agonist antibody that has been investigated in clinical trials for indolent lymphomas, diffuse large B cell lymphomas and Multiple Myeloma. In the clinical trials, dacetuzumab was administered intravenously at weekly doses ranging from 2 mg/kg to 16 mg/kg. In the vaccine-based immunotherapy regimen provided by the present disclosure, dacetuzumab can be administered intradermally, subcutaneously, or topically. It is preferred that it is administered intradermally. The effective amount of dacetuzumab to be administered in the vaccine-based immunotherapy regimen is generally below 16 mg/kg, typically in the range of 0.2 mg-14 mg/kg, or 0.5-8 mg/kg, or 1-5 mg/kg.

CTLA-4 Inhibitors.

Suitable anti-CTLA-4 antagonist agents for use in the vaccine-based immunotherapy regimen provided by the disclosure include, without limitation, anti-CTLA-4 antibodies (such as human anti-CTLA-4 antibodies, mouse anti-CTLA-4 antibodies, mammalian anti-CTLA-4 antibodies, humanized anti-CTLA-4 antibodies, monoclonal anti-CTLA-4 antibodies, polyclonal anti-CTLA-4 antibodies, chimeric anti-CTLA-4 antibodies, anti-CTLA-4 domain antibodies), fragments of anti-CTLA-4 antibodies (such as (single chain anti-CTLA-4 fragments, heavy chain anti-CTLA-4 fragments, and light chain anti-CTLA-4 fragments), and inhibitors of CTLA-4 that agonize the co-stimulatory pathway. In some embodiments, the CTLA-4 inhibitor is Ipilimumab or Tremelimumab.

Ipilimumab (also known as MEX-010 or MDX-101), marketed as YERVOY, is a human anti-human CTLA-4 antibody. Ipilimumab can also be referred to by its CAS Registry No. 477202-00-9, and is disclosed as antibody 10DI in PCT Publication No. WO01/14424, which is incorporated herein by reference in its entirety. Examples of pharmaceutical composition comprising Ipilimumab are provided in PCT Publication No. WO2007/67959. Ipilimumab is approved in the U.S. for the treatment of unresectable or metastatic melanoma. The recommended dose of Ipilimumab as monotherapy is 3 mg/kg by intravenous administration every 3 weeks for a total of 4 doses. In the methods provided by the present invention, Ipilimumab is administered locally, particularly intradermally or subcutaneously. The effective amount of Ipilimumab administered locally is typically in the range of 5-200 mg/dose per person. In some embodiments, the effective amount of Ipilimumab is in the range of 10-150 mg/dose per person per dose. In some particular embodiments, the effective amount of Ipilimumab is about 10, 25, 50, 75, 100, 125, 150, 175, or 200 mg/dose per person.

Tremelimumab (also known as CP-675,206) is a fully human IgG2 monoclonal antibody and has the CAS number 745013-59-6. Tremelimumab is disclosed as antibody 11.2.1 in U.S. Pat. No. 6,682,736, incorporated herein by reference in its entirety and for all purposes. The amino acid sequences of the heavy chain and light chain of Tremelimumab are set forth in SEQ IND NOs:42 and 43, respectively. Tremelimumab has been investigated in clinical trials for the treatment of various tumors, including melanoma and breast cancer; in which Tremelimumab was administered intravenously either as single dose or multiple doses every 4 or 12 weeks at the dose range of 0.01 and 15 mg/kg. In the regimens provided by the present invention, Tremelimumab is administered locally, particularly intradermally or subcutaneously. The effective amount of Tremelimumab administered intradermally or subcutaneously is typically in the range of 5-200 mg/dose per person. In some embodiments, the effective amount of Tremelimumab is in the range of 10-150 mg/dose per person per dose. In some particular embodiments, the effective amount of Tremelimumab is about 10, 25, 37.5, 40, 50, 75, 100, 125, 150, 175, or 200 mg/dose per person.

Toll-like Receptor (TLR) Agonists.

The term "toll-like receptor agonist" or "TLR agonist" refers to a compound that acts as an agonist of a toll-like receptor (TLR). This includes agonists of TLR1, TLR2, TLR3, TLR4, TLR5, TLR6, TLR7, TLR8, TLR9, TLR10, and TLR11 or a combination thereof. Unless otherwise indicated, reference to a TLR agonist compound can include the compound in any pharmaceutically acceptable form, including any isomer (e.g., diastereomer or enantiomer), salt, solvate, polymorph, and the like. In particular, if a compound is optically active, reference to the compound can include each of the compound's enantiomers as well as racemic mixtures of the enantiomers. Also, a compound may be identified as an agonist of one or more particular TLRs (e.g., a TLR7 agonist, a TLR8 agonist, or a TLR7/8 agonist).

In some embodiments, the TLR agonists are TLR9 agonists, particularly CpG oligonucleotides (or CpG.ODN). A CpG oligonucleotide is a short nucleic acid molecule containing a cytosine followed by a guanine linked by a phosphate bond in which the pyrimidine ring of the cytosine is unmethylated. A CpG motif is a pattern of bases that include an unmethylated central CpG surrounded by at least one base flanking (on the 3' and the 5' side of) the central CpG. CpG oligonucleotides include both D and K oligonucleotides. The entire CpG oligonucleotide can be unmethylated or portions may be unmethylated. Examples of CpG oligonucleotides useful in the methods provided by the present disclosure include those disclosed in U.S. Pat. Nos. 6,194,388, 6,207,646, 6,214,806, 628371, 6239116, and 6339068.

Examples of particular CpG oligonucleotides useful in the methods provided by the present disclosure include:

```
                                    (SEQ ID NO: 291)
5' TCGTCGTTTTGTCGTTTTGTCGTT3' (CpG 7909);

                                    (SEQ ID NO: 292)
5' TCGTCGTTTTTCGGTGCTTTT3' (CpG 24555);
and

                                    (SEQ ID NO: 293)
5' TCGTCGTTTTTCGGTCGTTTT3' (CpG 10103).
```

CpG7909, a synthetic 24mer single stranded oligonucleotide, has been extensively investigated for the treatment of cancer as a monotherapy and in combination with chemotherapeutic agents, as well as an adjuvant for vaccines against cancer and infectious diseases. It was reported that a single intravenous dose of CpG 7909 was well tolerated with no clinical effects and no significant toxicity up to 1.05 mg/kg, while a single dose subcutaneous CpG 7909 had a maximum tolerated dose (MTD) of 0.45 mg/kg with dose limiting toxicity of myalgia and constitutional effects. [See Zent, Clive S, et al: Phase I clinical trial of CpG 7909 (PF-03512676) in patients with previously treated chronic lymphocytic leukemia. Leukemia and Lymphoma, 53(2): 211-217(7)(2012)]. In the regimens provided by the present disclosure, CpG7909 may be administered by injection into the muscle or by any other suitable methods. It is preferred that it is administered locally in proximity to the vaccine draining lymph node, particularly by intradermal or subcutaneous administration. For use with a nucleic acid vaccine, such as a DNA vaccine, a CpG may be preferably co-formulated with the vaccine in a single formulation and administered by intramuscular injection coupled with electroporation. The effective amount of CpG7909 by intramuscular, intradermal, or subcutaneous administration is typically in the range of 10 μg/dose-10 mg/dose. In some embodiments, the effective amount of CpG7909 is in the range of 0.05 mg-14 mg/dose. In some particular embodiments, the effective amount of CpG7909 is about 0.05, 0.1, 0.2, 0.3, 0.4, 0.5, 05 1 mg/dose. Other CpG oligonucleotides, including CpG 24555 and CpG 10103, may be administered in similar manner and dose levels. In some particular embodiments, the present disclosure provides a method of enhancing the immunogenicity or therapeutic effect of a vaccine for the treatment of a neoplastic disorder in a human, comprising administering the human (1) an effective amount of at least one ISC inhibitor and (2) an effective amount of at least one IEC enhancer, wherein the at least one ISC inhibitor is protein kinase inhibitor selected from sorafenib tosylate, sunitinib malate, axitinib, erlotinib, gefitinib, axitinib, bosutinib, temsirolismus, or nilotinib and wherein the at least one IEC enhancer is selected from a CTLA-4 inhibitor, a TLR agonist, or a CD40 agonist. In some preferred embodiments, regimen comprises administering to the human (1) an effective amount of at least one ISC inhibitor and (2) effective amount of at least one IEC enhancer, wherein the at least one ISC inhibitor is a protein kinase inhibitor selected from axitinib, sorafenib tosylate, or sunitinib malate and wherein the at least one IEC enhancer is a CTLA-4 inhibitor selected from Ipilimumab or Tremelimumab. In some further preferred embodiments, the regimen comprises administering to the human (1) an effective amount of at least one ISC inhibitor and (2) an effective amount of at least two IEC enhancers, wherein the at least one ISC inhibitor is a protein kinase inhibitor selected from sunitinib or axitinib and wherein the at least two IEC enhancers are Tremelimumab and a TLR agonist selected from CpG7909, CpG2455, or CpG10103.

In some other embodiments, the present disclosure provides a method of treating prostate cancer in a human, comprising administering to the human (1) an effective amount of a vaccine capable of eliciting an immune response against a human PAA, (2) an effective amount of at least one ISC inhibitor, and (3) an effective amount of at least one IEC enhancer, wherein the at least one ISC inhibitor is a protein kinase inhibitor selected from sorafenib tosylate, sunitinib malate, axitinib, erlotinib, gefitinib, axitinib, bosutinib, temsirolismus, or nilotinib, and wherein the at least one IEC enhancer is selected from a CTLA-4 inhibitor, a TLR agonist, or a CD40 agonist. In some preferred embodiments, the method comprises administering to the human (1) an effective amount of a vaccine capable of eliciting an immune response against a human PAA, (2) an effective amount of at least one ISC inhibitor, and (3) an effective amount of at least one IEC enhancer, wherein the at least one ISC inhibitor is a protein kinase inhibitor selected from sorafenib tosylate, sunitinib malate, or axitinib and wherein the at least one IEC enhancer is a CTLA-4 inhibitor selected from Ipilimumab or Tremelimumab. In some further specific embodiments, the method comprises administering to the human (1) an effective amount of at least one ISC inhibitor and (2) an effective amount of at least two IEC enhancers, wherein the at least one ISC inhibitor is a protein kinase inhibitor selected from sunitinib or axitinib and wherein the at least two IEC enhancers are Tremelimumab and a TLR agonist selected from CpG7909, CpG2455, or CpG10103.

Additional therapeutic agents.

The vaccine-based immunotherapy regimen provided by the present disclosure may further comprise an additional therapeutic agent. A wide variety of cancer therapeutic agents may be used, including chemotherapeutic agents and hormone therapeutic agents. The term "chemotherapeutic agent" refers to a chemical or biological substance that can cause death of cancer cells, or interfere with growth, division, repair, and/or function of cancer cells. Examples of particular chemotherapeutic agents include: abiraterone acetate, cabazitaxel, degarelix, denosumab, docetaxel, enzalutamide, leuprolide acetate, prednisone, sipuleucel-T, and radium 223 dichloride. The term "hormone therapeutic agent" refers to a chemical or biological substance that inhibits or eliminates the production of a hormone, or inhibits or counteracts the effect of a hormone on the growth and/or survival of cancer cells. Examples of particular hormone therapeutic agents include leuprolide, goserelin, triptorelin, histrelin, bicalutamide, flutamide, and nilutamide. The VBIR provided by this disclosure may also be used in combination with other therapies, including (1) surgical methods that remove all or part of the organs or glands which participate in the production of the hormone, such as the ovaries, the testicles, the adrenal gland, and the pituitary gland, and (2) radiation treatment, in which the organs or glands of the patient are subjected to radiation in an amount sufficient to inhibit or eliminate the production of the targeted hormone.

E. EXAMPLES

The following examples are provided to illustrate certain embodiments of the invention. They should not be construed to limit the scope of the invention in any way. From the above discussion and these examples, one skilled in the art can ascertain the essential characteristics of the invention, and without departing from the spirit and scope thereof, can make various changes and modifications of the invention to adapt it to various usage and conditions.

Example 1. Antigens in Cytosolic, Secreted, and Membrane-Bound Formats Derived from the Human PSMA Protein 1A. Design of Immunogenic PSMA Polypeptides DNA constructs encoding immunogenic PSMA polypeptides in cytosolic, secreted, and modified formats were constructed based on the native human PSMA protein sequence and tested for their ability to induce anti-tumor effector immune responses. The structure and preparation of each of the human PSMA antigen formats are provided as follows.

1A1. Human PSMA cytosolic antigen. An immunogenic PSMA polypeptide in cytosolic form was designed to retain the immunogenic polypeptide inside the cell once it is expressed. The cytoplasmic domain (amino acids 1-19) and the transmembrane domain (amino acids 20-43) of the human PSMA were removed, resulting in a cytosolic PSMA polypeptide that consists of amino acids 44-750 (extracellular domain or ECD) of the human PSMA of SEQ ID NO: 1. The optimal Kozak sequence "MAS" may be added to the N-terminus of the polypeptide for enhancing the expression or to facilitate cloning.

1A2. Human PSMA secreted antigen. An immunogenic PSMA polypeptide in secreted form was designed to secret the polypeptide outside of the cell once it is expressed. The secreted polypeptide is made with amino acids 44-750 (ECD) of the human PSMA of SEQ ID NO:1 and the Ig Kappa secretory element that has the amino acid sequence ETDTLLLWVLLLWVPGSTGD (SEQ ID NO:294) and a two-amino acid linker (AA) in the N-terminal in order to maximize the secretion of the PSMA antigen once it is expressed.

1A3. Human PSMA membrane-bound antigen. An immunogenic PSMA membrane-bound polypeptide was designed to stabilize the polypeptide on the cell surface. The first 14 amino acids of the human PSMA protein were removed and the resultant immunogenic polypeptide consists of amino acids 15-750 of the human PSMA protein of SEQ ID NO:1. The immunogenic polypeptide that consists of amino acids 15-750 of the native human PSMA protein of SES ID NO: 1 and share 100% sequence identity with the native human PSMA protein is also referred to as "human PSMA modified," "hPSMA modified," or "hPSMAmod" antigen in the present disclosure. The following three immunogenic PSMA polypeptides (referred to as "shuffled PSMA modified antigens") that are variants of the human PSMA modified antigen (SEQ ID NO:9) were also generated:

(1) shuffled PSMA modified antigen 1 having the amino acid sequence of SEQ ID NO:3;

(2) shuffled PSMA modified antigen 2 having the amino acid sequence of SEQ ID NO:5; and (3) shuffled PSMA modified antigen 3 having the amino acid sequence of SEQ ID NO:7.

The nucleodie sequences encoding the shuffled PSMA modified antigens 1, 2, and 3 are set forth in SEQ ID NOs: 4, 6, and 8, respectively.

1B. Preparation of DNA Plasmids for Expressing the PSMA antigens

DNA constructs encoding the PSMA cytosolic, PSMA secreted, and PSMA modified antigens were cloned individually into PJV7563 vector that was suitable for in vivo testing in animals (FIG. 1). Both strands of the DNA in the PJV7563 vectors were sequenced to confirm the design integrity.

A large scale plasmid DNA preparation (Qiagen/CsCl) was produced from a sequence confirmed clone. The quality of the plasmid DNA was confirmed by high 260/280 ratio, high super coiled/nicked DNA ratio, low endotoxin levels (<10U/mg DNA) and negative bio burden.

1C. Expression of PSMA constructs in mammalian cells

The expression of the PSMA cytosolic, secreted, and modified antigens was determined by FACS. Mammalian 293 cells were transfected with the PJV7563 PMED vectors encoding the various immunogenic PSMA polypeptides. Three days later, the 293 cells were stained with mouse anti-PSMA antibody, followed with a fluorescent conjugated (FITC) rat anti-mouse secondary antibody. The results are presented tin Table 2. The data were reported as mean fluorescent intensity (MFI) over negative controls, confirmed that human PSMA modified antigen is expressed on the cell surface.

TABLE 2

Expression of Human PSMA Modified antigen on Cell Surface

| Samples | Average mean fluorescent intensity |
|---|---|
| Untransfected 293 cells | 231 |
| 293 cells transfected with full length human PSMA (SEQ ID NO: 1) | 6425 |
| 293 cells transfected with human PSMA modified antigen (SEQ ID NO: 9) | 12270 |

Example 2. Design of Various Immunogenic PSA Polypeptides

3A. Construction of Immunogenic PSA Polypeptides

Similar to what was described in Example 1 for the three different immunogenic PSMA polypeptide forms (e.g., the cytosolic, membrane-bound, and secreted forms), immunogenic PSA polypeptides in the three forms were also designed based on the human PSA sequence. An immunogenic PSA polypeptide in cytosolic form, which consists of amino acids 25-261 of the native human PSA, is constructed by deleting the secretory signal and the pro domain (amino acids 1-24). The amino acid sequence of this cytosolic immunogenic PSA polypeptide is provided in SEQ ID NO: 17. The secreted form of the PSA polypeptide is the native full length human PSA (amino acids 1-261). An immunogenic PSA polypeptide in membrane-bound form is constructed by linking the immunogenic PSA polypeptide cytosolic form (amino acids 25-261 of the native human PSA) to the human PSMA transmembrane domain (amino acids 15-54 of the human PSMA).

3B. Immune responses in Pasteur and HLA A24 mice Study design. Eight to 10 week old HLA A2 Pasteur mice or HLA A24 mice were immunized with DNA expressing the various PSA antigens using PMED provided in Example 3A in a prime/boost/boost regimen with two week intervals between each vaccination as described in Example 1. The antigen specific T and B cell responses were measured 7 days after the last immunization in an interferon-gamma (IFNγ) ELISPOT assay and sandwich ELISA.

ELISpot data shown in Table 3 indicates that immunogenic PSA polypeptides in both cytosolic and membrane-bound forms are capable of inducing T cells that recognize human tumor cells transduced with adenovirus to express the cytosolic PSA antigen (SKmel5-Ad-PSA) but not cells transduced with adenovirus to express eGFP (SKmel5-Ad-eGFP). These two antigens also elicited response to PSA protein. The PSA secreted antigen failed to induce T cells to both SKmel5-Ad-PSA or PSA protein. SFC>50 is considered positive.

TABLE 3

The induction of T cell responses by PSA antigens in Pasteur mice to PSA + HLA A2.1 + SKmel5 human cancer cells

| HLA A2.1 + human cancer cells or protein | IFN-γ SFC/1 × $10^6$ splenocytes (SD) | | |
|---|---|---|---|
| | PSA cytosolic | PSA membrane-bound | PSA secreted |
| SKmel5-Ad-eGFP | 7.7 (9.6) | 1.2 (1.4) | 2.9 (2.7) |
| SKmel5-Ad-PSA | 112.0 (169.3) | 546.1 (379.6) | 18.7 (18.5) |
| PSA protein | 108.8 (161.0) | 536.9 (380.9) | 20.6 (21) |

TABLE 4

The induction of anti-PSA antibody response as measured by a sandwich ELISA assay

| Antigen Forms | ELISA (OD = 1.0) Average (SD) | # of positive |
|---|---|---|
| PSA cytosolic | 99 (0) | 0/6 |
| PSA membrane-bound | 4838 (835) | 6/6 |
| PSA secreted | 1151 2410) | 2/6 |

Data in Table 4 demonstrates that immunogenic PSA polypeptides in both secreted and membrane-bound forms are capable of inducing anti-PSA antibody responses.

Example 3. Construction of Multi-Antigen Vaccine Constructs

In this Example, constructions of plasmids comprising a multi-antigen construct using different strategies are described. These plasmids share the same general plasmid backbone as pPJV7563. Unless otherwise specified, the genes included in the multi-antigen constructs encode (1) an immunogenic PSMA polypeptide of SEQ ID NO:9, (2) an immunogenic PSCA polypeptide comprising amino acids 2-125 of SEQ ID NO:21, and (3) an immunogenic PSA polypeptide of SEQ ID NO:17.

Example 3A. Plasmids Comprising a Dual Antigen Construct

3A1. Construction of Plasmid utilizing multiple promoters

Plasmid 460 (PSMA/PSCA Dual promoter). Plasmid 460 was constructed using the techniques of site-directed mutagenesis, PCR, and restriction fragment insertion. First, a Kpn I restriction site was introduced upstream of the CMV promoter in plasmid 5259 using site-directed mutagenesis with MD5 and MD6 primers according to manufacturer's protocol (Quickchange kit, Agilent Technologies, Santa Clara, Calif.). Second, an expression cassette consisting of a minimal CMV promoter, human PSMA, and rabbit B globulin transcription terminator was amplified by PCR from plasmid 5166 using primers that carried Kpn I restriction sites (MD7 and MD8). The PCR amplicon was digested with Kpn I and inserted into the newly introduced Kpn I site of calf intestinal alkaline phosphatase (CIP)-treated plasmid 5259.

3A2. Construction of dual antigen constructs utilizing 2A peptides

Plasmid 451 (PSMA-T2A-PSCA). Plasmid 451 was constructed using the techniques of overlapping PCR and restriction fragment exchange. First, the gene encoding human PSMA amino acids 15-750 was amplified by PCR using plasmid 5166 as a template with primers 119 and 117. The gene encoding full-length human PSCA was amplified by PCR using plasmid 5259 as a template with primers 118 and 120. PCR resulted in the addition of overlapping TAV 2A (T2A) sequences at the 3' end of PSMA and 5' end of PSCA. The amplicons were mixed together and amplified by PCR with primers 119 and 120. The PSMA-T2A-PSCA amplicon was digested with Nhe I and Bgl II and inserted into similarly digested plasmid 5166. A glycine-serine linker was included between PSMA and the T2A cassette to promote high cleavage efficiency.

Plasmid 454 (PSCA-F2A-PSMA). Plasmid 454 was created using the techniques of PCR and restriction fragment exchange. First, the gene encoding full-length human PSCA was amplified by PCR using plasmid 5259 as a template with primers 42 and 132. The amplicon was digested with BamH I and inserted into similarly digested, CIP-treated plasmid 5300. A glycine-serine linker was included between PSCA and the FMDV 2A (F2A) cassette to promote high cleavage efficiency.

Plasmid 5300 (PSA-F2A-PSMA) Plasmid 5300 was constructed using the techniques of overlapping PCR and restriction fragment exchange. First, the gene encoding PSA amino acids 25-261 was amplified by PCR from plasmid 5297 with primers MD1 and MD2. The gene encoding human PSMA amino acids 15-750 was amplified by PCR from plasmid 5166 with primers MD3 and MD4. PCR resulted in the addition of overlapping F2A sequences at the 3' end of PSA and 5' end of PSMA. The amplicons were mixed together and extended by PCR. The PSA-F2A-PSMA amplicon was digested with Nhe I and Bgl II and inserted into similarly digested plasmid pPJV7563.

3A3. Dual antigen constructs utilizing internal ribosomal entry sites Plasmid 449 (PSMA-mIRES-PSCA). Plasmid 449 was constructed using the techniques of overlapping PCR and restriction fragment exchange. First, the gene encoding full length human PSCA was amplified by PCR from plasmid 5259 with primers 124 and 123. The minimal EMCV IRES was amplified by PCR from pShuttle-IRES with primers 101 and 125. The overlapping amplicons were mixed together and amplified by PCR with primers 101 and 123. The IRES-PSCA amplicon was digested with Bgl II and BamH I and inserted into Bgl II-digested, CIP-treated plasmid 5166. In order to fix a spontaneous mutation within the IRES, the IRES containing Avr II to Kpn I sequence was replaced with an equivalent fragment from pShuttle-IRES.

Plasmid 603 (PSCA-pIRES-PSMA). Plasmid 603 was constructed using the techniques of PCR and seamless cloning. The gene encoding full length human PSCA attached at its 3' end to a preferred EMCV IRES was amplified from plasmid 455 by PCR with primers SD546 and SD547. The gene encoding human PSMA amino acids 15-750 was amplified by PCR from plasmid 5166 using primers SD548 and SD550. The two overlapping PCR amplicons were inserted into Nhe I and Bgl II-digested pPJV7563 by seamless cloning according to manufacturer's instructions (Invitrogen, Carlsbad, Calif.).

Plasmid 455 (PSCA-mIRES-PSA). Plasmid 455 was constructed using the techniques of overlapping PCR and restriction fragment exchange. First, the gene encoding human PSA amino acids 25-261 was amplified by PCR from plasmid 5297 with primers 115 and 114. The minimal EMCV IRES was amplified by PCR from pShuttle-IRES with primers 101 and 116. The overlapping amplicons were mixed together and amplified by PCR with primers 101 and 114. The IRES-PSA amplicon was digested with Bgl II and BamH I and inserted into Bgl II-digested, CIP-treated plasmid 5259. In order to fix a spontaneous mutation within this clone, the Bgl II to BstE II sequence was replaced with an equivalent fragment from a fresh overlapping PCR reaction.

Example 3B. Plasmids Comprising a Triple Antigen Construct

General Strategy. A number of dual antigen plasmids, including PSA-F2A-PSMA, PSMA-mIRES-PSCA, PSMA-T2A-PSCA, PSA-T2A-PSCA, PSCA-F2A-PSMA, PSCA-pIRES-PSMA, and PSMA-mIRES-PSA, were selected for incorporation in various combinations into triple antigen plasmid vectors. In all cases, the plasmid vectors were based on the parental pPJV7563 plasmid backbone. Four plasmid vectors (plasmids 456, 457, 458, and 459) utilized a single full CMV promoter with a rabbit B globulin transcription terminator to drive expression of all three antigens. Two other plasmid vectors (plasmids 846 and 850) incorporated a dual promoter strategy in combination with either an RES or 2A to drive expression of the three antigens. Plasmids with multiple 2A cassettes were engineered to carry different cassettes to minimize the likelihood of recombination between the first and second cassette during plasmid/vector amplification. Antigen expression was demonstrated by flow cytometry (FIGS. 7A and 7B) and western blotting (FIGS. 8A and 8B).

Plasmid 456 (PSA-F2A-PSMA-mIRES-PSCA). Plasmid 456 was constructed by restriction fragment exchange. Plasmid 5300 was digested with Nhe I and Hpa I and the ~1.8 kb insert was ligated into similarly digested plasmid 449.

Plasmid 457 (PSA-F2A-PSMA-T2A-PSCA). Plasmid 457 was constructed by restriction fragment exchange. Plasmid 5300 was digested with Nhe I and Hpa I and the ~1.8 kb insert was ligated into similarly digested plasmid 451.

Plasmid 458 (PSA-T2A-PSCA-F2A-PSMA). Plasmid 458 was constructed using the techniques of PCR and restriction fragment exchange. The gene encoding human PSA amino acids 25-261 was amplified by PCR from plasmid 5297 with primers 119 and 139, resulting in the addition of a T2A sequence and Nhe I restriction site at the 3' end. The amplicon was digested with Nhe I and inserted into similarly digested plasmid 454.

Plasmid 459 (PSCA-F2A-PSMA-mIRES-PSA). Plasmid 459 was constructed by restriction fragment exchange. Plasmid 454 was digested with Nhe I and Bgl II and the PSCA-F2A-PSMA containing insert was ligated into similarly digested plasmid 455.

Plasmid 846 (CBA-PSA, CMV-PSCA-pIRES-PSMA). Plasmid 846 was constructed using the techniques of PCR and seamless cloning. First, an expression cassette was synthesized that consisted of 1) the promoter and 5' untranslated region from the chicken beta actin (CBA) gene, 2) a hybrid chicken beta actin/rabbit beta globin intron, 3) the gene encoding human PSA amino acids 25-261, and 4) the bovine growth hormone terminator. This PSA expression cassette was amplified by PCR from plasmid 796 with primers 3SalICBA and 5SalIBGH. The amplicon was cloned into the SalI site of plasmid 603 using a GeneArt Seamless Cloning and Assembly Kit (Invitrogen, Carlsbad, Calif.). Upon delivery of this plasmid into a cell, PSA expression will be driven off the CBA promoter while PSCA and PSMA expression will be driven off the CMV promoter.

Plasmid 850 (CBA-PSA, CMV-PSCA-F2A-PSMA). Plasmid 850 was constructed using the techniques of PCR and seamless cloning. First, the CBA promoter-driven PSA expression cassette was amplified by PCR from plasmid 796 with primers 3SalICBA and 5SalIBGH. The amplicon was cloned into the SalI site of plasmid 454 using GeneArt Seamless Cloning. Upon delivery of this plasmid into a cell, PSA expression will be driven off the CBA promoter while PSCA and PSMA expression will be driven off the CMV promoter.

Plasmid 916 ((PSA-T2A-PSCA-F2A-PSMA). Plasmid 916 was constructed using the techniques of PCR and Gibson cloning. The genes encoding the three PAA polypeptides were amplified by PCR and ligated into the Nhe I/Bgl II sites of pPJV7563 by Gibson cloning techniques. The complete nucleotide sequence of Plasmid 916 is set forth in SEQ ID NO:62. Plasmid 458 and Plasmid 916 encode the same amino acid sequence that comprises the three immunogenic PAA polypeptides, which amino acid sequence is set forth in SEQ ID NO:60. The nucleotide sequence in Plasmid 916 that encodes the amino acid sequence comprising the three PAA polypeptides is codon-optimized and is also set forth in SEQ ID NO:61.

TABLE 21

List of Primers Used in the Construction of the Multi-antigen Plasmids

| Primer | Sequence (5' to 3') | Strand | SEQ ID NO |
|---|---|---|---|
| 42 | CGTTGACGCAAATGGGCGGTAGG | Sense | 83 |
| 101 | TCAGAGATCTGACCCCCTAACGTTAC | Sense | 84 |
| 114 | TGGCTATAGGATCCTCAGGGGTTGGC | Antisense | 85 |
| 115 | CACGATGGAAAAACACGATGATAATATGGCCAGCATTGTGGGAGGCTGGGAGTG | Sense | 86 |
| 116 | CCACAATGCTGGCCATATTATCATCGTGTTTTTCAAAGGAAAACCACGTCC | Antisense | 87 |
| 117 | CATCTCCACAGGTCAATAATGAACCCCTACCTTCGGATCCGGCTACTTCACTCAAAGTC | Antisense | 88 |
| 118 | GTTCATTATTGACCTGTGGAGATGTCGAAGAAAACCCAGGACCCGCAAGCAAGGCTGTGCTGCTTGCCCTG | Sense | 89 |
| 119 | TTGCCTCTCACATCTCGTCAATCTCCGCGAGGAC | Sense | 90 |
| 120 | GATCTTTTGTACAATATGATCTTGTGGCAATGTCCC | Antisense | 91 |
| 123 | TATAGGATCCCTATAGCTGGCCGGGTCC | Antisense | 92 |
| 124 | CACGATGATAATATGGCCAGCAAGGCTGTGCTGCTTGCC | Sense | 93 |
| 125 | CACAGCCTTGCTGGCCATATTATCATCGTGTTTTTCAAAGGAAAACCACGTCC | Antisense | 94 |
| 132 | TATAGGATCCTAGCTGGCCGGGTCCCCAGAG | Antisense | 95 |
| 139 | ATATGCTAGCGGGTCCTGGGTTTTCTTCGACATCTCCACAGGTCAATAATGAACCCCTACCTTCGGATCCGGGGTTGGCCACGATGGTGTCC | Antisense | 96 |
| SD546 | CTGTGACGAACATGGCTAGCAAGG | Sense | 97 |
| SD547 | ATTATCATCGTGTTTTTCAAAGGAAAACC | Antisense | 98 |
| SD548 | AAACACGATGATAATATGGCCACAACCATGGCGCGCCGCCCCGC | Sense | 99 |
| SD550 | TTTTGTTAGGGCCCAGATCTTTAGGC | Antisense | 100 |
| MD1 | GACGAACATGGCTAGCATTGTGGGAGGCTG | Sense | 101 |
| MD2 | CCACATCGCCTGCCAGTTTCAGCAGATCAAAGTTCAGGGTCTGGGATCCGGGGTTGGCCACGATGGTGTC | Antisense | 102 |
| MD3 | GATCTGCTGAAACTGGCAGGCGATGTGGAAAGCAACCCAGGCCCAATGGCAAGCGCGCGCCGCCCCGCGCTG | Sense | 103 |
| MD4 | GTTAGGGCCCAGATCTTTAGGCTACTTCACTCAAAGTC | Antisense | 104 |
| MD5 | CTTGTATTACTGTTTATGTAAGCAGACAGGGTACCAATATTGGCTATTGGCCATTGCATAC | Sense | 105 |

TABLE 21-continued

List of Primers Used in the Construction of the Multi-antigen Plasmids

| Primer | Sequence (5' to 3') | Strand | SEQ ID NO |
|---|---|---|---|
| MD6 | GTATGCAATGGCCAATAGCCAATATTGGTACCCTGTCTGCTTACATAAACAGTAATACAAG | Antisense | 106 |
| MD7 | CATGCATGGGTACCAATCTTCCGAGTGAGAGACACAAAAAATTCC | Sense | 107 |
| MD8 | GATCGATCGGTACCCTGCAGGTCGAGCACCAAAATCAACGGG | Antisense | 108 |
| 5SalIBGH | GTTTATGTAAGCAGACAGGTCGACCCATAGAGCCCACCGCATCCCCAGC | Antisense | 109 |
| 3SalICBA | TGGCCAATAGCCAATATTGTCGACTGGGTCGAGGTGAGCCCCACGTTCTG | Sense | 110 |

Example 3C. Triple Antigen Adenovirus Vectors

General Strategy. As with DNA plasmids, viral vectors can be engineered to deliver multiple prostate cancer antigens. The three multi-antigen expression strategies described above for multi-antigen constructs-dual promoters, 2A peptides, and internal ribosome entry sites—were incorporated in various combinations to create triple antigen adenovirus vectors. Briefly, the multi-antigen expression cassettes were cloned into a pShuttle-CMV plasmid modified to carry two copies of the tetracycline operator sequence (TetO2). Recombinant adenovirus serotype 5 vectors were created using the AdEasy Vector System according to manufacturer's protocols (Agilent Technologies, Inc., Santa Clara, Calif.). Viruses were amplified in HEK293 cells and purified by double cesium chloride banding according to standard protocols. Prior to in vivo studies, viral stocks were thoroughly characterized for viral particle concentration, infectivity titer, sterility, endotoxin, genomic and transgene integrity, transgene identity and expression.

Adenovirus-733 (PSA-F2A-PSMA-T2A-PSCA). Ad-733 is the viral equivalent of plasmid 457. Expression of the three antigens is driven off a single CMV promoter with a tetracycline operator for repressing transgene expression during large scale production in Tet repressor expressing HEK293 lines. Multi-antigen expression strategies include two different 2A sequences.

Adenovirus-734 (PSA-T2A-PSCA-F2A-PSMA). Ad-734 is the viral equivalent of plasmid 458. Expression of the three antigens is driven off a single CMV promoter with a tetracycline operator for repressing transgene expression during large scale production in Tet repressor expressing HEK293 lines. Multi-antigen expression strategies include two different 2A sequences.

Adenovirus-735 (PSCA-F2A-PSMA-mIRES-PSA). Ad-735 is the viral equivalent of plasmid 459. Expression of the three antigens is driven off a single CMV promoter with a tetracycline operator for repressing transgene expression during large scale production in Tet repressor expressing HEK293 lines. Multi-antigen expression strategies include a 2A sequence and an IRES.

Adenovirus-796 (CBA-PSA, CMV-PSCA-pIRES-PSMA). Ad-796 is the viral equivalent of plasmid 846. Expression of PSA is driven off the chicken beta actin promoter while PSCA and PSMA expression is driven off the CMV-TetO2 promoter.

Multi-antigen expression strategies include two promoters and an IRES.

Adenovirus-809 (CBA-PSA, CMV-PSCA-F2A-PSMA). Ad-809 is the viral equivalent of plasmid 850. Expression of PSA is driven off the chicken beta actin promoter while PSCA and PSMA expression is driven off the CMV-TetO2 promoter. Multi-antigen expression strategies include two promoters and a 2A sequence.

Example 4. Anti-Cancer Efficacy of Vaccine in Combination with Sunitinib and Anti-CTLA-4 Antibody The anti-tumor efficacy of a cancer vaccine in combination with sunitinib and anti-CTLA-4 monoclonal antibody (clone 9D9) was investigated in subcutaneous TUBO tumor bearing BALB/neuT mice.

Study Procedure. Briefly, ten mice per each group were daily orally dosed with either vehicle or sunitinib malate at 20 mg/kg starting at day 10 post tumor implant until day 64. Vaccination with DNA constructs that either encode no antigen (control vaccine) or a rat Her-2 antigen of SEQ Id NO: 54 (cancer vaccine) as adenovirus vectors initiated on day 13 subsequently followed by two weekly immunizations, two biweekly immunizations, and seven weekly immunizations of respective antigens (HBV antigens or rHer-2) by DNA. The groups of mice (closed circle and open triangle) that were treated with anti-murine CTLA-4 monoclonal antibody were intraperitoneally injected with 250 μg of the antibody on day 20, 27, 41, 55, 62, 69, 76, 83, 90, and 97 right after the PMED injections.

Figure 4:
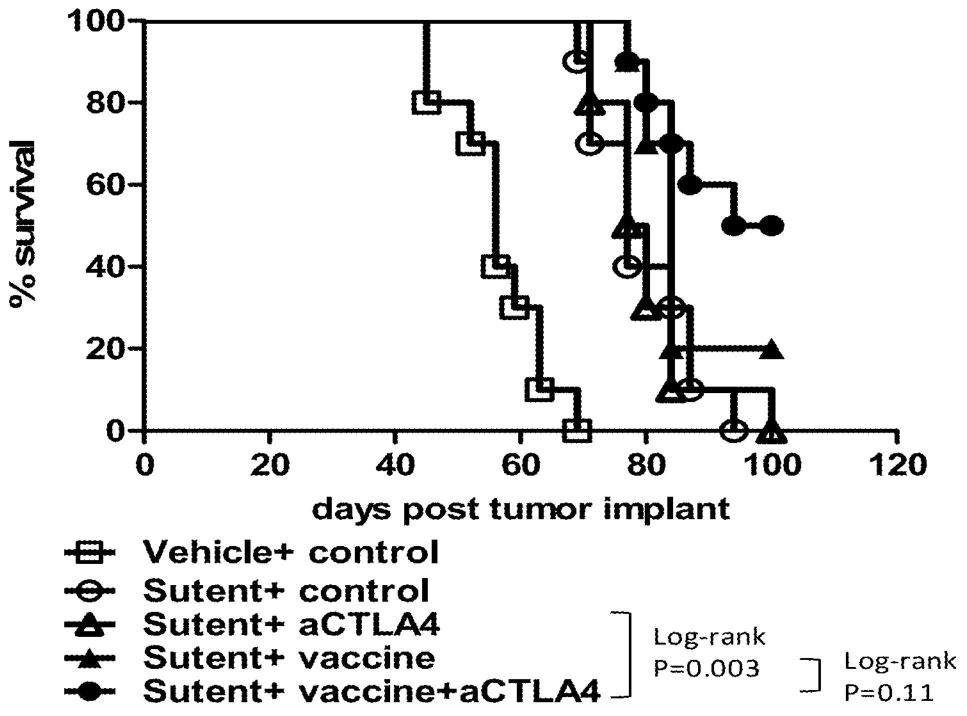
FIG. 4. Graph showing the Kaplan-Meier survival curves of the groups of mice from a representative study evaluating the effect of sunitinib malate (Sutent) and an anti-murine CTLA-4 monoclonal antibody (clone 9D9) on the antitumor efficacy of a cancer vaccine (vaccine) in subcutaneous TUBO tumor bearing BALB/neuT mice.

Results. FIG. 4 shows the Kaplan-Meier survival curve of the groups of mice from a representative study evaluating the anti-tumor efficacy of sunitinib and anti-murine CTLA-4 monoclonal antibody (clone 9D9) in combination with a cancer vaccine. Increased survival time was observed in mice treated with Sutent with control vaccine (open circle), anti-murine CTLA-4 monoclonal antibody (open triangle) or cancer vaccine (closed triangle). A further increase of survival was observed in mice treated with Sutent and cancer vaccine in combination with anti-murine CTLA-4 (closed circle). P values were calculated by log-rank test.

Example 5. Effect of CpG or CD40 Agonist on the Immune Responses Induced by Cancer Vaccine Immunogenicity Studies in BALB/c Mice The effect of local administration of immune modulators on the magnitude and quality of antigen specific immune responses induced by a cancer was investigated in BALB/c mice, in which the immune response was assessed by measuring rHER2 specific T cell responses using the IFNγ ELISPOT assay or intracellular cytokine staining assay. Briefly, 4 to 6 female BALB/c mice per group as indicated were immunized with DNA plasmid expression constructs encoding rHER2 antigen sequences (SEQ ID NO:54) by PMED delivery system. The immune modulators, CpG7909 (PF-03512676) and anti-CD40 monoclonal agonistic antibody, were administered locally by intradermal injections in proximity to the vaccine draining inguinal lymph node subsequently after the PMED actuations. Antigen specific T cell responses were measured by IFNγ ELISPOT or intracellular cytokine staining assay according to the procedure described below.

Intracellular Cytokine Staining (ICS) Assay

The rHer-2 specific polyfunctional (multi-cytokine positive) T cell immune responses were measured from splenocytes or PBMCs isolated from individual animals by ICS assay. Typically 1e6 splenocytes were incubated with Brefeldin A at 1 μg/ml and peptide stimulant (rHer-2 specific CD8p66, rHer-2 specific CD4p169 or irrelevant HBV p87) at 10 μg/ml for 5 hr at 37° C. in a 5% $CO_2$ incubator. After the stimulation, the splenocytes were washed and blocked with Fc□ block (anti-mouse CD16/CD32) for 10 min. at 4° C. followed by a 20 min staining with Live/dead aqua stain, anti-mouse CD3ePE-Cy7, anti-mouse CD8a Pacific blue, and anti-mouse CD45R/B220 PerCP-Cy5.5. The cells were washed, fixed with 4% paraformaldehyde overnight at 4° C., permeabilized with BD fix/perm solution for 30 min at RT and incubated with anti-mouse IFNγ APC, anti-mouse TNF□ Alexa488 and anti-mouse IL-2 PE for 30 min at RT. The cells were washed and 20,000 CD4 or CD8 T cells were acquired for analysis by flow cytometry. The total number of antigen specific single, double or triple cytokine positive T cells per total spleen of each animal is calculated by subtracting the rHer-2 specific responses to the irrelevant peptide HBV from the vaccine specific responses and normalized to the total number of splenocytes isolated from the spleen.

IFNγ ELISPOT Assay Results

Figure 5:
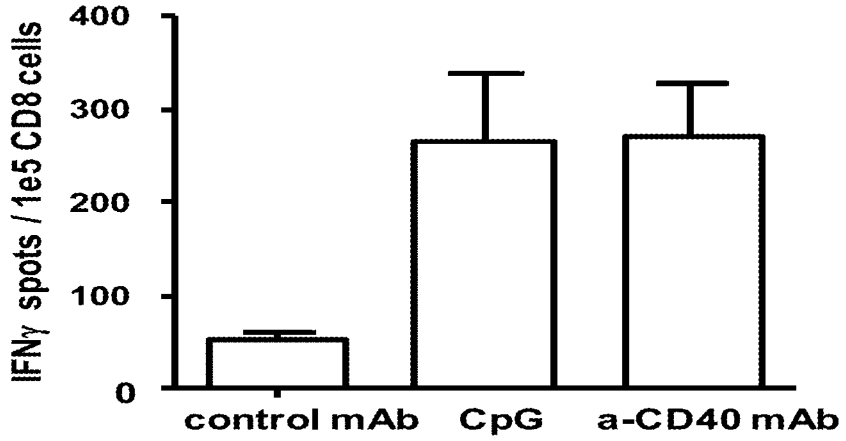
FIG. 5. Graph depicting the IFNγ ELISPOT results from a representative study evaluating the effect of CpG7909 and an anti-CD40 antibody (Bioxcell #BE0016-2) on the antigen specific T cell responses induced by a cancer vaccine (rHER2).

FIG. 5 shows the IFNγ ELISPOT results from groups of mice from a representative study evaluating the magnitude of antigen specific T cell responses induced by the rHER2 vaccine when given with the immune modulators as indicated. Briefly, each mouse per treatment group (n=4) was immunized with DNA plasmid expression constructs encoding rHER2 antigen sequences (SEQ ID NO:54) by PMED immediately followed by either 100 μg of control rat IgG monoclonal antibody (Bioxcell #BE0089: control mAb) or 50□g CpG7909 or 100 μg of anti-CD40 monoclonal antibody (Bioxcell #BE0016-2: a-CD40 mAb) as indicated. The antigen specific immune responses were measured by IFNγ ELISPOT assay from 5e5 splenocytes mixed with control or rHer-2 specific p66 peptides at 10 μg/ml concentration, 7 days after the PMED actuation. The number of total IFNγ secreting cells from splenocytes containing 1e5 CD8 T cells was calculated from the ELISPOT results from individual animals and the % of CD8 T cells in splenocytes and mean and standard error of mean of each group are plotted. As shown, both CpG7909 and the anti-CD40 monoclonal antibody significantly enhanced the magnitude of antigen specific immune responses induced by rHer-2 DNA compared to mice that received control antibodies.

Figure 6:
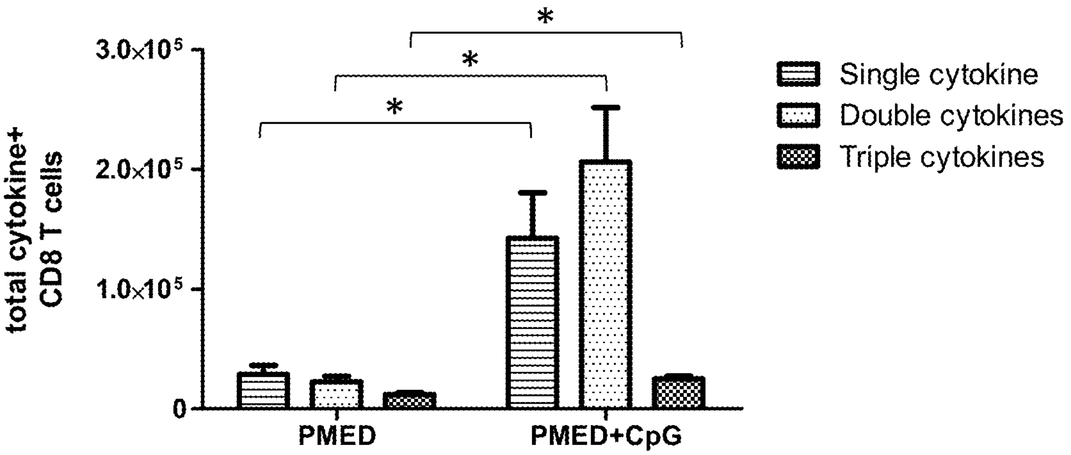
FIG. 6. Graphs depicting results of a representative study that evaluates the immunomodulatory activity of CpG7909 on the quality of the immune responses induced by a cancer vaccine (PMED) using intracellular cytokine staining assay, in which cytokine positive CD8 T cells were measured. (* indicates P<0.05 by Student's T-test).
Figure 7:
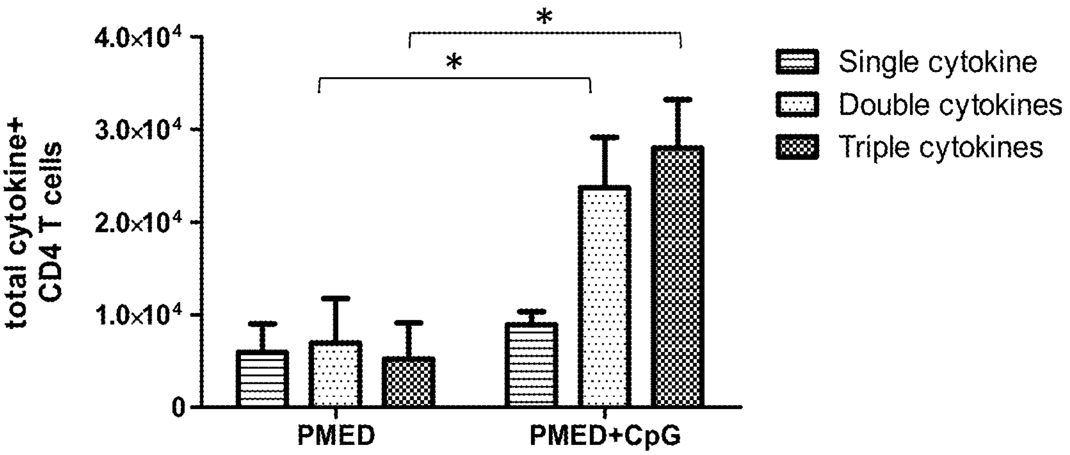
FIG. 7. Graphs depicting results of a representative study that evaluates the immunomodulatory activity of CpG7909 on the quality of the immune responses induced by a cancer vaccine (PMED) using intracellular cytokine staining assay, in which cytokine positive CD4 T cells (FIG. 7) were measured. (* indicates P<0.05 by Student's T-test).

Intracellular Cytokine Staining (ICS) Assay Results. FIGS. 6 and 7 show the results of a representative study that evaluates the immunomodulatory activity of CpG 7909 on the quality of the vaccine induced immune responses by intracellular cytokine staining assay. Briefly, each animal was immunized twice with the DNA plasmid expression constructs encoding rHER2 antigen sequences (SEQ ID NO: 54) delivered by PMED with a 4-week interval. The mice in each group (n=5) were given intradermal injections of either PBS (PMED group) or 50□g of CpG 7909 (PMED+CpG group) in proximity to the right side vaccine draining inguinal node immediately following both DNA immunizations by PMED. Seven days after the last immunization by PMED, an ICS assay was performed on the splenocytes isolated from each individual mice to detect antigen specific polyfunctional CD8 or CD4 T cells that secrete IFNγ, TNF 0 and/or IL-2. A significant increase in rHer-2 specific multi-cytokine positive CD8 and CD4 T cell responses were detected from mice treated with the local delivery of CpG 7909 compared to PBS. An increase in the single cytokine positive CD8 population was observed in the animals that received local delivery of CpG7909 administration compared to PBS.

Figure 8:
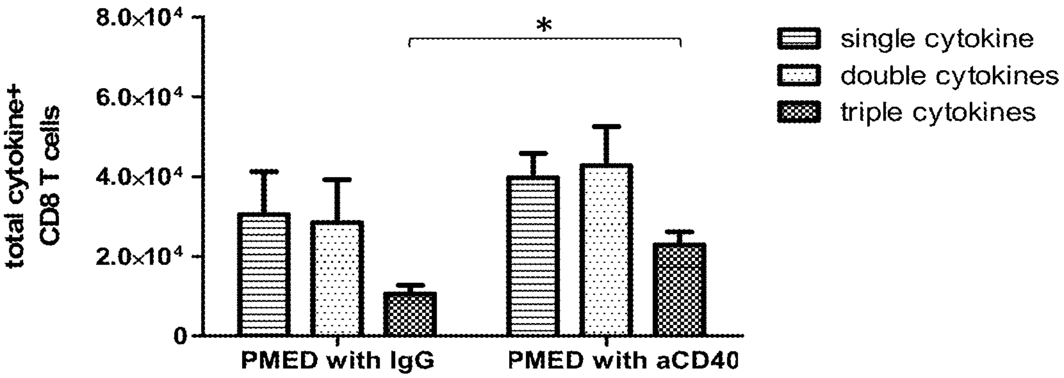
FIG. 8. Graphs depicting results of a representative study that evaluates the immunomodulatory activity of an agonistic anti-murine CD40 monoclonal antibody on the quality of the immune responses induced by a cancer vaccine (PMED) using intracellular cytokine staining assay, in which cytokine positive CD8 T cells were measured. (*indicates P<0.05 by Student's T-test)
Figure 9:
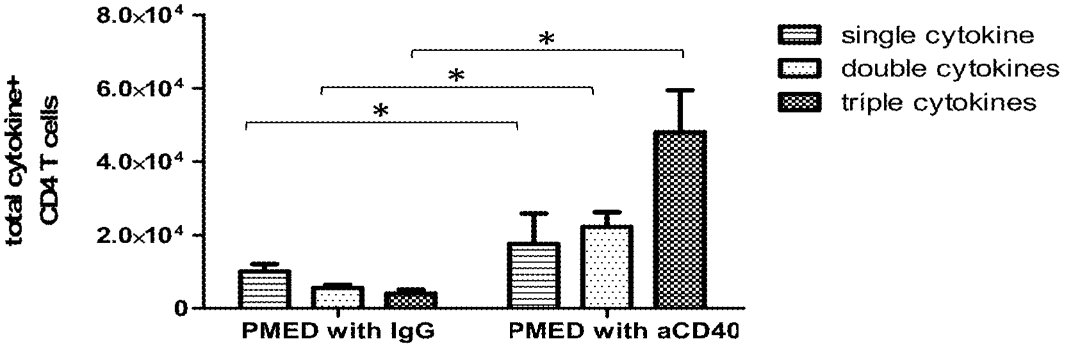
FIG. 9. Graphs depicting results of a representative study that evaluates the immunomodulatory activity of an agonistic anti-murine CD40 monoclonal antibody on the quality of the immune responses induced by a cancer vaccine (PMED) using intracellular cytokine staining assay, in which cytokine positive CD4 T cells were measured. (*indicates P<0.05 by Student's T-test)

FIGS. 8 and 9 show the results of a representative study that evaluates the immunomodulatory activity of an agonistic anti-CD40 monoclonal antibody on the quality of the vaccine induced immune responses by intracellular cytokine staining assay. Briefly, each animal was immunized twice by DNA plasmid expression constructs encoding rHER2 antigen sequences (SEQ ID NO: 54) delivered by PMED with a 4 week interval. The mice in each group (n=6) were given 100 □g of intradermal injections of either isotype IgG control (PMED with IgG) or anti-CD40 monoclonal antibody (PMED with aCD40) in proximity to the right side vaccine draining inguinal node, one day after the first immunization was administered by PMED. Seven days after the last PMED, an ICS assay was performed on the splenocytes isolated from each individual mice to detect rHer-2 specific polyfunctional CD8 or CD4 T cells that secrete IFN 0, TNF 0 and/or IL-2.. A significant increase in the rHer-2 specific triple-cytokine positive CD8 and CD4 T cell responses were detected from mice treated with the local delivery of anti-CD40 monoclonal antibody compared to isotype IgG control. There were also significant increases in rHer-2 specific single and double cytokine positive CD4 T cells by anti-CD40 monoclonal antibody given locally.

Example 6. Anti-Cancer Efficacy of Cancer Vaccine in Combination with Low Dose Sunitinib Anti-tumor efficacy of anti-cancer vaccine in combination with low dose sunitinib was investigated in BALB/neuT mice with spontaneous mammary pad tumors.

Animal treatment. Briefly, 13-14 weeks old female mice were orally given sunitinib malate (Sutent) at 5 mg/kg for 112 days twice a day. The control vaccine, which delivers no antigen, and cancer vaccine which delivers a rat Her-2 antigen of SEQ ID NO: 54 (rHer-2), were given by adenovirus injections on day 3 as a prime followed by 7 biweekly administrations by PMED of DNA delivering HBV antigens (control vaccine) or rHer-2 (cancer vaccine) respectively. The survival end point was determined when all ten mammary pads became tumor positive or when the volume of any of the mammary tumors reached 2000 $mm^3$.

Figure 10:
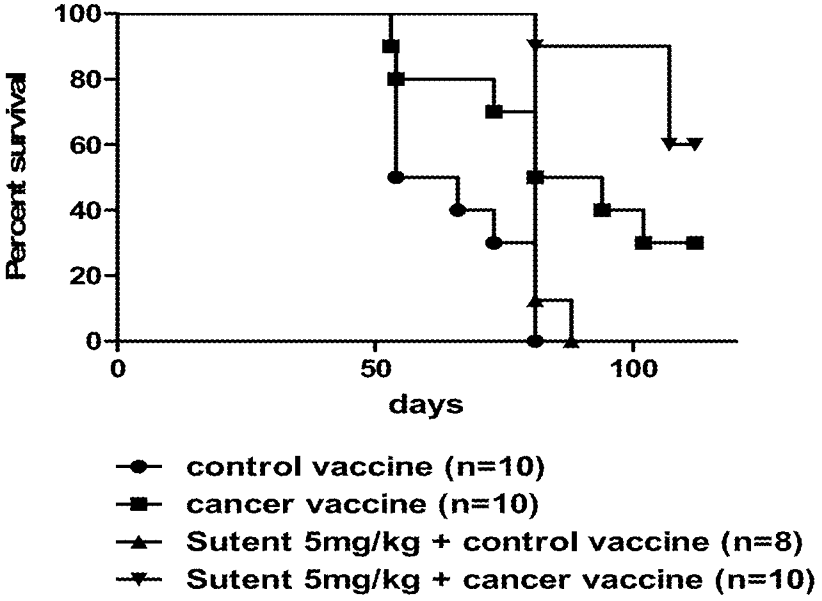
FIG. 10. Graph showing the Kaplan-Meier survival curves of the groups of mice from a representative study that evaluates the effect of low dose sunitinib malate (Sutent) on the anti-tumor efficacy of a cancer vaccine in spontaneous mammary tumor bearing BALB/neuT mice.

Results. The results are presented in FIG. 10. Compared to previously published pharmacokinetic profile of Sutent (Mendel, D., Laird, D., et al.: "In vivo antitumor activity of SU11248, a novel tyrosine kinase inhibitor targeting vascular endothelial growth factor and platelet-derived growth factor receptors: determination of a pharmacokinetic/pharmacodynamic relationship". Clinical Cancer Research, 203, 9:327-337), the $C_{Max}$ of Sutent in mice dosed twice a day at 5 mg/kg is expected to be significantly lower than the minimum blood levels necessary to achieve efficient anti-tumor efficacy in mice and man. The data shows a quick and temporary improvement in the survival of the mice treated with low dose Sutent monotherapy. However when given with the cancer vaccine, a more persistent and significant improvement of survival was observed (P<0.0001 by Log rank test).

Example 7. Enhancement of Vaccine-Induced Immune Responses by Local Administration of CpG The immune enhancement of local administration of CpG (PF-03512676) on the immune responses induced by a human PSMA nucleic acid provided by the invention was investigated in a monkey study, in which the immune response was assessed by measuring PSMA specific T cell responses using an IFNγ ELISPOT assay.

Animal Treatment and Sample Collection. Six groups of Chinese cynomolgus macaques, six (#1 to 6) per each test group, were immunized with a plasmid DNA encoding the human PSMA modified antigen (the polypeptide of SEQ ID NO:9) delivered by electroporation. Briefly, all animals received bilateral intramuscular injections of 5 mg of plasmid DNA followed by electroporation (DNA EP) on day 0. Subsequently right after the electroporation, group 2 received bilateral intramuscular injections of 2 mg of CpG mixed with 1 mg Alum in proximity to the DNA injection sites. Groups 3 and 4 received bilateral intramuscular injections of 2 mg of CpG delivered without alum in proximity to the DNA injection sites either on day 0 or day 3, respectively. Group 5 received 2 mg of bilateral intradermal injections of CpG delivered in proximity to the vaccine draining inguinal nodes on day 3. Group 6 received bilateral injections of 200 □g of CpG mixed with the DNA solution which was co-electroporated into the muscle on day 0.

IFNγ ELISPOT Assay Procedure. Peripheral blood samples were collected from each animal fifteen days after the DNA immunization. Peripheral blood mononuclear cells (PBMCs) were isolated from the blood samples and were subjected to an IFNγ ELISPOT assay to measure the PSMA specific T cell responses. Briefly, 4e5 PBMCs from individual animals were plated per well with pools of PSMA specific peptides or nonspecific control peptides (human HER2 peptide pool) each at 2 ug/ml in IFNγ ELISPOT plates. The composition of each of the PSMA specific peptide pool is provided in Table 24A. The plates were incubated for 16 hrs at 37° C. and 5% CO2 and washed and developed after incubation as per manufacturer's instruction. The number of IFNγ spot forming cells (SFC) was counted by CTL reader. Each condition was performed in duplicates.

Results. Table 6 shows the result of a representative IFNγ ELISPOT assay that evaluates and compares the IFNγ T cell responses induced by the vaccine without (group 1) or with CpG (PF-03512676) given locally by intramuscular (groups 2, 3, 4, and 5) or intradermal injections (group 6). The reported PSMA specific response was calculated by subtracting the average number of the SFC to the nonspecific control peptides (human HER2 peptide pool) from the average number of SFC to the PSMA peptide pools and normalized to the SFC observed with 1e6 PBMCs. ^indicates that the count is not accurate because the numbers of spots were too numerous to count. ND indicates not determined.

The PSMA specific IFNγ T cell responses were detected to multiple PSMA specific peptide pools in the absence of CpG (PF-03512676) in all six animals (group 1). The total responses to the PSMA peptides measured were modestly higher in a few animals that additionally received CpG (PF-03512676) either by intramuscular (group 4:3/6) or intradermal (group 5: 2/6) injections 3 days after DNA electroporation. However, when CpG was delivered subsequently right after electroporation on the same day (groups 2 and 3), there were several animals that failed to produce high responses (group 2: 4/6 and group3: 3/6) whether mixed or not mixed with Alum. However, higher net responses were detected in 4/6 animals when a ten-fold lower dose of CpG was co-electroporated with the DNA solution into the muscle (group 6) with a statistically higher response ($P<0.05$) to peptide pools H1 and R1 compared to animals that did not receive CpG (group 1). The data shows that low dose of CpG can effectively enhance IFNγ T cell responses induced by a DNA vaccine when co-electroporated into the muscle.

TABLE 6

PSMA specific IFNγ T cell responses induced by the DNA vaccine without (Group 1) or with CpG (Groups 2, 3, 4, 5 and 6) is measured by IFNγ ELISPOT assay from PBMCs, 15 days after DNA electroporation

| | | Recall Antigen | | | | | | |
|---|---|---|---|---|---|---|---|---|
| Group | Animal ID | P1 | P2 | P3 | H1 | H2 | R1 | R2 |
| 1 | #1 | 36 | 31 | 1 | 126 | 183 | 5 | 14 |
| | #2 | 6 | 3 | 13 | 61 | 524 | 6 | 141 |
| | #3 | 11 | 4 | 8 | 108 | 1049 | 3 | 56 |
| | #4 | 10 | 0 | 13 | 20 | 151 | 13 | 10 |
| | #5 | 8 | 6 | 11 | 39 | 469 | 14 | 18 |
| | #6 | 26 | 5 | 0 | 145 | 356 | 8 | 30 |
| 2 | #1 | 3 | 10 | 0 | 15 | 35 | 0 | 0 |
| | #2 | 0 | 0 | 8 | 4 | 6 | 13 | 0 |
| | #3 | 3 | 0 | 0 | 0 | 10 | 11 | 0 |
| | #4 | 6 | 209 | 4 | 111 | 414 | 23 | 9 |
| | #5 | 15 | 5 | 30 | 171 | 104 | 68 | 6 |
| | #6 | 0 | 0 | 0 | 9 | 9 | 6 | 8 |
| 3 | #1 | 14 | 19 | 8 | 123 | 1066 | 10 | 60 |
| | #2 | 14 | 16 | 20 | 384 | 393 | 104 | 8 |
| | #3 | 0 | 0 | 15 | 0 | 6 | 0 | 0 |
| | #4 | 0 | 0 | 0 | 33 | 21 | 0 | 4 |
| | #5 | 4 | 91 | 1 | 875 | ˆ1235 | 233 | 109 |
| | #6 | 0 | 0 | 0 | 0 | 3 | 0 | 0 |
| 4 | #1 | 0 | 33 | 15 | 1025 | ˆ1209 | 280 | 90 |
| | #2 | 0 | 313 | 3 | 23 | 656 | 6 | 31 |
| | #3 | 61 | 120 | 61 | 428 | 1190 | 143 | 53 |
| | #4 | 0 | 0 | 8 | 599 | 870 | 34 | 111 |
| | #5 | 0 | 1 | 8 | 19 | 226 | 10 | 36 |
| | #6 | 111 | 55 | 39 | 231 | 613 | 121 | 99 |
| 5 | #1 | 21 | 9 | 0 | 355 | 1131 | 73 | 5 |
| | #2 | 0 | 0 | 0 | 118 | 233 | 0 | 0 |
| | #3 | 0 | 0 | 0 | 18 | 129 | 0 | 0 |
| | #4 | 0 | 28 | 78 | 68 | 294 | 58 | 8 |
| | #5 | 25 | 0 | 28 | 329 | 1125 | 134 | 5 |
| | #6 | 0 | 0 | 0 | 23 | 39 | 4 | 0 |
| 6 | #1 | 0 | 0 | 13 | 650 | 1096 | 270 | 5 |
| | #2 | 34 | 1 | 74 | 124 | 474 | 29 | 15 |
| | #3 | 0 | 3 | 14 | 684 | 1074 | 126 | 64 |
| | #4 | 8 | 9 | 0 | 136 | 321 | 49 | 1 |
| | #5 | 13 | 23 | 35 | ND | ˆ1235 | 333 | 195 |
| | #6 | 0 | 0 | 0 | 421 | ˆ1201 | 138 | 29 |

Example 8. Enhancement of Vaccine-Induced Immune Responses by Local Administration of Anti-CTLA-4 Antibody The effect of low dose subcutaneous administration of anti-CTLA-4 monoclonal antibody (CP-675, 206) on the immune responses induced by a rhesus PSMA nucleic acid was investigated in a monkey study, in which the immune response was assessed by measuring PSMA specific T cell responses using an IFNγ ELISPOT assay. The rhesus PSMA nucleic acid used in the study has the sequence as set forth in SEQ ID NO: 56) and encodes an immunogenic PSMA polypeptide of SEQ ID NO: 55.

Animal Treatment and Sample Collection. Five groups of male Indian rhesus macaques, seven (#1 to 7) per each test group, were immunized with an adenovirus encoding a rhesus PSMA modified polypeptide delivered by bilateral intramuscular injections (2× 5e10 V.P.). Immediately following the adenovirus injections, group 1 received vehicle, and groups 2 to 4 received bilateral subcutaneous injections of anti-CTLA-4 antibody (CP-675, 206) at doses 2× 25 mg, 2× 16.7 mg and 2× 8.4 mg respectively in proximity to the vaccine draining lymph node.

Nine days after the immunization, peripheral blood mononuclear cells (PBMCs) were isolated from each animal and were subjected to an IFNγ ELISPOT assay to measure the rhesus PSMA specific T cell responses. Briefly, 4e5 PBMCs from individual animals were plated per well with pools of rhesus PSMA specific peptides (P1, P2, P3 or R1+R2 defined in Table 24A) or nonspecific control peptides (human HER2 peptide pool) each at 2 ug/ml in IFN□ ELISPOT plates. The plates were incubated for 16 hrs at 37° C. and 5% CO2 and washed and developed after incubation as per manufacturer's instruction. The number of IFNγ spot forming cells (SFC) was counted by CTL reader. Each condition was performed in duplicates. The average of the duplicates from the background adjusted SFC of the rhesus PSMA specific peptide pools was normalized to the response in 1e6 PBMCs. The individual and sum responses to the peptide pools from each individual animal are presented in Table 29.

IFNγ ELISPOT Assay Procedure. A capture antibody specific to IFNγ (□BD Bioscience, #51-2525kc) is coated onto a polyvinylidene fluoride (PVDF) membrane in a microplate overnight at 4° C. The plate is blocked with serum/protein to prevent nonspecific binding to the antibody. After blocking, effector cells (such as splenocytes isolated from immunized mice or PBMCs isolated from rhesus macaques) and targets (such as PSMA peptides from peptide library, target cells pulsed with antigen specific peptides or tumor cells expressing the relevant antigens) are added to the wells and incubated overnight at 37° C. in a 5% $CO_2$ incubator. Cytokine secreted by effector cells are captured by the coating antibody on the surface of the PVDF membrane. After removing the cells and culture media, 100 μl of a biotinylated polyclonal anti-humanIFNγ antibody was added to each of the wells for detection. The spots are visualized by adding streptavidin-horseradish peroxidase and the precipitate substrate, 3-amino-9-ethylcarbazole (AEC), to yield a red color spot as per manufacturer's (Mabtech) protocol. Each spot represents a single cytokine producing T cell.

Results. Table 7 shows the results of a representative IFNγ ELISPOT assay that compares the T cell responses induced by the vaccine without (group 1) or with (groups 2-4) anti-CTLA-4 monoclonal antibody (CP-675,206) given locally by subcutaneous injections in proximity to the vaccine draining lymph node. The vaccine generated an immune response (group1) that was significantly enhanced by the local administration of the anti-CTLA-4 antibody (CP-675, 206) at a dose of 50 mg (group 2, P=0.001 by Student's T-test using underestimated values). The response was also significantly enhanced by low doses of anti-CTLA-4 antibody at 33.4 mg (group3: P=0.004 by Student T-test using underestimated values) and 16.7 mg (group4: P=0.05 by Student T-test) respectively. The data suggests that low doses of anti-CTLA-4 delivered by subcutaneous injection can significantly enhance the vaccine induced immune responses.

TABLE 7

IFNγ T cell responses induced by the vaccine without (Group 1) or with subcutaneous injections of anti-CTLA-4 antibody (CP-675,206).

| Group | aCTLA4 dose, mg | animal ID | peptide pool P1 | P2 | P3 | R1 + R2 | Sum |
|---|---|---|---|---|---|---|---|
| 1 | NA | 1 | 21 | 0 | 0 | 108 | 129 |
| | | 2 | 59 | 480 | 28 | 353 | 920 |
| | | 3 | 133 | 29 | 359 | 305 | 826 |
| | | 4 | 0 | 28 | 1 | 35 | 64 |
| | | 5 | 41 | 6 | 30 | 99 | 176 |
| | | 6 | 1 | 0 | 849 | 169 | 1019 |
| | | 7 | 0 | 0 | 0 | 23 | 23 |
| 2 | 50.0 | 1 | ^1105 | 704 | ^1116 | ^1116 | ^4041 |
| | | 2 | 371 | 26 | 661 | 779 | 1837 |
| | | 3 | 393 | 559 | 216 | 198 | 1366 |
| | | 4 | ^1100 | ^1100 | 406 | 1078 | ^3684 |
| | | 5 | 778 | 325 | 554 | 419 | 2076 |
| | | 6 | ^1079 | ^1079 | 844 | ^1079 | ^4081 |
| | | 7 | 423 | 103 | 535 | 398 | 1459 |
| 3 | 33.4 | 1 | ^425 | ^425 | ^425 | ^425 | ^1700 |
| | | 2 | ^580 | ^580 | ^580 | ^580 | ^2320 |
| | | 3 | TNTC | TNTC | TNTC | TNTC | TNTC |
| | | 4 | 321 | 778 | 370 | 409 | 1878 |
| | | 5 | 331 | 466 | 311 | 446 | 1554 |
| | | 6 | 545 | 121 | ^631 | ^1194 | ^2491 |
| | | 7 | 446 | 299 | ^1078 | ^1060 | ^2883 |
| 4 | 16.7 | 1 | ^964 | 296 | ^964 | ^964 | ^3188 |
| | | 2 | 76 | 76 | 76 | 76 | 304 |
| | | 3 | ^984 | ^984 | ^984 | ^984 | ^3936 |
| | | 4 | 260 | 489 | 648 | ^1109 | ^2506 |
| | | 5 | 119 | 45 | 28 | 140 | 332 |
| | | 6 | 55 | 76 | 43 | 198 | 372 |
| | | 7 | 146 | 726 | 141 | 400 | 1413 |

^indicates that the count is underestimated due to the high spot numbers. TNTC means too numerous to count.

Example 9. Immunomodulation of Myeloid Derived Suppressor Cells by Low Dose Sunitinib The following example is provided to illustrate the immunomodulatory effects of low dose sunitinib on Myeloid Derived Suppressor Cells (MDSC) in vivo, in a non-tumor mouse model.

Study Procedures.

To generate MDSC enriched splenocytes, TUBO cells ($1\times10^6$) were implanted into the flanks of 5 BALB/neuT mice, and left for approx. 20-30 days until tumor volume reached between 1000-1500 $mm^3$. Mice were then sacrificed, spleens removed and the MDSC enriched splenocytes recovered. Splenocytes were labeled for 10 minutes with 5 μM CFSE, washed with PBS and counted. Labeled cells were subsequently resuspended at $5\times10^7$ splenocytes/ml in PBS solution and adoptively transferred via an i.v. tail vein injection into näive BALB/c recipient mice. Three days prior to adoptive transfer, the recipient mice began bi-daily dosing with vehicle or sunitinib malate (Sutent) at 5 mg/kg, 10 mg/kg and 20 mg/kg. Following adoptive transfer, recipient mice continued to receive bi-daily dosing of Vehicle or sunitinib for two further days, after which point the mice were sacrificed, spleens removed, splenocytes recovered and processed for phenotypic analysis.

Splenocytes were counted and resuspended at $5\times10^6$ cells/ml in FACS staining buffer (PBS, 0.2% (w/v) bovine serum albumin, and 0.02% (w/v) Sodium Azide). For flow cytometry staining of splenocytes, $2.5\times10^6$ cells were first incubated with anti-bodies to CD16/CD32, 10 minutes at 4° C., to block Fc receptors and minimize non-specific binding. Splenocytes were then stained for 20 minutes at 4° C. with appropriate fluorophore conjugated antibodies (Biolegend) to murine cell surface markers. For T cells (anti-CD3 (Pacific Blue), clone 17A2) and for MDSC (anti-GR-1 (APC), clone RB6-8C5 and anti-CD11 b (PerCp Cy5.5), clone M1/70). A live/dead stain was also included. Following antibody incubation, stained splenocytes were washed with 2 mls of FACS buffer, pelleted by centrifugation and resuspended in 0.2 ml of FACS buffer prior to data acquisition on a BD CANTO II flow cytometer. To monitor the effect of Sunitinib or Vehicle on the adoptively transferred MDSC survival, we calculated the percentage of CFSE+, CD3−,GR1+,CD11b+ in the live, singlet gate. We then determined the number of adoptively transferred MDSC per spleen by calculating what actual cell number the percentage represented of total splenocytes count. Data was analyzed by FloJo and Graph pad software.

Results. The data presented in Table 27 represents the mean number of adoptively transferred CSFE+,CD3−, GR1+,CD11b+ cells recovered per spleen (n=7/group), 2 days post adoptive transfer, from mice bi-daily dosed with either Vehicle or 5 mg/kg, 10 mg/kg and 20 mg/kg Sunitinib. Statistical significance was determined by one-way ANOVA using the Dunnett's multiple comparison test, comparing the Sunitinib dosed groups against the 0 mg/kg (vehicle) group. The data demonstrates that Sunitinib, dosed bi-daily, in vivo, has an immunomodulatory effect on MDSCs, even when dosed as low as 5 mg/kg, resulting in a statistically significant reduction in the numbers recovered when compared to the vehicle treated control group.

TABLE 8

| Mean number of CFSE+, CD3−, GR1+, CD11b+ MDSCs recovered from spleen | | | | |
|---|---|---|---|---|
| | Sunitinib Dose (mg/kg) | | | |
| | 0 (Vehicle) | 5 | 10 | 20 |
| MDSC #/spleen Mean +/− SEM | 17470 +/− 2017 | 10980 +/− 1082 | 4207 +/− 338 | 4440 +/− 440 |
| Statistical significance, p < 0.05 | NA | Yes | Yes | Yes |

Example 10. Immunogenicity of Triple Antigen Adenovirus and DNA Constructs

The following example is provided to illustrate the capability of triple antigen vaccine constructs (either in the form of adenovirus vector or DNA plasmid) expressing three antigens PSMA, PSCA and PSA provided by the invention to elicit specific T cell responses to all three encoded antigens in nonhuman primates.

In Vivo Study Procedures. The T cell immunogenicity of five adenovirus vectors each expressing three antigens (PSMA, PSCA and PSA; Ad-733, Ad-734, Ad-735, Ad-796 and Ad-809) provided by the invention were compared to the mix of three adenovirus vectors each only expressing a single antigen (PSMA, PSA or PSCA), 9 days post prime. The response to single adenovirus expressing a single antigen (groups 1-3) was evaluated to demonstrate the specificity. Briefly, Indian rhesus macaques (n=6 for groups 1 and 3, n=7 for group 2 and n=8 for groups 4-9) were intramuscularly injected with a total of 1e11 V.P. followed by intradermal injections of anti-CTLA-4 at 10 mg/kg on the same day. Nine days after the injections, peripheral blood mononuclear cells (PBMCs) were isolated from each animal and were subjected to an IFN□ ELISPOT assay to measure the PSMA, PSA and PSCA specific T cell responses.

Thirteen weeks after the adenovirus and anti-CTLA-4 injections when the T cell responses have contracted, the monkeys received DNA (Group 1: PSMA, plasmid 5166; Group 2: PSA, plasmid 5297; Group 3: PSCA, plasmid 5259; Group 4: mix of PSMA, PSA and PSCA, plasmids 5166, 5259 and 5297; Group 4: plasmid 457; Group 6: plasmid 458; Group 7: plasmid 459; Group 8: plasmid 796 and Group 9: plasmid 809) boost vaccinations delivered by electroporation. In summary, each animal received a total 5 mg of plasmid DNA provided by the invention which delivers the same expression cassette encoded in the adenovirus used in the prime. Nine days after the boost vaccination, peripheral blood mononuclear cells (PBMCs) were isolated from each animal and were subjected to an IFNγ ELISPOT assay.

IFNγ ELISPOT assay. Briefly, 4e5 PBMCs from individual animals were plated per well with PSMA specific peptide pools P1, P2, P3 or H1 and H2 (Table 9A), PSA specific pool 1 or 2 (Table 9B), PSCA specific pool (Table 10) or nonspecific control peptides (human HER2 peptide pool) each at 2 ug/ml in IFNγ ELISPOT plates. The plates were incubated for 16 hrs at 37° C. and 5% CO2 and washed and developed after incubation as per manufacturer's instruction. The number of IFNγ spot forming cells (SFC) was counted by CTL reader. Each condition was performed in duplicates. The average of the duplicates from the background adjusted SFC of the antigen specific peptide pools was normalized to the response in 1e6 PBMCs. The antigen specific responses in the tables present the sum of the responses to the corresponding antigen specific peptides or peptide pools.

Results: Table 11 represents a study that evaluates the T cell immunogenicity of five different adenoviruses each expressing all three antigens in comparison to the mixture of three adenoviruses each expressing a single antigen in Indian rhesus macaques by IFNγ ELISPOT. The majority of animals that only received Ad-PSMA (group 1) injections induced specific responses to PSMA but not to PSA or PSCA (Student's T-test, P<0.03. One animal (#4) that induced responses to PSCA preferentially was removed from the statistical analysis). The animals that only received injections of Ad-PSA (group 2) induced specific responses to PSA but not to PSMA or PSCA (Student's T-test, P<0.02). The animals that only received injections of Ad-PSCA (group 3) induced specific responses to PSCA but not to PSMA or PSA (Student's T-test, P<0.03). All five triple-antigen expressing adenovirus vectors (groups 5-9) induced IFN□ T cell responses to all three antigens which the magnitude varied by animal. The magnitude of the responses to PSCA induced by the triple antigen expressing adenoviruses was similar to the mix of individual vectors (group 4). However the magnitude of responses to PSMA induced by Ad-809 (group 9) and responses to PSA induced by Ad-796 (group 8) were each significantly superior to the mix (Student's T-test, P=0.04 and P=0.02) respectively. These results indicate that vaccinating with an adenovirus expressing triple antigens can elicit equivalent or superior T cell immune responses to vaccinating with the mix of individual adenoviruses in nonhuman primates. Table 12 shows the IFNγ ELISPOT results represents a study that evaluates the immunogenicity of the five different triple antigen expression cassettes provided in the invention delivered by an adenovirus prime in combination with anti-CTLA-4 followed by an electroporation boost of the corresponding plasmid DNA. The immune responses are compared to the mix of three constructs expressing a single antigen delivered similarly by an adenovirus prime with anti-CTLA-4 and DNA electroporation boost immunizations.

All of the animals that only received Ad-PSMA with anti-CTLA-4 followed by plasmid-PSMA (group 1) immunizations induced specific responses to PSMA but not to PSA or PSCA. Similarly all of the animals that only received Ad-PSA with anti-CTLA-4 followed by plasmid-PSA immunizations (group 2) induced specific responses to PSA but not to PSMA or PSCA and finally all of the animals that only received Ad-PSCA with anti-CTLA-4 followed by plasmid-PSCA (group 3) immunizations induced specific responses to PSCA but not to PSMA or PSA (Student's T-test, P<0.01).

All animals that have been immunized with either the triple-antigen expressing vectors (groups 5-9) or the mix (group 4) induced IFNγ T cell responses to all three antigens. The frequency of PSCA or PSA specific IFγ T cells detected were similar in all of these groups (groups 4-9) respectively. However construct groups 7 and 9 that received triple antigen expression vector vaccinations produced significantly higher frequency of responses to PSMA than the mix of three single antigen expressing constructs (group 4). These results indicate that adenovirus and DNA vaccines expressing triple antigens in one cassette can elicit equivalent or superior IFNγ T cell responses to the mix of adenoviruses and DNAs expressing the single antigens in nonhuman primates.

TABLE 9A

PSMA peptide pools*

| P1 | P2 | P3 | H1 | H2 | R1 | R2 |
|---|---|---|---|---|---|---|
| h 1-15 | h 249-263 | h 449-463 | h 33-47 | h 465-479 | r 33-47 | r 465-479 |
| h 5-19 | h 253-267 | h 453-467 | h 37-51 | h 469-483 | r 37-51 | r 469-483 |
| h 9-23 | h 257-271 | h 457-471 | h 41-55 | h 473-487 | r 41-55 | r 473-487 |
| h 13-27 | h 261-275 | h 485-499 | h 45-59 | h 477-491 | r 45-59 | r 477-491 |
| h 17-31 | h 265-279 | h 489-503 | h 61-75 | h 481-495 | r 61-75 | r 481-495 |
| h 21-35 | h 269-283 | h 493-507 | h 65-79 | h 537-551 | r 65-79 | r 537-551 |
| h 25-39 | h 273-287 | h 497-511 | h 69-83 | h 541-555 | r 69-83 | r 541-555 |
| h 29-43 | h 277-291 | h 501-515 | h 73-87 | h 545-559 | r 73-87 | r 545-559 |
| h 49-63 | h 281-295 | h 505-519 | h 97-111 | h 577-591 | r 97-111 | r 577-591 |
| h 53-67 | h 285-299 | h 509-523 | h 101-115 | h 581-595 | r 101-115 | r 581-595 |
| h 57-71 | h 289-303 | h 513-527 | h 105-119 | h 585-599 | r 105-119 | r 585-599 |
| h 77-91 | h 293-307 | h 517-531 | h 109-123 | h 589-603 | r 109-123 | r 589-603 |
| h 81-95 | h 297-311 | h 521-535 | h 137-151 | h 601-615 | r 137-151 | r 601-615 |
| h 85-99 | h 317-331 | h 525-539 | h 141-155 | h 605-619 | r 141-155 | r 605-619 |
| h 89-103 | h 321-335 | h 529-543 | h 145-159 | h 609-623 | r 145-159 | r 609-623 |
| h 93-107 | h 325-339 | h 533-547 | h 149-163 | h 613-627 | r 149-163 | r 613-627 |
| h 113-127 | h 329-343 | h 549-563 | h 209-223 | h 637-651 | r 209-223 | r 637-651 |
| h 117-131 | h 333-347 | h 553-567 | h 213-227 | h 641-655 | r 213-227 | r 641-655 |
| h 121-135 | h 353-367 | h 557-571 | h 217-231 | h 645-659 | r 217-231 | r 645-659 |
| h 125-139 | h 357-371 | h 561-575 | h 221-235 | h 649-663 | r 221-235 | r 649-663 |
| h 129-143 | h 361-375 | h 565-579 | h 301-315 | h 653-667 | r 301-315 | r 653-667 |
| h 133-147 | h 365-379 | h 569-583 | h 305-319 | h 657-671 | r 305-319 | r 657-671 |
| h 153-167 | h 369-383 | h 573-587 | h 309-323 | h 709-723 | r 309-323 | r 709-723 |
| h 157-171 | h 373-387 | h 593-607 | h 313-327 | h 713-727 | r 313-327 | r 713-727 |
| h 161-175 | h 377-391 | h 597-611 | h 337-351 | h 717-731 | r 337-351 | r 717-731 |
| h 165-179 | h 381-395 | h 617-631 | h 341-355 | h 721-735 | r 341-355 | r 721-735 |
| h 169-183 | h 385-399 | h 621-635 | h 345-359 | h 725-739 | r 345-359 | r 725-739 |
| h 173-187 | h 389-403 | h 625-639 | h 349-363 | h 729-743 | r 349-363 | r 729-743 |
| h 177-191 | h 393-407 | h 629-643 | h 461-475 | h 733-747 | r 461-475 | r 733-747 |
| h 181-195 | h 397-411 | h 633-647 | | | | |
| h 185-199 | h 401-415 | h 661-675 | | | | |
| h 189-203 | h 405-419 | h 665-679 | | | | |
| h 193-207 | h 409-423 | h 669-683 | | | | |
| h 197-211 | h 413-427 | h 673-687 | | | | |
| h 201-215 | h 417-431 | h 677-691 | | | | |
| h 205-219 | h 421-435 | h 681-695 | | | | |
| h 225-239 | h 425-439 | h 685-699 | | | | |
| h 229-243 | h 429-443 | h 689-703 | | | | |
| h 233-247 | h 433-447 | h 693-707 | | | | |
| h 237-251 | h 437-451 | h 697-711 | | | | |
| h 241-255 | h 441-455 | h 701-715 | | | | |
| h 245-259 | h 445-459 | h 705-719 | | | | |
| | | h737-750 | | | | |

TABLE 9B

PSA peptide pools: the amino acid position and sequence of fifteen amino acid peptides overlapping by thirteen amino acids from PSA peptide library is shown.

| PSA peptide pool 1 | | | PSA peptide pool 2 | | |
|---|---|---|---|---|---|
| amino acid no. | PSA peptide sequence | SEQ ID NO | amino acid no. | PSA peptide sequence | SEQ ID NO |
| 5-19 | VVFLTLSVTWIGAAP | 111 | 129-143 | PAELTDAVKVMDLPT | 172 |
| 9-23 | TLSVTWIGAAPLILS | 112 | 131-145 | ELTDAVKVMDLPTQE | 173 |
| 11-25 | SVTWIGAAPLILSRI | 113 | 133-147 | TDAVKVMDLPTQEPA | 174 |
| 13-27 | TWIGAAPLILSRIVG | 114 | 135-149 | AVKVMDLPTQEPALG | 175 |
| 15-29 | IGAAPLILSRIVGGW | 115 | 137-151 | KVMDLPTQEPALGTT | 176 |
| 17-31 | AAPLILSRIVGGWEC | 116 | 139-153 | MDLPTQEPALGTTCY | 177 |
| 19-33 | PLILSRIVGGWECEK | 117 | 141-155 | LPTQEPALGTTCYAS | 178 |
| 21-35 | ILSRIVGGWECEKHS | 118 | 143-157 | TQEPALGTTCYASGW | 179 |
| 23-37 | SRIVGGWECEKHSQP | 119 | 145-159 | EPALGTTCYASGWGS | 180 |

TABLE 9B-continued

PSA peptide pools: the amino acid position and sequence of fifteen amino acid peptides overlapping by thirteen amino acids from PSA peptide library is shown.

| PSA peptide pool 1 | | | PSA peptide pool 2 | | |
|---|---|---|---|---|---|
| amino acid no. | PSA peptide sequence | SEQ ID NO | amino acid no. | PSA peptide sequence | SEQ ID NO |
| 25-39 | IVGGWECEKHSQPWQ | 120 | 147-161 | ALGTTCYASGWGSIE | 181 |
| 27-41 | GGWECEKHSQPWQVL | 121 | 149-163 | GTTCYASGWGSIEPE | 182 |
| 29-43 | WECEKHSQPWQVLVA | 122 | 151-165 | TCYASGWGSIEPEEF | 183 |
| 31-45 | CEKHSQPWQVLVASR | 123 | 153-167 | YASGWGSIEPEEFLT | 184 |
| 33-47 | KHSQPWQVLVASRGR | 124 | 155-169 | SGWGSIEPEEFLTPK | 185 |
| 35-49 | SQPWQVLVASRGRAV | 125 | 157-171 | WGSIEPEEFLTPKKL | 186 |
| 37-51 | PWQVLVASRGRAVCG | 126 | 159-173 | SIEPEEFLTPKKLQC | 187 |
| 39-53 | QVLVASRGRAVCGGV | 127 | 161-175 | EPEEFLTPKKLQCVD | 188 |
| 41-55 | LVASRGRAVCGGVLV | 128 | 163-177 | EEFLTPKKLQCVDLH | 189 |
| 43-57 | ASRGRAVCGGVLVHP | 129 | 165-179 | FLTPKKLQCVDLHVI | 190 |
| 45-59 | RGRAVCGGVLVHPQW | 130 | 167-181 | TPKKLQCVDLHVISN | 191 |
| 47-61 | RAVCGGVLVHPQWVL | 131 | 169-183 | KKLQCVDLHVISNDV | 192 |
| 49-63 | VCGGVLVHPQWVLTA | 132 | 171-185 | LQCVDLHVISNDVCA | 193 |
| 51-65 | GGVLVHPQWVLTAAH | 133 | 173-187 | CVDLHVISNDVCAQV | 194 |
| 53-67 | VLVHPQWVLTAAHCI | 134 | 175-189 | DLHVISNDVCAQVHP | 195 |
| 55-69 | VHPQWVLTAAHCIRN | 135 | 177-191 | HVISNDVCAQVHPQK | 196 |
| 57-71 | PQWVLTAAHCIRNKS | 136 | 179-193 | ISNDVCAQVHPQKVT | 197 |
| 59-73 | WVLTAAHCIRNKSVI | 137 | 181-195 | NDVCAQVHPQKVTKF | 198 |
| 61-75 | LTAAHCIRNKSVILL | 138 | 183-197 | VCAQVHPQKVTKFML | 199 |
| 63-77 | AAHCIRNKSVILLGR | 139 | 185-199 | AQVHPQKVTKFMLCA | 200 |
| 65-79 | HCIRNKSVILLGRHS | 140 | 187-201 | VHPQKVTKFMLCAGR | 201 |
| 67-81 | IRNKSVILLGRHSLF | 141 | 189-203 | PQKVTKFMLCAGRWT | 202 |
| 69-83 | NKSVILLGRHSLFHP | 142 | 191-205 | KVTKFMLCAGRWTGG | 203 |
| 71-85 | SVILLGRHSLFHPED | 143 | 193-207 | TKFMLCAGRWTGGKS | 204 |
| 73-87 | ILLGRHSLFHPEDTG | 144 | 195-209 | FMLCAGRWTGGKSTC | 205 |
| 75-89 | LGRHSLFHPEDTGQV | 145 | 197-211 | LCAGRWTGGKSTCSG | 206 |
| 77-91 | RHSLFHPEDTGQVFQ | 146 | 199-213 | AGRWTGGKSTCSGDS | 207 |
| 79-93 | SLFHPEDTGQVFQVS | 147 | 201-215 | RWTGGKSTCSGDSGG | 208 |
| 81-95 | FHPEDTGQVFQVSHS | 148 | 203-217 | TGGKSTCSGDSGGPL | 209 |
| 83-97 | PEDTGQVFQVSHSFP | 149 | 205-219 | GKSTCSGDSGGPLVC | 210 |
| 85-99 | DTGQVFQVSHSFPHP | 150 | 207-221 | STCSGDSGGPLVCNG | 211 |
| 87-101 | GQVFQVSHSFPHPLY | 151 | 209-223 | CSGDSGGPLVCNGVL | 212 |
| 89-103 | VFQVSHSFPHPLYDM | 152 | 211-225 | GDSGGPLVCNGVLQG | 213 |
| 91-105 | QVSHSFPHPLYDMSL | 153 | 213-227 | SGGPLVCNGVLQGIT | 214 |
| 93-107 | SHSFPHPLYDMSLLK | 154 | 215-229 | GPLVCNGVLQGITSW | 215 |

TABLE 9B-continued

PSA peptide pools: the amino acid position and sequence of fifteen amino acid peptides overlapping by thirteen amino acids from PSA peptide library is shown.

| PSA peptide pool 1 | | | PSA peptide pool 2 | | |
|---|---|---|---|---|---|
| amino acid no. | PSA peptide sequence | SEQ ID NO | amino acid no. | PSA peptide sequence | SEQ ID NO |
| 95-109 | SFPHPLYDMSLLKNR | 155 | 217-231 | LVCNGVLQGITSWGS | 216 |
| 97-111 | PHPLYDMSLLKNRFL | 156 | 219-233 | CNGVLQGITSWGSEP | 217 |
| 99-113 | PLYDMSLLKNRFLRP | 157 | 221-235 | GVLQGITSWGSEPCA | 218 |
| 101-115 | YDMSLLKNRFLRPGD | 158 | 223-237 | LQGITSWGSEPCALP | 219 |
| 103-117 | MSLLKNRFLRPGDDS | 159 | 225-239 | GITSWGSEPCALPER | 220 |
| 105-119 | LLKNRFLRPGDDSSH | 160 | 227-241 | TSWGSEPCALPERPS | 221 |
| 107-121 | KNRFLRPGDDSSHDL | 161 | 229-243 | WGSEPCALPERPSLY | 222 |
| 109-123 | RFLRPGDDSSHDLML | 162 | 231-245 | SEPCALPERPSLYTK | 223 |
| 111-125 | LRPGDDSSHDLMLLR | 163 | 233-247 | PCALPERPSLYTKVV | 224 |
| 113-127 | PGDDSSHDLMLLRLS | 164 | 235-249 | ALPERPSLYTKVVHY | 225 |
| 115-129 | DDSSHDLMLLRLSEP | 165 | 237-251 | PERPSLYTKVVHYRK | 226 |
| 117-131 | SSHDLMLLRLSEPAE | 166 | 239-253 | RPSLYTKVVHYRKWI | 227 |
| 119-133 | HDLMLLRLSEPAELT | 167 | 241-255 | SLYTKVVHYRKWIKD | 228 |
| 121-135 | LMLLRLSEPAELTDA | 168 | 243-257 | YTKVVHYRKWIKDTI | 229 |
| 123-137 | LLRLSEPAELTDAVK | 169 | 245-259 | KVVHYRKWIKDTIVA | 230 |
| 125-139 | RLSEPAELTDAVKVM | 170 | 247-261 | VHYRKWIKDTIVANP | 231 |
| 127-141 | SEPAELTDAVKVMDL | 171 | 249-261 | YRKWIKDTIVANP | 232 |
| | | | 251-261 | KWIKDTIVANP | 233 |

TABLE 10

PSCA peptide pool: The amino acid position and sequence of fifteen amino acid peptides overlapping by thirteen amino acids from PSCA peptide library is shown.

| amino acid no. | PSCA peptide sequence | SEQ ID NO |
|---|---|---|
| 1-15 | MKAVLLALLMAGLAL | 234 |
| 3-17 | AVLLALLMAGLALQP | 235 |
| 5-19 | LLALLMAGLALQPGT | 236 |
| 7-21 | ALLMAGLALQPGTAL | 237 |
| 9-23 | LMAGLALQPGTALLC | 238 |
| 11-25 | AGLALQPGTALLCYS | 239 |
| 13-27 | LALQPGTALLCYSCK | 240 |
| 15-29 | LQPGTALLCYSCKAQ | 241 |
| 17-31 | PGTALLCYSCKAQVS | 242 |
| 19-33 | TALLCYSCKAQVSNE | 243 |
| 21-35 | LLCYSCKAQVSNEDC | 244 |

TABLE 10-continued

PSCA peptide pool: The amino acid position and sequence of fifteen amino acid peptides overlapping by thirteen amino acids from PSCA peptide library is shown.

| amino acid no. | PSCA peptide sequence | SEQ ID NO |
|---|---|---|
| 23-37 | CYSCKAQVSNEDCLQ | 245 |
| 25-39 | SCKAQVSNEDCLQVE | 246 |
| 27-41 | KAQVSNEDCLQVENC | 247 |
| 29-43 | QVSNEDCLQVENCTQ | 248 |
| 31-45 | SNEDCLQVENCTQLG | 249 |
| 33-47 | EDCLQVENCTQLGEQ | 250 |
| 35-49 | CLQVENCTQLGEQCW | 251 |
| 37-51 | QVENCTQLGEQCWTA | 252 |
| 39-53 | ENCTQLGEQCWTARI | 253 |
| 41-55 | CTQLGEQCWTARIRA | 254 |

TABLE 10-continued

PSCA peptide pool: The amino acid position and sequence of fifteen amino acid peptides overlapping by thirteen amino acids from PSCA peptide library is shown.

| amino acid no. | PSCA peptide sequence | SEQ ID NO |
|---|---|---|
| 43-57 | QLGEQCWTARIRAVG | 255 |
| 45-59 | GEQCWTARIRAVGLL | 256 |
| 47-61 | QCWTARIRAVGLLTV | 257 |
| 49-63 | WTARIRAVGLLTVIS | 258 |
| 51-65 | ARIRAVGLLTVISKG | 259 |
| 53-67 | IRAVGLLTVISKGCS | 260 |
| 55-69 | AVGLLTVISKGCSLN | 261 |
| 57-71 | GLLTVISKGCSLNCV | 262 |
| 59-73 | LTVISKGCSLNCVDD | 263 |
| 61-75 | VISKGCSLNCVDDSQ | 264 |
| 63-77 | SKGCSLNCVDDSQDY | 265 |
| 65-79 | GCSLNCVDDSQDYYV | 266 |
| 67-81 | SLNCVDDSQDYYVGK | 267 |
| 69-83 | NCVDDSQDYYVGKKN | 268 |
| 71-85 | VDDSQDYYVGKKNIT | 269 |
| 73-87 | DSQDYYVGKKNITCC | 270 |
| 75-89 | QDYYVGKKNITCCDT | 271 |
| 77-91 | YYVGKKNITCCDTDL | 272 |
| 79-93 | VGKKNITCCDTDLCN | 273 |
| 81-95 | KKNITCCDTDLCNAS | 274 |
| 83-97 | NITCCDTDLCNASGA | 275 |
| 85-99 | TCCDTDLCNASGAHA | 276 |
| 87-101 | CDTDLCNASGAHALQ | 277 |
| 89-103 | TDLCNASGAHALQPA | 278 |
| 91-105 | LCNASGAHALQPAAA | 279 |
| 93-107 | NASGAHALQPAAAIL | 280 |
| 95-109 | SGAHALQPAAAILAL | 281 |
| 97-111 | AHALQPAAAILALLP | 282 |
| 99-113 | ALQPAAAILALLPAL | 283 |
| 101-115 | QPAAAILALLPALGL | 284 |
| 103-117 | AAA!LALLPALGLLL | 285 |
| 105-119 | AILALLPALGLLLWG | 286 |
| 107-121 | LALLPALGLLLWGPG | 287 |
| 109-123 | LLPALGLLLWGPGQL | 288 |
| 111-125 | PALGLLLWGPGQL | 289 |

TABLE 11

IFNγ T cell responses induced by the single antigen (Group 1: Ad-PSMA, Group 2: Ad-PSA, Group 3: Ad-PSCA, Group 4: mix of Ad-PSMA, Ad-PSA and Ad-PSCA) or triple antigen expressing adenovirus vectors (Group 4: Ad-733; Group 6: Ad-734; Group 7: Ad-735; Group 8: Ad-796 and Group 9: Ad-809) after adenovirus prime with anti-CTLA-4 analyzed by ELISPOT assay.

| Response to | | animal ID | | | | | | | |
|---|---|---|---|---|---|---|---|---|---|
| PSMA peptides | | 1 | 2 | 3 | 4 | 5 | 6 | 7 | 8 |
| Group No. | 1 | 2356 | 988 | 1505 | 335 | 501 | 2145 | NA | NA |
| | 2 | 342 | 1776 | 154 | 329 | 158 | 438 | 321 | NA |
| | 3 | 0 | 1276 | 40 | 126 | 20 | 0 | NA | NA |
| | 4 | 304 | 1198 | 774 | 2007 | 1277 | 1310 | 1159 | 2774 |
| | 5 | 943 | 2670 | 2757 | 780 | 1082 | 2251 | 1566 | 544 |
| | 6 | 472 | 2092 | 4248 | 1369 | 1760 | 2964 | 1447 | 263 |
| | 7 | 2161 | 2202 | 939 | 869 | 3513 | 1654 | 3424 | 900 |
| | 8 | 1166 | 799 | 2566 | 663 | 1043 | 497 | 1334 | 560 |
| | 9 | 1621 | 3247 | 2031 | 980 | 2942 | 1882 | 1918 | 3805 |
| Response to | | animal ID | | | | | | | |
| PSA peptides | | 1 | 2 | 3 | 4 | 5 | 6 | 7 | 8 |
| Group No. | 1 | 0 | 0 | 0 | 48 | 0 | 42 | NA | NA |
| | 2 | 1419 | 1426 | 298 | 1223 | 1346 | 1120 | 1694 | NA |
| | 3 | 6 | 462 | 91 | 0 | 77 | 0 | NA | NA |
| | 4 | 790 | 1093 | 1611 | 790 | 186 | 783 | 2016 | 1964 |
| | 5 | 101 | 510 | 955 | 665 | 336 | 1512 | 1052 | 119 |
| | 6 | 236 | 673 | 2155 | 724 | 504 | 1600 | 930 | 83 |
| | 7 | 0 | 1086 | 494 | 663 | 2265 | 117 | 1712 | 84 |
| | 8 | 1893 | 2060 | 1490 | 1759 | 2352 | 1700 | 2232 | 1326 |
| | 9 | 1193 | 1432 | 207 | 1738 | 1886 | 949 | 492 | 1940 |
| Response to | | animal ID | | | | | | | |
| PSCA peptides | | 1 | 2 | 3 | 4 | 5 | 6 | 7 | 8 |
| Group No. | 1 | 795 | 425 | 874 | 1069 | 219 | 203 | NA | NA |
| | 2 | 669 | 713 | 391 | 199 | 164 | 560 | 461 | NA |
| | 3 | 510 | 1234 | 1099 | 1115 | 1194 | 339 | NA | NA |
| | 4 | 778 | 528 | 680 | 1101 | 165 | 531 | 1175 | 1009 |
| | 5 | 378 | 1061 | 1161 | 143 | 71 | 756 | 766 | 204 |
| | 6 | 118 | 380 | 1190 | 403 | 829 | 1225 | 148 | 261 |
| | 7 | 615 | 1141 | 794 | 564 | 1175 | 490 | 856 | 204 |
| | 8 | 968 | 1136 | 745 | 290 | 550 | 976 | 955 | 841 |
| | 9 | 929 | 434 | 1150 | 745 | 1120 | 246 | 1195 | 970 |

TABLE 12

IFNγ T cell responses induced by the single antigen (Group 1: PSMA, Group 2: PSA; Group 3: PSCA; Group 4: mix of PSMA, PSA and PSCA) or triple antigen expressing vectors (Groups 5-9) after adenovirus prime with anti-CTLA-4 and DNA electroporation boost immunizations analyzed by ELISPOT assay.

| Response to | | animal ID | | | | | | | |
|---|---|---|---|---|---|---|---|---|---|
| PSMA peptides | | 1 | 2 | 3 | 4 | 5 | 6 | 7 | 8 |
| Group No. | 1 | 1327 | 1535 | 1643 | 535 | 1506 | 1267 | NA | NA |
| | 2 | 15 | 266 | 26 | 191 | 10 | 46 | 1305 | NA |
| | 3 | 0 | 445 | 5 | 75 | 4 | 6 | NA | NA |
| | 4 | 365 | 675 | 731 | 1134 | 244 | 714 | 999 | 1683 |
| | 5 | 270 | 1623 | 2254 | 626 | 860 | 2245 | 1453 | 1046 |
| | 6 | 541 | 1151 | 2923 | 1094 | 1061 | 1746 | 691 | 489 |
| | 7 | 1183 | 1183 | 1453 | 1649 | 2844 | 1470 | 2321 | 991 |
| | 8 | 486 | 69 | 399 | 216 | 351 | 758 | 416 | 1389 |
| | 9 | 1430 | 2631 | 2015 | 475 | 1368 | 1826 | 1851 | 3141 |
| Response to | | animal ID | | | | | | | |
| PSA peptides | | 1 | 2 | 3 | 4 | 5 | 6 | 7 | 8 |
| Group No. | 1 | 0 | 0 | 0 | 1 | 0 | 26 | NA | NA |
| | 2 | 1883 | 1236 | 1574 | 393 | 461 | 941 | 1565 | NA |

TABLE 12-continued

IFNγ T cell responses induced by the single antigen (Group 1: PSMA, Group 2: PSA; Group 3: PSCA; Group 4: mix of PSMA, PSA and PSCA) or triple antigen expressing vectors (Groups 5-9) after adenovirus prime with anti-CTLA-4 and DNA electroporation boost immunizations analyzed by ELISPOT assay.

| | | | | | | | | | |
|---|---|---|---|---|---|---|---|---|---|
| | 3 | 33 | 30 | 9 | 13 | 8 | 11 | NA | NA |
| | 4 | 571 | 1129 | 1180 | 210 | 88 | 274 | 924 | 360 |
| | 5 | 50 | 1255 | 1344 | 628 | 210 | 638 | 948 | 1161 |
| | 6 | 88 | 228 | 1390 | 489 | 1006 | 908 | 683 | 51 |
| | 7 | 0 | 211 | 321 | 156 | 1509 | 56 | 199 | 85 |
| | 8 | 414 | 611 | 85 | 105 | 544 | 1080 | 331 | 1883 |
| | 9 | 434 | 821 | 556 | 343 | 1160 | 510 | 144 | 1115 |
| Response to PSCA | | animal ID | | | | | | | |
| peptides | | 1 | 2 | 3 | 4 | 5 | 6 | 7 | 8 |
| Group No. | 1 | 615 | 799 | 533 | 74 | 258 | 61 | NA | NA |
| | 2 | 194 | 170 | 133 | 133 | 8 | 66 | 405 | NA |
| | 3 | 819 | 1071 | 873 | 839 | 1045 | 724 | NA | NA |
| | 4 | 543 | 506 | 664 | 470 | 70 | 673 | 761 | 1235 |
| | 5 | 154 | 455 | 1218 | 109 | 218 | 1094 | 285 | 569 |
| | 6 | 56 | 293 | 603 | 506 | 745 | 911 | 63 | 165 |
| | 7 | 429 | 298 | 939 | 589 | 1226 | 263 | 803 | 451 |
| | 8 | 279 | 214 | 871 | 61 | 144 | 511 | 193 | 963 |
| | 9 | 379 | 191 | 1196 | 73 | 699 | 198 | 616 | 836 |

Example 11. Construction of C68 Vectors

11A. Vector AdC68-734 Construciton

AdC68-734 is a replication incompetent adenovirus vector based upon the chimpanzee adenovirus C68 that encodes three immunogenic PAA polypeptides—an immunogenic PSA polypeptide, immunogenic PSCA polypeptide, and immunogenic PSMA polypeptide. The vector sequence was designed in silico. First, the baseline full length C68 sequence was obtained from Genbank (Definition: Simian adenovirus 25, complete genome; accession number AC_000011.1). Five point mutations described in the literature were introduced into the sequence. (Roshorm, Y., M. G. Cottingham, et al. (2012). "T cells induced by recombinant chimpanzee adenovirus alone and in prime-boost regimens decrease chimeric EcoHIV/NDK challenge virus load." Eur J Immunol 42(12): 3243-3255) Next, 2.6 kilobases of the viral early transcription region 1 (E1) were deleted to render the vector replication incompetent, and 3.5 kilobases of the early transcription region 3 (E3) were removed to create space in the vector for the transgene expression cassette. (Tatsis, N., L. Tesema, et al. (2006). Chimpanzee-origin adenovirus vectors as vaccine carriers. Gene Ther. 13: 421-429) A highly efficient eukaryotic expression cassette was then introduced into the E1 region. The expression cassette included the following components: (A) Cytomegalovirus (CMV) immediate early enhancer/promoter, (B) Tet operator (binding site for the tetracycline repressor), (C) the multi-antigen construct comprising (1) nucleotide sequence encoding amino acids 25 through 261 of the human PSA, (2) Cis acting hydrolase element encoding a glycine-serine linker and Thosea asigna virus 2A peptide (T2A), (3) nucleotide sequence encoding amino acids 2 through 123 of the human PSCA, (4) Cis acting hydrolase element encoding a glycine-serine linker and Foot and Mouth Disease Virus 2A peptide (F2A), and (5) nucleotide sequence encoding amino acids 15 through 750 the human PSMA, and (D) SV40 polyA transcription termination signal. Finally, Pacl restriction sites were inserted at each end of the viral genome to facilitate the release of the genome from the parent Bacmid. Nucleotides from the Pacl restriction sites are removed during viral propagation and, therefore, are not incorporated into the genome of the vector product itself. A nucleotid sequence of the entire vector AdC68-734, including the Pacl restriction sites, is set forth in SEQ ID NO:58. The multi-antigen construct (PSA-T2A-PSCA-F2A-PSMA) incorporated in vector AdC68-734 (as well as in Plasmid 458) is also set forth in SEQ ID NO:61. The amino acid sequence encoded by the multi-agtigen construct of SEQ ID NO:61 is set forth in SEq ID NO:60. The components of vector AdC68-734 are provided in Table 13.

TABLE 13

Components of Vector AdC68-734

| Base Numbers | Feature |
|---|---|
| 1-8 | Pacl restriction site |
| 9-463 | Bases 1-455 of AC000011.1 (SEQ ID NO: 57) |
| 464-1096 | CMV enhancer/promoter |
| 1031-1070 | Tetracycline operator/repressor binding site |
| 1106-1825 | Sequence encoding amino acids 25 through 261 of the human PSA and the preceding methionine-alanine-serine linker |
| 1826-1831 | Linker encoding glycine - serine |
| 1832-1885 | Cis acting hydrolase element encoding a Thosea asigna virus 2A peptide |
| 1886-2257 | Sequence encoding amino acids 2 through 123 of the human PSCA and the preceding alanine-serine linker |
| 2258-2263 | Linker encoding glycine - serine |
| 2264-2323 | Cis acting hydrolase element encoding a Foot and Mouth Disease Virus 2A peptide |
| 2324-4543 | Sequence encoding amino acids 15 through 750 of the human PSMA and the preceding methionine-alanine-serine linker |
| 4541-4543 | Stop codon |
| 4596-4823 | SV40 polyA transcription termination signal |
| 4824-29622 | Bases 3013-27811 of AC000011.1 (SEQ ID NO: 57) |
| 29623-34811 | Bases 31331-36519 of AC000011.1 (SEQ ID NO: 57) |
| 10730 | C to G substitution at base 8919 of AC000011.1 (SEQ ID NO: 57) |
| 17569 | G to C substitution at base 15758 of AC000011.1 (SEQ ID NO: 57) |
| 18967 | A to T substitution at base 17156 of AC000011.1 (SEQ ID NO: 57) |
| 19245 | C to A substitution at base 17434 of AC000011.1 (SEQ ID NO: 57) |
| 33520 | G to C substitution at base 35228 of AC000011.1 (SEQ ID NO: 57) |
| 34812-34819 | Pacl restriction site |

Figure 11:
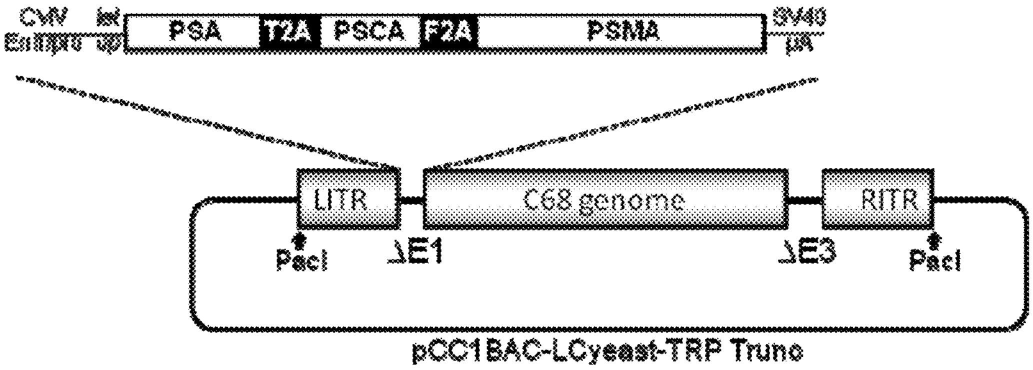
FIG. 11. Graph showing the genomic organization of the AdC68-734 vector. CMV Enh/pro=human cytomegalovirus immediate early enhancer and promoter; tet op=tetracycline operator; T2A=Thosea asigna virus 2A; F2A=Foot and Mouth Disease Virus 2A; SV40 pA=Simian Virus 40 polyadenylation signal; LITR=left inverted terminal repeat; RITR=right inverted terminal repeat.

Following in silico design, the 34,819 base-pair sequence was biochemically synthesized in a multi-stage process utilizing in vitro oligo synthesis and subsequent recombination-mediated intermediate assembly in *E. coli* and yeast. The viral genome was ultimately inserted into a bacterial artificial chromosome (pCC1BAC-LCyeast-TRP Trunc) for propagation. Next generation sequencing (MiSeq technology) was performed at multiple steps in the production process, including the final Bacmid 17.3.3.22 lot that was used to create the viral seed stock. Viral seed stock was generated by digesting Bacmid 17.3.3.22 with Pacl to release the AdC68-734 genome from the BAC backbone. The linearized nucleic acid was transfected into an E1 complimenting adherent HEK293 cell line and upon visible cytopathic effects and adenovirus foci formation, cultures were harvested by multiple rounds of freezing/thawing to release virus from the cells. Viruses were amplified and purified by standard techniques. The genetic organization of Bacmid 17.3.3.22 is provided in FIG. 11.

11B. Constructions of Additional C68 Vectors

Additional triple antigen C68 vectors were constructed in a similar fashion to AdC68-734. Some of the additional vectors involve functional deletions in the C68 genome that are slightly different from those in Vector AdC68-734, while others incorporate different multi-antigen constructs. Based on these examples and other description of the present disclosure, a person skilled in the art would be able construct additional vectors from C68 for expressing various multi-antigen constructs, all of which are within the scope of the present invention.

(1) AdC68X-734 and AdC68W-734

Vector AdC68X-734 was constructed from C68 by functional deletion of the E1 and E3 regions of the C68 genome through deletions of nucleotides 577-3403 (E1 region) and 27125-31831 (E2 region) of the C68 genome of SEQ ID NO:57 and by insertion of the triple antigen construct (PSA-T2A-PSCA-F2A-PSMA) of SEQ ID NO:61 in the deleted E1 region. Vector AdC68W-734 is identical to Vector AdC68-734 except that AdC68W-734 contains one or more mutations in the C68 NDA sequence.

(2) AdC68X-733 and AdC68X-735 Vectors AdC68X-733 and AdC68X-735 were created by replacing the triple antigen-construct incorporated in the AdC68X-734 vector with the triple antigen construct of SEQ ID NOs:65 and 66, respectively. The multi-antigen construct incorporated in vector AdC68X-733 (i.e, PSA-F2A-PSMA-T2A-PSCA) is the same as that incorporated in Plasmid 457 and the multi-antigen construct incorporated in vector AdC68X-735 (i.e., PSCA-F2A-PSMA-mIRES-PSA) is the same as that in Plasmid 459.

11C. Research Productivity Characterization

Various research grade lots of AdC68-734 were produced and tested for productivity. Bacmid was digested with Pacl to release the vector genome from the BAC backbone and the linearized nucleic acid was transfected into E1 complimenting adherent HEK293 cell lines. When extensive cytopathic effects and adenovirus foci were visible, cultures were harvested by multiple rounds of freezing/thawing to release virus from the cells. Viruses from these Passage 0 (P0) cultures were amplified at least one additional passage in tissue culture flasks and then used as seed stocks for research scale production runs (~0.5 to 3e13 total viral particles per lot). In total, 11 production runs were executed (five in HEK293 suspension cells and six in HEK293 adherent cells). The average specific productivity was 15,000+/−6,000 viral particles purified per initial infected cell, with a viral particle:infectious unit ratio of 55. Research scale productivities are summarized in Table 14.

TABLE 14

| Specific productivities and infectivities of research scale production lots | | |
|---|---|---|
| Lot | Specific productivity (purified viral particles/cell) | Viral particle:infectious unit ratio |
| 20039 | 17000 | 33 |
| 20424 | 19000 | 49 |
| 20542 | 12000 | 76 |
| 20609 | 25000 | 54 |
| 20626 | 16000 | 58 |
| 20671 | 19000 | ND |
| 130502 | 17000 | 51 |
| 130718* | 3500 | 52 |
| 130820 | 7400 | 55 |

TABLE 14-continued

| Specific productivities and infectivities of research scale production lots | | |
|---|---|---|
| Lot | Specific productivity (purified viral particles/cell) | Viral particle:infectious unit ratio |
| 130821 | 9300 | 70 |
| 130822 | 19000 | 54 |

*Late passage HEK293 suspension cells used in production

11 D. Antigen Expression

Figure 12:
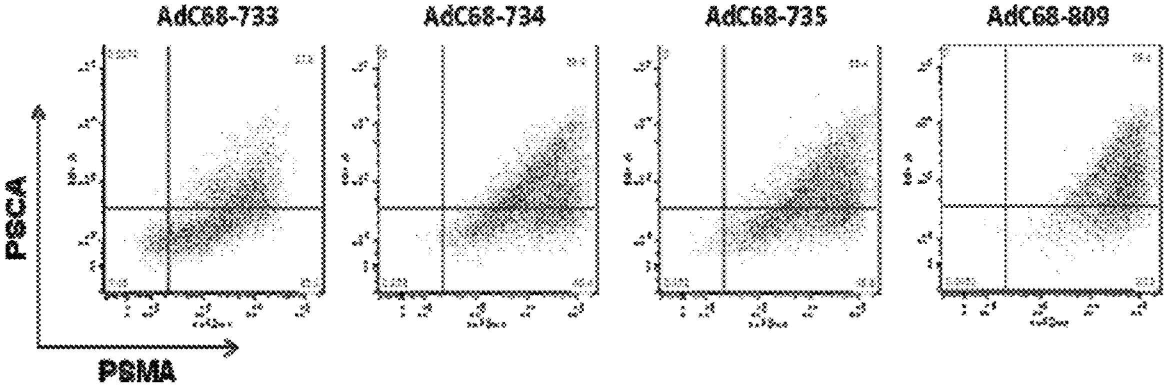
FIG. 12. Dot plots showing expression of PSMA and PSCA on the surface of A549 cells transduced with triple antigen expressing AdC68 vectors by flow cytometry.
Figure 13:
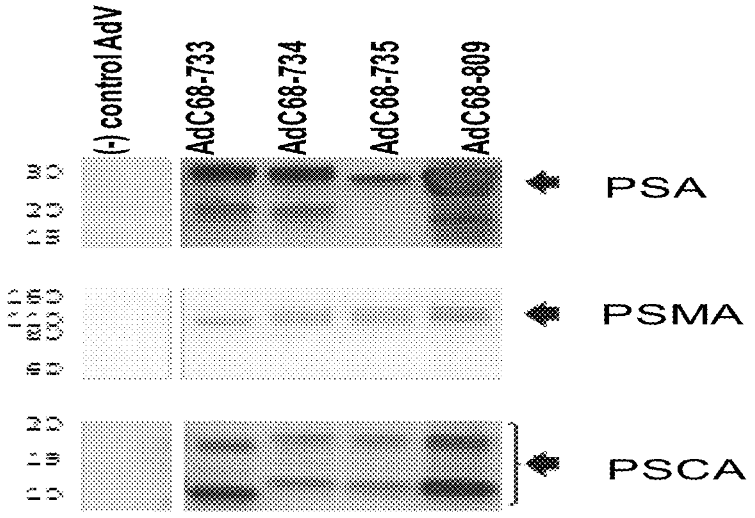
FIG. 13. Western blot from lysates of A549 infected by AdC68 vectors.

The surface expression of PSMA and PSCA was measured by flow cytometry (FIG. 12) and total cellular expression of PSMA, PSCA and PSA was measured by western blot analysis (FIG. 13) from AdC68-vector infected A549 cells at an M01=10,000.

Mock and AdC68 infected cells were stained with anti-PSCA (fluorescein isothiocyanate-conjugated monoclonal antibody 1G8 [1:200]) and PSMA antibodies (allophycocyanin-conjugated monoclonal antibody J591 [1:200]) for flow cytometric analysis, 2 days post infection. Surface expression of PSCA and PSMA were detected from majority of the cells infected with the different triple antigen-expressing AdC68 vectors with varying levels. Relatively higher levels of expression of PSCA and PSMA were detected from AdC68X-809 infected cells and lower levels were detected from AdC68X-733 infected cell. Two days after infection, total cellular lysates from approximately $1\times10^5$ infected cells were loaded onto each lane of a sodium dodecyl sulfate polyacrylamide gel. The gel was subsequently transferred to a membrane for the detection of PSA, PSMA, and PSCA proteins using primary antibodies specific to PSA, PSMA, and PSCA by western blot analysis. The expressions of all three antigens were detected in the infected cells to varying degrees. While relatively similar levels of PSMA and PSCA were detected from AdC68-734 and AdC68X-735 infected lysates, higher levels of PSA were detected from AdC68-734 lysates compared to those from AdC68X-735

11E. Immunogenicity

A head-to head comparison of the CD8 IFNγ responses induced by various triple antigen AdC68 vectors was performed. Each group of mice (n=5 per group) was immunized with AdC68-734, AdC68X-735, AdC68X-809, or Ad5-734 at 1e9 or 1 el 0 VP in the quadriceps. IFNγ CD8+ T cell responses in the mice were measured by collecting the spleens from each animal on day 13 post immunization. Splenocytes were isolated and subjected to an IFNγ ELISPOT assay to measure the PSMA, PSCA, and PSA-specific T cell responses. Briefly, 2.5 to $5\times10^5$ splenocytes from immunized animals were cultured in the presence of individual human PSMA, PSCA, or PSA-specific peptides at 10 μg/ml. The 15-mer peptides were previously defined to contain CD8+ T cell epitopes to each prostate antigen. Splenocytes cultured with medium alone served as a control. Each condition was performed in triplicate. The plates were incubated for 20 h at 37° C. and 5% $CO_2$, washed, and developed after incubation as per the manufacturer's instructions. The number of IFNγ SFC was counted by a CTL reader. The results show the average number of PSMA, PSCA, and PSA-specific SFCs with the medium alone background values subtracted, and normalized to $1\times10^6$ splenocytes.

In summary, all triple antigen expressing AdC68 vectors induced immune responses to all three antigens but to different magnitude. At 1e9 VP, the response to PSMA by the AdC68 vectors was similar to Ad5. The response to PSCA by the three AdC68 vectors was similar or lower than the response induced by Ad5 while the response to PSA was lower with Ad68-735 compared to all of the vectors tested. However at 1e10VP, AdC68-809 induced similar or better responses to all three antigens compared to AdC68-734, AdC68-735 or Ad5. Results are presented in Table 15.

TABLE 15

IFNγ T cellular Immunogenicity by AdC68 vectors co-expressing PSMA, PSA and PSCA in C57BL6 mice by IFNγ ELISPOT assay

| Construct | Ad5-734 | | AdC68-734 | | AdC68-809 | | AdC68-735 | |
|---|---|---|---|---|---|---|---|---|
| Titer, vp | 1e9 | 1e10 | 1e9 | 1e10 | 1e9 | 1e10 | 1e9 | 1e10 |
| PSMA | 473 | 1221 | 699 | 296 | 489 | 684 | 288 | 503 |
| | 491 | 831 | 143 | 513 | 221 | 687 | 203 | 261 |
| | 435 | 740 | 149 | 607 | 315 | 809 | 256 | 745 |
| | 248 | 596 | 224 | 116 | 347 | 317 | 317 | 1197 |
| | 709 | 711 | 269 | 681 | 296 | 536 | 320 | 368 |
| PSA | 1299 | 1472 | 1180 | 1741 | 1973 | 1979 | 533 | 695 |
| | 939 | 1025 | 1327 | 1985 | 841 | 1532 | 313 | 1615 |
| | 1096 | 797 | 672 | 780 | 1869 | 1979 | 277 | 1420 |
| | 989 | 933 | 904 | 635 | 1009 | 1669 | 535 | 616 |
| | 1971 | 1047 | 1309 | 1901 | 907 | 1920 | 824 | 403 |
| PSCA | 104 | 64 | 228 | 61 | 115 | 197 | 148 | 92 |
| | 160 | 80 | 11 | 41 | 59 | 92 | 80 | 897 |
| | 163 | 52 | 15 | 116 | 25 | 235 | 47 | 39 |
| | 119 | 223 | 32 | 57 | 24 | 96 | 107 | 33 |
| | 207 | 100 | 8 | 53 | 17 | 35 | 32 | 16 |

SEQ ID NO: 1. AMINO ACID SEQUENCE OF THE FULL LENGTH HUMAN PSMA

MWNLLHETDSAVATARRPRWLCAGALVLAGGFFLLGFLFGWFIKSSNEA

TNITPKHNMKAFLDELKAENIKKFLYNFTQIPHLAGTEQNFQLAKQIQS

QWKEFGLDSVELAHYDVLLSYPNKTHPNYISIINEDGNEIFNTSLFEPP

PPGYENVSDIVPPFSAFSPQGMPEGDLVYVNYARTEDFFKLERDMKINC

SGKIVIARYGKVFRGNKVKNAQLAGAKGVILYSDPADYFAPGVKSYPDG

WNLPGGGVQRGNILNLNGAGDPLTPGYPANEYAYRRGIAEAVGLPSIPV

HPIGYYDAQKLLEKMGGSAPPDSSWRGSLKVPYNVGPGFTGNFSTQKVK

MHIHSTNEVTRIYNVIGTLRGAVEPDRYVILGGHRDSWVFGGIDPQSGA

AVVHEIVRSFGTLKKEGWRPRRTILFASWDAEEFGLLGSTEWAEENSRL

LQERGVAYINADSSIEGNYTLRVDCTPLMYSLVHNLTKELKSPDEGFEG

KSLYESWTKKSPSPEFSGMPRISKLGSGNDFEVFFQRLGIASGRARYTK

NWETNKFSGYPLYHSVYETYELVEKFYDPMFKYHLTVAQVRGGMVFELA

NSIVLPFDCRDYAVVLRKYADKIYSISMKHPQEMKTYSVSFDSLFSAVK

NFTEIASKFSERLQDFDKSNPIVLRMMNDQLMFLERAFIDPLGLPDRPF

YRHVIYAPSSHNKYAGESFPGIYDALFDIESKVDPSKAWGEVKRQIYVA

AFTVQAAAETLSEVA

SEQ ID NO: 2. NUCLEOTIDE SEQUENCE ENCODING THE FULL LENGTH HUMAN PSMA OF SEQ ID NO: 1 atgtggaatctccttcacgaaaccgactcggctgtggccaccgcgcgcc gcccgcgctggctgtgcgctggggcgctggtgctggcgggtggcttctt tctcctcggcttcctcttcgggtggtttataaaatcctccaatgaagct actaacattactccaaagcataatatgaaagcatttttggatgaattga aagctgagaacatcaagaagttcttatataattttacacagataccaca -continued tttagcaggaacagaacaaaactttcagcttgcaaagcaaattcaatcc cagtggaaagaatttggcctggattctgttgagctagcacattatgatg tcctgttgtcctacccaaataagactcatcccaactacatctcaataat taatgaagatggaaatgagattttcaacacatcattatttgaaccacct cctccaggatatgaaaatgtttcggatattgtaccacctttcagtgctt tctctcctcaaggaatgccagagggcgatctagtgtatgttaactatgc acgaactgaagacttctttaaattggaacgggacatgaaaatcaattgc tctgggaaaattgtaattgccagatatgggaaagttttcagaggaaata aggttaaaaatgcccagctggcaggggccaaaggagtcattctctactc cgaccctgctgactactttgctcctggggtgaagtcctatccagatggt tggaatcttcctggaggtggtgtccagcgtggaaatatcctaaatctga atggtgcaggagaccctctcacaccaggttacccagcaaatgaatatgc ttataggcgtggaattgcagaggctgttggtcttccaagtattcctgtt catccaattggatactatgatgcacagaagctcctagaaaaaatgggtg gctcagcaccaccagatagcagctggagaggaagtctcaaagtgcccta caatgttggacctggctttactggaaacttttctacacaaaaagtcaag atgcacatccactctaccaatgaagtgacaagaatttacaatgtgatag gtactctcagaggagcagtggaaccagacagatatgtcattctgggagg tcaccgggactcatgggtgtttggtggtattgaccctcagagtggagca gctgttgttcatgaaattgtgaggagctttggaacactgaaaaaggaag ggtggagacctagaagaacaattttgtttgcaagctgggatgcagaaga atttggtcttcttggttctactgagtgggcagaggagaattcaagactc cttcaagagcgtggcgtggcttatattaatgctgactcatctatagaag gaaactacactctgagagttgattgtacaccgctgatgtacagcttggt acacaacctaacaaaagagctgaaaagccctgatgaaggctttgaaggc aaatctctttatgaaagttggactaaaaaaagtccttccccagagttca gtggcatgcccaggataagcaaattgggatctggaaatgattttgaggt gttcttccaacgacttggaattgcttcaggcagagcacggtatactaaa aattgggaaacaaacaaattcagcggctatccactgtatcacagtgtct atgaaacatatgagttggtggaaaagttttatgatccaatgtttaaata tcacctcactgtggcccaggttcgaggagggatggtgtttgagctagcc aattccatagtgctcccttttgattgtcgagattatgctgtagttttaa gaaagtatgctgacaaaatctacagtatttctatgaaacatccacagga aatgaagacatacagtgtatcatttgattcacttttttctgcagtaaag aattttacagaaattgcttccaagttcagtgagagactccaggactttg acaaaagcaacccaatagtattaagaatgatgaatgatcaactcatgtt tctggaaagagcatttattgatccattagggttaccagacaggcctttt tataggcatgtcatctatgctccaagcagccacaacaagtatgcagggg agtcattcccaggaatttatgatgctctgtttgatattgaaagcaaagt -continued ggacccttccaaggcctggggagaagtgaagagacagatttatgttgca gccttcacagtgcaggcagctgcagagactttgagtgaagtagcc

SEQ ID NO: 3. AMINO ACID SEQUENCE OF PSMA SHUFFLED ANTIGEN 1

SEQ ID NO: 4. NUCLEOTIDE SEQUENCE ENCODING AMINO ACID SEQUENCE OF PSMA SHUFFLED ANTIGEN 1 OF SEQ ID NO: 3

SEQ ID NO: 5. AMINO ACID SEQUENCE OF PSMA SHUFFLED ANTIGEN 2

SEQ ID NO: 6. NUCLEOTIDE SEQUENCE ENCODING AMINO ACID SEQUENCE OF PSMA SHUFFLED ANTIGEN 2 OF SEQ ID NO: 5

SEQ ID NO: 7. AMINO ACID SEQUENCE OF PSMA SHUFFLED ANTIGEN 3

SEQ ID NO: 8. NUCLEOTIDE SEQEUNCE ENCODING AMINO ACID SEQUENCE OF PSMA SHUFFLED ANTIGEN 3 OF SEQ ID NO: 7

SEQ ID NO: 9. AMINO ACID SEQUENCE OF A MEMBRANE-BOUND PSMA ANTIGEN

MASARRPRWLCAGALVLAGGFFLLGFLFGWFIKSSNEATNITPKHNMKA

FLDELKAENIKKFLYNFTQIPHLAGTEQNFQLAKQIQSQWKEFGLDSVE

LAHYDVLLSYPNKTHPNYISIINEDGNEIFNTSLFEPPPPGYENVSDIV

PPFSAFSPQGMPEGDLVYVNYARTEDFFKLERDMKINCSGKIVIARYGK

VFRGNKVKNAQLAGAKGVILYSDPADYFAPGVKSYPDGWNLPGGGVQRG

NILNLNGAGDPLTPGYPANEYAYRRGIAEAVGLPSIPVHPIGYYDAQKL

LEKMGGSAPPDSSWRGSLKVPYNVGPGFTGNFSTQKVKMHIHSTNEVTR

IYNVIGTLRGAVEPDRYVILGGHRDSWVFGGIDPQSGAAVVHEIVRSFG

TLKKEGWRPRRTILFASWDAEEFGLLGSTEWAEENSRLLQERGVAYINA

DSSIEGNYTLRVDCTPLMYSLVHNLTKELKSPDEGFEGKSLYESWTKKS

PSPEFSGMPRISKLGSGNDFEVFFQRLGIASGRARYTKNWETNKFSGYP

LYHSVYETYELVEKFYDPMFKYHLTVAQVRGGMVFELANSIVLPFDCRD

YAVVLRKYADKIYSISMKHPQEMKTYSVSFDSLFSAVKNFTEIASKFSE

RLQDFDKSNPIVLRMMNDQLMFLERAFIDPLGLPDRPFYRHVIYAPSSH

NKYAGESFPGIYDALFDIESKVDPSKAWGEVKRQIYVAAFTVQAAAETL

SEVA

SEQ ID NO: 10. NUCLEOTIDE SEQEUNCE ENCODING AMINO ACID SEQUENCE OF THE MEMBRANE-BOUND PSMA ANTIGEN OF SEQ ID NO: 9 atggctagcgcgcgccgcccgcgctggctgtgcgctggggcgctggtgc tggcgggtggcttctttctcctcggcttcctcttcgggtggtttataaa atcctccaatgaagctactaacattactccaaagcataatatgaaagca tttttggatgaattgaaagctgagaacatcaagaagttcttatataatt ttacacagataccacatttagcaggaacagaacaaaactttcagcttgc aaagcaaattcaatcccagtggaaagaatttggcctggattctgttgag ctggcacattatgatgtcctgttgtcctacccaaataagactcatccca actacatctcaataattaatgaagatggaaatgagattttcaacacatc attatttgaaccacctcctccaggatatgaaaatgtttcggatattgta ccacctttcagtgctttctctcctcaaggaatgccagagggcgatctag tgtatgttaactatgcacgaactgaagacttctttaaattggaacggga catgaaaatcaattgctctgggaaaattgtaattgccagatatgggaaa gttttcagaggaaataaggttaaaaatgcccagctggcaggggccaaag gagtcattctctactccgaccctgctgactactttgctcctggggtgaa gtcctatccagatggttggaatcttcctggaggtggtgtccagcgtgga aatatcctaaatctgaatggtgcaggagaccctctcacaccaggttacc cagcaaatgaatatgcttataggcgtggaattgcagaggctgttggtct tccaagtattcctgttcatccaattggatactatgatgcacagaagctc ctagaaaaaatgggtggctcagcaccaccagatagcagctggagaggaa gtctcaaagtgccctacaatgttggacctggctttactggaaacttttc tacacaaaaagtcaagatgcacatccactctaccaatgaagtgacaaga atttacaatgtgataggtactctcagaggagcagtggaaccagacagat atgtcattctgggaggtcaccgggactcatgggtgtttggtggtattga ccctcagagtggagcagctgttgttcatgaaattgtgaggagctttgga acactgaaaaaggaagggtggagacctagaagaacaattttgtttgcaa gctgggatgcagaagaatttggtcttcttggttctactgagtgggcaga ggagaattcaagactccttcaagagcgtggcgtggcttatattaatgct gactcatctatagaaggaaactacactctgagagttgattgtacaccgc tgatgtacagcttggtacacaacctaacaaaagagctgaaaagccctga tgaaggctttgaaggcaaatctctttatgaaagttggactaaaaaaagt ccttccccagagttcagtggcatgcccaggataagcaaattgggatctg gaaatgattttgaggtgttcttccaacgacttggaattgcttcaggcag agcacggtatactaaaaattgggaaacaaacaaattcagcggctatcca ctgtatcacagtgtctatgaaacatatgagttggtggaaaagttttatg atccaatgtttaaatatcacctcactgtggcccaggttcgaggagggat ggtgtttgagctggccaattccatagtgctccctttttgattgtcgagat tatgctgtagttttaagaaagtatgctgacaaaatctacagtatttcta tgaaacatccacaggaaatgaagacatacagtgtatcatttgattcact tttttctgcagtaaagaattttacagaaattgcttccaagttcagtgag agactccaggactttgacaaaagcaacccaatagtattaagaatgatga atgatcaactcatgtttctggaaagagcatttattgatccattagggtt accagacaggcctttttataggcatgtcatctatgctccaagcagccac aacaagtatgcaggggagtcattcccaggaatttatgatgctctgtttg atattgaaagcaaagtggacccttccaaggcctggggagaagtgaagag acagatttatgttgcagccttcacagtgcaggcagctgcagagactttg agtgaagtagcc

SEQ ID NO: 11. AMINO ACID SEQUENCE OF A CYTOSOLIC PSMA ANTIGEN

SEQ ID NO: 12. NUCLEOTIDE SEQEUNCE ENCODING AMINO ACID SEQUENCE OF THE CYTOSOLIC PSMA ANTIGEN OF SEQ ID NO: 11

-continued

SEQ ID NO: 13. AMINO ACID SEQUENCE OF A SECRETED PSMA ANTIGEN

SEQ ID NO: 14. NUCLEOTIDE SEQUENCE ENCODING AMINO ACID SEQUENCE OF THE SECRETED PSMA ANTIGEN OF SEQ ID NO: 13

SEQ ID NO: 15. AMINO ACID SEQUENCE OF THE FULL LENGTH HUMAN PSA

MASWVPVVFLTLSVTWIGAAPLILSRIVGGWECEKHSQPWQVLVASRGR
AVCGGVLVHPQWVLTAAHCIRNKSVILLGRHSLFHPEDTGQVFQVSHSF
PHPLYDMSLLKNRFLRPGDDSSHDLMLLRLSEPAELTDAVKVMDLPTQE
PALGTTCYASGWGSIEPEEFLTPKKLQCVDLHVISNDVCAQVHPQKVTK
FMLCAGRWTGGKSTCSGDSGGPLVCNGVLQGITSWGSEPCALPERPSLY
TKVVHYRKWIKDTIVANP

SEQ ID NO: 16. NUCLEOTIDE SEQUENCE ENCODING AMINO ACID SEQUENCE OF THE FULL LENGTH HUMAN PSA OF SEQ ID NO: 15 atggctagctgggtcccggttgtcttcctcaccctgtccgtgacgtgga
ttggcgctgcgcccctcatcctgtctcggattgtgggaggctgggagtg
cgagaagcattcccaaccctggcaggtgcttgtggcctctcgtggcagg
gcagtctgcggcggtgttctggtgcacccccagtgggtcctcacagctg
cccactgcatcaggaacaaaagcgtgatcttgctgggtcggcacagctt
gtttcatcctgaagacacaggccaggtatttcaggtcagccacagcttc
ccacacccgctctacgatatgagcctcctgaagaatcgattcctcaggc
caggtgatgactccagccacgacctcatgctgctccgcctgtcagagcc
tgccgagctcacggatgctgtgaaggtcatggacctgcccacccaggag
ccagcactggggaccacctgctacgcctcaggctggggcagcattgaac
cagaggagttcttgaccccaaagaaacttcagtgtgtggacctccatgt
tatttccaatgacgtgtgtgcgcaagttcaccctcagaaggtgaccaag
ttcatgctgtgtgctggacgctggacagggggcaaaagcacctgctcgg
gtgattctgggggcccacttgtctgtaatggtgtgcttcaaggtatcac
gtcatggggcagtgaaccatgtgccctgcccgaaaggccttccctgtac
accaaggtggtgcattaccggaagtggatcaaggacaccatcgtggcca
acccc

SEQ ID NO: 17. AMINO ACID SEQUENCE OF A CYTOSOLIC PSA ANTIGEN

MASIVGGWECEKHSQPWQVLVASRGRAVCGGVLVHPQWVLTAAHCIRNK
SVILLGRHSLFHPEDTGQVFQVSHSFPHPLYDMSLLKNRFLRPGDDSSH
DLMLLRLSEPAELTDAVKVMDLPTQEPALGTTCYASGWGSIEPEEFLTP
KKLQCVDLHVISNDVCAQVHPQKVTKFMLCAGRWTGGKSTCSGDSGGPL
VCNGVLQGITSWGSEPCALPERPSLYTKVVHYRKWIKDTIVANP

SEQ ID NO: 18. NUCLEOTIDE SEQEUNCE ENCODING AMINO ACID SEQUENCE OF THE CYTOSOLIC PSA ANTIGEN OF SEQ ID NO: 17 atggctagcattgtgggaggctgggagtgcgagaagcattcccaaccct
ggcaggtgcttgtggcctctcgtggcagggcagtctgcggcggtgttct
ggtgcacccccagtgggtcctcacagctgcccactgcatcaggaacaaa
agcgtgatcttgctgggtcggcacagcttgtttcatcctgaagacacag -continued gccaggtatttcaggtcagccacagcttcccacacccgctctacgatat
gagcctcctgaagaatcgattcctcaggccaggtgatgactccagccac
gacctcatgctgctccgcctgtcagagcctgccgagctcacggatgctg
tgaaggtcatggacctgcccacccaggagccagcactggggaccacctg
ctacgcctcaggctggggcagcattgaaccagaggagttcttgacccca
aagaaacttcagtgtgtggacctccatgttatttccaatgacgtgtgtg
cgcaagttcaccctcagaaggtgaccaagttcatgctgtgtgctggacg
ctggacagggggcaaaagcacctgctcgggtgattctgggggcccactt
gtctgtaatggtgtgcttcaaggtatcacgtcatggggcagtgaaccat
gtgccctgcccgaaaggccttccctgtacaccaaggtggtgcattaccg
gaagtggatcaaggacaccatcgtggccaacccc

SEQ ID NO: 19. AMINO ACID SEQUENCE OF A MEMBRANE-BOUND PSA ANTIGEN

MASARRPRWLCAGALVLAGGFFLLGFLFGWFIKSSNEATNITPGIVGGW
ECEKHSQPWQVLVASRGRAVCGGVLVHPQWVLTAAHCIRNKSVILLGRH
SLFHPEDTGQVFQVSHSFPHPLYDMSLLKNRFLRPGDDSSHDLMLLRLS
EPAELTDAVKVMDLPTQEPALGTTCYASGWGSIEPEEFLTPKKLQCVDL
HVISNDVCAQVHPQKVTKFMLCAGRWTGGKSTCSGDSGGPLVCNGVLQG
ITSWGSEPCALPERPSLYTKVVHYRKWIKDTIVANP

SEQ ID NO: 20. NUCLEOTIDE SEQUENCE ENCODING AMINO ACID SEQUENCE OF THE MEMBRANE-BOUND PSA ANTIGEN OF SEQ ID NO: 19 atggctagcgcgcgccgcccgcgctggctgtgcgctggggcgctggtgc
tggcgggtggcttctttctcctcggcttcctcttcgggtggtttataaa
atcctccaatgaagctactaacattactccaggaattgtgggaggctgg
gagtgcgagaagcattcccaaccctggcaggtgcttgtggcctctcgtg
gcagggcagtctgcggcggtgttctggtgcacccccagtgggtcctcac
agctgcccactgcatcaggaacaaaagcgtgatcttgctgggtcggcac
agcttgtttcatcctgaagacacaggccaggtatttcaggtcagccaca
gcttcccacacccgctctacgatatgagcctcctgaagaatcgattcct
caggccaggtgatgactccagccacgacctcatgctgctccgcctgtca
gagcctgccgagctcacggatgctgtgaaggtcatggacctgcccaccc
aggagccagcactggggaccacctgctacgcctcaggctggggcagcat
tgaaccagaggagttcttgaccccaaagaaacttcagtgtgtggacctc
catgttatttccaatgacgtgtgtgcgcaagttcaccctcagaaggtga
ccaagttcatgctgtgtgctggacgctggacagggggcaaaagcacctg
ctcgggtgattctgggggcccacttgtctgtaatggtgtgcttcaaggt
atcacgtcatggggcagtgaaccatgtgccctgcccgaaaggccttccc
tgtacaccaaggtggtgcattaccggaagtggatcaaggacaccatcgt
ggccaacccctga -continued SEQ ID NO: 21. AMINO ACID SEQUENCE OF THE FULL LENGTH HUMAN PSCA
MASKAVLLALLMAGLALQPGTALLCYSCKAQVSNEDCLQVENCTQLGEQ

CWTARIRAVGLLTVISKGCSLNCVDDSQDYYVGKKNITCCDTDLCNASG

AHALQPAAAILALLPALGLLLWGPGQL

SEQ ID NO: 22. NUCLEOTIDE SEQUENCE ENCODING AMINO ACIDSEQUENCE OF THE FULL LENGTH HUMAN PSCA OF SEQ ID NO: 21
atggctagcaaggctgtgctgcttgccctgttgatggcaggcttggccc tgcagccaggcactgccctgctgtgctactcctgcaaagcccaggtgag caacgaggactgcctgcaggtggagaactgcacccagctgggggagcag tgctggaccgcgcgcatccgcgcagttggcctcctgaccgtcatcagca aaggctgcagcttgaactgcgtggatgactcacaggactactacgtggg caagaagaacatcacgtgctgtgacaccgacttgtgcaacgccagcggg gcccatgccctgcagccggctgccgccatccttgcgctgctccctgcac tcggcctgctgctctggggacccggccagcta

SEQ ID NO: 23. NUCLEOTIDE SEQUENCE OF PLASMID 5166

SEQ ID NO: 24. NUCLEOTIDE SEQUENCE OF PLASMID 5259

SEQ ID NO: 25. NUCLEOTIDE SEQUENCE OF PLASMID 5297

SEQ ID NO: 26. NUCLEOTIDE SEQUENCE OF PLASMID 460

SEQ ID NO: 27. NUCLEOTIDE SEQUENCE OF PLASMID 451

SEQ ID NO: 28. NUCLEOTIDE SEQUENCE OF PLASMID 454

SEQ ID NO: 29. NUCLEOTIDE SEQUENCE OF PLASMID 5300

SEQ ID NO: 30. NUCLEOTIDE SEQUENCE OF PLASMID 449

SEQ ID NO: 31. NUCLEOTIDE SEQUENCE OF PLASMID 603

SEQ ID NO: 32. NUCLEOTIDE SEQUENCE OF PLASMID 455

SEQ ID NO: 33. NUCLEOTIDE SEQUENCE OF PLASMID 456

SEQ ID NO: 34. NUCLEOTIDE SEQUENCE OF PLASMID 457

SEQ ID NO: 35. NUCLEOTIDE SEQUENCE OF PLASMID 458
GGCGTAATGCTCTGCCAGTGTTACAACCAATTAACCAATTCTGATTAGA

AAAACTCATCGAGCATCAAATGAAACTGCAATTTATTCATATCAGGATT

ATCAATACCATATTTTTGAAAAAGCCGTTTCTGTAATGAAGGAGAAAAC

TCACCGAGGCAGTTCCATAGGATGGCAAGATCCTGGTATCGGTCTGCGA

TTCCGACTCGTCCAACATCAATACAACCTATTAATTTCCCCTCGTCAAA

AATAAGGTTATCAAGTGAGAAATCACCATGAGTGACGACTGAATCCGGT

GAGAATGGCAAAAGCTTATGCATTTCTTTCCAGACTTGTTCAACAGGCC

AGCCATTACGCTCGTCATCAAAATCACTCGCATCAACCAAACCGTTATT

CATTCGTGATTGCGCCTGAGCGAGACGAAATACGCGATCGCTGTTAAAA

GGACAATTACAAACAGGAATCAAATGCAACCGGCGCAGGAACACTGCCA

GCGCATCAACAATATTTTCACCTGAATCAGGATATTCTTCTAATACCTG

GAATGCTGTTTTCCCGGGGATCGCAGTGGTGAGTAACCATGCATCATCA

-continued

GGAGTACGGATAAAATGCTTGATGGTCGGAAGAGGCATAAATTCCGTCA

GCCAGTTTAGTCTGACCATCTCATCTGTAACATCATTGGCAACGCTACC

TTTGCCATGTTTCAGAAACAACTCTGGCGCATCGGGCTTCCCATACAAT

CGATAGATTGTCGCACCTGATTGCCCGACATTATCGCGAGCCCATTTAT

ACCCATATAAATCAGCATCCATGTTGGAATTTAATCGCGGCCTCGAGCA

AGACGTTTCCCGTTGAATATGGCTCATAACACCCCTTGTATTACTGTTT

ATGTAAGCAGACAGGTCGACAATATTGGCTATTGGCCATTGCATACGTT

GTATCTATATCATAATATGTACATTTATATTGGCTCATGTCCAATATGA

CCGCCATGTTGACATTGATTATTGACTAGTTATTAATAGTAATCAATTA

CGGGGTCATTAGTTCATAGCCCATATATGGAGTTCCGCGTTACATAACT

TACGGTAAATGGCCCGCCTGGCTGACCGCCCAACGACCCCCGCCCATTG

ACGTCAATAATGACGTATGTTCCCATAGTAACGCCAATAGGGACTTTCC

ATTGACGTCAATGGGTGGAGTATTTACGGTAAACTGCCCACTTGGCAGT

ACATCAAGTGTATCATATGCCAAGTCCGCCCCCTATTGACGTCAATGAC

GGTAAATGGCCCGCCTGGCATTATGCCCAGTACATGACCTTACGGGACT

TTCCTACTTGGCAGTACATCTACGTATTAGTCATCGCTATTACCATGGT

GATGCGGTTTTGGCAGTACACCAATGGGCGTGGATAGCGGTTTGACTCA

CGGGGATTTCCAAGTCTCCACCCCATTGACGTCAATGGGAGTTTGTTTT

GGCACCAAAATCAACGGGACTTTCCAAAATGTCGTAATAACCCCGCCCC

GTTGACGCAAATGGGCGGTAGGCGTGTACGGTGGGAGGTCTATATAAGC

AGAGCTCGTTTAGTGAACCGTCAGATCGCCTGGAGACGCCATCCACGCT

GTTTTGACCTCCATAGAAGACACCGGGACCGATCCAGCCTCCGCGGCCG

GGAACGGTGCATTGGAACGCGGATTCCCCGTGCCAAGAGTGACTCACCG

TCCGGATCTCAGCAAGCAGGTATGTACTCTCCAGGGTGGGCCTGGCTTC

CCCAGTCAAGACTCCAGGGATTTGAGGGACGCTGTGGGCTCTTCTCTTA

CATGTACCTTTTGCTTGCCTCAACCCTGACTATCTTCCAGGTCAGGATC

CCAGAGTCAGGGGTCTGTATTTTCCTGCTGGTGGCTCCAGTTCAGGAAC

AGTAAACCCTGCTCCGAATATTGCCTCTCACATCTCGTCAATCTCCGCG

AGGACTGGGGACCCTGTGACGAACATGGCTAGCATTGTGGGAGGCTGGG

AGTGCGAGAAGCATTCCCAACCCTGGCAGGTGCTTGTGGCCTCTCGTGG

CAGGGCAGTCTGCGGCGGTGTTCTGGTGCACCCCCAGTGGGTCCTCACA

GCTGCCCACTGCATCAGGAACAAAAGCGTGATCTTGCTGGGTCGGCACA

GCTTGTTTCATCCTGAAGACACAGGCCAGGTATTTCAGGTCAGCCACAG

CTTCCCACACCCGCTCTACGATATGAGCCTCCTGAAGAATCGATTCCTC

AGGCCAGGTGATGACTCCAGCCACGACCTCATGCTGCTCCGCCTGTCAG

AGCCTGCCGAGCTCACGGATGCTGTGAAGGTCATGGACCTGCCCACCCA

GGAGCCAGCACTGGGGACCACCTGCTACGCCTCAGGCTGGGGCAGCATT

GAACCAGAGGAGTTCTTGACCCCAAAGAAACTTCAGTGTGTGGACCTCC

ATGTTATTTCCAATGACGTGTGTGCGCAAGTTCACCCTCAGAAGGTGAC

CAAGTTCATGCTGTGTGCTGGACGCTGGACAGGGGGCAAAAGCACCTGC

TCGGGTGATTCTGGGGGCCCACTTGTCTGTAATGGTGTGCTTCAAGGTA

-continued

TCACGTCATGGGGCAGTGAACCATGTGCCCTGCCCGAAAGGCCTTCCCT

GTACACCAAGGTGGTGCATTACCGGAAGTGGATCAAGGACACCATCGTG

GCCAACCCCGGATCCGAAGGTAGGGGTTCATTATTGACCTGTGGAGATG

TCGAAGAAAACCCAGGACCCGCTAGCAAGGCTGTGCTGCTTGCCCTGTT

GATGGCAGGCTTGGCCCTGCAGCCAGGCACTGCCCTGCTGTGCTACTCC

TGCAAAGCCCAGGTGAGCAACGAGGACTGCCTGCAGGTGGAGAACTGCA

CCCAGCTGGGGGAGCAGTGCTGGACCGCGCGCATCCGCGCAGTTGGCCT

CCTGACCGTCATCAGCAAAGGCTGCAGCTTGAACTGCGTGGATGACTCA

CAGGACTACTACGTGGGCAAGAAGAACATCACGTGCTGTGACACCGACT

TGTGCAACGCCAGCGGGGCCCATGCCCTGCAGCCGGCTGCCGCCATCCT

TGCGCTGCTCCCTGCACTCGGCCTGCTGCTCTGGGGACCCGGCCAGCTA

GGATCCCAGACCCTGAACTTTGATCTGCTGAAACTGGCAGGCGATGTGG

AAAGCAACCCAGGCCCAATGGCAAGCGCGCGCCGCCCGCGCTGGCTGTG

CGCTGGGGCGCTGGTGCTGGCGGGTGGCTTCTTTCTCCTCGGCTTCCTC

TTCGGGTGGTTTATAAAATCCTCCAATGAAGCTACTAACATTACTCCAA

AGCATAATATGAAAGCATTTTTGGATGAATTGAAAGCTGAGAACATCAA

GAAGTTCTTATATAATTTTACACAGATACCACATTTAGCAGGAACAGAA

CAAAACTTTCAGCTTGCAAAGCAAATTCAATCCCAGTGGAAAGAATTTG

GCCTGGATTCTGTTGAGCTGGCACATTATGATGTCCTGTTGTCCTACCC

AAATAAGACTCATCCCAACTACATCTCAATAATTAATGAAGATGGAAAT

GAGATTTTCAACACATCATTATTTGAACCACCTCCTCCAGGATATGAAA

ATGTTTCGGATATTGTACCACCTTTCAGTGCTTTCTCTCCTCAAGGAAT

GCCAGAGGGCGATCTAGTGTATGTTAACTATGCACGAACTGAAGACTTC

TTTAAATTGGAACGGGACATGAAAATCAATTGCTCTGGGAAAATTGTAA

TTGCCAGATATGGGAAAGTTTTCAGAGGAAATAAGGTTAAAAATGCCCA

GCTGGCAGGGGCCAAAGGAGTCATTCTCTACTCCGACCCTGCTGACTAC

TTTGCTCCTGGGGTGAAGTCCTATCCAGATGGTTGGAATCTTCCTGGAG

GTGGTGTCCAGCGTGGAAATATCCTAAATCTGAATGGTGCAGGAGACCC

TCTCACACCAGGTTACCCAGCAAATGAATATGCTTATAGGCGTGGAATT

GCAGAGGCTGTTGGTCTTCCAAGTATTCCTGTTCATCCAATTGGATACT

ATGATGCACAGAAGCTCCTAGAAAAAATGGGTGGCTCAGCACCACCAGA

TAGCAGCTGGAGAGGAAGTCTCAAAGTGCCCTACAATGTTGGACCTGGC

TTTACTGGAAACTTTTCTACACAAAAAGTCAAGATGCACATCCACTCTA

CCAATGAAGTGACAAGAATTTACAATGTGATAGGTACTCTCAGAGGAGC

AGTGGAACCAGACAGATATGTCATTCTGGGAGGTCACCGGGACTCATGG

GTGTTTGGTGGTATTGACCCTCAGAGTGGAGCAGCTGTTGTTCATGAAA

TTGTGAGGAGCTTTGGAACACTGAAAAAGGAAGGGTGGAGACCTAGAAG

AACAATTTTGTTTGCAAGCTGGGATGCAGAAGAATTTGGTCTTCTTGGT

TCTACTGAGTGGGCAGAGGAGAATTCAAGACTCCTTCAAGAGCGTGGCG

TGGCTTATATTAATGCTGACTCATCTATAGAAGGAAACTACACTCTGAG

-continued

AGTTGATTGTACACCGCTGATGTACAGCTTGGTACACAACCTAACAAAA

GAGCTGAAAAGCCCTGATGAAGGCTTTGAAGGCAAATCTCTTTATGAAA

GTTGGACTAAAAAAAGTCCTTCCCCAGAGTTCAGTGGCATGCCCAGGAT

AAGCAAATTGGGATCTGGAAATGATTTTGAGGTGTTCTTCCAACGACTT

GGAATTGCTTCAGGCAGAGCACGGTATACTAAAAATTGGGAAACAAACA

AATTCAGCGGCTATCCACTGTATCACAGTGTCTATGAAACATATGAGTT

GGTGGAAAAGTTTTATGATCCAATGTTTAAATATCACCTCACTGTGGCC

CAGGTTCGAGGAGGGATGGTGTTTGAGCTGGCCAATTCCATAGTGCTCC

CTTTTGATTGTCGAGATTATGCTGTAGTTTTAAGAAAGTATGCTGACAA

AATCTACAGTATTTCTATGAAACATCCACAGGAAATGAAGACATACAGT

GTATCATTTGATTCACTTTTTTCTGCAGTAAAGAATTTTACAGAAATTG

CTTCCAAGTTCAGTGAGAGACTCCAGGACTTTGACAAAAGCAACCCAAT

AGTATTAAGAATGATGAATGATCAACTCATGTTTCTGGAAAGAGCATTT

ATTGATCCATTAGGGTTACCAGACAGGCCTTTTTATAGGCATGTCATCT

ATGCTCCAAGCAGCCACAACAAGTATGCAGGGGAGTCATTCCCAGGAAT

TTATGATGCTCTGTTTGATATTGAAAGCAAAGTGGACCCTTCCAAGGCC

TGGGGAGAAGTGAAGAGACAGATTTATGTTGCAGCCTTCACAGTGCAGG

CAGCTGCAGAGACTTTGAGTGAAGTAGCCTAAAGATCTGGGCCCCTAACA

AAACAAAAAGATGGGGTTATTCCCTAAACTTCATGGGTTACGTAATTGG

AAGTTGGGGGACATTGCCACAAGATCATATTGTACAAAAGATCAAACAC

TGTTTTAGAAAACTTCCTGTAAACAGGCCTATTGATTGGAAAGTATGTC

AAAGGATTGTGGGTCTTTTGGGCTTTGCTGCTCCATTTACACAATGTGG

ATATCCTGCCTTAATGCCTTTGTATGCATGTATACAAGCTAAACAGGCT

TTCACTTTCTCGCCAACTTACAAGGCCTTTCTAAGTAAACAGTACATGA

ACCTTTACCCCGTTGCTCGGCAACGGCCTGGTCTGTGCCAAGTGTTTGC

TGACGCAACCCCCACTGGCTGGGGCTTGGCCATAGGCCATCAGCGCATG

CGTGGAACCTTTGTGGCTCCTCTGCCGATCCATACTGCGGAACTCCTAG

CCGCTTGTTTTGCTCGCAGCCGGTCTGGAGCAAAGCTCATAGGAACTGA

CAATTCTGTCGTCCTCTCGCGGAAATATACATCGTTTCGATCTACGTAT

GATCTTTTTCCCTCTGCCAAAAATTATGGGGACATCATGAAGCCCCTTG

AGCATCTGACTTCTGGCTAATAAAGGAAATTTATTTTCATTGCAATAGT

GTGTTGGAATTTTTTGTGTCTCTCACTCGGAAGGAATTCTGCATTAATG

AATCGGCCAACGCGCGGGGAGAGGCGGTTTGCGTATTGGGCGCTCTTCC

GCTTCCTCGCTCACTGACTCGCTGCGCTCGGTCGTTCGGCTGCGGCGAG

CGGTATCAGCTCACTCAAAGGCGGTAATACGGTTATCCACAGAATCAGG

GGATAACGCAGGAAAGAACATGTGAGCAAAAGGCCAGCAAAAGGCCAGG

AACCGTAAAAAGGCCGCGTTGCTGGCGTTTTTCCATAGGCTCCGCCCCC

CTGACGAGCATCACAAAAATCGACGCTCAAGTCAGAGGTGGCGAAACCC

GACAGGACTATAAAGATACCAGGCGTTTCCCCCTGGAAGCTCCCTCGTG

CGCTCTCCTGTTCCGACCCTGCCGCTTACCGGATACCTGTCCGCCTTTC

TCCCTTCGGGAAGCGTGGCGCTTTCTCATAGCTCACGCTGTAGGTATCT

-continued

CAGTTCGGTGTAGGTCGTTCGCTCCAAGCTGGGCTGTGTGCACGAACCC

CCCGTTCAGCCCGACCGCTGCGCCTTATCCGGTAACTATCGTCTTGAGT

CCAACCCGGTAAGACACGACTTATCGCCACTGGCAGCAGCCACTGGTAA

CAGGATTAGCAGAGCGAGGTATGTAGGCGGTGCTACAGAGTTCTTGAAG

TGGTGGCCTAACTACGGCTACACTAGAAGAACAGTATTTGGTATCTGCG

CTCTGCTGAAGCCAGTTACCTTCGGAAAAAGAGTTGGTAGCTCTTGATC

CGGCAAACAAACCACCGCTGGTAGCGGTGGTTTTTTTGTTTGCAAGCAG

CAGATTACGCGCAGAAAAAAAGGATCTCAAGAAGATCCTTTGATCTTTT

CTACGGGGTCTGACGCTCAGTGGAACGAAAACTCACGTTAAGGGATTTT

GGTCATGAGATTATCAAAAAGGATCTTCACCTAGATCCTTTTAAATTAA

AAATGAAGTTTTAAATCAATCTAAAGTATATATGAGTAAACTTGGTCTG

ACAGTTACCAATGCTTAATCAGTGAGGCACCTATCTCAGCGATCTGTCT

ATTTCGTTCATCCATAGTTGCCTGACTC

SEQ ID NO: 36. NUCLEOTIDE SEQUENCE OF PLASMID 459

SEQ ID NO: 37. NUCLEOTIDE SEQUENCE OF PSHUTTLE IRES

SEQ ID NO: 38. Amino acid sequence of Her-2 antigen:

SEQ ID NO: 39. Nucleic acid sequence encoding the Her-2 antigen amino acid sequence of SEQ ID NO: 38

SEQ ID NO: 40. Amino acid sequence of heavy chain of the anti-CD40 antibody CP870,893:
MDWTWRILFLVAAATGAHSQVQLVQSGAEVKKPGASVKVSCKASGYTFT

GYYMHWVRQAPGQGLEWMGWINPDSGGTNYAQKFQGRVTMTRDTSISTA

YMELNRLRSDDTAVYYCARDQPLGYCTNGVCSYFDYWGQGTLVTVSSAS

TKGPSVFPLAPCSRSTSESTAALGCLVKDYFPEPVTVSWNSGALTSGVH

TFPAVLQSSGLYSLSSVVTVPSSNFGTQTYTCNVDHKPSNTKVDKTVER

KCCVECPPCPAPPVAGPSVFLFPPKPKDTLMISRTPEVTCVVVDVSHED

PEVQFNWYVDGVEVHNAKTKPREEQFNSTFRVVSVLTVVHQDWLNGKEY

KCKVSNKGLPAPIEKTISKTKGQPREPQVYTLPPSREEMTKNQVSLTCL

VKGFYPSDIAVEWESNGQPENNYKTTPPMLDSDGSFFLYSKLTVDKSRW

QQGNVFSCSVMHEALHNHYTQKSLSLSPGK.

SEQ ID NO: 41. Acid sequence of the light chain of the anti-CD40 antibody CP870,893:
MRLPAQLLGLLLLWFPGSRCDIQMTQSPSSVSASVGDRVTITCRASQGI

YSWLAWYQQKPGKAPNLLIYTASTLQSGVPSRFSGSGSGTDFTLTISSL

QPEDFATYYCQQANIFPLTFGGGTKVEIKRTVAAPSVFIFPPSDEQLKS

GTASVVCLLNNFYPREAKVQWKVDNALQSGNSQESVTEQDSKDSTYSLS

STLTLSKADYEKHKVYACEVTHQGLSSPVTKSFNRGEC.

SEQ ID NO: 42. Acid sequence of the heavy chain of the anti-CTLA-4 antibody Tremelimumab
QVQLVESGGGVVQPGRSLRLSCAASGFTFSSYGMHWVRQAPGKGLEWVA

VIWYDGSNKYYADSVKGRFTISRDNSKNTLYLQMNSLRAEDTAVYYCAR

DPRGATLYYYYYGMDVWGQGTTVTVSSASTKGPSVFPLAPCSRSTSEST

-continued

AALGCLVKDYFPEPVTVSWNSGALTSGVHTFPAVLQSSGLYSLSSVVTV

PSSNFGTQTYTCNVDHKPSNTKVDKTVERKCCVECPPCPAPPVAGPSVF

LFPPKPKDTLMISRTPEVTCVVVDVSHEDPEVQFNWYVDGVEVHNAKTK

PREEQFNSTFRVVSVLTVVHQDWLNGKEYKCKVSNKGLPAPIEKTISKT

KGQPREPQVYTLPPSREEMTKNQVSLTCLVKGFYPSDIAVEWESNGQPE

NNYKTTPPMLDSDGSFFLYSKLTVDKSRWQQGNVFSCSVMHEALHNHYT

QKSLSLSPGK

SEQ ID NO: 43. Acid sequence of the light chain of the anti-CTLA-4 antibody Tremelimumab
DIQMTQSPSSLSASVGDRVTITCRASQSINSYLDWYQQKPGKAPKLLIY

AASSLQSGVPSRFSGSGSGTDFTLTISSLQPEDFATYYCQQYYSTPFTF

GPGTKVEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC

SEQ ID NO: 44. Nucleotide sequence of CpG 7909
5'TCGTCGTTTTGTCGTTTTGTCGTT3'

SEQ ID NO: 45. Nucleotide sequence of CpG 24555
5'TCGTCGTTTTTCGGTGCTTTT3'

SEQ ID NO: 46. Nucleotide sequence of CpG 10103
5'TCGTCGTTTTTCGGTCGTTTT3'

SEQ ID NO: 47. Amino acid sequence of eGFP

SEQ ID NO: 48. Amino acid sequence of HBV core antigen

SEQ ID NO: 49. Amino acid sequence of HBV surface antigen

SEQ ID NO: 50. Amino acid sequence of Rhesus PSMA ECD protein:

SEQ ID NO: 51. Amino acid sequence of rat Her-2 p66 peptide (H-2d T cell epitope)

SEQ ID NO: 52. Amino acid sequence of rat Her-2 p169 peptide (H-2d T cell epitope)

SEQ ID NO: 53. Amino acid sequence of HBV core antigen p87 peptide

SEQ ID NO: 54. Amino acid sequence of a Rat Her-2 Antigen (rHer-2):

SEQ ID NO: 55. Amino Acid Sequence of Rhesus PSMA antigen:

SEQ ID NO: 56. Nucleotide sequence encoding the rhesus PSMA antigen of SEQ ID NO: 55"

SEQ ID NO: 57. Complete Genome of Simian Adenovirus 25 (C68)
ccatcttcaataatatacctcaaactttttgtgcgcgttaatatgcaaa tgaggcgtttgaatttggggaggaagggcggtgattggtcgagggatga gcgaccgttaggggcggggcgagtgacgttttgatgacgtggttgcgag gaggagccagtttgcaagttctcgtgggaaaagtgacgtcaaacgaggt gtggtttgaacacggaaatactcaatttttcccgcgctctctgacaggaa atgaggtgtttctgggcggatgcaagtgaaaacgggccattttcgcgcg aaaactgaatgaggaagtgaaaatctgagtaatttcgcgtttatggcag ggaggagtatttgccgagggccgagtagactttgaccgattacgtgggg -continued

```
gtttcgattaccgtgtttttcacctaaatttccgcgtacggtgtcaaag
tccggtgtttttacgtaggtgtcagctgatcgccagggtatttaaacct
gcgctctccagtcaagaggccactcttgagtgccagcgagaagagtttt
ctcctccgcgccgcgagtcagatctacactttgaaagatgaggcacctg
agagacctgcccgatgagaaaatcatcatcgcttccgggaacgagattc
tggaactggtggtaaatgccatgatgggcgacgaccctccggagccccc
caccccatttgagacaccttcgctgcacgatttgtatgatctggaggtg
gatgtgcccgaggacgatcccaatgaggaggcggtaaatgatttttta
gcgatgccgcgctgctagctgccgaggaggcttcgagctctagctcaga
cagcgactcttcactgcataccccctagacccggcagaggtgagaaaaag
atccccgagcttaaaggggaagagatggacttgcgctgctatgaggaat
gcttgcccccgagcgatgatgaggacgagcaggcgatccagaacgcagc

gagccagggagtgcaagccgccagcgagagctttgcgctggactgcccg
cctctgcccggacacggctgtaagtcttgtgaatttcatcgcatgaata
ctggagataaagctgtgttgtgtgcactttgctatatgagagcttacaa
ccattgtgtttacagtaagtgtgattaagttgaactttagagggaggca
gagagcagggtgactgggcgatgactggtttatttatgtatatatgttc
tttatataggtcccgtctctgacgcagatgatgagacccccactacaaa
gtccacttcgtcacccccagaaattggcacatctccacctgagaatatt
gttagaccagttcctgttagagccactgggaggagagcagctgtggaat
gtttggatgacttgctacagggtggggttgaacctttggacttgtgtac
ccggaaacgccccaggcactaagtgccacacatgtgtgtttacttgagg
tgatgtcagtatttatagggtgtggagtgcaataaaaaatgtgttgact
ttaagtgcgtggtttatgactcaggggtggggactgtgagtatataagc
aggtgcagacctgtgtggttagctcagagcggcatggagatttggacgg
tcttggaagactttcacaagactagacagctgctagagaacgcctcgaa
cggagtctcttacctgtggagattctgcttcggtggcgacctagctagg
ctagtctacagggccaaacaggattatagtgaacaatttgaggttattt
tgagagagtgttctggtctttttgacgctcttaacttgggccatcagtc
tcactttaaccagaggatttcgagagcccttgattttactactcctggc
agaaccactgcagcagtagcctttttttgcttttattcttgacaaatgga
gtcaagaaacccatttcagcagggattaccagctggatttcttagcagt
agctttgtggagaacatggaagtgccagcgcctgaatgcaatctccggc
tacttgccggtacagccgctagacactctgaggatcctgaatctccagg
agagtcccagggcacgccaacgtcgccagcagcagcagcaggaggagga
tcaagaagagaacccgagagccggcctggaccctccggcggaggaggag
gagtagctgacctgtttcctgaactgcgccgggtgctgactaggtcttc
gagtggtcgggagaggggggattaagcgggagaggcatgatgagactaat
cacagaactgaactgactgtgggtctgatgagtcgcaagcgcccagaaa
cagtgtggtggcatgaggtgcagtcgactggcacagatgaggtgtcggt
```

-continued

```
gatgcatgagaggttttctctagaacaagtcaagacttgttggttagag
cctgaggatgattgggaggtagccatcaggaattatgccaagctggctc
tgaggccagacaagaagtacaagattactaagctgataaatatcagaaa
tgcctgctacatctcagggaatggggctgaagtggagatctgtctccag
gaaagggtggctttcagatgctgcatgatgaatatgtacccgggagtgg
tgggcatggatggggttacctttatgaacatgaggttcaggggagatgg
gtataatggcacggtctttatggccaataccaagctgacagtccatggc
tgctccttctttgggtttaataacacctgcatcgaggcctggggtcagg
tcggtgtgaggggctgcagtttttcagccaactggatgggggtcgtggg
caggaccaagagtatgctgtccgtgaagaaatgcttgtttgagaggtgc
cacctgggggtgatgagcgagggcgaagccagaatccgccactgcgcct
ctaccgagacgggctgctttgtgctgtgcaagggcaatgctaagatcaa
gcataatatgatctgtggagcctcggacgagcgcggctaccagatgctg
acctgcgccggcgggaacagccatatgctggccaccgtacatgtggctt
cccatgctcgcaagccctggcccgagttcgagcacaatgtcatgaccag
gtgcaatatgcatctggggtcccgccgaggcatgttcatgccctaccag
tgcaacctgaattatgtgaaggtgctgctggagcccgatgccatgtcca
gagtgagcctgacgggggtgtttgacatgaatgtggaggtgtggaagat
tctgagatatgatgaatccaagaccaggtgccgagcctgcgagtgcgga
gggaagcatgccaggttccagcccgtgtgtgtggatgtgacggaggacc
tgcgacccgatcatttggtgttgccctgcaccgggacggagttcggttc
cagcggggaagaatctgactagagtgagtagtgttctggggcgggggag
gacctgcatgagggccagaataactgaaatctgtgcttttctgtgtgtt
gcagcagcatgagcggaagcggctcctttgagggaggggtattcagccc
ttatctgacggggcgtctcccctcctgggcgggagtgcgtcagaatgtg
atgggatccacggtggacggccggcccgtgcagcccgcgaactcttcaa
ccctgacctatgcaaccctgagctcttcgtcgttggacgcagctgccgc
cgcagctgctgcatctgccgccagcgccgtgcgcggaatggccatgggc
gccggctactacggcactctggtggccaactcgagttccaccaataatc
ccgccagcctgaacgaggagaagctgttgctgctgatggcccagctcga
ggccttgacccagcgcctgggcgagctgacccagcaggtggctcagctg
caggagcagacgcgggccgcggttgccacggtgaaatccaaataaaaaa
tgaatcaataaataaacggagacggttgttgattttaacacagagtctg
aatctttatttgatttttcgcgcgcggtaggccctggaccaccggtctc
gatcattgagcacccggtggatcttttccaggacccggtagaggtgggc
ttggatgttgaggtacatgggcatgagcccgtcccgggggtggaggtag
ctccattgcagggcctcgtgctcggggggtggtgttgtaaatcacccagt
catagcaggggcgcagggcatggtgttgcacaatatctttgaggaggag
actgatggccacgggcagccctttggtgtaggtgtttacaaatctgttg
agctgggagggatgcatgcgggggggagatgaggtgcatcttggcctgga
```

-continued

```
tcttgagattggcgatgttaccgcccagatcccgcctggggttcatgtt
gtgcaggaccaccagcacggtgtatccggtgcacttggggaatttatca
tgcaacttggaagggaaggcgtgaaagaatttggcgacgcctttgtgcc
cgcccaggttttccatgcactcatccatgatgatggcgatgggcccgtg
ggcggcggcctgggcaaagacgtttcgggggtcggacacatcatagttg
tggtcctgggtgaggtcatcataggccattttaatgaatttggggcgga
gggtgccggactgggggacaaaggtaccctcgatcccgggggcgtagtt
cccctcacagatctgcatctcccaggctttgagctcggaggggggggatc
atgtccacctgcggggcgataaagaacacggtttccggggcgggggaga
tgagctgggccgaaagcaagttccggagcagctgggacttgccgcagcc
ggtggggccgtagatgaccccgatgaccggctgcaggtggtagttgagg
gagagacagctgccgtcctcccggaggaggggggccacctcgttcatca
tctcgcgcacgtgcatgttctcgcgcaccagttccgccaggaggcgctc
tccccccagggataggagctcctggagcgaggcgaagtttttcagcggc
ttgagtccgtcggccatgggcattttggagagggtttgttgcaagagtt
ccaggcggtcccagagctcggtgatgtgctctacggcatctcgatccag
cagacctcctcgtttcgcgggttgggacggctgcgggagtagggcacca
gacgatgggcgtccagcgcagccagggtccggtccttccagggtcgcag
cgtccgcgtcagggtggtctccgtcacggtgaaggggtgcgcgccgggc
tgggcgcttgcgagggtgcgcttcaggctcatccggctggtcgaaaacc
gctcccgatcggcgccctgcgcgtcggccaggtagcaattgaccatgag
ttcgtagttgagcgcctcggccgcgtggcctttggcgcggagcttacct
ttggaagtctgcccgcaggcgggacagaggagggacttgagggcgtaga
gcttgggggcgaggaagacggactcgggggcgtaggcgtccgcgccgca
gtgggcgcagacggtctcgcactccacgagccaggtgaggtcgggctgg
tcggggtcaaaaaccagtttcccgccgttctttttgatgcgtttcttac
ctttggtctccatgagctcgtgtccccgctgggtgacaaagaggctgtc
cgtgtccccgtagaccgactttatgggccggtcctcgagcggtgtgccg
cggtcctcctcgtagaggaaccccgcccactccgagacgaaagcccggg
tccaggccagcacgaaggaggccacgtgggacgggtagcggtcgttgtc
caccagcgggtccaccttttccagggtatgcaaacacatgtccccctcg
tccacatccaggaaggtgattggcttgtaagtgtaggccacgtgaccgg
gggtcccggccgggggggtataaaagggtgcgggtccctgctcgtcctc
actgtcttccggatcgctgtccaggagcgccagctgttggggtaggtat
tccctctcgaaggcgggcatgacctcggcactcaggttgtcagtttcta
gaaacgaggaggatttgatattgacggtgccggcggagatgcctttcaa
gagcccctcgtccatctggtcagaaaagacgatctttttgttgtcgagc
ttggtggcgaaggagccgtagagggcgttggagaggagcttggcgatgg
agcgcatggtctggtttttttccttgtcggcgcgctccttggcggcgat
gttgagctgcacgtactcgcgcgccacgcacttccattcggggaagacg
gtggtcagctcgtcgggcacgattctgacctgccagccccgattatgca
```

-continued

```
gggtgatgaggtccacactggtggccacctcgccgcgcaggggctcatt
agtccagcagaggcgtccgcccttgcgcgagcagaagggggggcaggggg
tccagcatgacctcgtcggggggtcggcatcgatggtgaagatgccgg
gcaggaggtcggggtcaaagtagctgatggaagtggccagatcgtccag
ggcagcttgccattcgcgcacggccagcgcgcgctcgtagggactgagg
ggcgtgccccagggcatgggatgggtaagcgcggaggcgtacatgccgc
agatgtcgtagacgtagaggggctcctcgaggatgccgatgtaggtggg
gtagcagcgcccccccgcggatgctggcgcgcacgtagtcatacagctcg
tgcgagggggcgaggagccccgggcccaggttggtgcgactgggctttt
cggcgcggtagacgatctggcggaaaatggcatgcgagttggaggagat
ggtgggcctttggaagatgttgaagtgggcgtggggcagtccgaccgag
tcgcggatgaagtgggcgtaggagtcttgcagcttggcgacgagctcgg
cggtgactaggacgtccagagcgcagtagtcgagggtctcctggatgat
gtcatacttgagctgtccctttttgtttccacagctcgcggttgagaagg
aactcttcgcggtccttccagtactcttcgagggggaacccgtcctgat
ctgcacggtaagagcctagcatgtagaactggttgacggccttgtaggc
gcagcagcccttctccacggggagggcgtaggcctgggcggccttgcgc
agggaggtgtgcgtgagggcgaaagtgtccctgaccatgaccttgagga
actggtgcttgaagtcgatatcgtcgcagccccccctgctcccagagctg
gaagtccgtgcgcttcttgtaggcggggttgggcaaagcgaaagtaaca
tcgttgaagaggatcttgcccgcgcggggcataaagttgcgagtgatgc
ggaaaggttggggcacctcggcccggttgttgatgacctgggcggcgag
cacgatctcgtcgaagccgttgatgttgtggcccacgatgtagagttcc
acgaatcgcggacggcccttgacgtggggcagtttcttgagctcctcgt
aggtgagctcgtcggggtcgctgagcccgtgctgctcgagcgcccagtc
ggcgagatgggggttggcgcggaggaaggaagtccagagatccacggcc
agggcggtttgcagacggtcccggtactgacggaactgctgcccgacgg
ccatttttttcgggggtgacgcagtagaaggtgcgggggtccccgtgcca
gcgatcccatttgagctggagggcgagatcgagggcgagctcgacgagc
cggtcgtccccggagagtttcatgaccagcatgaaggggacgagctgct
tgccgaaggaccccatccaggtgtaggtttccacatcgtaggtgaggaa
gagcctttcggtgcgaggatgcgagccgatggggaagaactggatctcc
tgccaccaattggaggaatggctgttgatgtgatggaagtagaaatgcc
gacggcgcgccgaacactcgtgcttgtgtttatacaagcggccacagtg
ctcgcaacgctgcacgggatgcacgtgctgcacgagctgtacctgagtt
cctttgacgaggaatttcagtgggaagtggagtcgtggcgcctgcatct
cgtgctgtactacgtcgtggtggtcggcctggccctcttctgcctcgat
ggtggtcatgctgacgagcccgcgcgggaggcaggtccagacctcggcg
cgagcgggtcggagagcgaggacgagggcgcgcaggccggagctgtcca
gggtcctgagacgctgcggagtcaggtcagtgggcagcggcggcgcgcg
```

-continued gttgacttgcaggagtttttccagggcgcgcgggaggtccagatggtac ttgatctccaccgcgccattggtggcgacgtcgatggcttgcagggtcc cgtgcccctggggtgtgaccaccgtcccccgtttcttcttgggcggctg gggcgacgggggcggtgcctcttccatggttagaagcggcggcgaggac gcgcgccgggcggcaggggcggctcggggcccggaggcaggggcggcag gggcacgtcggcgccgcgcgcgggtaggttctggtactgcgcccggaga agactggcgtgagcgacgacgcgacggttgacgtcctggatctgacgcc tctgggtgaaggccacgggacccgtgagtttgaacctgaaagagagttc gacagaatcaatctcggtatcgttgacggcggcctgccgcaggatctct tgcacgtcgcccgagttgtcctggtaggcgatctcggtcatgaactgct cgatctcctcctcttgaaggtctccgcggccggcgcgctccacggtggc cgcgaggtcgttggagatgcggcccatgagctgcgagaaggcgttcatg cccgcctcgttccagacgcggctgtagaccacgacgccctcgggatcgc cggcgcgcatgaccacctgggcgaggttgagctccacgtggcgcgtgaa gaccgcgtagttgcagaggcgctggtagaggtagttgagcgtggtggcg atgtgctcggtgacgaagaaatacatgatccagcggcggagcggcatct cgctgacgtcgcccagcgcctccaaacgttccatggcctcgtaaaagtc cacggcgaagttgaaaaactgggagttgcgcgccgagacggtcaactcc tcctccagaagacggatgagctcggcgatggtggcgcgcacctcgcgct cgaaggcccccgggagttcctccacttcctcttcttcctcctccactaa catctcttctacttcctcctcaggcggcagtggtggcgggggagggggc ctgcgtcgccggcggcgcacgggcagacggtcgatgaagcgctcgatgg tctcgccgcgccggcgtcgcatggtctcggtgacggcgcgcccgtcctc gcggggccgcagcgtgaagacgccgccgcgcatctccaggtggccgggg gggtccccgttgggcagggagagggcgctgacgatgcatcttatcaatt gccccgtagggactccgcgcaaggacctgagcgtctcgagatccacggg atctgaaaaccgctgaacgaaggcttcgagccagtcgcagtcgcaaggt aggctgagcacggtttcttctggcgggtcatgttggttgggagcggggc gggcgatgctgctggtgatgaagttgaaataggcggttctgagacggcg gatggtggcgaggagcaccaggtctttgggcccggcttgctggatgcgc agacggtcggccatgccccaggcgtggtcctgacacctggccaggtcct tgtagtagtcctgcatgagccgctccacgggcacctcctcctcgcccgc gcggccgtgcatgcgcgtgagcccgaagccgcgctggggctggacgagc gccaggtcggcgacgacgcgctcggcgaggatggcttgctggatctggg tgagggtggtctggaagtcatcaaagtcgacgaagcggtggtaggctcc ggtgttgatggtgtaggagcagttggccatgacggaccagttgacggtc tggtggcccggacgcacgagctcgtggtacttgaggcgcgagtaggcgc gcgtgtcgaagatgtagtcgttgcaggtgcgcaccaggtactggtagcc gatgaggaagtgcggcggcggctggcggtagagcggccatcgctcggtg gcgggggcgccgggcgcgaggtcctcgagcatggtgcggtggtagccgt agatgtacctggacatccaggtgatgccggcggcggtggtggaggcgcg -continued cgggaactcgcggacgcggttccagatgttgcgcagcggcaggaagtag ttcatggtgggcacggtctggcccgtgaggcgcgcgcagtcgtggatgc tctatacgggcaaaaacgaaagcggtcagcggctcgactccgtggcctg gaggctaagcgaacgggttgggctgcgcgtgtaccccggttcgaatctc gaatcaggctggagccgcagctaacgtggtattggcactcccgtctcga cccaagcctgcaccaaccctccaggatacggaggcgggtcgttttgcaa ctttttttggaggccggatgagactagtaagcgcggaaagcggccgac cgcgatggctcgctgccgtagtctggagaagaatcgccagggttgcgtt gcggtgtgccccggttcgaggccggccggattccgcggctaacgagggc gtggctgccccgtcgtttccaagaccccatagccagccgacttctccag ttacggagcgagcccctcttttgttttgtttgtttttgccagatgcatc ccgtactgcggcagatgcgcccccaccaccctccaccgcaacaacagcc ccctccacagccggcgcttctgccccegccccagcagcaacttccagcc acgaccgccgcggccgccgtgagcggggctggacagagttatgatcacc agctggccttggaagagggcgaggggctggcgcgcctgggggcgtcgtc gccggagcggcacccgcgcgtgcagatgaaaagggacgctcgcgaggcc tacgtgcccaagcagaacctgttcagagacaggagcggcgaggagcccg aggagatgcgcgcggcccggttccacgcggggcgggagctgcggcgcgg cctggaccgaaagagggtgctgagggacgaggatttcgaggcggacgag ctgacggggatcagccccgcgcgcgcgcacgtggccgcggccaacctgg tcacggcgtacgagcagaccgtgaaggaggagagcaacttccaaaaatc cttcaacaaccacgtgcgcaccctgatcgcgcgcgaggaggtgaccctg ggcctgatgcacctgtgggacctgctggaggccatcgtgcagaacccca ccagcaagccgctgacggcgcagctgttcctggtggtgcagcatagtcg ggacaacgaagcgttcagggaggcgctgctgaatatcaccgagcccgag ggccgctggctcctggacctggtgaacattctgcagagcatcgtggtgc aggagcgcgggctgccgctgtccgagaagctggcggccatcaacttctc ggtgctgagtttgggcaagtactacgctaggaagatctacaagaccccg tacgtgcccatagacaaggaggtgaagatcgacgggttttacatgcgca tgaccctgaaagtgctgaccctgagcgacgatctgggggtgtaccgcaa cgacaggatgcaccgtgcggtgagcgccagcaggcggcgcgagctgagc gaccaggagctgatgcatagtctgcagcgggccctgaccggggccggga ccgagggggagagctactttgacatgggcgcggacctgcactggcagcc cagccgccgggccttggaggcggcggcaggaccctacgtagaagaggtg gacgatgaggtggacgaggagggcgagtacctggaagactgatggcgcg accgtatttttgctagatgcaacaacaacagccacctcctgatcccgcg atgcgggcggcgctgcagagccagccgtccggcattaactcctcggacg attggacccaggccatgcaacgcatcatggcgctgacgacccgcaaccc cgaagcctttagacagcagccccaggccaaccggctctcggccatcctg gaggccgtggtgccctcgcgctccaaccccacgcacgagaaggtcctgg -continued ccatcgtgaacgcgctggtggagaacaaggccatccgcggcgacgaggc cggcctggtgtacaacgcgctgctggagcgcgtggcccgctacaacagc accaacgtgcagaccaacctggaccgcatggtgaccgacgtgcgcgagg ccgtggcccagcgcgagcggttccaccgcgagtccaacctgggatccat ggtggcgctgaacgccttcctcagcacccagcccgccaacgtgccccgg ggccaggaggactacaccaacttcatcagcgccctgcgcctgatggtga ccgaggtgccccagagcgaggtgtaccagtccgggccggactacttctt ccagaccagtcgccagggcttgcagaccgtgaacctgagccaggctttc aagaacttgcagggcctgtggggcgtgcaggccccggtcggggaccgcg cgacggtgtcgagcctgctgacgccgaactcgcgcctgctgctgctgct ggtggccccttcacggacagcggcagcatcaaccgcaactcgtacctg ggctacctgattaacctgtaccgcgaggccatcggccaggcgcacgtgg acgagcagacctaccaggagatcacccacgtgagccgcgccctgggcca ggacgacccgggcaacctggaagccaccctgaactttttgctgaccaac cggtcgcagaagatcccgccccagtacgcgctcagcaccgaggaggagc gcatcctgcgttacgtgcagcagagcgtgggcctgttcctgatgcagga gggggccacccccagcgccgcgctcgacatgaccgcgcgcaacatggag cccagcatgtacgccagcaaccgcccgttcatcaataaactgatggact acttgcatcgggcggccgccatgaactctgactatttcaccaacgccat cctgaatccccactggctcccgccgccggggttctacacgggcgagtac gacatgcccgaccccaatgacgggttcctgtgggacgatgtggacagca gcgtgttctcccccgaccgggtgctaacgagcgccccttgtggaagaa ggaaggcagcgaccgacgcccgtcctcggcgctgtccggccgcgagggt gctgccgcggcggtgcccgaggccgccagtcctttcccgagcttgccct tctcgctgaacagtatccgcagcagcgagctgggcaggatcacgcgccc gcgcttgctgggcgaagaggagtacttgaatgactcgctgttgagaccc gagcgggagaagaacttccccaataacgggatagaaagcctggtggaca agatgagccgctggaagacgtatgcgcaggagcacagggacgatccccg ggcgtcgcagggggccacgagccggggcagcgccgcccgtaaacgccgg tggcacgacaggcagcggggacagatgtgggacgatgaggactccgccg acgacagcagcgtgttggacttgggtgggagtggtaacccgttcgctca cctgcgcccccgtatcgggcgcatgatgtaagagaaaccgaaaataaat gatactcaccaaggccatggcgaccagcgtgcgttcgtttcttctctgt tgttgttgtatctagtatgatgaggcgtgcgtacccggagggtcctcct ccctcgtacgagagcgtgatgcagcaggcgatggcggcggcggcgatgc agcccccgctggaggctccttacgtgcccccgcggtacctggcgcctac ggaggggcggaacagcattcgttactcggagctggcacccttgtacgat accacccggttgtacctggtggacaacaagtcggcggacatcgcctcgc tgaactaccagaacgaccacagcaacttcctgaccaccgtggtgcagaa caatgacttcacccccacggaggccagcacccagaccatcaactttgac gagcgctcgcggtggggcggccagctgaaaaccatcatgcacaccaaca -continued tgcccaacgtgaacgagttcatgtacagcaacaagttcaaggcgcgggt gatggtctcccgcaagacccccaatggggtgacagtgacagaggattat gatggtagtcaggatgagctgaagtatgaatgggtggaatttgagctgc ccgaaggcaacttctcggtgaccatgaccatcgacctgatgaacaacgc catcatcgacaattacttggcggtggggcggcagaacggggtgctggag agcgacatcggcgtgaagttcgacactaggaacttcaggctgggctggg accccgtgaccgagctggtcatgcccggggtgtacaccaacgaggcttt ccatcccgatattgtcttgctgcccggctgcggggtggacttcaccgag agccgcctcagcaacctgctgggcattcgcaagaggcagcccttccagg aaggcttccagatcatgtacgaggatctggagggggcaacatccccgc gctcctggatgtcgacgcctatgagaaaagcaaggaggatgcagcagct gaagcaactgcagccgtagctaccgcctctaccgaggtcaggggcgata attttgcaagcgccgcagcagtggcagcggccgaggcggctgaaaccga aagtaagatagtcattcagccggtggagaaggatagcaagaacaggagc tacaacgtactaccggacaagataaacaccgcctaccgcagctggtacc tagcctacaactatggcgaccccgagaagggcgtgcgctcctggacgct gctcaccacctcggacgtcacctgcggcgtggagcaagtctactggtcg ctgcccgacatgatgcaagacccggtcaccttccgctccacgcgtcaag ttagcaactacccggtggtgggcgccgagctcctgcccgtctactccaa gagcttcttcaacgagcaggccgtctactcgcagcagctgcgcgccttc acctcgcttacgcacgtcttcaaccgcttccccgagaaccagatcctcg tccgcccgcccgcgcccaccattaccaccgtcagtgaaaacgttcctgc tctcacagatcacgggaccctgccgctgcgcagcagtatccggggagtc cagcgcgtgaccgttactgacgccagacgccgcacctgcccctacgtct acaaggccctgggcatagtcgcgccgcgcgtcctctcgagccgcacctt ctaaatgtccattctcatctcgcccagtaataacaccggttggggcctg cgcgcgcccagcaagatgtacggaggcgctcgccaacgctccacgcaac accccgtgcgcgtgcgcgggcacttccgcgctccctggggcgccctcaa gggccgcgtgcggtcgcgcaccaccgtcgacgacgtgatcgaccaggtg gtggccgacgcgcgcaactacaccccccgccgccgcgcccgtctccaccg tggacgccgtcatcgacagcgtggtggcggacgcgcgccggtacgcccg cgccaagagccggcggcggcgcatcgcccggcggcaccggagcaccccc gccatgcgcgcggcgcgagccttgctgcgcagggccaggcgcacgggac gcagggccatgctcagggcggccagacgcgcggcttcaggcgccagcgc cggcaggacccggagacgcgcggccacggcggcggcagcggccatcgcc agcatgtcccgcccgcggcgagggaacgtgtactgggtgcgcgacgccg ccaccggtgtgcgcgtgcccgtgcgcacccgcccccctcgcacttgaag atgttcacttcgcgatgttgatgtgtcccagcggcgaggaggatgtcca agcgcaaattcaaggaagagatgctccaggtcatcgcgcctgagatcta cggccctgcggtggtgaaggaggaaagaaagccccgcaaaatcaagcgg -continued gtcaaaaaggacaaaaaggaagaagaaagtgatgtggacggattggtgg agtttgtgcgcgagttcgcccccggcggcgcgtgcagtggcgcgggcg gaaggtgcaaccggtgctgagacccggcaccaccgtggtcttcacgccc ggcgagcgctccggcaccgcttccaagcgctcctacgacgaggtgtacg gggatgatgatattctggagcaggcggccgagcgcctgggcgagtttgc ttacggcaagcgcagccgttccgcaccgaaggaagaggcggtgtccatc ccgctggaccacggcaaccccacgccgagcctcaagcccgtgaccttgc agcaggtgctgccgaccgcggcgccgcgccgggggttcaagcgcgaggg cgaggatctgtaccccaccatgcagctgatggtgcccaagcgccagaag ctggaagacgtgctggagaccatgaaggtggacccggacgtgcagcccg aggtcaaggtgcggcccatcaagcaggtggccccgggcctgggcgtgca gaccgtggacatcaagattcccacggagcccatggaaacgcagaccgag cccatgatcaagcccagcaccagcaccatggaggtgcagacggatccct ggatgccatcggctcctagtcgaagaccccggcgcaagtacggcgcggc cagcctgctgatgcccaactacgcgctgcatccttccatcatccccacg ccgggctaccgcggcacgcgcttctaccgcggtcataccagcagccgcc gccgcaagaccaccactcgccgccgccgtcgccgcaccgccgctgcaac cacccctgccgccctggtgcggagagtgtaccgccgcggccgcgcacct ctgaccctgccgcgcgcgcgctaccacccgagcatcgccatttaaactt tcgccagctttgcagatcaatggccctcacatgccgccttcgcgttccc attacgggctaccgaggaagaaaaccgcgccgtagaaggctggcgggga acgggatgcgtcgccaccaccaccggcggcggcgcgccatcagcaagcg gttgggggggaggcttcctgcccgcgctgatccccatcatcgccgcggcg atcggggcgatccccggcattgcttccgtggcggtgcaggcctctcagc gccactgagacacacttggaaacatcttgtaataaacccatggactctg acgctcctggtcctgtgatgtgttttcgtagacagatggaagacatcaa tttttcgtccctggctccgcgacacggcacgcggccgttcatgggcacc tggagcgacatcggcaccagccaactgaacgggggcgccttcaattgga gcagtctctggagcgggcttaagaatttcgggtccacgcttaaaaccta tggcagcaaggcgtggaacagcaccacagggcaggcgctgagggataag ctgaaagagcagaacttccagcagaaggtggtcgatgggctcgcctcgg gcatcaacggggtggtggacctggccaaccaggccgtgcagcggcagat caacagccgcctggacccggtgccgcccgccggctccgtggagatgccg caggtggaggaggagctgcctccccctggacaagcggggcgagaagcgac cccgccccgatgcggaggagacgctgctgacgcacacggacgagccgcc cccgtacgaggaggcggtgaaactgggtctgcccaccacgcggcccatc gcgcccctggccaccggggtgctgaaacccgaaaagcccgcgaccctgg acttgcctcctccccagccttcccgcccctctacagtggctaagcccct gccgccggtggccgtggcccgcgcgcgacccgggggcaccgcccgccct catgcgaactggcagagcactctgaacagcatcgtgggtctgggagtgc agagtgtgaagcgccgccgctgctattaaacctaccgtagcgcttaact -continued tgcttgtctgtgtgtgtatgtattatgtcgccgccgccgctgtccacca gaaggaggagtgaagaggcgcgtcgccgagttgcaagatggccacccca tcgatgctgccccagtgggcgtacatgcacatcgccggacaggacgctt cggagtacctgagtccgggtctggtgcagtttgcccgcgccacagacac ctacttcagtctggggaacaagtttaggaaccccacggtggcgcccacg cacgatgtgaccaccgaccgcagccagcggctgacgctgcgcttcgtgc ccgtggaccgcgaggacaacacctactcgtacaaagtgcgctacacgct ggccgtgggcgacaaccgcgtgctggacatggccagcacctactttgac atccgcggcgtgctggatcggggccctagcttcaaaccctactccggca ccgcctacaacagtctggcccccaagggagcacccaacacttgtcagtg gacatataaagccgatggtgaaactgccacagaaaaaacctatacatat ggaaatgcacccgtgcagggcattaacatcacaaaagatggtattcaac ttggaactgacaccgatgatcagccaatctacgcagataaaacctatca gcctgaacctcaagtgggtgatgctgaatggcatgacatcactggtact gatgaaaagtatggaggcagagctcttaagcctgataccaaaatgaagc cttgttatggttcttttgccaagcctactaataaagaaggaggtcaggc aaatgtgaaaacaggaacaggcactactaaagaatatgacatagacatg gctttctttgacaacagaagtgcggctgctgctggcctagctccagaaa ttgttttgtatactgaaaatgtggatttggaaactccagatacccatat tgtatacaaagcaggcacagatgacagcagctcttctattaatttgggt cagcaagccatgcccaacagacctaactacattggtttcagagacaact ttatcgggctcatgtactacaacagcactggcaatatgggggtgctggc cggtcaggcttctcagctgaatgctgtggttgacttgcaagacagaaac accgagctgtcctaccagctcttgcttgactctctgggtgacagaaccc ggtatttcagtatgtggaatcaggcggtggacagctatgatcctgatgt gcgcattattgaaaatcatggtgtggaggatgaacttcccaactattgt ttccctctggatgctgttggcagaacagatacttatcagggaattaagg ctaatggaactgatcaaaccacatggaccaaagatgacagtgtcaatga tgctaatgagataggcaagggtaatccattcgccatggaaatcaacatc caagccaacctgtggaggaacttcctctacgccaacgtggccctgtacc tgcccgactcttacaagtacacgccggccaatgttaccctgcccaccaa caccaacacctacgattacatgaacggccgggtggtggcgccctcgctg gtggactcctacatcaacatcggggcgcgctggtcgctggatcccatgg acaacgtgaaccccttcaaccaccaccgcaatgcggggctgcgctaccg ctccatgctcctgggcaacgggcgctacgtgcccttccacatccaggtg ccccagaaatttttcgccatcaagagcctcctgctcctgcccgggtcct acacctacgagtggaacttccgcaaggacgtcaacatgatcctgcagag ctccctcggcaacgacctgcgcacggacggggcctccatctccttcacc agcatcaacctctacgccaccttcttccccatggcgcacaacacggcct ccacgctcgaggccatgctgcgcaacgacaccaacgaccagtccttcaa -continued cgactacctctcggcggccaacatgctctaccccatcccggccaacgcc
accaacgtgcccatctccatcccctcgcgcaactgggccgccttccgcg
gctggtccttcacgcgtctcaagaccaaggagacgccctcgctgggctc
cgggttcgacccctacttcgtctactcgggctccatcccctacctcgac
ggcaccttctacctcaaccacaccttcaagaaggtctccatcaccttcg
actcctccgtcagctggcccggcaacgaccggctcctgacgcccaacga
gttcgaaatcaagcgcaccgtcgacggcgagggctacaacgtggcccag
tgcaacatgaccaaggactggttcctggtccagatgctggcccactaca
acatcggctaccagggcttctacgtgcccgagggctacaaggaccgcat
gtactccttcttccgcaacttccagcccatgagccgccaggtggtggac
gaggtcaactacaaggactaccaggccgtcaccctggcctaccagcaca
acaactcgggcttcgtcggctacctcgcgcccaccatgcgccagggcca
gccctaccccgccaactacccctacccgctcatcggcaagagcgccgtc
accagcgtcacccagaaaaagttcctctgcgacagggtcatgtggcgca
tccccttctccagcaacttcatgtccatgggcgcgctcaccgacctcgg
ccagaacatgctctatgccaactccgcccacgcgctagacatgaatttc
gaagtcgaccccatggatgagtccacccttctctatgttgtcttcgaag
tcttcgacgtcgtccgagtgcaccagccccaccgcggcgtcatcgaggc
cgtctacctgcgcacccccttctcggccggtaacgccaccacctaagct
cttgcttcttgcaagccatggccgcgggctccggcgagcaggagctcag
ggccatcatccgcgacctgggctgcgggccctacttcctgggcaccttc
gataagcgcttcccgggattcatggccccgcacaagctggcctgcgcca
tcgtcaacacggccggccgcgagaccgggggcgagcactggctggcctt
cgcctggaacccgcgctcgaacacctgctacctcttcgaccccttcggg
ttctcggacgagcgcctcaagcagatctaccagttcgagtacgagggcc
tgctgcgccgcagcgccctggccaccgaggaccgctgcgtcaccctgga
aaagtccacccagaccgtgcagggtccgcgctcggccgcctgcgggctc
ttctgctgcatgttcctgcacgccttcgtgcactggcccgaccgcccca
tggacaagaaccccaccatgaacttgctgacgggggtgcccaacggcat
gctccagtcgccccaggtggaacccaccctgcgccgcaaccaggaggcg
ctctaccgcttcctcaactcccactccgcctactttcgctcccaccgcg
cgcgcatcgagaaggccaccgccttcgaccgcatgaatcaagacatgta
aaccgtgtgtgtatgttaaatgtctttaataaacagcactttcatgtta
cacatgcatctgagatgatttatttagaaatcgaaagggttctgccggg
tctcggcatggcccgcgggcagggacacgttgcggaactggtacttggc
cagccacttgaactcggggatcagcagtttgggcagcggggtgtcgggg
aaggagtcggtccacagcttccgcgtcagttgcagggcgcccagcaggt
cgggcgcggagatcttgaaatcgcagttgggacccgcgttctgcgcgcg
ggagttgcggtacacggggttgcagcactggaacaccatcagggccggg
tgcttcacgctcgccagcaccgtcgcgtcggtgatgctctccacgtcga
ggtcctcggcgttggccatcccgaagggggtcatcttgcaggtctgcct -continued tcccatggtgggcacgcacccgggcttgtggttgcaatcgcagtgcagg
gggatcagcatcatctgggcctggtcggcgttcatccccgggtacatgg
ccttcatgaaagcctccaattgcctgaacgcctgctgggccttggctcc
ctcggtgaagaagaccccgcaggacttgctagagaactggttggtggcg
cacccggcgtcgtgcacgcagcagcgcgcgtcgttgttggccagctgca
ccacgctgcgcccccagcggttctgggtgatcttggcccggtcggggtt
ctccttcagcgcgcgctgcccgttctcgctcgccacatccatctcgatc
atgtgctccttctggatcatggtggtcccgtgcaggcaccgcagcttgc
cctcggcctcggtgcacccgtgcagccacagcgcgcacccggtgcactc
ccagttcttgtgggcgatctgggaatgcgcgtgcacgaagccctgcagg
aagcggcccatcatggtggtcagggtcttgttgctagtgaaggtcagcg
gaatgccgcggtgctcctcgttgatgtacaggtggcagatgcggcggta
cacctcgccctgctcgggcatcagctggaagttggctttcaggtcggtc
tccacgcggtagcggtccatcagcatagtcatgatttccataccettct
cccaggccgagacgatgggcaggctcatagggttcttcaccatcatctt
agcgctagcagccgcggccagggggtcgctctcgtccagggtctcaaag
ctccgcttgccgtccttctcggtgatccgcaccgggggtagctgaagc
ccacggccgccagctcctcctcggcctgtctttcgtcctcgctgtcctg
gctgacgtcctgcaggaccacatgcttggtcttgcggggtttcttcttg
ggcggcagcggcggcggagatgttggagatggcgagggggagcgcgagt
tctcgctcaccactactatctcttcctcttcttggtccgaggccacgcg
gcggtaggtatgtctcttcgggggcagaggcggaggcgacgggctctcg
ccgccgcgacttggcggatggctggcagagccccttccgcgttcggggg
tgcgctcccggcggcgctctgactgacttcctccgcggccggccattgt
gttctcctagggaggaacaacaagcatggagactcagccatcgccaacc
tcgccatctgcccccaccgccgacgagaagcagcagcagcagaatgaaa
gcttaaccgccccgccgcccagccccgccacctccgacgcggccgtccc
agacatgcaagagatggaggaatccatcgagattgacctgggctatgtg
acgcccgcggagcacgaggaggagctggcagtgcgcttttcacaagaag
agatacaccaagaacagccagagcaggaagcagagaatgagcagagtca
ggctgggctcgagcatgacggcgactacctccacctgagcggggggag
gacgcgctcatcaagcatctggcccggcaggccaccatcgtcaaggatg
cgctgctcgaccgcaccgaggtgcccctcagcgtggaggagctcagccg
cgcctacgagttgaacctcttctcgccgcgcgtgcccccccaagcgccag
cccaatggcacctgcgagcccaacccgcgcctcaacttctacccggtct
tcgcggtgcccgaggccctggccacctaccacatctttttcaagaacca
aaagatccccgtctcctgccgcgccaaccgcacccgcgccgacgccctt
ttcaacctgggtcccggcgcccgcctacctgatatcgcctccttggaag
aggttcccaagatcttcgagggtctgggcagcgacgagactcgggccgc
gaacgctctgcaaggagaaggaggagagcatgagcaccacagcgccctg -continued gtcgagttggaaggcgacaacgcgcggctggcggtgctcaaacgcacgg
tcgagctgacccatttcgcctacccggctctgaacctgccccccaaagt
catgagcgcggtcatggaccaggtgctcatcaagcgcgcgtcgcccatc
tccgaggacgagggcatgcaagactccgaggagggcaagcccgtggtca
gcgacgagcagctggcccggtggctgggtcctaatgctagtccccagag
tttggaagagcggcgcaaactcatgatggccgtggtcctggtgaccgtg
gagctggagtgcctgcgccgcttcttcgccgacgcggagaccctgcgca
aggtcgaggagaacctgcactacctcttcaggcacgggttcgtgcgcca
ggcctgcaagatctccaacgtggagctgaccaacctggtctcctacatg
ggcatcttgcacgagaaccgcctggggcagaacgtgctgcacaccaccc
tgcgcggggaggcccggcgcgactacatccgcgactgcgtctacctcta
cctctgccacacctggcagacgggcatgggcgtgtggcagcagtgtctg
gaggagcagaacctgaaagagctctgcaagctcctgcagaagaacctca
agggtctgtggaccgggttcgacgagcgcaccaccgcctcggacctggc
cgacctcattttccccgagcgcctcaggctgacgctgcgcaacggcctg
cccgactttatgagccaaagcatgttgcaaaactttcgctctttcatcc
tcgaacgctccggaatcctgcccgccacctgctccgcgctgccctcgga
cttcgtgccgctgaccttccgcgagtgccccccgccgctgtggagccac
tgctacctgctgcgcctggccaactacctggcctaccactcggacgtga
tcgaggacgtcagcggcgagggcctgctcgagtgccactgccgctgcaa
cctctgcacgccgcaccgctccctggcctgcaacccccagctgctgagc
gagacccagatcatcggcaccttcgagttgcaagggcccagcgaaggcg
agggttcagccgccaaggggggtctgaaactcaccccggggctgtggac
ctcggcctacttgcgcaagttcgtgcccgaggactaccatcccttcgag
atcaggttctacgaggaccaatcccatccgcccaaggccgagctgtcgg
cctgcgtcatcacccaggggggcgatcctggcccaattgcaagccatcca
gaaatcccgccaagaattcttgctgaaaaagggccgcggggtctacctc
gacccccagaccggtgaggagctcaaccccggcttcccccaggatgccc
cgaggaaacaagaagctgaaagtggagctgccgcccgtggaggatttgg
aggaagactgggagaacagcagtcaggcagaggaggaggagatggagga
agactgggacagcactcaggcagaggaggacagcctgcaagacagtctg
gaggaagacgaggaggaggcagaggaggaggtggaagaagcagccgccg
ccagaccgtcgtcctcggcgggggagaaagcaagcagcacggataccat
ctccgctccgggtcggggtcccgctcgaccacacagtagatgggacgag
accggacgattcccgaaccccaccacccagaccggtaagaaggagcggc
agggatacaagtcctggcgggggcacaaaaacgccatcgtctcctgctt
gcaggcctgcgggggcaacatctccttcacccggcgctacctgctcttc
caccgcggggtgaactttccccgcaacatcttgcattactaccgtcacc
tccacagcccctactacttccaagaagaggcagcagcagcagaaaaaga
ccagcagaaaaccagcagctagaaaatccacagcggcggcagcaggtgg
actgaggatcgcggcgaacgagccggcgcaaacccgggagctgaggaac
cggatctttcccaccctctatgccatcttccagcagagtcgggggcagg
agcaggaactgaaagtcaagaaccgttctctgcgctcgctcacccgcag
ttgtctgtatcacaagagcgaagaccaacttcagcgcactctcgaggac
gccgaggctctcttcaacaagtactgcgcgctcactcttaaagagtagc
ccgcgcccgcccagtcgcagaaaaaggcgggaattacgtcacctgtgcc
cttcgccctagccgcctccacccatcatcatgagcaaagagattcccac
gccttacatgtggagctaccagccccagatgggcctggccgccggtgcc
gcccaggactactccacccgcatgaattggctcagcgccgggcccgcga
tgatctcacgggtgaatgacatccgcgcccaccgaaaccagatactcct
agaacagtcagcgctcaccgccacgccccgcaatcacctcaatccgcgt
aattggcccgccgccctggtgtaccaggaaattccccagcccacgaccg
tactacttccgcgagacgcccaggccgaagtccagctgactaactcagg
tgtccagctggcgggcggcgccaccctgtgtcgtcaccgccccgctcag
ggtataaagcggctggtgatccggggcagaggcacacagctcaacgacg
aggtggtgagctcttcgctgggtctgcgacctgacggagtcttccaact
cgccggatcggggagatcttccttcacgcctcgtcaggccgtcctgact
ttggagagttcgtcctcgcagccccgctcgggtggcatcggcactctcc
agttcgtggaggagttcactccctcggtctacttcaaccccttctccgg
ctcccccggccactacccggacgagttcatcccgaacttcgacgccatc
agcgagtcggtggacggctacgattgaatgtcccatggtggcgcagctg
acctagctcggcttcgacacctggaccactgccgccgcttccgctgctt
cgctcgggatctcgccgagtttgcctactttgagctgcccgaggagcac
cctcagggcccggcccacggagtgcggatcgtcgtcgaaggggggcctcg
actcccacctgcttcggatcttcagccagcgtccgatcctggtcgagcg
cgagcaaggacagacccttctgactctgtactgcatctgcaaccacccc
ggcctgcatgaaagtctttgttgtctgctgtgtactgagtataataaaa
gctgagatcagcgactactccggacttccgtgtgttcctgaatccatca
accagtctttgttcttcaccgggaacgagaccgagctccagctccagtg
taagccccacaagaagtacctcacctggctgttccagggctccccgatc
gccgttgtcaaccactgcgacaacgacggagtcctgctgagcggccctg
ccaaccttacttttttccacccgcagaagcaagctccagctcttccaacc
cttcctccccgggacctatcagtgcgtctcgggaccctgccatcacacc
ttccacctgatcccgaataccacagcgtcgctccccgctactaacaacc
aaactaacctccaccaacgccaccgtcgcgacctttctgaatctaatac
taccacccacaccggaggtgagctccgaggtcaaccaacctctgggatt
tactacggcccctgggaggtggttgggttaatagcgctaggcctagttg
cgggtgggcttttggttctctgctacctatacctcccttgctgttcgta
cttagtggtgctgtgttgctggtttaagaaatggggaagatcaccctag
tgagctgcggtgcgctggtggcggtgttgctttcgattgtgggactggg
cggtgcggctgtagtgaaggagaaggccgatccctgcttgcatttcaat -continued cccaacaaatgccagctgagttttcagcccgatggcaatcggtgcgcgg
tactgatcaagtgcggatgggaatgcgagaacgtgagaatcgagtacaa
taacaagactcggaacaatactctcgcgtccgtgtggcagcccggggac
cccgagtggtacaccgtctctgtccccggtgctgacggctccccgcgca
ccgtgaataatactttcatttttgcgcacatgtgcgacacggtcatgtg
gatgagcaagcagtacgatatgtggcccccacgaaggagaacatcgtg
gtcttctccatcgcttacagcctgtgcacggcgctaatcaccgctatcg
tgtgcctgagcattcacatgctcatcgctattcgccccagaaataatgc
cgaaaaagaaaaacagccataacgtttttttcacaccttttcagacc
atggcctctgttaaattttgcttttatttgccagtctcattgccgtca
ttcatggaatgagtaatgagaaaattactatttacactggcactaatca
cacattgaaaggtccagaaaaagccacagaagtttcatggtattgttat
tttaatgaatcagatgtatctactgaactctgtggaaacaataacaaaa
aaaatgagagcattactctcatcaagtttcaatgtggatctgacttaac
cctaattaacatcactagagactatgtaggtatgtattatggaactaca
gcaggcatttcggacatggaattttatcaagtttctgtgtctgaaccca
ccacgcctagaatgaccacaaccacaaaaactacacctgttaccactat
gcagctcactaccaataacattttgccatgcgtcaaatggtcaacaat
agcactcaacccaccccacccagtgaggaaattcccaaatccatgattg
gcattattgttgctgtagtggtgtgcatgttgatcatcgccttgtgcat
ggtgtactatgccttctgctacagaaagcacagactgaacgacaagctg
gaacacttactaagtgttgaattttaatttttagaaccatgaagatcc
taggccttttaatttttctatcattacctctgctctatgcaattctga
caatgaggacgttactgtcgttgtcggatcaaattatacactgaaaggt
ccagcgaagggtatgctttcgtggtattgctattttggatctgacacta
cagaaactgaattatgcaatcttaagaatggcaaaattcaaaattctaa
aattaacaattatatatgcaatggtactgatctgatactcctcaatatc
acgaaatcatatgctggcagttacacctgccctggagatgatgctgaca
gtatgatttttacaaagtaactgttgttgatcccactactccacctcc
acccaccacaactactcacaccacacacacagatcaaaccgcagcagag
gaggcagcaaagttagccttgcaggtccaagacagttcatttgttggca
ttacccctacacctgatcagcggtgtccggggctgctagtcagcggcat
tgtcggtgtgctttcgggattagcagtcataatcatctgcatgttcatt
tttgcttgctgctatagaaggctttaccgacaaaaatcagacccactgc
tgaacctctatgtttaatttttccagagtcatgaaggcagttagcgct
ctagtttttgttctttgattggcattgtttttgcaatcctattccta
aagttagctttattaaagatgtgaatgttactgagggggcaatgtgac
actggtaggtgtagagggtgctgaaaacaccacctggacaaaataccac
ctcaatgggtggaaagatatttgcaattggagtgtattagtttatacat
gtgagggagttaatcttaccattgtcaatgccacctcagctcaaaatgg
tagaattcaaggacaaagtgtcagtgtatctaatgggtattttacccaa -continued catacttttatctatgacgttaaagtcataccactgcctacgcctagcc
cacctagcactaccacacagacaacccacactacacagacaaccacata
cagtacattaaatcagcctaccaccactacagcagcagaggttgccagc
tcgtctggggtccgagtggcatttttgatgtgggccccatctagcagtc
ccactgctagtaccaatgagcagactactgaatttttgtccactgtcga
gagccacaccacagctacctccagtgccttctctagcaccgccaatctc
tcctcgctttcctctacaccaatcagtcccgctactactcctagccccg
ctcctcttcccactcccctgaagcaaacagacggcggcatgcaatggca
gatcaccctgctcattgtgatcgggttggtcatcctggccgtgttgctc
tactacatcttctgccgccgcattcccaacgcgcaccgcaagccggtct
acaagcccatcattgtcgggcagccggagccgcttcaggtggaaggggg
tctaaggaatcttctcttctcttttacagtatggtgattgaactatgat
tcctagacaattcttgatcactattcttatctgcctcctccaagtctgt
gccaccctcgctctggtggccaacgccagtccagactgtattgggccct
tcgcctcctacgtgctctttgccttcaccacctgcatctgctgctgtag
catagtctgcctgcttatcaccttcttccagttcattgactggatcttt
gtgcgcatcgcctacctgcgccaccaccccagtaccgcgaccagcgag
tggcgcggctgctcaggctcctctgataagcatgcgggctctgctactt
ctcgcgcttctgctgttagtgctcccccgtcccgtcgacccccggtccc
ccacccagtcccccgaggaggtccgcaaatgcaaattccaagaaccctg
gaaattcctcaaatgctaccgccaaaaatcagacatgcatcccagctgg
atcatgatcattgggatcgtgaacattctggcctgcaccctcatctcct
ttgtgatttacccctgctttgactttggttggaactcgccagaggcgct
ctatctcccgcctgaacctgacacaccaccacagcaacctcaggcacac
gcactaccaccactacagcctaggccacaatacatgcccatattagact
atgaggccgagccacagcgacccatgctccccgctattagttacttcaa
tctaaccggcggagatgactgacccactggccaacaacaacgtcaacga
ccttctcctggacatggacggccgcgcctcggagcagcgactcgcccaa
cttcgcattcgccagcagcaggagagagccgtcaaggagctgcaggatg
cggtggccatccaccagtgcaagagaggcatcttctgcctggtgaaaca
ggccaagatctcctacgaggtcactccaaacgaccatcgcctctcctac
gagctcctgcagcagcgccagaagttcacctgcctggtcggagtcaacc
ccatcgtcatcacccagcagtctggcgataccaaggggtgcatccactg
ctcctgcgactcccccgactgcgtccacactctgatcaagaccctctgc
ggcctccgcgacctcctccccatgaactaatcaccccccttatccagtga
aataaagatcatattgatgatgattttacagaaataaaaaataatcatt
tgatttgaaataaagatacaatcatattgatgatttgagtttaacaaaa
aaataaagaatcacttacttgaaatctgataccaggtctctgtccatgt
tttctgccaacaccacttcactcccctcttcccagctctggtactgcag
gccccggcgggctgcaaacttcctccacacgctgaaggggatgtcaaat -continued

```
tcctcctgtccctcaatcttcattttatcttctatcagatgtccaaaaa
gcgcgtccgggtggatgatgacttcgaccccgtctacccctacgatgca
gacaacgcaccgaccgtgcccttcatcaacccccccttcgtctcttcag
atggattccaagagaagcccctgggggtgttgtccctgcgactggccga
ccccgtcaccaccaagaacggggaaatcaccctcaagctgggagagggg
gtggacctcgattcctcgggaaaactcatctccaacacggccaccaagg
ccgccgcccctctcagtttttccaacaacaccatttcccttaacatgga
tcaccccttttacactaaagatggaaaattatccttacaagtttctcca
ccattaaatatactgagaacaagcattctaaacacactagctttaggtt
ttggatcaggtttaggactccgtggctctgccttggcagtacagttagt
ctctccacttacatttgatactgatggaaacataaagcttaccttagac
agaggtttgcatgttacaacaggagatgcaattgaaagcaacataagct
gggctaaaggtttaaaatttgaagatggagccatagcaaccaacattgg
aaatgggttagagtttggaagcagtagtacagaaacaggtgttgatgat
gcttacccaatccaagttaaacttggatctggccttagctttgacagta
caggagccataatggctggtaacaaagaagacgataaactcactttgtg
gacaacacctgatccatcaccaaactgtcaaatactcgcagaaaatgat
gcaaaactaacactttgcttgactaaatgtggtagtcaaatactggcca
ctgtgtcagtcttagttgtaggaagtggaaacctaaaccccattactgg
caccgtaagcagtgctcaggtgtttctacgttttgatgcaaacggtgtt
cttttaacagaacattctacactaaaaaaatactgggggtataggcagg
gagatagcatagatggcactccatataccaatgctgtaggattcatgcc
caatttaaaagcttatccaaagtcacaaagttctactactaaaaataat
atagtagggcaagtatacatgaatggagatgtttcaaaacctatgcttc
tcactataaccctcaatggtactgatgacagcaacagtacatattcaat
gtcattttcatacacctggactaatggaagctatgttggagcaacattt
ggggctaactcttataccttctcatacatcgcccaagaatgaacactgt
atcccaccctgcatgccaacccttcccaccccactctgtggaacaaact
ctgaaacacaaaataaaataaagttcaagtgttttattgattcaacagt
tttacaggattcgagcagttatttttcctccaccctcccaggacatgga
atacaccaccctctccccccgcacagccttgaacatctgaatgccattg
gtgatggacatgcttttggtctccacgttccacacagtttcagagcgag
ccagtctcgggtcggtcagggagatgaaaccctccgggcactcccgcat
ctgcacctcacagctcaacagctgaggattgtcctcggtggtcgggatc
acggttatctggaagaagcagaagagcggcggtgggaatcatagtccgc
gaacgggatcggccggtggtgtcgcatcaggccccgcagcagtcgctgc
cgccgccgctccgtcaagctgctgctcagggggtccgggtccagggact
ccctcagcatgatgcccacggccctcagcatcagtcgtctggtgcggcg
ggcgcagcagcgcatgcggatctcgctcaggtcgctgcagtacgtgcaa
cacagaaccaccaggttgttcaacagtccatagttcaacacgctccagc
cgaaactcatcgcgggaaggatgctacccacgtggccgtcgtaccagat
```

-continued

```
cctcaggtaaatcaagtggtgcccccctccagaacacgctgcccacgtac
atgatctccttgggcatgtggcggttcaccacctcccggtaccacatca
ccctctggttgaacatgcagccccggatgatcctgcggaaccacagggc
cagcaccgccccgcccgccatgcagcgaagagaccccgggtcccggcaa
tggcaatggaggacccaccgctcgtacccgtggatcatctgggagctga
acaagtctatgttggcacagcacaggcatatgctcatgcatctcttcag
cactctcaactcctcgggggtcaaaaccatatcccagggcacggggaac
tcttgcaggacagcgaaccccgcagaacagggcaatcctcgcacagaac
ttacattgtgcatggacagggtatcgcaatcaggcagcaccgggtgatc
ctccaccagagaagcgcgggtctcggtctcctcacagcgtggtaagggg
gccggccgatacgggtgatggcgggacgcggctgatcgtgttcgcgacc
gtgtcatgatgcagttgctttcggacattttcgtacttgctgtagcaga
acctggtccgggcgctgcacaccgatcgccggcggcggtctcggcgctt
ggaacgctcggtgttgaaattgtaaaacagccactctctcagaccgtgc
agcagatctagggcctcaggagtgatgaagatcccatcatgcctgatgg
ctctgatcacatcgaccaccgtggaatgggccagacccagccagatgat
gcaattttgttgggtttcggtgacggcgggggagggaagaacaggaaga
accatgattaacttttaatccaaacggtctcggagtacttcaaaatgaa
gatcgcggagatggcacctctcgcccccgctgtgttggtggaaaataac
agccaggtcaaaggtgatacggttctcgagatgttccacggtggcttcc
agcaaagcctccacgcgcacatccagaaacaagacaatagcgaaagcgg
gagggttctctaattcctcaatcatcatgttacactcctgcaccatccc
cagataattttcatttttccagccttgaatgattcgaactagttcgtga
ggtaaatccaagccagccatgataaagagctcgcgcagagcgccctcca
ccggcattcttaagcacaccctcataattccaagatattctgctcctgg
ttcacctgcagcagattgacaagcggaatatcaaaatctctgccgcgat
ccctgagctcctccctcagcaataactgtaagtactctttcatatcctc
tccgaaatttttagccataggaccaccaggaataagattagggcaagcc
acagtacagataaaccgaagtcctccccagtgagcattgccaaatgcaa
gactgctataagcatgctggctagacccggtgatatcttccagataact
ggacagaaaatcgcccaggcaatttttaagaaaatcaacaaaagaaaaa
tcctccaggtggacgtttagagcctcgggaacaacgatgaagtaaatgc
aagcggtgcgttccagcatggttagttagctgatctgtagaaaaaacaa
aaatgaacattaaaccatgctagcctggcgaacaggtgggtaaatcgtt
ctctccagcaccaggcaggccacggggtctccggcgcgaccctcgtaaa
aattgtcgctatgattgaaaaccatcacagagagacgttcccggtggcc
ggcgtgaatgattcgacaagatgaatacaccccccggaacattggcgtcc
gcgagtgaaaaaaagcgcccgaggaagcaataaggcactacaatgctca
gtctcaagtccagcaaagcgatgccatgcggatgaagcacaaaattctc
aggtgcgtacaaaatgtaattactcccctcctgcacaggcagcaaagcc
```

-continued cccgatccctccaggtacacatacaaagcctcagcgtccatagcttacc gagcagcagcacacaacaggcgcaagagtcagagaaaggctgagctcta acctgtccacccgctctctgctcaatatatagcccagatctacactgac gtaaaggccaaagtctaaaaatacccgccaaataatcacacacgcccag cacacgcccagaaaccggtgacacactcaaaaaaatacgcgcacttcct caaacgcccaaaactgccgtcatttccgggttcccacgctacgtcatca aaacacgactttcaaattccgtcgaccgttaaaaacgtcacccgccccg cccctaacggtcgcccgtctctcagccaatcagcgccccgcatccccaa attcaaacacctcatttgcatattaacgcgcacaaaaagtttgaggtat attattgatgatgg SEQ ID NO: 58. Complete Sequence of the AdC68-734 Vector TTAATTAAccatcttcaataatatacctcaaacttttttgtgcgcgttaa tatgcaaatgaggcgtttgaatttggggaggaagggcggtgattggtcg agggatgagcgaccgttaggggcggggcgagtgacgttttgatgacgtg gttgcgaggaggagccagtttgcaagttctcgtgggaaaagtgacgtca aacgaggtgtggtttgaacacggaaatactcaattttcccgcgctctct gacaggaaatgaggtgtttctgggcggatgcaagtgaaaacgggccatt ttcgcgcgaaaactgaatgaggaagtgaaaatctgagtaatttcgcgtt tatggcagggaggagtatttgccgagggccgagtagactttgaccgatt acgtgggggtttcgattaccgtgtttttcacctaaatttccgcgtacgg tgtcaaagtccggtgtttttactactgtaatagtaatcaattacggggt cattagttcatagcccatatatggagttccgcgttacataacttacggt aaatggcccgcctggctgaccgcccaacgacccccgcccattgacgtca ataatgacgtatgttcccatagtaacgccaatagggactttccattgac gtcaatgggtggagtatttacggtaaactgcccacttggcagtacatca agtgtatcatatgccaagtacgccccctattgacgtcaatgacggtaaa tggcccgcctggcattatgcccagtacatgaccttatgggactttccta cttggcagtacatctacgtattagtcatcgctattaccatggtgatgcg gttttggcagtacatcaatgggcgtggatagcggtttgactcacgggga tttccaagtctccaccccattgacgtcaatgggagtttgttttggcacc aaaatcaacgggactttccaaaatgtcgtaacaactccgccccattgac gcaaatgggcggtaggcgtgtacggtgggaggtctatataagcagagct gtccctatcagtgatagagatctccctatcagtgatagagagtttagtg aaccgtcagatccgctagggtaccaacATGGCTAGCATCGTCGGAGGGT

GGGAGTGCGAAAAGCACTCACAGCCATGGCAGGTCCTGGTCGCCTCGCG

CGGACGCGCCGTGTGTGGAGGTGTGCTGGTCCACCCGCAGTGGGTGTTG

ACTGCGGCCCATTGCATCAGAAATAAGTCCGTGATCCTCTTGGGGAGAC

ATTCCCTGTTTCACCCCGAAGATACTGGACAGGTGTTCCAAGTGAGCCA

CTCCTTCCCGCATCCACTGTACGACATGAGCCTGCTGAAGAACCGCTTT

CTGCGGCCAGGGGACGACTCATCACACGATTTGATGCTGCTTCGGCTCT

CGGAACCGGCCGAGCTCACCGACGCAGTGAAGGTCATGGACCTCCCTAC

-continued

GCAAGAGCCTGCTCTCGGTACCACTTGTTACGCATCGGGATGGGGCTCC

ATCGAGCCGGAAGAATTCCTGACCCCGAAAAAGCTGCAGTGCGTGGATC

TGCACGTGATTTCGAATGACGTGTGCGCGCAAGTGCATCCACAAAAGGT

CACTAAGTTCATGCTGTGCGCCGGAAGGTGGACCGGCGGAAAATCGACC

TGTTCCGGCGACAGCGGAGGCCCACTCGTGTGCAACGGTGTGCTGCAGG

GCATCACTAGCTGGGGATCAGAACCGTGCGCGCTTCCGGAGCGGCCCTC

GCTCTACACGAAGGTGGTGCACTACCGCAAATGGATTAAAGATACCATC

GTCGCAAACCCTggatccgaaggtaggggttcattattgacctgtggag atgtcgaagaaaacccaggacccGCTAGCAAAGCAGTGCTGCTGGCGCT

CCTGATGGCTGGACTCGCGCTGCAGCCTGGAACCGCCCTGCTCTGTTAC

TCGTGCAAGGCCCAAGTCTCGAATGAGGACTGTTTGCAAGTGGAAAACT

GCACCCAGCTCGGAGAACAATGCTGGACTGCACGGATCCGCGCTGTCGG

CCTGCTGACCGTGATCTCCAAAGGGTGCTCATTGAACTGCGTGGACGAT

AGCCAGGACTACTACGTGGGAAAGAAGAATATCACTTGTTGCGACACGG

ATCTTTGCAACGCGTCCGGAGCGCACGCCCTGCAGCCAGCAGCCGCCAT

TCTGGCCCTGCTTCCGGCCCTGGGGTTGCTGCTCTGGGGTCCGGGCCAG

CTCggatcccagaccctgaactttgatctgctgaaactggcaggcgatg tggaaagcaacccaggcccaATGGCTAGCGCTCGCAGACCGCGGTGGCT

GTGTGCAGGGGCGCTCGTCCTGGCGGGTGGCTTCTTTTTGCTCGGCTTT

CTTTTCGGATGGTTCATCAAATCGTCAAACGAAGCTACCAATATCACCC

CGAAGCACAACATGAAGGCCTTTCTGGATGAGCTGAAGGCTGAGAACAT

TAAGAAGTTCCTCTACAACTTCACCCAGATCCCACATTTGGCGGGCACT

GAGCAGAACTTTCAGTTGGCTAAGCAGATCCAGAGCCAGTGGAAGGAAT

TCGGCCTGGACTCCGTCGAGCTGGCGCATTACGATGTGCTGCTGAGCTA

CCCTAATAAGACTCATCCGAACTATATCTCGATTATCAATGAGGACGGA

AACGAAATCTTTAACACGTCCCTCTTCGAGCCGCCACCGCCTGGATACG

AGAACGTGTCAGATATCGTGCCTCCGTTCTCGGCCTTCTCGCCCCAGGG

AATGCCCGAAGGGGACCTGGTGTACGTGAACTACGCAAGGACCGAGGAC

TTCTTCAAGTTGGAGCGGGATATGAAGATCAATTGCAGCGGAAAGATCG

TCATCGCCCGCTACGGCAAAGTGTTCCGCGGCAACAAGGTGAAGAATGC

ACAGTTGGCAGGCGCCAAGGGCGTCATCCTCTACTCGGATCCTGCCGAC

TACTTCGCTCCTGGCGTGAAATCCTACCCTGATGGTTGGAATCTGCCAG

GAGGAGGGGTGCAGAGGGGAAATATCCTGAACCTGAACGGTGCCGGTGA

CCCACTTACTCCGGGTTACCCGGCCAACGAATACGCGTACAGGCGGGGT

ATCGCGGAAGCCGTCGGACTGCCGTCCATCCCGGTCCATCCGATTGGTT

ACTACGACGCCCAGAAGCTCCTCGAAAAGATGGGAGGCAGCGCCCCTCC

GGACTCGTCATGGAGAGGCTCGCTGAAGGTGCCATACAACGTGGGACCC

GGATTCACTGGAAATTTCAGCACTCAAAAAGTGAAGATGCACATTCACT

CCACTAACGAAGTCACCAGGATCTACAACGTCATCGGAACCCTCCGGGG

AGCGGTGGAACCGGACCGCTACGTGATCCTCGGTGGACACCGGGATAGC

-continued

TGGGTGTTCGGAGGAATCGATCCTCAATCGGGCGCAGCCGTCGTCCATG

AAATCGTCAGGTCCTTTGGTACTCTTAAGAAGGAGGGCTGGCGCCCTAG

ACGCACTATTCTGTTCGCCTCGTGGGATGCCGAAGAATTTGGTCTGCTC

GGCAGCACCGAATGGGCTGAGGAAAACTCCCGCCTGCTCCAAGAACGCG

GAGTGGCGTACATCAATGCCGACTCATCCATCGAAGGAAACTACACGCT

GCGGGTGGACTGCACTCCACTGATGTACTCGCTCGTGCACAACCTGACC

AAAGAACTCAAATCCCCAGACGAAGGATTCGAGGGAAAATCGCTGTACG

AGTCGTGGACCAAGAAGAGCCCATCCCCGGAGTTCAGCGGGATGCCGCG

GATCTCAAAGCTCGGATCAGGAAATGATTTCGAAGTGTTCTTTCAGAGG

CTGGGAATTGCGTCGGGAAGGGCTCGGTACACGAAAAACTGGGAAACTA

ACAAGTTCTCGGGATACCCGCTGTACCACTCGGTGTATGAAACTTACGA

ACTGGTGGAGAAATTCTACGATCCTATGTTTAAGTACCACCTGACTGTG

GCCCAAGTGAGAGGCGGAATGGTGTTCGAGTTGGCCAATTCAATTGTGC

TGCCATTCGATTGCCGCGACTACGCCGTGGTGCTGAGAAAGTACGCAGA

CAAAATCTACTCAATCAGCATGAAGCACCCACAAGAGATGAAAACCTAC

TCAGTCTCCTTCGACTCCCTCTTCTCCGCGGTGAAGAACTTCACCGAGA

TCGCGAGCAAATTCTCGGAGCGCCTTCAAGATTTTGACAAATCCAATCC

GATCGTCCTCCGCATGATGAATGACCAGCTCATGTTTCTCGAACGGGCC

TTCATCGATCCACTGGGACTTCCGGACCGGCCGTTTTACCGCCACGTGA

TCTACGCGCCCTCGTCGCATAACAAGTATGCTGGAGAGAGCTTCCCGGG

TATCTACGACGCATTGTTCGACATTGAGTCCAAGGTGGATCCGTCCAAA

GCCTGGGGTGAAGTGAAGCGCCAAATCTACGTGGCGGCCTTTACCGTCC

AGGCGGCAGCAGAAACCTTGAGCGAGGTGGCTTGActcgagcctaagct tctagataagatatccgatccaccggatctagataactgatcataatca gccataccacatttgtagaggttttacttgctttaaaaaacctcccaca cctccccctgaacctgaaacataaaatgaatgcaattgttgttgttaac ttgtttattgcagcttataatggttacaaataaagcaatagcatcacaa atttcacaaataaagcatttttttcactgcattctagttgtggtttgtc caaactcatcaatgtatcttatatgctggccaccgtacatgtggcttcc catgctcgcaagccctggcccgagttcgagcacaatgtcatgaccaggt gcaatatgcatctggggtcccgccgaggcatgttcatgccctaccagtg caacctgaattatgtgaaggtgctgctggagcccgatgccatgtccaga gtgagcctgacgggggtgtttgacatgaatgtggaggtgtggaagattc tgagatatgatgaatccaagaccaggtgccgagcctgcgagtgcggagg gaagcatgccaggttccagcccgtgtgtgtggatgtgacggaggacctg cgacccgatcatttggtgttgccctgcaccgggacggagttcggttcca gcggggaagaatctgactagagtgagtagtgttctggggcgggggagga cctgcatgagggccagaataactgaaatctgtgcttttctgtgtgttgc agcagcatgagcggaagcggctcctttgagggaggggtattcagccctt atctgacggggcgtctcccctcctgggcgggagtgcgtcagaatgtgat gggatccacggtggacggccggcccgtgcagcccgcgaactcttcaacc -continued ctgacctatgcaaccctgagctcttcgtcgttggacgcagctgccgccg cagctgctgcatctgccgccagcgccgtgcgcggaatggccatgggcgc cggctactacggcactctggtggccaactcgagttccaccaataatccc gccagcctgaacgaggagaagctgttgctgctgatggcccagctcgagg ccttgacccagcgcctgggcgagctgacccagcaggtggctcagctgca ggagcagacgcgggccgcggttgccacggtgaaatccaaataaaaaatg aatcaataaataaacggagacggttgttgattttaacacagagtctgaa tctttatttgattttcgcgcgcggtaggccctggaccaccggtctcga tcattgagcacccggtggatcttttccaggacccggtagaggtgggctt ggatgttgaggtacatgggcatgagcccgtcccgggggtggaggtagct ccattgcagggcctcgtgctcgggggtggtgttgtaaatcacccagtca tagcaggggcgcagggcatggtgttgcacaatatctttgaggaggagac tgatggccacgggcagccctttggtgtaggtgtttacaaatctgttgag ctgggagggatgcatgcgggggagatgaggtgcatcttggcctggatc ttgagattggcgatgttaccgcccagatcccgcctggggttcatgttgt gcaggaccaccagcacggtgtatccggtgcacttggggaatttatcatg caacttggaagggaaggcgtgaaagaatttggcgacgcctttgtgcccg cccaggttttccatgcactcatccatgatgatggcgatgggcccgtggg cggcggcctgggcaaagacgtttcgggggtcggacacatcatagttgtg gtcctgggtgaggtcatcataggccattttaatgaatttggggcggagg gtgccggactgggggacaaaggtaccctcgatcccgggggcgtagttcc cctcacagatctgcatctcccaggctttgagctcggagggggggatcat gtccacctgcggggcgataaagaacacggtttccggggcgggggagatg agctgggccgaaagcaagttccggagcagctgggacttgccgcagccgg tggggccgtagatgaccccgatgaccggctgcaggtggtagttgaggga gagacagctgccgtcctcccggaggagggggccacctcgttcatcatc tcgcgcacgtgcatgttctcgcgcaccagttccgccaggaggcgctctc cccccagggataggagctcctggagcgaggcgaagtttttcagcggctt gagtccgtcggccatgggcattttggagagggtttgttgcaagagttcc aggcggtcccagagctcggtgatgtgctctacggcatctcgatccagca gacctcctcgtttcgcgggttgggacggctgcgggagtagggcaccaga cgatgggcgtccagcgcagccagggtccggtccttccagggtcgcagcg tccgcgtcagggtggtctccgtcacggtgaaggggtgcgcgccgggctg ggcgcttgcgagggtgcgcttcaggctcatccggctggtcgaaaaccgc tcccgatcggcgccctgcgcgtcggccaggtagcaattgaccatgagtt cgtagttgagcgcctcggccgcgtggcctttggcgcggagcttaccttt ggaagtctgcccgcaggcgggacagaggagggacttgagggcgtagagc ttgggggcgaggaagacggactcgggggcgtaggcgtccgcgccgcagt gggcgcagacggtctcgcactccacgagccaggtgaggtcgggctggtc ggggtcaaaaaccagtttcccgccgttctttttgatgcgtttcttacct -continued ttggtctccatgagctcgtgtccccgctgggtgacaaagaggctgtccg tgtccccgtagaccgactttatgggccggtcctcgagcggtgtgccgcg gtcctcctcgtagaggaaccccgcccactccgagacgaaagcccgggtc caggccagcacgaaggaggccacgtgggacgggtagcggtcgttgtcca ccagcgggtccaccttttccagggtatgcaaacacatgtccccctcgtc cacatccaggaaggtgattggcttgtaagtgtaggccacgtgaccgggg gtcccggccgggggggtataaaagggtgcgggtccctgctcgtcctcac tgtcttccggatcgctgtccaggagcgccagctgttggggtaggtattc cctctcgaaggcgggcatgacctcggcactcaggttgtcagtttctaga aacgaggaggatttgatattgacggtgccggcggagatgcctttcaaga gcccctcgtccatctggtcagaaaagacgatctttttgttgtcgagctt ggtggcgaaggagccgtagagggcgttggagaggagcttggcgatggag cgcatggtctggtttttttccttgtcggcgcgctccttggcggcgatgt tgagctgcacgtactcgcgcgccacgcacttccattcggggaagacggt ggtcagctcgtcgggcacgattctgacctgccagccccgattatgcagg gtgatgaggtccacactggtggccacctcgccgcgcaggggctcattag tccagcagaggcgtccgcccttgcgcgagcagaagggggggcagggggtc cagcatgacctcgtcggggggggtcggcatcgatggtgaagatgccgggc aggaggtcggggtcaaagtagctgatggaagtggccagatcgtccaggg cagcttgccattcgcgcacggccagcgcgcgctcgtagggactgagggg cgtgccccagggcatgggatgggtaagcgcggaggcgtacatgccgcag atgtcgtagacgtagaggggctcctcgaggatgccgatgtaggtggggt agcagcgccccccgcggatgctggcgcgcacgtagtcatacagctcgtg cgagggggcgaggagccccgggcccaggttggtgcgactgggcttttcg gcgcggtagacgatctggcggaaaatggcatgcgagttggaggagatgg tgggcctttggaagatgttgaagtgggcgtggggcagtccgaccgagtc gcggatgaagtgggcgtaggagtcttgcagcttggcgacgagctcggcg gtgactaggacgtccagagcgcagtagtcgagggtctcctggatgatgt catacttgagctgtcccttttgtttccacagctcgcggttgagaaggaa ctcttcgcggtccttccagtactcttcgaggggggaacccgtcctgatct gcacggtaagagcctagcatgtagaactggttgacggccttgtaggcgc agcagcccttctccacggggagggcgtaggcctgggcggccttgcgcag ggaggtgtgcgtgagggcgaaagtgtccctgaccatgaccttgaggaac tggtgcttgaagtcgatatcgtcgcagccccccctgctcccagagctgga agtccgtgcgcttcttgtaggcggggttgggcaaagcgaaagtaacatc gttgaagaggatcttgcccgcgcggggcataaagttgcgagtgatgcgg aaaggttggggcacctcggcccggttgttgatgacctgggcggcgagca cgatctcgtcgaagccgttgatgttgtggcccacgatgtagagttccac gaatcgcggacggcccttgacgtggggcagtttcttgagctcctcgtag gtgagctcgtcggggtcgctgagcccgtgctgctcgagcgcccagtcgg cgagatgggggttggcgcggaggaaggaagtccagagatccacggccag -continued ggcggtttgcagacggtcccggtactgacggaactgctgcccgacggcc atttttttcggggggtgacgcagtagaaggtgcgggggtccccgtgccagc gatcccatttgagctggagggcgagatcgagggcgagctcgacgagccg gtcgtccccggagagtttcatgaccagcatgaaggggacgagctgcttg ccgaaggaccccatccaggtgtaggtttccacatcgtaggtgaggaaga gcctttcggtgcgaggatgcgagccgatggggaagaactggatctcctg ccaccaattggaggaatggctgttgatgtgatggaagtagaaatgccga cggcgcgccgaacactcgtgcttgtgtttatacaagcggccacagtgct cgcaacgctgcacgggatgcacgtgctgcacgagctgtacctgagttcc tttgacgaggaatttcagtgggaagtggagtcgtggcgcctgcatctcg tgctgtactacgtcgtggtggtcggcctggccctcttctgcctcgatgg tggtcatgctgacgagcccgcgcgggaggcaggtccagacctcggcgcg agcgggtcggagagcgaggacgagggcgcgcaggccggagctgtccagg gtcctgagacgctgcggagtcaggtcagtgggcagcggcggcgcgcggt tgacttgcaggagtttttccagggcgcgcgggaggtccagatggtactt gatctccaccgcgccattggtggcgacgtcgatggcttgcagggtcccg tgccccctggggtgtgaccaccgtcccccgtttcttcttgggcggctggg gcgacgggggcggtgcctcttccatggttagaagcggcggcgaggacgc gcgccgggcggcaggggcggctcggggcccggaggcaggggcggcaggg gcacgtcggcgccgcgcgcgggtaggttctggtactgcgcccggagaag actggcgtgagcgacgacgcgacggttgacgtcctggatctgacgcctc tgggtgaaggccacgggacccgtgagtttgaacctgaaagagagttcga cagaatcaatctcggtatcgttgacggcggcctgccgcaggatctcttg cacgtcgcccgagttgtcctggtaggcgatctcggtcatgaactgctcg atctcctcctcttgaaggtctccgcggccggcgcgctccacggtggccg cgaggtcgttggagatgcggcccatgagctgcgagaaggcgttcatgcc cgcctcgttccagacgcggctgtagaccacgacgccctcgggatcgcGg gcgcgcatgaccacctgggcgaggttgagctccacgtggcgcgtgaaga ccgcgtagttgcagaggcgctggtagaggtagttgagcgtggtggcgat gtgctcggtgacgaagaaatacatgatccagcggcggagcggcatctcg ctgacgtcgcccagcgcctccaaacgttccatggcctcgtaaaagtcca cggcgaagttgaaaaactgggagttgcgcgccgagacggtcaactcctc ctccagaagacggatgagctcggcgatggtggcgcgcacctcgcgctcg aaggcccccgggagttcctccacttcctcttcttcctcctccactaaca tctcttctacttcctcctcaggcggcagtggtggcgggggagggggcct gcgtcgccggcggcgcacgggcagacggtcgatgaagcgctcgatggtc tcgccgcgccggcgtcgcatggtctcggtgacggcgcgcccgtcctcgc ggggccgcagcgtgaagacgccgccgcgcatctccaggtggccgggggg gtccccgttgggcagggagagggcgctgacgatgcatcttatcaattgc cccgtagggactccgcgcaaggacctgagcgtctcgagatccacgggat -continued ctgaaaaccgctgaacgaaggcttcgagccagtcgcagtcgcaaggtag
gctgagcacggtttcttctggcgggtcatgttggttgggagcggggcgg
gcgatgctgctggtgatgaagttgaaataggcggttctgagacggcgga
tggtggcgaggagcaccaggtctttgggcccggcttgctggatgcgcag
acggtcggccatgccccaggcgtggtcctgacacctggccaggtccttg
tagtagtcctgcatgagccgctccacgggcacctcctcctcgcccgcgc
ggccgtgcatgcgcgtgagcccgaagccgcgctggggctggacgagcgc
caggtcggcgacgacgcgctcggcgaggatggcttgctggatctgggtg
agggtggtctggaagtcatcaaagtcgacgaagcggtggtaggctccgg
tgttgatggtgtaggagcagttggccatgacggaccagttgacggtctg
gtggcccggacgcacgagctcgtggtacttgaggcgcgagtaggcgcgc
gtgtcgaagatgtagtcgttgcaggtgcgcaccaggtactggtagccga
tgaggaagtgcggcggcggctggcggtagagcggccatcgctcggtggc
gggggcgccgggcgcgaggtcctcgagcatggtgcggtggtagccgtag
atgtacctggacatccaggtgatgccggcggcggtggtggaggcgcgcg
ggaactcgcggacgcggttccagatgttgcgcagcggcaggaagtagtt
catggtgggcacggtctggcccgtgaggcgcgcgcagtcgtggatgctc
tatacgggcaaaaacgaaagcggtcagcggctcgactccgtggcctgga
ggctaagcgaacgggttgggctgcgcgtgtaccccggttcgaatctcga
atcaggctggagccgcagctaacgtggtattggcactcccgtctcgacc
caagcctgcaccaaccctccaggatacggaggcgggtcgttttgcaact
ttttttggaggccggatgagactagtaagcgcggaaagcggccgaccg
cgatggctcgctgccgtagtctggagaagaatcgccagggttgcgttgc
ggtgtgccccggttcgaggccggccggattccgcggctaacgagggcgt
ggctgccccgtcgtttccaagaccccatagccagccgacttctccagtt
acggagcgagcccctcttttgttttgtttgtttttgccagatgcatccc
gtactgcggcagatgcgcccccaccaccctccaccgcaacaacagcccc
ctccacagccggcgcttctgcccccgccccagcagcaacttccagccac
gaccgccgcggccgccgtgagcggggctggacagagttatgatcaccag
ctggccttggaagagggcgaggggctggcgcgcctgggggcgtcgtcgc
cggagcggcacccgcgcgtgcagatgaaaagggacgctcgcgaggccta
cgtgcccaagcagaacctgttcagagacaggagcggcgaggagcccgag
gagatgcgcgcggcccggttccacgcggggcgggagctgcggcgcggcc
tggaccgaaagagggtgctgagggacgaggatttcgaggcggacgagct
gacggggatcagccccgcgcgcgcgcacgtggccgcggccaacctggtc
acggcgtacgagcagaccgtgaaggaggagagcaacttccaaaaatcct
tcaacaaccacgtgcgcaccctgatcgcgcgcgaggaggtgaccctggg
cctgatgcacctgtgggacctgctggaggccatcgtgcagaaccccacc
agcaagccgctgacggcgcagctgttcctggtggtgcagcatagtcggg
acaacgaagcgttcagggaggcgctgctgaatatcaccgagcccgaggg
ccgctggctcctggacctggtgaacattctgcagagcatcgtggtgcag -continued gagcgcgggctgccgctgtccgagaagctggcggccatcaacttctcgg
tgctgagtttgggcaagtactacgctaggaagatctacaagaccccgta
cgtgcccatagacaaggaggtgaagatcgacgggttttacatgcgcatg
accctgaaagtgctgaccctgagcgacgatctggggggtgtaccgcaacg
acaggatgcaccgtgcggtgagcgccagcaggcggcgcgagctgagcga
ccaggagctgatgcatagtctgcagcgggccctgaccggggccgggacc
gaggggggagagctactttgacatgggcgcggacctgcactggcagccca
gccgccgggccttggaggcggcggcaggaccctacgtagaagaggtgga
cgatgaggtggacgaggagggcgagtacctggaagactgatggcgcgac
cgtatttttgctagatgcaacaacaacagccacctcctgatcccgcgat
gcgggcggcgctgcagagccagccgtccggcattaactcctcggacgat
tggacccaggccatgcaacgcatcatggcgctgacgacccgcaaccccg
aagcctttagacagcagccccaggccaaccggctctcggccatcctgga
ggccgtggtgccctcgcgctccaaccccacgcacgagaaggtcctggcc
atcgtgaacgcgctggtggagaacaaggccatccgcggcgacgaggccg
gcctggtgtacaacgcgctgctggagcgcgtggcccgctacaacagcac
caacgtgcagaccaacctggaccgcatggtgaccgacgtgcgcgaggcc
gtggcccagcgcgagcggttccaccgcgagtccaacctgggatccatgg
tggcgctgaacgccttcctcagcacccagcccgccaacgtgccccgggg
ccaggaggactacaccaacttcatcagcgccctgcgcctgatggtgacc
gaggtgccccagagcgaggtgtaccagtccgggccggactacttcttcc
agaccagtcgccagggcttgcagaccgtgaacctgagccaggctttcaa
gaacttgcagggcctgtggggcgtgcaggccccggtcggggaccgcgcg
acggtgtcgagcctgctgacgccgaactcgcgcctgctgctgctgctgg
tggccccccttcacggacagcggcagcatcaaccgcaactcgtacctggg
ctacctgattaacctgtaccgcgaggccatcggccaggcgcacgtggac
gagcagacctaccaggagatcacccacgtgagccgcgccctgggccagg
acgacccgggcaacctggaagccaccctgaactttttgctgaccaaccg
gtcgcagaagatcccgccccagtacgcgctcagcaccgaggaggagcgc
atcctgcgttacgtgcagcagagcgtgggcctgttcctgatgcaggagg
gggccacccccagcgccgcgctcgacatgaccgcgcgcaacatggagcc
cagcatgtacgccagcaaccgcccgttcatcaataaactgatggactac
ttgcatcgggcggccgccatgaactctgactatttcaccaacgccatcc
tgaatccccactggctcccgccgccggggttctacacgggcgagtacga
catgcccgaccccaatgacgggttcctgtgggacgatgtggacagcagc
gtgttctcccccccgaccgggtgctaacgagcgccccttgtggaagaagg
aaggcagcgaccgacgcccgtcctcggcgctgtccggccgcgagggtgc
tgccgcggcggtgcccgaggccgccagtcctttcccgagcttgcccttc
tcgctgaacagtatccgcagcagcgagctgggcaggatcacgcgcccgc
gcttgctgggcgaagaggagtacttgaatgactcgctgttgagacccga -continued gcgggagaagaacttccccaataacgggatagaaagcctggtggacaag atgagccgctggaagacgtatgcgcaggagcacagggacgatccccggg cgtcgcagggggccacgagccggggcagcgccgcccgtaaacgccggtg gcacgacaggcagcggggacagatgtgggacgatgaggactccgccgac gacagcagcgtgttggacttgggtgggagtggtaacccgttcgctcacc tgcgcccccgtatcgggcgcatgatgtaagagaaaccgaaaataaatga tactcaccaaggccatggcgaccagcgtgcgttcgtttcttctctgttg ttgttgtatctagtatgatgaggcgtgcgtacccggagggtcctcctcc ctcgtacgagagcgtgatgcagcaggcgatggcggcggcggcgatgcag cccccgctggaggctccttacgtgcccccgcggtacctggcgcctacgg aggggcggaacagcattcgttactcggagctggcacccttgtacgatac cacccggttgtacctggtggacaacaagtcggcggacatcgcctcgctg aactaccagaacgaccacagcaacttcctgaccaccgtggtgcagaaca atgacttcacccccacggaggccagcacccagaccatcaactttgacga gcgctcgcggtggggcggccagctgaaaaccatcatgcacaccaacatg cccaacgtgaacgagttcatgtacagcaacaagttcaaggcgcgggtga tggtctcccgcaagacccccaatggggtgacagtgacagaggattatga tggtagtcaggatgagctgaagtatgaatgggtggaatttgagctgccc gaaggcaacttctcggtgaccatgaccatcgacctgatgaacaacgcca tcatcgacaattacttggcggtggggcggcagaacggggtgctggagag cgacatcggcgtgaagttcgacactaggaacttcaggctgggctgggac cccgtgaccgagctggtcatgcccggggtgtacaccaacgaggctttcc atcccgatattgtcttgctgcccggctgcggggtggacttcaccgagag ccgcctcagcaacctgctgggcattcgcaagaggcagcccttccaggaa ggcttccagatcatgtacgaggatctggagggggcaacatccccgcgc tcctggatgtcgacgcctatgagaaaagcaaggaggatgcagcagctga agcaactgcagccgtagctaccgcctctaccgaggtcaggggcgataat tttgcaagcgccgcagcagtggcagcggccgaggcggctgaaaccgaaa gtaagatagtcattcagccggtggagaaggatagcaagaacaggagcta caacgtactaccggacaagataaacaccgcctaccgcagctggtaccta gcctacaactatggcgaccccgagaagggcgtgcgctcctggacgctgc tcaccacctcggacgtcacctgcggcgtggagcaagtctactggtcgct gcccgacatgatgcaagacccggtcaccttccgctccacgcgtcaagtt agcaactacccggtggtgggcgccgagctcctgcccgtctactccaaga gcttcttcaacgagcaggccgtctactcgcagcagctgcgcgccttcac ctcgcttacgcacgtcttcaaccgcttccccgagaaccagatcctcgtc cgcccgcccgcgcccaccattaccaccgtcagtgaaaacgttcctgctc tcacagatcacgggaccctgccgctgcgcagcagtatccggggagtcca gcgcgtgaccgttactgacgccagacgccgcacctgcccctacgtctac aaggccctgggcatagtcgcgccgcgcgtcctctcgagccgcaccttct aaatgtccattctcatctcgcccagtaataacaccggttggggcctgcg -continued cgcgcccagcaagatgtacggaggcgctcgccaacgctccacgcaacac cccgtgcgcgtgcgcgggcacttccgcgctccctggggcgccctcaagg gccgcgtgcggtcgcgcaccaccgtcgacgacgtgatcgaccaggtggt ggccgacgcgcgcaactacacccccgccgccgcgcccgtctccaccgtg gacgccgtcatcgacagcgtggtggcCgacgcgcgccggtacgcccgcg ccaagagccggcggcggcgcatcgcccggcggcaccggagcacccccgc catgcgcgcggcgcgagccttgctgcgcagggccaggcgcacgggacgc agggccatgctcagggcggccagacgcgcggcttcaggcgccagcgccg gcaggacccggagacgcgcggccacggcggcggcagcggccatcgccag catgtcccgcccgcggcgagggaacgtgtactgggtgcgcgacgccgcc accggtgtgcgcgtgcccgtgcgcacccgcccccctcgcacttgaagat gttcacttcgcgatgttgatgtgtcccagcggcgaggaggatgtccaag cgcaaattcaaggaagagatgctccaggtcatcgcgcctgagatctacg gccctgcggtggtgaaggaggaaagaaagccccgcaaaatcaagcgggt caaaaaggacaaaaaggaagaagaaagtgatgtggacggattggtggag tttgtgcgcgagttcgcccccggcggcgcgtgcagtggcgcgggcgga aggtgcaaccggtgctgagacccggcaccaccgtggtcttcacgcccgg cgagcgctccggcaccgcttccaagcgctcctacgacgaggtgtacggg gatgatgatattctggagcaggcggccgagcgcctgggcgagtttgctt acggcaagcgcagccgttccgcaccgaaggaagaggcggtgtccatccc gctggaccacggcaaccccacgccgagcctcaagcccgtgaccttgcag caggtgctgccgaccgcggcgccgcgccgggggttcaagcgcgagggcg aggatctgtaccccaccatgcagctgatggtgcccaagcgccagaagct ggaagacgtgctggagaccatgaaggtggacccggacgtgcagcccgag gtcaaggtgcggcccatcaagcaggtggccccgggcctgggcgtgcaga ccgtggacatcaagattcccacggagcccatggaaacgcagaccgagcc catgatcaagcccagcaccagcaccatggaggtgcagacggatccctgg atgccatcggctcctagtcgaagaccccggcgcaagtacggcgcggcca gcctgctgatgcccaactacgcgctgcatccttccatcatccccacgcc gggctaccgcggcacgcgcttctaccgcggtcataccagcagccgccgc cgcaagaccaccactcgccgccgccgtcgccgcaccgccgctgcaacca cccctgccgccctggtgcggagagtgtaccgccgcggccgcgcacctct gaccctgccgcgcgcgcgctaccacccgagcatcgccatttaaactttc gccTgctttgcagatcaatggccctcacatgccgccttcgcgttcccat tacgggctaccgaggaagaaaaccgcgccgtagaaggctggcggggaac gggatgcgtcgccaccaccaccggcggcggcgcgccatcagcaagcggt tggggggaggcttcctgcccgcgctgatccccatcatcgccgcggcgat cggggcgatccccggcattgcttccgtggcggtgcaggcctctcagcgc cactgagacacacttggaaacatcttgtaataaaccAatggactctgac gctcctggtcctgtgatgtgttttcgtagacagatggaagacatcaatt -continued tttcgtccctggctccgcgacacggcacgcggccgttcatgggcacctg
gagcgacatcggcaccagccaactgaacgggggcgccttcaattggagc
agtctctggagcgggcttaagaatttcgggtccacgcttaaaacctatg
gcagcaaggcgtggaacagcaccacagggcaggcgctgagggataagct
gaaagagcagaacttccagcagaaggtggtcgatgggctcgcctcgggc
atcaacggggtggtggacctggccaaccaggccgtgcagcggcagatca
acagccgcctggacccggtgccgcccgccggctccgtggagatgccgca
ggtggaggaggagctgcctccccctggacaagcggggcgagaagcgaccc
cgccccgatgcggaggagacgctgctgacgcacacggacgagccgcccc
cgtacgaggaggcggtgaaactgggtctgcccaccacgcggcccatcgc
gcccctggccaccggggtgctgaaacccgaaaagcccgcgaccctggac
ttgcctcctccccagccttcccgcccctctacagtggctaagcccctgc
cgccggtggccgtggcccgcgcgcgacccgggggcaccgcccgccctca
tgcgaactggcagagcactctgaacagcatcgtgggtctgggagtgcag
agtgtgaagcgccgccgctgctattaaacctaccgtagcgcttaacttg
cttgtctgtgtgtgtatgtattatgtcgccgccgccgctgtccaccaga
aggaggagtgaagaggcgcgtcgccgagttgcaagatggccaccccatc
gatgctgccccagtgggcgtacatgcacatcgccggacaggacgcttcg
gagtacctgagtccgggtctggtgcagtttgcccgcgccacagacacct
acttcagtctggggaacaagtttaggaaccccacggtggcgcccacgca
cgatgtgaccaccgaccgcagccagcggctgacgctgcgcttcgtgccc
gtggaccgcgaggacaacacctactcgtacaaagtgcgctacacgctgg
ccgtgggcgacaaccgcgtgctggacatggccagcacctactttgacat
ccgcggcgtgctggatcggggccctagcttcaaaccctactccggcacc
gcctacaacagtctggcccccaagggagcacccaacacttgtcagtgga
catataaagccgatggtgaaactgccacagaaaaaacctatacatatgg
aaatgcacccgtgcagggcattaacatcacaaaagatggtattcaactt
ggaactgacaccgatgatcagccaatctacgcagataaaacctatcagc
ctgaacctcaagtgggtgatgctgaatggcatgacatcactggtactga
tgaaaagtatggaggcagagctcttaagcctgataccaaaatgaagcct
tgttatggttcttttgccaagcctactaataaagaaggaggtcaggcaa
atgtgaaaacaggaacaggcactactaaagaatatgacatagacatggc
tttctttgacaacagaagtgcggctgctgctggcctagctccagaaatt
gttttgtatactgaaaatgtggatttggaaactccagatacccatattg
tatacaaagcaggcacagatgacagcagctcttctattaatttgggtca
gcaagccatgcccaacagacctaactacattggtttcagagacaacttt
atcgggctcatgtactacaacagcactggcaatatgggggtgctggccg
gtcaggcttctcagctgaatgctgtggttgacttgcaagacagaaacac
cgagctgtcctaccagctcttgcttgactctctgggtgacagaacccgg
tatttcagtatgtggaatcaggcggtggacagctatgatcctgatgtgc
gcattattgaaaatcatggtgtggaggatgaacttcccaactattgttt -continued ccctctggatgctgttggcagaacagatacttatcagggaattaaggct
aatggaactgatcaaaccacatggaccaaagatgacagtgtcaatgatg
ctaatgagataggcaagggtaatccattcgccatggaaatcaacatcca
agccaacctgtggaggaacttcctctacgccaacgtggccctgtacctg
cccgactcttacaagtacacgccggccaatgttaccctgcccaccaaca
ccaacacctacgattacatgaacggccgggtggtggcgccctcgctggt
ggactcctacatcaacatcggggcgcgctggtcgctggatcccatggac
aacgtgaaccccttcaaccaccaccgcaatgcggggctgcgctaccgct
ccatgctcctgggcaacgggcgctacgtgcccttccacatccaggtgcc
ccagaaatttttcgccatcaagagcctcctgctcctgcccgggtcctac
acctacgagtggaacttccgcaaggacgtcaacatgatcctgcagagct
ccctcggcaacgacctgcgcacggacggggcctccatctccttcaccag
catcaacctctacgccaccttcttccccatggcgcacaacacggcctcc
acgctcgaggccatgctgcgcaacgacaccaacgaccagtccttcaacg
actacctctcggcggccaacatgctctaccccatcccggccaacgccac
caacgtgcccatctccatcccctcgcgcaactgggccgccttccgcggc
tggtccttcacgcgtctcaagaccaaggagacgccctcgctgggctccg
ggttcgacccctacttcgtctactcgggctccatcccctacctcgacgg
caccttctacctcaaccacaccttcaagaaggtctccatcaccttcgac
tcctccgtcagctggcccggcaacgaccggctcctgacgcccaacgagt
tcgaaatcaagcgcaccgtcgacggcgagggctacaacgtggcccagtg
caacatgaccaaggactggttcctggtccagatgctggcccactacaac
atcggctaccagggcttctacgtgcccgagggctacaaggaccgcatgt
actccttcttccgcaacttccagcccatgagccgccaggtggtggacga
ggtcaactacaaggactaccaggccgtcaccctggcctaccagcacaac
aactcgggcttcgtcggctacctcgcgcccaccatgcgccagggccagc
cctaccccgccaactacccctacccgctcatcggcaagagcgccgtcac
cagcgtcacccagaaaaagttcctctgcgacagggtcatgtggcgcatc
cccttctccagcaacttcatgtccatgggcgcgctcaccgacctcggcc
agaacatgctctatgccaactccgcccacgcgctagacatgaatttcga
agtcgaccccatggatgagtccacccttctctatgttgtcttcgaagtc
ttcgacgtcgtccgagtgcaccagccccaccgcggcgtcatcgaggccg
tctacctgcgcacccccttctcggccggtaacgccaccacctaagctct
tgcttcttgcaagccatggccgcgggctccggcgagcaggagctcaggg
ccatcatccgcgacctgggctgcgggccctacttcctgggcaccttcga
taagcgcttcccgggattcatggccccgcacaagctggcctgcgccatc
gtcaacacggccggccgcgagaccgggggcgagcactggctggccttcg
cctggaacccgcgctcgaacacctgctacctcttcgaccccttcgggtt
ctcggacgagcgcctcaagcagatctaccagttcgagtacgagggcctg
ctgcgccgcagcgccctggccaccgaggaccgctgcgtcaccctggaaa -continued agtccacccagaccgtgcagggtccgcgctcggccgcctgcgggctctt ctgctgcatgttcctgcacgccttcgtgcactggcccgaccgccccatg gacaagaaccccaccatgaacttgctgacgggggtgcccaacggcatgc tccagtcgccccaggtggaacccaccctgcgccgcaaccaggaggcgct ctaccgcttcctcaactcccactccgcctactttcgctcccaccgcgcg cgcatcgagaaggccaccgccttcgaccgcatgaatcaagacatgtaaa ccgtgtgtgtatgttaaatgtctttaataaacagcactttcatgttaca catgcatctgagatgatttatttagaaatcgaaagggttctgccgggtc tcggcatggcccgcgggcagggacacgttgcggaactggtacttggcca gccacttgaactcggggatcagcagtttgggcagcggggtgtcggggaa ggagtcggtccacagcttccgcgtcagttgcagggcgcccagcaggtcg ggcgcggagatcttgaaatcgcagttgggacccgcgttctgcgcgcggg agttgcggtacacggggttgcagcactggaacaccatcagggccgggtg cttcacgctcgccagcaccgtcgcgtcggtgatgctctccacgtcgagg tcctcggcgttggccatcccgaagggggtcatcttgcaggtctgccttc ccatggtgggcacgcacccgggcttgtggttgcaatcgcagtgcagggg gatcagcatcatctgggcctggtcggcgttcatccccgggtacatggcc ttcatgaaagcctccaattgcctgaacgcctgctgggccttggctccct cggtgaagaagaccccgcaggacttgctagagaactggttggtggcgca cccggcgtcgtgcacgcagcagcgcgcgtcgttgttggccagctgcacc acgctgcgcccccagcggttctgggtgatcttggcccggtcggggttct ccttcagcgcgcgctgcccgttctcgctcgccacatccatctcgatcat gtgctccttctggatcatggtggtcccgtgcaggcaccgcagcttgccc tcggcctcggtgcacccgtgcagccacagcgcgcacccggtgcactccc agttcttgtgggcgatctgggaatgcgcgtgcacgaagccctgcaggaa gcggcccatcatggtggtcagggtcttgttgctagtgaaggtcagcgga atgccgcggtgctcctcgttgatgtacaggtggcagatgcggcggtaca cctcgccctgctcgggcatcagctggaagttggctttcaggtcggtctc cacgcggtagcggtccatcagcatagtcatgatttccataccct tctcc caggccgagacgatgggcaggctcatagggttcttcaccatcatcttag cgctagcagccgcggccaggggggtcgctctcgtccagggtctcaaagct ccgcttgccgtccttctcggtgatccgcaccggggggtagctgaagccc acggccgccagctcctcctcggcctgtctttcgtcctcgctgtcctggc tgacgtcctgcaggaccacatgcttggtcttgcggggtttcttcttggg cggcagcggcggcggagatgttggagatggcgagggggagcgcgagttc tcgctcaccactactatctcttcctcttcttggtccgaggccacgcggc ggtaggtatgtctcttcgggggcagaggcggaggcgacgggctctcgcc gccgcgacttggcggatggctggcagagccccttccgcgttcgggggtg cgctcccggcggcgctctgactgacttcctccgcggccggccattgtgt tctcctagggaggaacaacaagcatggagactcagccatcgccaacctc gccatctgcccccaccgccgacgagaagcagcagcagcagaatgaaagc -continued ttaaccgccccgccgcccagccccgccacctccgacgcggccgtcccag acatgcaagagatggaggaatccatcgagattgacctgggctatgtgac gcccgcggagcacgaggaggagctggcagtgcgcttttcacaagaagag atacaccaagaacagccagagcaggaagcagagaatgagcagagtcagg ctgggctcgagcatgacggcgactacctccacctgagcgggggggagga cgcgctcatcaagcatctggcccggcaggccaccatcgtcaaggatgcg ctgctcgaccgcaccgaggtgcccctcagcgtggaggagctcagccgcg cctacgagttgaacctcttctcgccgcgcgtgcccccaagcgccagcc caatggcacctgcgagcccaacccgcgcctcaacttctacccggtcttc gcggtgcccgaggccctggccacctaccacatctttttcaagaaccaaa agatccccgtctcctgccgcgccaaccgcacccgcgccgacgcccttt t caacctgggtcccggcgcccgcctacctgatatcgcctccttggaagag gttcccaagatcttcgagggtctgggcagcgacgagactcgggccgcga acgctctgcaaggagaaggaggagagcatgagcaccacagcgccctggt cgagttggaaggcgacaacgcgcggctggcggtgctcaaacgcacggtc gagctgacccatttcgcctacccggctctgaacctgcccccaaagtca tgagcgcggtcatggaccaggtgctcatcaagcgcgcgtcgcccatctc cgaggacgagggcatgcaagactccgaggagggcaagcccgtggtcagc gacgagcagctggcccggtggctgggtcctaatgctagtccccagagtt tggaagagcggcgcaaactcatgatggccgtggtcctggtgaccgtgga gctggagtgcctgcgccgcttcttcgccgacgcggagaccctgcgcaag gtcgaggagaacctgcactacctcttcaggcacgggttcgtgcgccagg cctgcaagatctccaacgtggagctgaccaacctggtctcctacatggg catcttgcacgagaaccgcctggggcagaacgtgctgcacaccaccctg cgcggggaggcccggcgcgactacatccgcgactgcgtctacctctacc tctgccacacctggcagacgggcatgggcgtgtggcagcagtgtctgga ggagcagaacctgaaagagctctgcaagctcctgcagaagaacctcaag ggtctgtggaccgggttcgacgagcgcaccaccgcctcggacctggccg acctcattttccccgagcgcctcaggctgacgctgcgcaacggcctgcc cgactttatgagccaaagcatgttgcaaaactttcgctctttcatcctc gaacgctccggaatcctgcccgccacctgctccgcgctgccctcggact tcgtgccgctgaccttccgcgagtgcccccgccgctgtggagccactg ctacctgctgcgcctggccaactacctggcctaccactcggacgtgatc gaggacgtcagcggcgagggcctgctcgagtgccactgccgctgcaacc tctgcacgccgcaccgctccctggcctgcaacccccagctgctgagcga gacccagatcatcggcaccttcgagttgcaagggcccagcgaaggcgag ggttcagccgccaaggggggtctgaaactcaccccggggctgtggacct cggcctacttgcgcaagttcgtgcccgaggactaccatcccttcgagat caggttctacgaggaccaatcccatccgcccaaggccgagctgtcggcc tgcgtcatcacccagggggcgatcctggcccaattgcaagccatccaga -continued aatcccgccaagaattcttgctgaaaaagggccgcggggtctacctcga cccccagaccggtgaggagctcaaccccggcttcccccaggatgccccg aggaaacaagaagctgaaagtggagctgccgcccgtggaggatttggag gaagactgggagaacagcagtcaggcagaggaggaggagatggaggaag actgggacagcactcaggcagaggaggacagcctgcaagacagtctgga ggaagacgaggaggaggcagaggaggaggtggaagaagcagccgccgcc agaccgtcgtcctcggcgggggagaaagcaagcagcacggataccatct ccgctccgggtcggggtcccgctcgaccacacagtagatgggacgagac cggacgattcccgaaccccaccacccagaccggtaagaaggagcggcag ggatacaagtcctggcgggggcacaaaaacgccatcgtctcctgcttgc aggcctgcgggggcaacatctccttcacccggcgctacctgctcttcca ccgcggggtgaactttccccgcaacatcttgcattactaccgtcacctc cacagcccctactacttccaagaagaggcagcagcagcagaaaaagacc agcagaaaaccagcagctagaaaatccacagcggcggcagcaggtggac tgaggatcgcggcgaacgagccggcgcaaacccgggagctgaggaaccg gatctttcccaccctctatgccatcttccagcagagtcgggggcaggag caggaactgaaagtcaagaaccgttctctgcgctcgctcacccgcagtt gtctgtatcacaagagcgaagaccaacttcagcgcactctcgaggacgc cgaggctctcttcaacaagtactgcgcgctcactcttaaagagtagccc gcgcccgcccagtcgcagaaaaaggcgggaattacgtcacctgtgccct tcgccctagccgcctccacccatcatcatgagcaaagagattcccacgc cttacatgtggagctaccagccccagatgggcctggccgccggtgccgc ccaggactactccacccgcatgaattggctcagcgccgggcccgcgatg atctcacgggtgaatgacatccgcgcccaccgaaaccagatactcctag aacagtcagcgctcaccgccacgccccgcaatcacctcaatccgcgtaa ttggcccgccgccctggtgtaccaggaaattccccagcccacgaccgta ctacttccgcgagacgcccaggccgaagtccagctgactaactcaggtg tccagctggcgggcggcgccaccctgtgtcgtcaccgccccgctcaggg tataaagcggctggtgatccggggcagaggcacacagctcaacgacgag gtggtgagctcttcgctgggtctgcgacctgacggagtcttccaactcg ccggatcggggagatcttccttcacgcctcgtcaggccgtcctgacttt ggagagttcgtcctcgcagccccgctcgggtggcatcggcactctccag ttcgtggaggagttcactccctcggtctacttcaaccccttctccggct cccccggccactacccggacgagttcatcccgaacttcgacgccatcag cgagtcggtggacggctacgattgaatgtcccatggtggcgcagctgac ctagctcggcttcgacacctggaccactgccgccgcttccgctgcttcg ctcgggatctcgccgagtttgcctactttgagctgcccgaggagcaccc tcagggcccggcccacggagtgcggatcgtcgtcgaagggggcctcgac tcccacctgcttcggatcttcagccagcgtccgatcctggtcgagcgcg agcaaggacagacccttctgactctgtactgcatctgcaaccaccccgg cctgcatgaaagtctttgttgtctgctgtgtactgagtataataaaagc -continued tgagatcagcgactactccggacttccgtgtgttcctgaatccatcaac cagtctttgttcttcaccgggaacgagaccgagctccagctccagtgta agccccacaagaagtacctcacctggctgttccagggctccccgatcgc cgttgtcaaccactgcgacaacgacggagtcctgctgagcggccctgcc aaccttactttttccacccgcagaagcaagctccagctcttccaaccct tcctccccgggacctatcagtgcgtctcgggaccctgccatcacacctt ccacctgatcccgaataccacagcgtcgctccccgctactaacaaccaa actaacctccaccaacgccaccgtcgctaggccacaatacatgcccata ttagactatgaggccgagccacagcgacccatgctccccgctattagtt acttcaatctaaccggcggagatgactgacccactggccaacaacaacg tcaacgaccttctcctggacatggacggccgcgcctcggagcagcgact cgcccaacttcgcattcgccagcagcaggagagagccgtcaaggagctg caggatgcggtggccatccaccagtgcaagagaggcatcttctgcctgg tgaaacaggccaagatctcctacgaggtcactccaaacgaccatcgcct ctcctacgagctcctgcagcagcgccagaagttcacctgcctggtcgga gtcaaccccatcgtcatcacccagcagtctggcgataccaaggggtgca tccactgctcctgcgactcccccgactgcgtccacactctgatcaagac cctctgcggcctccgcgacctcctccccatgaactaatcaccccccttat ccagtgaaataaagatcatattgatgatgattttacagaaataaaaaat aatcatttgatttgaaataaagatacaatcatattgatgatttgagttt aacaaaaaaataaagaatcacttacttgaaatctgataccaggtctctg tccatgttttctgccaacaccacttcactcccctcttcccagctctggt actgcaggccccggcgggctgcaaacttcctccacacgctgaaggggat gtcaaattcctcctgtccctcaatcttcattttatcttctatcagatgt ccaaaaagcgcgtccgggtggatgatgacttcgaccccgtctaccccta cgatgcagacaacgcaccgaccgtgcccttcatcaacccccccttcgtc tcttcagatggattccaagagaagcccctgggggtgttgtccctgcgac tggccgaccccgtcaccaccaagaacggggaaatcaccctcaagctggg agagggggtggacctcgattcctcgggaaaactcatctccaacacggcc accaaggccgccgcccctctcagtttttccaacaacaccatttccctta acatggatcaccccttttacactaaagatggaaaattatccttacaagt ttctccaccattaaatatactgagaacaagcattctaaacacactagct ttaggttttggatcaggtttaggactccgtggctctgccttggcagtac agttagtctctccacttacatttgatactgatggaaacataaagcttac cttagacagaggtttgcatgttacaacaggagatgcaattgaaagcaac ataagctgggctaaaggtttaaaatttgaagatggagccatagcaacca acattggaaatgggttagagtttggaagcagtagtacagaaacaggtgt tgatgatgcttacccaatccaagttaaacttggatctggccttagcttt gacagtacaggagccataatggctggtaacaaagaagacgataaactca ctttgtggacaacacctgatccatcaccaaactgtcaaatactcgcaga -continued aaatgatgcaaaactaacactttgcttgactaaatgtggtagtcaaata ctggccactgtgtcagtcttagttgtaggaagtggaaacctaaacccca ttactggcaccgtaagcagtgctcaggtgtttctacgttttgatgcaaa cggtgttcttttaacagaacattctacactaaaaaaatactgggggtat aggcagggagatagcatagatggcactccatataccaatgctgtaggat tcatgcccaatttaaaagcttatccaaagtcacaaagttctactactaa aaataatatagtagggcaagtatacatgaatggagatgtttcaaaacct atgcttctcactataaccctcaatggtactgatgacagcaacagtacat attcaatgtcattttcatacacctggactaatggaagctatgttggagc aacatttggggctaactcttataccttctcatacatcgcccaagaatga acactgtatcccaccctgcatgccaacccttcccaccccactctgtgga acaaactctgaaacacaaaataaaataaagttcaagtgttttattgatt caacagttttacaggattcgagcagttatttttcctccaccctcccagg acatggaatacaccaccctctccccccgcacagccttgaacatctgaat gccattggtgatggacatgcttttggtctccacgttccacacagtttca gagcgagccagtctcgggtcggtcagggagatgaaaccctccgggcact cccgcatctgcacctcacagctcaacagctgaggattgtcctcggtggt cgggatcacggttatctggaagaagcagaagagcggcggtgggaatcat agtccgcgaacgggatcggccggtggtgtcgcatcaggccccgcagcag tcgctgccgccgccgctccgtcaagctgctgctcagggggtccgggtcc agggactccctcagcatgatgcccacggccctcagcatcagtcgtctgg tgcggcgggcgcagcagcgcatgcggatctcgctcaggtcgctgcagta cgtgcaacacagaaccaccaggttgttcaacagtccatagttcaacacg ctccagccgaaactcatcgcgggaaggatgctacccacgtggccgtcgt accagatcctcaggtaaatcaagtggtgccccctccagaacacgctgcc cacgtacatgatctccttgggcatgtggcggttcaccacctcccggtac cacatcaccctctggttgaacatgcagccccggatgatcctgcggaacc acagggccagcaccgccccgcccgccatgcagcgaagagaccccgggtc ccggcaatggcaatggaggacccaccgctcgtacccgtggatcatctgg gagctgaacaagtctatgttggcacagcacaggcatatgctcatgcatc tcttcagcactctcaactcctcgggggtcaaaaccatatcccagggcac ggggaactcttgcaggacagcgaaccccgcagaacagggcaatcctcgc acagaacttacattgtgcatggacagggtatcgcaatcaggcagcaccg ggtgatcctccaccagagaagcgcgggtctcggtctcctcacagcgtgg taagggggccggccgatacgggtgatggcgggacgcggctgatcgtgtt cgcgaccgtgtcatgatgcagttgctttcggacattttcgtacttgctg tagcagaacctggtccgggcgctgcacaccgatcgccggcggcggtctc ggcgcttggaacgctcggtgttgaaattgtaaaacagccactctctcag accgtgcagcagatctagggcctcaggagtgatgaagatcccatcatgc ctgatggctctgatcacatcgaccaccgtggaatgggccagacccagcc agatgatgcaattttgttgggtttcggtgacggcgggggagggaagaac -continued aggaagaaccatgattaacttttaatccaaacggtctcggagtacttca aaatgaagatcgcggagatggcacctctcgccccgctgtgttggtgga aaataacagccaggtcaaaggtgatacggttctcgagatgttccacggt ggcttccagcaaagcctccacgcgcacatccagaaacaagacaatagcg aaagcgggagggttctctaattcctcaatcatcatgttacactcctgca ccatccccagataattttcatttttccagccttgaatgattcgaactag ttcCtgaggtaaatccaagccagccatgataaagagctcgcgcagagcg ccctccaccggcattcttaagcacaccctcataattccaagatattctg ctcctggttcacctgcagcagattgacaagcggaatatcaaaatctctg ccgcgatccctgagctcctccctcagcaataactgtaagtactctttca tatcctctccgaaatttttagccataggaccaccaggaataagattagg gcaagccacagtacagataaaccgaagtcctccccagtgagcattgcca aatgcaagactgctataagcatgctggctagacccggtgatatcttcca gataactggacagaaaatcgcccaggcaatttttaagaaaatcaacaaa agaaaaatcctccaggtggacgtttagagcctcgggaacaacgatgaag taaatgcaagcggtgcgttccagcatggttagttagctgatctgtagaa aaaacaaaaatgaacattaaaccatgctagcctggcgaacaggtgggta aatcgttctctccagcaccaggcaggccacggggtctccggcgcgaccc tcgtaaaaattgtcgctatgattgaaaaccatcacagagagacgttccc ggtggccggcgtgaatgattcgacaagatgaatacaccccccggaacatt ggcgtccgcgagtgaaaaaaagcgcccgaggaagcaataaggcactaca atgctcagtctcaagtccagcaaagcgatgccatgcggatgaagcacaa aattctcaggtgcgtacaaaatgtaattactcccctcctgcacaggcag caaagcccccgatccctccaggtacacatacaaagcctcagcgtccata gcttaccgagcagcagcacacaacaggcgcaagagtcagagaaaggctg agctctaacctgtccacccgctctctgctcaatatatagcccagatcta cactgacgtaaaggccaaagtctaaaaatacccgccaaataatcacaca cgcccagcacacgcccagaaaccggtgacacactcaaaaaaatacgcgc acttcctcaaacgcccaaaactgccgtcatttccgggttcccacgctac gtcatcaaaacacgactttcaaattccgtcgaccgttaaaaacgtcacc cgccccgcccctaacggtcgcccgtctctcagccaatcagcgccccgca tccccaaattcaaacacctcatttgcatattaacgcgcacaaaaagttt gaggtatattattgatgatggTTAATTAA SEQ ID NO: 59: Nucleotide Seqeunce of Preferred EMCV IRES (pIRES)

TAACGTTACTGGCCGAAGCCGCTTGGAATAAGGCCGGTGTGCGTTTGTC

TATATGTTATTTTCCACCATATTGCCGTCTTTTGGCAATGTGAGGGCCC

GGAAACCTGGCCCTGTCTTCTTGACGAGCATTCCTAGGGGTCTTTCCCC

TCTCGCCAAAGGAATGCAAGGTCTGTTGAATGTCGTGAAGGAAGCAGTT

CCTCTGGAAGCTTCTTGAAGACAAACAACGTCTGTAGCGACCCTTTGCA

GGCAGCGGAACCCCCCACCTGGCGACAGGTGCCTCTGCGGCCAAAAGCC

-continued

ACGTGTATAAGATACACCTGCAAAGGCGGCACAACCCCAGTGCCACGTT

GTGAGTTGGATAGTTGTGGAAAGAGTCAAATGGCTCTCCTCAAGCGTAT

TCAACAAGGGGCTGAAGGATGCCCAGAAGGTACCCCATTGTATGGGATC

TGATCTGGGGCCTCGGTGCACATGCTTTACATGTGTTTAGTCGAGGTTA

AAAAACGTCTAGGCCCCCCGAACCACGGGGACGTGGTTTTCCTTTGAAA

AACACGATGATAATATGGCCACAACCATG (The minimal EMCV IRES (mIRES) lacks the underlined 15 nucleotides)

SEQ ID NO: 60. Amino Acid Sequence Comprising an Immunogenic PSA, PSCA, and PSMA Polypeptide (Encoded by by Plasmid 916 and Vectors AdC68-734 and AdC68W-734)

MASIVGGWECEKHSQPWQVLVASRGRAVCGGVLVHPQWVLTAAHCIRNK

SVILLGRHSLFHPEDTGQVFQVSHSFPHPLYDMSLLKNRFLRPGDDSSH

DLMLLRLSEPAELTDAVKVMDLPTQEPALGTTCYASGWGSIEPEEFLTP

KKLQCVDLHVISNDVCAQVHPQKVTKFMLCAGRWTGGKSTCSGDSGGPL

VCNGVLQGITSWGSEPCALPERPSLYTKVVHYRKWIKDTIVANPGSEGR

GSLLTCGDVEENPGPASKAVLLALLMAGLALQPGTALLCYSCKAQVSNE

DCLQVENCTQLGEQCWTARIRAVGLLTVISKGCSLNCVDDSQDYYVGKK

NITCCDTDLCNASGAHALQPAAAILALLPALGLLLWGPGQLGSQTLNFD

LLKLAGDVESNPGPMASARRPRWLCAGALVLAGGFFLLGFLFGWFIKSS

NEATNITPKHNMKAFLDELKAENIKKFLYNFTQIPHLAGTEQNFQLAKQ

IQSQWKEFGLDSVELAHYDVLLSYPNKTHPNYISIINEDGNEIFNTSLF

EPPPPGYENVSDIVPPFSAFSPQGMPEGDLVYVNYARTEDFFKLERDMK

INCSGKIVIARYGKVFRGNKVKNAQLAGAKGVILYSDPADYFAPGVKSY

PDGWNLPGGGVQRGNILNLNGAGDPLTPGYPANEYAYRRGIAEAVGLPS

IPVHPIGYYDAQKLLEKMGGSAPPDSSWRGSLKVPYNVGPGFTGNFSTQ

KVKMHIHSTNEVTRIYNVIGTLRGAVEPDRYVILGGHRDSWVFGGIDPQ

SGAAVVHEIVRSFGTLKKEGWRPRRTILFASWDAEEFGLLGSTEWAEEN

SRLLQERGVAYINADSSIEGNYTLRVDCTPLMYSLVHNLTKELKSPDEG

FEGKSLYESWTKKSPSPEFSGMPRISKLGSGNDFEVFFQRLGIASGRAR

YTKNWETNKFSGYPLYHSVYETYELVEKFYDPMFKYHLTVAQVRGGMVF

ELANSIVLPFDCRDYAVVLRKYADKIYSISMKHPQEMKTYSVSFDSLFS

AVKNFTEIASKFSERLQDFDKSNPIVLRMMNDQLMFLERAFIDPLGLPD

RPFYRHVIYAPSSHNKYAGESFPGIYDALFDIESKVDPSKAWGEVKRQI

YVAAFTVQAAAETLSEVA

SEQ ID NO: 61. Nucleotide Sequence Encoding the Amino Acid Sequence of SEQ ID NO: 60.

atggctagcatcgtcggagggtgggagtgcgaaaagcactcacagccat ggcaggtcctggtcgcctcgcgcggacgcgccgtgtgtggaggtgtgct ggtccacccgcagtgggtgttgactgcggcccattgcatcagaaataag tccgtgatcctcttggggagacattccctgtttcaccccgaagatactg gacaggtgttccaagtgagccactccttcccgcatccactgtacgacat gagcctgctgaagaaccgctttctgcggccaggggacgactcatcacac gatttgatgctgcttcggctctcggaaccggccgagctcaccgacgcag -continued tgaaggtcatggacctccctacgcaagagcctgctctcggtaccacttg ttacgcatcgggatggggctccatcgagccggaagaattcctgaccccg aaaaagctgcagtgcgtggatctgcacgtgatttcgaatgacgtgtgcg cgcaagtgcatccacaaaaggtcactaagttcatgctgtgcgccggaag gtggaccggcggaaaatcgacctgttccggcgacagcggaggcccactc gtgtgcaacggtgtgctgcagggcatcactagctggggatcagaaccgt gcgcgcttccggagcggccctcgctctacacgaaggtggtgcactaccg caaatggattaaagataccatcgtcgcaaaccctggatccgaaggtagg ggttcattattgacctgtggagatgtcgaagaaaacccaggacccgcta gcaaagcagtgctgctggcgctcctgatggctggactcgcgctgcagcc tggaaccgccctgctctgttactcgtgcaaggcccaagtctcgaatgag gactgtttgcaagtggaaaactgcacccagctcggagaacaatgctgga ctgcacggatccgcgctgtcggcctgctgaccgtgatctccaaagggtg ctcattgaactgcgtggacgatagccaggactactacgtgggaaagaag aatatcacttgttgcgacacggatctttgcaacgcgtccggagcgcacg ccctgcagccagcagccgccattctggccctgcttccggccctggggtt gctgctctggggtccgggccagctcggatcccagaccctgaactttgat ctgctgaaactggcaggcgatgtggaaagcaacccaggcccaatggcta gcgctcgcagaccgcggtggctgtgtgcaggggcgctcgtcctggcggg tggcttctttttgctcggctttcttttcggatggttcatcaaatcgtca aacgaagctaccaatatcaccccgaagcacaacatgaaggcctttctgg atgagctgaaggctgagaacattaagaagttcctctacaacttcaccca gatcccacatttggcgggcactgagcagaactttcagttggctaagcag atccagagccagtggaaggaattcggcctggactccgtcgagctggcgc attacgatgtgctgctgagctaccctaataagactcatccgaactatat ctcgattatcaatgaggacggaaacgaaatctttaacacgtccctcttc gagccgccaccgcctggatacgagaacgtgtcagatatcgtgcctccgt tctcggccttctcgccccagggaatgcccgaaggggacctggtgtacgt gaactacgcaaggaccgaggacttcttcaagttggagcgggatatgaag atcaattgcagcggaaagatcgtcatcgcccgctacggcaaagtgttcc gcggcaacaaggtgaagaatgcacagttggcaggcgccaagggcgtcat cctctactcggatcctgccgactacttcgctcctggcgtgaaatcctac cctgatggttggaatctgccaggaggaggggtgcagaggggaaatatcc tgaacctgaacggtgccggtgacccacttactccgggttacccggccaa cgaatacgcgtacaggcggggtatcgcggaagccgtcggactgccgtcc atcccggtccatccgattggttactacgacgcccagaagctcctcgaaa agatgggaggcagcgcccctccggactcgtcatggagaggctcgctgaa ggtgccatacaacgtgggacccggattcactggaaatttcagcactcaa aaagtgaagatgcacattcactccactaacgaagtcaccaggatctaca acgtcatcggaaccctccggggagcggtggaaccggaccgctacgtgat -continued cctcggtggacaccgggatagctgggtgttcggaggaatcgatcctcaa tcgggcgcagccgtcgtccatgaaatcgtcaggtcctttggtactctta agaaggagggctggcgccctagacgcactattctgttcgcctcgtggga tgccgaagaatttggtctgctcggcagcaccgaatgggctgaggaaaac tcccgcctgctccaagaacgcggagtggcgtacatcaatgccgactcat ccatcgaaggaaactacacgctgcgggtggactgcactccactgatgta ctcgctcgtgcacaacctgaccaaagaactcaaatccccagacgaagga ttcgagggaaaatcgctgtacgagtcgtggaccaagaagagcccatccc cggagttcagcgggatgccgcggatctcaaagctcggatcaggaaatga tttcgaagtgttctttcagaggctgggaattgcgtcgggaagggctcgg tacacgaaaaactgggaaactaacaagttctcgggatacccgctgtacc actcggtgtatgaaacttacgaactggtggagaaattctacgatcctat gtttaagtaccacctgactgtggcccaagtgagaggcggaatggtgttc gagttggccaattcaattgtgctgccattcgattgccgcgactacgccg tggtgctgagaaagtacgcagacaaaatctactcaatcagcatgaagca cccacaagagatgaaaacctactcagtctccttcgactccctcttctcc gcggtgaagaacttcaccgagatcgcgagcaaattctcggagcgccttc aagattttgacaaatccaatccgatcgtcctccgcatgatgaatgacca gctcatgtttctcgaacgggccttcatcgatccactgggacttccggac cggccgttttaccgccacgtgatctacgcgccctcgtcgcataacaagt atgctggagagagcttcccgggtatctacgacgcattgttcgacattga gtccaaggtggatccgtccaaagcctggggtgaagtgaagcgccaaatc tacgtggcggcctttaccgtccaggcggcagcagaaaccttgagcgagg tggct SEQ ID NO: 62. Nucleotide Sequence of Plasmid 916
ggcgtaatgctctgccagtgttacaaccaattaaccaattctgattaga aaaactcatcgagcatcaaatgaaactgcaatttattcatatcaggatt atcaataccatatttttgaaaaagccgtttctgtaatgaaggagaaaac tcaccgaggcagttccataggatggcaagatcctggtatcggtctgcga ttccgactcgtccaacatcaatacaacctattaatttcccctcgtcaaa aataaggttatcaagtgagaaatcaccatgagtgacgactgaatccggt gagaatggcaaaagcttatgcatttctttccagacttgttcaacaggcc agccattacgctcgtcatcaaaatcactcgcatcaaccaaaccgttatt cattcgtgattgcgcctgagcgagacgaaatacgcgatcgctgttaaaa ggacaattacaaacaggaatcaaatgcaaccggcgcaggaacactgcca gcgcatcaacaatattttcacctgaatcaggatattcttctaatacctg gaatgctgttttcccggggatcgcagtggtgagtaaccatgcatcatca ggagtacggataaaatgcttgatggtcggaagaggcataaattccgtca gccagtttagtctgaccatctcatctgtaacatcattggcaacgctacc tttgccatgtttcagaaacaactctggcgcatcgggcttcccatacaat cgatagattgtcgcacctgattgcccgacattatcgcgagcccatttat -continued acccatataaatcagcatccatgttggaatttaatcgcggcctcgagca agacgtttcccgttgaatatggctcataacaccccttgtattactgttt atgtaagcagacaggtcgacaatattggctattggccattgcatacgtt gtatctatatcataatatgtacatttatattggctcatgtccaatatga ccgccatgttgacattgattattgactagttattaatagtaatcaatta cggggtcattagttcatagcccatatatggagttccgcgttacataact tacggtaaatggcccgcctggctgaccgcccaacgacccccgcccattg acgtcaataatgacgtatgttcccatagtaacgccaatagggactttcc attgacgtcaatgggtggagtatttacggtaaactgcccacttggcagt acatcaagtgtatcatatgccaagtccgccccctattgacgtcaatgac ggtaaatggcccgcctggcattatgcccagtacatgaccttacgggact ttcctacttggcagtacatctacgtattagtcatcgctattaccatggt gatgcggttttggcagtacaccaatgggcgtggatagcggtttgactca cggggatttccaagtctccaccccattgacgtcaatgggagtttgtttt ggcaccaaaatcaacgggactttccaaaatgtcgtaataaccccgcccc gttgacgcaaatgggcggtaggcgtgtacggtgggaggtctatataagc agagctcgtttagtgaaccgtcagatcgcctggagacgccatccacgct gttttgacctccatagaagacaccgggaccgatccagcctccgcggccg ggaacggtgcattggaacgcggattccccgtgccaagagtgactcaccg tccggatctcagcaagcaggtatgtactctccagggtgggcctggcttc cccagtcaagactccagggatttgagggacgctgtgggctcttctctta catgtaccttttgcttgcctcaaccctgactatcttccaggtcaggatc ccagagtcaggggtctgtattttcctgctggtggctccagttcaggaac agtaaaccctgctccgaatattgcctctcacatctcgtcaatctccgcg aggactggggaccctgtgacgaacatggctagcatcgtcggagggtggg agtgcgaaaagcactcacagccatggcaggtcctggtcgcctcgcgcgg acgcgccgtgtgtggaggtgtgctggtccacccgcagtgggtgttgact gcggcccattgcatcagaaataagtccgtgatcctcttggggagacatt ccctgtttcaccccgaagatactggacaggtgttccaagtgagccactc cttcccgcatccactgtacgacatgagcctgctgaagaaccgctttctg cggccaggggacgactcatcacacgatttgatgctgcttcggctctcgg aaccggccgagctcaccgacgcagtgaaggtcatggacctccctacgca agagcctgctctcggtaccacttgttacgcatcgggatggggctccatc gagccggaagaattcctgaccccgaaaaagctgcagtgcgtggatctgc acgtgatttcgaatgacgtgtgcgcgcaagtgcatccacaaaaggtcac taagttcatgctgtgcgccggaaggtggaccggcggaaaatcgacctgt tccggcgacagcggaggcccactcgtgtgcaacggtgtgctgcagggca tcactagctggggatcagaaccgtgcgcgcttccggagcggccctcgct ctacacgaaggtggtgcactaccgcaaatggattaaagataccatcgtc gcaaaccctggatccgaaggtaggggttcattattgacctgtggagatg tcgaagaaaacccaggacccgctagcaaagcagtgctgctggcgctcct -continued

```
gatggctggactcgcgctgcagcctggaaccgccctgctctgttactcg
tgcaaggcccaagtctcgaatgaggactgtttgcaagtggaaaactgca
cccagctcggagaacaatgctggactgcacggatccgcgctgtcggcct
gctgaccgtgatctccaaagggtgctcattgaactgcgtggacgatagc
caggactactacgtgggaaagaagaatatcacttgttgcgacccggatc
tttgcaacgcgtccggagcgcacgccctgcagccagcagccgccattct
ggccctgcttccggccctggggttgctgctctggggtccgggccagctc
ggatcccagaccctgaactttgatctgctgaaactggcaggcgatgtgg
aaagcaacccaggcccaatggctagcgctcgcagaccgcggtggctgtg
tgcaggggcgctcgtcctggcgggtggcttctttttgctcggctttctt
ttcggatggttcatcaaatcgtcaaacgaagctaccaatatcaccccga
agcacaacatgaaggcctttctggatgagctgaaggctgagaacattaa
gaagttcctctacaacttcacccagatcccacatttggcgggcactgag
cagaactttcagttggctaagcagatccagagccagtggaaggaattcg
gcctggactccgtcgagctggcgcattacgatgtgctgctgagctaccc
taataagactcatccgaactatatctcgattatcaatgaggacggaaac
gaaatctttaacacgtccctcttccagccgccaccgcctggatacgaga
acgtgtcagatatcgtgcctccgttctcggccttctcgccccagggaat
gcccgaaggggacctggtgtacgtgaactacgcaaggaccgaggacttc
ttcaagttggagcgggatatgaagatcaattgcagcggaaagatcgtca
tcgcccgctacggcaaagtgttccgcggcaacaaggtgaagaatgcaca
gttggcaggcgccaagggcgtcatcctctactcggatcctgccgactac
ttcgctcctggcgtgaaatcctaccctgatggttggaatctgccaggag
gaggggtgcagaggggaaatatcctgaacctgaacggtgccggtgaccc
acttactccgggttacccggccaacgaatacgcgtacaggcggggtatc
gcggaagccgtcggactgccgtccatcccggtccatccgattggttact
acgacgcccagaagctcctcgaaaagatgggaggcagcgcccctccgga
ctcgtcatggagaggctcgctgaaggtgccatacaacgtgggacccgga
ttcactggaaatttcagcactcaaaaagtgaagatgcacattcactcca
ctaacgaagtcaccaggatctacaacgtcatcggaaccctccggggagc
ggtggaaccggaccgctacgtgatcctcggtggacaccgggatagctgg
gtgttcggaggaatcgatcctcaatcgggcgcagccgtcgtccatgaaa
tcgtcaggtcctttggtactcttaagaaggagggctggcgccctagacg
cactattctgttcgcctcgtgggatgccgaagaatttggtctgctcggc
agcaccgaatgggctgaggaaaactcccgcctgctccaagaacgcggag
tggcgtacatcaatgccgactcatccatcgaaggaaactacacgctgcg
ggtggactgcactccactgatgtactcgctcgtgcacaacctgaccaaa
gaactcaaatccccagacgaaggattcgagggaaaatcgctgtacgagt
cgtggaccaagaagagcccatccccggagttcagcgggatgccgcggat
ctcaaagctcggatcaggaaatgatttcgaagtgttctttcagaggctg
```

-continued

```
ggaattgcgtcgggaagggctcggtacacgaaaaactgggaaactaaca
agttctcgggatacccgctgtaccactcggtgtatgaaacttacgaact
ggtggagaaattctacgatcctatgtttaagtaccacctgactgtggcc
caagtgagaggcggaatggtgttcgagttggccaattcaattgtgctgc
cattcgattgccgcgactacgccgtggtgctgagaaagtacgcagacaa
aatctactcaatcagcatgaagcacccacaagagatgaaaacctactca
gtctccttcgactccctcttctccgcggtgaagaacttcaccgagatcg
cgagcaaattctcggagcgccttcaagattttgacaaatccaatccgat
cgtcctccgcatgatgaatgaccagctcatgtttctcgaacgggccttc
atcgatccactgggacttccggaccggccgttttaccgccacgtgatct
acgcgccctcgtcgcataacaagtatgctggagagagcttcccgggtat
ctacgacgcattgttcgacattgagtccaaggtggatccgtccaaagcc
tggggtgaagtgaagcgccaaatctacgtggcggcctttaccgtccagg
cggcagcagaaaccttgagcgaggtggcttaaagatctgggccctaaca
aaacaaaaagatggggttattccctaaacttcatgggttacgtaattgg
aagttgggggacattgccacaagatcatattgtacaaaagatcaaacac
tgttttagaaaacttcctgtaaacaggcctattgattggaaagtatgtc
aaaggattgtgggtcttttgggctttgctgctccatttacacaatgtgg
atatcctgccttaatgcctttgtatgcatgtatacaagctaaacaggct
ttcactttctcgccaacttacaaggcctttctaagtaaacagtacatga
acctttaccccgttgctcggcaacggcctggtctgtgccaagtgtttgc
tgacgcaacccccactggctggggcttggccataggccatcagcgcatg
cgtggaacctttgtggctcctctgccgatccatactgcggaactcctag
ccgcttgttttgctcgcagccggtctggagcaaagctcataggaactga
caattctgtcgtcctctcgcggaaatatacatcgtttcgatctacgtat
gatctttttccctctgccaaaaattatggggacatcatgaagccccttg
agcatctgacttctggctaataaaggaaatttattttcattgcaatagt
gtgttggaatttttgtgtctctcactcggaaggaattctgcattaatg
aatcggccaacgcgcggggagaggcggtttgcgtattgggcgctcttcc
gcttcctcgctcactgactcgctgcgctcggtcgttcggctgcggcgag
cggtatcagctcactcaaaggcggtaatacggttatccacagaatcagg
ggataacgcaggaaagaacatgtgagcaaaaggccagcaaaaggccagg
aaccgtaaaaaggccgcgttgctggcgtttttccataggctccgccccc
ctgacgagcatcacaaaaatcgacgctcaagtcagaggtggcgaaaccc
gacaggactataaagataccaggcgtttccccctggaagctccctcgtg
cgctctcctgttccgaccctgccgcttaccggatacctgtccgcctttc
tcccttcgggaagcgtggcgctttctcatagctcacgctgtaggtatct
cagttcggtgtaggtcgttcgctccaagctgggctgtgtgcacgaaccc
cccgttcagcccgaccgctgcgccttatccggtaactatcgtcttgagt
ccaacccggtaagacacgacttatcgccactggcagcagccactggtaa
caggattagcagagcgaggtatgtaggcggtgctacagagttcttgaag
```

-continued tggtggcctaactacggctacactagaagaacagtatttggtatctgcg ctctgctgaagccagttaccttcggaaaaagagttggtagctcttgatc cggcaaacaaaccaccgctggtagcggtggtttttttgtttgcaagcag cagattacgcgcagaaaaaaaggatctcaagaagatcctttgatctttt ctacggggtctgacgctcagtggaacgaaaactcacgttaagggatttt ggtcatgagattatcaaaaaggatcttcacctagatccttttaaattaa aaatgaagttttaaatcaatctaaagtatatatgagtaaacttggtctg acagttaccaatgcttaatcagtgaggcacctatctcagcgatctgtct atttcgttcatccatagttgcctgactc SEQ ID NO: 63. Complete Sequence of the AdC68W-734 Vector ccatcttcaataatatacctcaaactttttgtgcgcgttaatatgcaaa tgaggcgtttgaatttggggaggaagggcggtgattggtcgagggatga gcgaccgttaggggcggggcgagtgacgttttgatgacgtggttgcgag gaggagccagtttgcaagttctcgtgggaaaagtgacgtcaaacgaggt gtggtttgaacacggaaatactcaattttcccgcgctctctgacaggaa atgaggtgtttctgggcggatgcaagtgaaaacgggccattttcgcgcg aaaactgaatgaggaagtgaaaatctgagtaatttcgcgtttatggcag ggaggagtatttgccgagggccgagtagactttgaccgattacgtgggg gtttcgattaccgtgtttttcacctaaatttccgcgtacggtgtcaaag tccggtgtttttactactgtaatagtaatcaattacggggtcattagtt catagcccatatatggagttccgcgttacataacttacggtaaatggcc cgcctggctgaccgcccaacgacccccgcccattgacgtcaataatgac gtatgttcccatagtaacgccaatagggactttccattgacgtcaatgg gtggagtatttacggtaaactgcccacttggcagtacatcaagtgtatc atatgccaagtacgccccctattgacgtcaatgacggtaaatggcccgc ctggcattatgcccagtacatgaccttatgggactttcctacttggcag tacatctacgtattagtcatcgctattaccatggtgatgcggttttggc agtacatcaatgggcgtggatagcggtttgactcacggggatttccaag tctccaccccattgacgtcaatgggagtttgttttggcaccaaaatcaa cgggactttccaaaatgtcgtaacaactccgccccattgacgcaaatgg gcggtaggcgtgtacggtgggaggtctatataagcagagctgtccctat cagtgatagagatctccctatcagtgatagagagtttagtgaaccgtca gatccgctagggtaccaacATGGCTAGCATCGTCGGAGGGTGGGAGTGC

GAAAAGCACTCACAGCCATGGCAGGTCCTGGTCGCCTCGCGCGGACGCG

CCGTGTGTGGAGGTGTGCTGGTCCACCCGCAGTGGGTGTTGACTGCGGC

CCATTGCATCAGAAATAAGTCCGTGATCCTCTTGGGGAGACATTCCCTG

TTTCACCCCGAAGATACTGGACAGGTGTTCCAAGTGAGCCACTCCTTCC

CGCATCCACTGTACGACATGAGCCTGCTGAAGAACCGCTTTCTGCGGCC

AGGGGACGACTCATCACACGATTTGATGCTGCTTCGGCTCTCGGAACCG

GCCGAGCTCACCGACGCAGTGAAGGTCATGGACCTCCCTACGCAAGAGC

-continued

CTGCTCTCGGTACCACTTGTTACGCATCGGGATGGGGCTCCATCGAGCC

GGAAGAATTCCTGACCCCGAAAAAGCTGCAGTGCGTGGATCTGCACGTG

ATTTCGAATGACGTGTGCGCGCAAGTGCATCCACAAAAGGTCACTAAGT

TCATGCTGTGCGCCGGAAGGTGGACCGGCGGAAAATCGACCTGTTCCGG

CGACAGCGGAGGCCCACTCGTGTGCAACGGTGTGCTGCAGGGCATCACT

AGCTGGGGATCAGAACCGTGCGCGCTTCCGGAGCGGCCCTCGCTCTACA

CGAAGGTGGTGCACTACCGCAAATGGATTAAAGATACCATCGTCGCAAA

CCCTggatccgaaggtaggggttcattattgacctgtggagatgtcgaa gaaaacccaggacccGCTAGCAAAGCAGTGCTGCTGGCGCTCCTGATGG

CTGGACTCGCGCTGCAGCCTGGAACCGCCCTGCTCTGTTACTCGTGCAA

GGCCCAAGTCTCGAATGAGGACTGTTTGCAAGTGGAAAACTGCACCCAG

CTCGGAGAACAATGCTGGACTGCACGGATCCGCGCTGTCGGCCTGCTGA

CCGTGATCTCCAAAGGGTGCTCATTGAACTGCGTGGACGATAGCCAGGA

CTACTACGTGGGAAAGAAGAATATCACTTGTTGCGACACGGATCTTTGC

AACGCGTCCGGAGCGCACGCCCTGCAGCCAGCAGCCGCCATTCTGGCCC

TGCTTCCGGCCCTGGGGTTGCTGCTCTGGGGTCCGGGCCAGCTCggatc ccagaccctgaactttgatctgctgaaactggcaggcgatgtggaaagc aacccaggcccaATGGCTAGCGCTCGCAGACCGCGGTGGCTGTGTGCAG

GGGCGCTCGTCCTGGCGGGTGGCTTCTTTTTGCTCGGCTTTCTTTTCGG

ATGGTTCATCAAATCGTCAAACGAAGCTACCAATATCACCCCGAAGCAC

AACATGAAGGCCTTTCTGGATGAGCTGAAGGCTGAGAACATTAAGAAGT

TCCTCTACAACTTCACCCAGATCCCACATTTGGCGGGCACTGAGCAGAA

CTTTCAGTTGGCTAAGCAGATCCAGAGCCAGTGGAAGGAATTCGGCCTG

GACTCCGTCGAGCTGGCGCATTACGATGTGCTGCTGAGCTACCCTAATA

AGACTCATCCGAACTATATCTCGATTATCAATGAGGACGGAAACGAAAT

CTTTAACACGTCCCTCTTCGAGCCGCCACCGCCTGGATACGAGAACGTG

TCAGATATCGTGCCTCCGTTCTCGGCCTTCTCGCCCCAGGGAATGCCCG

AAGGGGACCTGGTGTACGTGAACTACGCAAGGACCGAGGACTTCTTCAA

GTTGGAGCGGGATATGAAGATCAATTGCAGCGGAAAGATCGTCATCGCC

CGCTACGGCAAAGTGTTCCGCGGCAACAAGGTGAAGAATGCACAGTTGG

CAGGCGCCAAGGGCGTCATCCTCTACTCGGATCCTGCCGACTACTTCGC

TCCTGGCGTGAAATCCTACCCTGATGGTTGGAATCTGCCAGGAGGAGGG

GTGCAGAGGGGAAATATCCTGAACCTGAACGGTGCCGGTGACCCACTTA

CTCCGGGTTACCCGGCCAACGAATACGCGTACAGGCGGGGTATCGCGGA

AGCCGTCGGACTGCCGTCCATCCCGGTCCATCCGATTGGTTACTACGAC

GCCCAGAAGCTCCTCGAAAAGATGGGAGGCAGCGCCCCTCCGGACTCGT

CATGGAGAGGCTCGCTGAAGGTGCCATACAACGTGGGACCCGGATTCAC

TGGAAATTTCAGCACTCAAAAAGTGAAGATGCACATTCACTCCACTAAC

GAAGTCACCAGGATCTACAACGTCATCGGAACCCTCCGGGGAGCGGTGG

AACCGGACCGCTACGTGATCCTCGGTGGACACCGGGATAGCTGGGTGTT

CGGAGGAATCGATCCTCAATCGGGCGCAGCCGTCGTCCATGAAATCGTC

-continued

AGGTCCTTTGGTACTCTTAAGAAGGAGGGCTGGCGCCCTAGACGCACTA
TTCTGTTCGCCTCGTGGGATGCCGAAGAATTTGGTCTGCTCGGCAGCAC
CGAATGGGCTGAGGAAAACTCCCGCCTGCTCCAAGAACGCGGAGTGGCG
TACATCAATGCCGACTCATCCATCGAAGGAAACTACACGCTGCGGGTGG
ACTGCACTCCACTGATGTACTCGCTCGTGCACAACCTGACCAAAGAACT
CAAATCCCCAGACGAAGGATTCGAGGGAAAATCGCTGTACGAGTCGTGG
ACCAAGAAGAGCCCATCCCCGGAGTTCAGCGGGATGCCGCGGATCTCAA
AGCTCGGATCAGGAAATGATTTCGAAGTGTTCTTTCAGAGGCTGGGAAT
TGCGTCGGGAAGGGCTCGGTACACGAAAAACTGGGAAACTAACAAGTTC
TCGGGATACCCGCTGTACCACTCGGTGTATGAAACTTACGAACTGGTGG
AGAAATTCTACGATCCTATGTTTAAGTACCACCTGACTGTGGCCCAAGT
GAGAGGCGGAATGGTGTTCGAGTTGGCCAATTCAATTGTGCTGCCATTC
GATTGCCGCGACTACGCCGTGGTGCTGAGAAAGTACGCAGACAAAATCT
ACTCAATCAGCATGAAGCACCCACAAGAGATGAAAACCTACTCAGTCTC
CTTCGACTCCCTCTTCTCCGCGGTGAAGAACTTCACCGAGATCGCGAGC
AAATTCTCGGAGCGCCTTCAAGATTTTGACAAATCCAATCCGATCGTCC
TCCGCATGATGAATGACCAGCTCATGTTTCTCGAACGGGCCTTCATCGA
TCCACTGGGACTTCCGGACCGGCCGTTTTACCGCCACGTGATCTACGCG
CCCTCGTCGCATAACAAGTATGCTGGAGAGAGCTTCCCGGGTATCTACG
ACGCATTGTTCGACATTGAGTCCAAGGTGGATCCGTCCAAAGCCTGGGG
TGAAGTGAAGCGCCAAATCTACGTGGCGGCCTTTACCGTCCAGGCGGCA
GCAGAAACCTTGAGCGAGGTGGCTTGActcgagcctaagcttctagata
agatatccgatccaccggatctagataactgatcataatcagccatacc
acatttgtagaggttttacttgctttaaaaaacctcccacacctccccc
tgaacctgaaacataaaatgaatgcaattgttgttgttaacttgtttat
tgcagcttataatggttacaaataaagcaatagcatcacaaatttcaca
aataaagcatttttttcactgcattctagttgtggtttgtccaaactca
tcaatgtatcttatatgctggccaccgtacatgtggcttcccatgctcg
caagccctggcccgagttcgagcacaatgtcatgaccaggtgcaatatg
catctggggtcccgccgaggcatgttcatgccctaccagtgcaacctga
attatgtgaaggtgctgctggagcccgatgccatgtccagagtgagcct
gacgggggtgtttgacatgaatgtggaggtgtggaagattctgagatat
gatgaatccaagaccaggtgccgagcctgcgagtgcggagggaagcatg
ccaggttccagcccgtgtgtgtggatgtgacggaggacctgcgacccga
tcatttggtgttgccctgcaccgggacggagttcggttccagcggggaa
gaatctgactagagtgagtagtgttctggggcgggggaggacctgcatg
agggccagaataactgaaatctgtgcttttctgtgtgttgcagcagcat
gagcggaagcggctcctttgagggaggggtattcagcccttatctgacg
ggcgtctcccctcctgggcgggagtgcgtcagaatgtgatgggatcca
cggtggacggccggcccgtgcagcccgcgaactcttcaaccctgaccta -continued tgcaaccctgagctcttcgtcgttggacgcagctgccgccgcagctgct
gcatctgccgccagcgccgtgcgcggaatggccatgggcgccggctact
acggcactctggtggccaactcgagttccaccaataatcccgccagcct
gaacgaggagaagctgttgctgctgatggcccagctcgaggccttgacc
cagcgcctgggcgagctgacccagcaggtggctcagctgcaggagcaga
cgcgggccgcggttgccacggtgaaatccaaataaaaaatgaatcaata
aataaacggagacggttgttgattttaacacagagtctgaatctttatt
tgatttttcgcgcgcggtaggccctggaccaccggtctcgatcattgag
cacccggtggatcttttccaggacccggtagaggtgggcttggatgttg
aggtacatgggcatgagcccgtcccgggggtggaggtagctccattgca
gggcctcgtgctcgggggtggtgttgtaaatcacccagtcatagcaggg
gcgcagggcatggtgttgcacaatatctttgaggaggagactgatggcc
acgggcagccctttggtgtaggtgtttacaaatctgttgagctgggagg
gatgcatgcgggggggagatgaggtgcatcttggcctggatcttgagatt
ggcgatgttaccgcccagatcccgcctggggttcatgttgtgcaggacc
accagcacggtgtatccggtgcacttggggaatttatcatgcaacttgg
aagggaaggcgtgaaagaatttggcgacgcctttgtgcccgcccaggtt
ttccatgcactcatccatgatgatggcgatgggcccgtgggcggcggcc
tgggcaaagacgtttcgggggtcggacacatcatagttgtggtcctggg
tgaggtcatcataggccattttaatgaatttggggcggagggtgccgga
ctgggggacaaaggtaccctcgatcccgggggcgtagttcccctcacag
atctgcatctcccaggctttgagctcggagggggggatcatgtccacct
gcggggcgataaagaacacggtttccggggcgggggagatgagctgggc
cgaaagcaagttccggagcagctgggacttgccgcagccggtggggccg
tagatgaccccgatgaccggctgcaggtggtagttgagggagagacagc
tgccgtcctcccggaggagggggccacctcgttcatcatctcgcgcac
gtgcatgttctcgcgcaccagttccgccaggaggcgctctcccccccagg
gataggagctcctggagcgaggcgaagtttttcagcggcttgagtccgt
cggccatgggcattttggagagggtttgttgcaagagttccaggcggtc
ccagagctcggtgatgtgctctacggcatctcgatccagcagacctcct
cgtttcgcgggttgggacggctgcgggagtagggcaccagacgatgggc
gtccagcgcagccagggtccggtccttccagggtcgcagcgtccgcgtc
agggtggtctccgtcacggtgaaggggtgcgcgccgggctgggcgcttg
cgagggtgcgcttcaggctcatccggctggtcgaaaaccgctcccgatc
ggcgccctgcgcgtcggccaggtagcaattgaccatgagttcgtagttg
agcgcctcggccgcgtggcctttggcgcggagcttacctttggaagtct
gcccgcaggcgggacagaggagggacttgagggcgtagagcttgggggc
gaggaagacggactcgggggcgtaggcgtccgcgccgcagtgggcgcag
acggtctcgcactccacgagccaggtgaggtcgggctggtcggggtcaa
aaaccagtttcccgccgttctttttgatgcgtttcttacctttggtctc
catgagctcgtgtccccgctgggtgacaaagaggctgtccgtgtccccg -continued

```
tagaccgactttatgggccggtcctcgagcggtgtgccgcggtcctcct
cgtagaggaaccccgcccactccgagacgaaagcccgggtccaggccag
cacgaaggaggccacgtgggacgggtagcggtcgttgtccaccagcggg
tccaccttttccagggtatgcaaacacatgtccccctcgtccacatcca
ggaaggtgattggcttgtaagtgtaggccacgtgaccgggggtcccggc
cggggggtataaaagggtgcgggtccctgctcgtcctcactgtcttcc
ggatcgctgtccaggagcgccagctgttggggtaggtattccctctcga
aggcgggcatgacctcggcactcaggttgtcagtttctagaaacgagga
ggatttgatattgacggtgccggcggagatgcctttcaagagcccctcg
tccatctggtcagaaaagacgatctttttgttgtcgagcttggtggcga
aggagccgtagagggcgttggagaggagcttggcgatggagcgcatggt
ctggtttttttccttgtcggcgcgctccttggcggcgatgttgagctgc
acgtactcgcgcgccacgcacttccattcggggaagacggtggtcagct
cgtcgggcacgattctgacctgccagccccgattatgcagggtgatgag
gtccacactggtggccacctcgccgcgcaggggctcattagtccagcag
aggcgtccgcccttgcgcgagcagaagggggggcagggggtccagcatga
cctcgtcggggggggtcggcatcgatggtgaagatgccgggcaggaggtc
ggggtcaaagtagctgatggaagtggccagatcgtccagggcagcttgc
cattcgcgcacggccagcgcgcgctcgtagggactgaggggcgtgcccc
agggcatgggatgggtaagcgcggaggcgtacatgccgcagatgtcgta
gacgtagaggggctcctcgaggatgccgatgtaggtggggtagcagcgc
cccccgcggatgctggcgcgcacgtagtcatacagctcgtgcgaggggg
cgaggagccccgggcccaggttggtgcgactgggcttttcggcgcggta
gacgatctggcggaaaatggcatgcgagttggaggagatggtgggcctt
tggaagatgttgaagtgggcgtggggcagtccgaccgagtcgcggatga
agtgggcgtaggagtcttgcagcttggcgacgagctcggcggtgactag
gacgtccagagcgcagtagtcgagggtctcctggatgatgtcatacttg
agctgtccctttttgtttccacagctcgcggttgagaaggaactcttcgc
ggtccttccagtactcttcgaggggggaacccgtcctgatctgcacggta
agagcctagcatgtagaactggttgacggccttgtaggcgcagcagccc
ttctccacggggagggcgtaggcctgggcggccttgcgcagggaggtgt
gcgtgagggcgaaagtgtccctgaccatgaccttgaggaactggtgctt
gaagtcgatatcgtcgcagccccccctgctcccagagctggaagtccgtg
cgcttcttgtaggcggggttgggcaaagcgaaagtaacatcgttgaaga
ggatcttgcccgcgcggggcataaagttgcgagtgatgcggaaaggttg
gggcacctcggcccggttgttgatgacctgggcggcgagcacgatctcg
tcgaagccgttgatgttgtggcccacgatgtagagttccacgaatcgcg
gacggcccttgacgtggggcagtttcttgagctcctcgtaggtgagctc
gtcggggtcgctgagcccgtgctgctcgagcgcccagtcggcgagatgg
gggttggcgcggaggaaggaagtccagagatccacggccagggcggttt
```

-continued

```
gcagacggtcccggtactgacggaactgctgcccgacggccatttttc
gggggtgacgcagtagaaggtgcgggggtccccgtgccagcgatcccat
ttgagctggagggcgagatcgagggcgagctcgacgagccggtcgtccc
cggagagtttcatgaccagcatgaaggggacgagctgcttgccgaagga
ccccatccaggtgtaggtttccacatcgtaggtgaggaagagcctttcg
gtgcgaggatgcgagccgatggggaagaactggatctcctgccaccaat
tggaggaatggctgttgatgtgatggaagtagaaatgccgacggcgcgc
cgaacactcgtgcttgtgtttatacaagcggccacagtgctcgcaacgc
tgcacgggatgcacgtgctgcacgagctgtacctgagttcctttgacga
ggaatttcagtgggaagtggagtcgtggcgcctgcatctcgtgctgtac
tacgtcgtggtggtcggcctggccctcttctgcctcgatggtggtcatg
ctgacgagcccgcgcgggaggcaggtccagacctcggcgcgagcgggtc
ggagagcgaggacgagggcgcgcaggccggagctgtccagggtcctgag
acgctgcggagtcaggtcagtgggcagcggcggcgcgcggttgacttgc
aggagtttttccagggcgcgcgggaggtccagatggtacttgatctcca
ccgcgccattggtggcgacgtcgatggcttgcagggtcccgtgcccctg
gggtgtgaccaccgtcccccgtttcttcttgggcggctggggcgacggg
ggcggtgcctcttccatggttagaagcggcggcgaggacgcgcgccggg
cggcaggggcggctcggggcccggaggcaggggcggcaggggcacgtcg
gcgccgcgcgcgggtaggttctggtactgcgcccggagaagactggcgt
gagcgacgacgcgacggttgacgtcctggatctgacgcctctgggtgaa
ggccacgggacccgtgagtttgaacctgaaagagagttcgacagaatca
atctcggtatcgttgacggcggcctgccgcaggatctcttgcacgtcgc
ccgagttgtcctggtaggcgatctcggtcatgaactgctcgatctcctc
ctcttgaaggtctccgcggccggcgcgctccacggtggccgcgaggtcg
ttggagatgcggcccatgagctgcgagaaggcgttcatgcccgcctcgt
tccagacgcggctgtagaccacgacgccctcgggatcgcGggcgcgcat
gaccacctgggcgaggttgagctccacgtggcgcgtgaagaccgcgtag
ttgcagaggcgctggtagaggtagttgagcgtggtggcgatgtgctcgg
tgacgaagaaatacatgatccagcggcggagcggcatctcgctgacgtc
gcccagcgcctccaaacgttccatggcctcgtaaaagtccacggcgaag
ttgaaaaactgggagttgcgcgccgagacggtcaactcctcctccagaa
gacggatgagctcggcgatggtggcgcgcacctcgcgctcgaaggcccc
cgggagttcctccacttcctcttcttcctcctccactaacatctcttct
acttcctcctcaggcggcagtggtggcgggggagggggcctgcgtcgcc
ggcggcgcacgggcagacggtcgatgaagcgctcgatggtctcgccgcg
ccggcgtcgcatggtctcggtgacggcgcgcccgtcctcgcggggccgc
agcgtgaagacgccgccgcgcatctccaggtggccgggggggtccccgt
tgggcagggagagggcgctgacgatgcatcttatcaattgccccgtagg
gactccgcgcaaggacctgagcgtctcgagatccacgggatctgaaaac
cgctgaacgaaggcttcgagccagtcgcagtcgcaaggtaggctgagca
```

-continued cggtttcttctggcgggtcatgttggttgggagcggggcgggcgatgct
gctggtgatgaagttgaaataggcggttctgagacggcggatggtggcg
aggagcaccaggtctttgggcccggcttgctggatgcgcagacggtcgg
ccatgccccaggcgtggtcctgacacctggccaggtccttgtagtagtc
ctgcatgagccgctccacgggcacctcctcctcgcccgcgcggccgtgc
atgcgcgtgagcccgaagccgcgctggggctggacgagcgccaggtcgg
cgacgacgcgctcggcgaggatggcttgctggatctgggtgagggtggt
ctggaagtcatcaaagtcgacgaagcggtggtaggctccggtgttgatg
gtgtaggagcagttggccatgacggaccagttgacggtctggtggcccg
gacgcacgagctcgtggtacttgaggcgcgagtaggcgcgcgtgtcgaa
gatgtagtcgttgcaggtgcgcaccaggtactggtagccgatgaggaag
tgcggcggcggctggcggtagagcggccatcgctcggtggcgggggcgc
cgggcgcgaggtcctcgagcatggtgcggtggtagccgtagatgtacct
ggacatccaggtgatgccggcggcggtggtggaggcgcgcgggaactcg
cggacgcggttccagatgttgcgcagcggcaggaagtagttcatggtgg
gcacggtctggcccgtgaggcgcgcgcagtcgtggatgctctatacggg
caaaaacgaaagcggtcagcggctcgactccgtggcctggaggctaagc
gaacgggttgggctgcgcgtgtaccccggttcgaatctcgaatcaggct
ggagccgcagctaacgtggtattggcactcccgtctcgacccaagcctg
caccaaccctccaggatacggaggcgggtcgttttgcaactttttttg
gaggccggatgagactagtaagcgcggaaagcggccgaccgcgatggct
cgctgccgtagtctggagaagaatcgccagggttgcgttgcggtgtgcc
ccggttcgaggccggccggattccgcggctaacgagggcgtggctgccc
cgtcgtttccaagaccccatagccagccgacttctccagttacggagcg
agcccctcttttgttttgtttgtttttgccagatgcatcccgtactgcg
gcagatgcgcccccaccaccctccaccgcaacaacagccccctccacag
ccggcgcttctgcccccgccccagcagcaacttccagccacgaccgccg
cggccgccgtgagcggggctggacagagttatgatcaccagctggcctt
ggaagagggcgaggggctggcgcgcctgggggcgtcgtcgccggagcgg
cacccgcgcgtgcagatgaaaagggacgctcgcgaggcctacgtgccca
agcagaacctgttcagagacaggagcggcgaggagcccgaggagatgcg
cgcggcccggttccacgcggggcgggagctgcggcgcggcctggaccga
aagagggtgctgagggacgaggatttcgaggcggacgagctgacgggga
tcagccccgcgcgcgcgcacgtggccgcggccaacctggtcacggcgta
cgagcagaccgtgaaggaggagagcaacttccaaaaatccttcaacaac
cacgtgcgcaccctgatcgcgcgcgaggaggtgaccctgggcctgatgc
acctgtgggacctgctggaggccatcgtgcagaaccccaccagcaagcc
gctgacggcgcagctgttcctggtggtgcagcatagtcgggacaacgaa
gcgttcagggaggcgctgctgaatatcaccgagcccgagggccgctggc
tcctggacctggtgaacattctgcagagcatcgtggtgcaggagcgcgg
gctgccgctgtccgagaagctggcggccatcaacttctcggtgctgagt
ttgggcaagtactacgctaggaagatctacaagaccccgtacgtgccca
tagacaaggaggtgaagatcgacgggttttacatgcgcatgaccctgaa
agtgctgaccctgagcgacgatctgggggtgtaccgcaacgacaggatg
caccgtgcggtgagcgccagcaggcggcgcgagctgagcgaccaggagc
tgatgcatagtctgcagcgggccctgaccggggccgggaccgaggggga
gagctactttgacatgggcgcggacctgcactggcagcccagccgccgg
gccttggaggcggcggcaggaccctacgtagaagaggtggacgatgagg
tggacgaggagggcgagtacctggaagactgatggcgcgaccgtatttt
tgctagatgcaacaacaacagccacctcctgatcccgcgatgcgggcgg
cgctgcagagccagccgtccggcattaactcctcggacgattggaccca
ggccatgcaacgcatcatggcgctgacgacccgcaaccccgaagccttt
agacagcagccccaggccaaccggctctcggccatcctggaggccgtgg
tgccctcgcgctccaaccccacgcacgagaaggtcctggccatcgtgaa
cgcgctggtggagaacaaggccatccgcggcgacgaggccggcctggtg
tacaacgcgctgctggagcgcgtggcccgctacaacagcaccaacgtgc
agaccaacctggaccgcatggtgaccgacgtgcgcgaggccgtggccca
gcgcgagcggttccaccgcgagtccaacctgggatccatggtggcgctg
aacgccttcctcagcacccagcccgccaacgtgccccggggccaggagg
actacaccaacttcatcagcgccctgcgcctgatggtgaccgaggtgcc
ccagagcgaggtgtaccagtccgggccggactacttcttccagaccagt
cgccagggcttgcagaccgtgaacctgagccaggctttcaagaacttgc
agggcctgtggggcgtgcaggccccggtcggggaccgcgcgacggtgtc
gagcctgctgacgccgaactcgcgcctgctgctgctgctggtggccccc
ttcacggacagcggcagcatcaaccgcaactcgtacctgggctacctga
ttaacctgtaccgcgaggccatcggccaggcgcacgtggacgagcagac
ctaccaggagatcacccacgtgagccgcgccctgggccaggacgacccg
ggcaacctggaagccaccctgaactttttgctgaccaaccggtcgcaga
agatcccgccccagtacgcgctcagcaccgaggaggagcgcatcctgcg
ttacgtgcagcagagcgtgggcctgttcctgatgcaggagggggccacc
cccagcgccgcgctcgacatgaccgcgcgcaacatggagcccagcatgt
acgccagcaaccgcccgttcatcaataaactgatggactacttgcatcg
ggcggccgccatgaactctgactatttcaccaacgccatcctgaatccc
cactggctcccgccgccggggttctacacgggcgagtacgacatgcccg
accccaatgacgggttcctgtgggacgatgtggacagcagcgtgttctc
cccccgaccgggtgctaacgagcgccccttgtggaagaaggaaggcagc
gaccgacgcccgtcctcggcgctgtccggccgcgagggtgctgccgcgg
cggtgcccgaggccgccagtcctttcccgagcttgcccttctcgctgaa
cagtatccgcagcagcgagctgggcaggatcacgcgcccgcgcttgctg
ggcgaagaggagtacttgaatgactcgctgttgagacccgagcgggaga
agaacttccccaataacgggatagaaagcctggtggacaagatgagccg -continued ctggaagacgtatgcgcaggagcacagggacgatccccgggcgtcgcag ggggccacgagccggggcagcgccgcccgtaaacgccggtggcacgaca ggcagcggggacagatgtgggacgatgaggactccgccgacgacagcag cgtgttggacttgggtgggagtggtaacccgttcgctcacctgcgcccc cgtatcgggcgcatgatgtaagagaaaccgaaaataaatgatactcacc aaggccatggcgaccagcgtgcgttcgtttcttctctgttgttgttgta tctagtatgatgaggcgtgcgtacccggagggtcctcctccctcgtacg agagcgtgatgcagcaggcgatggcggcggcggcgatgcagccccccgct ggaggctccttacgtgcccccgcggtacctggcgcctacggaggggcgg aacagcattcgttactcggagctggcacccttgtacgataccacccggt tgtacctggtggacaacaagtcggcggacatcgcctcgctgaactacca gaacgaccacagcaacttcctgaccaccgtggtgcagaacaatgacttc acccccacggaggccagcacccagaccatcaactttgacgagcgctcgc ggtggggcggccagctgaaaaccatcatgcacaccaacatgcccaacgt gaacgagttcatgtacagcaacaagttcaaggcgcgggtgatggtctcc cgcaagacccccaatggggtgacagtgacagaggattatgatggtagtc aggatgagctgaagtatgaatgggtggaatttgagctgcccgaaggcaa cttctcggtgaccatgaccatcgacctgatgaacaacgccatcatcgac aattacttggcggtggggcggcagaacggggtgctggagagcgacatcg gcgtgaagttcgacactaggaacttcaggctgggctgggaccccgtgac cgagctggtcatgcccggggtgtacaccaacgaggctttccatcccgat attgtcttgctgcccggctgcggggtggacttcaccgagagccgcctca gcaacctgctgggcattcgcaagaggcagcccttccaggaaggcttcca gatcatgtacgaggatctggagggggcaacatccccgcgctcctggat gtcgacgcctatgagaaaagcaaggaggatgcagcagctgaagcaactg cagccgtagctaccgcctctaccgaggtcaggggcgataattttgcaag cgccgcagcagtggcagcggccgaggcggctgaaaccgaaagtaagata gtcattcagccggtggagaaggatagcaagaacaggagctacaacgtac taccggacaagataaacaccgcctaccgcagctggtacctagcctacaa ctatggcgaccccgagaagggcgtgcgctcctggacgctgctcaccacc tcggacgtcacctgcggcgtggagcaagtctactggtcgctgcccgaca tgatgcaagacccggtcaccttccgctccacgcgtcaagttagcaacta cccggtggtgggcgccgagctcctgcccgtctactccaagagcttcttc aacgagcaggccgtctactcgcagcagctgcgcgccttcacctcgctta cgcacgtcttcaaccgcttccccgagaaccagatcctcgtccgcccgcc cgcgcccaccattaccaccgtcagtgaaaacgttcctgctctcacagat cacgggaccctgccgctgcgcagcagtatccggggagtccagcgcgtga ccgttactgacgccagacgccgcacctgcccctacgtctacaaggccct gggcatagtcgcgccgcgcgtcctctcgagccgcaccttctaaatgtcc attctcatctcgcccagtaataacaccggttggggcctgcgcgcgccca -continued gcaagatgtacggaggcgctcgccaacgctccacgcaacaccccgtgcg cgtgcgcgggcacttccgcgctccctggggcgccctcaagggccgcgtg cggtcgcgcaccaccgtcgacgacgtgatcgaccaggtggtggccgacg cgcgcaactacacccccgccgccgcgcccgtctccaccgtggacgccgt catcgacagcgtggtggcCgacgcgcgccggtacgcccgcgccaagagc cggcggcggcgcatcgcccggcggcaccggagcaccccgccatgcgcg cggcgcgagccttgctgcgcagggccaggcgcacgggacgcagggccat gctcagggcggccagacgcgcggcttcaggcgccagcgccggcaggacc cggagacgcgcggccacggcggcggcagcggccatcgccagcatgtccc gcccgcggcgagggaacgtgtactgggtgcgcgacgccgccaccggtgt gcgcgtgcccgtgcgcacccgcccccctcgcacttgaagatgttcactt cgcgatgttgatgtgtcccagcggcgaggaggatgtccaagcgcaaatt caaggaagagatgctccaggtcatcgcgcctgagatctacggccctgcg gtggtgaaggaggaaagaaagccccgcaaaatcaagcgggtcaaaaagg acaaaaaggaagaagaaagtgatgtggacggattggtggagtttgtgcg cgagttcgcccccggcggcgcgtgcagtggcgcgggcggaaggtgcaa ccggtgctgagacccggcaccaccgtggtcttcacgcccggcgagcgct ccggcaccgcttccaagcgctcctacgacgaggtgtacggggatgatga tattctggagcaggcggccgagcgcctgggcgagtttgcttacggcaag cgcagccgttccgcaccgaaggaagaggcggtgtccatcccgctggacc acggcaaccccacgccgagcctcaagcccgtgaccttgcagcaggtgct gccgaccgcggcgccgcgccgggggttcaagcgcgagggcgaggatctg taccccaccatgcagctgatggtgcccaagcgccagaagctggaagacg tgctggagaccatgaaggtggacccggacgtgcagcccgaggtcaaggt gcggcccatcaagcaggtggccccgggcctgggcgtgcagaccgtggac atcaagattcccacggagcccatggaaacgcagaccgagcccatgatca agcccagcaccagcaccatggaggtgcagacggatccctggatgccatc ggctcctagtcgaagaccccggcgcaagtacggcgcggccagcctgctg atgcccaactacgcgctgcatccttccatcatccccacgccgggctacc gcggcacgcgcttctaccgcggtcataccagcagccgccgccgcaagac caccactcgccgccgccgtcgccgcaccgccgctgcaaccacccctgcc gccctggtgcggagagtgtaccgccgcggccgcgcacctctgaccctgc cgcgcgcgcgctaccacccgagcatcgccatttaaactttcgccTgctt tgcagatcaatggccctcacatgccgccttcgcgttcccattacgggct accgaggaagaaaaccgcgccgtagaaggctggcggggaacgggatgcg tcgccaccaccaccggcggcggcgcgccatcagcaagcggttgggggga ggcttcctgcccgcgctgatccccatcatcgccgcggcgatcggggcga tccccggcattgcttccgtggcggtgcaggcctctcagcgccactgaga cacacttggaaacatcttgtaataaaccAatggactctgacgctcctgg tcctgtgatgtgttttcgtagacagatggaagacatcaatttttcgtcc ctggctccgcgacacggcacgcggccgttcatgggcacctggagcgaca -continued tcggcaccagccaactgaacgggggcgccttcaattggagcagtctctg gagcgggcttaagaatttcgggtccacgcttaaaacctatggcagcaag gcgtggaacagcaccacagggcaggcgctgagggataagctgaaagagc agaacttccagcagaaggtggtcgatgggctcgcctcgggcatcaacgg ggtggtggacctggccaaccaggccgtgcagcggcagatcaacagccgc ctggacccggtgccgcccgccggctccgtggagatgccgcaggtggagg aggagctgcctcccctggacaagcggggcgagaagcgaccccgccccga tgcggaggagacgctgctgacgcacacggacgagccgcccccgtacgag gaggcggtgaaactgggtctgcccaccacgcggcccatcgcgcccctgg ccaccggggtgctgaaacccgaaaagcccgcgaccctggacttgcctcc tccccagccttcccgcccctctacagtggctaagcccctgccgccggtg gccgtggcccgcgcgcgacccgggggcaccgcccgccctcatgcgaact ggcagagcactctgaacagcatcgtgggtctgggagtgcagagtgtgaa gcgccgccgctgctattaaacctaccgtagcgcttaacttgcttgtctg tgtgtgtatgtattatgtcgccgccgccgctgtccaccagaaggaggag tgaagaggcgcgtcgccgagttgcaagatggccaccccatcgatgctgc cccagtgggcgtacatgcacatcgccggacaggacgcttcggagtacct gagtccgggtctggtgcagtttgcccgcgccacagacacctacttcagt ctggggaacaagtttaggaaccccacggtggcgcccacgcacgatgtga ccaccgaccgcagccagcggctgacgctgcgcttcgtgcccgtggaccg cgaggacaacacctactcgtacaaagtgcgctacacgctggccgtgggc gacaaccgcgtgctggacatggccagcacctactttgacatccgcggcg tgctggatcggggccctagcttcaaaccctactccggcaccgcctacaa cagtctggcccccaagggagcacccaacacttgtcagtggacatataaa gccgatggtgaaactgccacagaaaaaacctatacatatggaaatgcac ccgtgcagggcattaacatcacaaaagatggtattcaacttggaactga caccgatgatcagccaatctacgcagataaaacctatcagcctgaacct caagtgggtgatgctgaatggcatgacatcactggtactgatgaaaagt atggaggcagagctcttaagcctgataccaaaatgaagccttgttatgg ttcttttgccaagcctactaataaagaaggaggtcaggcaaatgtgaaa acaggaacaggcactactaaagaatatgacatagacatggctttctttg acaacagaagtgcggctgctgctggcctagctccagaaattgttttgta tactgaaaatgtggatttggaaactccagatacccatattgtatacaaa gcaggcacagatgacagcagctcttctattaatttgggtcagcaagcca tgcccaacagacctaactacattggtttcagagacaactttatcgggct catgtactacaacagcactggcaatatgggggtgctggccggtcaggct tctcagctgaatgctgtggttgacttgcaagacagaaacaccgagctgt cctaccagctcttgcttgactctctgggtgacagaacccggtatttcag tatgtggaatcaggcggtggacagctatgatcctgatgtgcgcattatt gaaaatcatggtgtggaggatgaacttcccaactattgtttccctctgg -continued atgctgttggcagaacagatacttatcagggaattaaggctaatggaac tgatcaaaccacatggaccaaagatgacagtgtcaatgatgctaatgag ataggcaagggtaatccattcgccatggaaatcaacatccaagccaacc tgtggaggaacttcctctacgccaacgtggccctgtacctgcccgactc ttacaagtacacgccggccaatgttaccctgcccaccaacaccaacacc tacgattacatgaacggccgggtggtggcgccctcgctggtggactcct acatcaacatcggggcgcgctggtcgctggatcccatggacaacgtgaa ccccttcaaccaccaccgcaatgcggggctgcgctaccgctccatgctc ctgggcaacgggcgctacgtgcccttccacatccaggtgccccagaaat tttcgccatcaagagcctcctgctcctgcccgggtcctacacctacga gtggaacttccgcaaggacgtcaacatgatcctgcagagctccctcggc aacgacctgcgcacggacggggcctccatctccttcaccagcatcaacc tctacgccaccttcttccccatggcgcacaacacggcctccacgctcga ggccatgctgcgcaacgacaccaacgaccagtccttcaacgactacctc tcggcggccaacatgctctaccccatcccggccaacgccaccaacgtgc ccatctccatcccctcgcgcaactgggccgccttccgcggctggtcctt cacgcgtctcaagaccaaggagacgccctcgctgggctccgggttcgac ccctacttcgtctactcgggctccatcccctacctcgacggcaccttct acctcaaccacaccttcaagaaggtctccatcaccttcgactcctccgt cagctggcccggcaacgaccggctcctgacgcccaacgagttcgaaatc aagcgcaccgtcgacggcgagggctacaacgtggcccagtgcaacatga ccaaggactggttcctggtccagatgctggcccactacaacatcggcta ccagggcttctacgtgcccgagggctacaaggaccgcatgtactccttc ttccgcaacttccagcccatgagccgccaggtggtggacgaggtcaact acaaggactaccaggccgtcaccctggcctaccagcacaacaactcggg cttcgtcggctacctcgcgcccaccatgcgccagggccagccctacccc gccaactacccctacccgctcatcggcaagagcgccgtcaccagcgtca cccagaaaaagttcctctgcgacagggtcatgtggcgcatccccttctc cagcaacttcatgtccatgggcgcgctcaccgacctcggccagaacatg ctctatgccaactccgcccacgcgctagacatgaatttcgaagtcgacc ccatggatgagtccacccttctctatgttgtcttcgaagtcttcgacgt cgtccgagtgcaccagccccaccgcggcgtcatcgaggccgtctacctg cgcacccccttctcggccggtaacgccaccacctaagctcttgcttctt gcaagccatggccgcgggctccggcgagcaggagctcagggccatcatc cgcgacctgggctgcgggccctacttcctgggcaccttcgataagcgct tcccgggattcatggccccgcacaagctggcctgcgccatcgtcaacac ggccggccgcgagaccgggggcgagcactggctggccttcgcctggaac ccgcgctcgaacacctgctacctcttcgaccccttcgggttctcggacg agcgcctcaagcagatctaccagttcgagtacgagggcctgctgcgccg cagcgccctggccaccgaggaccgctgcgtcaccctggaaaagtccacc cagaccgtgcagggtccgcgctcggccgcctgcgggctcttctgctgca -continued tgttcctgcacgccttcgtgcactggcccgaccgccccatggacaagaa
ccccaccatgaacttgctgacgggggtgcccaacggcatgctccagtcg
ccccaggtggaacccaccctgcgccgcaaccaggaggcgctctaccgct
tcctcaactcccactccgcctactttcgctcccaccgcgcgcgcatcga
gaaggccaccgccttcgaccgcatgaatcaagacatgtaaaccgtgtgt
gtatgttaaatgtctttaataaacagcactttcatgttacacatgcatc
tgagatgatttatttagaaatcgaaagggttctgccgggtctcggcatg
gcccgcgggcagggacacgttgcggaactggtacttggccagccacttg
aactcggggatcagcagtttgggcagcggggtgtcggggaaggagtcgg
tccacagcttccgcgtcagttgcagggcgcccagcaggtcgggcgcgga
gatcttgaaatcgcagttgggacccgcgttctgcgcgcgggagttgcgg
tacacggggttgcagcactggaacaccatcagggccgggtgcttcacgc
tcgccagcaccgtcgcgtcggtgatgctctccacgtcgaggtcctcggc
gttggccatcccgaaggggggtcatcttgcaggtctgccttcccatggtg
ggcacgcacccgggcttgtggttgcaatcgcagtgcagggggatcagca
tcatctgggcctggtcggcgttcatccccgggtacatggccttcatgaa
agcctccaattgcctgaacgcctgctgggccttggctccctcggtgaag
aagaccccgcaggacttgctagagaactggttggtggcgcacccggcgt
cgtgcacgcagcagcgcgcgtcgttgttggccagctgcaccacgctgcg
cccccagcggttctgggtgatcttggcccggtcggggttctccttcagc
gcgcgctgcccgttctcgctcgccacatccatctcgatcatgtgctcct
tctggatcatggtggtcccgtgcaggcaccgcagcttgccctcggcctc
ggtgcacccgtgcagccacagcgcgcacccggtgcactcccagttcttg
tgggcgatctgggaatgcgcgtgcacgaagccctgcaggaagcggccca
tcatggtggtcagggtcttgttgctagtgaaggtcagcggaatgccgcg
gtgctcctcgttgatgtacaggtggcagatgcggcggtacacctcgccc
tgctcgggcatcagctggaagttggctttcaggtcggtctccacgcggt
agcggtccatcagcatagtcatgatttccataccttctcccaggccga
gacgatgggcaggctcatagggttcttcaccatcatcttagcgctagca
gccgcggccaggggggtcgctctcgtccagggtctcaaagctccgcttgc
cgtccttctcggtgatccgcaccggggggtagctgaagcccacggccgc
cagctcctcctcggcctgtctttcgtcctcgctgtcctggctgacgtcc
tgcaggaccacatgcttggtcttgcggggtttcttcttgggcggcagcg
gcggcggagatgttggagatggcgagggggagcgcgagttctcgctcac
cactactatctcttcctcttcttggtccgaggccacgcggcggtaggta
tgtctcttcgggggcagaggcggaggcgacgggctctcgccgccgcgac
ttggcggatggctggcagagccccttccgcgttcgggggtgcgctcccg
gcggcgctctgactgacttcctccgcggccggccattgtgttctcctag
ggaggaacaacaagcatggagactcagccatcgccaacctcgccatctg
cccccaccgccgacgagaagcagcagcagcagaatgaaagcttaaccgc
cccgccgcccagccccgccacctccgacgcggccgtcccagacatgcaa
gagatggaggaatccatcgagattgacctgggctatgtgacgcccgcgg
agcacgaggaggagctggcagtgcgcttttcacaagaagagatacacca
agaacagccagagcaggaagcagagaatgagcagagtcaggctgggctc
gagcatgacggcgactacctccacctgagcggggggggaggacgcgctca
tcaagcatctggcccggcaggccaccatcgtcaaggatgcgctgctcga
ccgcaccgaggtgcccctcagcgtggaggagctcagccgcgcctacgag
ttgaacctcttctcgccgcgcgtgccccccaagcgccagcccaatggca
cctgcgagcccaacccgcgcctcaacttctacccggtcttcgcggtgcc
cgaggccctggccacctaccacatctttttcaagaaccaaaagatcccc
gtctcctgccgcgccaaccgcacccgcgccgacgcccttttcaacctgg
gtcccggcgcccgcctacctgatatcgcctccttggaagaggttcccaa
gatcttcgagggtctgggcagcgacgagactcgggccgcgaacgctctg
caaggagaaggaggagagcatgagcaccacagcgccctggtcgagttgg
aaggcgacaacgcgcggctggcggtgctcaaacgcacggtcgagctgac
ccatttcgcctacccggctctgaacctgcccccccaaagtcatgagcgcg
gtcatggaccaggtgctcatcaagcgcgcgtcgcccatctccgaggacg
agggcatgcaagactccgaggagggcaagcccgtggtcagcgacgagca
gctggcccggtggctgggtcctaatgctagtccccagagtttggaagag
cggcgcaaactcatgatggccgtggtcctggtgaccgtggagctggagt
gcctgcgccgcttcttcgccgacgcggagaccctgcgcaaggtcgagga
gaacctgcactacctcttcaggcacgggttcgtgcgccaggcctgcaag
atctccaacgtggagctgaccaacctggtctcctacatgggcatcttgc
acgagaaccgcctggggcagaacgtgctgcacaccaccctgcgcgggga
ggcccggcgcgactacatccgcgactgcgtctacctctacctctgccac
acctggcagacgggcatgggcgtgtggcagcagtgtctggaggagcaga
acctgaaagagctctgcaagctcctgcagaagaacctcaagggtctgtg
gaccgggttcgacgagcgcaccaccgcctcggacctggccgacctcatt
ttccccgagcgcctcaggctgacgctgcgcaacggcctgcccgacttta
tgagccaaagcatgttgcaaaactttcgctctttcatcctcgaacgctc
cggaatcctgcccgccacctgctccgcgctgccctcggacttcgtgccg
ctgaccttccgcgagtgcccccgccgctgtggagccactgctacctgc
tgcgcctggccaactacctggcctaccactcggacgtgatcgaggacgt
cagcggcgagggcctgctcgagtgccactgccgctgcaacctctgcacg
ccgcaccgctccctggcctgcaacccccagctgctgagcgagacccaga
tcatcggcaccttcgagttgcaagggcccagcgaaggcgagggttcagc
cgccaagggggggtctgaaactcaccccggggctgtggacctcggcctac
ttgcgcaagttcgtgcccgaggactaccatcccttcgagatcaggttct
acgaggaccaatcccatccgcccaaggccgagctgtcggcctgcgtcat
cacccaggggggcgatcctggcccaattgcaagccatccagaaatcccgc
caagaattcttgctgaaaaagggccgcggggtctacctcgaccccaga -continued ccggtgaggagctcaaccccggcttcccccaggatgccccgaggaaaca
agaagctgaaagtggagctgccgcccgtggaggatttggaggaagactg
ggagaacagcagtcaggcagaggaggaggagatggaggaagactgggac
agcactcaggcagaggaggacagcctgcaagacagtctggaggaagacg
aggaggaggcagaggaggaggtggaagaagcagccgccgccagaccgtc
gtcctcggcgggggagaaagcaagcagcacggataccatctccgctccg
ggtcggggtcccgctcgaccacacagtagatgggacgagaccggacgat
tcccgaaccccaccacccagaccggtaagaaggagcggcagggatacaa
gtcctggcgggggcacaaaaacgccatcgtctcctgcttgcaggcctgc
gggggcaacatctccttcacccggcgctacctgctcttccaccgcgggg
tgaactttccccgcaacatcttgcattactaccgtcacctccacagccc
ctactacttccaagaagaggcagcagcagcagaaaaagaccagcagaaa
accagcagctagaaaatccacagcggcggcagcaggtggactgaggatc
gcggcgaacgagccggcgcaaacccgggagctgaggaaccggatctttc
ccaccctctatgccatcttccagcagagtcgggggcaggagcaggaact
gaaagtcaagaaccgttctctgcgctcgctcacccgcagttgtctgtat
cacaagagcgaagaccaacttcagcgcactctcgaggacgccgaggctc
tcttcaacaagtactgcgcgctcactcttaaagagtagcccgcgcccgc
ccagtcgcagaaaaaggcgggaattacgtcacctgtgcccttcgcccta
gccgcctccacccatcatcatgagcaaagagattcccacgccttacatg
tggagctaccagccccagatgggcctggccgccggtgccgcccaggact
actccacccgcatgaattggctcagcgccgggcccgcgatgatctcacg
ggtgaatgacatccgcgcccaccgaaaccagatactcctagaacagtca
gcgctcaccgccacgccccgcaatcacctcaatccgcgtaattggcccg
ccgccctggtgtaccaggaaattccccagcccacgaccgtactacttcc
gcgagacgcccaggccgaagtccagctgactaactcaggtgtccagctg
gcgggcggcgccaccctgtgtcgtcaccgccccgctcagggtataaagc
ggctggtgatccggggcagaggcacacagctcaacgacgaggtggtgag
ctcttcgctgggtctgcgacctgacggagtcttccaactcgccggatcg
gggagatcttccttcacgcctcgtcaggccgtcctgactttggagagtt
cgtcctcgcagccccgctcgggtggcatcggcactctccagttcgtgga
ggagttcactccctcggtctacttcaaccccttctccggctcccccggc
cactacccggacgagttcatcccgaacttcgacgccatcagcgagtcgg
tggacggctacgattgaatgtcccatggtggcgcagctgacctagctcg
gcttcgacacctggaccactgccgccgcttccgctgcttcgctcgggat
ctcgccgagtttgcctactttgagctgcccgaggagcaccctcagggcc
cggcccacggagtgcggatcgtcgtcgaaggggggcctcgactcccacct
gcttcggatcttcagccagcgtccgatcctggtcgagcgcgagcaagga
cagacccttctgactctgtactgcatctgcaaccaccccggcctgcatg
aaagtctttgttgtctgctgtgtactgagtataataaaagctgagatca -continued gcgactactccggacttccgtgtgttcctgaatccatcaaccagtcttt
gttcttcaccgggaacgagaccgagctccagctccagtgtaagccccac
aagaagtacctcacctggctgttccagggctccccgatcgccgttgtca
accactgcgacaacgacggagtcctgctgagcggccctgccaaccttac
tttttccacccgcagaagcaagctccagctcttccaacccttcctcccc
gggacctatcagtgcgtctcgggaccctgccatcacaccttccacctga
tcccgaataccacagcgtcgctccccgctactaacaaccaaactaacct
ccaccaacgccaccgtcgctaggccacaatacatgcccatattagacta
tgaggccgagccacagcgacccatgctccccgctattagttacttcaat
ctaaccggcggagatgactgacccactggccaacaacaacgtcaacgac
cttctcctggacatggacggccgcgcctcggagcagcgactcgcccaac
ttcgcattcgccagcagcaggagagagccgtcaaggagctgcaggatgc
ggtggccatccaccagtgcaagagaggcatcttctgcctggtgaaacag
gccaagatctcctacgaggtcactccaaacgaccatcgcctctcctacg
agctcctgcagcagcgccagaagttcacctgcctggtcggagtcaaccc
catcgtcatcacccagcagtctggcgataccaaggggtgcatccactgc
tcctgcgactcccccgactgcgtccacactctgatcaagaccctctgcg
gcctccgcgacctcctccccatgaactaatcaccccccttatccagtgaa
ataaagatcatattgatgatgattttacagaaataaaaaataatcattt
gatttgaaataaagatacaatcatattgatgatttgagtttaacaaaaa
aataaagaatcacttacttgaaatctgataccaggtctctgtccatgtt
ttctgccaacaccacttcactcccctcttcccagctctggtactgcagg
ccccggcgggctgcaaacttcctccacacgctgaaggggatgtcaaatt
cctcctgtccctcaatcttcattttatcttctatcagatgtccaaaaag
cgcgtccgggtggatgatgacttcgaccccgtctacccctacgatgcag
acaacgcaccgaccgtgcccttcatcaacccccccttcgtctcttcaga
tggattccaagagaagcccctgggggtgttgtccctgcgactggccgac
cccgtcaccaccaagaacggggaaatcaccctcaagctgggagaggggg
tggacctcgattcctcgggaaaactcatctccaacacggccaccaaggc
cgccgcccctctcagtttttccaacaacaccatttcccttaacatggat
caccccttttacactaaagatggaaaattatccttacaagtttctccac
cattaaatatactgagaacaagcattctaaacacactagctttaggttt
tggatcaggtttaggactccgtggctctgccttggcagtacagttagtc
tctccacttacatttgatactgatggaaacataaagcttaccttagaca
gaggtttgcatgttacaacaggagatgcaattgaaagcaacataagctg
ggctaaaggtttaaaatttgaagatggagccatagcaaccaacattgga
aatgggttagagtttggaagcagtagtacagaaacaggtgttgatgatg
cttacccaatccaagttaaacttggatctggccttagctttgacagtac
aggagccataatggctggtaacaaagaagacgataaactcactttgtgg
acaacacctgatccatcaccaaactgtcaaatactcgcagaaaatgatg
caaaactaacactttgcttgactaaatgtggtagtcaaatactggccac -continued tgtgtcagtcttagttgtaggaagtggaaacctaaaccccattactggc accgtaagcagtgctcaggtgtttctacgttttgatgcaaacggtgttc ttttaacagaacattctacactaaaaaaatactggggggtataggcaggg agatagcatagatggcactccatataccaatgctgtaggattcatgccc aatttaaaagcttatccaaagtcacaaagttctactactaaaaataata tagtagggcaagtatacatgaatggagatgtttcaaaacctatgcttct cactataaccctcaatggtactgatgacagcaacagtacatattcaatg tcattttcatacacctggactaatggaagctatgttggagcaacatttg gggctaactcttataccttctcatacatcgcccaagaatgaacactgta tcccaccctgcatgccaacccttcccaccccactctgtggaacaaactc tgaaacacaaaataaaataaagttcaagtgttttattgattcaacagtt ttacaggattcgagcagttatttttcctccaccctcccaggacatggaa tacaccaccctctccccccgcacagccttgaacatctgaatgccattgg tgatggacatgcttttggtctccacgttccacacagtttcagagcgagc cagtctcgggtcggtcagggagatgaaaccctccgggcactcccgcatc tgcacctcacagctcaacagctgaggattgtcctcggtggtcgggatca cggttatctggaagaagcagaagagcggcggtgggaatcatagtccgcg aacgggatcggccggtggtgtcgcatcaggccccgcagcagtcgctgcc gccgccgctccgtcaagctgctgctcagggggtccgggtccagggactc cctcagcatgatgcccacggccctcagcatcagtcgtctggtgcggcgg gcgcagcagcgcatgcggatctcgctcaggtcgctgcagtacgtgcaac acagaaccaccaggttgttcaacagtccatagttcaacacgctccagcc gaaactcatcgcgggaaggatgctacccacgtggccgtcgtaccagatc ctcaggtaaatcaagtggtgcccctccagaacacgctgcccacgtaca tgatctccttgggcatgtggcggttcaccacctcccggtaccacatcac cctctggttgaacatgcagccccggatgatcctgcggaaccacagggcc agcaccgccccgcccgccatgcagcgaagagaccccgggtcccggcaat ggcaatggaggacccaccgctcgtacccgtggatcatctgggagctgaa caagtctatgttggcacagcacaggcatatgctcatgcatctcttcagc actctcaactcctcgggggtcaaaaccatatcccagggcacggggaact cttgcaggacagcgaaccccgcagaacagggcaatcctcgcacagaact tacattgtgcatggacagggtatcgcaatcaggcagcaccgggtgatcc tccaccagagaagcgcgggtctcggtctcctcacagcgtggtaagggggg ccggccgatacgggtgatggcgggacgcggctgatcgtgttcgcgaccg tgtcatgatgcagttgctttcggacattttcgtacttgctgtagcagaa cctggtccgggcgctgcacaccgatcgccggcggcggtctcggcgcttg gaacgctcggtgttgaaattgtaaaacagccactctctcagaccgtgca gcagatctagggcctcaggagtgatgaagatcccatcatgcctgatggc tctgatcacatcgaccaccgtggaatgggccagacccagccagatgatg caattttgttgggtttcggtgacggcgggggagggaagaacaggaagaa -continued ccatgattaacttttaatccaaacggtctcggagtacttcaaaatgaag atcgcggagatggcacctctcgccccccgctgtgttggtggaaaataaca gccaggtcaaaggtgatacggttctcgagatgttccacggtggcttcca gcaaagcctccacgcgcacatccagaaacaagacaatagcgaaagcggg agggttctctaattcctcaatcatcatgttacactcctgcaccatcccc agataattttcatttttccagccttgaatgattcgaactagttcCtgag gtaaatccaagccagccatgataaagagctcgcgcagagcgccctccac cggcattcttaagcacaccctcataattccaagatattctgctcctggt tcacctgcagcagattgacaagcggaatatcaaaatctctgccgcgatc cctgagctcctccctcagcaataactgtaagtactctttcatatcctct ccgaaatttttagccataggaccaccaggaataagattagggcaagcca cagtacagataaaccgaagtcctccccagtgagcattgccaaatgcaag actgctataagcatgctggctagacccggtgatatcttccagataactg gacagaaaatcgcccaggcaatttttaagaaaatcaacaaaagaaaaat cctccaggtggacgtttagagcctcgggaacaacgatgaagtaaatgca agcggtgcgttccagcatggttagttagctgatctgtagaaaaaaacaaa aatgaacattaaaccatgctagcctggcgaacaggtgggtaaatcgttc tctccagcaccaggcaggccacggggtctccggcgcgaccctcgtaaaa attgtcgctatgattgaaaaccatcacagagagacgttcccggtggccg gcgtgaatgattcgacaagatgaatacacccccggaacattggcgtccg cgagtgaaaaaaagcgcccgaggaagcaataaggcactacaatgctcag tctcaagtccagcaaagcgatgccatgcggatgaagcacaaaattctca ggtgcgtacaaaatgtaattactcccctcctgcacaggcagcaaagccc ccgatccctccaggtacacatacaaagcctcagcgtccatagcttaccg agcagcagcacacaacaggcgcaagagtcagagaaaggctgagctctaa cctgtccacccgctctctgctcaatatatagcccagatctacactgacg taaaggccaaagtctaaaaatacccgccaaataatcacacacgcccagc acacgcccagaaaccggtgacacactcaaaaaaatacgcgcacttcctc aaacgcccaaaactgccgtcatttccgggttcccacgctacgtcatcaa aacacgactttcaaattccgtcgaccgttaaaaacgtcacccgccccgc ccctaacggtcgcccgtctctcagccaatcagcgccccgcatccccaaa ttcaaacGcctcatttgcatattaacgcgcacaaaaagtttgaggtata ttattgatgatgg SEQ ID NO: 64. Amino Acid Sequence Comprising an Immunogenic PSA, PSMA, and PSCA Polypeptide (Encoded by Plasmid 457 and Vector AdC68X-733)

MASIVGGWECEKHSQPWQVLVASRGRAVCGGVLVHPQWVLTAAHCIRNK

SVILLGRHSLFHPEDTGQVFQVSHSFPHPLYDMSLLKNRFLRPGDDSSH

DLMLLRLSEPAELTDAVKVMDLPTQEPALGTTCYASGWGSIEPEEFLTP

KKLQCVDLHVISNDVCAQVHPQKVTKFMLCAGRWTGGKSTCSGDSGGPL

VCNGVLQGITSWGSEPCALPERPSLYTKVVHYRKWIKDTIVANPGSQTL

NFDLLKLAGDVESNPGPMASARRPRWLCAGALVLAGGFFLLGFLFGWFI

-continued

KSSNEATNITPKHNMKAFLDELKAENIKKFLYNFTQIPHLAGTEQNFQL
AKQIQSQWKEFGLDSVELAHYDVLLSYPNKTHPNYISIINEDGNEIFNT
SLFEPPPPGYENVSDIVPPFSAFSPQGMPEGDLVYVNYARTEDFFKLER
DMKINCSGKIVIARYGKVFRGNKVKNAQLAGAKGVILYSDPADYFAPGV
KSYPDGWNLPGGGVQRGNILNLNGAGDPLTPGYPANEYAYRRGIAEAVG
LPSIPVHPIGYYDAQKLLEKMGGSAPPDSSWRGSLKVPYNVGPGFTGNF
STQKVKMHIHSTNEVTRIYNVIGTLRGAVEPDRYVILGGHRDSWVFGGI
DPQSGAAVVHEIVRSFGTLKKEGWRPRRTILFASWDAEEFGLLGSTEWA
EENSRLLQERGVAYINADSSIEGNYTLRVDCTPLMYSLVHNLTKELKSP
DEGFEGKSLYESWTKKSPSPEFSGMPRISKLGSGNDFEVFFQRLGIASG
RARYTKNWETNKFSGYPLYHSVYETYELVEKFYDPMFKYHLTVAQVRGG
MVFELANSIVLPFDCRDYAVVLRKYADKIYSISMKHPQEMKTYSVSFDS
LFSAVKNFTEIASKFSERLQDFDKSNPIVLRMMNDQLMFLERAFIDPLG
LPDRPFYRHVIYAPSSHNKYAGESFPGIYDALFDIESKVDPSKAWGEVK
RQIYVAAFTVQAAAETLSEVAGSEGRGSLLTCGDVEENPGPASKAVLLA
LLMAGLALQPGTALLCYSCKAQVSNEDCLQVENCTQLGEQCWTARIRAV
GLLTVISKGCSLNCVDDSQDYYVGKKNITCCDTDLCNASGAHALQPAAA
ILALLPALGLLLWGPGQL

SEQ ID NO: 65. Nucleotide Sequence Encoding the Amino Acid Sequence of SEQ ID NO: 64

ATGGCTAGCATCGTCGGAGGGTGGGAGTGCGAAAAGCACTCACAGCCAT
GGCAGGTCCTGGTCGCCTCGCGCGGACGCGCCGTGTGTGGAGGTGTGCT
GGTCCACCCGCAGTGGGTGTTGACTGCGGCCCATTGCATCAGAAATAAG
TCCGTGATCCTCTTGGGGAGACATTCCCTGTTTCACCCCGAAGATACTG
GACAGGTGTTCCAAGTGAGCCACTCCTTCCCGCATCCACTGTACGACAT
GAGCCTGCTGAAGAACCGCTTTCTGCGGCCAGGGGACGACTCATCACAC
GATTTGATGCTGCTTCGGCTCTCGGAACCGGCCGAGCTCACCGACGCAG
TGAAGGTCATGGACCTCCCTACGCAAGAGCCTGCTCTCGGTACCACTTG
TTACGCATCGGGATGGGGCTCCATCGAGCCGGAAGAATTCCTGACCCCG
AAAAAGCTGCAGTGCGTGGATCTGCACGTGATTTCGAATGACGTGTGCG
CGCAAGTGCATCCACAAAAGGTCACTAAGTTCATGCTGTGCGCCGGAAG
GTGGACCGGCGGAAAATCGACCTGTTCCGGCGACAGCGGAGGCCCACTC
GTGTGCAACGGTGTGCTGCAGGGCATCACTAGCTGGGGATCAGAACCGT
GCGCGCTTCCGGAGCGGCCCTCGCTCTACACGAAGGTGGTGCACTACCG
CAAATGGATTAAAGATACCATCGTCGCAAACCCTggatcccagaccctg
aactttgatctgctgaaactggcaggcgatgtggaaagcaacccaggcc
caATGGCTAGCGCTCGCAGACCGCGGTGGCTGTGTGCAGGGGCGCTCGT
CCTGGCGGGTGGCTTCTTTTTGCTCGGCTTTCTTTTCGGATGGTTCATC
AAATCGTCAAACGAAGCTACCAATATCACCCCGAAGCACAACATGAAGG
CCTTTCTGGATGAGCTGAAGGCTGAGAACATTAAGAAGTTCCTCTACAA
CTTCACCCAGATCCCACATTTGGCGGGCACTGAGCAGAACTTTCAGTTG
GCTAAGCAGATCCAGAGCCAGTGGAAGGAATTCGGCCTGGACTCCGTCG -continued AGCTGGCGCATTACGATGTGCTGCTGAGCTACCCTAATAAGACTCATCC
GAACTATATCTCGATTATCAATGAGGACGGAAACGAAATCTTTAACACG
TCCCTCTTCGAGCCGCCACCGCCTGGATACGAGAACGTGTCAGATATCG
TGCCTCCGTTCTCGGCCTTCTCGCCCCAGGGAATGCCCGAAGGGGACCT
GGTGTACGTGAACTACGCAAGGACCGAGGACTTCTTCAAGTTGGAGCGG
GATATGAAGATCAATTGCAGCGGAAAGATCGTCATCGCCCGCTACGGCA
AAGTGTTCCGCGGCAACAAGGTGAAGAATGCACAGTTGGCAGGCGCCAA
GGGCGTCATCCTCTACTCGGATCCTGCCGACTACTTCGCTCCTGGCGTG
AAATCCTACCCTGATGGTTGGAATCTGCCAGGAGGAGGGGTGCAGAGGG
GAAATATCCTGAACCTGAACGGTGCCGGTGACCCACTTACTCCGGGTTA
CCCGGCCAACGAATACGCGTACAGGCGGGGTATCGCGGAAGCCGTCGGA
CTGCCGTCCATCCCGGTCCATCCGATTGGTTACTACGACGCCCAGAAGC
TCCTCGAAAAGATGGGAGGCAGCGCCCCTCCGGACTCGTCATGGAGAGG
CTCGCTGAAGGTGCCATACAACGTGGGACCCGGATTCACTGGAAATTTC
AGCACTCAAAAAGTGAAGATGCACATTCACTCCACTAACGAAGTCACCA
GGATCTACAACGTCATCGGAACCCTCCGGGGAGCGGTGGAACCGGACCG
CTACGTGATCCTCGGTGGACACCGGGATAGCTGGGTGTTCGGAGGAATC
GATCCTCAATCGGGCGCAGCCGTCGTCCATGAAATCGTCAGGTCCTTTG
GTACTCTTAAGAAGGAGGGCTGGCGCCCTAGACGCACTATTCTGTTCGC
CTCGTGGGATGCCGAAGAATTTGGTCTGCTCGGCAGCACCGAATGGGCT
GAGGAAAACTCCCGCCTGCTCCAAGAACGCGGAGTGGCGTACATCAATG
CCGACTCATCCATCGAAGGAAACTACACGCTGCGGGTGGACTGCACTCC
ACTGATGTACTCGCTCGTGCACAACCTGACCAAAGAACTCAAATCCCCA
GACGAAGGATTCGAGGGAAAATCGCTGTACGAGTCGTGGACCAAGAAGA
GCCCATCCCCGGAGTTCAGCGGGATGCCGCGGATCTCAAAGCTCGGATC
AGGAAATGATTTCGAAGTGTTCTTTCAGAGGCTGGGAATTGCGTCGGGA
AGGGCTCGGTACACGAAAAACTGGGAAACTAACAAGTTCTCGGGATACC
CGCTGTACCACTCGGTGTATGAAACTTACGAACTGGTGGAGAAATTCTA
CGATCCTATGTTTAAGTACCACCTGACTGTGGCCCAAGTGAGAGGCGGA
ATGGTGTTCGAGTTGGCCAATTCAATTGTGCTGCCATTCGATTGCCGCG
ACTACGCCGTGGTGCTGAGAAAGTACGCAGACAAAATCTACTCAATCAG
CATGAAGCACCCACAAGAGATGAAAACCTACTCAGTCTCCTTCGACTCC
CTCTTCTCCGCGGTGAAGAACTTCACCGAGATCGCGAGCAAATTCTCGG
AGCGCCTTCAAGATTTTGACAAATCCAATCCGATCGTCCTCCGCATGAT
GAATGACCAGCTCATGTTTCTCGAACGGGCCTTCATCGATCCACTGGGA
CTTCCGGACCGGCCGTTTTACCGCCACGTGATCTACGCGCCCTCGTCGC
ATAACAAGTATGCTGGAGAGAGCTTCCCGGGTATCTACGACGCATTGTT
CGACATTGAGTCCAAGGTGGATCCGTCCAAAGCCTGGGGTGAAGTGAAG
CGCCAAATCTACGTGGCGGCCTTTACCGTCCAGGCGGCAGCAGAAACCT
TGAGCGAGGTGGCTggatccgaaggtaggggttcattattgacctgtgg -continued agatgtcgaagaaaacccaggacccGCTAGCAAAGCAGTGCTGCTGGCG

CTCCTGATGGCTGGACTCGCGCTGCAGCCTGGAACCGCCCTGCTCTGTT

ACTCGTGCAAGGCCCAAGTCTCGAATGAGGACTGTTTGCAAGTGGAAAA

CTGCACCCAGCTCGGAGAACAATGCTGGACTGCACGGATCCGCGCTGTC

GGCCTGCTGACCGTGATCTCCAAAGGGTGCTCATTGAACTGCGTGGACG

ATAGCCAGGACTACTACGTGGGAAAGAAGAATATCACTTGTTGCGACAC

GGATCTTTGCAACGCGTCCGGAGCGCACGCCCTGCAGCCAGCAGCCGCC

ATTCTGGCCCTGCTTCCGGCCCTGGGGTTGCTGCTCTGGGGTCCGGGCC

AGCTC

SEQ ID NO: 66. Nucleotide Sequence of the Multi-antigen Construct (PSCA-F2A-PSMA-mIRES-PSA) Incorporated in Plasmid 459 and Vector AdC68X-735

ATGGCTAGCAAAGCAGTGCTGCTGGCGCTCCTGATGGCTGGACTCGCGC

TGCAGCCTGGAACCGCCCTGCTCTGTTACTCGTGCAAGGCCCAAGTCTC

GAATGAGGACTGTTTGCAAGTGGAAAACTGCACCCAGCTCGGAGAACAA

TGCTGGACTGCACGGATCCGCGCTGTCGGCCTGCTGACCGTGATCTCCA

AAGGGTGCTCATTGAACTGCGTGGACGATAGCCAGGACTACTACGTGGG

AAAGAAGAATATCACTTGTTGCGACACGGATCTTTGCAACGCGTCCGGA

GCGCACGCCCTGCAGCCAGCAGCCGCCATTCTGGCCCTGCTTCCGGCCC

TGGGGTTGCTGCTCTGGGGTCCGGGCCAGCTCggatcccagaccctgaa ctttgatctgctgaaactggcaggcgatgtggaaagcaacccaggccca

ATGGCTAGCGCTCGCAGACCGCGGTGGCTGTGTGCAGGGGCGCTCGTCC

TGGCGGGTGGCTTCTTTTTGCTCGGCTTTCTTTTCGGATGGTTCATCAA

ATCGTCAAACGAAGCTACCAATATCACCCCGAAGCACAACATGAAGGCC

TTTCTGGATGAGCTGAAGGCTGAGAACATTAAGAAGTTCCTCTACAACT

TCACCCAGATCCCACATTTGGCGGGCACTGAGCAGAACTTTCAGTTGGC

TAAGCAGATCCAGAGCCAGTGGAAGGAATTCGGCCTGGACTCCGTCGAG

CTGGCGCATTACGATGTGCTGCTGAGCTACCCTAATAAGACTCATCCGA

ACTATATCTCGATTATCAATGAGGACGGAAACGAAATCTTTAACACGTC

CCTCTTCGAGCCGCCACCGCCTGGATACGAGAACGTGTCAGATATCGTG

CCTCCGTTCTCGGCCTTCTCGCCCCAGGGAATGCCCGAAGGGGACCTGG

TGTACGTGAACTACGCAAGGACCGAGGACTTCTTCAAGTTGGAGCGGGA

TATGAAGATCAATTGCAGCGGAAAGATCGTCATCGCCCGCTACGGCAAA

GTGTTCCGCGGCAACAAGGTGAAGAATGCACAGTTGGCAGGCGCCAAGG

GCGTCATCCTCTACTCGGATCCTGCCGACTACTTCGCTCCTGGCGTGAA

ATCCTACCCTGATGGTTGGAATCTGCCAGGAGGAGGGGTGCAGAGGGGA

AATATCCTGAACCTGAACGGTGCCGGTGACCCACTTACTCCGGGTTACC

CGGCCAACGAATACGCGTACAGGCGGGGTATCGCGGAAGCCGTCGGACT

GCCGTCCATCCCGGTCCATCCGATTGGTTACTACGACGCCCAGAAGCTC

CTCGAAAAGATGGGAGGCAGCGCCCCTCCGGACTCGTCATGGAGAGGCT

CGCTGAAGGTGCCATACAACGTGGGACCCGGATTCACTGGAAATTTCAG

CACTCAAAAAGTGAAGATGCACATTCACTCCACTAACGAAGTCACCAGG

-continued

ATCTACAACGTCATCGGAACCCTCCGGGGAGCGGTGGAACCGGACCGCT

ACGTGATCCTCGGTGGACACCGGGATAGCTGGGTGTTCGGAGGAATCGA

TCCTCAATCGGGCGCAGCCGTCGTCCATGAAATCGTCAGGTCCTTTGGT

ACTCTTAAGAAGGAGGGCTGGCGCCCTAGACGCACTATTCTGTTCGCCT

CGTGGGATGCCGAAGAATTTGGTCTGCTCGGCAGCACCGAATGGGCTGA

GGAAAACTCCCGCCTGCTCCAAGAACGCGGAGTGGCGTACATCAATGCC

GACTCATCCATCGAAGGAAACTACACGCTGCGGGTGGACTGCACTCCAC

TGATGTACTCGCTCGTGCACAACCTGACCAAAGAACTCAAATCCCCAGA

CGAAGGATTCGAGGGAAAATCGCTGTACGAGTCGTGGACCAAGAAGAGC

CCATCCCCGGAGTTCAGCGGGATGCCGCGGATCTCAAAGCTCGGATCAG

GAAATGATTTCGAAGTGTTCTTTCAGAGGCTGGGAATTGCGTCGGGAAG

GGCTCGGTACACGAAAAACTGGGAAACTAACAAGTTCTCGGGATACCCG

CTGTACCACTCGGTGTATGAAACTTACGAACTGGTGGAGAAATTCTACG

ATCCTATGTTTAAGTACCACCTGACTGTGGCCCAAGTGAGAGGCGGAAT

GGTGTTCGAGTTGGCCAATTCAATTGTGCTGCCATTCGATTGCCGCGAC

TACGCCGTGGTGCTGAGAAAGTACGCAGACAAAATCTACTCAATCAGCA

TGAAGCACCCACAAGAGATGAAAACCTACTCAGTCTCCTTCGACTCCCT

CTTCTCCGCGGTGAAGAACTTCACCGAGATCGCGAGCAAATTCTCGGAG

CGCCTTCAAGATTTTGACAAATCCAATCCGATCGTCCTCCGCATGATGA

ATGACCAGCTCATGTTTCTCGAACGGGCCTTCATCGATCCACTGGGACT

TCCGGACCGGCCGTTTTACCGCCACGTGATCTACGCGCCCTCGTCGCAT

AACAAGTATGCTGGAGAGAGCTTCCCGGGTATCTACGACGCATTGTTCG

ACATTGAGTCCAAGGTGGATCCGTCCAAAGCCTGGGGTGAAGTGAAGCG

CCAAATCTACGTGGCGGCCTTTACCGTCCAGGCGGCAGCAGAAACCTTG

AGCGAGGTGGCTTGAagatctgacccccctaacgttactggccgaagccg cttggaataaggccggtgtgcgtttgtctatatgttattttccaccata ttgccgtcttttggcaatgtgagggcccggaaacctggccctgtcttct tgacgagcattcctaggggtctttcccctctcgccaaaggaatgcaagg tctgttgaatgtcgtgaaggaagcagttcctctggaagcttcttgaaga caaacaacgtctgtagcgaccctttgcaggcagcggaaccccccacctg gcgacaggtgcctctgcggccaaaagccacgtgtataagatacacctgc aaaggcggcacaaccccagtgccacgttgtgagttggatagttgtggaa agagtcaaatggctctcctcaagcgtattcaacaaggggctgaaggatg cccagaaggtaccccattgtatgggatctgatctggggcctcggtgcac atgctttacatgtgtttagtcgaggttaaaaaacgtctaggccccccga accacggggacgtggttttcctttgaaaaacacgatgataatATGGCTA

GCATCGTCGGAGGGTGGGAGTGCGAAAAGCACTCACAGCCATGGCAGGT

CCTGGTCGCCTCGCGCGGACGCGCCGTGTGTGGAGGTGTGCTGGTCCAC

CCGCAGTGGGTGTTGACTGCGGCCCATTGCATCAGAAATAAGTCCGTGA

TCCTCTTGGGGAGACATTCCCTGTTTCACCCCGAAGATACTGGACAGGT

GTTCCAAGTGAGCCACTCCTTCCCGCATCCACTGTACGACATGAGCCTG

-continued

CTGAAGAACCGCTTTCTGCGGCCAGGGGACGACTCATCACACGATTTGA

TGCTGCTTCGGCTCTCGGAACCGGCCGAGCTCACCGACGCAGTGAAGGT

CATGGACCTCCCTACGCAAGAGCCTGCTCTCGGTACCACTTGTTACGCA

TCGGGATGGGGCTCCATCGAGCCGGAAGAATTCCTGACCCCGAAAAAGC

TGCAGTGCGTGGATCTGCACGTGATTTCGAATGACGTGTGCGCGCAAGT

GCATCCACAAAAGGTCACTAAGTTCATGCTGTGCGCCGGAAGGTGGACC

GGCGGAAAATCGACCTGTTCCGGCGACAGCGGAGGCCCACTCGTGTGCA

ACGGTGTGCTGCAGGGCATCACTAGCTGGGGATCAGAACCGTGCGCGCT

TCCGGAGCGGCCCTCGCTCTACACGAAGGTGGTGCACTACCGCAAATGG

ATTAAAGATACCATCGTCGCAAACCCT

The invention claimed is:

1. A method of treating prostate cancer in a human, which comprises administering to the human an effective amount of a C68 DNA vector, wherein the C68 DNA vector comprises: (1) a C68 nucleotide sequence; and (2) a multi-antigen construct, wherein the C68 nucleotide sequence is the sequence of SEQ ID NO: 57 lacking at least one gene selected from the group consisting of E1A, E1B, E2A, E2B, E3, E4, L1, L2, L3, L4 and L5 genes, wherein the multi-antigen construct encodes only two different immunogenic PAA polypeptides selected from the group consisting of:

(1) an immunogenic PSMA polypeptide and an immunogenic PSA polypeptide; and (2) an immunogenic PSA polypeptide and an immunogenic PSCA polypeptide, wherein the two immunogenic PAA polypeptides are each encoded by a coding nucleotide sequence, and wherein the immunogenic PSA polypeptide consists of an amino acid sequence selected from the group consisting of:

(1) an amino acid sequence consisting of amino acids 27-263 of SEQ ID NO: 15; and (2) the amino acid sequence of SEQ ID NO:17.

2. The method according to claim 1, wherein the immunogenic PSCA polypeptide comprises an amino acid sequence selected from the group consisting of:

(1) the amino acid sequence of SEQ ID NO:21;

(2) an amino acid sequence comprising amino acids 2-125 of SEQ ID NO:21; and (3) an amino acid sequence comprising amino acids 4-125 Of SEQ ID NO:21.

3. The method according to claim 2, wherein the immunogenic PSMA polypeptide comprises an amino acid sequence selected from the group consisting of:

(1) an amino acid sequence consisting of amino acids 15-750 of SEQ ID NO:1;

(2) the amino acid sequence of SEQ ID NO:3;

(3) the amino acid sequence of SEQ ID NO:5;

(4) the amino acid sequence of SEQ ID NO:7;

(5) an amino acid sequence comprising amino acids 4-739 of SEQ ID NO:9;

(6) an amino acid sequence comprising amino acids 4-739 of SEQ ID NO:3;

(7) an amino acid sequence comprising amino acids 4-739 of SEQ ID NO:5;

(8) an amino acid sequence comprising amino acids 4-739 of SEQ ID NO:7; and (9) the amino acid sequence of SEQ ID NO:9.

4. The method according to claim 3, wherein the C68 nucleotide sequence is the sequence of SEQ ID NO: 57 lacking the genes of E1A, E1B, and E3.

5. The method according to claim 4, wherein the multi-antigen construct further comprises a separator sequence between the coding nucleotide sequences encoding the immunogenic PAA polypeptides.

6. The method according to claim 5, wherein the separator sequence is selected from the group consisting of:

(1) a nucleotide sequence encoding a 2A peptide sequence; and (2) an internal ribosomal entry site (IRES) sequence.

7. The method according to claim 6, wherein the 2A peptide sequence is selected from the group consisting of the 2A-peptide sequence of FMDV, ERAV, PTV1, EMC-B, EMCV, TME-GD7, ERBV, TaV, DrosC, CrPV, ABPV, IFV, Porcine rotavirus, human rotavirus, *T brucei* TSR1, and *T cruzi* AP endonuclease.

8. The method according to claim 7, wherein the 2A peptide sequence is selected from the group consisting of a FMDV 2A-peptide sequence and a TAV 2A peptide sequence.

9. The method according to claim 6, wherein the IRES sequence is an EMCV IRES sequence.

10. The method according to claim 1, wherein the nucleotide sequence encoding the immunogenic PSA polypeptide is set forth in SEQ ID NO: 18.

11. The method according to claim 10, wherein the nucleotide sequence encoding the immunogenic PSCA polypeptide is selected from the group consisting of:

(1) the nucleotide sequence of SEQ ID NO:22;

(2) a nucleotide sequence comprising nucleotides 10-372 of SEQ ID NO:22;

(3) a degenerate variant of the nucleotide sequence of SEQ ID NO:22; and (4) a degenerate variant of the nucleotide sequence comprising nucleotides 10-372 of SEQ ID NO:22.

12. The method according to claim 11, wherein the nucleotide sequence encoding the immunogenic PSMA polypeptide is selected from the group consisting of:

(1) the nucleotide sequence of SEQ ID NO:4;
(2) the nucleotide sequence of SEQ ID NO:6;
(3) the nucleotide sequence of SEQ ID NO:8;
(4) the nucleotide sequence of SEQ ID NO:10;
(5) a nucleotide sequence comprising nucleotides 43-2250 of SEQ ID NO:2;
(6) a nucleotide sequence comprising nucleotides 10-2217 of SEQ ID NO:4;
(7) a nucleotide sequence comprising nucleotides 10-2217 of SEQ ID NO:6;
(8) a nucleotide sequence comprising nucleotides 10-2217 of SEQ ID NO:8;
(9) a nucleotide sequence comprising nucleotides 10-2217 of SEQ ID NO:10;
(10) a nucleotide sequence comprising nucleotides 2333-4543 of SEQ ID NO:58;
(11) a nucleotide sequence comprising nucleotides 2324-4543 of SEQ ID NO:58; and
(12) a degenerate variant of any of the nucleotide sequences provided in (1)-(11).

13. The method according to claim 1, further comprising administering to the human an effective amount of an immune modulator.

14. The method according to claim 13, wherein the immune modulator is an immune-effector-cell enhancer.

15. The method according to claim 13, wherein the immune modulator is selected from the group consisting of a TNFR agonist, a CTLA-4 antagonist, a TLR agonist, a PD-1 antagonist, and a PD L-1 antagonist.

16. The method according to claim 13, wherein the immune modulator is a CTLA-4 antagonist.

17. The method according to claim 16, wherein the CTLA-4 antagonist is an anti-CTLA-4 antibody.

18. The method according to claim 13, wherein the immune modulator is a PD-1 antagonist.

19. A method of treating prostate cancer in a human, which comprises administering to the human an effective amount of a pharmaceutical composition comprising a C68 vector and a pharmaceutically acceptable excipient, wherein the C68 vector comprises: (1) a C68 nucleotide sequence; and (2) a multi-antigen construct, wherein the C68 nucleotide sequence is the sequence of SEQ ID NO: 57 lacking at least one gene selected from the group consisting of E1A, E1B, E2A, E2B, E3, E4, L1, L2, L3, L4 and L5 genes, wherein the multi-antigen construct encodes only two different immunogenic PAA polypeptides selected from the group consisting of:

(1) an immunogenic PSMA polypeptide and an immunogenic PSA polypeptide; and
(2) an immunogenic PSA polypeptide and an immunogenic PSCA polypeptide, and wherein the immunogenic PSA polypeptide consists of the amino acid sequence of SEQ ID NO:17.

* * * * *